US012522638B2

(12) United States Patent
Chang et al.

(10) Patent No.: US 12,522,638 B2
(45) Date of Patent: Jan. 13, 2026

(54) IL12 RECEPTOR AGONISTS AND METHODS OF USE THEREOF

(71) Applicant: Regeneron Pharmaceuticals, Inc., Tarrytown, NY (US)

(72) Inventors: Aaron Chang, White Plains, NY (US); Jiaxi Wu, Elmsford, NY (US); Tong Zhang, New Rochelle, NY (US); Nicolin Bloch, Ossining, NY (US); Erica Ullman, Yorktown Heights, NY (US); Eric Smith, New York, NY (US); Chia-Yang Lin, Scarsdale, NY (US); Samuel Davis, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 5 days.

(21) Appl. No.: 17/813,122

(22) Filed: Jul. 18, 2022

(65) Prior Publication Data

US 2023/0051304 A1 Feb. 16, 2023

Related U.S. Application Data

(60) Provisional application No. 63/337,038, filed on Apr. 29, 2022, provisional application No. 63/281,580, filed on Nov. 19, 2021, provisional application No. 63/233,084, filed on Aug. 13, 2021, provisional application No. 63/223,534, filed on Jul. 19, 2021.

(51) Int. Cl.

| | |
|---|---|
| ***C07K 14/54*** | (2006.01) |
| ***A61K 47/68*** | (2017.01) |
| ***A61P 37/04*** | (2006.01) |
| ***C07K 16/24*** | (2006.01) |
| ***C07K 16/28*** | (2006.01) |
| ***C07K 16/30*** | (2006.01) |
| *A61K 38/00* | (2006.01) |

(52) U.S. Cl.

CPC ...... *C07K 14/5434* (2013.01); *A61K 47/6845* (2017.08); *A61P 37/04* (2018.01); *C07K 16/244* (2013.01); *C07K 16/2833* (2013.01); *C07K 16/30* (2013.01); *A61K 38/00* (2013.01); *C07K 2317/30* (2013.01); *C07K 2317/52* (2013.01); *C07K 2317/55* (2013.01); *C07K 2317/622* (2013.01); *C07K 2317/75* (2013.01); *C07K 2319/00* (2013.01)

(58) Field of Classification Search

CPC ............ C07K 14/5434; C07K 2317/52; C07K 2317/75; A61K 47/6845

See application file for complete search history.

(56) References Cited

U.S. PATENT DOCUMENTS

| | | | | |
|---|---|---|---|---|
| 9,447,159 | B2 | 9/2016 | Ast et al. | |
| 10,696,722 | B2 | 6/2020 | Kim et al. | |
| 2019/0194283 | A1 | 6/2019 | Hauskins et al. | |
| 2020/0283489 | A1* | 9/2020 | Winston | C07K 16/18 |
| 2022/0162280 | A1 | 5/2022 | Fu et al. | |
| 2023/0220031 | A1* | 7/2023 | Garcia | A61P 35/00 424/85.2 |

FOREIGN PATENT DOCUMENTS

| | | | |
|---|---|---|---|
| CA | 3147126 | | 9/2021 |
| EP | 3766512 | A1 | 1/2021 |
| WO | WO2017062953 | | 4/2017 |
| WO | WO2018023093 | A1 | 2/2018 |
| WO | WO2019209965 | | 10/2019 |
| WO | WO2020072821 | | 4/2020 |
| WO | WO2021016640 | | 1/2021 |
| WO | WO2021062406 | | 4/2021 |
| WO | WO2021067863 | | 4/2021 |
| WO | WO2021189139 | | 9/2021 |
| WO | WO2021202678 | | 10/2021 |
| WO | WO2021212083 | | 10/2021 |
| WO | WO2022155263 | A2 | 7/2022 |
| WO | WO2022236292 | | 11/2022 |

OTHER PUBLICATIONS

Almagro JC, Fransson J. Humanization of antibodies. Front Biosci. Jan. 1, 2008;13:1619-33. (Year: 2008).*

Yoon C, Johnston SC, Tang J, Stahl M, Tobin JF, Somers WS. Charged residues dominate a unique interlocking topography in the heterodimeric cytokine interleukin-12. EMBO J. Jul. 17, 2000;19(14):3530-41. (Year: 2000).*

Esch, Alessandra, et al. "Deciphering site 3 interactions of interleukin 12 and interleukin 23 with their cognate murine and human receptors." Journal of Biological Chemistry 295.30 (2020): 10478-10492.

Glassman, Caleb R., et al. "Structural basis for IL-12 and IL-23 receptor sharing reveals a gateway for shaping actions on T versus NK cells." Cell 184.4 (2021): 983-999.

Morris et al., 2021, "WTX-330, a conditionally activated IL-12 Indukine therapy, releases IL-12 selectively in the tumor microenvironment to activate anti-tumor immune responses and induce regressions in mouse tumor models," Society for Immunotherapy of Cancer (SITC). Poster.

Mansurov et al., 2022, "Masking the immunotoxicity of interleukin-12 by fusing it with a domain of its receptor via a tumor-protease-cleavable linker" Nature Biomedical Engineering 6: 819-829.

Patel et al., 2021, "XTX301, A Protein-engineered IL-12, Exhibits Tumor-selective Activity in Mice Without Peripheral Toxicities And Is Well Tolerated In Non-Human Primates", Society for Immunotherapy of Cancer (SITC). Poster.

International Search Report and Written Opinion for PCT/US2022/073832, mailed Mar. 28, 2023.

International Search Report and Written Opinion for PCT/US2024/011444 mailed Apr. 26, 2024.

Xue, Diyuan, et al. "A tumor-specific pro-IL-12 activates preexisting cytotoxic T cells to control established tumors." Science immunology 7.67 (2022): eabi6899.

* cited by examiner

*Primary Examiner* — Aurora M Fontainhas
*Assistant Examiner* — Jennifer A Benavides
(74) *Attorney, Agent, or Firm* — Biospark Intellectual Property Law

(57) ABSTRACT

The present disclosure relates to IL12 receptor agonists with improved therapeutic profiles.

13 Claims, 73 Drawing Sheets

Specification includes a Sequence Listing.

Monovalent:
IL12(p35xp40)-Fc

Monovalent:
IL12*(p35*xp40*)-Fc

Monovalent:
Fc-IL12(p35xp40)

Monovalent:
Fc-IL12*(p35*xp40*)

Monovalent:
Fc-p40-p35 x Fc

Monovalent:
Fc-IL12(p35-p40)

Bivalent:
IL12(p40-p35)-Fc

Bivalent:
IL12*(p40*-p35*)-Fc

Bivalent:
IL12(p35-p40)-Fc

Bivalent:
Fc-IL12(p40-p35)

Bivalent:
Fc-IL12(p35-p40)

p40(mutein)-p35-Fc

Fc-p40(mutein)-p35 p40-p35(mutein)-Fc

Fc-p40-p35(mutein)

Fc-p40(mutein-p35
(mutein)

p40(D2-D3)-p35-Fc

Fc-p40-(D2-D3)-p35

Fc-p35-p40(D2-D3)

Monovalent:
Fc-p40-p35-IL12Rβ2
x Fc

Monovalent:
Fc-p40-p35-IL12Rβ1
x Fc

Monovalent:
Fc-IL12Rβ1-p40-p35
x Fc

Monovalent:
Fc-p40-p35
x Fc-IL12Rβ1

Monovalent:
Fc-p40-p35
x Fc-IL12Rβ2

Monovalent:
Fc-p35-IL12Rβ2
x Fc-p40

Monovalent:
Fc-p35
x Fc-p40-IL12Rβ1

Monovalent:
Fc-IL12Rβ1-p40-p35
x Fc-IL12Rβ2

Monovalent:
Fc-p40-p35-αp40
x Fc

Monovalent:
Fc-p40-p35-αp35
x Fc

Monovalent:
Fc-p40-p35
x Fc-αp40

Monovalent:
Fc-p40-p35
x Fc-αp35

Monovalent:
Fc-p40(mutein)-p35
x Fc-IL12Rβ2

Monovalent:
Fc-IL12Rβ1-p40-p35(mutein)
x Fc

Monovalent:
Fc-p35
x Fc
x IL12Rβ1-p40

Monovalent:
Fc-p35
x Fc-IL12Rβ2
x p40

Monovalent:
Fc-p35
x Fc-IL12Rβ2
x IL12Rβ1-p40

*Disulfide removal reduces HMW species in p35-p40 orientation on denaturing gel

Monovalent:
Fc-p40-p35 x Fc-αp35Fab

Monovalent:
Fc-p40-p35 x Fc-αp40Fab

Monovalent:
Targeting Moiety-Fc-p40-p35
x Targeting Moiety-Fc-αp35Fab

Monovalent:
Targeting Moiety-Fc-p40-p35
x Targeting Moiety-Fc-αp40Fab

SEQUENCE LISTING

```
Sequence total quantity: 136
SEQ ID NO: 1           moltype = AA  length = 9
FEATURE                Location/Qualifiers
source                 1..9
                       mol_type = protein
                       organism = synthetic construct
SEQUENCE: 1
YMLDLQPET                                                              9

SEQ ID NO: 2           moltype = AA  length = 9
FEATURE                Location/Qualifiers
source                 1..9
                       mol_type = protein
                       organism = synthetic construct
SEQUENCE: 2
LLMGTLGIV                                                              9

SEQ ID NO: 3           moltype = AA  length = 5
FEATURE                Location/Qualifiers
source                 1..5
                       mol_type = protein
                       organism = synthetic construct
VARIANT                3
                       note = Any amino acid
SEQUENCE: 3
```

-continued

```
WSXWS                                                        5

SEQ ID NO: 4          moltype = AA  length = 6
FEATURE               Location/Qualifiers
source                1..6
                      mol_type = protein
                      organism = Homo sapiens
SEQUENCE: 4
WSEWAS                                                       6

SEQ ID NO: 5          moltype = AA  length = 328
FEATURE               Location/Qualifiers
source                1..328
                      mol_type = protein
                      organism = Homo sapiens
SEQUENCE: 5
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                               328

SEQ ID NO: 6          moltype = AA  length = 219
FEATURE               Location/Qualifiers
source                1..219
                      mol_type = protein
                      organism = Homo sapiens
SEQUENCE: 6
MCPARSLLLV ATLVLLDHLS LARNLPVATP DPGMFPCLHH SQNLLRAVSN MLQKARQTLE  60
FYPCTSEEID HEDITKDKTS TVEACLPLEL TKNESCLNSR ETSFITNGSC LASRKTSFMM  120
ALCLSSIYED LKMYQVEFKT MNAKLLMDPK RQIFLDQNML AVIDELMQAL NFNSETVPQK  180
SSLEEPDFYK TKIKLCILLH AFRIRAVTID RVMSYLNAS                    219

SEQ ID NO: 7          moltype = AA  length = 127
FEATURE               Location/Qualifiers
source                1..127
                      mol_type = protein
                      organism = synthetic construct
SEQUENCE: 7
EVQLVESGGG LVQPGRSLRL SCVASGFTFN DYAMHWVRQA PGKGLEWVSV ISWNSDSIGY  60
ADSVKGRFTI SRDNAKNSLY LQMHSLRAED TALYYCAKDN HYGSGSYYYY QYGMDVWGQG  120
TTVTVSS                                                      127

SEQ ID NO: 8          moltype = AA  length = 108
FEATURE               Location/Qualifiers
source                1..108
                      mol_type = protein
                      organism = synthetic construct
SEQUENCE: 8
AEIVMTQSPA TLSVSPGERA TLSCRASQSV SSNLAWYQQK PGQAPRLLIY GASTRATGIP  60
ARFSGSGSGT EFTLTISSLQ SEDFAVYYCQ HYINWPLTFG GGTKVEIK          108

SEQ ID NO: 9          moltype = AA  length = 107
FEATURE               Location/Qualifiers
source                1..107
                      mol_type = protein
                      organism = synthetic construct
SEQUENCE: 9
EIVMTQSPAT LSVSPGERAT LSCRASHSVS RNSAWYQQKP GQAPRLLIYG ASTRATGIPA  60
RFSGSGSGTE FTLTISSLQS EDFAIYYCQQ YNNWPLTFGG GTKVEIK           107

SEQ ID NO: 10         moltype = AA  length = 107
FEATURE               Location/Qualifiers
source                1..107
                      mol_type = protein
                      organism = synthetic construct
SEQUENCE: 10
EIVMTQSPAT LSVSPGERAT LSCRASQSVS SNLAWYQQKP GQAPRLLIYG ASTRATGIPA  60
RFSGSGSGTE FTLTISSLQS EDFAVYYCQH YINWPLTFGG GTKVEIK           107

SEQ ID NO: 11         moltype = AA  length = 107
FEATURE               Location/Qualifiers
source                1..107
                      mol_type = protein
                      organism = synthetic construct
SEQUENCE: 11
EIVMTQSPAT LSVSPGERAT LSCRASQSVS RNLAWYQQKP GQAPRLLIYG ASTRATGIPA  60
RFSGSGSGTD FTLTISSLQS EDFAVYYCQQ YNNWPLTFGG GTKVVIK           107
```

```
SEQ ID NO: 12          moltype = AA  length = 107
FEATURE                Location/Qualifiers
source                 1..107
                       mol_type = protein
                       organism = synthetic construct
SEQUENCE: 12
EIVMTQSPAT LSVSPGERAT LSCRASQRIS SNLAWYQQKP GQAPRLLIYG ASTRATGSPA  60
RFSGSGSGTD FTLTISSLQS EDVAVYYCQQ HHNWPLTFGG GTKVEIK                107

SEQ ID NO: 13          moltype = AA  length = 106
FEATURE                Location/Qualifiers
source                 1..106
                       mol_type = protein
                       organism = synthetic construct
SEQUENCE: 13
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                 106

SEQ ID NO: 14          moltype = AA  length = 117
FEATURE                Location/Qualifiers
source                 1..117
                       mol_type = protein
                       organism = synthetic construct
SEQUENCE: 14
EVQLLESGGV LVQPGGSLRL SCAASGFTFS NFGMTWVRQA PGKGLEWVSG ISGGGRDTYF  60
ADSVKGRFTI SRDNSKNTLY LQMNSLKGED TAVYYCVKWG NIYFDYWGQG TLVTVSS     117

SEQ ID NO: 15          moltype = AA  length = 107
FEATURE                Location/Qualifiers
source                 1..107
                       mol_type = protein
                       organism = synthetic construct
SEQUENCE: 15
DIQMTQSPSS LSASVGDSIT ITCRASLSIN TFLNWYQQKP GKAPNLLIYA ASSLHGGVPS  60
RFSGSGSGTD FTLTIRTLQP EDFATYYCQQ SSNTPFTFGP GTVVDFR                107

SEQ ID NO: 16          moltype = AA  length = 15
FEATURE                Location/Qualifiers
source                 1..15
                       mol_type = protein
                       organism = synthetic construct
SEQUENCE: 16
GGGGSGGGGS GGGGS                                                   15

SEQ ID NO: 17          moltype = AA  length = 231
FEATURE                Location/Qualifiers
source                 1..231
                       mol_type = protein
                       organism = synthetic construct
SEQUENCE: 17
DKRVESKYGP CPPCPAPPVA GPSVFLFPPK PKDTLMISRT PEVTCVVVDV SQEDPEVQFN  60
WYVDGVEVHN AKTKPREEQF NSTYRVVSVL TVLHQDWLNG KEYKCKVSNK GLPSSIEKTI  120
SKAKGQPREP QVYTLPPSQE EMTKNQVSLT CLVKGFYPSD IAVEWESNGQ PENNYKTTPP  180
VLDSDGSFFL YSRLTVDKSR WQEGNVFSCS VMHEALHNHY TQKSLSLSLG K           231

SEQ ID NO: 18          moltype = AA  length = 235
FEATURE                Location/Qualifiers
source                 1..235
                       mol_type = protein
                       organism = synthetic construct
SEQUENCE: 18
DKKVEPKSCD KTHTCPPCPA PPVAGPSVFL FPPKPKDTLM ISRTPEVTCV VVDVSQEDPE  60
VQFNWYVDGV EVHNAKTKPR EEQFNSTYRV VSVLTVLHQD WLNGKEYKCK VSNKGLPSSI  120
EKTISKAKGQ PREPQVYTLP PSRDELTKNQ VSLTCLVKGF YPSDIAVEWE SNGQPENNYK  180
TTPPVLDSDG SFFLYSKLTV DKSRWQQGNV FSCSVMHEAL HNHYTQKSLS LSPGK       235

SEQ ID NO: 19          moltype = AA  length = 329
FEATURE                Location/Qualifiers
source                 1..329
                       mol_type = protein
                       organism = synthetic construct
SEQUENCE: 19
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVSQ EDPEVQFNWY VDGVEVHNAK TKPREEQFNS  180
TYRVVSVLTV LHQDWLNGKE YKCKVSNKGL PSSIEKTISK AKGQPREPQV YTLPPSRDEL  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPGK                                    329
```

```
SEQ ID NO: 20          moltype = AA  length = 326
FEATURE                Location/Qualifiers
source                 1..326
                       mol_type = protein
                       organism = synthetic construct
SEQUENCE: 20
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APPVAGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNHYTQKSL SLSLGK                                      326

SEQ ID NO: 21          moltype = AA  length = 329
FEATURE                Location/Qualifiers
source                 1..329
                       mol_type = protein
                       organism = synthetic construct
SEQUENCE: 21
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVSQ EDPEVQFNWY VDGVEVHNAK TKPREEQFNS  180
TYRVVSVLTV LHQDWLNGKE YKCKVSNKGL PSSIEKTISK AKGQPREPQV YTLPPSRDEL  240
TKNQVSLTCL VKGFYPSDIA VEWESNGQPE NNYKTTPPVL DSDGSFFLYS KLTVDKSRWQ  300
QGNVFSCSVM HEALHNRFTQ KSLSLSPGK                                   329

SEQ ID NO: 22          moltype = AA  length = 326
FEATURE                Location/Qualifiers
source                 1..326
                       mol_type = protein
                       organism = synthetic construct
SEQUENCE: 22
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APPVAGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNRFTQKSL SLSLGK                                      326

SEQ ID NO: 23          moltype = AA  length = 11
FEATURE                Location/Qualifiers
source                 1..11
                       mol_type = protein
                       organism = synthetic construct
VARIANT                1..10
                       note = This region may encompass 1-10 residues
SEQUENCE: 23
GGGGGGGGGG S                                                     11

SEQ ID NO: 24          moltype = AA  length = 11
FEATURE                Location/Qualifiers
source                 1..11
                       mol_type = protein
                       organism = synthetic construct
VARIANT                2..11
                       note = This region may encompass 1-10 residues
SEQUENCE: 24
SGGGGGGGGG G                                                     11

SEQ ID NO: 25          moltype = AA  length = 5
FEATURE                Location/Qualifiers
source                 1..5
                       mol_type = protein
                       organism = synthetic construct
SEQUENCE: 25
GGGGS                                                            5

SEQ ID NO: 26          moltype = AA  length = 5
FEATURE                Location/Qualifiers
source                 1..5
                       mol_type = protein
                       organism = synthetic construct
SEQUENCE: 26
GGGGS                                                            5

SEQ ID NO: 27          moltype = AA  length = 4
FEATURE                Location/Qualifiers
source                 1..4
```

```
                        mol_type = protein
                        organism = synthetic construct
SEQUENCE: 27
GGGG                                                                         4

SEQ ID NO: 28           moltype = AA  length = 5
FEATURE                 Location/Qualifiers
source                  1..5
                        mol_type = protein
                        organism = synthetic construct
SEQUENCE: 28
GGGGG                                                                        5

SEQ ID NO: 29           moltype = AA  length = 6
FEATURE                 Location/Qualifiers
source                  1..6
                        mol_type = protein
                        organism = synthetic construct
SEQUENCE: 29
GGGGGG                                                                       6

SEQ ID NO: 30           moltype = AA  length = 7
FEATURE                 Location/Qualifiers
source                  1..7
                        mol_type = protein
                        organism = synthetic construct
SEQUENCE: 30
GGGGGGG                                                                      7

SEQ ID NO: 31           moltype = AA  length = 8
FEATURE                 Location/Qualifiers
source                  1..8
                        mol_type = protein
                        organism = synthetic construct
SEQUENCE: 31
GGGGGGGG                                                                     8

SEQ ID NO: 32           moltype = AA  length = 9
FEATURE                 Location/Qualifiers
source                  1..9
                        mol_type = protein
                        organism = synthetic construct
SEQUENCE: 32
GGGGGGGGG                                                                    9

SEQ ID NO: 33           moltype = AA  length = 5
FEATURE                 Location/Qualifiers
source                  1..5
                        mol_type = protein
                        organism = synthetic construct
SEQUENCE: 33
GSGGS                                                                        5

SEQ ID NO: 34           moltype = AA  length = 4
FEATURE                 Location/Qualifiers
source                  1..4
                        mol_type = protein
                        organism = synthetic construct
SEQUENCE: 34
GGGS                                                                         4

SEQ ID NO: 35           moltype = AA  length = 4
FEATURE                 Location/Qualifiers
source                  1..4
                        mol_type = protein
                        organism = synthetic construct
SEQUENCE: 35
GGSG                                                                         4

SEQ ID NO: 36           moltype = AA  length = 5
FEATURE                 Location/Qualifiers
source                  1..5
                        mol_type = protein
                        organism = synthetic construct
SEQUENCE: 36
GGSGG                                                                        5

SEQ ID NO: 37           moltype = AA  length = 5
FEATURE                 Location/Qualifiers
```

```
source                  1..5
                        mol_type = protein
                        organism = synthetic construct
SEQUENCE: 37
GSGSG                                                                5

SEQ ID NO: 38           moltype = AA  length = 5
FEATURE                 Location/Qualifiers
source                  1..5
                        mol_type = protein
                        organism = synthetic construct
SEQUENCE: 38
GSGGG                                                                5

SEQ ID NO: 39           moltype = AA  length = 5
FEATURE                 Location/Qualifiers
source                  1..5
                        mol_type = protein
                        organism = synthetic construct
SEQUENCE: 39
GGGSG                                                                5

SEQ ID NO: 40           moltype = AA  length = 5
FEATURE                 Location/Qualifiers
source                  1..5
                        mol_type = protein
                        organism = synthetic construct
SEQUENCE: 40
GSSSG                                                                5

SEQ ID NO: 41           moltype = AA  length = 15
FEATURE                 Location/Qualifiers
source                  1..15
                        mol_type = protein
                        organism = synthetic construct
SEQUENCE: 41
GCGASGGGGS GGGGS                                                     15

SEQ ID NO: 42           moltype = AA  length = 10
FEATURE                 Location/Qualifiers
source                  1..10
                        mol_type = protein
                        organism = synthetic construct
SEQUENCE: 42
GGGGSGGGGS                                                           10

SEQ ID NO: 43           moltype = AA  length = 15
FEATURE                 Location/Qualifiers
source                  1..15
                        mol_type = protein
                        organism = synthetic construct
SEQUENCE: 43
GGGASGGGGS GGGGS                                                     15

SEQ ID NO: 44           moltype = AA  length = 15
FEATURE                 Location/Qualifiers
source                  1..15
                        mol_type = protein
                        organism = synthetic construct
SEQUENCE: 44
GGGGSGGGGS GGGGS                                                     15

SEQ ID NO: 45           moltype = AA  length = 10
FEATURE                 Location/Qualifiers
source                  1..10
                        mol_type = protein
                        organism = synthetic construct
SEQUENCE: 45
GGGASGGGGS                                                           10

SEQ ID NO: 46           moltype = AA  length = 20
FEATURE                 Location/Qualifiers
source                  1..20
                        mol_type = protein
                        organism = synthetic construct
SEQUENCE: 46
GGGGSGGGGS GGGGSGGGGS                                                20

SEQ ID NO: 47           moltype = AA  length = 5
```

```
FEATURE                 Location/Qualifiers
source                  1..5
                        mol_type = protein
                        organism = synthetic construct
SEQUENCE: 47
GCGGS                                                                   5

SEQ ID NO: 48           moltype = AA  length = 4
FEATURE                 Location/Qualifiers
source                  1..4
                        mol_type = protein
                        organism = synthetic construct
SEQUENCE: 48
CPPC                                                                    4

SEQ ID NO: 49           moltype = AA  length = 4
FEATURE                 Location/Qualifiers
source                  1..4
                        mol_type = protein
                        organism = Homo sapiens
SEQUENCE: 49
CPSC                                                                    4

SEQ ID NO: 50           moltype = AA  length = 20
FEATURE                 Location/Qualifiers
source                  1..20
                        mol_type = protein
                        organism = synthetic construct
SEQUENCE: 50
EPKSCDKTHT CPPCPAPPVA                                                   20

SEQ ID NO: 51           moltype = AA  length = 17
FEATURE                 Location/Qualifiers
source                  1..17
                        mol_type = protein
                        organism = synthetic construct
SEQUENCE: 51
ESKYGPPCPP CPAPPVA                                                      17

SEQ ID NO: 52           moltype = AA  length = 15
FEATURE                 Location/Qualifiers
source                  1..15
                        mol_type = protein
                        organism = synthetic construct
SEQUENCE: 52
CPPCPAPGGG GPSVF                                                        15

SEQ ID NO: 53           moltype = AA  length = 14
FEATURE                 Location/Qualifiers
source                  1..14
                        mol_type = protein
                        organism = synthetic construct
SEQUENCE: 53
CPPCPAPGGG PSVF                                                         14

SEQ ID NO: 54           moltype = AA  length = 13
FEATURE                 Location/Qualifiers
source                  1..13
                        mol_type = protein
                        organism = synthetic construct
SEQUENCE: 54
CPPCPAPGGP SVF                                                          13

SEQ ID NO: 55           moltype = AA  length = 12
FEATURE                 Location/Qualifiers
source                  1..12
                        mol_type = protein
                        organism = synthetic construct
SEQUENCE: 55
CPPCPAPGPS VF                                                           12

SEQ ID NO: 56           moltype = AA  length = 306
FEATURE                 Location/Qualifiers
source                  1..306
                        mol_type = protein
                        organism = Homo sapiens
SEQUENCE: 56
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
```

```
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                            306

SEQ ID NO: 57          moltype = AA  length = 313
FEATURE                Location/Qualifiers
source                 1..313
                       mol_type = protein
                       organism = Mus sp.
SEQUENCE: 57
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRS                                                    313

SEQ ID NO: 58          moltype = AA  length = 197
FEATURE                Location/Qualifiers
source                 1..197
                       mol_type = protein
                       organism = Homo sapiens
SEQUENCE: 58
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                197

SEQ ID NO: 59          moltype = AA  length = 193
FEATURE                Location/Qualifiers
source                 1..193
                       mol_type = protein
                       organism = Mus sp.
SEQUENCE: 59
RVIPVSGPAR CLSQSRNLLK TTDDMVKTAR EKLKHYSCTA EDIDHEDITR DQTSTLKTCL  60
PLELHKNESC LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSA                                                    193

SEQ ID NO: 60          moltype = AA  length = 228
FEATURE                Location/Qualifiers
source                 1..228
                       mol_type = protein
                       organism = synthetic construct
SEQUENCE: 60
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGK              228

SEQ ID NO: 61          moltype = AA  length = 228
FEATURE                Location/Qualifiers
source                 1..228
                       mol_type = protein
                       organism = synthetic construct
SEQUENCE: 61
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGK              228

SEQ ID NO: 62          moltype = AA  length = 228
FEATURE                Location/Qualifiers
source                 1..228
                       mol_type = protein
                       organism = synthetic construct
SEQUENCE: 62
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGK              228

SEQ ID NO: 63          moltype = AA  length = 227
FEATURE                Location/Qualifiers
source                 1..227
                       mol_type = protein
                       organism = synthetic construct
SEQUENCE: 63
```

```
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGK                227

SEQ ID NO: 64          moltype = AA  length = 443
FEATURE                Location/Qualifiers
source                 1..443
                       mol_type = protein
                       organism = synthetic construct
SEQUENCE: 64
QVQLVESGGG LVKPGGSLRL SCAASGFTFS NYYMSWVRQA PGKGLEWISY ISGRGSTIFY  60
ADSVKGRITI SRDNAKNSLF LQMNSLRAED TAVYFCVKDR GGYSPYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPP VAGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 65          moltype = AA  length = 215
FEATURE                Location/Qualifiers
source                 1..215
                       mol_type = protein
                       organism = synthetic construct
SEQUENCE: 65
DIQMTQSPSS LSASVGDRVT ITCRASQSIS TYLNWYQQKP GKAPKLLIYT ASSLQSGVPS  60
RFSGSGSGTD FTLTISSLQP EDFATYYCQQ SYSTPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 66          moltype = AA  length = 220
FEATURE                Location/Qualifiers
source                 1..220
                       mol_type = protein
                       organism = synthetic construct
SEQUENCE: 66
DGIWSTDILK DQKEPKNKTF LRCEAKNYSG RFTCWWLTTI STDLTFSVKS SRGSSDPQGV  60
TCGAATLSAE RVRGDNKEYE YSVECQEDSA CPAAEESLPI EVMVDAVHKL KYENYTSSFF  120
IRDIIKPDPP KNLQLKPLKN SRQVEVSWEY PDTWSTPHSY FSLTFCVQVQ GKSKREKKDR  180
VFTDKTSATV ICRKNASISV RAQDRYYSSS WSEWASVPCS                        220

SEQ ID NO: 67          moltype = AA  length = 436
FEATURE                Location/Qualifiers
source                 1..436
                       mol_type = protein
                       organism = synthetic construct
SEQUENCE: 67
RVIPVSGPAR CLSQSRNLLK TTDDMVKTAR EKLKHYSCTA EDIDHEDITR DQTSTLKTCL  60
PLELHKNESC LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSAGGGGSGG GGSGGGGSES KYGPPCPPCP APPVAGPSVF LFPPKPKDTL  240
MISRTPEVTC VVVDVSQEDP EVQFNWYVDG VEVHNAKTKP REEQFNSTYR VVSVLTVLHQ  300
DWLNGKEYKC KVSNKGLPSS IEKTISKAKG QPREPQVYTL PPSQEEMTKN QVSLWCLVKG  360
FYPSDIAVEW ESNGQPENNY KTTPPVLDSD GSFFLYSRLT VDKSRWQEGN VFSCSVMHEA  420
LHNHYTQKSL SLSLGK                                                  436

SEQ ID NO: 68          moltype = AA  length = 556
FEATURE                Location/Qualifiers
source                 1..556
                       mol_type = protein
                       organism = synthetic construct
SEQUENCE: 68
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGGGSGG GGSGGGGSES KYGPPCPPCP APPVAGPSVF LFPPKPKDTL  360
MISRTPEVTC VVVDVSQEDP EVQFNWYVDG VEVHNAKTKP REEQFNSTYR VVSVLTVLHQ  420
DWLNGKEYKC KVSNKGLPSS IEKTISKAKG QPREPQVYTL PPSQEEMTKN QVSLSCAVKG  480
FYPSDIAVEW ESNGQPENNY KTTPPVLDSD GSFFLVSRLT VDKSRWQEGN VFSCSVMHEA  540
LHNRFTQKSL SLSPGK                                                  556

SEQ ID NO: 69          moltype = AA  length = 436
FEATURE                Location/Qualifiers
source                 1..436
                       mol_type = protein
                       organism = synthetic construct
```

```
SEQUENCE: 69
RVIPVSGPAR CLSQSRNLLK TTDDMVKTAR EKLKHYSCTA EDIDHEDITR DQTSTLKTCL  60
PLELHKNESS LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSAGGGGSGG GGSGGGGSES KYGPPCPPCP APPVAGPSVF LFPPKPKDTL  240
MISRTPEVTC VVVDVSQEDP EVQFNWYVDG VEVHNAKTKP REEQFNSTYR VVSVLTVLHQ  300
DWLNGKEYKC KVSNKGLPSS IEKTISKAKG QPREPQVYTL PPSQEEMTKN QVSLWCLVKG  360
FYPSDIAVEW ESNGQPENNY KTTPPVLDSD GSFFLYSRLT VDKSRWQEGN VFSCSVMHEA  420
LHNHYTQKSL SLSLGK                                                 436

SEQ ID NO: 70          moltype = AA  length = 556
FEATURE                Location/Qualifiers
source                 1..556
                       mol_type = protein
                       organism = synthetic construct
SEQUENCE: 70
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTSPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGGGSGG GGSGGGGSES KYGPPCPPCP APPVAGPSVF LFPPKPKDTL  360
MISRTPEVTC VVVDVSQEDP EVQFNWYVDG VEVHNAKTKP REEQFNSTYR VVSVLTVLHQ  420
DWLNGKEYKC KVSNKGLPSS IEKTISKAKG QPREPQVYTL PPSQEEMTKN QVSLSCAVKG  480
FYPSDIAVEW ESNGQPENNY KTTPPVLDSD GSFFLVSRLT VDKSRWQEGN VFSCSVMHEA  540
LHNRFTQKSL SLSPGK                                                 556

SEQ ID NO: 71          moltype = AA  length = 436
FEATURE                Location/Qualifiers
source                 1..436
                       mol_type = protein
                       organism = synthetic construct
SEQUENCE: 71
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSRVIPVSG PARCLSQSRN LLKTTDDMVK TAREKLKHYS CTAEDIDHED ITRDQTSTLK  300
TCLPLELHKN ESCLATRETS STTRGSCLPP QKTSLMMTLC LGSIYEDLKM YQTEFQAINA  360
ALQNHNHQQI ILDKGMLVAI DELMQSLNHN GETLRQKPPV GEADPYRVKM KLCILLHAFS  420
TRVVTINRVM GYLSSA                                                 436

SEQ ID NO: 72          moltype = AA  length = 556
FEATURE                Location/Qualifiers
source                 1..556
                       mol_type = protein
                       organism = synthetic construct
SEQUENCE: 72
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRS                                                 556

SEQ ID NO: 73          moltype = AA  length = 764
FEATURE                Location/Qualifiers
source                 1..764
                       mol_type = protein
                       organism = synthetic construct
SEQUENCE: 73
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGGGSGG GGSGGGGSRV IPVSGPARCL SQSRNLLKTT DDMVKTAREK  360
LKHYSCTAED IDHEDITRDQ TSTLKTCLPL ELHKNESCLA TRETSSTTRG SCLPPQKTSL  420
MMTLCLGSIY EDLKMYQTEF QAINAALQNH NHQQIILDKG MLVAIDELMQ SLNHNGETLR  480
QKPPVGEADP YRVKMKLCIL LHAFSTRVVT INRVMGYLSS AGGGGSGGGG SGGGGSESKY  540
GPPCPPCPAP PVAGPSVFLF PPKPKDTLMI SRTPEVTCVV VDVSQEDPEV QFNWYVDGVE  600
VHNAKTKPRE EQFNSTYRVV SVLTVLHQDW LNGKEYKCKV SNKGLPSSIE KTISKAKGQP  660
REPQVYTLPP SQEEMTKNQV SLTCLVKGFY PSDIAVEWES NGQPENNYKT TPPVLDSDGS  720
FFLYSRLTVD KSRWQEGNVF SCSVMHEALH NHYTQKSLSL SLGK                  764
```

```
SEQ ID NO: 74          moltype = AA  length = 764
FEATURE                Location/Qualifiers
source                 1..764
                       mol_type = protein
                       organism = synthetic construct
SEQUENCE: 74
MWELEKDVYV VEVDWTPDAP GETVNLTCDT PEEDDITWTS DQRHGVIGSG KTLTITVKEF  60
LDAGQYTCHK GGETLSHSHL LLHKKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTSPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSGGGGSGG GGSGGGGSRV IPVSGPARCL SQSRNLLKTT DDMVKTAREK  360
LKHYSCTAED IDHEDITRDQ TSTLKTCLPL ELHKNESSLA TRETSSTTRG SCLPPQKTSL  420
MMTLCLGSIY EDLKMYQTEF QAINAALQNH NHQQIILDKG MLVAIDELMQ SLNHNGETLR  480
QKPPVGEADP YRVKMKLCIL LHAFSTRVVT INRVMGYLSS AGGGGSGGGG SGGGGSESKY  540
GPPCPPCPAP PVAGPSVFLF PPKPKDTLMI SRTPEVTCVV VDVSQEDPEV QFNWYVDGVE  600
VHNAKTKPRE EQFNSTYRVV SVLTVLHQDW LNGKEYKCKV SNKGLPSSIE KTISKAKGQP  660
REPQVYTLPP SQEEMTKNQV SLTCLVKGFY PSDIAVEWES NGQPENNYKT TPPVLDSDGS  720
FFLYSRLTVD KSRWQEGNVF SCSVMHEALH NHYTQKSLSL SLGK              764

SEQ ID NO: 75          moltype = AA  length = 774
FEATURE                Location/Qualifiers
source                 1..774
                       mol_type = protein
                       organism = synthetic construct
SEQUENCE: 75
RVIPVSGPAR CLSQSRNLLK TTDDMVKTAR EKLKHYSCTA EDIDHEDITR DQTSTLKTCL  60
PLELHKNESC LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSAGGGGSGG GGSGGGGSGG GGSGGGGSMW ELEKDVYVVE VDWTPDAPGE  240
TVNLTCDTPE EDDITWTSDQ RHGVIGSGKT LTITVKEFLD AGQYTCHKGG ETLSHSHLLL  300
HKKENGIWST EILKNFKNKT FLKCEAPNYS GRFTCSWLVQ RNMDLKFNIK SSSSSPDSRA  360
VTCGMASLSA EKVTLDQRDY EKYSVSCQED VTCPTAEETL PIELALEARQ QNKYENYSTS  420
FFIRDIIKPD PPKNLQMKPL KNSQVEVSWE YPDSWSTPHS YFSLKFFVRI QRKKEKMKET  480
EEGCNQKGAF LVEKTSTEVQ CKGGNVCVQA QDRYYNSSCS KWACVPCRVR SGGGGSGGGG  540
SGGGGSESKY GPPCPPCPAP PVAGPSVFLF PPKPKDTLMI SRTPEVTCVV VDVSQEDPEV  600
QFNWYVDGVE VHNAKTKPRE EQFNSTYRVV SVLTVLHQDW LNGKEYKCKV SNKGLPSSIE  660
KTISKAKGQP REPQVYTLPP SQEEMTKNQV SLTCLVKGFY PSDIAVEWES NGQPENNYKT  720
TPPVLDSDGS FFLYSRLTVD KSRWQEGNVF SCSVMHEALH NHYTQKSLSL SLGK       774

SEQ ID NO: 76          moltype = AA  length = 774
FEATURE                Location/Qualifiers
source                 1..774
                       mol_type = protein
                       organism = synthetic construct
SEQUENCE: 76
RVIPVSGPAR CLSQSRNLLK TTDDMVKTAR EKLKHYSCTA EDIDHEDITR DQTSTLKTCL  60
PLELHKNESS LATRETSSTT RGSCLPPQKT SLMMTLCLGS IYEDLKMYQT EFQAINAALQ  120
NHNHQQIILD KGMLVAIDEL MQSLNHNGET LRQKPPVGEA DPYRVKMKLC ILLHAFSTRV  180
VTINRVMGYL SSAGGGGSGG GGSGGGGSGG GGSGGGGSMW ELEKDVYVVE VDWTPDAPGE  240
TVNLTCDTPE EDDITWTSDQ RHGVIGSGKT LTITVKEFLD AGQYTCHKGG ETLSHSHLLL  300
HKKENGIWST EILKNFKNKT FLKCEAPNYS GRFTCSWLVQ RNMDLKFNIK SSSSSPDSRA  360
VTCGMASLSA EKVTLDQRDY EKYSVSCQED VTSPTAEETL PIELALEARQ QNKYENYSTS  420
FFIRDIIKPD PPKNLQMKPL KNSQVEVSWE YPDSWSTPHS YFSLKFFVRI QRKKEKMKET  480
EEGCNQKGAF LVEKTSTEVQ CKGGNVCVQA QDRYYNSSCS KWACVPCRVR SGGGGSGGGG  540
SGGGGSESKY GPPCPPCPAP PVAGPSVFLF PPKPKDTLMI SRTPEVTCVV VDVSQEDPEV  600
QFNWYVDGVE VHNAKTKPRE EQFNSTYRVV SVLTVLHQDW LNGKEYKCKV SNKGLPSSIE  660
KTISKAKGQP REPQVYTLPP SQEEMTKNQV SLTCLVKGFY PSDIAVEWES NGQPENNYKT  720
TPPVLDSDGS FFLYSRLTVD KSRWQEGNVF SCSVMHEALH NHYTQKSLSL SLGK       774

SEQ ID NO: 77          moltype = AA  length = 764
FEATURE                Location/Qualifiers
source                 1..764
                       mol_type = protein
                       organism = synthetic construct
SEQUENCE: 77
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                 764
```

```
SEQ ID NO: 78          moltype = AA  length = 764
FEATURE                Location/Qualifiers
source                 1..764
                       mol_type = protein
                       organism = synthetic construct
SEQUENCE: 78
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES SLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                764

SEQ ID NO: 79          moltype = AA  length = 774
FEATURE                Location/Qualifiers
source                 1..774
                       mol_type = protein
                       organism = synthetic construct
SEQUENCE: 79
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSRVIPVSG PARCLSQSRN LLKTTDDMVK TAREKLKHYS CTAEDIDHED ITRDQTSTLK  300
TCLPLELHKN ESCLATRETS STTRGSCLPP QKTSLMMTLC LGSIYEDLKM YQTEFQAINA  360
ALQNHNHQQI ILDKGMLVAI DELMQSLNHN GETLRQKPPV GEADPYRVKM KLCILLHAFS  420
TRVVTINRVM GYLSSAGGGG SGGGGSGGGG SGGGGSGGGG SMWELEKDVY VVEVDWTPDA  480
PGETVNLTCD TPEEDDITWT SDQRHGVIGS GKTLTITVKE FLDAGQYTCH KGGETLSHSH  540
LLLHKKENGI WSTEILKNFK NKTFLKCEAP NYSGRFTCSW LVQRNMDLKF NIKSSSSSPD  600
SRAVTCGMAS LSAEKVTLDQ RDYEKYSVSC QEDVTCPTAE ETLPIELALE ARQQNKYENY  660
STSFFIRDII KPDPPKNLQM KPLKNSQVEV SWEYPDSWST PHSYFSLKFF VRIQRKKEKM  720
KETEEGCNQK GAFLVEKTST EVQCKGGNVC VQAQDRYYNS SCSKWACVPC RVRS        774

SEQ ID NO: 80          moltype = AA  length = 774
FEATURE                Location/Qualifiers
source                 1..774
                       mol_type = protein
                       organism = synthetic construct
SEQUENCE: 80
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSRVIPVSG PARCLSQSRN LLKTTDDMVK TAREKLKHYS CTAEDIDHED ITRDQTSTLK  300
TCLPLELHKN ESSLATRETS STTRGSCLPP QKTSLMMTLC LGSIYEDLKM YQTEFQAINA  360
ALQNHNHQQI ILDKGMLVAI DELMQSLNHN GETLRQKPPV GEADPYRVKM KLCILLHAFS  420
TRVVTINRVM GYLSSAGGGG SGGGGSGGGG SGGGGSGGGG SMWELEKDVY VVEVDWTPDA  480
PGETVNLTCD TPEEDDITWT SDQRHGVIGS GKTLTITVKE FLDAGQYTCH KGGETLSHSH  540
LLLHKKENGI WSTEILKNFK NKTFLKCEAP NYSGRFTCSW LVQRNMDLKF NIKSSSSSPD  600
SRAVTCGMAS LSAEKVTLDQ RDYEKYSVSC QEDVTSPTAE ETLPIELALE ARQQNKYENY  660
STSFFIRDII KPDPPKNLQM KPLKNSQVEV SWEYPDSWST PHSYFSLKFF VRIQRKKEKM  720
KETEEGCNQK GAFLVEKTST EVQCKGGNVC VQAQDRYYNS SCSKWACVPC RVRS        774

SEQ ID NO: 81          moltype = AA  length = 764
FEATURE                Location/Qualifiers
source                 1..764
                       mol_type = protein
                       organism = synthetic construct
SEQUENCE: 81
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
```

```
TLRQKPPVGE ADPARVKMKL CILLHAFSTR VVTINRVMGY LSSA                764

SEQ ID NO: 82          moltype = AA  length = 764
FEATURE                Location/Qualifiers
source                 1..764
                       mol_type = protein
                       organism = synthetic construct
SEQUENCE: 82
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPVRVKMKL CILLHAFSTR VVTINRVMGY LSSA                764

SEQ ID NO: 83          moltype = AA  length = 764
FEATURE                Location/Qualifiers
source                 1..764
                       mol_type = protein
                       organism = synthetic construct
SEQUENCE: 83
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPRRVKMKL CILLHAFSTR VVTINRVMGY LSSA                764

SEQ ID NO: 84          moltype = AA  length = 764
FEATURE                Location/Qualifiers
source                 1..764
                       mol_type = protein
                       organism = synthetic construct
SEQUENCE: 84
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPERVKMKL CILLHAFSTR VVTINRVMGY LSSA                764

SEQ ID NO: 85          moltype = AA  length = 764
FEATURE                Location/Qualifiers
source                 1..764
                       mol_type = protein
                       organism = synthetic construct
SEQUENCE: 85
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
```

```
TSLMMTLCLG SIYEDLKMYQ TEFQAINAAL QNHNHQQIIL DKGMLVAIDE LMQSLNHNGE  720
TLRQKPPVGE ADPYRVKAKL CILLHAFSTR VVTINRVMGY LSSA                   764

SEQ ID NO: 86          moltype = AA  length = 764
FEATURE                Location/Qualifiers
source                 1..764
                       mol_type = protein
                       organism = synthetic construct
SEQUENCE: 86
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKEKL CILLHAFSTR VVTINRVMGY LSSA                   764

SEQ ID NO: 87          moltype = AA  length = 764
FEATURE                Location/Qualifiers
source                 1..764
                       mol_type = protein
                       organism = synthetic construct
SEQUENCE: 87
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEAD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                   764

SEQ ID NO: 88          moltype = AA  length = 764
FEATURE                Location/Qualifiers
source                 1..764
                       mol_type = protein
                       organism = synthetic construct
SEQUENCE: 88
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDATP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                   764

SEQ ID NO: 89          moltype = AA  length = 764
FEATURE                Location/Qualifiers
source                 1..764
                       mol_type = protein
                       organism = synthetic construct
SEQUENCE: 89
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP AAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
```

```
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                   764

SEQ ID NO: 90          moltype = AA  length = 764
FEATURE                Location/Qualifiers
source                 1..764
                       mol_type = protein
                       organism = synthetic construct
SEQUENCE: 90
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPAAADIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                   764

SEQ ID NO: 91          moltype = AA  length = 764
FEATURE                Location/Qualifiers
source                 1..764
                       mol_type = protein
                       organism = synthetic construct
SEQUENCE: 91
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTAILAN FANATFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                   764

SEQ ID NO: 92          moltype = AA  length = 678
FEATURE                Location/Qualifiers
source                 1..678
                       mol_type = protein
                       organism = synthetic construct
SEQUENCE: 92
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSNGIWSTE ILKNFKNKTF LKCEAPNYSG RFTCSWLVQR NMDLKFNIKS SSSSPDSRAV  300
TCGMASLSAE KVTLDQRDYE KYSVSCQEDV TCPTAEETLP IELALEARQQ NKYENYSTSF  360
FIRDIIKPDP PKNLQMKPLK NSQVEVSWEY PDSWSTPHSY FSLKFFVRIQ RKKEKMKETE  420
EGCNQKGAFL VEKTSTEVQC KGGNVCVQAQ DRYYNSSCSK WACVPCRVRS GGGGSGGGGS  480
GGGGSRVIPV SGPARCLSQS RNLLKTTDDM VKTAREKLKH YSCTAEDIDH EDITRDQTST  540
LKTCLPLELH KNESCLATRE TSSTTRGSCL PPQKTSLMMT LCLGSIYEDL KMYQTEFQAI  600
NAALQNHNHQ QIILDKGMLV AIDELMQSLN HNGETLRQKP PVGEADPYRV KMKLCILLHA  660
FSTRVVTINR VMGYLSSA                                                678

SEQ ID NO: 93          moltype = AA  length = 678
FEATURE                Location/Qualifiers
source                 1..678
                       mol_type = protein
                       organism = synthetic construct
SEQUENCE: 93
NGIWSTEILK NFKNKTFLKC EAPNYSGRFT CSWLVQRNMD LKFNIKSSSS SPDSRAVTCG  60
MASLSAEKVT LDQRDYEKYS VSCQEDVTCP TAEETLPIEL ALEARQQNKY ENYSTSFFIR  120
DIIKPDPPKN LQMKPLKNSQ VEVSWEYPDS WSTPHSYFSL KFFVRIQRKK EKMKETEEGC  180
NQKGAFLVEK TSTEVQCKGG NVCVQAQDRY YNSSCSKWAC VPCRVRSGGG GSGGGGSGGG  240
GSRVIPVSGP ARCLSQSRNL LKTTDDMVKT AREKLKHYSC TAEDIDHEDI TRDQTSTLKT  300
CLPLELHKNE SCLATRETSS TTRGSCLPPQ KTSLMMTLCL GSIYEDLKMY QTEFQAINAA  360
LQNHNHQQII LDKGMLVAID ELMQSLNHNG ETLRQKPPVG EADPYRVKMK LCILLHAFST  420
RVVTINRVMG YLSSAGGGGS GGGGSGGGGS ESKYGPPCPP CPAPPVAGPS VFLFPPKPKD  480
TLMISRTPEV TCVVVDVSQE DPEVQFNWYV DGVEVHNAKT KPREEQFNST YRVVSVLTVL  540
HQDWLNGKEY KCKVSNKGLP SSIEKTISKA KGQPREPQVY TLPPSQEEMT KNQVSLTCLV  600
```

```
KGFYPSDIAV EWESNGQPEN NYKTTPPVLD SDGSFFLYSR LTVDKSRWQE GNVFSCSVMH  660
EALHNHYTQK SLSLSLGK                                               678

SEQ ID NO: 94          moltype = AA  length = 764
FEATURE                Location/Qualifiers
source                 1..764
                       mol_type = protein
                       organism = synthetic construct
SEQUENCE: 94
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KAALDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                  764

SEQ ID NO: 95          moltype = AA  length = 764
FEATURE                Location/Qualifiers
source                 1..764
                       mol_type = protein
                       organism = synthetic construct
SEQUENCE: 95
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KAALDAGQYT CHKGGETLSH SHLLLHAKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                  764

SEQ ID NO: 96          moltype = AA  length = 764
FEATURE                Location/Qualifiers
source                 1..764
                       mol_type = protein
                       organism = synthetic construct
SEQUENCE: 96
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDATP DAPGETVNLT CDTPEEDDIT WTSDQRHGVI GSGKTLTITV  300
KEALDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                  764

SEQ ID NO: 97          moltype = AA  length = 764
FEATURE                Location/Qualifiers
source                 1..764
                       mol_type = protein
                       organism = synthetic construct
SEQUENCE: 97
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTAILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNAYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
```

```
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                  764

SEQ ID NO: 98          moltype = AA  length = 774
FEATURE                Location/Qualifiers
source                 1..774
                       mol_type = protein
                       organism = synthetic construct
SEQUENCE: 98
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SGGGGSGGGG SRVIPVSGPA RCLSQSRNLL  600
KTTDDMVKTA REKLKHYSCT AEDIDHEDIT RDQTSTLKTC LPLELHKNES SLATRETSST  660
TRGSCLPPQK TSLMMTLCLG SIYEDLKMYQ TEFQAINAAL QNHNHQQIIL DKGMLVAIDE  720
LMQSLNHNGE TLRQKPPVGE ADPYRVKMKL CILLHAFSTR VVTINRVMGY LSSA        774

SEQ ID NO: 99          moltype = AA  length = 774
FEATURE                Location/Qualifiers
source                 1..774
                       mol_type = protein
                       organism = synthetic construct
SEQUENCE: 99
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SGGGGSGGGG SRVIPVSGPA RCLSQSRNLL  600
KTTDDMVKTA REKLKHYSCT AEDIDHEDIT RDQTSTLKTC LPLELHKNES SLATRETSST  660
TRGSCLPPQK TSLMMTLCLG SIYEDLKMYQ TEFQAINAAL QNHNHQQIIL DKGMLVAIDE  720
LMQSLNHNGE TLRQKPPVGE ADPYRVKMKL CILLHAFSTR VVTINAVMGY LSSA        774

SEQ ID NO: 100         moltype = AA  length = 774
FEATURE                Location/Qualifiers
source                 1..774
                       mol_type = protein
                       organism = synthetic construct
SEQUENCE: 100
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SGGGGSGGGG SRVIPVSGPA RCLSQSRNLL  600
KTTDDMVKTA REKLKHYSCT AEDIDHEDIT RDQTSTLKTC LPLELHKNES SLATRETSST  660
TRGSCLPPQK TSLMMTLCLG SIYEDLKMYQ TEFQAINAAL QNHNHQQIIL DKGMLVAIDE  720
LMQSLNHNGE TLRQKPPVGE ADPYRVKMKL CILLHAFSTR VVTINKVMGY LSSA        774

SEQ ID NO: 101         moltype = AA  length = 774
FEATURE                Location/Qualifiers
source                 1..774
                       mol_type = protein
                       organism = synthetic construct
SEQUENCE: 101
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSVFSLK FFVRIQRKKE KMKETEEGCN QKGAFLVEKT STEVQCKGGN VCVQAQDRYY  540
```

```
NSSCSKWACV PCRVRSGGGG SGGGGSGGGG SGGGGSGGGG SRVIPVSGPA RCLSQSRNLL  600
KTTDDMVKTA REKLKHYSCT AEDIDHEDIT RDQTSTLKTC LPLELHKNES SLATRETSST  660
TRGSCLPPQK TSLMMTLCLG SIYEDLKMYQ TEFQAINAAL QNHNHQQIIL DKGMLVAIDE  720
LMQSLNHNGE TLRQKPPVGE ADPYRVKMKL CILLHAFSTR VVTINRVMGY LSSA        774

SEQ ID NO: 102          moltype = AA  length = 774
FEATURE                 Location/Qualifiers
source                  1..774
                        mol_type = protein
                        organism = synthetic construct
SEQUENCE: 102
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSFFSLK FFVRIQRKKE KMKETEEGCN QKGAFLVEKT STEVQCKGGN VCVQAQDRYY  540
NSSCSKWACV PCRVRSGGGG SGGGGSGGGG SGGGGSGGGG SRVIPVSGPA RCLSQSRNLL  600
KTTDDMVKTA REKLKHYSCT AEDIDHEDIT RDQTSTLKTC LPLELHKNES SLATRETSST  660
TRGSCLPPQK TSLMMTLCLG SIYEDLKMYQ TEFQAINAAL QNHNHQQIIL DKGMLVAIDE  720
LMQSLNHNGE TLRQKPPVGE ADPYRVKMKL CILLHAFSTR VVTINRVMGY LSSA        774

SEQ ID NO: 103          moltype = AA  length = 774
FEATURE                 Location/Qualifiers
source                  1..774
                        mol_type = protein
                        organism = synthetic construct
SEQUENCE: 103
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTSPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRFY  540
NSSCSKWACV PCRVRSGGGG SGGGGSGGGG SGGGGSGGGG SRVIPVSGPA RCLSQSRNLL  600
KTTDDMVKTA REKLKHYSCT AEDIDHEDIT RDQTSTLKTC LPLELHKNES SLATRETSST  660
TRGSCLPPQK TSLMMTLCLG SIYEDLKMYQ TEFQAINAAL QNHNHQQIIL DKGMLVAIDE  720
LMQSLNHNGE TLRQKPPVGE ADPYRVKMKL CILLHAFSTR VVTINRVMGY LSSA        774

SEQ ID NO: 104          moltype = AA  length = 922
FEATURE                 Location/Qualifiers
source                  1..922
                        mol_type = protein
                        organism = synthetic construct
SEQUENCE: 104
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSAGGGGSG GGGSGGGGSG  780
GGGSGGGGSQ LGASGPGDGC CVEKTSFPEG ASGSPLGPRN LSCYRVSKTD YECSWQYDGP  840
EDNVSHVLWC CFVPPNHTHT GQERCRYFSS GPDRTVQFWE QDGIPVLSKV NFWVESRLGN  900
RTMKSQKISQ YLYNWTKTTP PL                                           922

SEQ ID NO: 105          moltype = AA  length = 896
FEATURE                 Location/Qualifiers
source                  1..896
                        mol_type = protein
                        organism = synthetic construct
SEQUENCE: 105
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
```

```
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSAGGGGSG GGGSGGGGSG  780
GGGSNIDVCK LGTVTVQPAP VIPLGSAANI SCSLNPKQGC SHYPSSNELI LLKFVNDVLV  840
ENLHGKKVHD HTGHSSTFQV TNLSLGMTLF VCKLNCSNSQ KKPPVPVCGV EISVGV      896

SEQ ID NO: 106          moltype = AA  length = 901
FEATURE                 Location/Qualifiers
source                  1..901
                        mol_type = protein
                        organism = synthetic construct
SEQUENCE: 106
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSNIDVCKL GTVTVQPAPV IPLGSAANIS CSLNPKQGCS HYPSSNELIL LKFVNDVLVE  300
NLHGKKVHDH TGHSSTFQVT NLSLGMTLFV CKLNCSNSQK KPPVPVCGVE ISVGVGGGGS  360
GGGGSGGGGS GGGGSGGGGS MWELEKDVYV VEVDWTPDAP GETVNLTCDT PEEDDITWTS  420
DQRHGVIGSG KTLTITVKEF LDAGQYTCHK GGETLSHSHL LLHKKENGIW STEILKNFKN  480
KTFLKCEAPN YSGRFTCSWL VQRNMDLKFN IKSSSSSPDS RAVTCGMASL SAEKVTLDQR  540
DYEKYSVSCQ EDVTCPTAEE TLPIELALEA RQQNKYENYS TSFFIRDIIK PDPPKNLQMK  600
PLKNSQVEVS WEYPDSWSTP HSYFSLKFFV RIQRKKEKMK ETEEGCNQKG AFLVEKTSTE  660
VQCKGGNVCV QAQDRYYNSS CSKWACVPCR VRSGGGGSGG GGSGGGGSRV IPVSGPARCL  720
SQSRNLLKTT DDMVKTAREK LKHYSCTAED IDHEDITRDQ TSTLKTCLPL ELHKNESCLA  780
TRETSSTTRG SCLPPQKTSL MMTLCLGSIY EDLKMYQTEF QAINAALQNH NHQQIILDKG  840
MLVAIDELMQ SLNHNGETLR QKPPVGEADP YRVKMKLCIL LHAFSTRVVT INRVMGYLSS  900
A                                                                 901

SEQ ID NO: 107          moltype = AA  length = 764
FEATURE                 Location/Qualifiers
source                  1..764
                        mol_type = protein
                        organism = synthetic construct
SEQUENCE: 107
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                  764

SEQ ID NO: 108          moltype = AA  length = 998
FEATURE                 Location/Qualifiers
source                  1..998
                        mol_type = protein
                        organism = synthetic construct
SEQUENCE: 108
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSAGGGGSG GGGSGGGGSG  780
GGGSNIDVCK LGTVTVQPAP VIPLGSAANI SCSLNPKQGC SHYPSSNELI LLKFVNDVLV  840
ENLHGKKVHD HTGHSSTFQV TNLSLGMTLF VCKLNCSNSQ KKPPVPVCGV EISVGVAPEP  900
PQNISCVQEG ENGTVACSWN SGKVTYLKTN YTLQLSGPNN LTCQKQCFSD NRQNCNRLDL  960
GINLSPDLAE SRFIVRVTAI NDLGNSSSLP HTFTFLDI                          998

SEQ ID NO: 109          moltype = AA  length = 1028
```

```
FEATURE               Location/Qualifiers
source                1..1028
                      mol_type = protein
                      organism = synthetic construct
SEQUENCE: 109
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSAGGGGSG GGGSGGGGSG  780
GGGSGGGGSQ LGASGPGDGC CVEKTSFPEG ASGSPLGPRN LSCYRVSKTD YECSWQYDGP  840
EDNVSHVLWC CFVPPNHTHT GQERCRYFSS GPDRTVQFWE QDGIPVLSKV NFWVESRLGN  900
RTMKSQKISQ YLYNWTKTTP PLGHIKVSQS HRQLRMDWNV SEEAGAEVQF RRRMPTTNWT  960
LGDCGPQVNS GSGVLGDIRG SMSESCLCPS ENMAQEIQIR RRRRLSSGAP GGPWSDWSMP  1020
VCVPPEVL                                                         1028

SEQ ID NO: 110        moltype = AA  length = 912
FEATURE               Location/Qualifiers
source                1..912
                      mol_type = protein
                      organism = synthetic construct
SEQUENCE: 110
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGGGG SGGGGSGGGG SMWELEKDVY VVEVDWTPDA PGETVNLTCD  420
TPEEDDITWT SDQRHGVIGS GKTLTITVKE FLDAGQYTCH KGGETLSHSH LLLHKKENGI  480
WSTEILKNFK NKTFLKCEAP NYSGRFTCSW LVQRNMDLKF NIKSSSSSPD SRAVTCGMAS  540
LSAEKVTLDQ RDYEKYSVSC QEDVTCPTAE ETLPIELALE ARQQNKYENY STSFFIRDII  600
KPDPPKNLQM KPLKNSQVEV SWEYPDSWST PHSYFSLKFF VRIQRKKEKM KETEEGCNQK  660
GAFLVEKTST EVQCKGGNVC VQAQDRYYNS SCSKWACVPC RVRSGGGGSG GGGSGGGGSR  720
VIPVSGPARC LSQSRNLLKT TDDMVKTARE KLKHYSCTAE DIDHEDITRD QTSTLKTCLP  780
LELHKNESCL ATRETSSTTR GSCLPPQKTS LMMTLCLGSI YEDLKMYQTE FQAINAALQN  840
HNHQQIILDK GMLVAIDELM QSLNHNGETL RQKPPVGEAD PYRVKMKLCI LLHAFSTRVV  900
TINRVMGYLS SA                                                    912

SEQ ID NO: 111        moltype = AA  length = 482
FEATURE               Location/Qualifiers
source                1..482
                      mol_type = protein
                      organism = synthetic construct
SEQUENCE: 111
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGHIK VSQSHRQLRM DWNVSEEAGA EVQFRRRMPT TNWTLGDCGP  420
QVNSGSGVLG DIRGSMSESC LCPSENMAQE IQIRRRRRLS SGAPGGPWSD WSMPVCVPPE  480
VL                                                               482

SEQ ID NO: 112        moltype = AA  length = 815
FEATURE               Location/Qualifiers
source                1..815
                      mol_type = protein
                      organism = synthetic construct
SEQUENCE: 112
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGSMWELEKD VYVVEVDWTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SGGGGSQLGA SGPGDGCCVE KTSFPEGASG  600
```

```
SPLGPRNLSC YRVSKTDYEC SWQYDGPEDN VSHVLWCCFV PPNHTHTGQE RCRYFSSGPD  660
RTVQFWEQDG IPVLSKVNFW VESRLGNRTM KSQKISQYLY NWTKTTPPLG HIKVSQSHRQ  720
LRMDWNVSEE AGAEVQFRRR MPTTNWTLGD CGPQVNSGSG VLGDIRGSMS ESCLCPSENM  780
AQEIQIRRRR RLSSGAPGGP WSDWSMPVCV PPEVL                             815

SEQ ID NO: 113          moltype = AA  length = 912
FEATURE                 Location/Qualifiers
source                  1..912
                        mol_type = protein
                        organism = synthetic construct
SEQUENCE: 113
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGGGG SGGGGSGGGG SMWELEKDVY VVEVDWTPDA PGETVNLTCD  420
TPEEDDITWT SDQRHGVIGS GKTLTITVKE FLDAGQYTCH KGGETLSHSH LLLHKKENGI  480
WSTEILKNFK NKTFLKCEAP NYSGRFTCSW LVQRNMDLKF NIKSSSSSPD SRAVTCGMAS  540
LSAEKVTLDQ RDYEKYSVSC QEDVTCPTAE ETLPIELALE ARQQNKYENY STSFFIRDII  600
KPDPPKNLQM KPLKNSQVEV SWEYPDSWST PHSYFSLKFF VRIQRKKEKM KETEEGCNQK  660
GAFLVEKTST EVQCKGGNVC VQAQDRYYNS SCSKWACVPC RVRSGGGGSG GGGSGGGGSR  720
VIPVSGPARC LSQSRNLLKT TDDMVKTARE KLKHYSCTAE DIDHEDITRD QTSTLKTCLP  780
LELHKNESCL ATRETSSTTR GSCLPPQKTS LMMTLCLGSI YEDLKMYQTE FQAINAALQN  840
HNHQQIILDK GMLVAIDELM QSLNHNGETL RQKPPVGEAD PYRVKMKLCI LLHAFSTRVV  900
TINRVMGYLS SA                                                      912

SEQ ID NO: 114          moltype = AA  length = 376
FEATURE                 Location/Qualifiers
source                  1..376
                        mol_type = protein
                        organism = synthetic construct
SEQUENCE: 114
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPL                                                  376

SEQ ID NO: 115          moltype = AA  length = 355
FEATURE                 Location/Qualifiers
source                  1..355
                        mol_type = protein
                        organism = synthetic construct
SEQUENCE: 115
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGSNIDVCKL GTVTVQPAPV IPLGSAANIS CSLNPKQGCS HYPSSNELIL LKFVNDVLVE  300
NLHGKKVHDH TGHSSTFQVT NLSLGMTLFV CKLNCSNSQK KPPVPVCGVE ISVGV       355

SEQ ID NO: 116          moltype = AA  length = 456
FEATURE                 Location/Qualifiers
source                  1..456
                        mol_type = protein
                        organism = synthetic construct
SEQUENCE: 116
QLGASGPGDG CCVEKTSFPE GASGSPLGPR NLSCYRVSKT DYECSWQYDG PEDNVSHVLW  60
CCFVPPNHTH TGQERCRYFS SGPDRTVQFW EQDGIPVLSK VNFWVESRLG NRTMKSQKIS  120
QYLYNWTKTT PPLGGGGSGG GGSMWELEKD VYVVEVDWTP DAPGETVNLT CDTPEEDDIT  180
WTSDQRHGVI GSGKTLTITV KEFLDAGQYT CHKGGETLSH SHLLLHKKEN GIWSTEILKN  240
FKNKTFLKCE APNYSGRFTC SWLVQRNMDL KFNIKSSSSS PDSRAVTCGM ASLSAEKVTL  300
DQRDYEKYSV SCQEDVTCPT AEETLPIELA LEARQQNKYE NYSTSFFIRD IIKPDPPKNL  360
QMKPLKNSQV EVSWEYPDSW STPHSYFSLK FFVRIQRKKE KMKETEEGCN QKGAFLVEKT  420
STEVQCKGGN VCVQAQDRYY NSSCSKWACV PCRVRS                            456

SEQ ID NO: 117          moltype = AA  length = 764
FEATURE                 Location/Qualifiers
source                  1..764
                        mol_type = protein
                        organism = synthetic construct
SEQUENCE: 117
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
```

```
SDGSFFLYSR LTVDKSRWQE GNVFSCSVMH EALHNHYTQK SLSLSLGKGG GGSGGGGSGG  240
GGSMWELEKD VYVVEVDGTP DAPGETVNLT CDTPEEDDIT WTSDQRHGVI GSGKTLTITV  300
KEFLDAGQYT CHKGGETLSH SHLLLHKKEN GIWSTEILKN FKNKTFLKCE APNYSGRFTC  360
SWLVQRNMDL KFNIKSSSSS PDSRAVTCGM ASLSAEKVTL DQRDYEKYSV SCQEDVTCPT  420
AEETLPIELA LEARQQNKYE NYSTSFFIRD IIKPDPPKNL QMKPLKNSQV EVSWEYPDSW  480
STPHSYFSLK FFVRIQRKKE KMKETEEGCN QKGAFLVEKT STEVQCKGGN VCVQAQDRYY  540
NSSCSKWACV PCRVRSGGGG SGGGGSGGGG SRVIPVSGPA RCLSQSRNLL KTTDDMVKTA  600
REKLKHYSCT AEDIDHEDIT RDQTSTLKTC LPLELHKNES CLATRETSST TRGSCLPPQK  660
TSLMMTLCLG SIYEDLKMYQ TEFQAINAAL QNHNHQQIIL DKGMLVAIDE LMQSLNHNGE  720
TLRQKPPVGE ADPYRVKMKL CILLHAFSTR VVTINRVMGY LSSA                 764

SEQ ID NO: 118          moltype = AA  length = 912
FEATURE                 Location/Qualifiers
source                  1..912
                        mol_type = protein
                        organism = synthetic construct
SEQUENCE: 118
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGGGG SGGGGSGGGG SMWELEKDVY VVEVDWTPDA PGETVNLTCD  420
TPEEDDITWT SDQRHGVIGS GKTLTITVKE FLDAGQYTCH KGGETLSHSH LLLHKKENGI  480
WSTEILKNFK NKTFLKCEAP NYSGRFTCSW LVQRNMDLKF NIKSSSSSPD SRAVTCGMAS  540
LSAEKVTLDQ RDYEKYSVSC QEDVTCPTAE ETLPIELALE ARQQNKYENY STSFFIRDII  600
KPDPPKNLQM KPLKNSQVEV SWEYPDSWST PHSYFSLKFF VRIQRKKEKM KETEEGCNQK  660
GAFLVEKTST EVQCKGGNVC VQAQDRYYNS SCSKWACVPC RVRSGGGGSG GGGSGGGGSR  720
VIPVSGPARC LSQSRNLLKT TDDMVKTARE KLKHYSCTAE DIDHEDITRD QTSTLKTCLP  780
LELHKNESCL ATRETSSTTR GSCLPPQKTS LMMTLCLGSI YEDLKMYQTE FQAINAALQN  840
HNHQQIILDK GMLVAIDELM QSLNHNGETL RQKPPVGEAD PGRVKMKLCI LLHAFSTRVV  900
TINRVMGYLS SA                                                     912

SEQ ID NO: 119          moltype = AA  length = 912
FEATURE                 Location/Qualifiers
source                  1..912
                        mol_type = protein
                        organism = synthetic construct
SEQUENCE: 119
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGGGG SGGGGSGGGG SMWELEKDVY VVEVDWTPDA PGETVNLTCD  420
TPEEDDITWT SDQRHGVIGS GKTLTITVKE FLDAGQYTCH KGGETLSHSH LLLHKKENGI  480
WSTEILKNFK NKTFLKCEAP NYSGRFTCSW LVQRNMDLKF NIKSSSSSPD SRAVTCGMAS  540
LSAEKVTLDQ RDYEKYSVSC QEDVTCPTAE ETLPIELALE ARQQNKYENY STSFFIRDII  600
KPDPPKNLQM KPLKNSQVEV SWEYPDSWST PHSYFSLKFF VRIQRKKEKM KETEEGCNQK  660
GAFLVEKTST EVQCKGGNVC VQAQDRYYNS SCSKWACVPC RVRSGGGGSG GGGSGGGGSR  720
VIPVSGPARC LSQSRNLLKT TDDMVKTARE KLKHYSCTAE DIDHEDITRD QTSTLKTCLP  780
LELHKNESCL ATRETSSTTR GSCLPPQKTS LMMTLCLGSI YEDLKMYQTE FQAINAALQN  840
HNHQQIILDK GMLVAIDELM QSLNHNGETL RQKPPVGEAD PLRVKMKLCI LLHAFSTRVV  900
TINRVMGYLS SA                                                     912

SEQ ID NO: 120          moltype = AA  length = 912
FEATURE                 Location/Qualifiers
source                  1..912
                        mol_type = protein
                        organism = synthetic construct
SEQUENCE: 120
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGGGG SGGGGSGGGG SMWELEKDVY VVEVDWTPDA PGETVNLTCD  420
TPEEDDITWT SDQRHGVIGS GKTLTITVKE FLDAGQYTCH KGGETLSHSH LLLHKKENGI  480
WSTEILKNFK NKTFLKCEAP NYSGRFTCSW LVQRNMDLKF NIKSSSSSPD SRAVTCGMAS  540
LSAEKVTLDQ RDYEKYSVSC QEDVTCPTAE ETLPIELALE ARQQNKYENY STSFFIRDII  600
KPDPPKNLQM KPLKNSQVEV SWEYPDSWST PHSYFSLKFF VRIQRKKEKM KETEEGCNQK  660
GAFLVEKTST EVQCKGGNVC VQAQDRYYNS SCSKWACVPC RVRSGGGGSG GGGSGGGGSR  720
VIPVSGPARC LSQSRNLLKT TDDMVKTARE KLKHYSCTAE DIDHEDITRD QTSTLKTCLP  780
LELHKNESCL ATRETSSTTR GSCLPPQKTS LMMTLCLGSI YEDLKMYQTE FQAINAALQN  840
HNHQQIILDK GMLVAIDELM QSLNHNGETL RQKPPVGEAD PVRVKMKLCI LLHAFSTRVV  900
TINRVMGYLS SA                                                     912
```

```
SEQ ID NO: 121          moltype = AA  length = 912
FEATURE                 Location/Qualifiers
source                  1..912
                        mol_type = protein
                        organism = synthetic construct
SEQUENCE: 121
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSQLGASGP GDGCCVEKTS FPEGASGSPL GPRNLSCYRV SKTDYECSWQ YDGPEDNVSH  300
VLWCCFVPPN HTHTGQERCR YFSSGPDRTV QFWEQDGIPV LSKVNFWVES RLGNRTMKSQ  360
KISQYLYNWT KTTPPLGGGG SGGGGSGGGG SMWELEKDVY VVEVDWTPDA PGETVNLTCD  420
TPEEDDITWT SDQRHGVIGS GKTLTITVKE FLDAGQYTCH KGGETLSHSH LLLHKKENGI  480
WSTEILKNFK NKTFLKCEAP NYSGRFTCSW LVQRNMDLKF NIKSSSSSPD SRAVTCGMAS  540
LSAEKVTLDQ RDYEKYSVSC QEDVTCPTAE ETLPIELALE ARQQNKYENY STSFFIRDII  600
KPDPPKNLQM KPLKNSQVEV SWEYPDSWST PHSYFSLKFF VRIQRKKEKM KETEEGCNQK  660
GAFLVEKTST EVQCKGGNVC VQAQDRYYNS SCSKWACVPC RVRSGGGGSG GGGSGGGGSR  720
VIPVSGPARC LSQSRNLLKT TDDMVKTARE KLKHYSCTAE DIDHEDITRD QTSTLKTCLP  780
LELHKNESCL ATRETSSTTR GSCLPPQKTS LMMTLCLGSI YEDLKMYQTE FQAINAALQN  840
HNHQQIILDK GMLVAIDELM QSLNHNGETL RQKPPVGEAD PARVKMKLCI LLHAFSTRVV  900
TINRVMGYLS SA                                                      912

SEQ ID NO: 122          moltype = AA  length = 457
FEATURE                 Location/Qualifiers
source                  1..457
                        mol_type = protein
                        organism = synthetic construct
SEQUENCE: 122
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGSNIDVCKL GTVTVQPAPV IPLGSAANIS CSLNPKQGCS HYPSSNELIL LKFVNDVLVE  300
NLHGKKVHDH TGHSSTFQVT NLSLGMTLFV CKLNCSNSQK KPPVPVCGVE ISVGVAPEPP  360
QNISCVQEGE NGTVACSWNS GKVTYLKTNY TLQLSGPNNL TCQKQCFSDN RQNCNRLDLG  420
INLSPDLAES RFIVRVTAIN DLGNSSSLPH TFTFLDI                           457

SEQ ID NO: 123          moltype = AA  length = 243
FEATURE                 Location/Qualifiers
source                  1..243
                        mol_type = protein
                        organism = synthetic construct
SEQUENCE: 123
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGKGG GGSGGGGSGG  240
GGS                                                                243

SEQ ID NO: 124          moltype = AA  length = 907
FEATURE                 Location/Qualifiers
source                  1..907
                        mol_type = protein
                        organism = synthetic construct
SEQUENCE: 124
QLGASGPGDG CCVEKTSFPE GASGSPLGPR NLSCYRVSKT DYECSWQYDG PEDNVSHVLW  60
CCFVPPNHTH TGQERCRYFS SGPDRTVQFW EQDGIPVLSK VNFWVESRLG NRTMKSQKIS  120
QYLYNWTKTT PPLGGGGSGG GGSMWELEKD VYVVEVDWTP DAPGETVNLT CDTPEEDDIT  180
WTSDQRHGVI GSGKTLTITV KEFLDAGQYT CHKGGETLSH SHLLLHKKEN GIWSTEILKN  240
FKNKTFLKCE APNYSGRFTC SWLVQRNMDL KFNIKSSSSS PDSRAVTCGM ASLSAEKVTL  300
DQRDYEKYSV SCQEDVTCPT AEETLPIELA LEARQQNKYE NYSTSFFIRD IIKPDPPKNL  360
QMKPLKNSQV EVSWEYPDSW STPHSYFSLK FFVRIQRKKE KMKETEEGCN QKGAFLVEKT  420
STEVQCKGGN VCVQAQDRYY NSSCSKWACV PCRVRSGGGG SGGGGSGGGG SRVIPVSGPA  480
RCLSQSRNLL KTTDDMVKTA REKLKHYSCT AEDIDHEDIT RDQTSTLKTC LPLELHKNES  540
CLATRETSST TRGSCLPPQK TSLMMTLCLG SIYEDLKMYQ TEFQAINAAL QNHNHQQIIL  600
DKGMLVAIDE LMQSLNHNGE TLRQKPPVGE ADPYRVKMKL CILLHAFSTR VVTINRVMGY  660
LSSAGGGGSG GGGSGGGGSE SKYGPPCPPC PAPPVAGPSV FLFPPKPKDT LMISRTPEVT  720
CVVVDVSQED PEVQFNWYVD GVEVHNAKTK PREEQFNSTY RVVSVLTVLH QDWLNGKEYK  780
CKVSNKGLPS SIEKTISKAK GQPREPQVYT LPPSQEEMTK NQVSLWCLVK GFYPSDIAVE  840
WESNGQPENN YKTTPPVLDS DGSFFLYSRL TVDKSRWQEG NVFSCSVMHE ALHNHYTQKS  900
LSLSLGK                                                            907

SEQ ID NO: 125          moltype = AA  length = 761
FEATURE                 Location/Qualifiers
source                  1..761
                        mol_type = protein
                        organism = synthetic construct
```

```
SEQUENCE: 125
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGKGG GGSGGGGSGG  240
GGSIWELKKD VYVVELDWYP DAPGEMVVLT CDTPEEDGIT WTLDQSSEVL GSGKTLTIQV  300
KEFGDAGQYT CHKGGEVLSH SLLLLHKKED GIWSTDILKD QKEPKNKTFL RCEAKNYSGR  360
FTCWWLTTIS TDLTFSVKSS RGSSDPQGVT CGAATLSAER VRGDNKEYEY SVECQEDSAC  420
PAAEESLPIE VMVDAVHKLK YENYTSSFFI RDIIKPDPPK NLQLKPLKNS RQVEVSWEYP  480
DTWSTPHSYF SLTFCVQVQG KSKREKKDRV FTDKTSATVI CRKNASISVR AQDRYYSSSW  540
SEWASVPCSG GGGSGGGGSG GGGSRNLPVA TPDPGMFPCL HHSQNLLRAV SNMLQKARQT  600
LEFYPCTSEE IDHEDITKDK TSTVEACLPL ELTKNESCLN SRETSFITNG SCLASRKTSF  660
MMALCLSSIY EDLKMYQVEF KTMNAKLLMD PKRQIFLDQN MLAVIDELMQ ALNFNSETVP  720
QKSSLEEPDF YKTKIKLCIL LHAFRIRAVT IDRVMSYLNA S                    761

SEQ ID NO: 126          moltype = AA  length = 215
FEATURE                 Location/Qualifiers
source                  1..215
                        mol_type = protein
                        organism = Mus sp.
SEQUENCE: 126
MCQSRYLLFL ATLALLNHLS LARVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSA                           215

SEQ ID NO: 127          moltype = AA  length = 335
FEATURE                 Location/Qualifiers
source                  1..335
                        mol_type = protein
                        organism = Mus sp.
SEQUENCE: 127
MCPQKLTISW FAIVLLVSPL MAMWELEKDV YVVEVDWTPD APGETVNLTC DTPEEDDITW  60
TSDQRHGVIG SGKTLTITVK EFLDAGQYTC HKGGETLSHS HLLLHKKENG IWSTEILKNF  120
KNKTFLKCEA PNYSGRFTCS WLVQRNMDLK FNIKSSSSSP DSRAVTCGMA SLSAEKVTLD  180
QRDYEKYSVS CQEDVTCPTA EETLPIELAL EARQQNKYEN YSTSFFIRDI IKPDPPKNLQ  240
MKPLKNSQVE VSWEYPDSWS TPHSYFSLKF FVRIQRKKEK MKETEEGCNQ KGAFLVEKTS  300
TEVQCKGGNV CVQAQDRYYN SSCSKWACVP CRVRS                           335

SEQ ID NO: 128          moltype = AA  length = 189
FEATURE                 Location/Qualifiers
source                  1..189
                        mol_type = protein
                        organism = Homo sapiens
SEQUENCE: 128
MLGSRAVMLL LLLPWTAQGR AVPGGSSPAW TQCQQLSQKL CTLAWSAHPL VGHMDLREEG  60
DEETTNDVPH IQCGDGCDPQ GLRDNSQFCL QRIHQGLIFY EKLLGSDIFT GEPSLLPDSP  120
VGQLHASLLG LSQLLQPEGH HWETQQIPSL SPSQPWQRLL LRFKILRSLQ AFVAVAARVF  180
AHGAATLSP                                                        189

SEQ ID NO: 129          moltype = AA  length = 243
FEATURE                 Location/Qualifiers
source                  1..243
                        mol_type = protein
                        organism = Homo sapiens
SEQUENCE: 129
MGQTAGDLGW RLSLLLLPLL LVQAGVWGFP RPPGRPQLSL QELRREFTVS LHLARKLLSE  60
VRGQAHRFAE SHLPGVNLYL LPLGEQLPDV SLTFQAWRRL SDPERLCFIS TTLQPFHALL  120
GGLGTQGRWT NMERMQLWAM RLDLRDLQRH LRFQVLAAGF NLPEEEEEEE EEEEEEEKGL  180
LPGALGSALQ GPAQVSWPQL LSTYRLLHSL ELVLSRAVRE LLLLSKAGHS VWPLGFPTLS  240
PQP                                                              243

SEQ ID NO: 130          moltype = AA  length = 212
FEATURE                 Location/Qualifiers
source                  1..212
                        mol_type = protein
                        organism = Homo sapiens
SEQUENCE: 130
MNSFSTSAFG PVAFSLGLLL VLPAAFPAPV PPGEDSKDVA APHRQPLTSS ERIDKQIRYI  60
LDGISALRKE TCKNSNMCES SKEALAENNL NLPKMAEKDG CFQSGFNEET CLVKIITGLL  120
EFEVYLEYLQ NRFESSEEQA RAVQMSTKVL IQFLQKKAKN LDAITTPDPT TNASLLTKLQ  180
AQNQWLQDMT THLILRSFKE FLQSSLRALR QM                              212

SEQ ID NO: 131          moltype = AA  length = 200
FEATURE                 Location/Qualifiers
source                  1..200
                        mol_type = protein
                        organism = Homo sapiens
SEQUENCE: 131
```

```
MAFTEHSPLT PHRRDLCSRS IWLARKIRSD LTALTESYVK HQGLNKNINL DSADGMPVAS  60
TDQWSELTEA ERLQENLQAY RTFHVLLARL LEDQQVHFTP TEGDFHQAIH TLLLQVAAFA  120
YQIEELMILL EYKIPRNEAD GMPINVGDGG LFEKKLWGLK VLQELSQWTV RSIHDLRFIS  180
SHQTGIPARG SHYIANNKKM                                            200

SEQ ID NO: 132          moltype = AA  length = 225
FEATURE                 Location/Qualifiers
source                  1..225
                        mol_type = protein
                        organism = Homo sapiens
SEQUENCE: 132
MDLRAGDSWG MLACLCTVLW HLPAVPALNR TGDPGPGPSI QKTYDLTRYL EHQLRSLAGT  60
YLNYLGPPFN EPDFNPPRLG AETLPRATVD LEVWRSLNDK LRLTQNYEAY SHLLCYLRGL  120
NRQAATAELR RSLAHFCTSL QGLLGSIAGV MAALGYPLPQ PLPGTEPTWT PGPAHSDFLQ  180
KMDDFWLLKE LQTWLWRSAK DFNRLKKKMQ PPAAAVTLHL GAHGF                 225

SEQ ID NO: 133          moltype = AA  length = 662
FEATURE                 Location/Qualifiers
source                  1..662
                        mol_type = protein
                        organism = Homo sapiens
SEQUENCE: 133
MEPLVTWVVP LLFLFLLSRQ GAACRTSECC FQDPPYPDAD SGSASGPRDL RCYRISSDRY  60
ECSWQYEGPT AGVSHFLRCC LSSGRCCYFA AGSATRLQFS DQAGVSVLYT VTLWVESWAR  120
NQTEKSPEVT LQLYNSVKYE PPLGDIKVSK LAGQLRMEWE TPDNQVGAEV QFRHRTPSSP  180
WKLGDCGPQD DDTESCLCPL EMNVAQEFQL RRRQLGSQGS SWSKWSSPVC VPPENPPQPQ  240
VRFSVEQLGQ DGRRRLTLKE QPTQLELPEG CQGLAPGTEV TYRLQLHMLS CPCKAKATRT  300
LHLGKMPYLS GAAYNVAVIS SNQFGPGLNQ TWHIPADTHT EPVALNISVG TNGTTMYWPA  360
RAQSMTYCIE WQPVGQDGGL ATCSLTAPQD PDPAGMATYS WSRESGAMGQ EKCYYITIFA  420
SAHPEKLTLW STVLSTYHFG GNASAAGTPH HVSVKNHSLD SVSVDWAPSL LSTCPGVLKE  480
YVVRCRDEDS KQVSEHPVQP TETQVTLSGL RAGVAYTVQV RADTAWLRGV WSQPQRFSIE  540
VQVSDWLIFF ASLGSFLSIL LVGVLGYLGL NRAARHLCPP LPTPCASSAI EFPGGKETWQ  600
WINPVDFQEE ASLQEALVVE MSWDKGERTE PLEKTELPEG APELALDTEL SLEDGDRCKA  660
KM                                                               662

SEQ ID NO: 134          moltype = AA  length = 522
FEATURE                 Location/Qualifiers
source                  1..522
                        mol_type = protein
                        organism = Homo sapiens
SEQUENCE: 134
CRTSECCFQD PPYPDADSGS ASGPRDLRCY RISSDRYECS WQYEGPTAGV SHFLRCCLSS  60
GRCCYFAAGS ATRLQFSDQA GVSVLYTVTL WVESWARNQT EKSPEVTLQL YNSVKYEPPL  120
GDIKVSKLAG QLRMEWETPD NQVGAEVQFR HRTPSSPWKL GDCGPQDDDT ESCLCPLEMN  180
VAQEFQLRRR QLGSQGSSWS KWSSPVCVPP ENPPQPQVRF SVEQLGQDGR RRLTLKEQPT  240
QLELPEGCQG LAPGTEVTYR LQLHMLSCPC KAKATRTLHL GKMPYLSGAA YNVAVISSNQ  300
FGPGLNQTWH IPADTHTEPV ALNISVGTNG TTMYWPARAQ SMTYCIEWQP VGQDGGLATC  360
SLTAPQDPDP AGMATYSWSR ESGAMGQEKC YYITIFASAH PEKLTLWSTV LSTYHFGGNA  420
SAAGTPHHVS VKNHSLDSVS VDWAPSLLST CPGVLKEYVV RCRDEDSKQV SEHPVQPTET  480
QVTLSGLRAG VAYTVQVRAD TAWLRGVWSQ PQRFSIEVQV SD                    522

SEQ ID NO: 135          moltype = AA  length = 862
FEATURE                 Location/Qualifiers
source                  1..862
                        mol_type = protein
                        organism = Homo sapiens
SEQUENCE: 135
MAHTFRGCSL AFMFIITWLL IKAKIDACKR GDVTVKPSHV ILLGSTVNIT CSLKPRQGCF  60
HYSRRNKLIL YKFDRRINFH HGHSLNSQVT GLPLGTTLFV CKLACINSDE IQICGAEIFV  120
GVAPEQPQNL SCIQKGEQGT VACTWERGRD THLYTEYTLQ LSGPKNLTWQ KQCKDIYCDY  180
LDFGINLTPE SPESNFTAKV TAVNSLGSSS SLPSTFTFLD IVRPLPPWDI RIKFQKASVS  240
RCTLYWRDEG LVLLNRLRYR PSNSRLWNMV NVTKAKGRHD LLDLKPFTEY EFQISSKLHL  300
YKGSWSDWSE SLRAQTPEEE PTGMLDVWYM KRHIDYSRQQ ISLFWKNLSV SEARGKILHY  360
QVTLQELTGG KAMTQNITGH TSWTTVIPRT GNWAVAVSAA NSKGSSLPTR INIMNLCEAG  420
LLAPRQVSAN SEGMDNILVT WQPPRKDPSA VQEYVVEWRE LHPGGDTQVP LNWLRSRPYN  480
VSALISENIK SYICYEIRVY ALSGDQGGCS SILGNSKHKA PLSGPHINAI TEEKGSILIS  540
WNSIPVQEQM GCLLHYRIYW KERDSNSQPQ LCEIPYRVSQ NSHPINSLQP RVTYVLWMTA  600
LTAAGESSHG NEREFCLQGK ANWMAFVAPS ICIAIIMVGI FSTHYFQQKV FVLLAALRPQ  660
WCSREIPDPA NSTCAKKYPI AEEKTQLPLD RLLIDWPTPE DPEPLVISEV LHQVTPVFRH  720
PPCSNWPQRE KGIQGHQASE KDMMHSASSP PPPRALQAES RQLVDLYKVL ESRGSDPKPE  780
NPACPWTVLP AGDLPTHDGY LPSNIDDLPS HEAPLADSLE ELEPQHISLS VFPSSSLHPL  840
TFSCGDKLTL DQLKMRCDSL ML                                          862

SEQ ID NO: 136          moltype = AA  length = 599
FEATURE                 Location/Qualifiers
source                  1..599
                        mol_type = protein
                        organism = Homo sapiens
SEQUENCE: 136
```

-continued

```
KIDACKRGDV TVKPSHVILL GSTVNITCSL KPRQGCFHYS RRNKLILYKF DRRINFHHGH  60
SLNSQVTGLP LGTTLFVCKL ACINSDEIQI CGAEIFVGVA PEQPQNLSCI QKGEQGTVAC  120
TWERGRDTHL YTEYTLQLSG PKNLTWQKQC KDIYCDYLDF GINLTPESPE SNFTAKVTAV  180
NSLGSSSSLP STFTFLDIVR PLPPWDIRIK FQKASVSRCT LYWRDEGLVL LNRLRYRPSN  240
SRLWNMVNVT KAKGRHDLLD LKPFTEYEFQ ISSKLHLYKG SWSDWSESLR AQTPEEEPTG  300
MLDVWYMKRH IDYSRQQISL FWKNLSVSEA RGKILHYQVT LQELTGGKAM TQNITGHTSW  360
TTVIPRTGNW AVAVSAANSK GSSLPTRINI MNLCEAGLLA PRQVSANSEG MDNILVTWQP  420
PRKDPSAVQE YVVEWRELHP GGDTQVPLNW LRSRPYNVSA LISENIKSYI CYEIRVYALS  480
GDQGGCSSIL GNSKHKAPLS GPHINAITEE KGSILISWNS IPVQEQMGCL LHYRIYWKER  540
DSNSQPQLCE IPYRVSQNSH PINSLQPRVT YVLWMTALTA AGESSHGNER EFCLQGKAN   599
```

IL12 RECEPTOR AGONISTS AND METHODS OF USE THEREOF

1. CROSS-REFERENCE TO RELATED APPLICATIONS

This application claims the priority benefit of U.S. provisional application No. 63/223,534 filed Jul. 19, 2021; U.S. provisional application No. 63/233,084 filed Aug. 13, 2021; U.S. provisional application No. 63/281,580 filed Nov. 19, 2021; and U.S. provisional application No. 63/337,038 filed Apr. 29, 2022, the contents of each of which are incorporated herein in their entireties by reference thereto.

2. SEQUENCE LISTING

The instant application contains a Sequence Listing which has been submitted electronically in XML file format and is hereby incorporated by reference in its entirety. Said XML copy, created on Jul. 8, 2024, is named RGN-009US-_SL.xml and is 172,597 bytes in size.

3. BACKGROUND

Interleukin 12 (IL-12 or IL12) is a pro-inflammatory cytokine having an important role in both innate and adaptive immunity. Hamza et al., 2010, Int. J. Mol. Sci., 11(3): 789-806. IL12 functions primarily as a 70 kDa heterodimer consisting of disulfide-linked p35 and p40 subunits. Id. A variety of different immune cells, including B cells, dendritic cells, macrophages, monocytes, and neutrophils express IL12 when stimulated (Tugues et al., 2015, Cell Death Differ., 22:237-246), with the active heterodimer forming following protein synthesis. Binding of IL12 to the IL12 receptor complex on T and natural killer (NK) cells leads to signaling via signal transducer and activator of transcription 4 (STAT4) and signal transducer and activator of transcription 3 (STAT3), and subsequent interferon gamma (IFN-γ) production and secretion. Ullrich et al., 2020, EXCLI J., 19:1563-1589. Signaling downstream of IFN-γ includes activation of T-box transcription factor TBX21 (Tbet) and induces pro-inflammatory functions of T helper 1 ($T_H1$) cells. Id.

Due to its ability to activate NK cells and cytotoxic T cells, IL12 has been studied as an anti-cancer therapeutic since the early 1990's. Lasek et al., 2014, Cancer Immunol. Immunother. 63(5):419-435. However, in most patients, repeated administration of IL12 led to adaptive response and a progressive decline of IL12-induced IFN-γ blood levels. Id. Further, severe toxicity resulted from the concomitant induction of IFN-γ along with other cytokines (e.g., TNF-α) and/or chemokines (IP-10 or MIG). Id. Different dosing and timing protocols were developed in an attempt to minimize IFN-γ toxicity and improve IL12 efficacy. Id. These approaches had minimal effect and have not significantly improved patient survival. Id.

Despite the general acceptance in the field of IL12 therapies being developed for immunotherapy, including anticancer therapy, IL12 molecules have generally displayed poor therapeutic indices, with high, toxic doses required to confer modest anti-cancer effects.

Thus, there is a need in the art for novel IL12 therapies with improved therapeutic efficacy and safety profiles.

4. SUMMARY

The present disclosure provides novel IL12 receptor agonists. In certain aspects, IL12 receptor agonists address the drawbacks of IL12 therapy and are characterized by improved therapeutic profiles by virtue of improved half-lives and/or improved safety profiles. In certain aspects, IL12 receptor agonists address the aggregation problems associated with traditional IL12 fusion constructs, for example fusion proteins comprising p35, p40 and an Fc domain. The IL12 receptor agonists of the disclosure typically comprise or consist of IL12 muteins that vary from native IL12 by primary amino acid sequence of p35 and/or p40 and/or by the inclusion of additional domains or moieties not normally present in IL12. Exemplary IL12 receptor agonists are disclosed in Section 6.2, numbered embodiments 3 to 847.

The present disclosure further provides variant p35 and p40 moieties that incorporate amino acid substitutions that contribute to improved therapeutic profiles, e.g., by attenuating IL12 activity due to reduced receptor binding. Exemplary p35 and p40 moieties, including exemplary p35 moieties useful for incorporating into IL12 receptor agonists, are disclosed in Section 6.3 and numbered embodiments 1, 2, 676 to 719 and 589 to 674.

The disclosure further provides nucleic acids encoding the IL12 receptor agonists, the IL12 muteins, the p35 moieties and the p40 moieties of the disclosure. The nucleic acids encoding the IL12 receptor agonist and IL12 muteins that are composed of two or more polypeptide chains can be a single nucleic acid (e.g., a vector encoding all polypeptide chains) or a plurality of nucleic acids (e.g., two or more vectors encoding the different polypeptide chains). The disclosure further provides host cells and cell lines engineered to express the nucleic acids and the IL12 receptor agonists, the IL12 muteins, the p35 moieties, and the p40 moieties of the disclosure. The disclosure further provides methods of producing an IL12 receptor agonist, an IL12 mutein, a p35 moiety and the p40 moieties of the disclosure. Exemplary nucleic acids, host cells, cell lines, and methods of producing the IL12 receptor agonists, the IL12 muteins, the p35 moieties and the p40 moieties are described in Section 6.9 and numbered embodiments 848 to 850, infra.

The disclosure further provides pharmaceutical compositions comprising the IL12 receptor agonists, the IL12 muteins, the p35 moieties and the p40 moieties of the disclosure. Exemplary pharmaceutical compositions are described in Section 6.10 and numbered embodiment 851, infra.

Further provided herein are methods of using the IL12 receptor agonists, the IL12 muteins, the p35 moieties, the p40 moieties and the pharmaceutical compositions of the disclosure, e.g., for treating cancerous conditions. Exemplary methods are described in Section 6.11 and numbered embodiments 852 to 860, infra.

5. BRIEF DESCRIPTION OF THE FIGURES

FIG. 1 is a diagram representing the structure of IL12 (left), the IL12 receptor complex (middle), and IL12 signaling (right).

FIGS. 2A-2P are cartoons representing p35 and p40 moieties having the structural organization of IL12 (FIG. 2A) and various embodiments of monovalent IL12-Fc fusion proteins (FIGS. 2B-2G) and bivalent IL12-Fc fusion proteins (FIGS. 2H-2O) that the IL12 receptor agonists of the disclosure can comprise or consist of. In the embodiments of FIGS. 2B-2P, IL12 moieties can be attached to either the N-terminus of the Fc (FIGS. 2B, 2C, 2H-2J and 2N) or the C-terminus of the Fc (FIGS. 2D-2G, 2K-2M, 2O and 2P). When attached to Fc according to the embodiments of FIGS. 2B-2M, the IL12 moieties can be arranged in the order (N- to C-terminus) of p40 moiety-p35 moiety (FIGS. 2F, 2H, 2I, 2K, and 2M) or p35 moiety-p40 moiety (FIGS. 2G, 2J, and 2L). Alternatively, the p40 moiety can be provided in the form of a p40 monomer. Stars occurring between the p40 and p35 moieties indicate an optionally removed disulfide bond between the subunits. While only certain IL12 moieties are indicated to have a removed disulfide bond between the p40 and p35 moieties, any of IL12-Fc fusion proteins of FIGS. 2A-2O can the disulfide bond between the p40 and p35 moieties removed. Examples of suitable p35 and p40 moieties that can be incorporated into the IL12 fusion proteins of FIGS. 2A-2O are disclosed in, e.g., Section 6.3. The CH2 and CH3 domains shown in FIGS. 2B to 2P form an Fc domain which is a type of multimerization moiety. Fc domains and other multimerization moieties that can be used in the IL12 receptor agonists are described in Section 6.6. The Fc domains in heterodimeric IL12-Fc fusion proteins (e.g., as shown in FIGS. 2B through 2G and 2P) can incorporate any combination of mutations suitable for heterodimerization or selective purification (e.g., knob-in-hole and/or star mutations), for example as described in Section 6.6.1.2 (not shown).

FIGS. 3A-3I are cartoons representing p35 and p40 moieties having the structural orientation of IL12 (FIG. 3A) and various embodiments of IL12-Fc fusion proteins (FIGS. 3B-3I) that can be combined with one another to form a bivalent IL12-Fc fusion protein that the IL12 receptor agonists of the disclosure can comprise or consist of. The p40 moiety can include D1, D2, and D3 domains (FIGS. 3B-3F), or only the D2 and D3 domains (FIGS. 3G-3I). Examples of suitable p35 and p40 moieties that can be incorporated into the IL12 fusion proteins of FIGS. 3A-3I are disclosed in, e.g., Section 6.3. Asterisks occurring on either the p40 moiety or the p35 moiety indicate the optional presence of a mutation in the IL12 moiety, for example one or more of the mutations described in Section 6.3. The CH2 and CH3 domains shown in FIGS. 3B to 3I form an Fc domain which is a type of multimerization moiety. Fc domains and other multimerization moieties that can be used in the IL12 receptor agonists are described in Section 6.6.

FIGS. 4A-4W are cartoons representing the structural orientation of additional embodiments of IL12-Fc fusion proteins that the IL12 receptor agonists of the disclosure can comprise or consist of, incorporating a masking moiety in the form of an IL12 receptor (IL12R) β1 receptor moiety or IL12Rβ2 receptor moiety (FIGS. 4B-4N and 4S-4W) or an anti-IL12 antibody fragment (FIGS. 4O-4R). Examples of suitable p35 and p40 moieties that can be incorporated into the IL12 fusion proteins of FIGS. 4A-4W are disclosed in, e.g., Section 6.3. Examples of suitable IL12 receptor moieties are disclosed in, e.g., Sections 6.4.1 and 6.4.2. Examples of suitable IL12 antibody-based masking moieties are disclosed in, e.g., Section 6.4.3. The CH2 and CH3 domains shown in FIGS. 4B to 4W form an Fc domain which is a type of multimerization moiety. Fc domains and other multimerization moieties that can be used in the IL12 receptor agonists are described in Section 6.6. The Fc domains in heterodimeric IL12-Fc fusion proteins (e.g., as shown in FIGS. 4F through 4W) can incorporate any combination of mutations suitable for heterodimerization or selective purification (e.g., knob-in-hole and/or star mutations), for example as described in Section 6.6.1.2 (not shown).

FIGS. 5A-5S and 5V-5X are cartoons representing the structural orientation of additional embodiments of IL12-Fc fusion proteins that the IL12 receptor agonists of the disclosure can comprise or consist of, incorporating a Fab domain of an antibody (e.g., an anti-PD1 (αPD1) antibody) as a targeting moiety. Examples of suitable p35 and p40 moieties that can be incorporated into the IL12 fusion proteins of FIGS. 5A-5X are disclosed in, e.g., Section 6.3. Examples of suitable targeting moieties are disclosed in, e.g., Section 6.5. The CH2 and CH3 domains shown in FIGS. 5B to 5S and 5V to 5X form an Fc domain which is a type of multimerization moiety. Fc domains and other multimerization moieties that can be used in the IL12 receptor agonists are described in Section 6.6. The Fc domains in heterodimeric IL12-Fc fusion proteins (e.g., as shown in FIGS. 5B, 5C, 5E, 5G through 5S, and 5V though 5X) can incorporate any combination of mutations suitable for heterodimerization or selective purification (e.g., knob-in-hole and/or star mutations), for example as described in Section 6.6.1.2 (not shown). In some aspects, the IL12-Fc fusion proteins are masked, e.g., by a receptor (as shown in FIGS. 5H through 5K, 5O, 5R, 5S, and 5V through 5X) or an antibody (as shown in FIGS. 5L through 5N). Although the antibodies in FIGS. 5L through 5N are depicted as Fvs, in particular scFvs, the scFvs may be substituted with Fabs, as shown in FIGS. 39A-39B.

FIG. 6 discloses SEQ ID NOS 126 and 6, respectively, in order of appearance.

FIG. 7 discloses SEQ ID NOS 127 and 5, respectively, in order of appearance.

Figure 8:
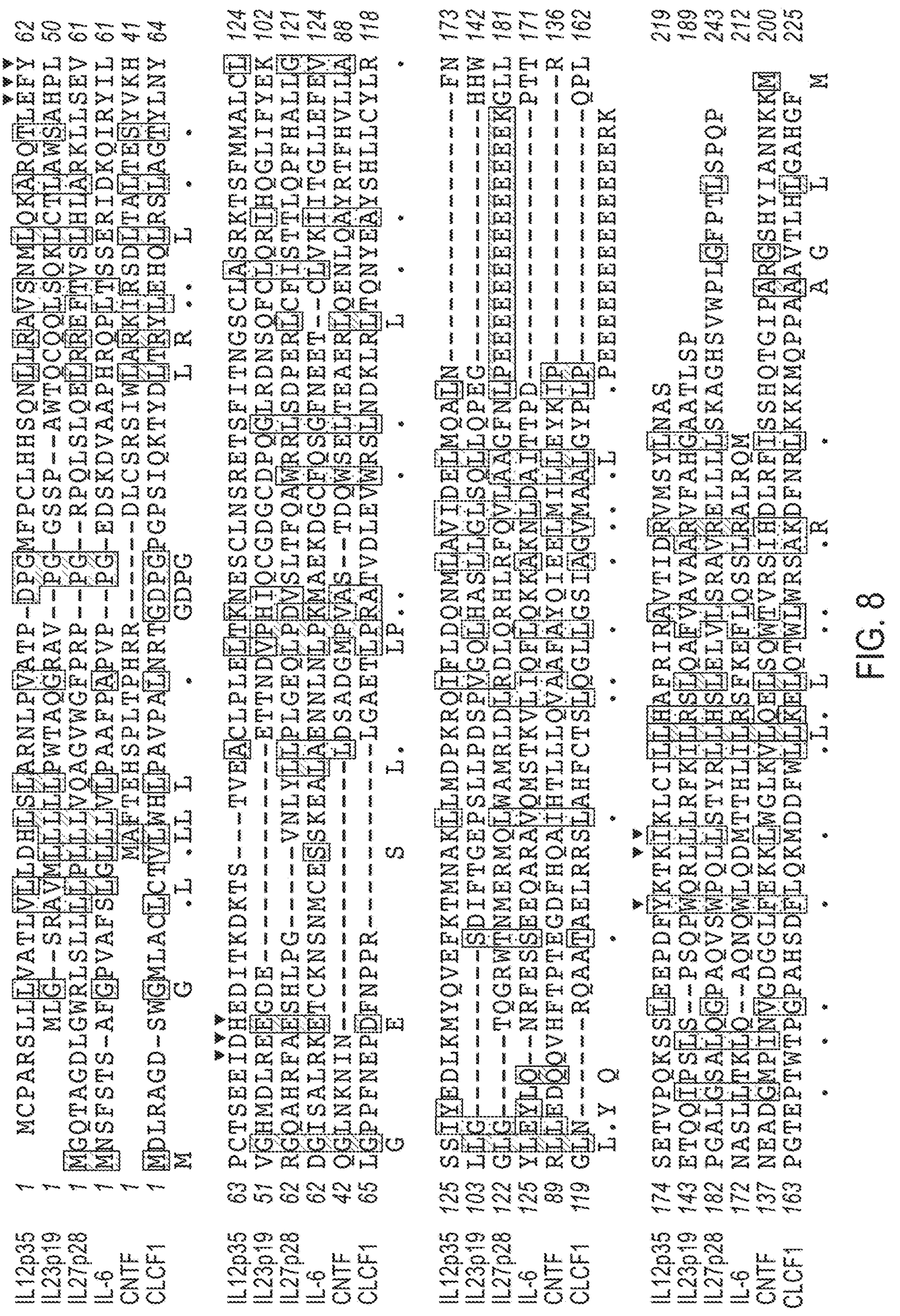

FIG. 8 depicts a sequence alignment of human IL12 p35 with other representative IL6 family cytokines. Arrows depict positions of representative amino acid substitutions. FIG. 8 discloses SEQ ID NOS 6, 128-132, respectively, in order of appearance.

Figure 9:
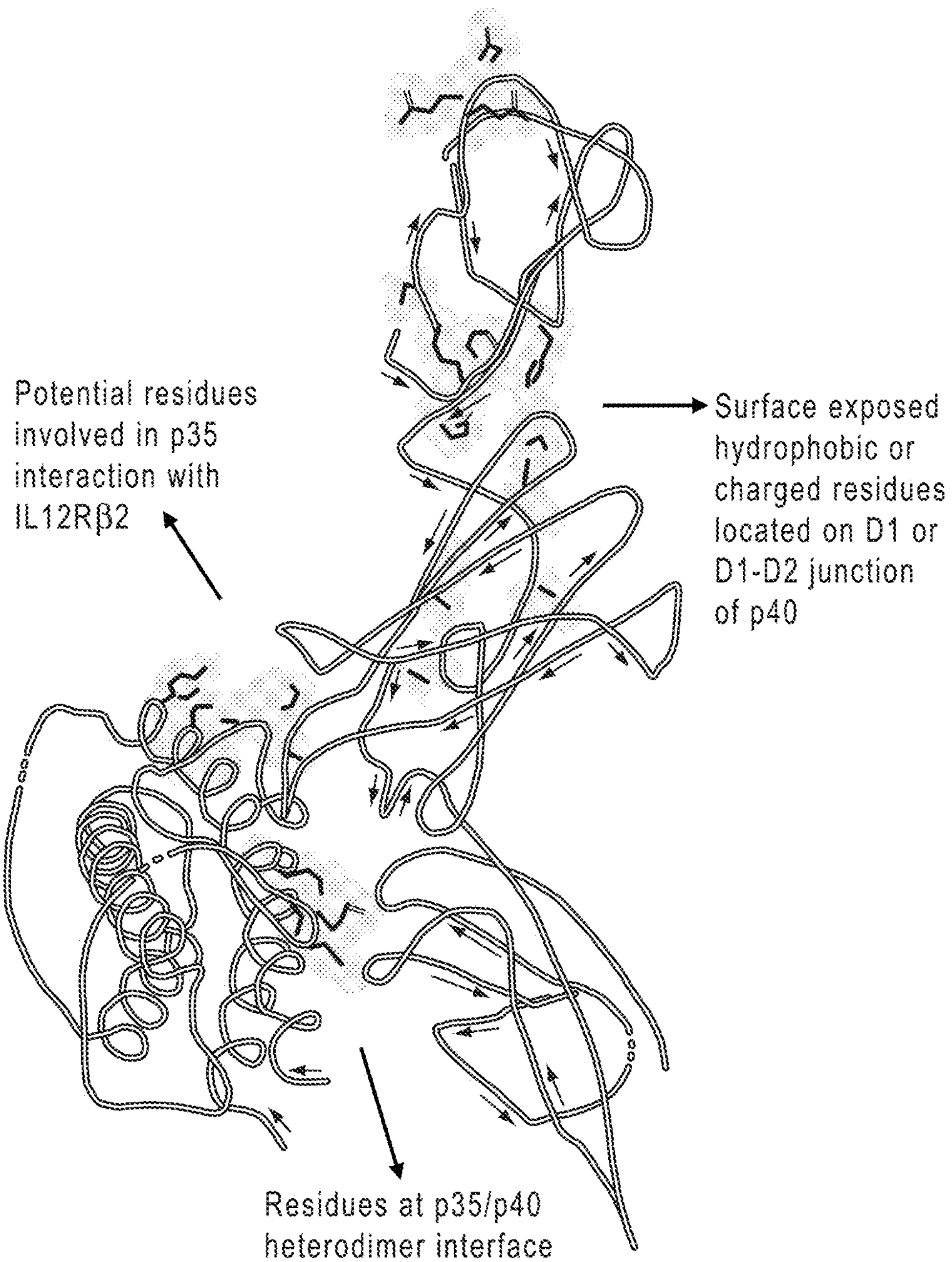

FIG. 9 depicts the 3-dimensional structure of IL12 (p35 and p40), highlighting potential residues involved in p35 interaction with IL12Rβ2, residues at the p35/p40 heterodimer interface, and surface-exposed residues located on D1 or the D1-D2 junction of p40 potentially involved in interaction with IL12Rβ1.

Figure 10A:
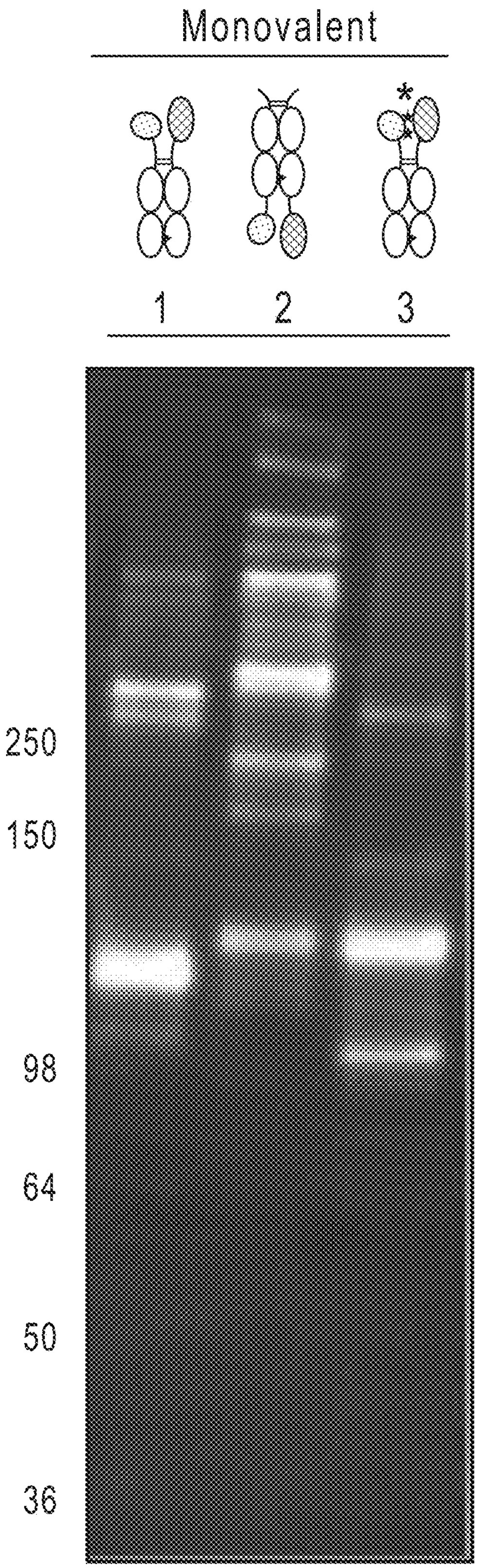
Figure 10B:
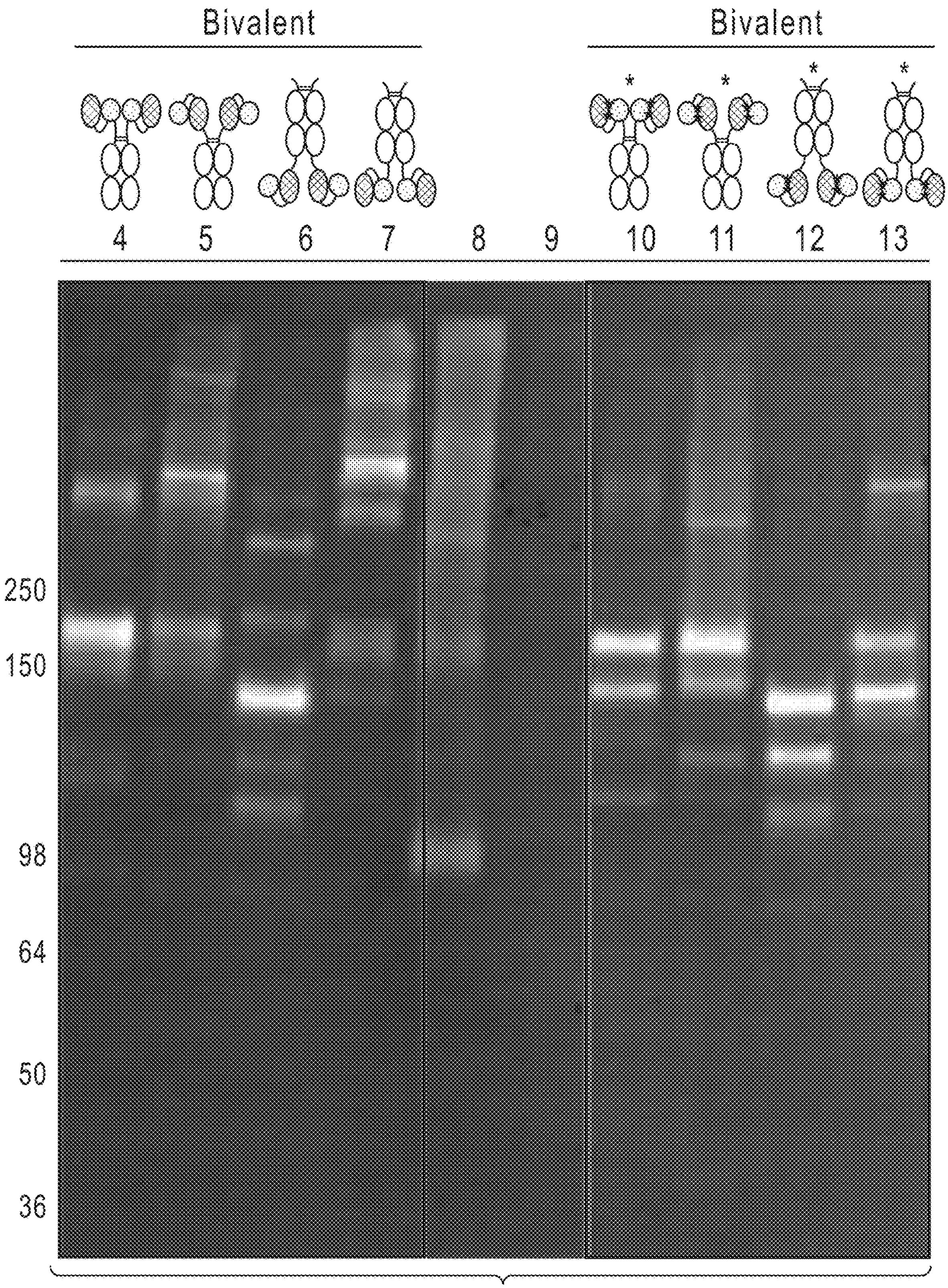

FIGS. 10A-10B are photographs of SDS-PAGE gels depicting the size of IL12-Fc fusion proteins. FIG. 10A: lane 1) Monovalent: IL12(p35×p40)-Fc; lane 2) Monovalent: Fc-IL12(p35×p40); lane 3) Monovalent: IL12*(p35*×p40*)-Fc. FIG. 10B: lane 4) Bivalent: IL12(p40-p35)-Fc; lane 5) Bivalent: IL12(p35-p40)-Fc; lane 6) Bivalent: Fc-IL12(p40-p35); lane 7) Bivalent: Fc-IL12(p35-p40); lane 10) Bivalent: IL12*(p40*-p35*)-Fc; lane 11) Bivalent: IL12*(p35*-p40*)-Fc; lane 12) Bivalent: Fc-IL12*(p40*-p35*); lane 13) Bivalent: Fc-IL12*(p35*-p40*).

Figure 11:
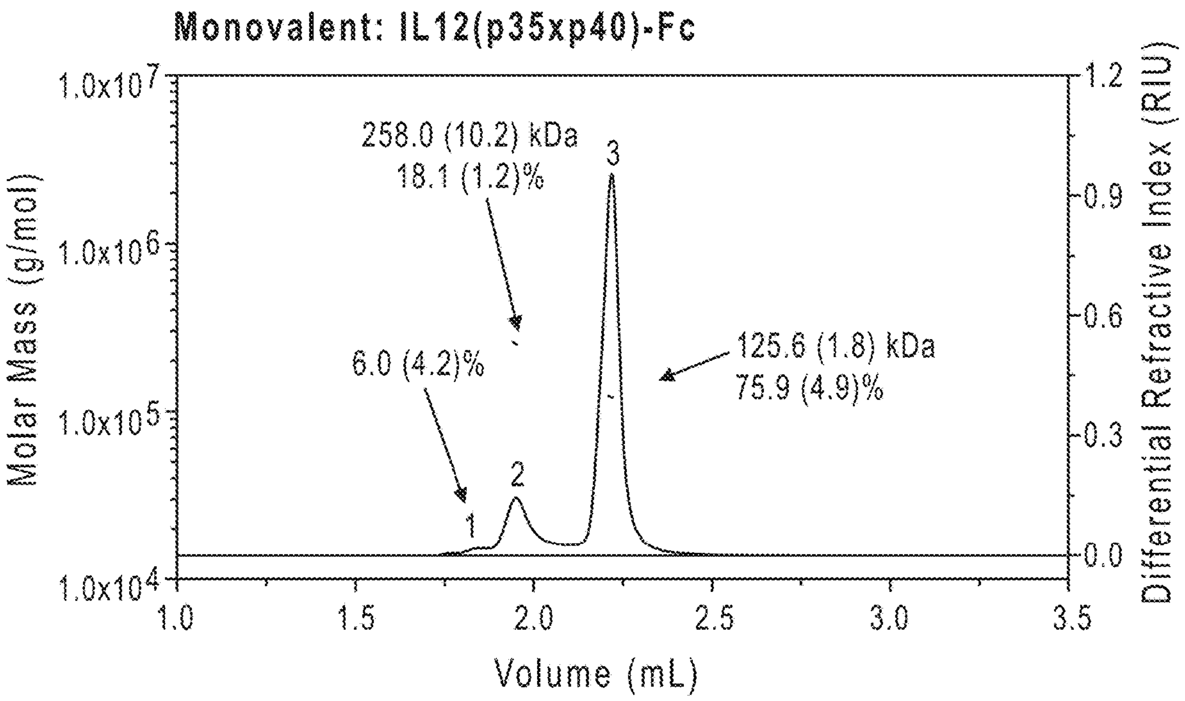

FIG. 11 depicts a trace from size-exclusion ultra-performance liquid chromatography (SEC) coupled with multi-angle light scattering (MALS) (SEC-MALS), indicating the size and arrangement of monovalent: IL12(p35×p40)-Fc. The fusion protein's predicted molecular weight is 110.5 kDa. The fusion protein has 6 predicted glycosylation sites, resulting in an estimated MW of 122.5 kDa with glycosylation. The fusion protein displayed monomeric protein of 125.6 kDa with ~75% peak area and two HMW species (peak 2, Mw~258 kDa, 18.1% peak area), (peak 1, 6.0% peak area).

Figure 12:
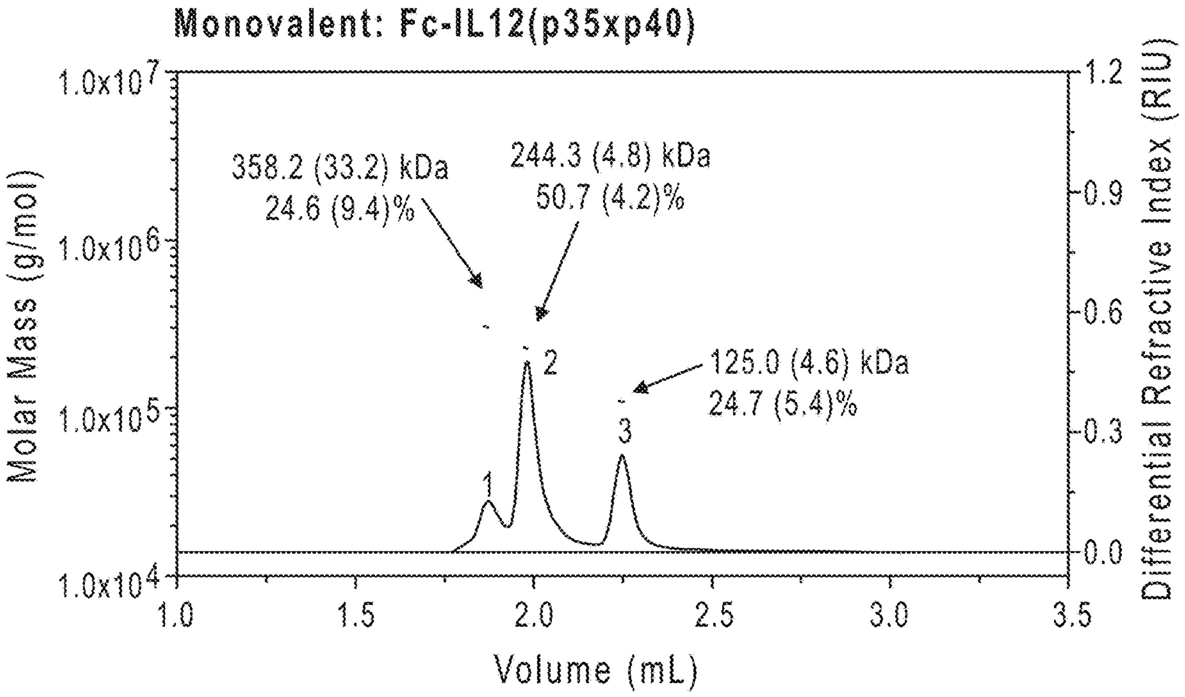

FIG. 12 depicts a trace from SEC-MALS, indicating the size and arrangement of Fc-monovalent: Fc-IL12(p35×p40). The fusion protein's predicted molecular weight is 110.5 kDa. The fusion protein has 6 predicted glycosylation sites, resulting in an estimated MW of 122.5 kDa with glycosylation. The fusion protein displayed primarily as a potential dimeric protein of 244.3 kDa, at ~50% total peak area. Putative monomer and trimeric oligomers were also detected (peaks 1 and 3, respectively).

Figure 13:
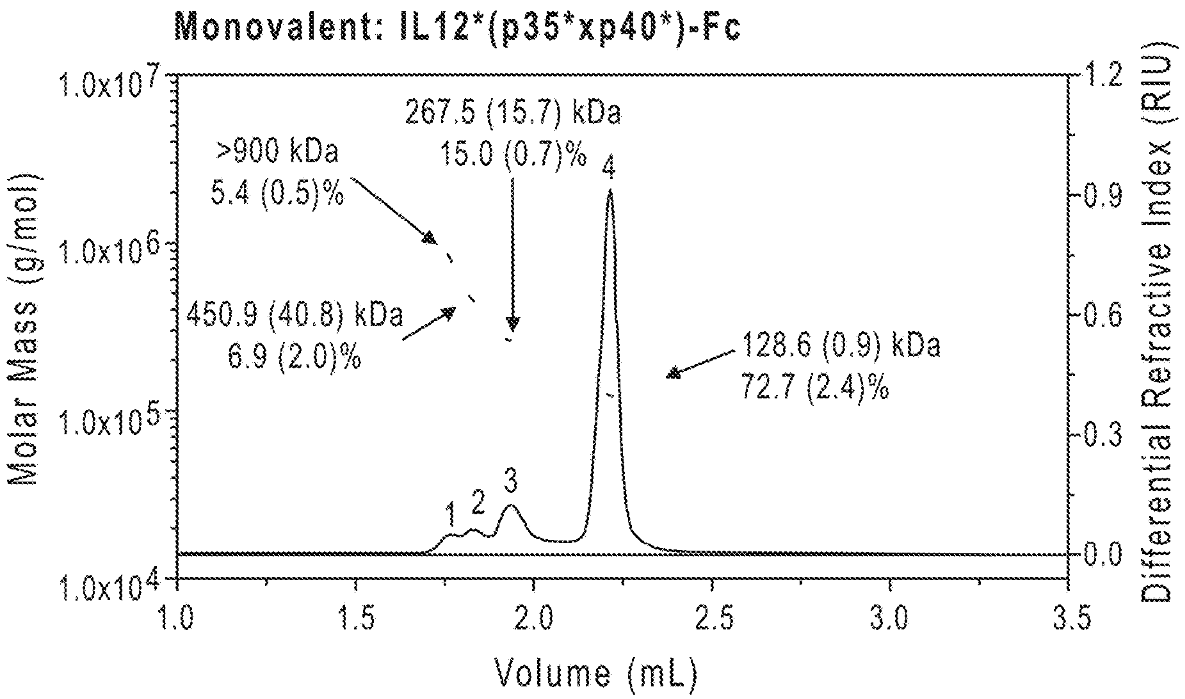

FIG. 13 depicts a trace from SEC-MALS, indicating the size and arrangement of monovalent: IL12*(p35*×p40*)-Fc. The fusion protein's predicted molecular weight is 110.5 kDa. The fusion protein has 6 predicted glycosylation sites, resulting in an estimated MW of 122.5 kDa with glycosylation. The fusion protein displayed monomeric protein of 128.6 kDa, at ~72% peak area with putative dimeric and tetrameric oligomers detected (peaks 2 and 3).

Figure 14:
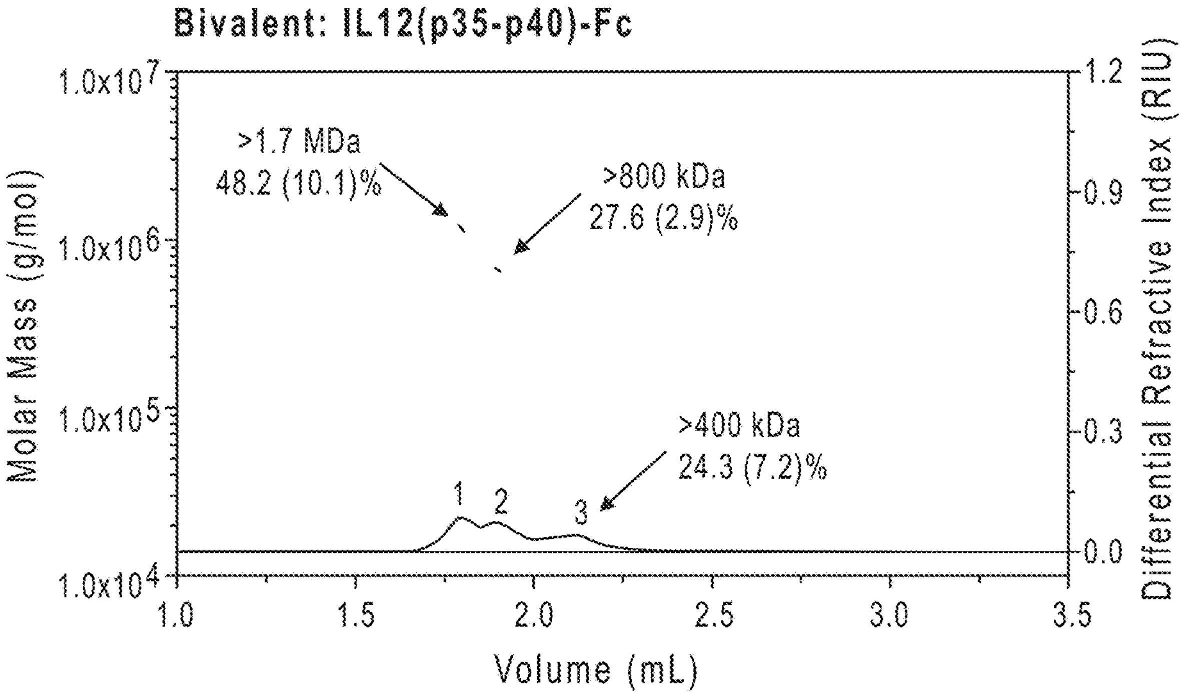

FIG. 14 depicts a trace from SEC-MALS, indicating the size and arrangement of bivalent: IL12(p35-p40)-Fc. The fusion protein's predicted molecular weight is 170.0 kDa. The fusion protein has 10 predicted glycosylation sites, resulting in an estimated MW of 190.0 kDa with glycosylation. The fusion protein exhibited mostly aggregated protein, with high molecular weight specie ~45% of the total peak area and an apparent molar mass of 1.7 MDa.

Figure 15:
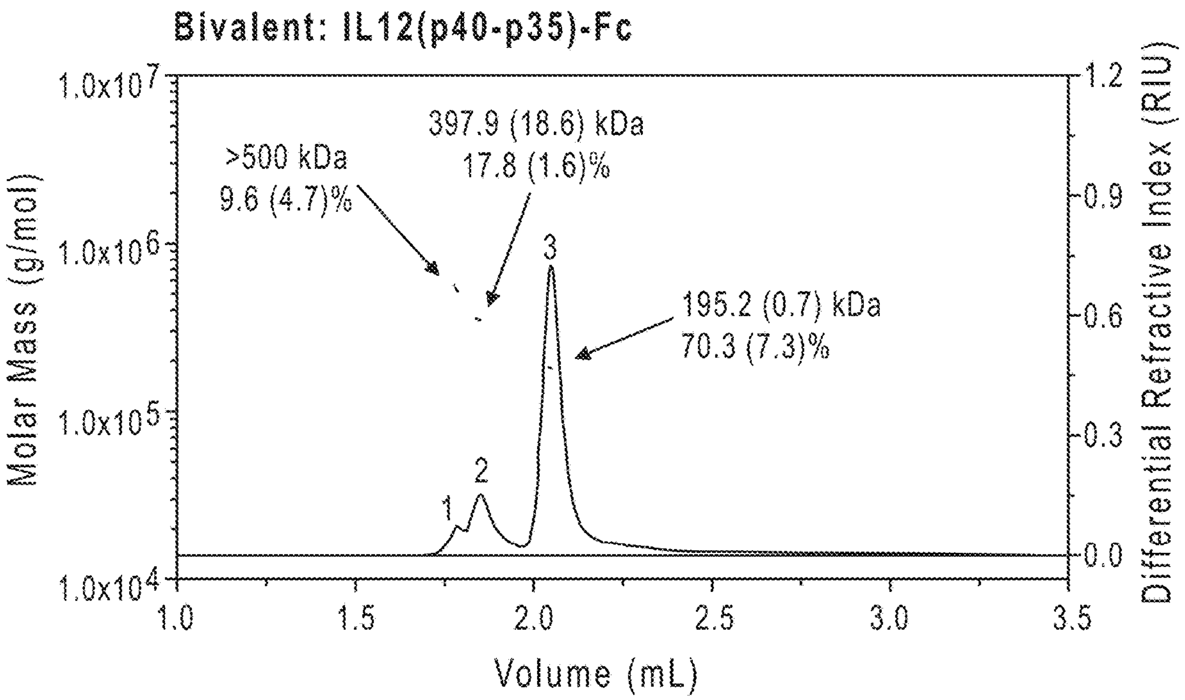

FIG. 15 depicts a trace from SEC-MALS, indicating the size and arrangement of bivalent: IL12(p40-p35)-Fc. The fusion protein's predicted molecular weight is 171.2 kDa. The fusion protein has 12 predicted glycosylation sites, resulting in an estimated MW of 195.2 kDa with glycosylation. The fusion protein exhibited monomeric protein of 195.2 kDa at ~70% total peak area. A putative dimer was also detected (peak 2).

Figure 16:
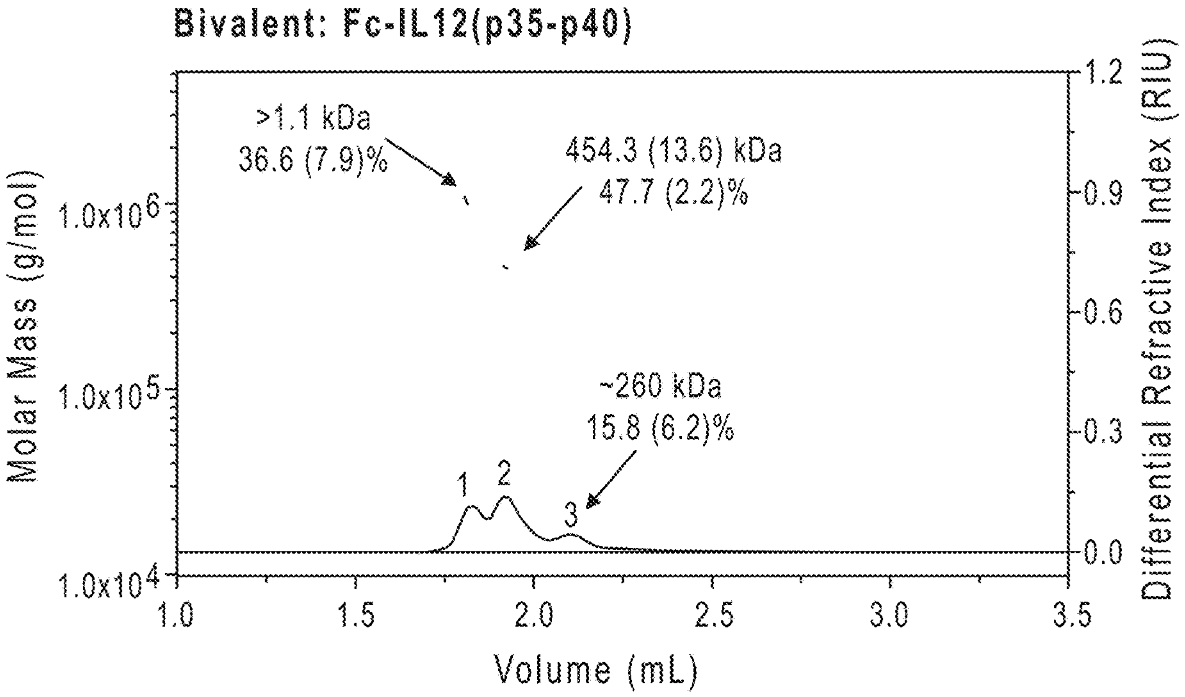

FIG. 16 depicts a trace from SEC-MALS, indicating the size and arrangement of Fc-bivalent: Fc-IL12(p35-p40). The fusion protein's predicted molecular weight is 171.2 kDa. The fusion protein has 12 predicted glycosylation sites, resulting in an estimated MW of 195.2 kDa with glycosylation. The fusion protein exhibited mostly aggregated protein, with the predominant species being ~450 kDa at 47.7% peak area.

Figure 17:
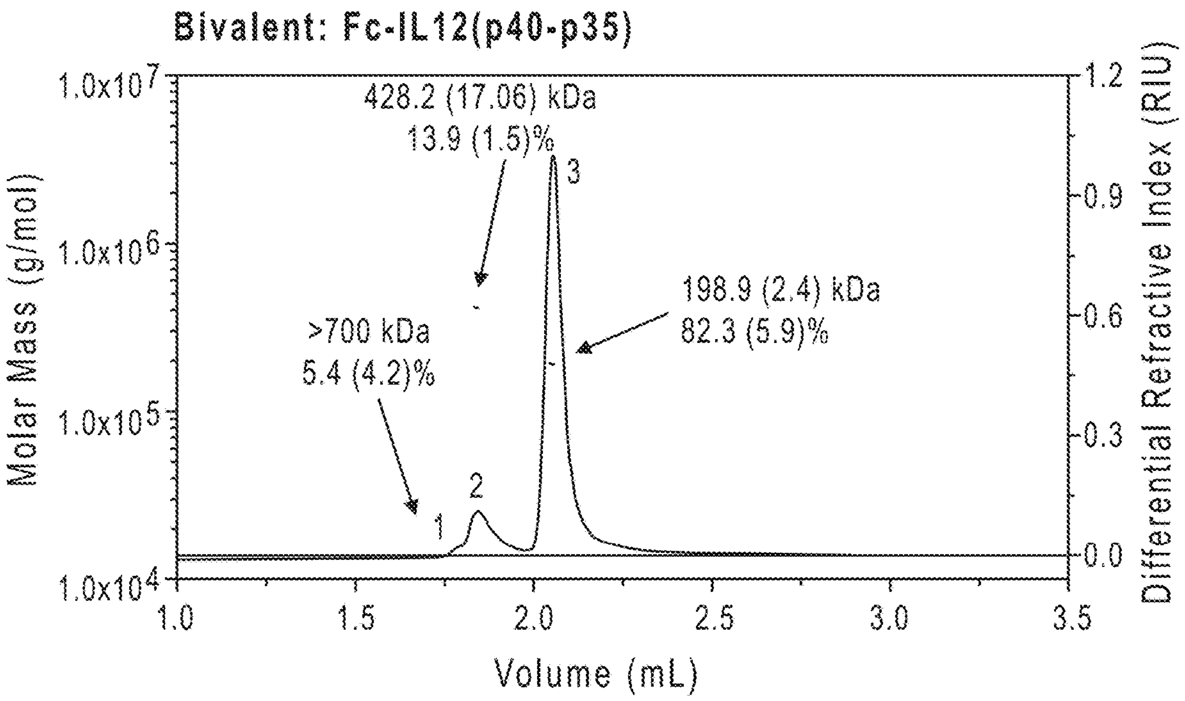

FIG. 17 depicts a trace from SEC-MALS, indicating the size and arrangement of bivalent: Fc-IL12(p40-p35). The fusion protein's predicted molecular weight is 170 kDa. The fusion protein has 10 predicted glycosylation sites, resulting in an estimated MW of 190.0 kDa with glycosylation. The fusion protein exhibited monomeric protein of 198.9 kDa at ~82% total peak area. A putative dimer was also detected (peak 2).

Figure 18:
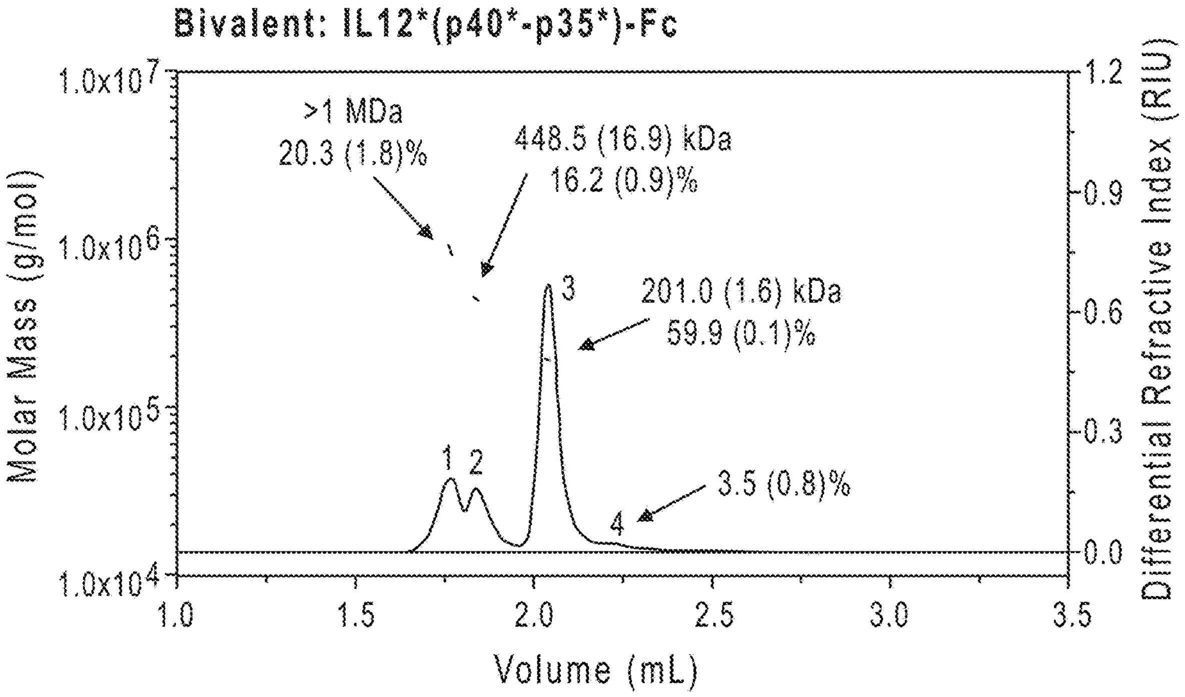

FIG. 18 depicts a trace from SEC-MALS, indicating the size and arrangement of bivalent: IL12*(p40*-p35*)-Fc. The fusion protein's predicted molecular weight is 171.2 kDa. The fusion protein has 12 predicted glycosylation sites, resulting in an estimated MW of 195.2 kDa with glycosylation. The fusion protein consisted of predominantly monomeric species (~60% total peak area) with an apparent molar mass of 201.0 kDa.

Figure 19:
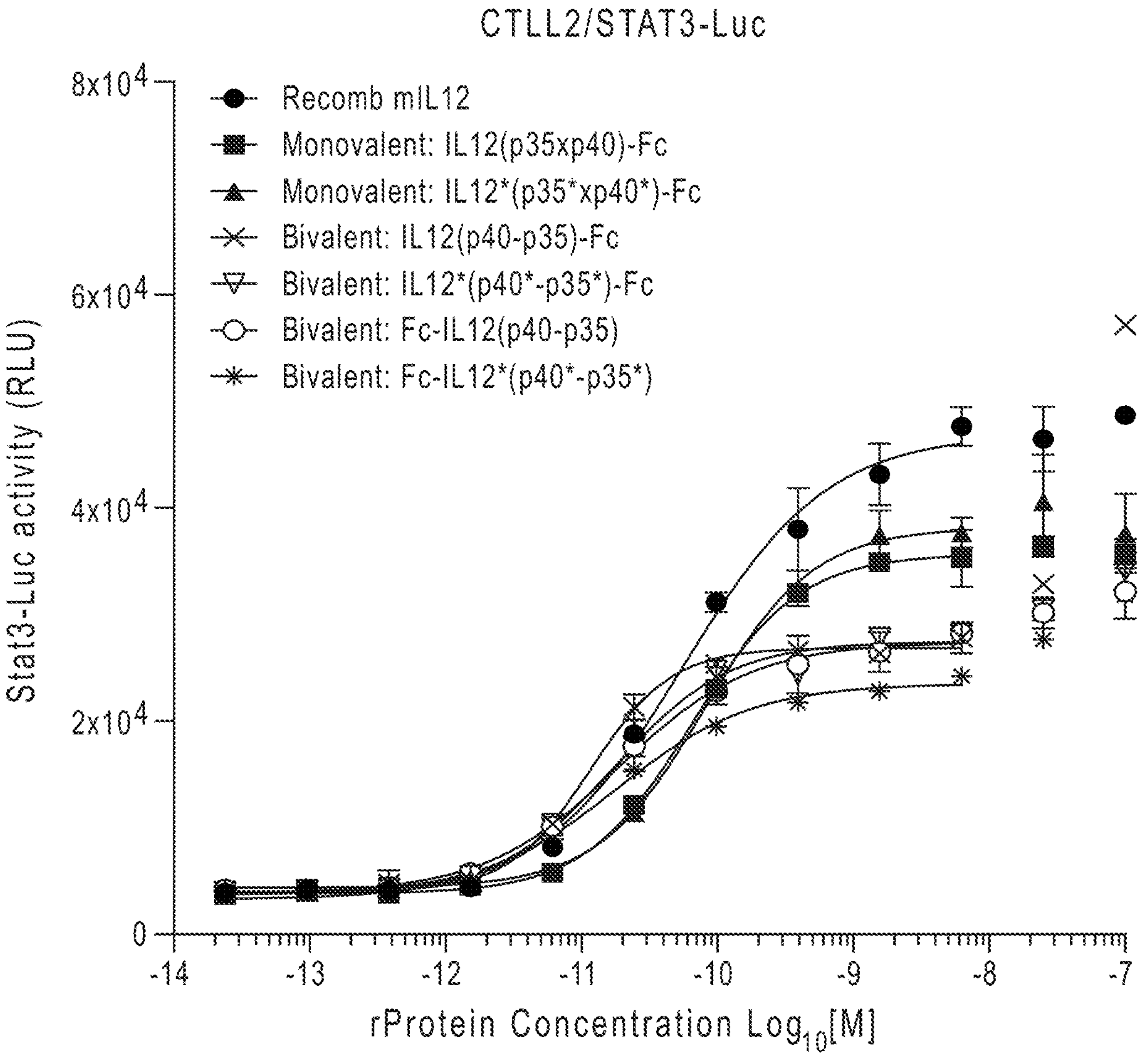

FIG. 19 presents curves illustrating the bioactivity of the noted control or IL12-Fc fusion protein on CTLL2/STAT3-Luc cells.

Figure 20A:
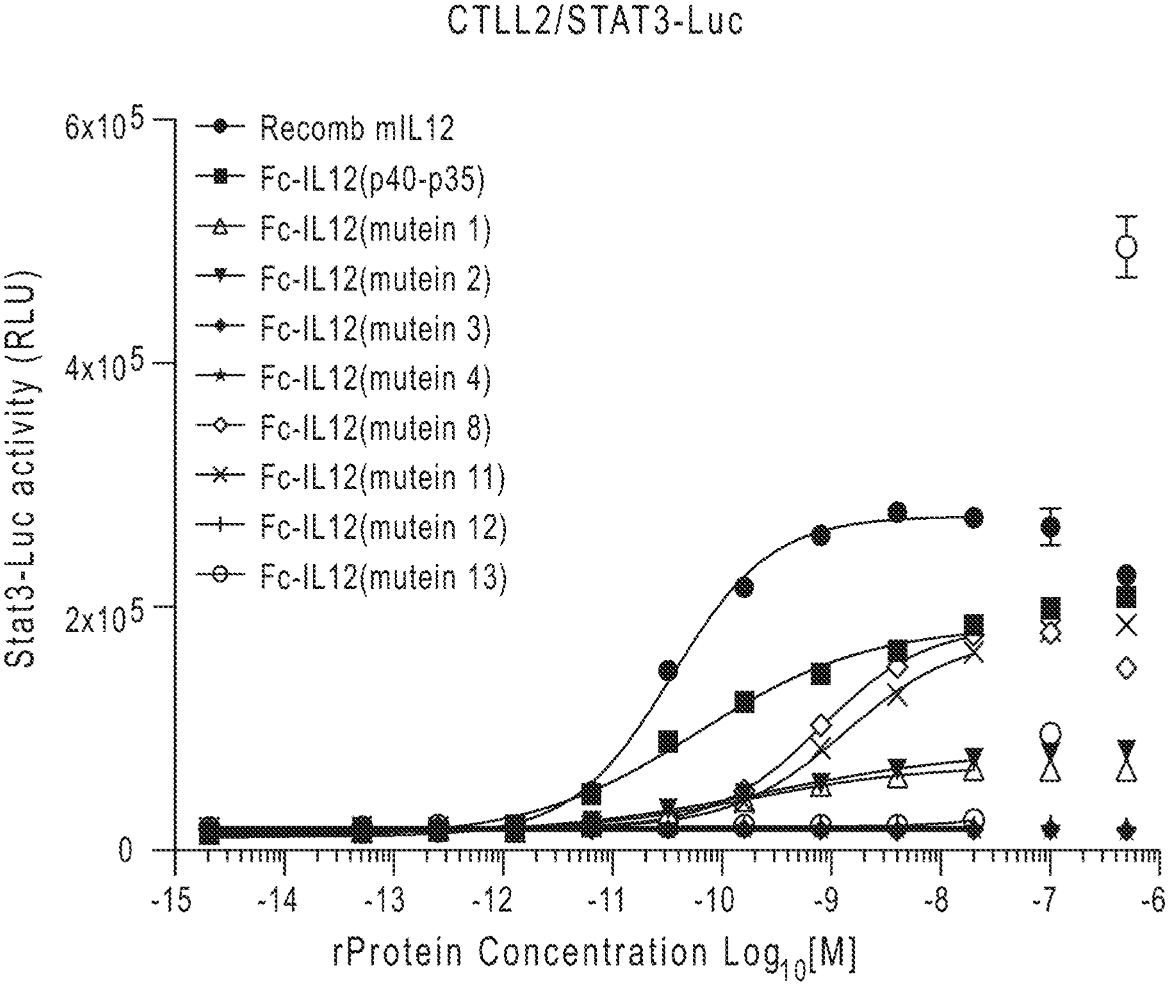
Figure 20B:
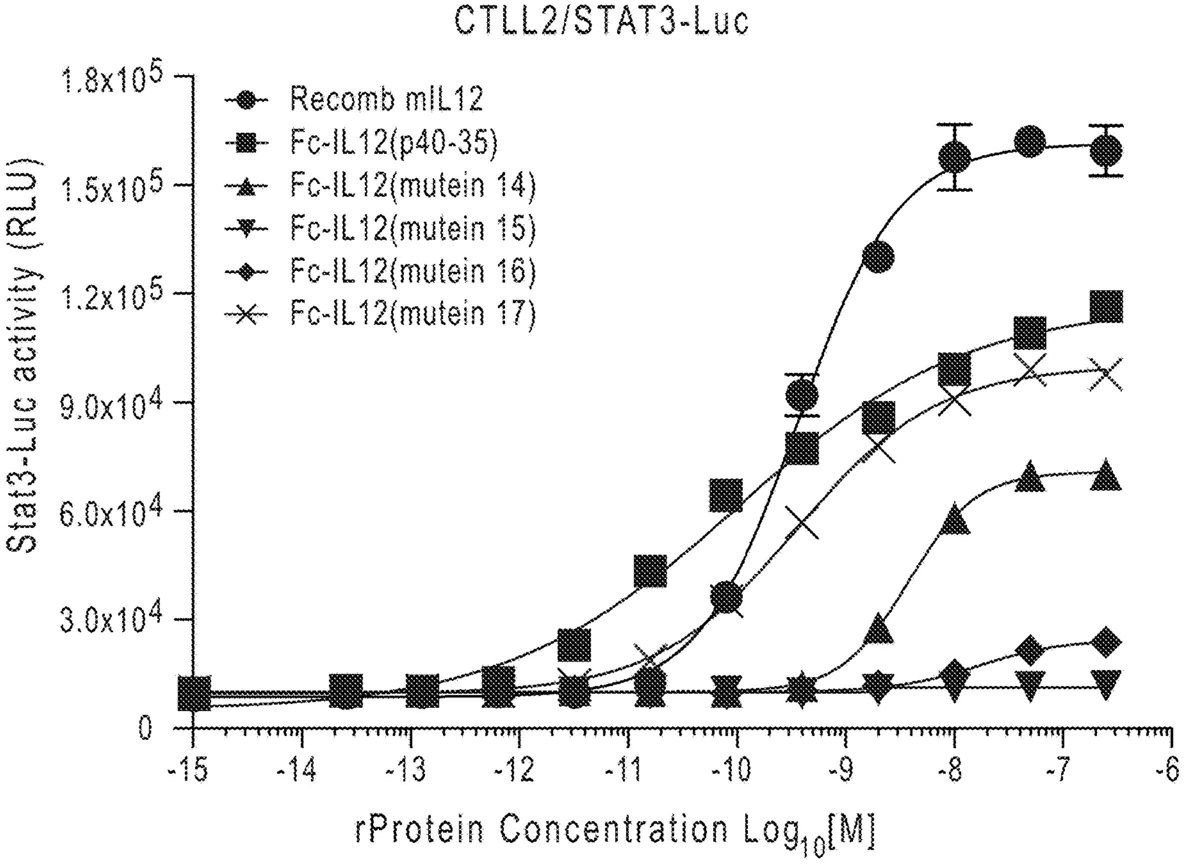

FIG. 20A-20B presents curves illustrating the bioactivity of the noted control or IL12-Fc fusion protein or mutein on CTLL2/STAT3-Luc cells.

Figure 21:
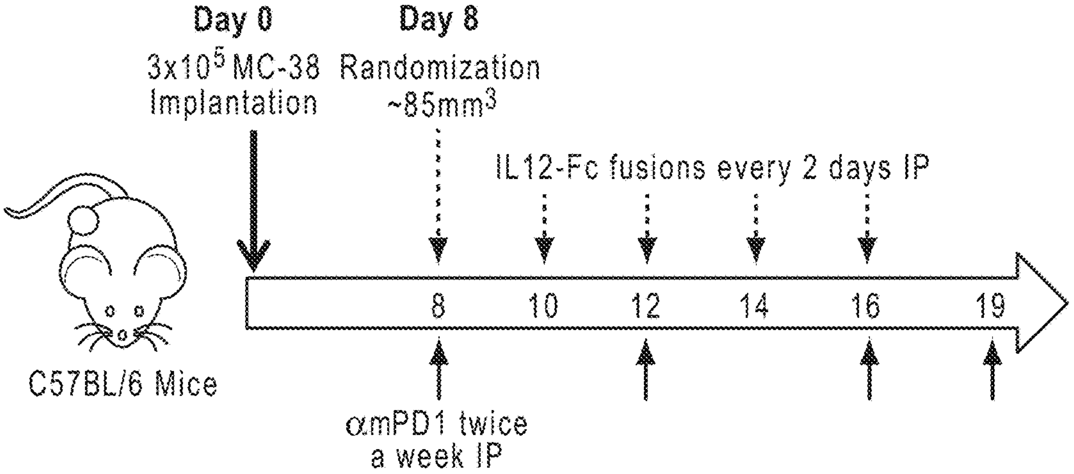

FIG. 21 is a schematic representing an experimental protocol for implantation of C57BL/6 mice with MC38 cancer cells and subsequent dosing with test fusion proteins.

Figure 22:
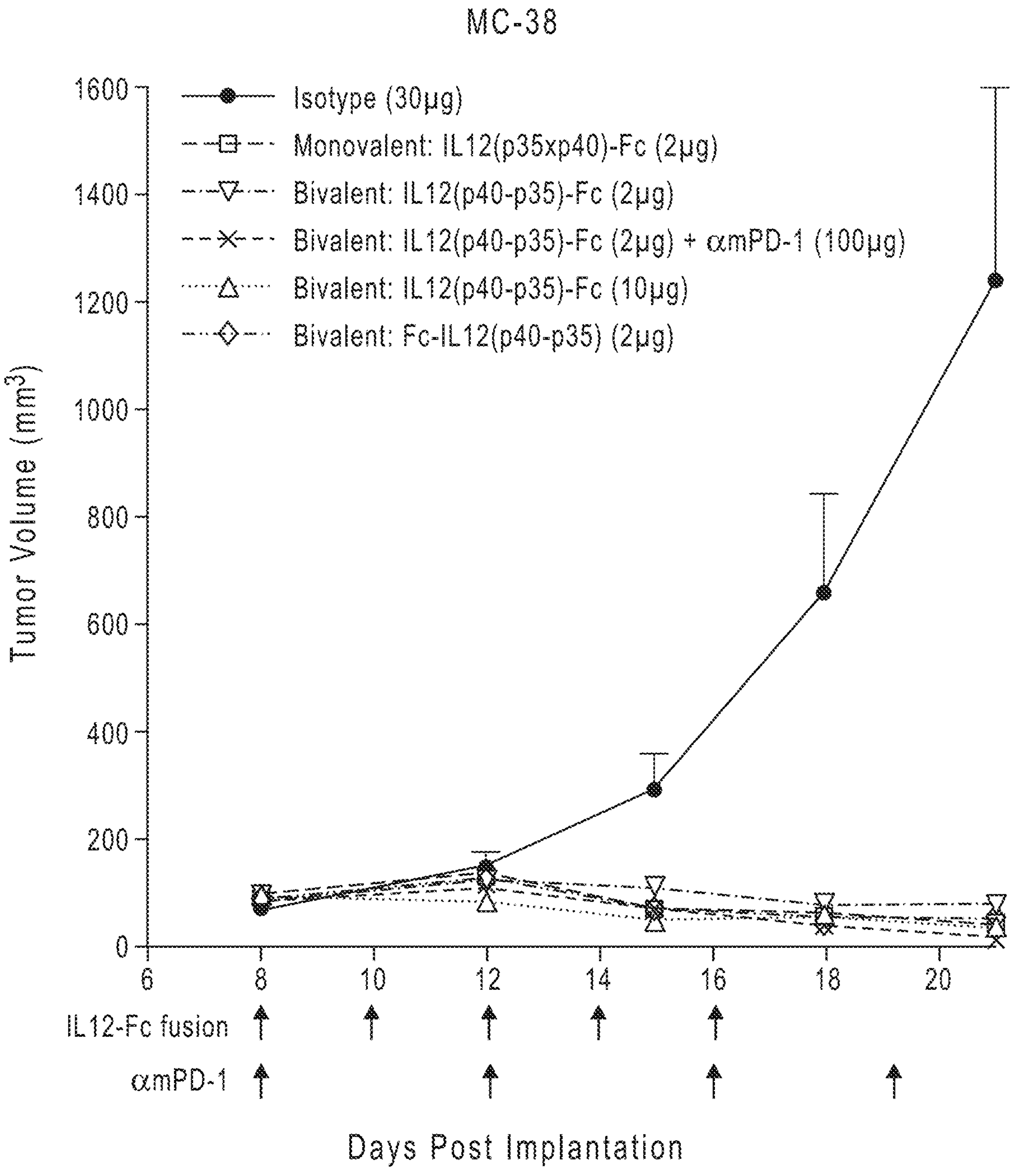
Figure 23A:
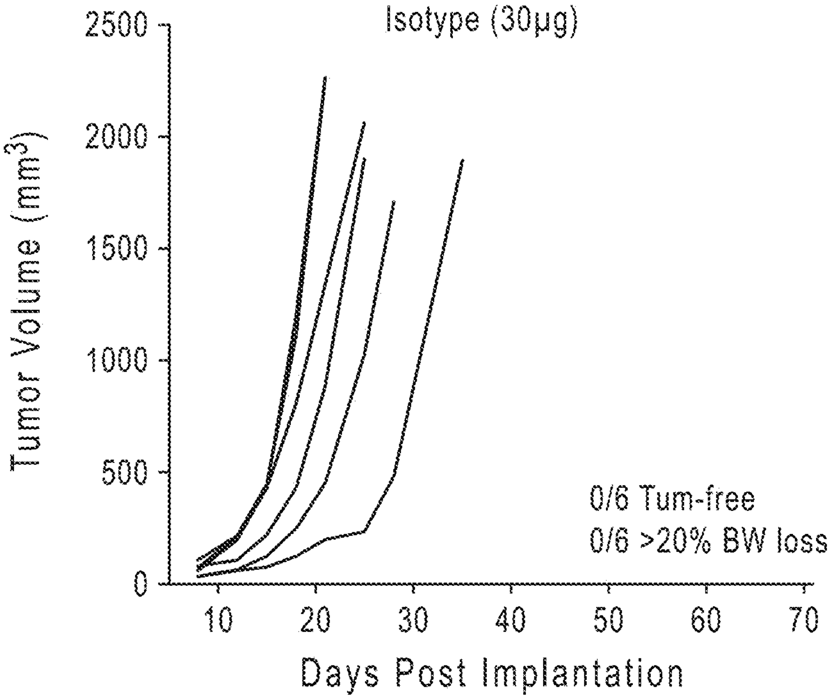
Figure 23B:
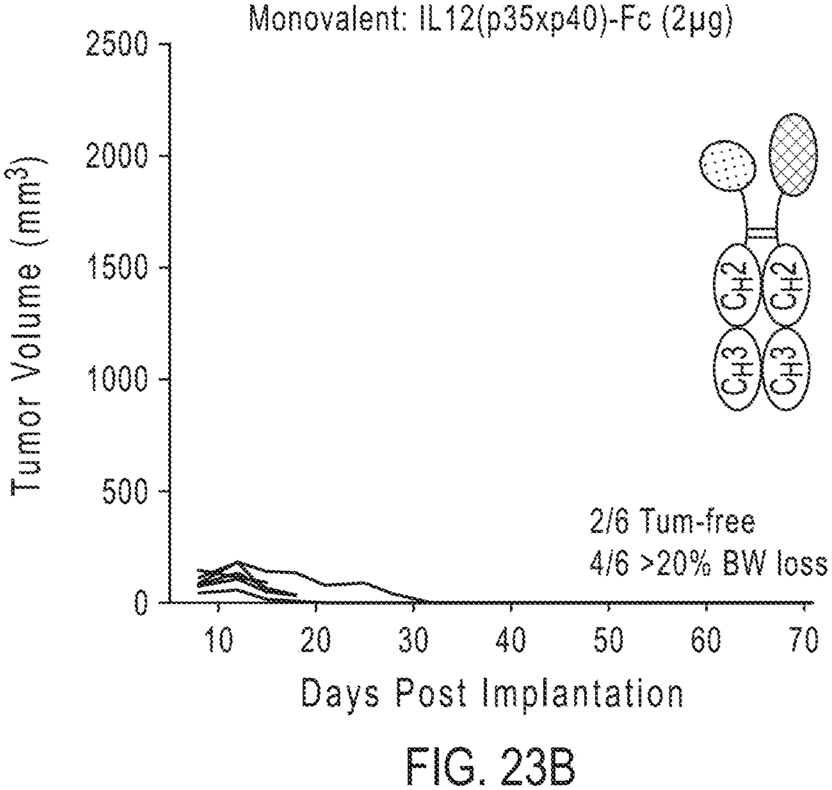
Figure 23C:
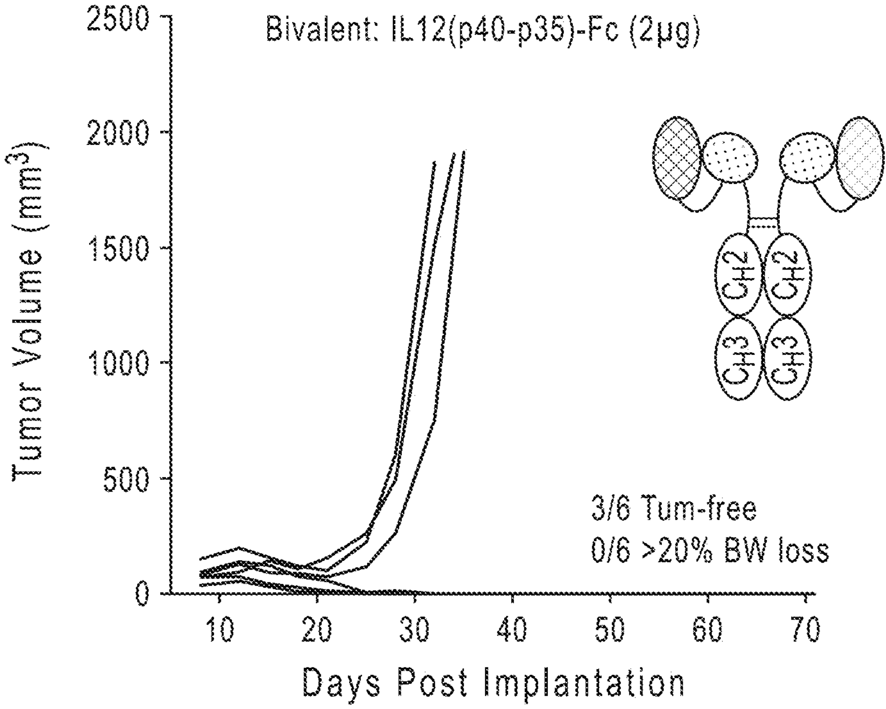
Figure 23D:
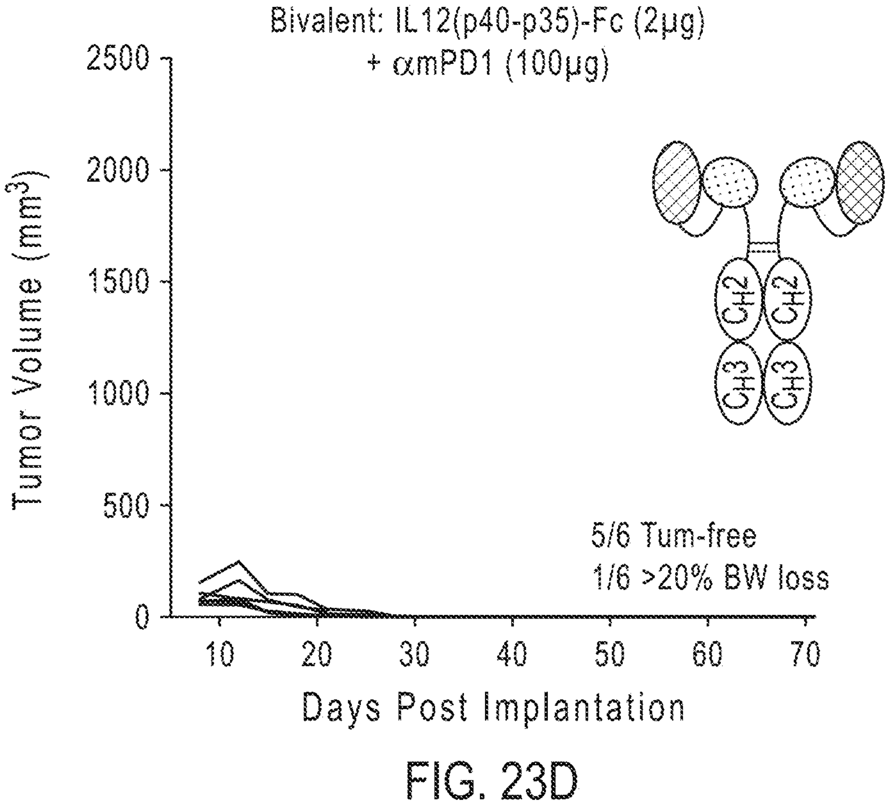
Figure 23E:
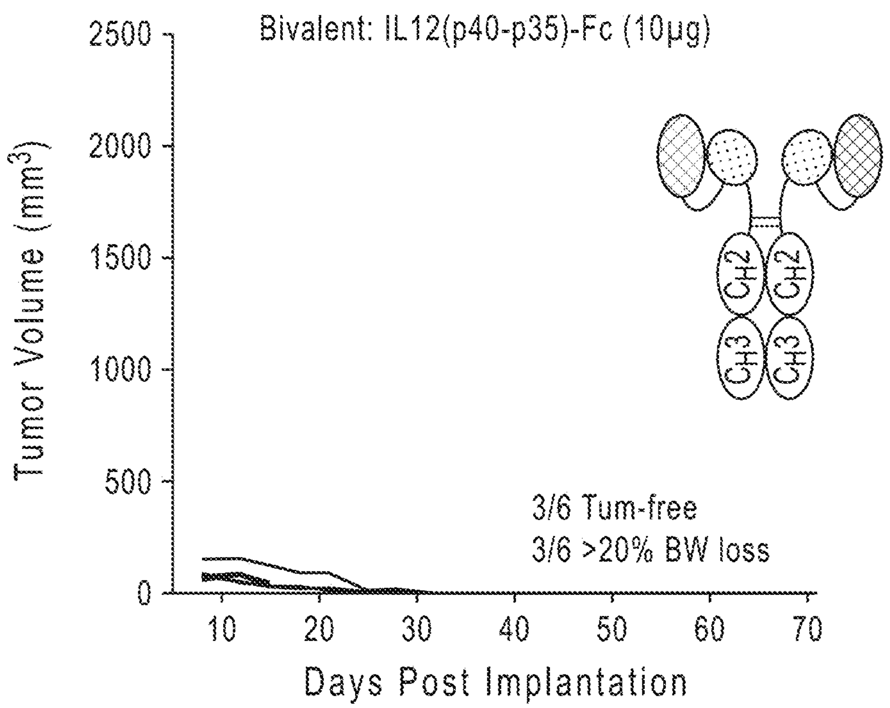
Figure 23F:
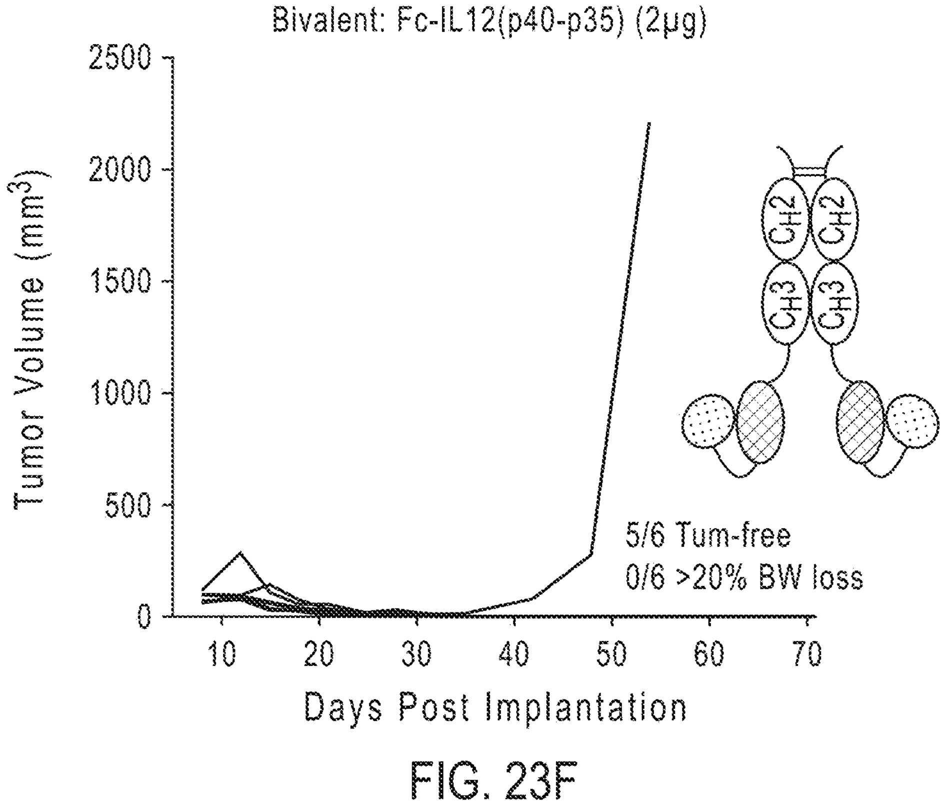

FIG. 22 is a graph depicting the effect of the noted control or fusion protein on tumor volume in an MC38 tumor model.

FIGS. 23A-23F is a graph depicting the effect of the noted control or fusion protein on individual tumor growth in an MC38 tumor model.

Figure 24:
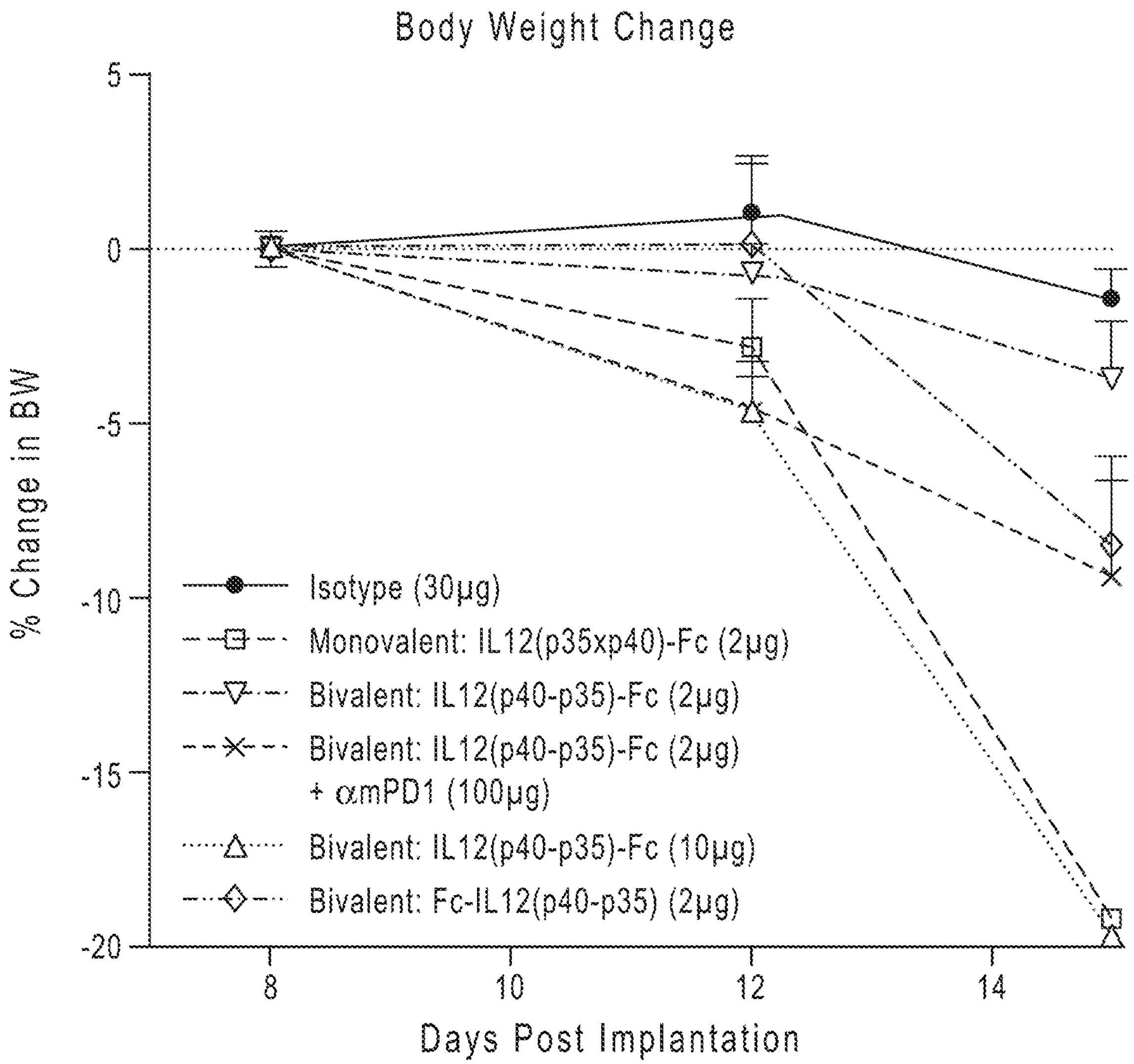

FIG. 24 is a graph depicting the effect of the noted control or fusion protein on mouse bodyweight change in an MC38 tumor model.

Figure 25A:
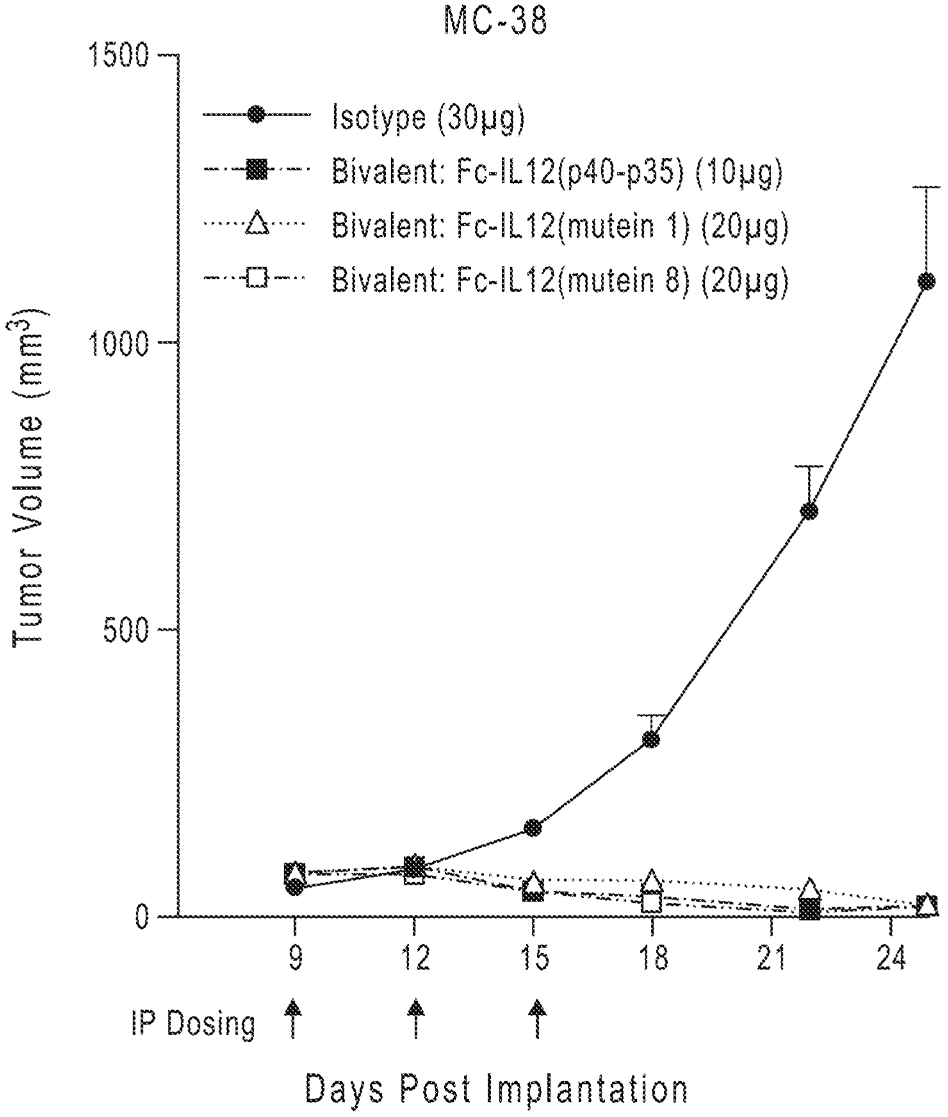
Figure 25B:
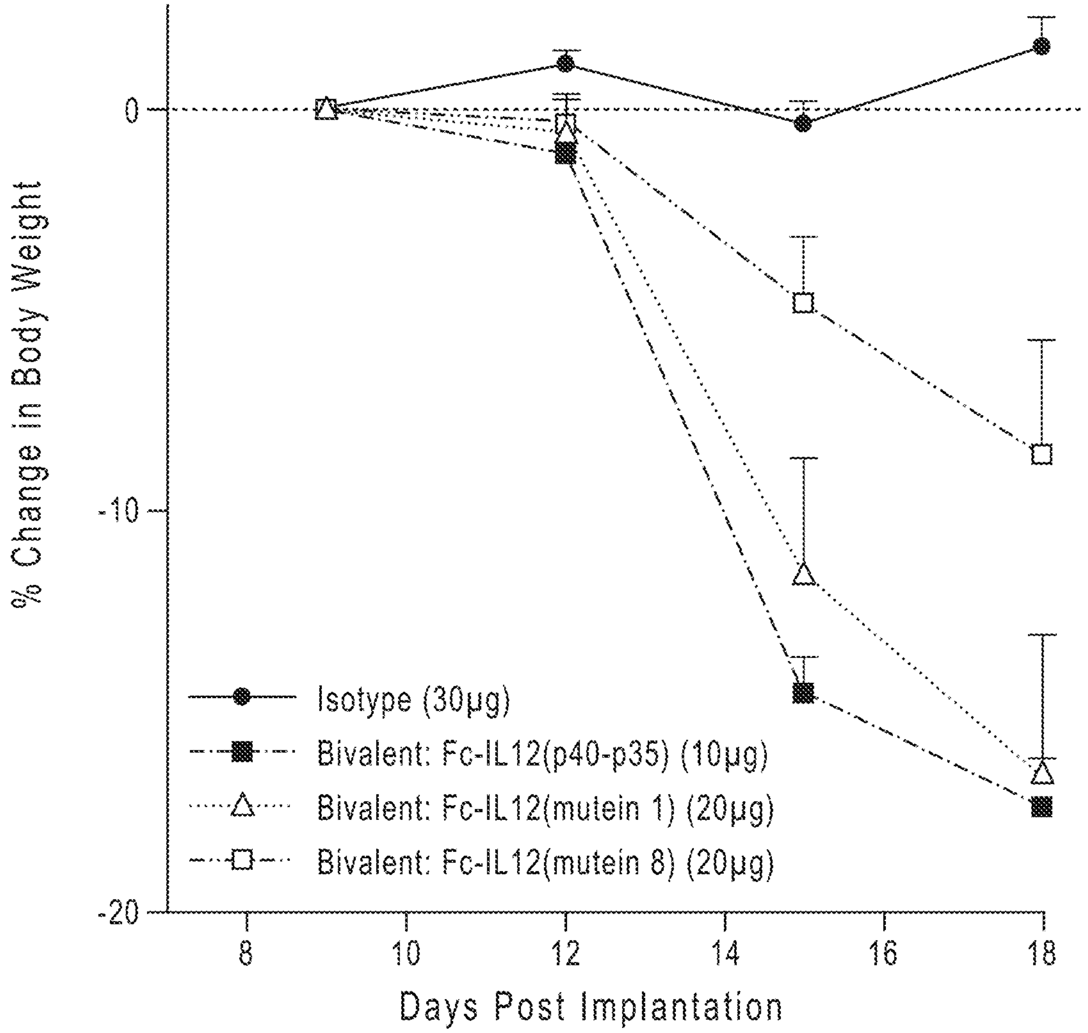

FIGS. 25A-25B depicts the effect of the noted control or fusion protein or mutein fusion protein on tumor volume and bodyweight change in an MC38 tumor model.

Figure 26A:
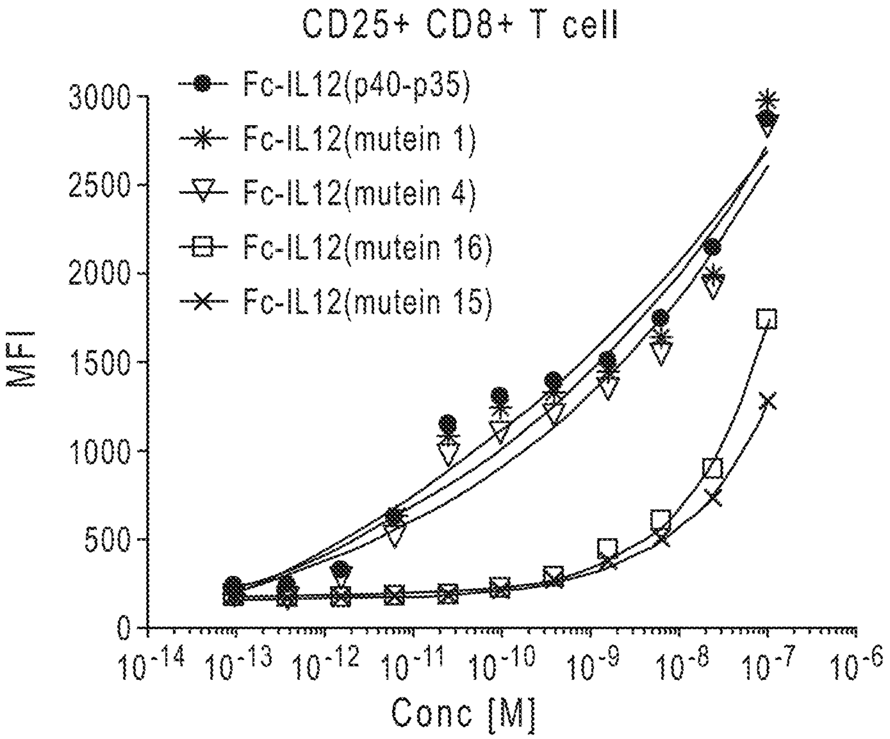
Figure 26B:
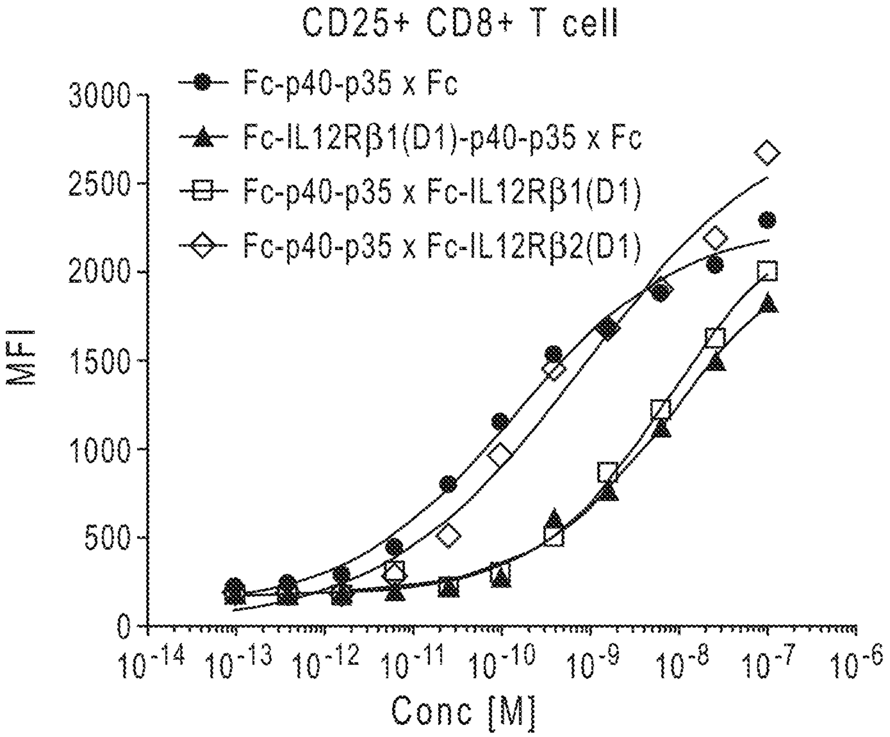

FIGS. 26A-26B depict traces from a binding assay, indicating binding of the noted IL12-Fc fusion proteins to primary mouse T cells.

Figure 27A:
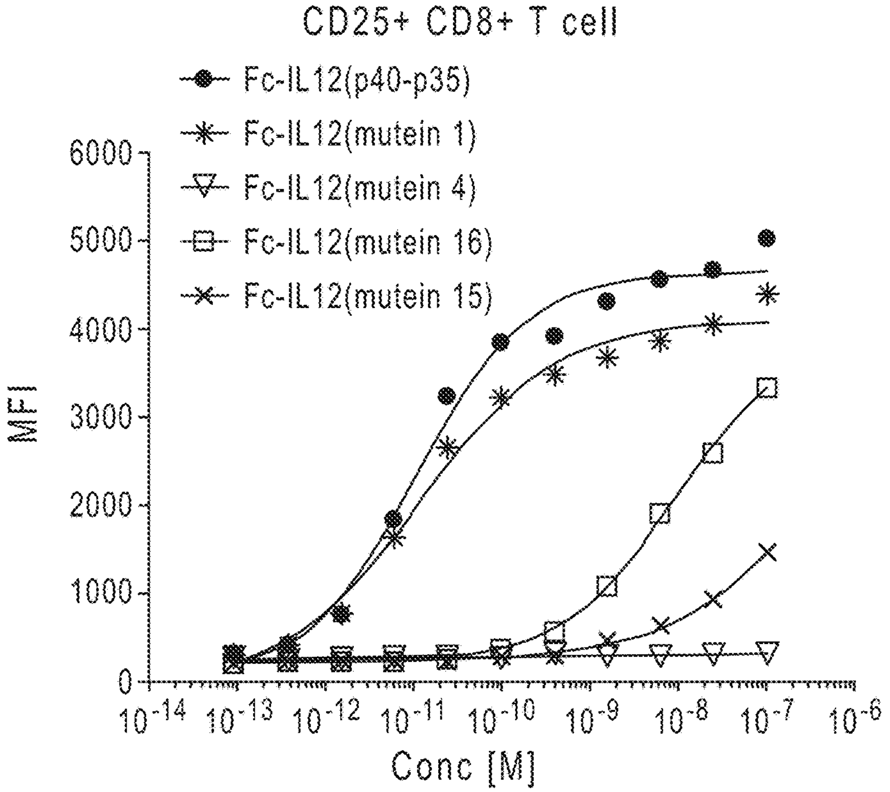
Figure 27B:
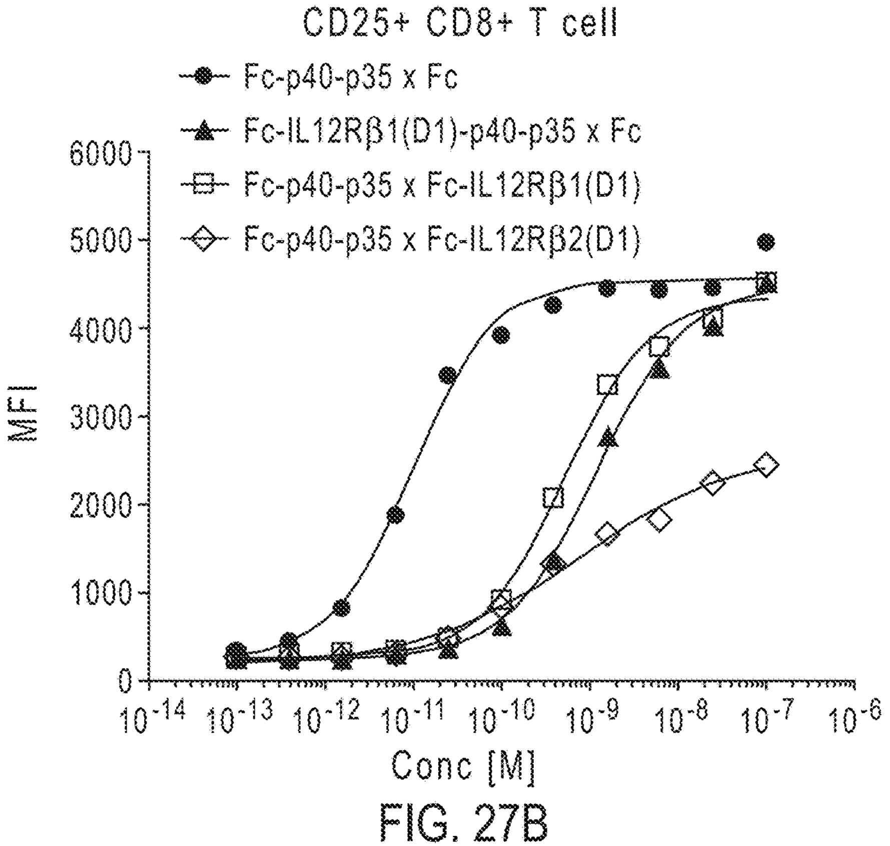

FIGS. 27A-27B depict traces from a pSTAT4-based bioassay, indicating the effect of the noted IL12-Fc fusion proteins on pSTAT4 activity in primary mouse T cells.

Figure 28:
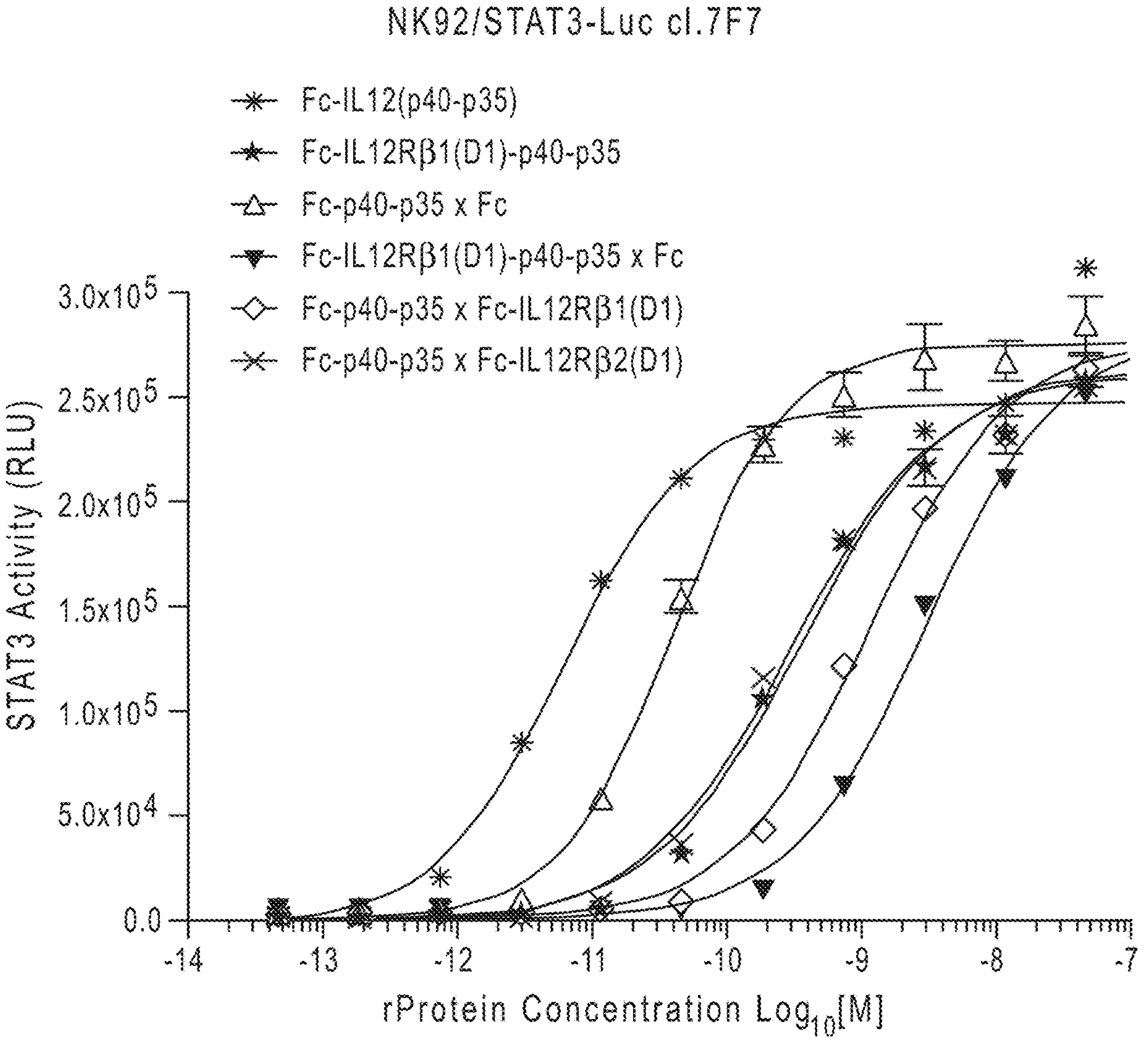

FIG. 28 depicts traces from a STAT3-based bioassay, indicating the effect of the noted IL12-Fc fusion proteins on STAT3 activity in NK92 cells (NK92/STAT3-Luc cl.7F7).

Figure 29:
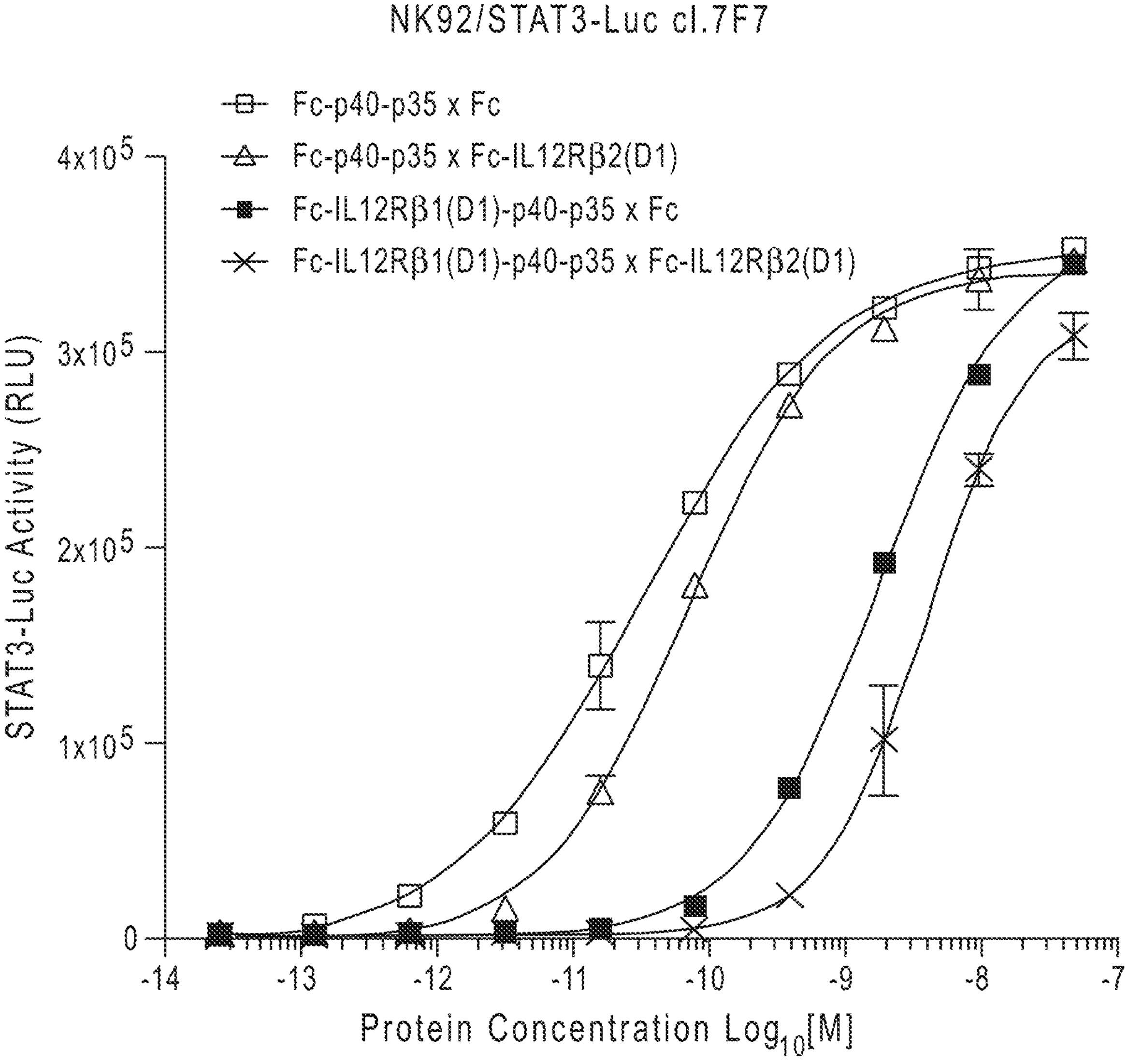

FIG. 29 depicts traces from a STAT3-based bioassay, indicated the effect of the noted IL12-Fc fusion proteins on STAT3 activity in NK92 cells (NK92/STAT3-Luc cl.7F7).

Figure 30:
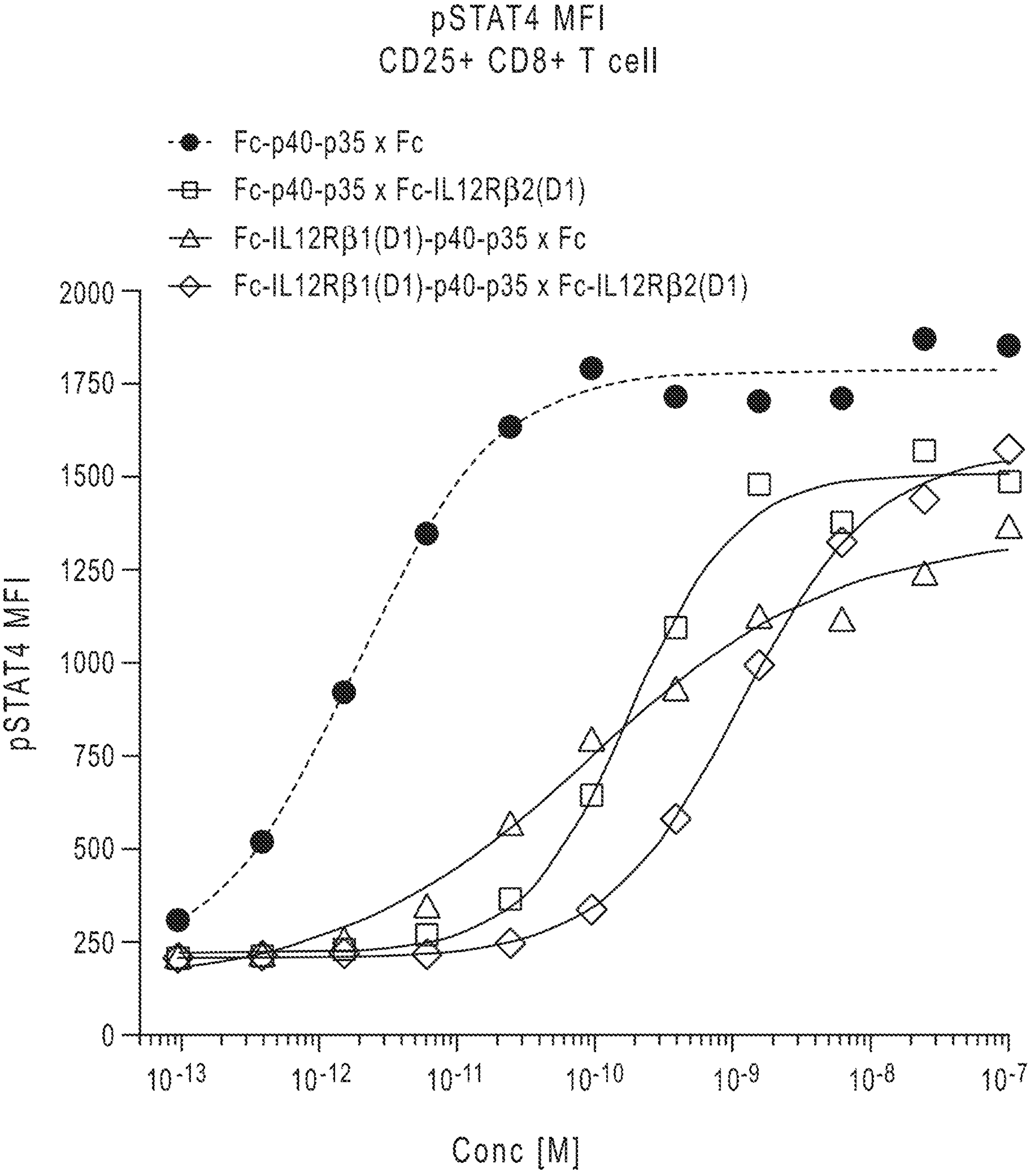

FIG. 30 depicts traces from a pSTAT4-based bioassay, indicating the effect of the noted IL12-Fc fusion proteins on pSTAT4 activity in primary mouse T cells.

Figure 31:
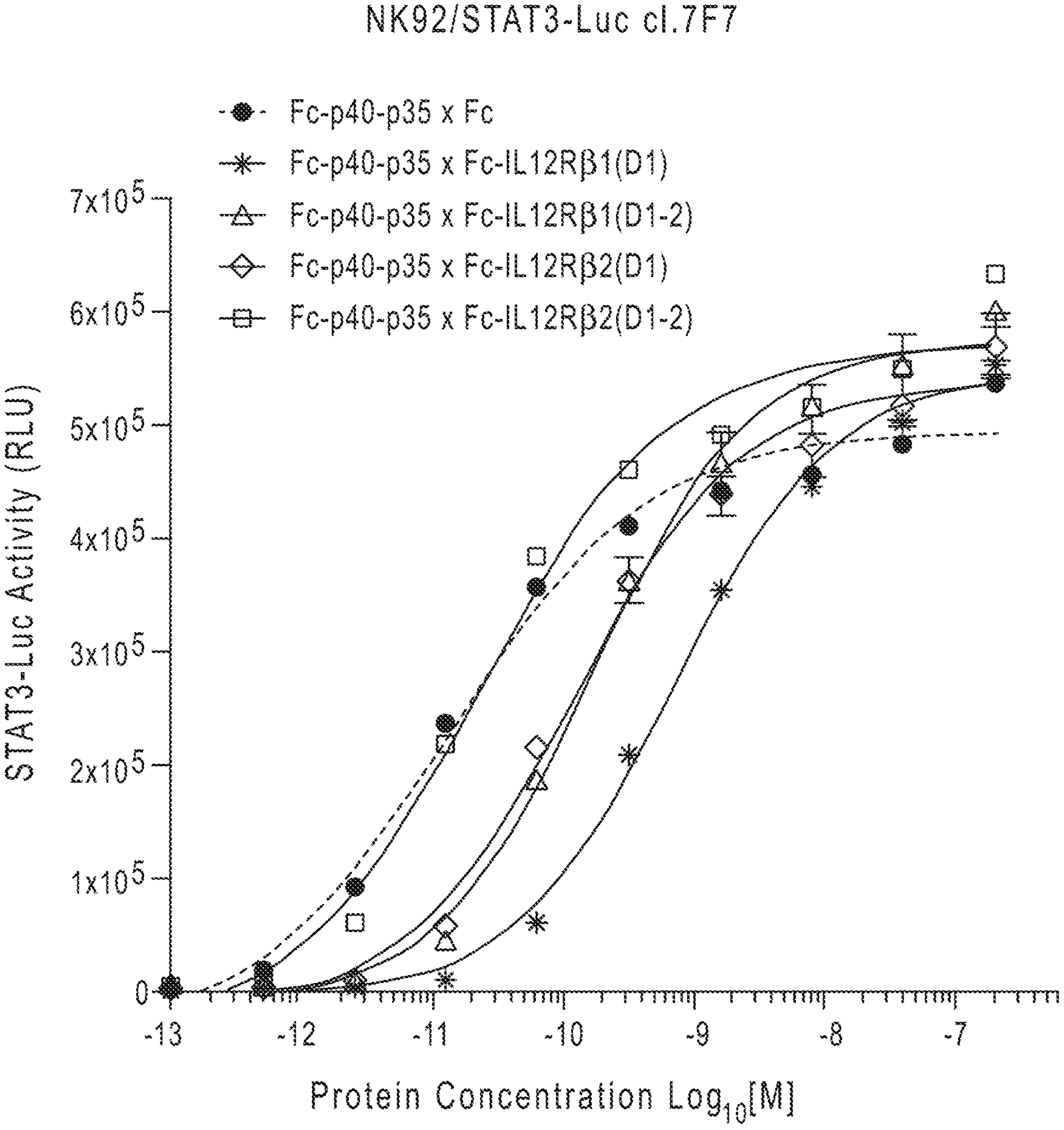

FIG. 31 depicts traces from a STAT3-based bioassay, indicating the effect of the noted IL12-Fc fusion proteins on STAT3 activity in NK92 cells (NK92/STAT3-Luc cl.7F7).

Figure 32:
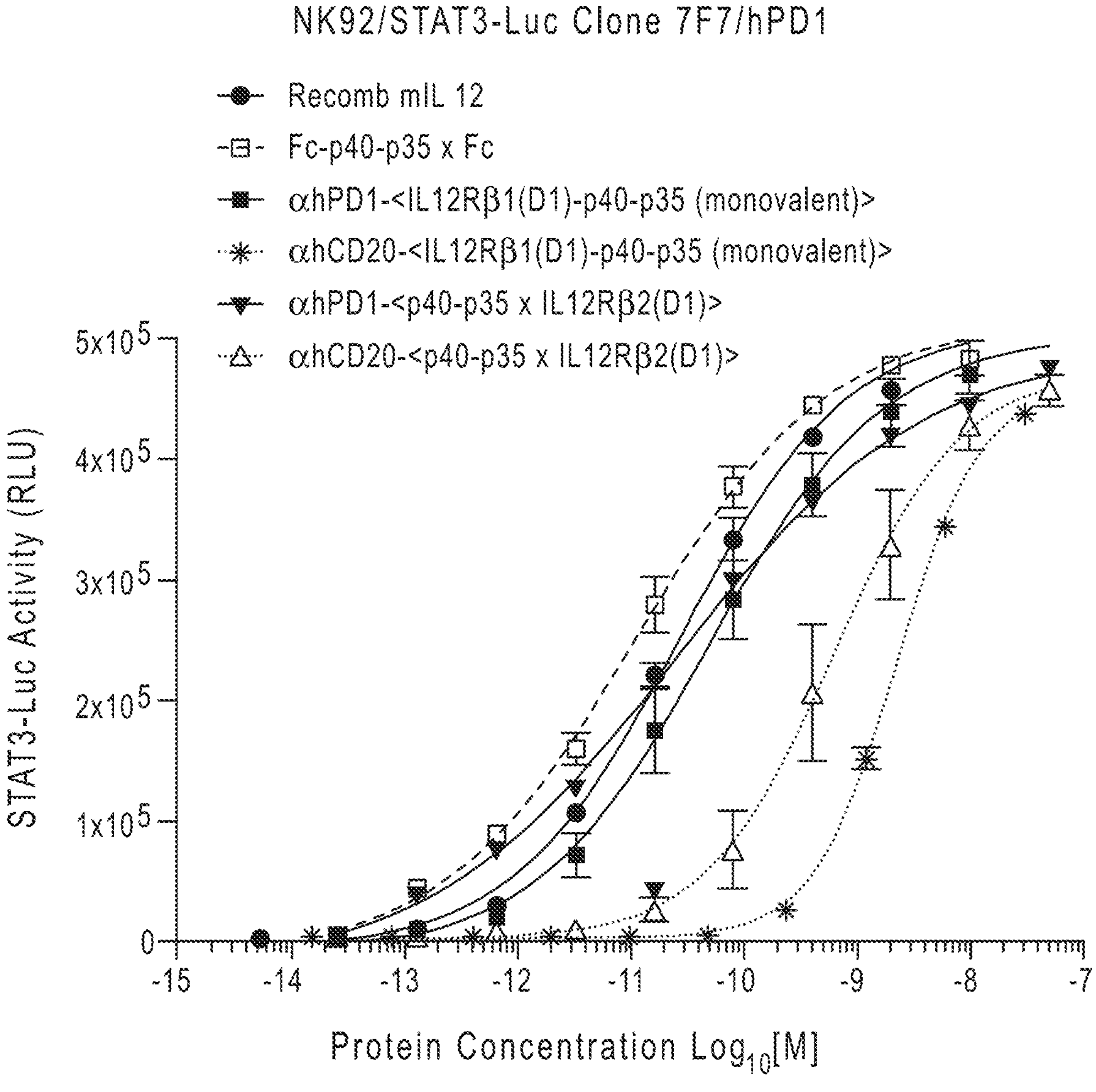

FIG. 32 depicts traces from a STAT3-based bioassay, indicating the effect of the noted IL12-Fc fusion proteins on STAT3 activity in target-expressing cells compared to an untargeted control construct.

Figure 33:
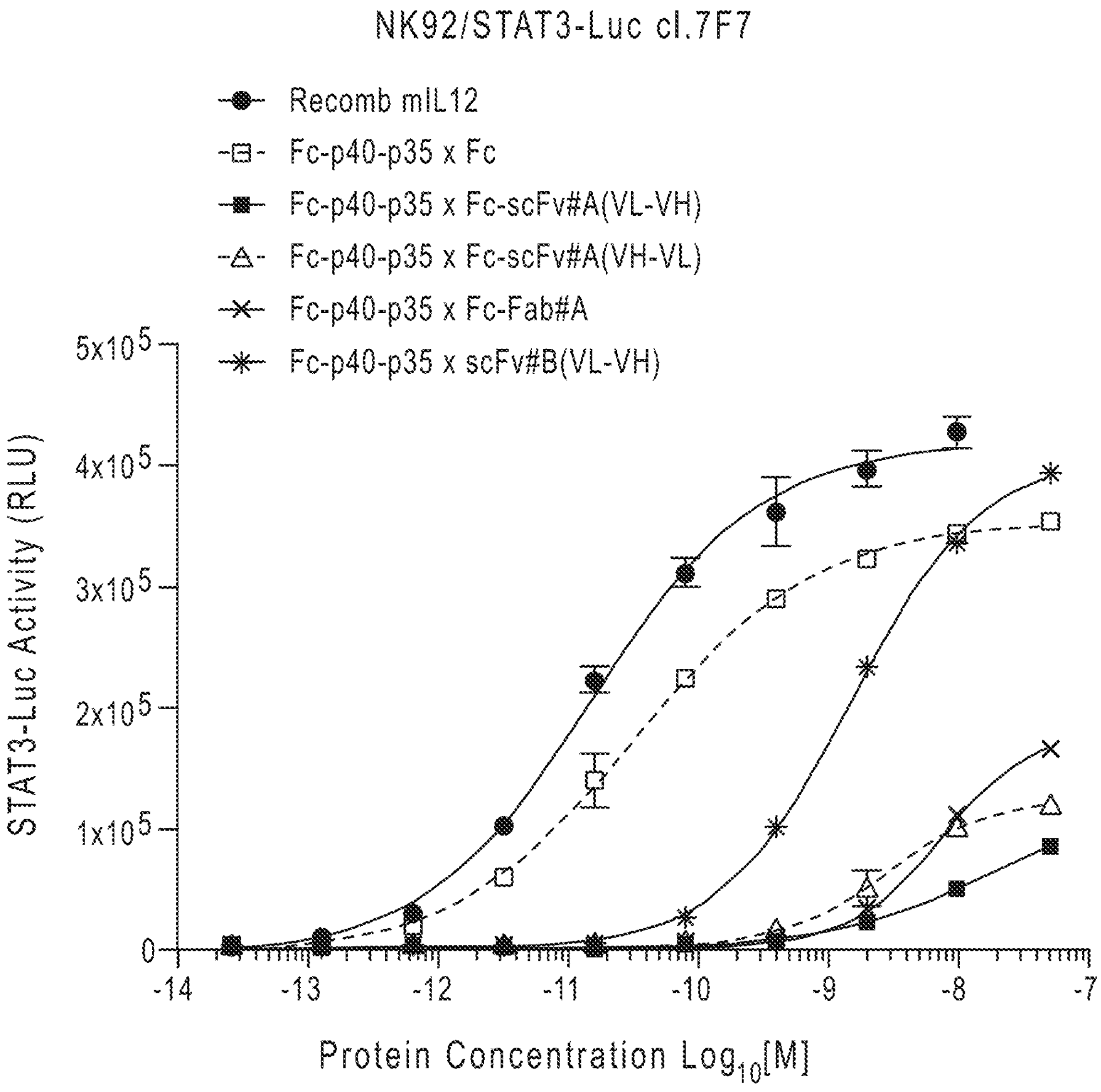

FIG. 33 depicts traces from a STAT3-based bioassay, indicating the effect of the noted IL12-Fc fusion proteins on STAT3 activity in human NK92 cells (NK92/STAT3-Luc cl.7F7).

Figure 34:
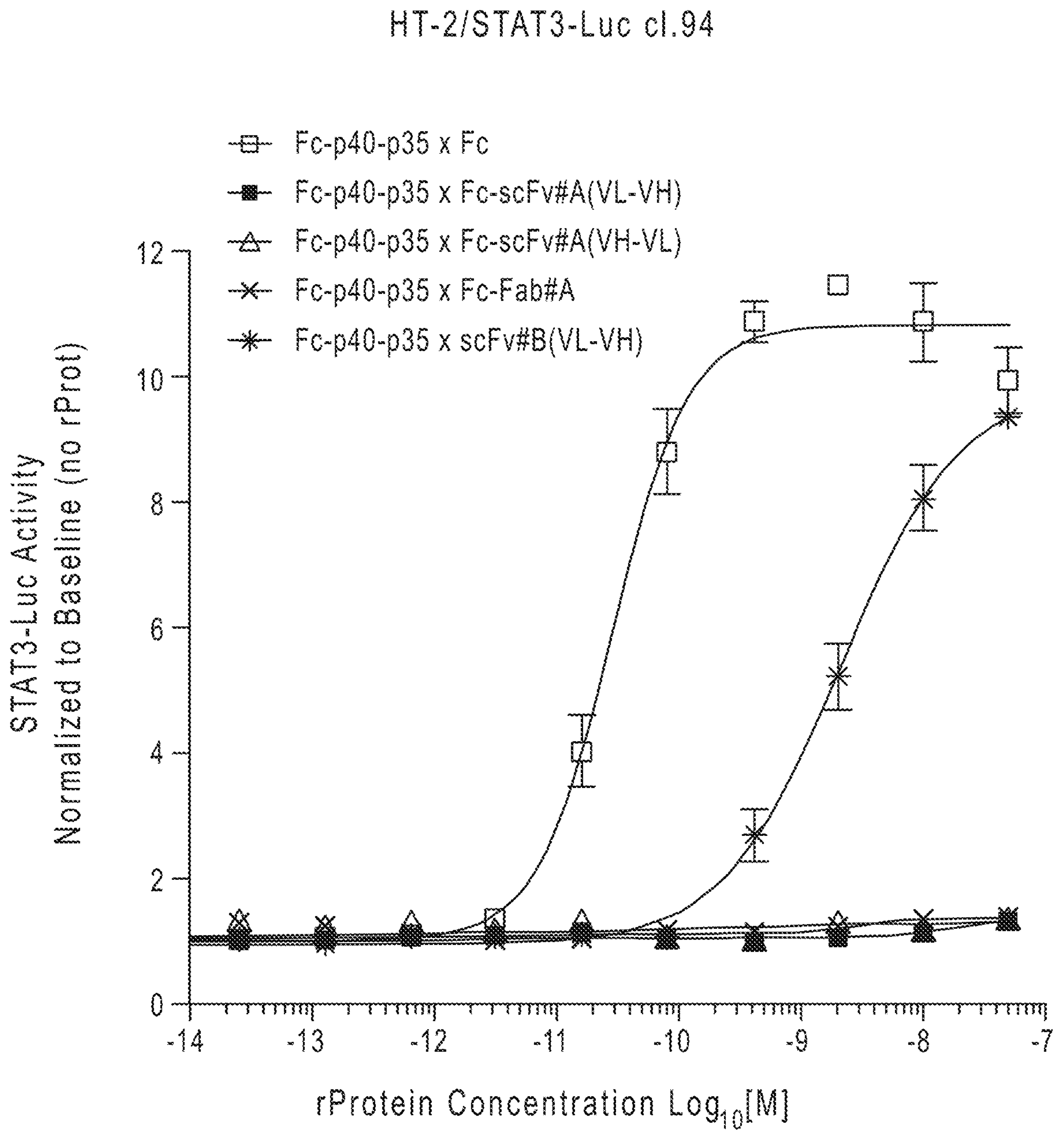

FIG. 34 depicts traces from a STAT3-based bioassay, indicating the effect of the noted IL12-Fc fusion proteins on STAT3 activity in murine HT-2 cells.

Figure 35A:
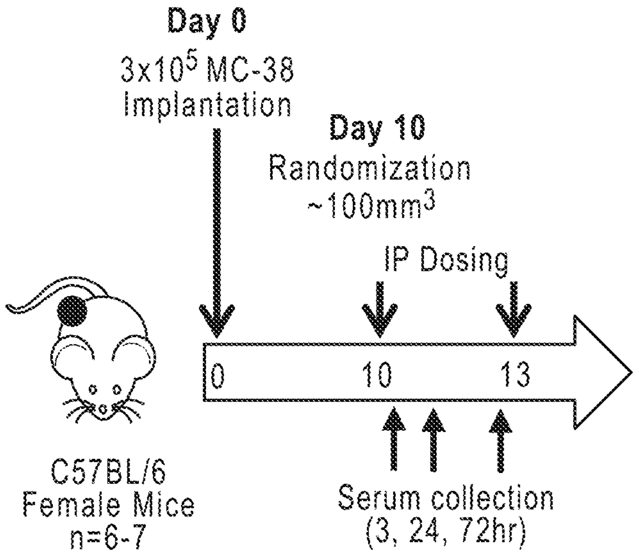
Figure 35B:
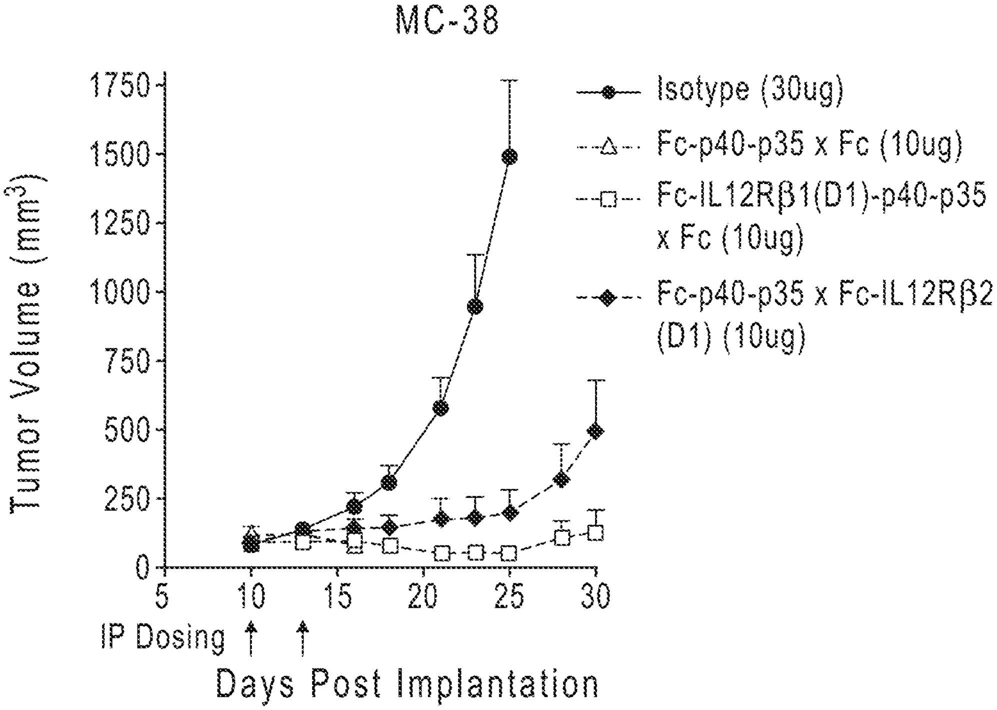
Figure 35C:
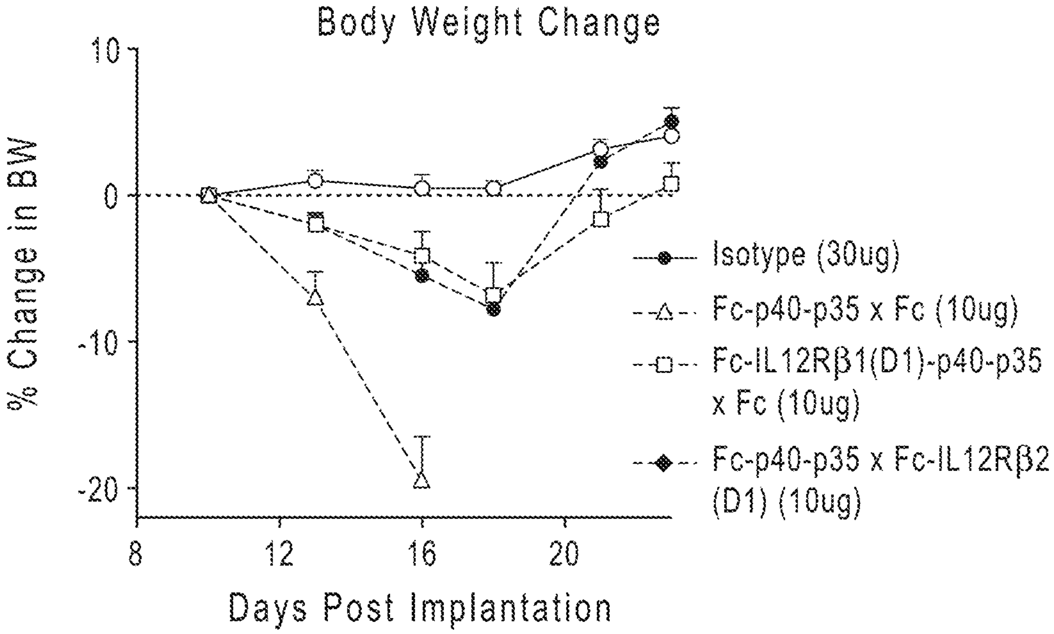

FIGS. 35A-35C depict that receptor-masked Fc-IL12 reduces toxicity and retains a level of anti-tumor activity in vivo.

FIGS. 36A-36E depict PD1-targeted-receptor-masked-IL12 has target enhanced anti-tumor efficacy without body weight loss and reduced systemic IFNγ.

Figure 37A:
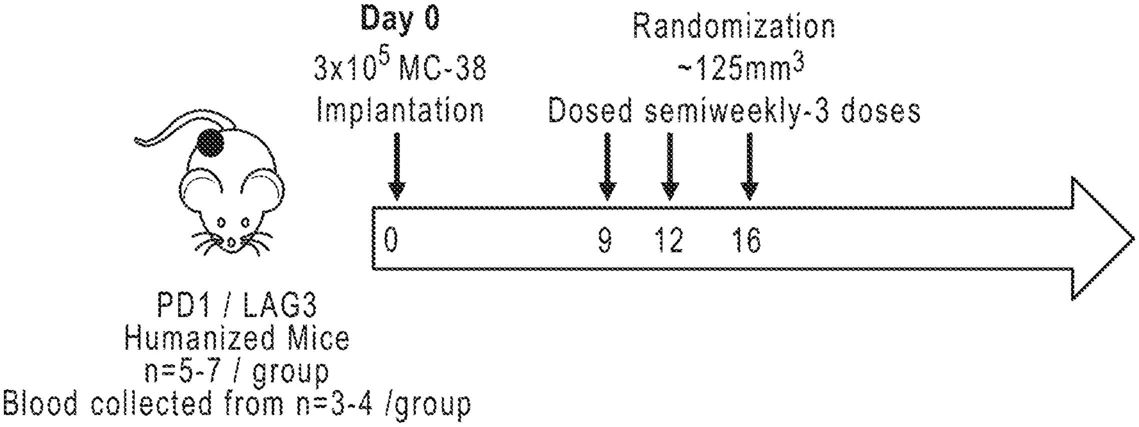
Figure 37B:
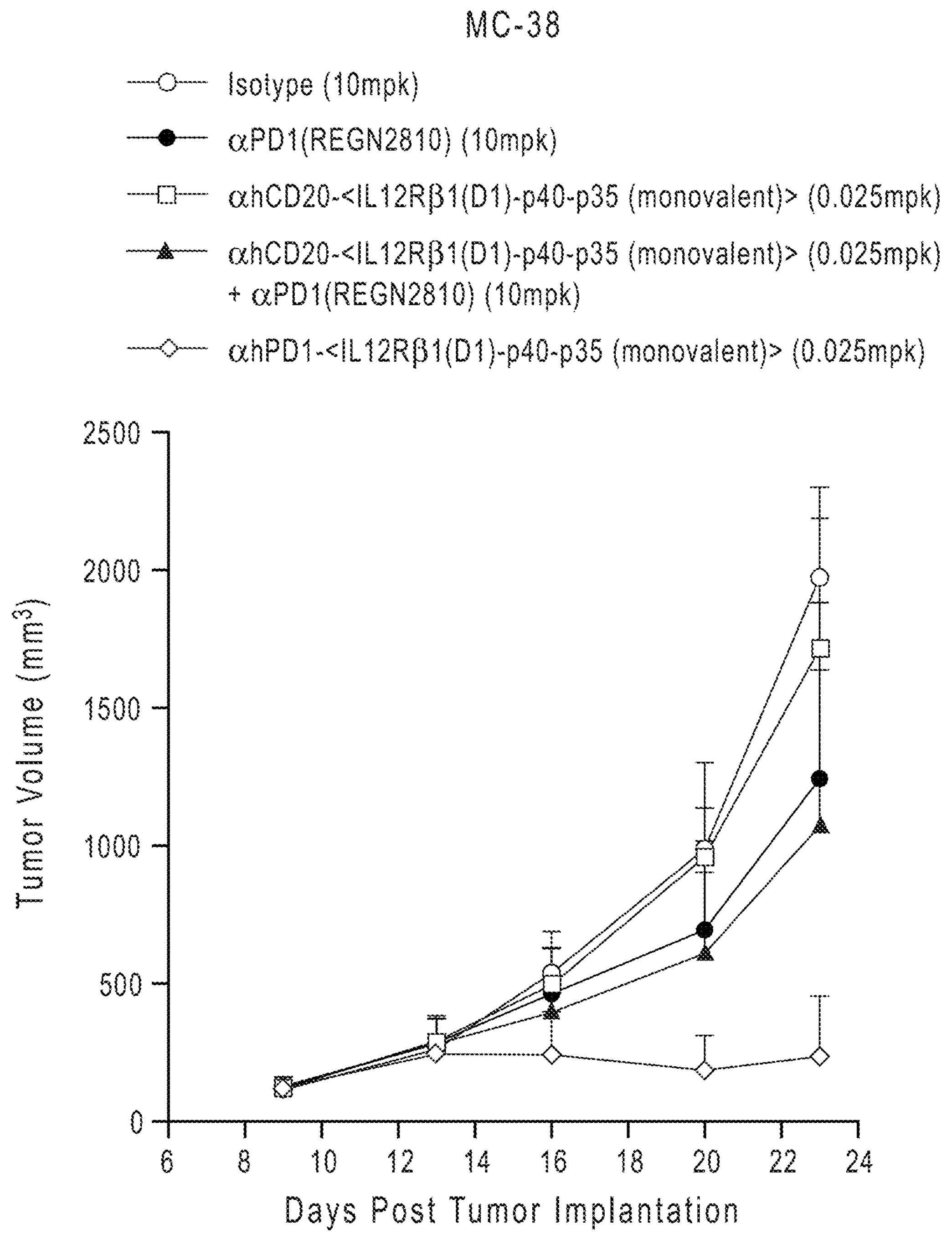

FIGS. 37A-37B depict PD1-targeted-receptor-masked-IL12 has superior anti-tumor efficacy than PD-1 blockade or the combination of untargeted-receptor-masked-IL12 and PD-1 blockade FIGS. 38A-38C-5 depict PD1-targeted-receptor-masked-IL12 has target enhanced anti-tumor efficacy without body weight loss and minimal systemic IFNγ.

Figure 5A:
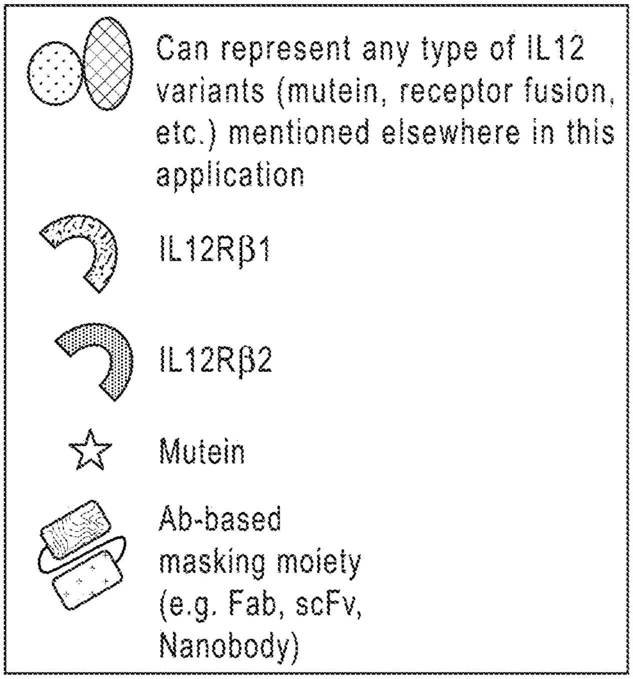
FIGS. 5T-5U are cartoons representing exemplary mechanisms of action of targeted IL12-Fc fusion proteins disclosed herein, e.g., in FIGS. 5B through 5S and 5V through 5X.
Figure 5B:
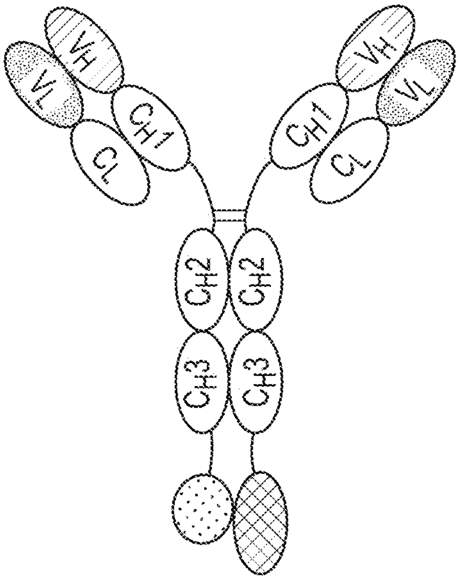
Figure 5C:
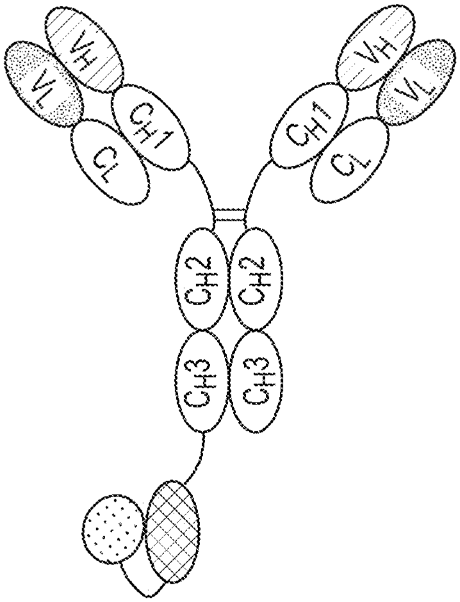
Figure 5D:
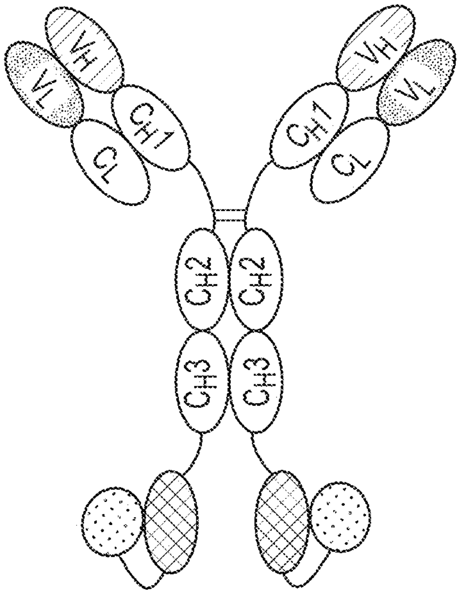
Figure 39A:
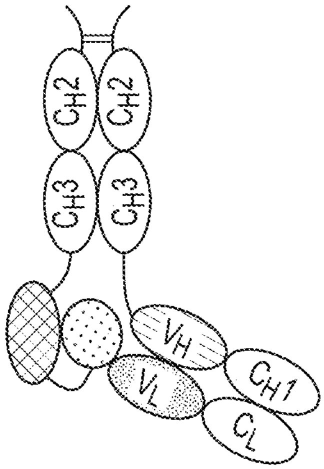
Figure 39B:
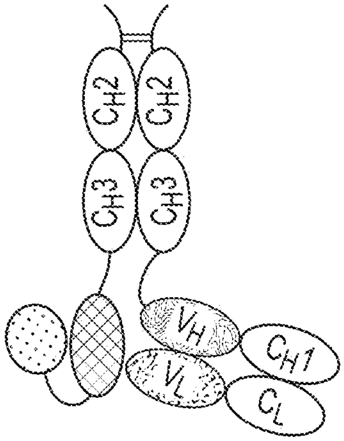
Figure 39C:
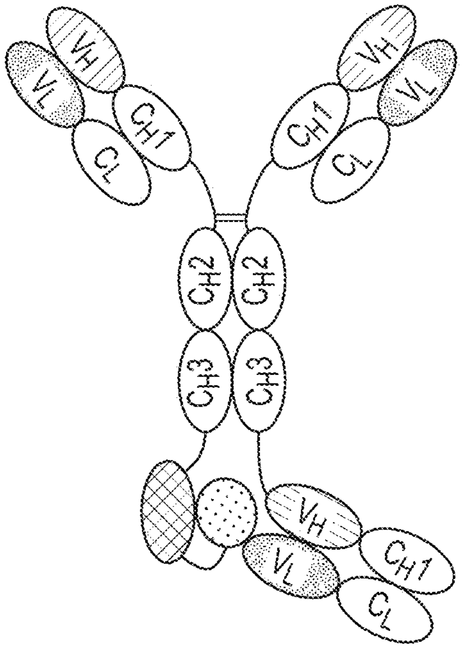
Figure 39D:
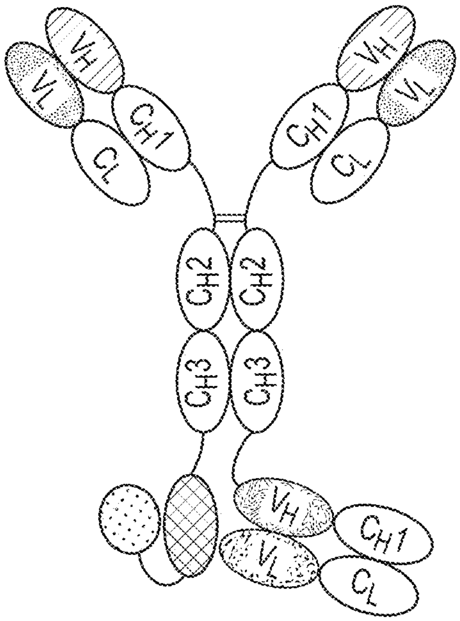

FIGS. 39A-39D are cartoons representing exemplary antibody masked IL12/Fc fusion constructs. Although the masking antibodies are depicted as Fabs, the Fabs may be substituted with Fvs, as shown in FIGS. 5L through 5N. The constructs depicted in FIGS. 39A and 39B can further include targeting moieties. FIGS. 39C and 39D represent embodiments of the constructs in FIGS. 39A and 39B, respectively, with targeting moieties at their N-termini. In FIGS. 39C and 39D, the targeting moieties are represented as Fabs; however, other formats can be used. Thus, the embodiments described herein (including in Section 6.2, the Group A and Group B numbered embodiments and claims) encompassing the formats of FIGS. 39A and 39B may further include a targeting moiety, e.g., a targeting moiety as described in Section 6.5.2, with the Fab format exemplified in FIGS. 39 and 39D.

Figure 40A:
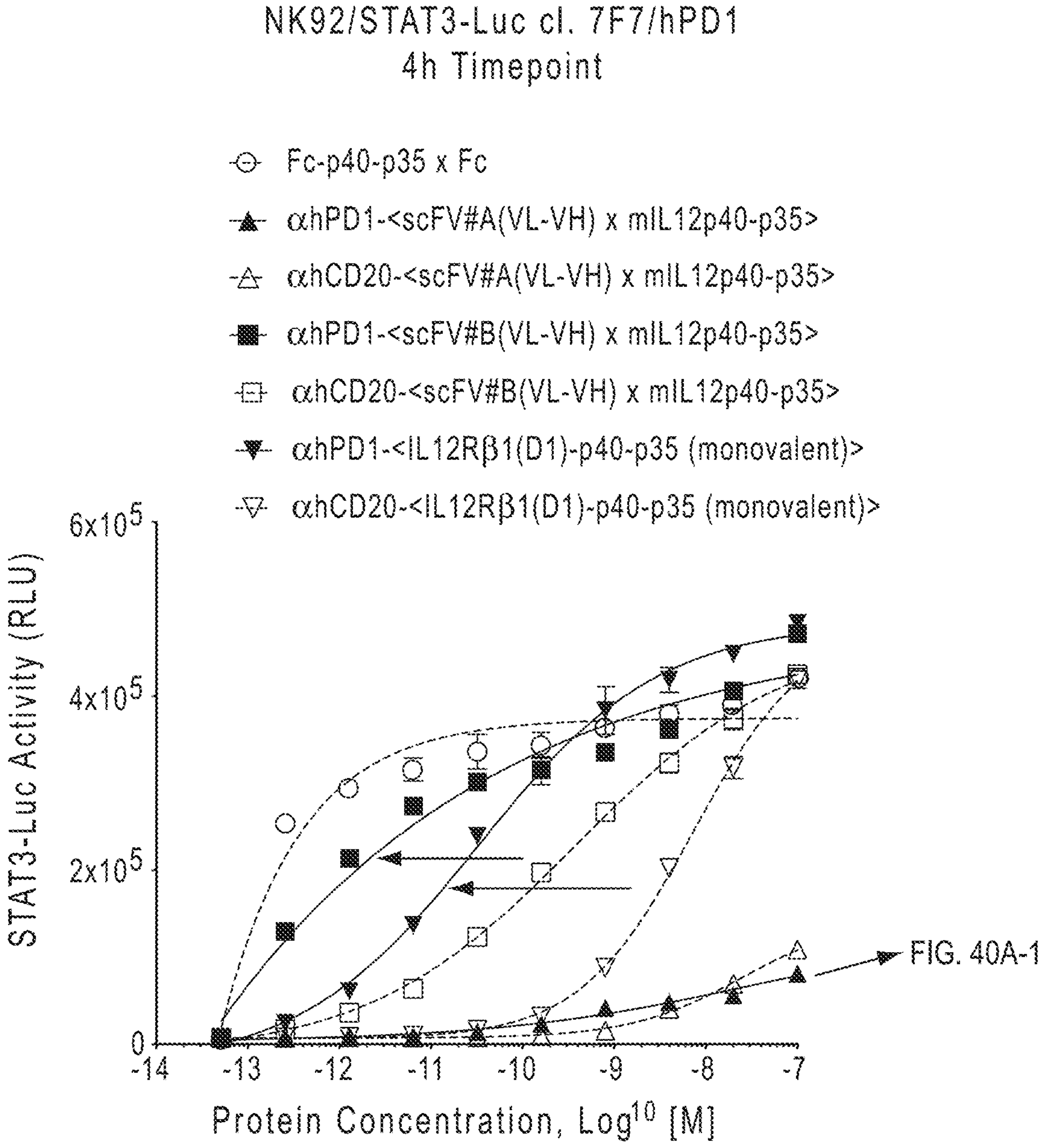
Figures 1, 40A:
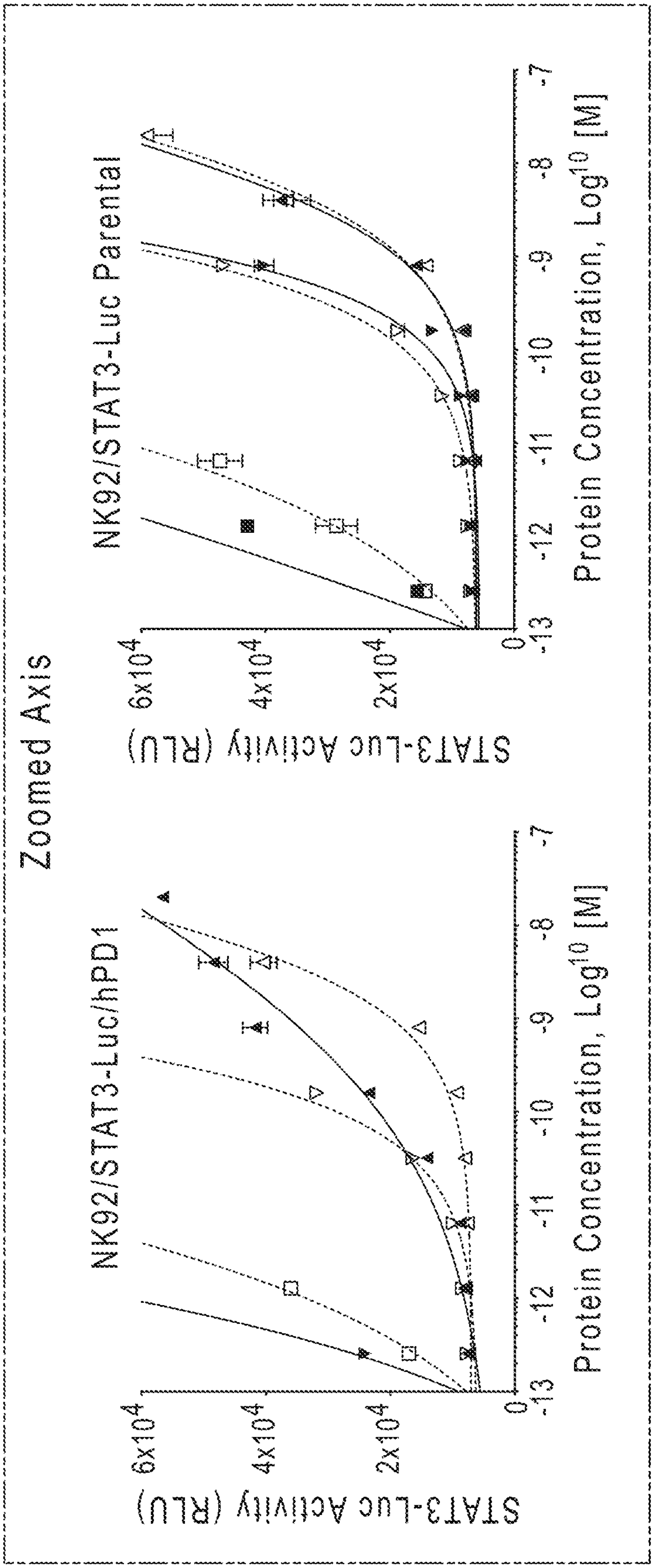
Figure 40B:
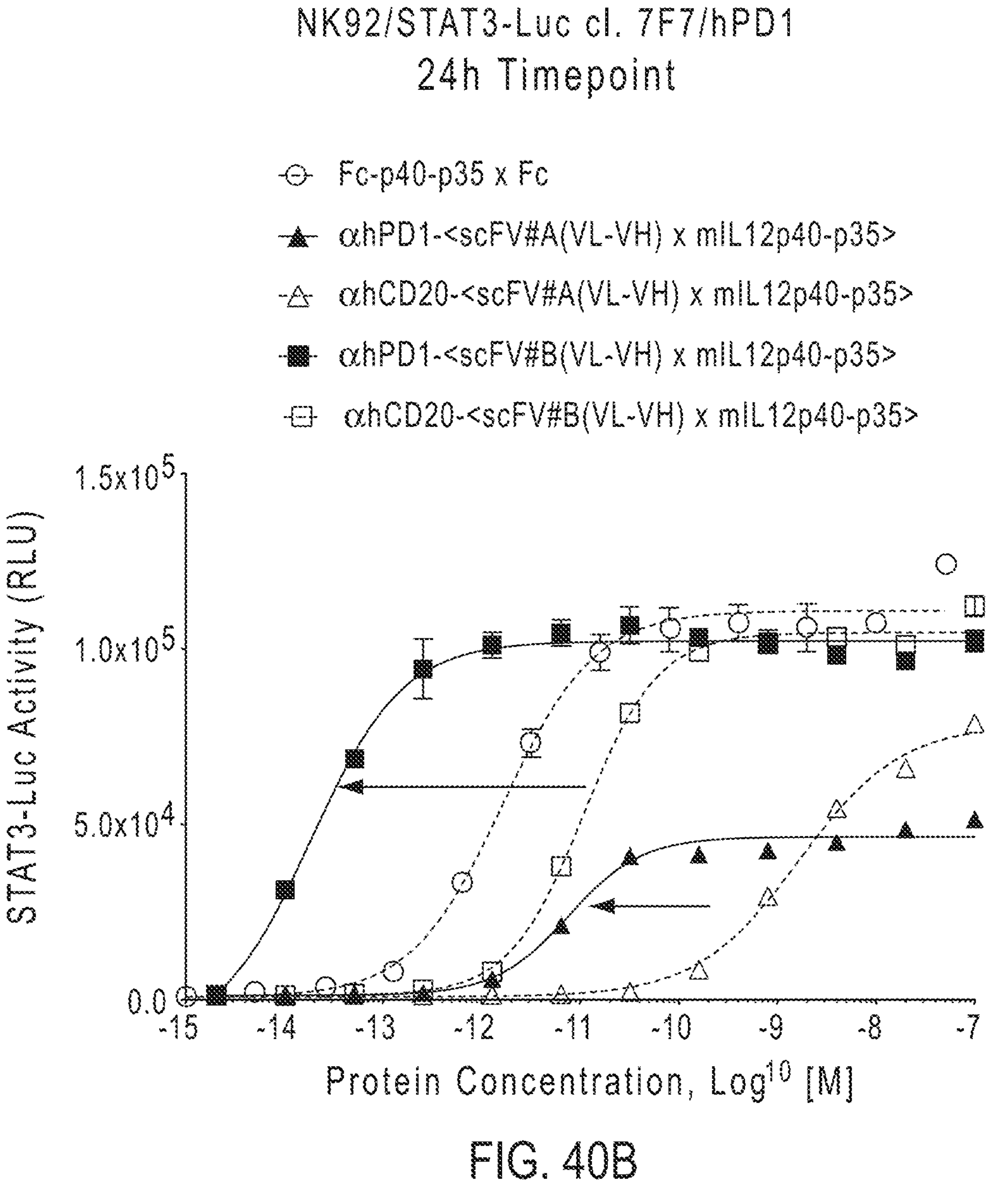

FIGS. 40A-40B depict traces from STAT3-based bioassay in NK92 cells for PD1 targeted mIL12 with R1 masks or scFv masks.

FIGS. 41A-41D depict PD1-targeted-antibody-masked-IL12 has tumor-growth inhibition without body weight loss and minimal systemic IFNγ.

Figure 42:
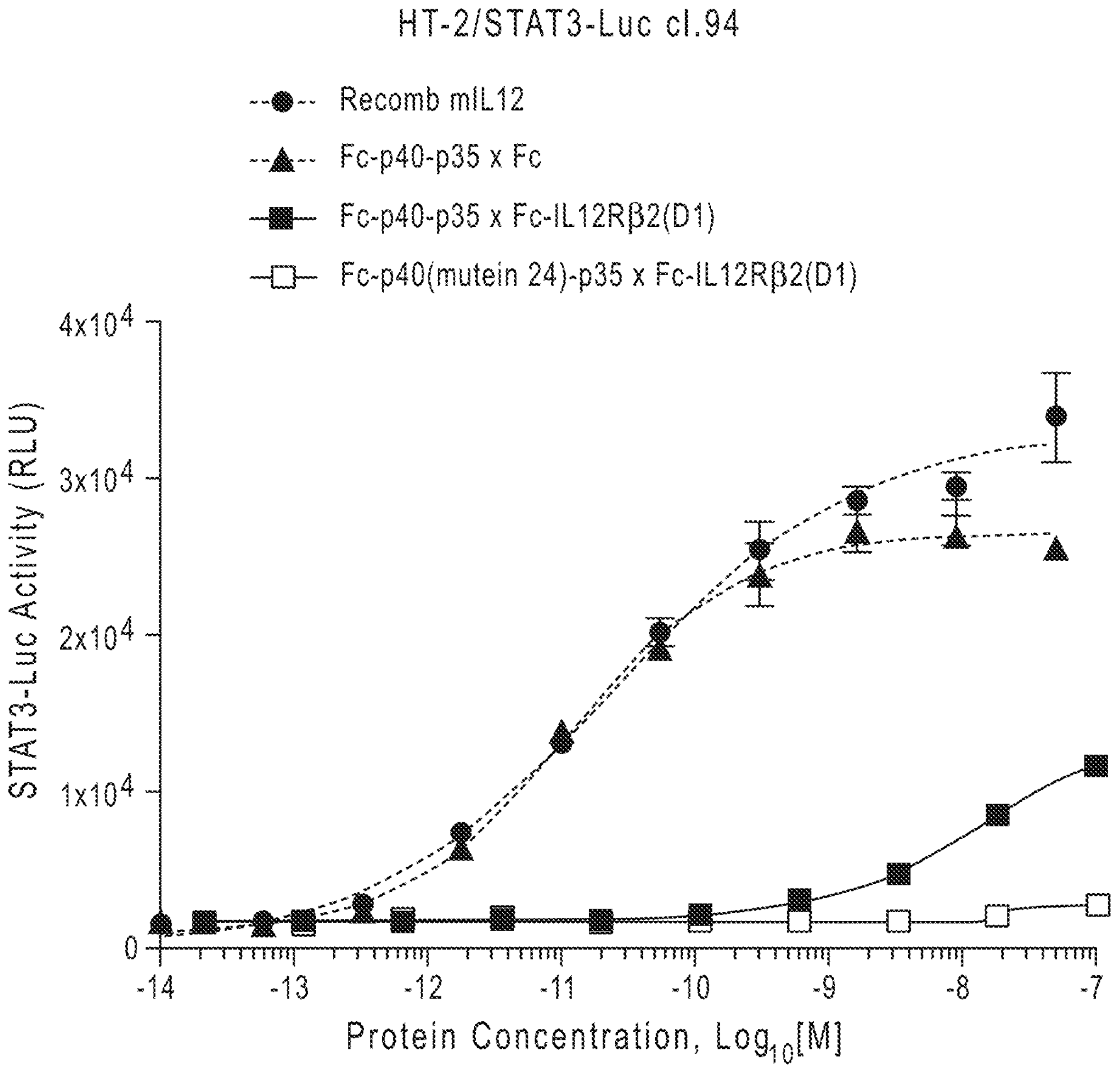

FIG. 42 depict that the combination of receptor mask for one IL12 subunit and p40 mutein further attenuates activity compared to receptor mask alone.

Figure 43:
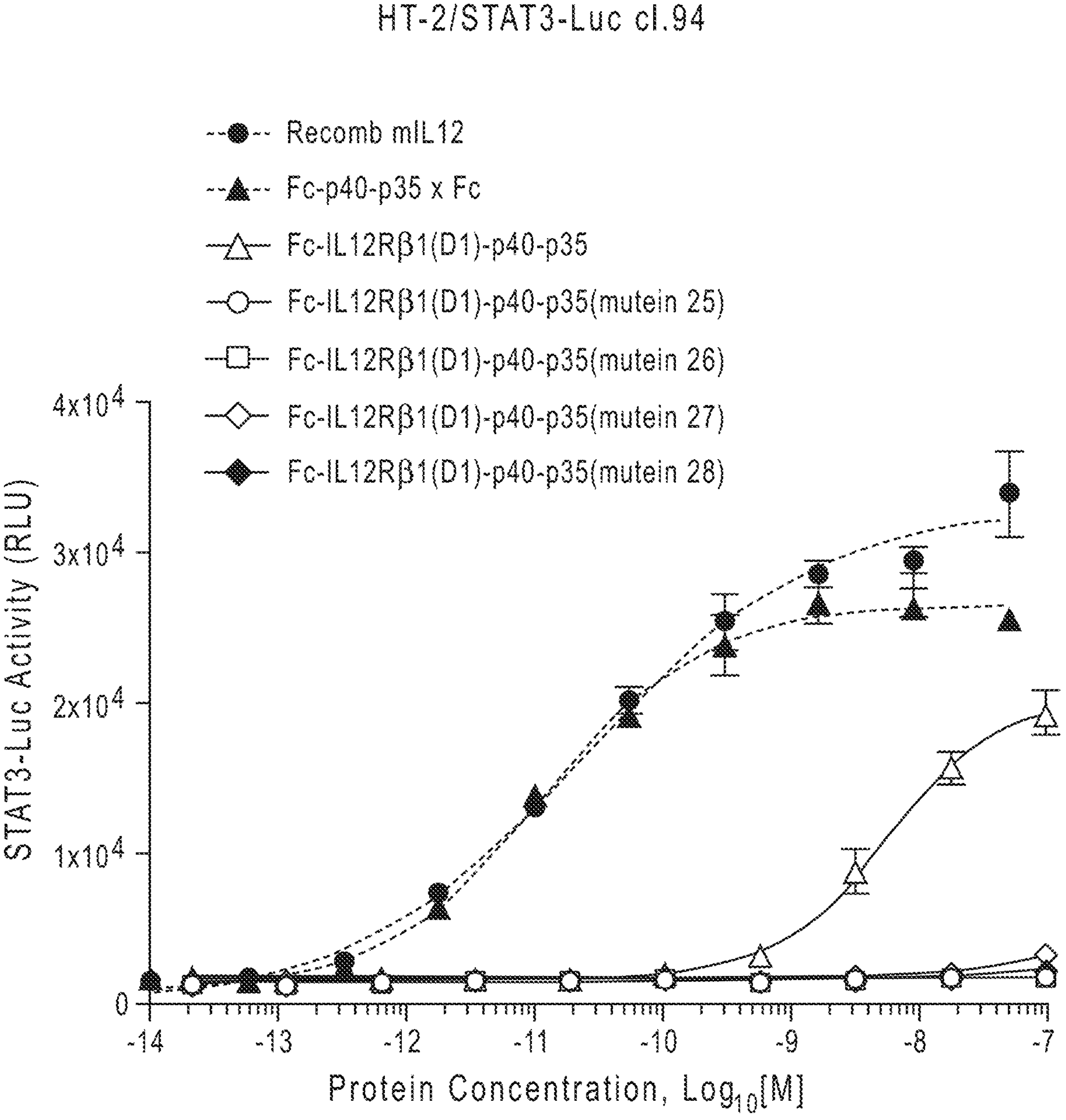

FIG. 43 depicts that the combination of receptor mask for one IL12 subunit and p35 mutein further attenuates activity compared to receptor mask alone.

Figure 44:
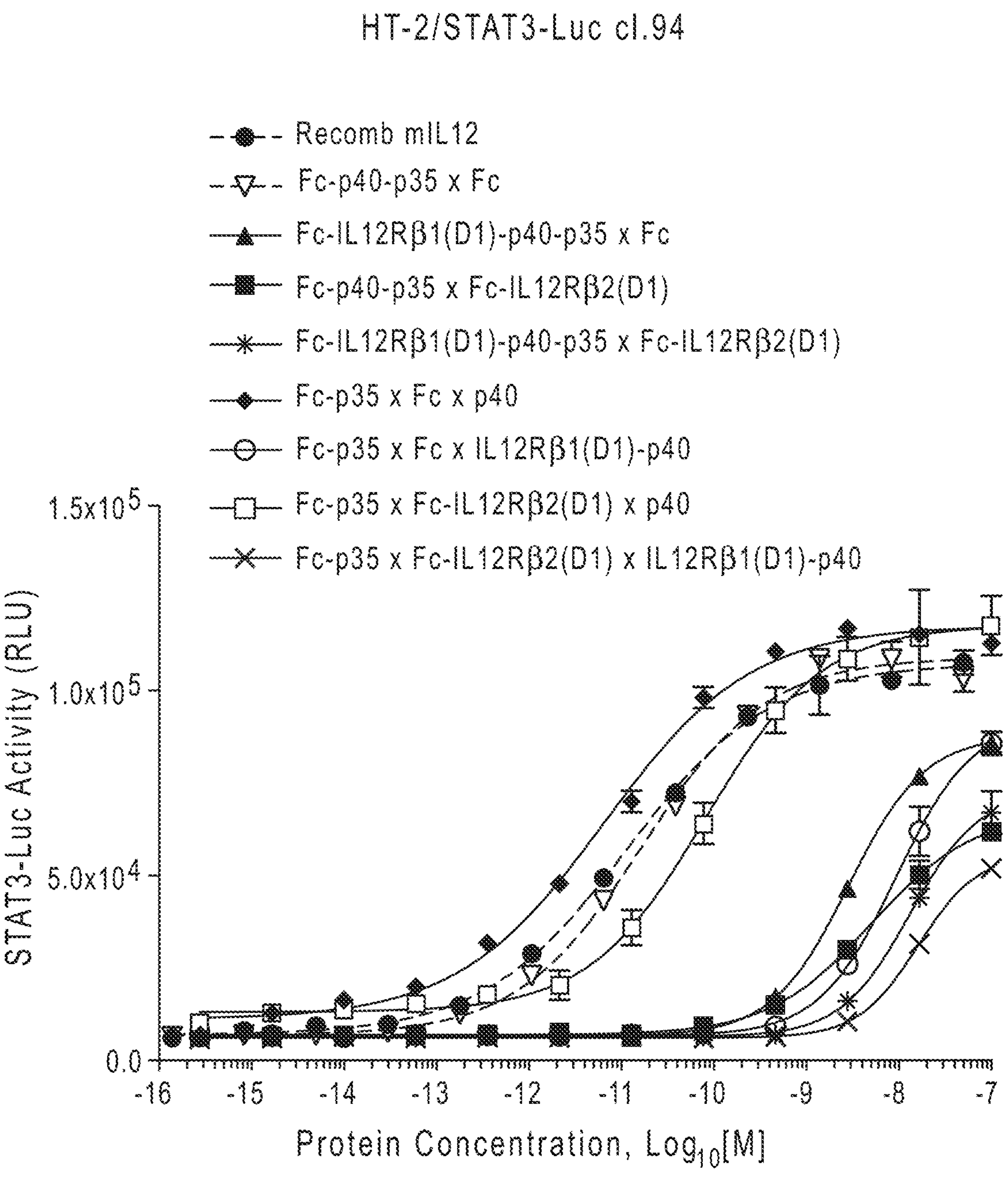

FIG. 44 depicts that '3 chain' format protein constructs with receptor masks attenuate IL12 bioactivity.

Figure 45:
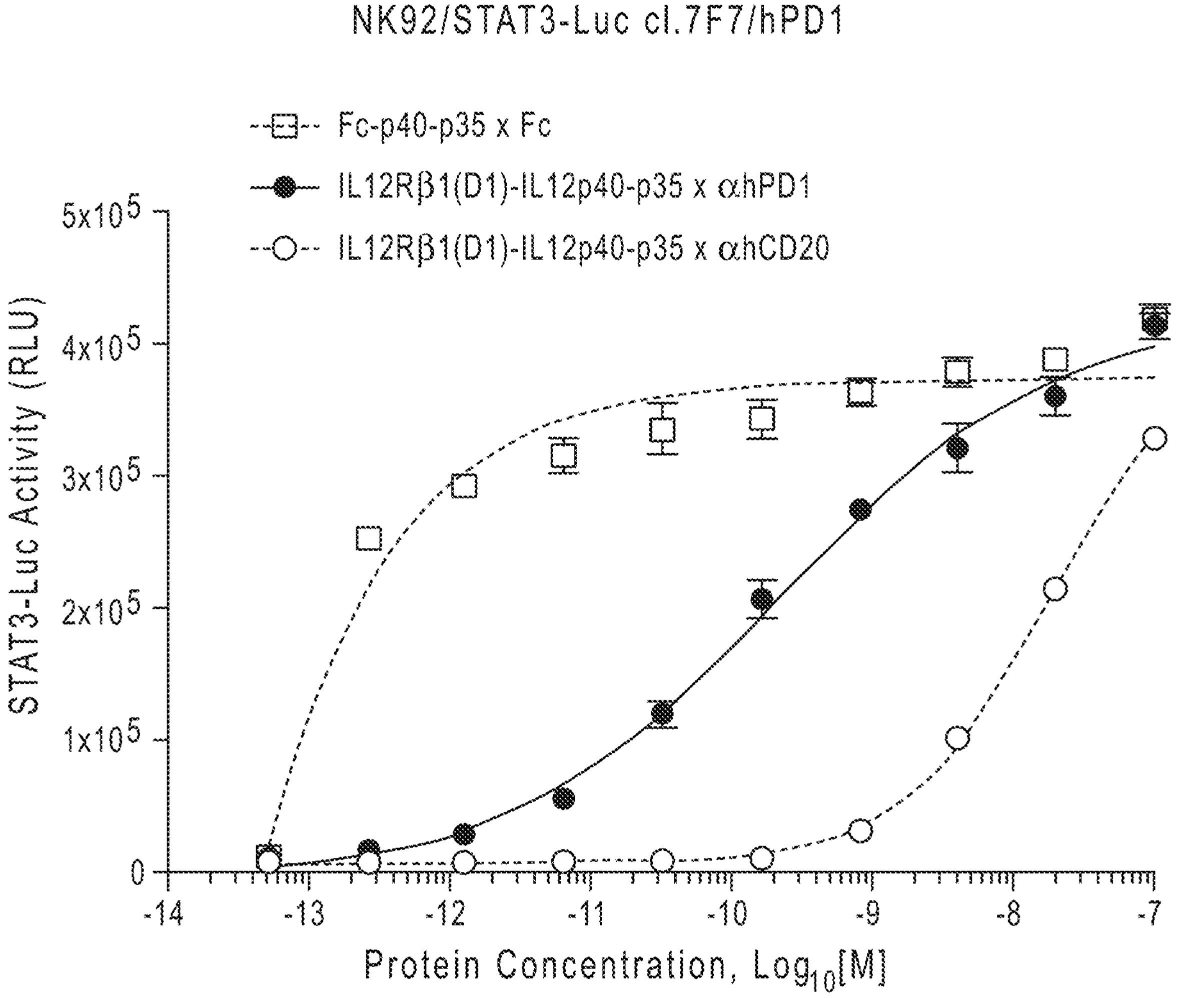

FIG. 45 depicts an exemplary format of receptor-masked IL12 that has target-enhanced bioactivity.

Figure 46A:
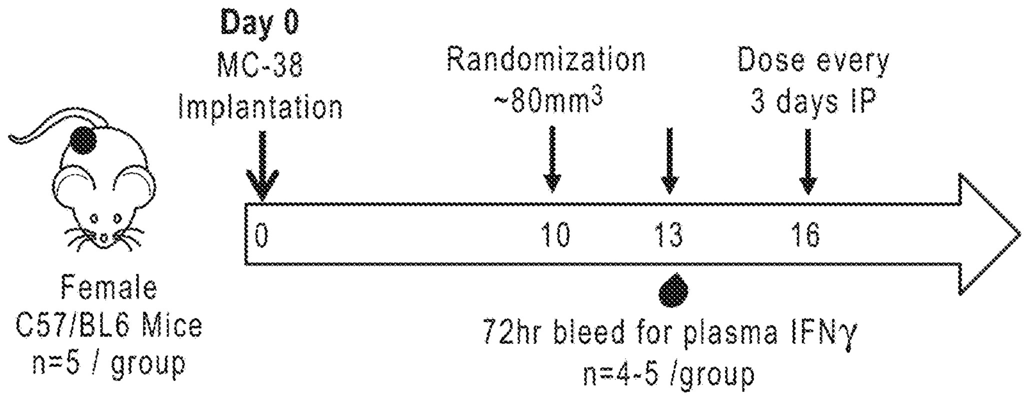
Figure 46B:
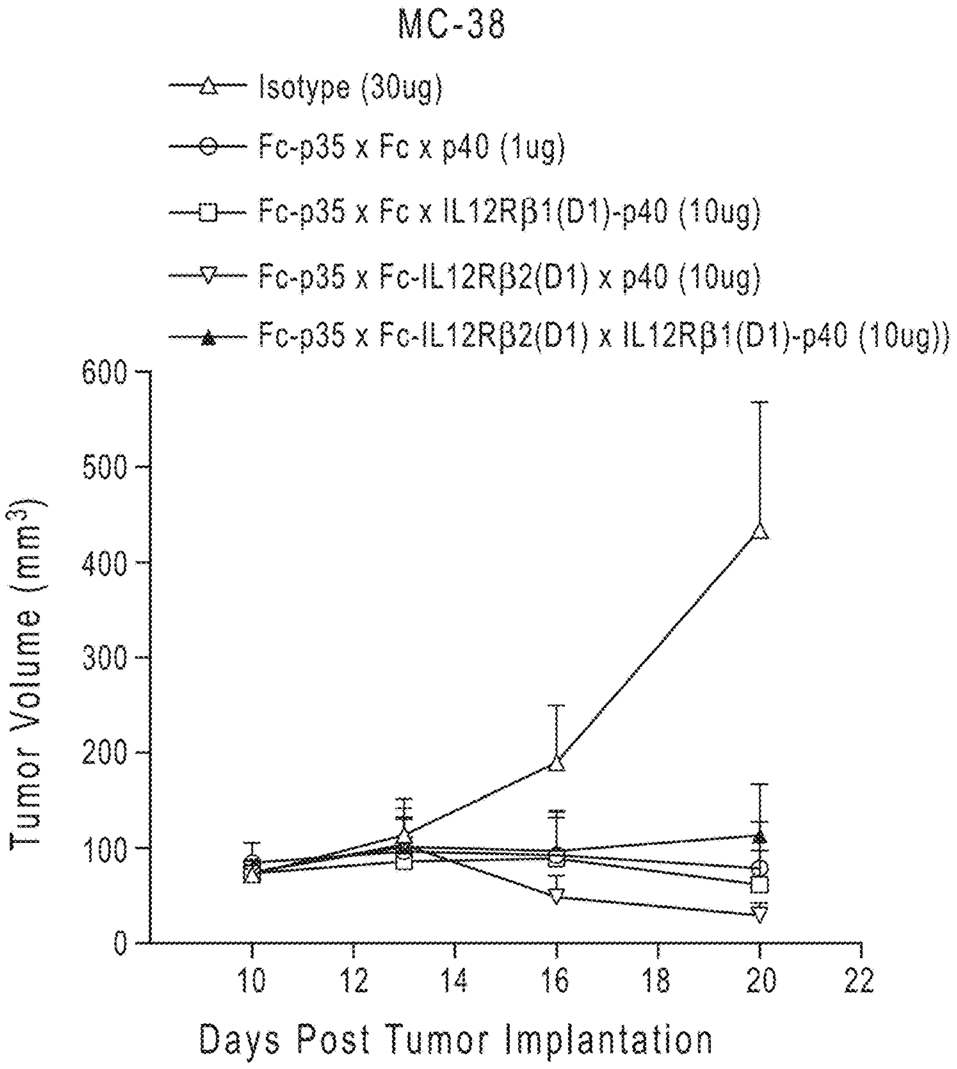
Figure 46C:
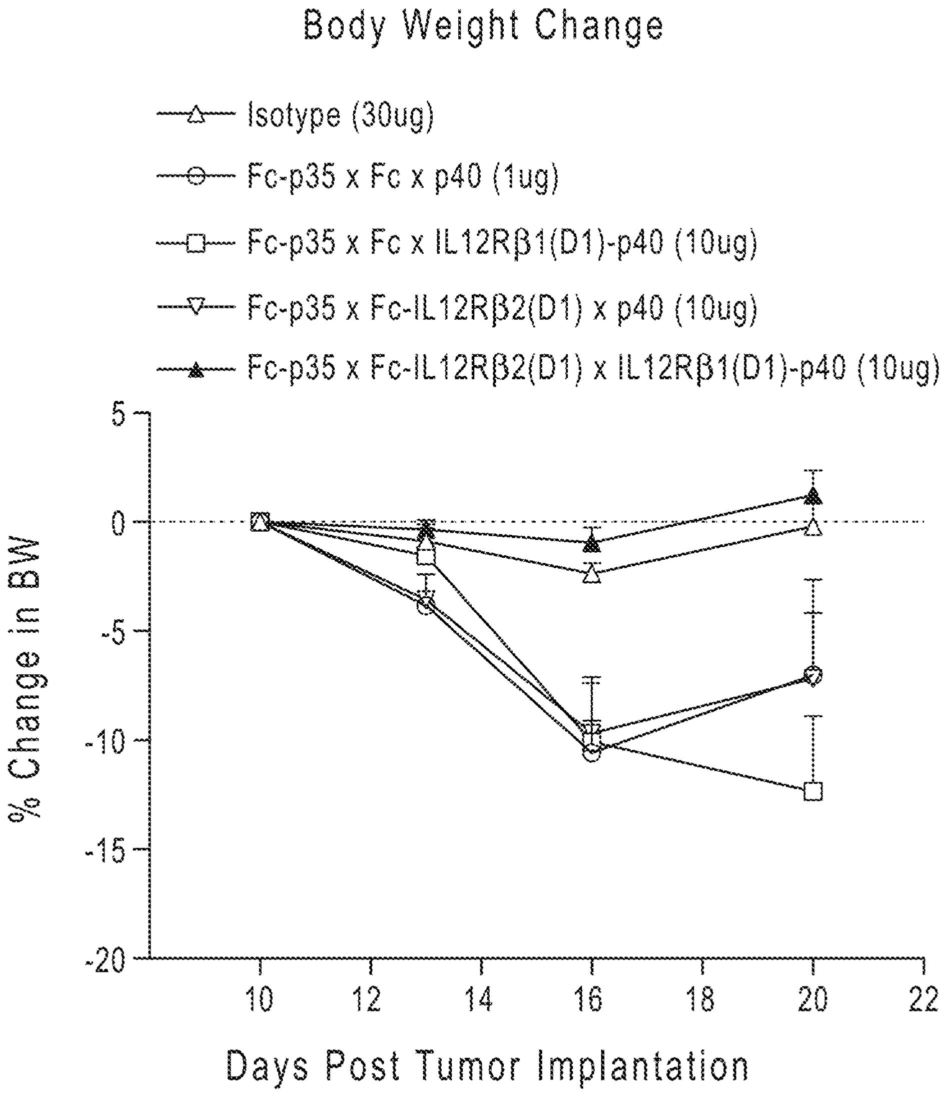
Figure 46D:
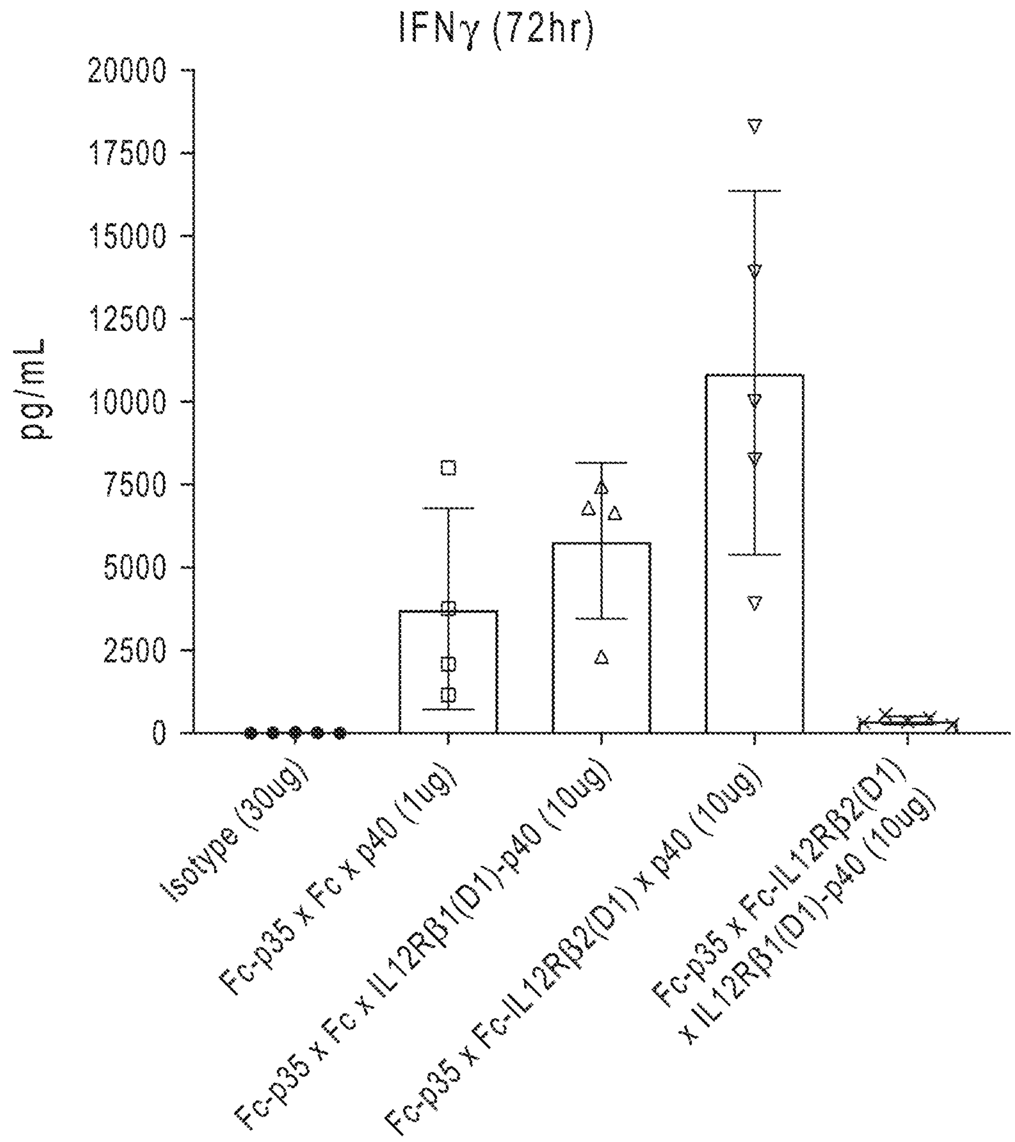

FIGS. 46A-46D depict a protocol for in vivo administration of '3 chain' format protein constructs with receptor masks (FIG. 46A) and resulting activity on tumor growth (FIG. 46B), weight loss (FIG. 46C) and IFNγ production (FIG. 46D).

6. DETAILED DESCRIPTION

6.1. Definitions

About, Approximately: The terms "about", "approximately" and the like are used throughout the specification in front of a number to show that the number is not necessarily exact (e.g., to account for fractions, variations in measurement accuracy and/or precision, timing, etc.). It should be understood that a disclosure of "about X" or "approximately X" where X is a number is also a disclosure of "X." Thus, for example, a disclosure of an embodiment in which one sequence has "about X % sequence identity" to another sequence is also a disclosure of an embodiment in which the sequence has "X % sequence identity" to the other sequence.

And, or: Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

Antigen Binding Domain or ABD: The term "antigen binding domain" or "ABD" as used herein refers to the portion of a targeting moiety that is capable of specific, non-covalent, and reversible binding to a target molecule.

Associated: The term "associated" in the context of an IL12 receptor agonist or a component thereof (e.g., an IL12 p40 moiety; an IL12 p35 moiety; a targeting moiety such as an antibody) refers to a functional relationship between two or more polypeptide chains. In particular, the term "associated" means that two or more polypeptides are associated with one another, e.g., non-covalently through molecular interactions or covalently through one or more disulfide bridges or chemical cross-linkages, so as to produce a functional IL12 receptor agonist. Examples of associations that might be present in an IL12 receptor agonist of the disclosure include (but are not limited to) associations between IL12 p40 and p35 moieties, associations between homodimeric or heterodimeric Fc domains in an Fc region, associations between VH and VL regions in a Fab or scFv, associations between CH1 and CL in a Fab, and associations between CH3 and CH3 in a domain substituted Fab.

Bivalent: The term "bivalent" as used herein in reference to IL12 and/or a targeting moiety in an IL12 receptor agonist means an IL12 receptor agonist that has two IL12 heterodimers (i.e., two p40×p35 heterodimers) and/or targeting moieties, respectively. Typically, IL12 receptor agonists that are bivalent for an IL12 moiety and/or a targeting moiety are dimeric (either homodimeric or heterodimeric).

Cancer: The term "cancer" refers to a disease characterized by the uncontrolled (and often rapid) growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, adrenal gland cancer, autonomic ganglial cancer, biliary tract cancer, bone cancer, endometrial cancer, eye cancer, fallopian tube cancer, genital tract cancers, large intestinal cancer, cancer of the meninges, oesophageal cancer, peritoneal cancer, pituitary cancer, penile cancer, placental cancer, pleura cancer, salivary gland cancer, small intestinal cancer, stomach cancer, testicular cancer, thymus cancer, thyroid cancer, upper aerodigestive cancers, urinary tract cancer, vaginal cancer, vulva cancer, lymphoma, leukemia, lung cancer and the like.

Complementarity Determining Region or CDR: The terms "complementarity determining region" or "CDR," as used herein, refer to the sequences of amino acids within antibody variable regions which confer antigen specificity and binding affinity. In general, there are three CDRs in each heavy chain variable region (CDR-H1, CDR-H2, CDR-H3) and three CDRs in each light chain variable region (CDR1-L1, CDR-L2, CDR-L3). Exemplary conventions that can be used to identify the boundaries of CDRs include, e.g., the Kabat definition, the Chothia definition, the ABM definition and the IMGT definition. See, e.g., Kabat, 1991, "Sequences of Proteins of Immunological Interest," National Institutes of Health, Bethesda, Md. (Kabat numbering scheme); Al-Lazikani et al., 1997, J. Mol. Biol. 273:927-948 (Chothia numbering scheme); Martin et al., 1989, Proc. Natl. Acad. Sci. USA 86:9268-9272 (ABM numbering scheme); and Lefranc et al., 2003, Dev. Comp. Immunol. 27:55-77 (IMGT numbering scheme). Public databases are also available for identifying CDR sequences within an antibody.

EC50: The term "EC50" refers to the half maximal effective concentration of a molecule (such as an IL12 receptor agonist) which induces a response halfway between the baseline and maximum after a specified exposure time. The EC50 essentially represents the concentration of an antibody or IL12 receptor agonist where 50% of its maximal effect is observed. In certain embodiments, the EC50 value equals the concentration of an IL12 receptor agonist that gives half-maximal STAT3 activation in an assay as described in Section 8.1.2.

Epitope: An epitope, or antigenic determinant, is a portion of an antigen (e.g., target molecule) recognized by an antibody or other antigen-binding moiety as described herein. An epitope can be linear or conformational.

Fab: The term "Fab" in the context of a targeting moiety of the disclosure refers to a pair of polypeptide chains, the first comprising a variable heavy (VH) domain of an antibody N-terminal to a first constant domain (referred to herein as C1), and the second comprising variable light (VL)

domain of an antibody N-terminal to a second constant domain (referred to herein as C2) capable of pairing with the first constant domain. In a native antibody, the VH is N-terminal to the first constant domain (CH1) of the heavy chain and the VL is N-terminal to the constant domain of the light chain (CL). The Fabs of the disclosure can be arranged according to the native orientation or include domain substitutions or swaps that facilitate correct VH and VL pairings. For example, it is possible to replace the CH1 and CL domain pair in a Fab with a CH3-domain pair to facilitate correct modified Fab-chain pairing in heterodimeric molecules. It is also possible to reverse CH1 and CL, so that the CH1 is attached to VL and CL is attached to the VH, a configuration generally known as Crossmab.

Fc Domain and Fc Region: The term "Fc domain" refers to a portion of the heavy chain that pairs with the corresponding portion of another heavy chain. The term "Fc region" refers to the region of antibody-based binding molecules formed by association of two heavy chain Fc domains. The two Fc domains within the Fc region may be the same or different from one another. In a native antibody the Fc domains are typically identical, but one or both Fc domains might advantageously be modified to allow for heterodimerization, e.g., via a knob-in-hole interaction.

Host cell: The term "host cell" as used herein refers to cells into which a nucleic acid of the disclosure has been introduced. The terms "host cell" and "recombinant host cell" are used interchangeably herein. It is understood that such terms refer to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein. Typical host cells are eukaryotic host cells, such as mammalian host cells. Exemplary eukaryotic host cells include yeast and mammalian cells, for example vertebrate cells such as a mouse, rat, monkey or human cell line, for example HKB11 cells, PER.C6 cells, HEK cells or CHO cells.

IL12 Agonist or IL12 Receptor Agonist: The terms "IL12 agonist" and "IL12 receptor agonist" are used interchangeably herein to refer to a molecule comprising or consisting of an IL12 mutein and which has IL12 activity. The IL12 activity can be greater than, lower than, or equal to the activity of wild type or recombinant IL12 (e.g., human or murine IL12) in one or more in vitro or in vivo biological assays, for example the STAT3-driven luciferase-based reporter assay described in Section 8.1.2 or the MC38 synergistic tumor model described in Section 8.1.3. In various embodiments, the IL12 agonist has activity, relative to recombinant IL12, ranging from 5% to 90%, from 5% to 85%, from 5% to 80%, from 10% to 80%, from 15% to 80%, from 20% to 80%, from 25% to 80%, from 30% to 80%, from 35% to 80%, from 45% to 80%, from 50% to 80%, from 5% to 70%, from 10% to 70%, from 15% to 70%, from 20% to 70%, from 25% to 70%, from 30% to 70%, from 35% to 70%, from 45% to 70%, or from 50% to 70%.

IL12 Moiety: The term "IL12 Moiety" refers to a p35 moiety or a p40 moiety. Thus, the related term "intra-IL12 moiety linker" refers to a linker connecting two IL12 moieties, e.g., a p35 moiety and a p40 moiety.

IL12 Mutein: An "IL12 mutein" is a variant IL12 molecule composed or one or more polypeptide chains (e.g., one, two, three or four polypeptide chains) comprising an IL12 p35 (referred to as "p35") moiety and an IL12 p40 ("p40") moiety in association with one another and which varies from native IL12 by (a) primary amino acid sequence and/or (b) association with additional domains not naturally associated with IL12, for example (i) a multimerization moiety (e.g., dimerization domain such as an Fc domain) domain and/or (ii) a targeting moiety and/or (iii) a stabilization moiety and/or (iv) an IL12βR moiety.

In some embodiments, the term mutein refers to a structure (a) with or without a targeting moiety and/or (b) with or without a stabilization moiety and/or (c) with or without a multimerization moiety. In the context of the IL12 agonists of the disclosure, the term "IL12 mutein" sometimes refers to the core components of a variant IL12 molecule, namely the p35 and p40 moieties and sometimes also the multimerization moieties, such as Fc domains and any/or associated linker moieties, and it is to be understood that the term "IL12 mutein" extends also to IL12 molecules comprising additional features, e.g., one or more targeting moieties, one or more stabilization moieties, one or more multimerization moieties, one or more IL12R moieties, one or more linker moieties, and any combination of the foregoing, unless the context dictates otherwise.

The IL12 mutein can thus comprise a p35 and/or p40 moiety with one or more amino acid substitutions, deletions and/or insertions compared to wild type p35 and/or p40.

As disclosed herein, a p35 moiety may include an IL12Rβ2 moiety and a p40 moiety may include an IL12Rβ1 moiety. The p35 moiety and the IL12Rβ2 moiety may be on the same or on different polypeptide chains. The p40 moiety and the IL12Rβ1 moiety may be on the same or different polypeptide chains. The IL12Rβ1 and the IL12Rβ2 moieties generally serve as masking moieties and when present are thus typically configured to interact with the p40 moiety and the p35 moiety, respectively.

In some embodiments, the IL12 mutein has one or more mutations in its p35 subunit or its p40 subunit, or one or more mutations in both its p35 subunit and its p40 subunit. Exemplary mutations, e.g., substitutions, are disclosed, inter alia, in Section 6.3 and subsections thereof, in Tables 1 and 2, as well as in numbered embodiments 1, 2, 676 to 719 and 589 to 674. The p35 and p40 subunits of an IL12 mutein can be included in the same polypeptide chain, or can be included on different polypeptide chains. Exemplary configurations of the IL12 muteins and agonists of the disclosure are disclosed, inter alia, in FIGS. 2A through 5X, Section 6.2, and in numbered embodiments 3 to 847.

In some embodiments, the IL12 mutein comprises a masking moiety. Exemplary masking moieties of the disclosure as disclosed, inter alia, in FIGS. 4B-4E, 4G-4W, 5H-5O, 5R-5S, 5V-5X and 39A-39D, and Section 6.4, as well as in numbered embodiments disclosed in Section 7 below that reference these figures and/or their constituent Exemplary Monomers.

In some embodiments, the IL12 mutein comprises a receptor-based masking moiety. In other embodiments, the IL12 mutein comprises an antibody-based masking moiety. Exemplary antibody-based masking moieties and IL12 receptor agonists comprising them are disclosed in, inter alia, in FIGS. 4O-4R, 5L-5N and 39A-39D, Sections 6.2 and 6.4, and in numbered embodiments disclosed in Section 7 below that references these figures and/or their constituent Exemplary Monomers. Exemplary receptor-based masking moieties and IL12 receptor agonists comprising them are disclosed in, inter alia, in FIGS. 4B to 4E, 4G to 4N, 4S to 4W, 5H to 5K, 5O, 5R, 5S, and 5V-5X, Sections 6.2 and 6.4, and in numbered embodiments disclosed in Section 7 below that references these figures and/or their constituent Exemplary Monomers.

The IL12 mutein can be monovalent for p35 and p40 (i.e., has a single p35 moiety and a single p40 moiety) or multivalent for p35 and p40 (i.e., has multiple p35 moieties and p40 moieties). In some embodiments, the IL12 mutein is divalent for p35 and p40 (i.e., has two p35 moieties and two p40 moieties). When an IL12 mutein is multivalent for p35 and p40, the multiple p35 moieties can be the same or different from one another and/or the multiple p40 moieties can be the same or different from one another.

An IL12 mutein can have altered function (e.g., receptor binding, affinity, cytokine activity) and/or altered pharmacokinetics as compared to wild type IL12.

IL12 p35 moiety or p35 moiety: An IL12 p35 moiety or a p35 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12Rβ2 binding portion of a mammalian, e.g., human or murine, p35 (sometimes referred to as the alpha subunit of IL12 or IL12α), optionally with one or amino acid substitutions as defined in Section 6.3.2 below. The sequence of human p35 has the Uniprot identifier P29459 (uniprot.org/uniprot/P29459). The sequence of murine p35 has the Uniprot identifier P43431 (uniprot.org/uniprot/P43431).

p35 comprises a signal sequence (at amino acids 1-22 of human p35). In native IL12, p35 has four conserved cysteine residues that form two inter-strand disulfide bonds, which bridge C64 and C96 as well as C85 and C123 of human p35. p35 also includes a cysteine (C74 of human p35) that forms an inter-chain bond with p40 (at amino acid C177 of human p40)).

The p35 moiety preferably comprises an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a mature a mammalian p35, e.g., human or murine p35 (corresponding to amino acids 23-219 of human p35), optionally with one or amino acid substitutions as defined in Section 6.3.2 below.

In various embodiments, the p35 moiety of an IL12 mutein of the disclosure retains any combination of (a) none, either, or both inter-strand disulfide bonds and/or (b) the cysteine that forms an inter-chain bond with p40.

IL12 p40 moiety or p40 moiety: An IL12 p40 moiety or a p40 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12Rβ1 binding portion of a mammalian, e.g., human or murine, p40 (sometimes referred to as the beta subunit of IL12 or IL12β), optionally with one or amino acid substitutions as defined in Section 6.3.1 below. The sequence of human p40 has the Uniprot identifier P29460 (uniprot.org/uniprot/P29460). The sequence of murine p40 has the Uniprot identifier P43432 (uniprot.org/uniprot/P43432). p40 comprises a signal sequence (at amino acids 1-22 of human p40), an Ig-like C2-type domain referred to as D1 (at amino acids 23 to 106 of human p40), a first fibronectin type-III domain referred to as D2 (at amino acids 107 to 236 of human p40) and a second fibronectin type-III domain referred to as D3 (at amino acids 237 to 328 of human p40). In native IL12, the D2 domain of p40 has four conserved cysteine residues which form two inter-strand disulfide bonds, which bridge C109 and C120 and C148 and C171 in human p40 and the D3 domain also contains an inter-strain disulfide bond, which bridges C278 and C305 in human p40. D2 also includes a cysteine (C177 in human p40) that forms an inter-chain bond with p35 (at amino acid C74 of human p35). D3 also contains the highly conserved WSXWS motif (SEQ ID NO: 3) (WSEWAS (SEQ ID NO: 4) in human p40).

The p40 moiety preferably includes a D2 domain and a D3 domain (or an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the D2 and D3 domains) of a mammalian, e.g., human or murine, p40, optionally with one or amino acid substitutions as defined in Section 6.3.1 below.

The p40 moiety can also include a D1 domain or an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the D1 domain of a mammalian, e.g., human or murine, p40, optionally with one or amino acid substitutions as defined in Section 6.3.1 below.

In various embodiments, the p40 moiety of an IL12 mutein of the disclosure retains any combination of (a) none, any one, any two or all three inter-strand disulfide bonds and/or (b) the cysteine that forms an inter-chain bond with p35 and/or (c) the conserved WSXWS motif (SEQ ID NO: 3).

IL12Rβ1 moiety: An IL12Rβ1 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12 p40 binding portion of a mammalian, e.g., human or murine, IL12 receptor subunit beta-1 (IL12Rβ1). The IL12 p40 binding portion of IL12Rβ1 comprises or consists of the extracellular domain of the receptor subunit. The sequence of human IL12Rβ1 has the Uniprot identifier P42701 (uniprot.org/uniprot/P42701) (SEQ ID NO: 133), with amino acids 24 to 545 (SEQ ID NO: 134) making up the extracellular domain. The sequence of murine IL12Rβ1 has the Uniprot identifier Q60837 (uniprot.org/uniprot/Q60837), with amino acids 20 to 565 making up the extracellular domain. IL12Rβ1 comprises a signal sequence (at amino acids 1-23 of human IL12Rβ1), an extracellular p40-binding domain (at amino acids 24 to 545 of human IL12Rβ1 (SEQ ID NO:134)), a helical transmembrane domain (at amino acids 546 to 570 of human IL12Rβ1) and a cytoplasmic domain (at amino acids 571 to 662 of human IL12RÆ1).

The IL12Rβ1 moiety preferably includes an extracellular domain (or an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the extracellular domain) of a mammalian, e.g., human or murine, IL12Rβ1.

IL12Rβ moiety: As used herein, the term IL12Rβ moiety refers to an IL12Rβ1 or an IL12Rβ2 moiety.

IL12Rβ2 moiety: An IL12Rβ2 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12 p35 binding portion of a mammalian, e.g., human or murine, IL12 receptor subunit beta-2 (IL12Rβ2). The IL12 p35 binding portion of IL12Rβ2 comprises or consists of the extracellular domain of the receptor subunit. The sequence of human IL12Rβ2 has the Uniprot identifier Q99665 (uniprot.org/uniprot/Q99665) (SEQ ID NO: 135), with amino acids 24 to 622 (SEQ ID NO: 136) making up the extracellular domain. The sequence of murine IL12Rβ2 has the Uniprot identifier P97378 (uniprot.org/uniprot/Q60837), with amino acids 24 to 637 making up the extracellular domain. IL12Rβ2 comprises a signal sequence (at amino acids 1-23 of human IL12Rβ2), an extracellular p40-binding domain (at amino acids 24 to 622 of human IL12Rβ2 (SEQ ID NO: 136)), a helical transmembrane domain (at amino acids 623 to 643 of human IL12Rβ2) and a cytoplasmic domain (at amino acids 644 to 862 of human IL12Rβ2).

The IL12Rβ2 moiety preferably includes an extracellular domain (or an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the extracellular domain) of a mammalian, e.g., human or murine, IL12Rβ2.

Major histocompatibility complex and MHC: These terms refer to naturally occurring MHC molecules, individual chains of MHC molecules (e.g., MHC class I α (heavy) chain, β2 microglobulin, MHC class II α chain, and MHC class II β chain), individual subunits of such chains of MHC molecules (e.g., α1, α2, and/or α3 subunits of MHC class I α chain, α1-α2 subunits of MHC class II α chain, β1-β2 subunits of MHC class II β chain) as well as portions (e.g., the peptide-binding portions, e.g., the peptide-binding grooves), mutants, and various derivatives thereof (including fusions proteins), wherein such portion, mutants, and derivatives retain the ability to display an antigenic peptide for recognition by a T-cell receptor (TCR), e.g., an antigen-specific TCR. An MHC class I molecule comprises a peptide binding groove formed by the α1 and α2 domains of the heavy a chain that can stow a peptide of around 8-10 amino acids. Despite the fact that both classes of MHC bind a core of about 9 amino acids (e.g., 5 to 17 amino acids) within peptides, the open-ended nature of MHC class II peptide binding groove (the α1 domain of a class II MHC a polypeptide in association with the β1 domain of a class II MHC β polypeptide) allows for a wider range of peptide lengths. Peptides binding MHC class II usually vary between 13 and 17 amino acids in length, though shorter or longer lengths are not uncommon. As a result, peptides may shift within the MHC class II peptide binding groove, changing which 9-mer sits directly within the groove at any given time. Conventional identifications of particular MHC variants are used herein. The terms encompass "human leukocyte antigen" or "HLA".

Masking Moiety or IL12 Masking Moiety: The terms "masking moiety" (in relation to IL12) and "IL12 masking moiety" refer to a moiety capable of reversibly binding with a p35 moiety and/or a p40 moiety. In some embodiments, the masking moiety is an IL12Rβ moiety (e.g., an IL12Rβ1 or IL12Rβ2 moiety). In other embodiments, the masking moiety is an anti-IL12 (e.g., an anti-p35 or anti-p40) antibody fragment.

Monomer and IL12 Monomer: The terms monomer and IL12 monomer as used herein refer to a molecule comprising a first polypeptide chain which (a) comprises a p35 moiety and a p40 moiety and is capable of associating with a second polypeptide chain; (b) comprises a p35 moiety and is capable of associating with a p40 moiety on a second polypeptide chain; (c) comprises a p40 moiety and is capable of associating with a p35 moiety on a second polypeptide chain; (d) comprises a multimerization moiety (e.g., an Fc domain) and is capable of associating with a corresponding multimerization moiety (e.g., another Fc domain) on a second polypeptide chain; or (e) any combination of (a), (b), (c), and (d) above. Thus, monomers are capable of associating with other monomers through a p35/p40 moiety pairing and/or a multimerization moiety (e.g., Fc domain) pairing. In some embodiments, one or more of associations between monomers are stabilized through inter-chain disulfide bridges, e.g., at the p35/p40 interface or through hinge sequences or other portions of Fc domains. Thus, a monomer of the disclosure is capable of associating with another monomer to form a dimer. The dimers can be homodimeric, in which each constituent monomer is identical, or heterodimeric, in which case each constituent monomer is different. As used herein, the reference to a "monomer" does not preclude the presence of a second polypeptide chain that does not comprise a p35, p40 or multimerization moiety, for example a light chain of a Fab domain. Thus, a "dimer" of two monomers may include more than two polypeptide chains, e.g., may include three or four polypeptide chains.

Monomeric p40 or Monomeric p40 polypeptide chain: The terms "monomeric p40", "monomeric p40 polypeptide chain" and the like refer to a polypeptide chain comprising an IL12-p40 moiety without a dimerization moiety, e.g., without an Fc domain. Monomeric p40 polypeptide chains can optionally include a p40 masking moiety (e.g., a p40-binding portion of IL12Rβ1 or an anti-p40 antibody-based masking moiety). Such polypeptide chains are sometimes referred to herein as a "masked monomeric p40".

Monovalent: The term "monovalent" as used herein in reference to IL12 and/or a targeting moiety in an IL12 receptor agonist means an IL12 receptor agonist that has only a single IL12 heterodimer (i.e., one p40×p35 heterodimer) and/or targeting moiety, respectively.

Operably linked: The term "operably linked" as used herein refers to a functional relationship between two or more regions of a polypeptide chain in which the two or more regions are linked so as to produce a functional polypeptide, or two or more nucleic acid sequences, e.g., to produce an in-frame fusion of two polypeptide components or to link a regulatory sequence to a coding sequence.

Peptide-MHC complex, pMHC complex, peptide-in-groove: A "peptide-MHC complex," "pMHC complex," and "peptide-in-groove" refer to (i) an MHC domain (e.g., a human MHC molecule or portion thereof (e.g., the peptide-binding groove thereof and e.g., the extracellular portion thereof), (ii) an antigenic peptide, and, optionally, (iii) a β2 microglobulin domain (e.g., a human β2 microglobulin or portion thereof), where the MHC domain, the antigenic peptide and optional β2 microglobulin domain are complexed in such a manner that permits specific binding to a T-cell receptor. In some embodiments, a pMHC complex comprises at least the extracellular domains of a human HLA class I/human β2 microglobulin molecule and/or a human HLA class II molecule.

Single Chain Fv or scFv: The term "single chain Fv" or "scFv" as used herein refers to a polypeptide chain comprising the VH and VL domains of antibody, where these domains are present in a single polypeptide chain.

Specifically (or selectively) binds: The term "specifically (or selectively) binds" as used herein means that a targeting moiety, e.g., an antibody, or antigen binding domain ("ABD") thereof, forms a complex with a target molecule that is relatively stable under physiologic conditions. Specific binding can be characterized by a $K_D$ of about $5\times10^{-2}$M or less (e.g., less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, or less than $10^{-10}$M). Methods for determining the binding affinity of an antibody or an antibody fragment, e.g., an IL12 receptor agonist or a component targeting moiety, to a target molecule are well known in the art and include, for example, equilibrium dialysis, surface plasmon resonance (e.g., Biacore assays), fluorescent-activated cell sorting (FACS) binding assays and the like. An IL12 receptor agonist of the disclosure comprising a targeting moiety or an ABD thereof that specifically binds a target molecule from one species can, however, have cross-reactivity to the target molecule from one or more other species.

Subject: The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

Target Molecule: The term "target molecule" as used herein refers to any biological molecule (e.g., protein, carbohydrate, lipid or combination thereof) expressed on a cell surface or in the extracellular matrix that can be specifically bound by a targeting moiety in an IL12 receptor agonist of the disclosure.

Targeting Moiety: The term "targeting moiety" as used herein refers to any molecule or binding portion (e.g., an immunoglobulin or an antigen binding fragment) thereof that can bind to a cell surface or extracellular matrix molecule at a site to which an IL12 receptor agonist of the disclosure is to be localized, for example on tumor cells or on lymphocytes in the tumor microenvironment. The targeting moiety can also have a functional activity in addition to localizing an IL12 receptor agonist to a particular site. For example, a targeting moiety that is an anti-PD1 antibody or an antigen binding portion thereof can also exhibit anti-tumor activity or enhance the anti-tumor activity by an IL12 mutein by inhibiting PD1 signaling.

Treat, Treatment, Treating: As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more IL12 receptor agonists of the disclosure. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

Tumor: The term "tumor" is used interchangeably with the term "cancer" herein, e.g., both terms encompass solid and liquid, e.g., diffuse or circulating, tumors. As used herein, the term "cancer" or "tumor" includes premalignant, as well as malignant cancers and tumors.

Tumor-Associated Antigen: The term "tumor-associated antigen" or "TAA" refers to a molecule (typically a protein, carbohydrate, lipid or some combination thereof) that is expressed on the surface of a cancer cell, either entirely or as a fragment (e.g., MHC/peptide), and which is useful for the preferential targeting of a pharmacological agent to the cancer cell. In some embodiments, a TAA is a marker expressed by both normal cells and cancer cells, e.g., a lineage marker, e.g., CD19 on B cells. In some embodiments, a TAA is a cell surface molecule that is overexpressed in a cancer cell in comparison to a normal cell, for instance, 1-fold over expression, 2-fold overexpression, 3-fold overexpression or more in comparison to a normal cell. In some embodiments, a TAA is a cell surface molecule that is inappropriately synthesized in the cancer cell, for instance, a molecule that contains deletions, additions or mutations in comparison to the molecule expressed on a normal cell. In some embodiments, a TAA will be expressed exclusively on the cell surface of a cancer cell, entirely or as a fragment (e.g., MHC/peptide), and not synthesized or expressed on the surface of a normal cell. Accordingly, the term "TAA" encompasses antigens that are specific to cancer cells, sometimes known in the art as tumor-specific antigens ("TSAs").

Universal Light Chain: The term "universal light chain" as used herein in the context of a targeting moiety refers to a light chain polypeptide capable of pairing with the heavy chain region of the targeting moiety and also capable of pairing with other heavy chain regions. Universal light chains are also known as "common light chains."

VH: The term "VH" refers to the variable region of an immunoglobulin heavy chain of an antibody, including the heavy chain of an scFv or a Fab.

VL: The term "VL" refers to the variable region of an immunoglobulin light chain, including the light chain of an scFv or a Fab.

6.2. IL12 Receptor Agonists

The present disclosure provides IL12 receptor agonists comprising or consisting of an IL12 mutein. The IL12 muteins comprise a p35 moiety and a p40 moiety and differ from wild type IL12 by (a) primary amino acid sequence (e.g., an amino acid insertion, deletion, or substitutions as compared to p35 and/or p40 or any combination of the foregoing) and/or (b) association with additional domains not naturally associated with IL12, for example (i) a multimerization moiety (e.g., dimerization domain such as an Fc domain) domain and/or (ii) a targeting moiety and/or (iii) a stabilization moiety and/or (iv) an IL12β receptor (IL12βR1 and/or IL12βR2) sequence.

The IL12 receptor agonists of the disclosure and/or the IL12 muteins in the IL12 receptor agonists of the disclosure can have amino acid modifications that result in a reduction of binding affinity of to an IL12 receptor complex (e.g., a receptor complex comprising IL12Rβ1 and IL12Rβ2) as compared to wild type IL12. Overall, the IL12 receptor agonists of the disclosure and/or the IL12 muteins in the IL12 receptor agonists of the disclosure can have normal or attenuated binding (i.e., reduced affinity) to the IL12 receptor complex (e.g., by up to 10-fold, by up to 50-fold, by up to 100-fold, by up to 200 fold, by up to 500-fold, by up to 1,000-fold, by up to 2,000-fold or by up to 5,000-fold). In some embodiments, binding is attenuated by 100- to 5,000-fold, by 200- to 2,000-fold, by 500- to 2,000-fold or by 500- to 1,000-fold. Binding can be attenuated through one or more amino acid substitutions in the p35 and/or p40 sequences and/or the inclusion of one or more IL12Rβ moieties in the IL12 receptor agonist.

In certain embodiments, the IL12 receptor agonists and IL12 muteins of the disclosure have one or more amino acid substitutions in an IL12 p40 moiety, an IL12 p35 moiety, or both IL12 p40 and p35 moieties that reduce binding to the IL12 receptor complex, for example as disclosed in Section 6.3 and subsections thereof. For example, in some embodiments, an IL12 mutein can have up to 100-fold to 1,000-fold attenuated binding to human IL12 receptor complex as compared to wild-type human IL12. Exemplary amino acid substitutions are disclosed in Sections 6.3.1 and 6.3.2 and include substitutions at W37 of full-length human or murine p40 that reduce binding to IL12Rβ1, e.g., the substitution W37A.

Certain aspects of the disclosure relate to IL12 receptor agonists comprising: (a) a first polypeptide chain comprising, in an N- to C-terminal orientation, a first targeting moiety or targeting moiety component, a first Fc domain and a p35 moiety; (b) a second polypeptide chain comprising in an N- to C-terminal orientation, a second targeting moiety or targeting moiety component and a second Fc domain; (c) a p40 moiety between the first Fc domain and the p35 moiety or in the form of a monomeric p40; (d) an IL12Rβ moiety or an IL12 antibody fragment configured to mask the p35 moiety or the p40 moiety. The p40 moiety and/or p35 moiety may have an attenuating substitution, e.g., as described in Section 6.3. In some embodiments, the p40 moiety has an amino acid substitution at the position corresponding to amino acid W37 of full length human p40 or amino acid W37 of full length murine p40, e.g., the substitution W37A.

Further aspects of the disclosure relate to IL12 receptor agonists comprising an IL12 mutein, wherein the IL12 receptor agonist has at least 500-fold attenuation as compared to wild-type IL12, wherein the IL12 receptor agonist comprises: (a) a first polypeptide chain and a second polypeptide chain dimerized through a first Fc domain and a second Fc domain; (b) an optional first targeting moiety or targeting moiety component on the first polypeptide chain and an optional second targeting moiety or targeting moiety component on the second polypeptide chain; (c) a p35 moiety and a p40 moiety; and (d) an IL12Rβ moiety or an IL12 antibody fragment configured to mask the p35 moiety or the p40 moiety.

Yet further aspects of the disclosure relate to IL12 receptor agonists comprising on a first polypeptide chain and a second polypeptide chain dimerized through a first Fc domain and a second Fc domain: (a) an optional first targeting moiety and an optional second targeting moiety; (b) an IL12 mutein comprising a p35 moiety and a p40 moiety, wherein: (i) the p35 moiety comprises an attenuating amino acid substitution, optionally wherein the attenuating amino acid substitution is at (A) amino acid Y189 of full length human p35 or amino acid Y185 of full length murine p35, wherein the substitution is optionally A, V, R or E; (B) amino acid I193 of full length human p35 or amino acid M189 of full length murine p35, wherein the substitution is optionally A, V, or E; (C) amino acid R211 of full length human p35 or amino acid R207 of full length murine p35, wherein the substitution is optionally A or K; or (D) any combination of (A)-(C); and/or (ii) the p40 moiety comprises an attenuating amino acid substitution optionally wherein the attenuating amino acid substitution is at (A) amino acid K28 of full length human p40 or amino acid K28 of full length murine p40, wherein the substitution is optionally A; (B) amino acid W37 of full length human p40 or amino acid W37 of full length murine p40, wherein the substitution is optionally A; (C) amino acid D115 of full length human p40 or amino acid E115 of full length murine p40, wherein the substitution is optionally A; (D) amino acid K118 of full length human p40 or amino acid K118 of full length murine p40, wherein the substitution is optionally A; (E) amino acid K126 of full length human p40 or amino acid K126 of full length murine p40, wherein the substitution is optionally A; (F) amino acid Y268 of full length human p40 or amino acid Y265 of full length murine p40, wherein the substitution is optionally V or F; (G) amino acid Y314 of full length human p40 or amino acid Y318 of full length murine p40, wherein the substitution is optionally F; or (H) any combination of (A) to (G); and (c) an IL12Rβ moiety or an IL12 antibody fragment configured to mask the p35 moiety or the p40 moiety.

Binding affinity of p40 to IL12Rβ1 and of p35 to IL12Rβ2 can be assayed by surface plasmon resonance (SPR) techniques (analyzed on a Biacore instrument) (Liljeblad et al., 2000, Glyco J 17:323-329).

In some embodiments, the IL12 receptor agonists and IL12 muteins of the disclosure may comprise IL12 receptor sequences, for example IL12Rβ1 and/or IL12Rβ2 sequences, as described in Section 6.4 and subsections thereof, which is believed to attenuate side effects of IL12 receptor agonist treatment.

An IL12 receptor agonist or IL12 mutein can be composed of one or more polypeptides. In some embodiments, the IL12 receptor agonist is composed of a plurality of (e.g., two) monomers comprising p40 and/or p35 moieties and in some embodiments also comprising multimerization moieties.

An IL12 receptor agonist or IL12 mutein may further include and/or one or more targeting moieties and/or one or more stabilization moieties and/or one or more IL12βR moieties. Exemplary multimerization moieties are described in Section 6.6 and include Fc domains that confer homodimerization or heterodimerization capability to the IL12 receptor agonist. Free IL12 has poor pharmacokinetics (a serum half-life of about 5 h to about 20 h) and, without being bound by theory, it is believed that the inclusion of a multimerization domain, such as an Fc domain, improves serum stability and the pharmacokinetic profile of an IL12 receptor agonist. Thus, the Fc domain can be a dual-purpose domain, conferring stabilization properties of a stabilization moiety as described in Section 6.7.

Exemplary targeting moieties are described in Section 6.4 and include an antigen binding domain (e.g., a scFv or Fab) that binds to a tumor associated antigen, binds to a tumor microenvironment antigen, or binds to tumor lymphocytes, as well as a peptide-MHC complex that recognizes tumor lymphocytes.

In some embodiments, the IL12 receptor agonist includes one or more masking moieties.

In some embodiments, the IL12 receptor agonist comprises one or more IL12Rβ-based masking moieties, e.g., an IL12Rβ1 moiety, an IL12Rβ2 moiety, or both an IL12Rβ1 moiety and an IL12Rβ1 moiety. Exemplary IL12Rβ1 moieties are described in Section 6.4.1. Exemplary IL12Rβ2 moieties are described in Section 6.4.2.

In other embodiments, the IL12 receptor agonist comprises one or more antibody-based masking moieties, e.g., an anti-p35 antibody-based masking moiety or an anti-p40 antibody based masking moiety. In some embodiments, the antibody-based masking moiety is an Fv (e.g., an scFv). In other embodiments, the antibody-based masking moiety is a Fab.

In some embodiments, the IL12 agonist of the disclosure is composed of two monomers, optionally in association with one or more additional polypeptide chains (e.g., in association with a polypeptide chain comprising the light chain of a Fab targeting moiety). The monomers can be identical, thereby forming a homodimer, or different, thereby forming a heterodimer. The multimerization moieties of each monomer of an IL12 receptor agonist can be configured to dimerize together. Exemplary multimerization moieties are described in Section 6.6 and include Fc domains.

It has been discovered that incorporating a p40 moiety and p35 moiety C-terminal to an Fc domain configured with the p40 moiety N-terminal to the p35 moiety improves expression yield and reduced aggregation, resulting in higher quality preparations of the IL12 receptor agonists of the disclosure. When the p35 moiety is immediately C-terminal to an Fc domain (with or without a linker separating the p35 moiety and the Fc domain), expression and aggregation can be improved by providing the p40 moiety as a monomeric p40 moiety, on a separate polypeptide chain lacking an Fc domain. Accordingly, in some embodiments, the IL12 agonist of the disclosure further comprises a monomeric p40 polypeptide chain associated with a p35 moiety in one of the two monomers.

In some embodiments, an IL12 mutein or IL12 agonist can include one or more linker sequences connecting the various components of its one or more polypeptide chains, for example (1) the p35 moiety and the p40 moiety of IL12 when present on the same polypeptide chain, (2) a p35 moiety and a multimerization domain (e.g., an Fc domain), (3) a p40 moiety and a multimerization domain (e.g., an Fc domain), (4) a p35 moiety and a targeting moiety or component thereof (e.g., an scFv or a heavy chain of a Fab), (5) a p40 moiety and a targeting moiety or component thereof (e.g., an scFv or a heavy chain of a Fab), (6) a multimerization domain (e.g. an Fc domain) and a targeting moiety or component thereof (e.g., an scFv or a heavy chain of a Fab), (7) a p35 moiety, a p40 moiety, a multimerization domain or a targeting moiety or component thereof and an IL12βR moiety, e.g., an IL12βR1 or an IL12βR2 moiety, or (8) any combination of the foregoing. Exemplary linkers are described in Section 6.8.

Most IL12 muteins and IL12 agonists are multimeric, e.g., dimeric, by virtue of association of a p35 and a p40 moiety present on different polypeptide chains and/or by virtue of association of multimerization moieties configured to associate with one another (e.g., Fc domains). The present disclosure generally refers to polypeptide chains containing a p35 moiety, a p40 moiety and/or a multimerization moiety (e.g., a first Fc domain) that is capable of associating with another polypeptide chain containing a p40 moiety, a p35 moiety and/or a corresponding multimerization moiety (e.g., a second Fc domain), respectively, as "monomers" or "IL12 monomers". Below are some illustrative examples of IL12 monomers of the disclosure, described in an N-to-C terminal orientation. Individual elements of each monomer are described in detail herein, for example in the subsections that follow and the numbered embodiments.

(1) Exemplary Monomer 1: IL12 p35 moiety-optional linker-multimerization moiety (see, e.g., FIG. 2B, left monomer, FIG. 2C, left monomer, and FIG. 2N (both monomers)).

(2) Exemplary Monomer 2: IL12 p40 moiety-optional linker-multimerization moiety (see, e.g., FIG. 2B, right monomer and FIG. 2C, right monomer).

(3) Exemplary Monomer 3: Multimerization moiety-optional linker-IL12 p35 moiety (see, e.g., FIG. 2D (left monomer), FIG. 2E (left monomer), FIG. 2O (both monomers), FIG. 2P (left monomer), FIG. 4M (left monomer), FIG. 4U (left monomer), FIG. 4V (left monomer), and FIG. 4W (left monomer)).

(4) Exemplary Monomer 4: Multimerization moiety-optional linker-IL12 p40 moiety (see, e.g., FIG. 2D (right monomer), FIG. 2E (right monomer), and FIG. 4L (right monomer)).

(5) Exemplary Monomer 5: IL12 p40 moiety-optional linker-IL12 p35 moiety-optional linker-multimerization moiety (see, e.g., FIG. 2H (both monomers), FIG. 2I (both monomers), FIG. 3B, FIG. 3D, FIG. 3G, FIG. 5E (right monomer), FIG. 5P (left monomer), and FIG. 5Q (left monomer)).

(6) Exemplary Monomer 6: IL12 p35 moiety-optional linker-IL12 p40 moiety-optional linker-multimerization moiety (see, e.g., FIG. 2J, both monomers).

Figure 2A:
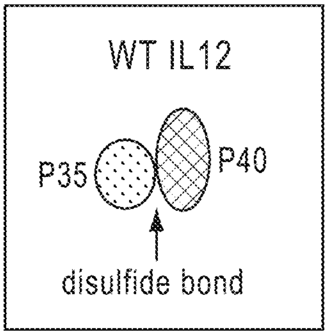
Figure 2B:
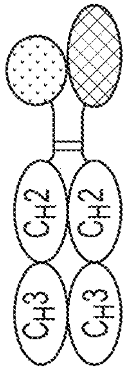
Figure 2C:
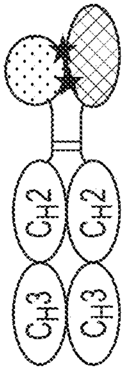
Figure 2D:
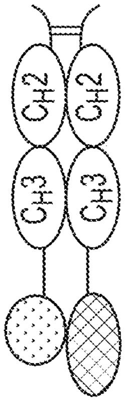
Figure 2E:
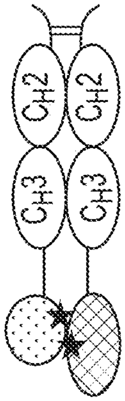
Figure 2F:
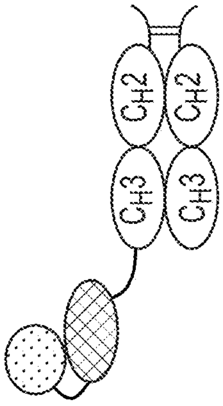
Figure 2G:
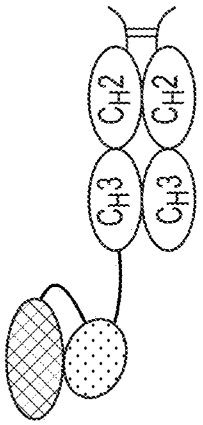
Figure 2H:
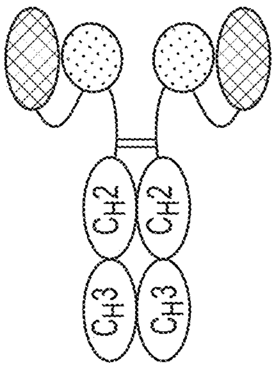
Figure 2I:
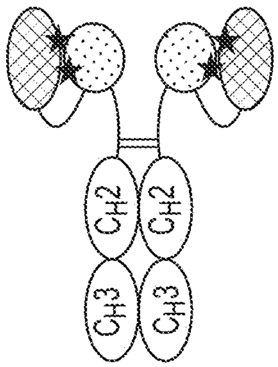
Figure 2J:
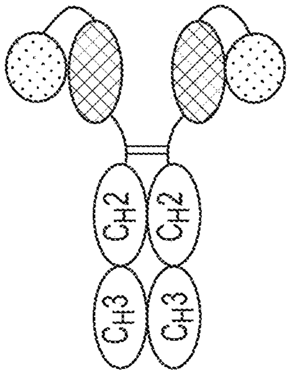
Figure 2K:
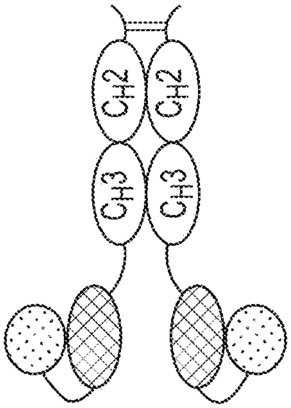
Figure 2L:
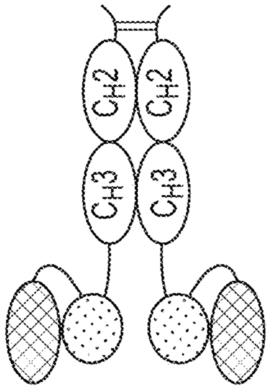
Figure 3A:
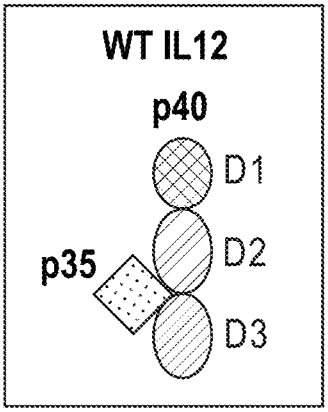
Figure 3B:
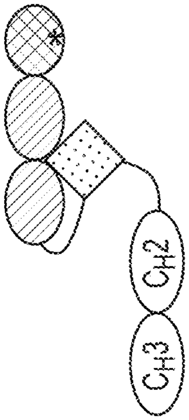
Figure 3C:
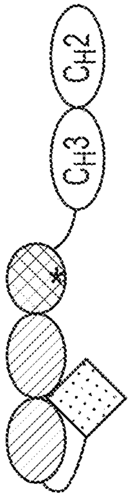
Figure 3D:
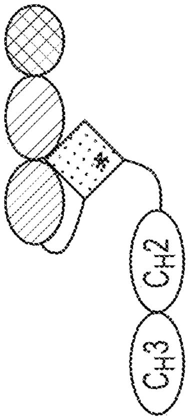
Figure 3E:
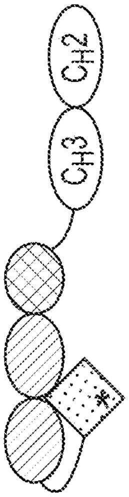
Figure 3F:
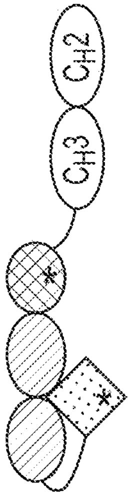
Figure 3G:
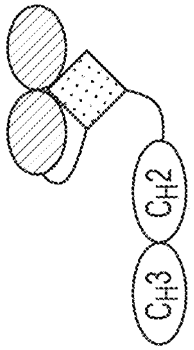
Figure 3H:
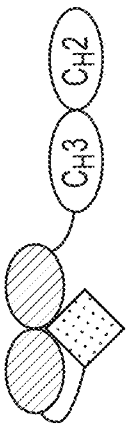
Figure 3I:
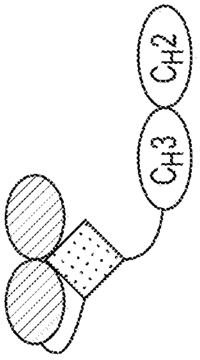

(7) Exemplary Monomer 7: Multimerization moiety-optional linker-IL12 p35 moiety-optional linker-IL12 p40 moiety (see, e.g., FIG. 2G (left monomer), FIG. 2L (both monomers), FIG. 3I).

(8) Exemplary Monomer 8: Multimerization moiety-optional linker-IL12 p40 moiety-optional linker-IL12 p35 moiety (see, e.g., FIG. 2F (left monomer), FIG. 2K (both monomers), FIG. 2M (both monomers), FIG. 3C, FIG. 3E, FIG. 3F, FIG. 3H, FIG. 4F (left monomer), FIG. 4J (left monomer), FIG. 4K (left monomer), FIG. 4S (left monomer), FIG. 39A (left monomer), and FIG. 39B (left monomer)).

(9) Exemplary Monomer 9: Multimerization moiety-optional linker-IL12Rβ moiety (e.g., an IL12Rβ1 moiety or IL12Rβ2 moiety)-optional linker-IL12 p40 moiety-optional linker-IL12 p35 moiety (see, e.g., FIG. 4C (both monomers), FIG. 4E (both monomers), FIG. 4I (left monomer), FIG. 4N (left monomer), and FIG. 4T (left monomer)). In some embodiments, the IL12Rβ moiety is an IL12Rβ1 moiety. In other embodiments, the IL12Rβ moiety is an IL12Rβ2 moiety.

(10) Exemplary Monomer 10: Multimerization moiety-optional linker-IL12Rβ moiety (e.g., an IL12Rβ1 moiety or IL12Rβ2 moiety)-optional linker-IL12 p35 moiety-optional linker-IL12 p40 moiety. In some embodiments, the IL12Rβ moiety is an IL12Rβ1 moiety. In other embodiments, the IL12Rβ moiety is an IL12Rβ2 moiety.

(11) Exemplary Monomer 11: Multimerization moiety-optional linker-IL12 p40 moiety-optional linker-IL12 p35 moiety-optional linker-IL12Rβ moiety (e.g., an IL12Rβ1 moiety or IL12Rβ2 moiety) (see, e.g., FIG. 4B (both monomers), FIG. 4D (both monomers), FIG. 4G (left monomer), and FIG. 4H (left monomer)). In some embodiments, the IL12Rβ moiety is an IL12Rβ1 moiety. In other embodiments, the IL12Rβ moiety is an IL12Rβ2 moiety.

(12) Exemplary Monomer 12: Multimerization moiety-optional linker-IL12 p35 moiety-optional linker-IL12 p40 moiety-optional linker-IL12Rβ moiety (e.g., an IL12Rβ1 moiety or IL12Rβ2 moiety).

(13) Exemplary Monomer 13: IL12 p40 moiety-optional linker-IL12 p35 moiety-optional linker-IL12Rβ moiety (e.g., an IL12Rβ1 moiety or IL12Rβ2 moiety)-optional linker-multimerization moiety. In some embodiments, the IL12Rβ moiety is an IL12Rβ1 moiety. In other embodiments, the IL12Rβ moiety is an IL12Rβ2 moiety.

(14) Exemplary Monomer 14: IL12 p35 moiety-optional linker-IL12 p40 moiety-optional linker-IL12Rβ moiety (e.g., an IL12Rβ1 moiety or IL12Rβ2 moiety)-optional linker-multimerization moiety. In some embodiments, the IL12Rβ moiety is an IL12Rβ1 moiety. In other embodiments, the IL12Rβ moiety is an IL12Rβ2 moiety.

(15) Exemplary Monomer 15: IL12Rβ moiety (e.g., an IL12Rβ1 moiety or IL12Rβ2 moiety)-optional linker-IL12 p40 moiety-optional linker-IL12 p35 moiety-optional linker-multimerization moiety (see, e.g., FIG. 5O (left monomer)). In some embodiments, the IL12Rβ moiety is an IL12Rβ1 moiety. In other embodiments, the IL12Rβ moiety is an IL12Rβ2 moiety.

(16) Exemplary Monomer 16: IL12Rβ moiety (e.g., an IL12Rβ1 moiety or IL12Rβ2 moiety)-optional linker-IL12 p35 moiety-optional linker-IL12 p40 moiety-optional linker-multimerization moiety. In some embodiments, the IL12Rβ moiety is an IL12Rβ1 moiety. In other embodiments, the IL12Rβ moiety is an IL12Rβ2 moiety.

(17) Exemplary Monomer 17: IL12 p35 moiety-optional linker-multimerization moiety-optional linker-targeting moiety (see, e.g., FIG. 5G, left monomer).

(18) Exemplary Monomer 18: IL12 p40 moiety-optional linker-multimerization moiety-optional linker-targeting moiety (see, e.g., FIG. 5G, right monomer).

(19) Exemplary Monomer 19: Targeting moiety-optional linker-multimerization moiety-optional linker-IL12 p35 moiety (see, e.g., FIG. 5B (left monomer), FIG. 5V (left monomer), FIG. 5W (left monomer), and FIG. 5X (left monomer)).

(20) Exemplary Monomer 20: Targeting moiety-optional linker-multimerization moiety-optional linker-IL12 p40 moiety (see, e.g., FIG. 5B, right monomer).

(21) Exemplary Monomer 21: Targeting moiety-optional linker-IL12 p35 moiety-optional linker-multimerization moiety.

(22) Exemplary Monomer 22: Targeting moiety-optional linker-IL12 p40 moiety-optional linker-multimerization moiety.

(23) Exemplary Monomer 23: Multimerization moiety-optional linker-IL12 p35 moiety-optional linker-targeting moiety.

(24) Exemplary Monomer 24: Multimerization moiety-optional linker-IL12 p40 moiety-optional linker-targeting moiety.

(25) Exemplary Monomer 25: IL12 p40 moiety-optional linker-IL12 p35 moiety-optional linker-multimerization moiety-optional linker-targeting moiety (see, e.g., FIG. 5F, both monomers).

(26) Exemplary Monomer 26: IL12 p35 moiety-optional linker-IL12 p40 moiety-optional linker-multimerization moiety-optional linker-targeting moiety.

(27) Exemplary Monomer 27: Targeting moiety-optional linker-multimerization moiety-optional linker-IL12 p35 moiety-optional linker-IL12 p40 moiety.

(28) Exemplary Monomer 28: Targeting moiety-optional linker-multimerization moiety-optional linker-IL12 p40 moiety-optional linker-IL12 p35 moiety (see, e.g., FIG. 5C (left monomer), FIG. 5D (both monomers), FIG. 5I (left monomer), FIG. 5J (left monomer), FIG. 5M (left monomer), FIG. 5N (left monomer), FIG. 39C (left monomer) and FIG. 39D (left monomer)).

(29) Exemplary Monomer 29: Targeting moiety-optional linker-IL12 p40 moiety-optional linker-IL12 p35 moiety-optional linker-multimerization moiety.

(30) Exemplary Monomer 30: Targeting moiety-optional linker-IL12 p35 moiety-optional linker-IL12 p40 moiety-optional linker-multimerization moiety.

(31) Exemplary Monomer 31: Multimerization moiety-optional linker-IL12 p35 moiety-optional linker-IL12 p40 moiety-optional linker-targeting moiety.

(32) Exemplary Monomer 32: Multimerization moiety-optional linker-IL12 p40 moiety-optional linker-IL12 p35 moiety-optional linker-targeting moiety.

(33) Exemplary Monomer 33: Targeting moiety-optional linker-multimerization moiety (see, e.g., FIG. 5C (right monomer), FIG. 5E (left monomer), FIG. 5H (right monomer), FIG. 5L (right monomer), FIG. 5O (right monomer), FIG. 5P (right monomer), FIG. 5Q (right monomer), FIG. 5R (right monomer) and FIG. 5V (right monomer)).

(34) Exemplary Monomer 34: Multimerization moiety-optional linker-targeting moiety.

(35) Exemplary Monomer 35: Targeting moiety-optional linker-multimerization moiety-optional linker-IL12Rβ moiety (e.g., an IL12Rβ1 moiety or IL12Rβ2 moiety)-optional linker-IL12 p40 moiety-optional linker-IL12 p35 moiety (see, e.g., FIG. 5H (left monomer), FIG. 5K (left monomer), and FIG. 5R (left monomer)). In some embodiments, the IL12Rβ moiety is an IL12Rβ1 moiety. In other embodiments, the IL12Rβ moiety is an IL12Rβ2 moiety.

(36) Exemplary Monomer 36: Targeting moiety-optional linker-multimerization moiety-optional linker-IL12Rβ moiety (e.g., an IL12Rβ1 moiety or IL12Rβ2 moiety)-optional linker-IL12 p35 moiety-optional linker-IL12 p40 moiety. In some embodiments, the IL12Rβ moiety is an IL12Rβ1 moiety. In other embodiments, the IL12Rβ moiety is an IL12Rβ2 moiety.

(37) Exemplary Monomer 37: Targeting moiety-optional linker-multimerization moiety-optional linker-IL12 p40 moiety-optional linker-IL12 p35 moiety-optional linker-IL12Rβ moiety (e.g., an IL12Rβ1 moiety or IL12Rβ2 moiety). In some embodiments, the IL12Rβ moiety is an IL12Rβ1 moiety. In other embodiments, the IL12Rβ moiety is an IL12Rβ2 moiety.

(38) Exemplary Monomer 38: Targeting moiety-optional linker-multimerization moiety-optional linker-IL12 p35 moiety-optional linker-IL12 p40 moiety-optional linker-IL12Rβ moiety (e.g., an IL12Rβ1 moiety or IL12Rβ2 moiety). In some embodiments, the IL12Rβ moiety is an IL12Rβ1 moiety. In other embodiments, the IL12Rβ moiety is an IL12Rβ2 moiety.

(39) Exemplary Monomer 39: Multimerization moiety-optional linker-IL12Rβ moiety (e.g., an IL12Rβ1 moiety or IL12Rβ2 moiety)-optional linker-IL12 p40 moiety-optional linker-IL12 p35 moiety-optional linker-targeting moiety. In some embodiments, the IL12Rβ moiety is an IL12Rβ1 moiety. In other embodiments, the IL12Rβ moiety is an IL12Rβ2 moiety.

(40) Exemplary Monomer 40: Multimerization moiety-optional linker-IL12Rβ moiety (e.g., an IL12Rβ1 moiety or IL12Rβ2 moiety)-optional linker-IL12 p35 moiety-optional linker-IL12 p40 moiety-optional linker-targeting moiety. In some embodiments, the IL12Rβ moiety is an IL12Rβ1 moiety. In other embodiments, the IL12Rβ moiety is an IL12Rβ2 moiety.

(41) Exemplary Monomer 41: Multimerization moiety-optional linker-IL12 p40 moiety-optional linker-IL12 p35 moiety-optional linker-IL12Rβ moiety (e.g., an IL12Rβ1 moiety or IL12Rβ2 moiety)-optional linker-targeting moiety. In some embodiments, the IL12Rβ moiety is an IL12Rβ1 moiety. In other embodiments, the IL12Rβ moiety is an IL12Rβ2 moiety.

(42) Exemplary Monomer 42: Multimerization moiety-optional linker-IL12 p35 moiety-optional linker-IL12 p40 moiety-optional linker-IL12Rβ moiety (e.g., an IL12Rβ1 moiety or IL12Rβ2 moiety)-optional linker-targeting moiety. In some embodiments, the IL12Rβ moiety is an IL12Rβ1 moiety. In other embodiments, the IL12Rβ moiety is an IL12Rβ2 moiety.

(43) Exemplary Monomer 43: IL12 p40 moiety-optional linker-IL12 p35 moiety-optional linker-IL12Rβ moiety (e.g., an IL12Rβ1 moiety or IL12Rβ2 moiety)-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(44) Exemplary Monomer 44: IL12 p35 moiety-optional linker-IL12 p40 moiety-optional linker-IL12Rβ moiety (e.g., an IL12Rβ1 moiety or IL12Rβ2 moiety)-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(45) Exemplary Monomer 45: IL12Rβ moiety (e.g., an IL12Rβ1 moiety or IL12Rβ2 moiety)-optional linker-IL12 p40 moiety-optional linker-IL12 p35 moiety-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(46) Exemplary Monomer 46: IL12Rβ moiety (e.g., an IL12Rβ1 moiety or IL12Rβ2 moiety)-optional linker-IL12 p35 moiety-optional linker-IL12 p40 moiety-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(47) Exemplary Monomer 47: Targeting moiety-optional linker-IL12 p40 moiety-optional linker-IL12 p35 moiety-optional linker-IL12Rβ moiety (e.g., an IL12Rβ1 moiety or IL12Rβ2 moiety)-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(48) Exemplary Monomer 48: Targeting moiety-optional linker-IL12 p35 moiety-optional linker-IL12 p40 moiety-optional linker-IL12Rβ moiety (e.g., an IL12Rβ1 moiety or IL12Rβ2 moiety)-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(49) Exemplary Monomer 49: Targeting moiety-optional linker-IL12Rβ moiety (e.g., an IL12Rβ1 moiety or IL12Rβ2 moiety)-optional linker-IL12 p40 moiety-optional linker-IL12 p35 moiety-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(50) Exemplary Monomer 50: Targeting moiety-optional linker-IL12Rβ moiety (e.g., an IL12Rβ1 moiety or IL12Rβ2 moiety)-optional linker-IL12 p35 moiety-optional linker-IL12 p40 moiety-optional linker-multimerization moiety-optional linker-targeting moiety. In some embodiments, the IL12Rβ moiety is an IL12Rβ1 moiety. In other embodiments, the IL12Rβ moiety is an IL12Rβ2 moiety.

(51) Exemplary Monomer 51: Multimerization moiety-optional linker-IL12Rβ moiety (e.g., an IL12Rβ1 moiety or IL12Rβ2 moiety) (see, e.g., FIG. 4J (right monomer), FIG. 4K (right monomer), FIG. 4N (right monomer), FIG. 4S (right monomer), FIG. 4V (right monomer), and FIG. 4W (right monomer)). In some embodiments, the IL12Rβ moiety is an IL12Rβ1 moiety. In other embodiments, the IL12Rβ moiety is an IL12Rβ2 moiety.

(52) Exemplary Monomer 52: IL12Rβ moiety (e.g., an IL12Rβ1 moiety or IL12Rβ2 moiety)-optional linker-multimerization moiety.

(53) Exemplary Monomer 53: Multimerization moiety-optional linker-IL12 p35 moiety-optional linker-IL12Rβ moiety (e.g., an IL12Rβ1 moiety or IL12Rβ2 moiety) (see e.g., FIG. 4L (left monomer)). In some embodiments, the IL12Rβ moiety is an IL12Rβ1 moiety. In other embodiments, the IL12Rβ moiety is an IL12Rβ2 moiety.

(54) Exemplary Monomer 54: Multimerization moiety-optional linker-IL12 p40 moiety-optional linker-IL12Rβ moiety (e.g., an IL12Rβ1 moiety or IL12Rβ2 moiety) (see e.g., FIG. 4M (right monomer)). In some embodiments, the IL12Rβ moiety is an IL12Rβ1 moiety. In other embodiments, the IL12Rβ moiety is an IL12Rβ2 moiety.

(55) Exemplary Monomer 55: Multimerization moiety-optional linker-IL12 p40 moiety-optional linker-IL12 p35 moiety-optional linker-antibody-based masking moiety (see e.g., FIG. 4O (left monomer) and FIG. 4P (left monomer)).

(56) Exemplary Monomer 56: Multimerization moiety-optional linker-antibody-based masking moiety (see e.g., FIG. 4Q (right monomer), FIG. 4R (right monomer), FIG. 39A (right monomer), and FIG. 39B (right monomer)).

(57) Exemplary Monomer 57: Targeting moiety-optional linker-multimerization moiety-optional linker-IL12Rβ moiety (e.g., an IL12Rβ1 moiety or IL12Rβ2 moiety) (see e.g., FIG. 5I (right monomer), FIG. 5J (right monomer), FIG. 5K (right monomer), FIG. 5S (right monomer), FIG. 5W (right monomer) and FIG. 5X (right monomer)). In some embodiments, the IL12Rβ moiety is an IL12Rβ1 moiety. In other embodiments, the IL12Rβ moiety is an IL12Rβ2 moiety.

(58) Exemplary Monomer 58: Targeting moiety-optional linker-multimerization moiety-optional linker-IL12 p40 moiety-optional linker-IL12 p35 moiety-optional linker-antibody-based masking moiety (see e.g., FIG. 5L (left monomer)).

(59) Exemplary Monomer 59: Targeting moiety-optional linker-multimerization moiety-optional linker-antibody-based masking moiety (see e.g., FIG. 5M (right monomer), FIG. 5N (right monomer), FIG. 39C (right monomer) and FIG. 39D (right monomer)).

(60) Exemplary Monomer 60: Multimerization moiety (see e.g., FIG. 2F (right monomer), FIG. 2G (right monomer), FIG. 4O (right monomer), FIG. 4P (right monomer), FIG. 4T (right monomer) and FIG. 4U (right monomer)).

(61) Exemplary Monomer 61: IL12Rβ moiety (e.g., an IL12Rβ1 moiety or IL12Rβ2 moiety)-optional linker-IL12p40 moiety-optional linker-IL12p35 moiety-optional linker-multimerization moiety. In some embodiments, the IL12Rβ moiety is an IL12Rβ1 moiety. In other embodiments, the IL12Rβ moiety is an IL12Rβ2 moiety.

(62) Exemplary Monomer 62: IL12Rβ moiety (e.g., an IL12Rβ1 moiety or IL12Rβ2 moiety)-optional linker-multimerization moiety. In some embodiments, the IL12Rβ moiety is an IL12Rβ1 moiety. In other embodiments, the IL12Rβ moiety is an IL12Rβ2 moiety.

(63) Exemplary Monomer 63: Targeting moiety-optional linker-multimerization moiety-optional linker-IL12 p40 moiety-optional linker-IL12 p35 moiety (see, e.g., FIG. 5S (left monomer)).

Figure 2M:
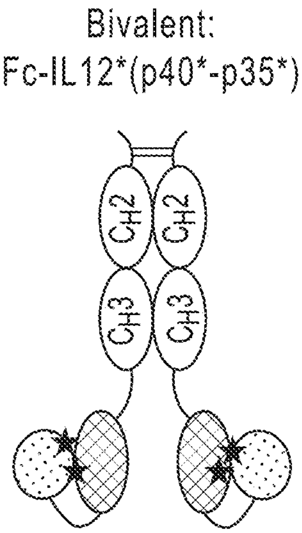
Figure 2N:
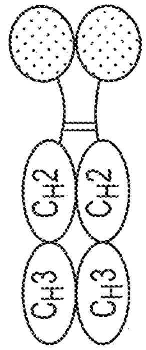

In some embodiments, the present disclosure provides an IL12 receptor agonist comprising two monomers according to Exemplary Monomer 1 (see, e.g., FIG. 2N).

In some embodiments, the present disclosure provides an IL12 receptor agonist comprising Exemplary Monomer 1 and Exemplary Monomer 2 (see, e.g., FIGS. 2B and 2C).

Figure 2O:
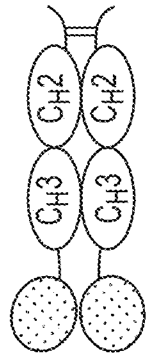

In some embodiments, the present disclosure provides an IL12 receptor agonist comprising two monomers according to Exemplary Monomer 3 (see, e.g., FIG. 2O).

In some embodiments, the present disclosure provides an IL12 receptor agonist comprising Exemplary Monomer 3 and Exemplary Monomer 4 (see, e.g., FIGS. 2D and 2E).

Figure 4A:
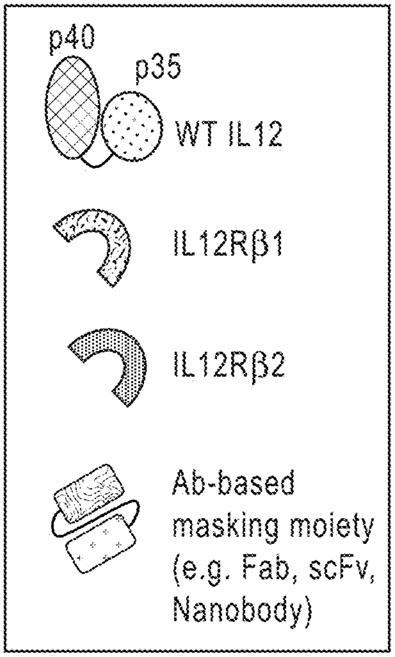
Figure 4B:
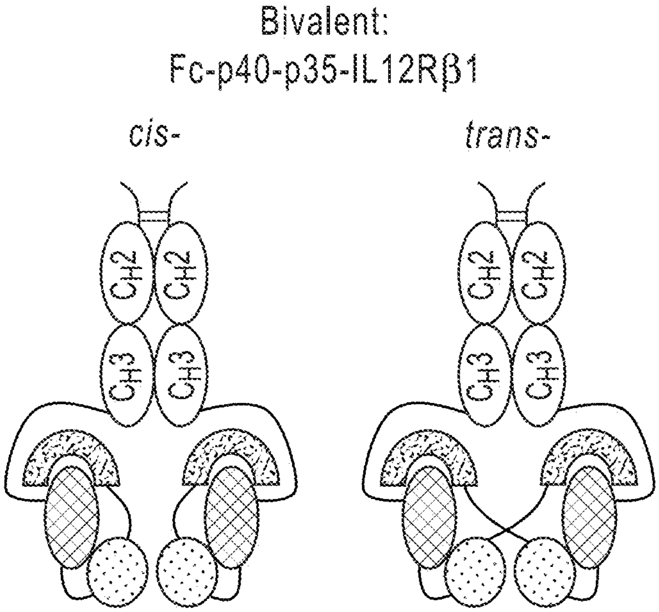
Figure 4C:
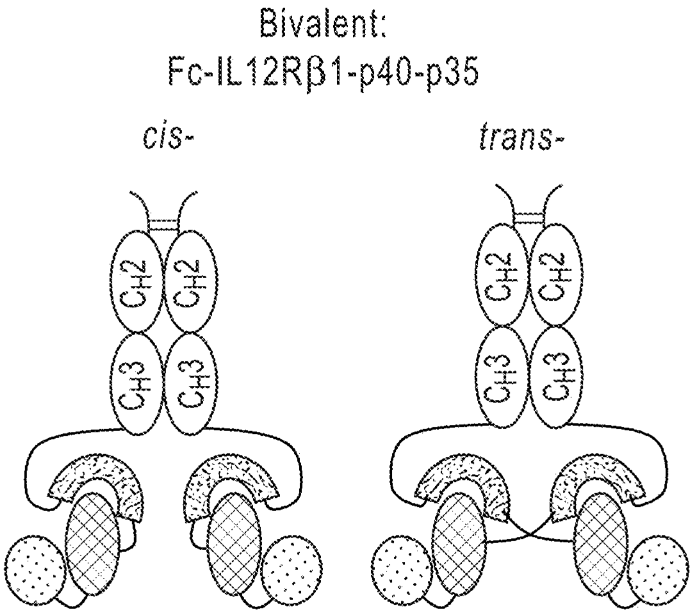
Figure 4D:
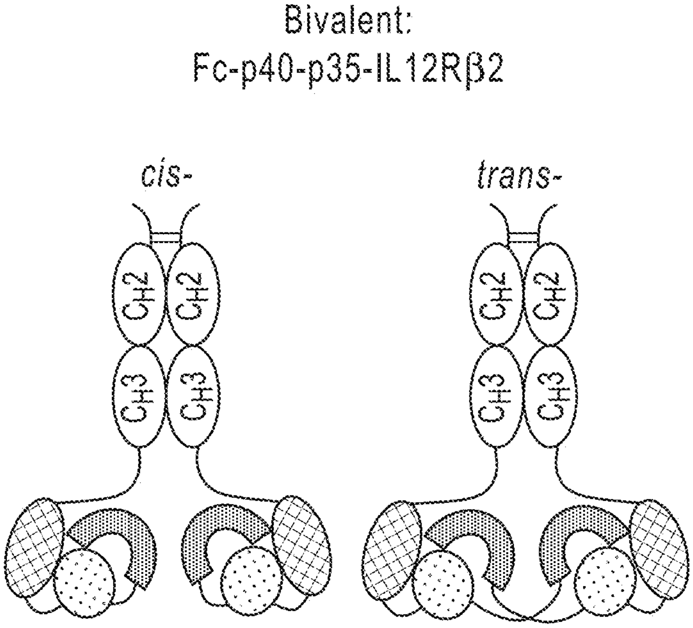
Figure 4E:
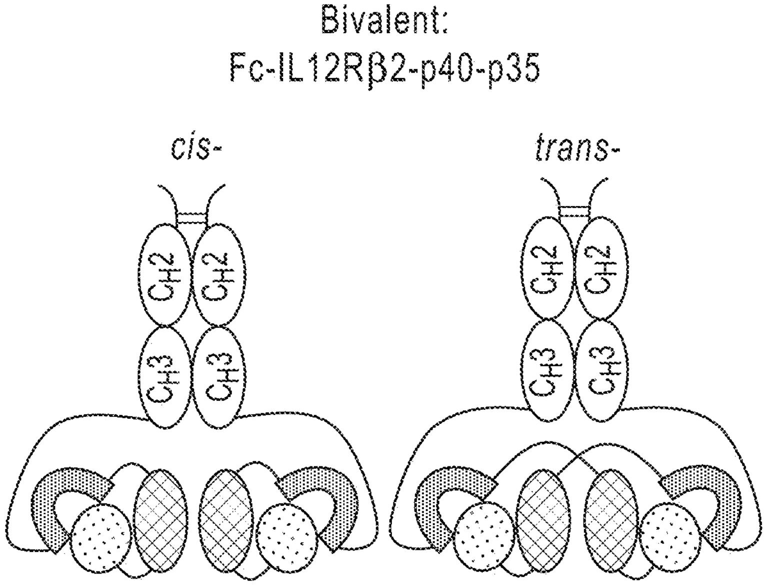
Figure 4F:
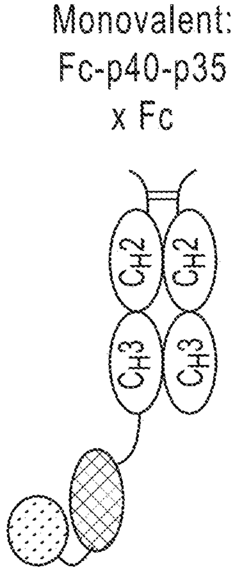
Figure 4G:
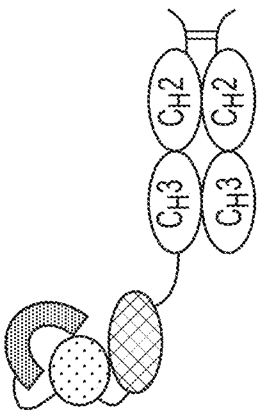
Figure 4H:
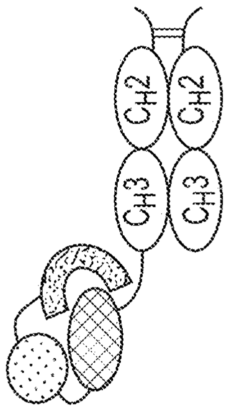
Figure 4I:
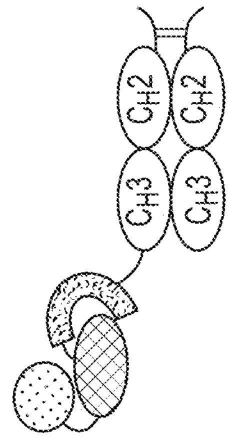
Figure 4J:
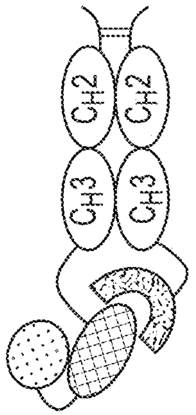
Figure 4K:
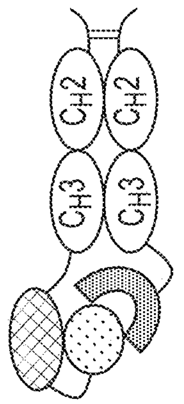
Figure 4L:
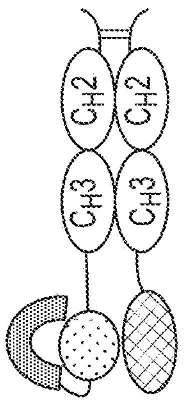
Figure 4M:
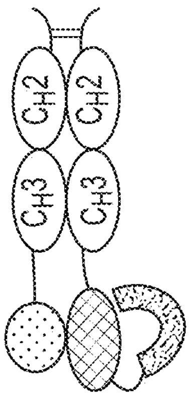
Figure 4N:
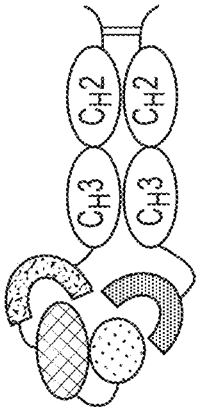
Figure 4O:
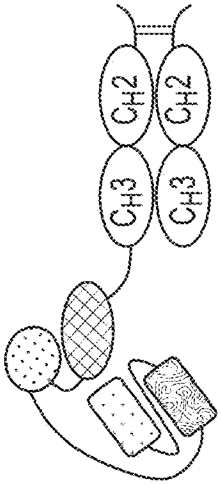
Figure 4P:
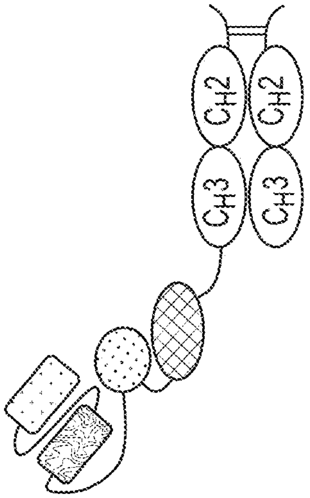
Figure 4Q:
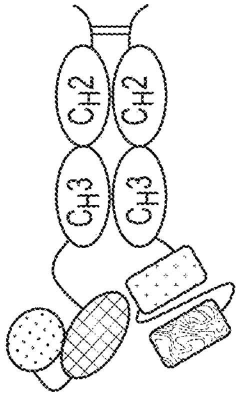
Figure 4R:
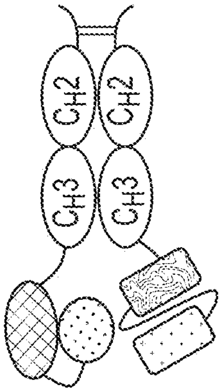
Figure 4S:
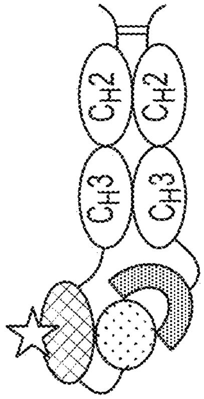
Figure 4T:
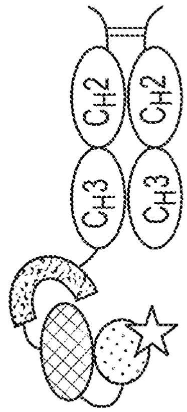
Figure 4U:
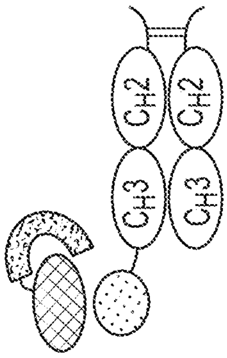
Figure 4V:
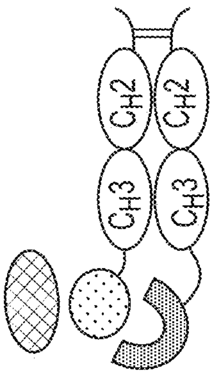
Figure 4W:
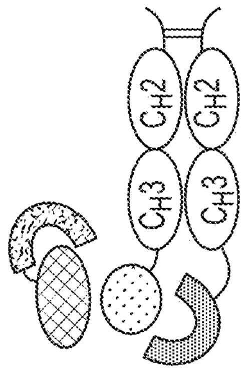

In some embodiments, the present disclosure provides an IL12 receptor agonist comprising Exemplary Monomer 3 and Exemplary Monomer 51, where Exemplary Monomer 3 is associated with monomeric p40 (see, e.g., FIG. 4V (left monomer), and FIG. 4W (left monomer)). In some embodiments, the monomeric p40 is masked, monomeric p40 (see, e.g., FIG. 4U and FIG. 4W). The mask can be, e.g., an IL12Rβ1-based or an anti-p40 antibody-based mask.

In some embodiments, the present disclosure provides an IL12 receptor agonist comprising Exemplary Monomer 3 and Exemplary Monomer 54 (see e.g., FIG. 4M).

Figure 2P:
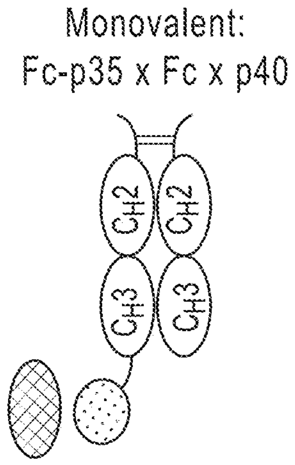

In some embodiments, the present disclosure provides an IL12 receptor agonist comprising Exemplary Monomer 3 and Exemplary Monomer 60, where Exemplary Monomer 3 is associated with monomeric p40 (see e.g., FIG. 2P (left monomer) and FIG. 4U (left monomer)). In some embodiments, the monomeric p40 is masked, monomeric p40 (see, e.g., FIG. 4U). The mask can be, e.g., an IL12Rβ1-based or an anti-p40 antibody-based mask.

In some embodiments, the present disclosure provides an IL12 receptor agonist comprising Exemplary Monomer 4 and Exemplary Monomer 53 (see e.g., FIG. 4L).

In some embodiments, the present disclosure provides an IL12 receptor agonist comprising two monomers according to Exemplary Monomer 5 (see e.g., FIGS. 2H and 2I).

Figure 5E:
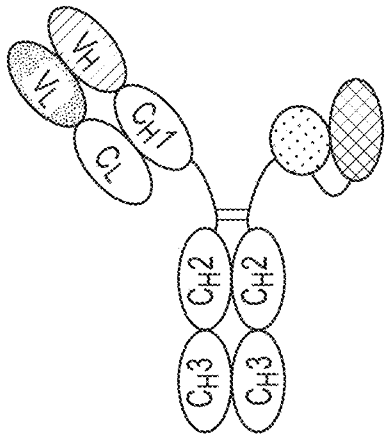
Figure 5F:
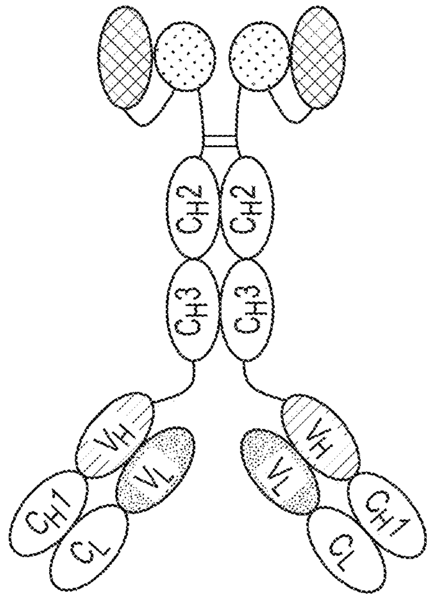
Figure 5G:
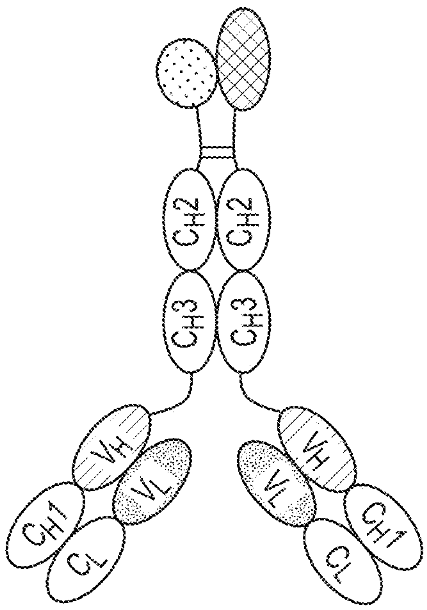
Figure 5H:
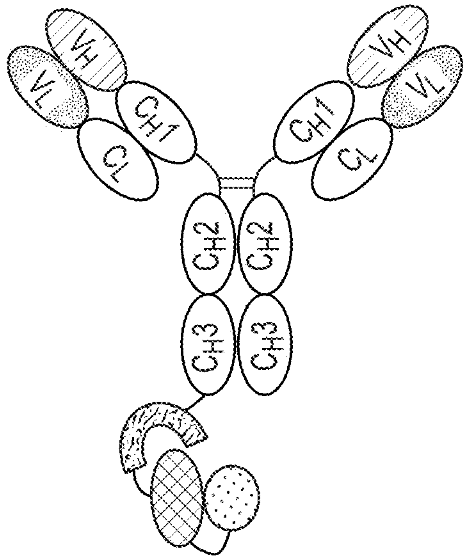
Figure 5I:
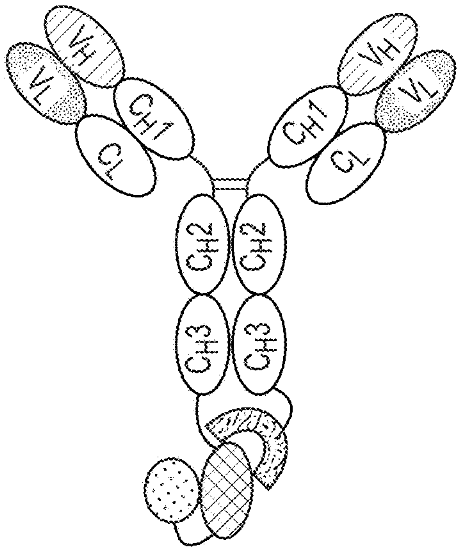
Figure 5J:
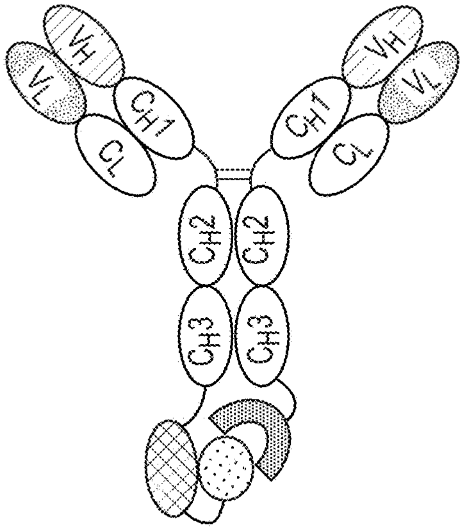
Figure 5K:
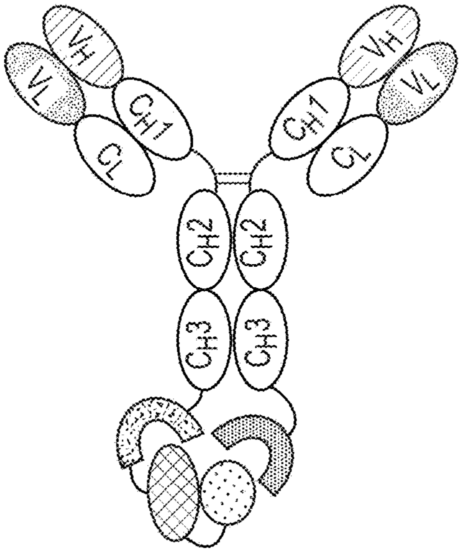
Figure 5L:
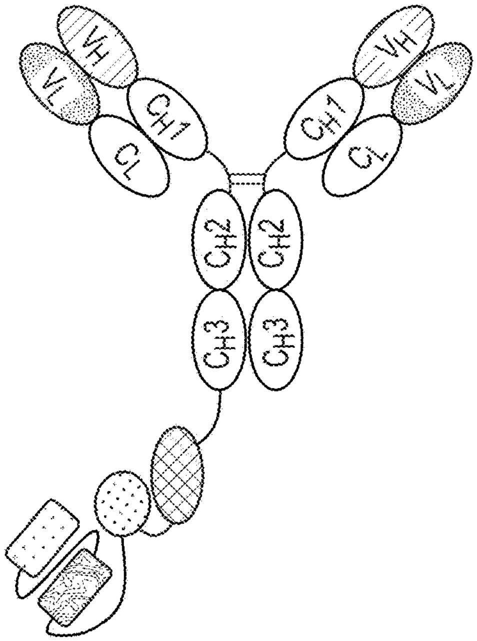
Figure 5M:
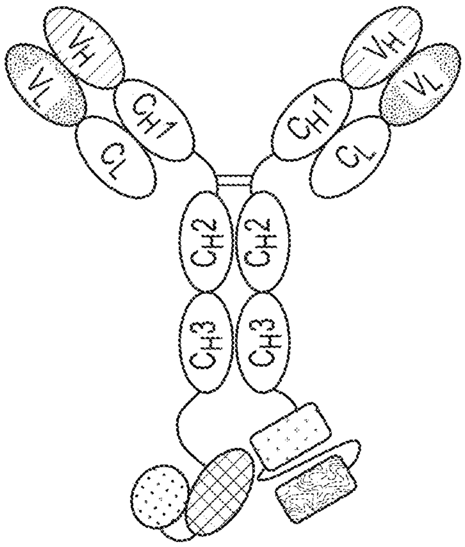
Figure 5N:
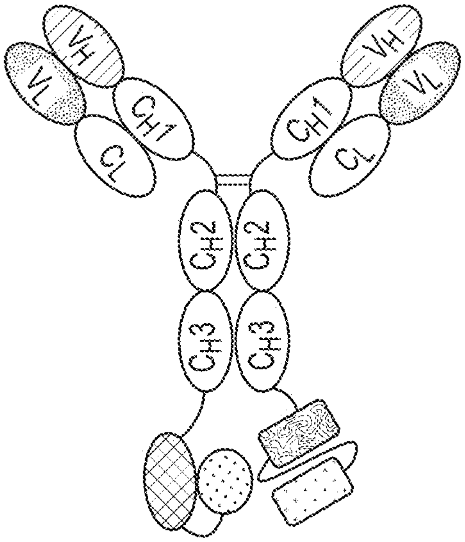
Figure 5O:
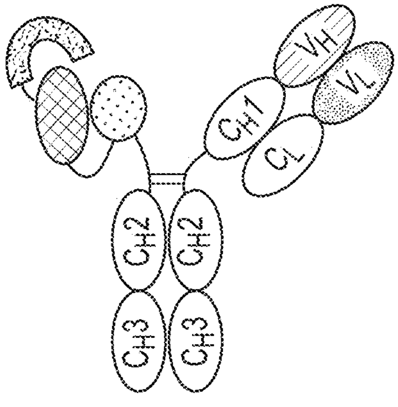
Figure 5P:
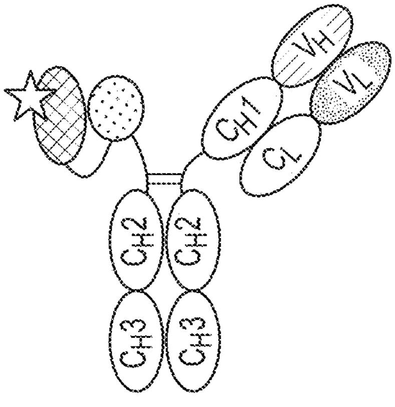
Figure 5Q:
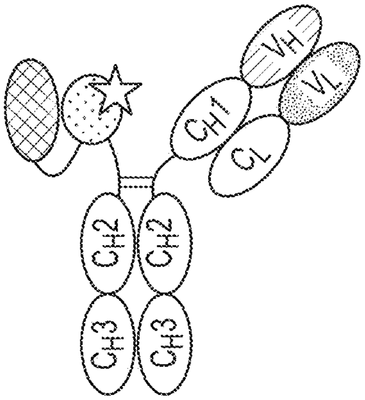

In some embodiments, the present disclosure provides an IL12 receptor agonist comprising Exemplary Monomer 5 and Exemplary Monomer 33 (see e.g., FIGS. 5E, 5P and 5Q).

In some embodiments, the present disclosure provides an IL12 receptor agonist comprising two monomers according to Exemplary Monomer 6 (see e.g., FIG. 2J).

In some embodiments, the present disclosure provides an IL12 receptor agonist comprising two monomers according to Exemplary Monomer 7 (see e.g., FIG. 2L).

In some embodiments, the present disclosure provides an IL12 receptor agonist comprising Exemplary Monomer 7 and Exemplary Monomer 60 (see e.g., FIG. 2G).

In some embodiments, the present disclosure provides an IL12 receptor agonist comprising two monomers according to Exemplary Monomer 8 (see e.g., FIGS. 2K and 2M).

In some embodiments, the present disclosure provides an IL12 receptor agonist comprising Exemplary Monomer 8 and Exemplary Monomer 60 (see e.g., FIGS. 2F and 4F).

In some embodiments, the present disclosure provides an IL12 receptor agonist comprising Exemplary Monomer 8 and Exemplary Monomer 51 (see e.g., FIGS. 4J, 4K and 4S).

In some embodiments, the present disclosure provides an IL12 receptor agonist comprising Exemplary Monomer 8 and Exemplary Monomer 56 (see, e.g., FIGS. 4Q, 4R, 39A and 39B).

In some embodiments, the present disclosure provides an IL12 receptor agonist comprising two monomers according to Exemplary Monomer 9 (see e.g., FIG. 4C and FIG. 4E). The IL12Rβ moieties in the monomers according to Exemplary Monomer 9 can both be IL12Rβ1 moieties, can both be IL12Rβ2 moieties, or can be a combination of IL12Rβ1 and IL12Rβ2 moieties.

In some embodiments, the present disclosure provides an IL12 receptor agonist comprising Exemplary Monomer 9 and Exemplary Monomer 60 (see e.g., FIG. 4I and FIG. 4T).

In some embodiments, the present disclosure provides an IL12 receptor agonist comprising two monomers according to Exemplary Monomer 11 (see e.g., FIG. 4B and FIG. 4D). The IL12Rβ moieties in the monomers according to Exemplary Monomer 11 can both be IL12Rβ1 moieties, can both be IL12Rβ2 moieties, or can be a combination of IL12Rβ1 and IL12Rβ2 moieties.

In some embodiments, the present disclosure provides an IL12 receptor agonist comprising Exemplary Monomer 11 and Exemplary Monomer 60 (see e.g., FIGS. 4G and 4H).

In some embodiments, the present disclosure provides an IL12 receptor agonist comprising Exemplary Monomer 15 and Exemplary Monomer 33 (see, e.g., FIG. 5O). In one embodiment, the IL12Rβ moiety in Exemplary Monomer 15 is an IL12Rβ1 moiety. In another embodiment, the IL12Rβ moiety in Exemplary Monomer 15 is an IL12Rβ2 moiety.

In some embodiments, the present disclosure provides an IL12 receptor agonist comprising Exemplary Monomer 17 and Exemplary Monomer 18 (see e.g., FIG. 5G).

In some embodiments, the present disclosure provides an IL12 receptor agonist comprising Exemplary Monomer 19 and Exemplary Monomer 20 (see e.g., FIG. 5B).

Figure 5R:
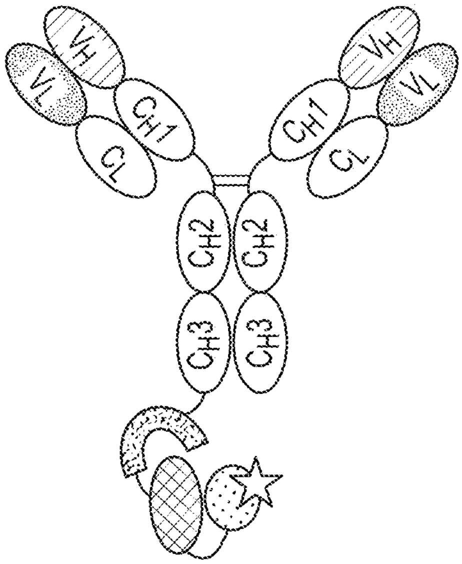
Figure 5S:
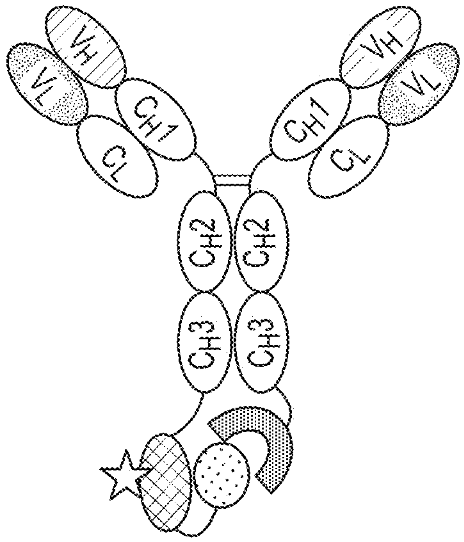
Figure 5T:
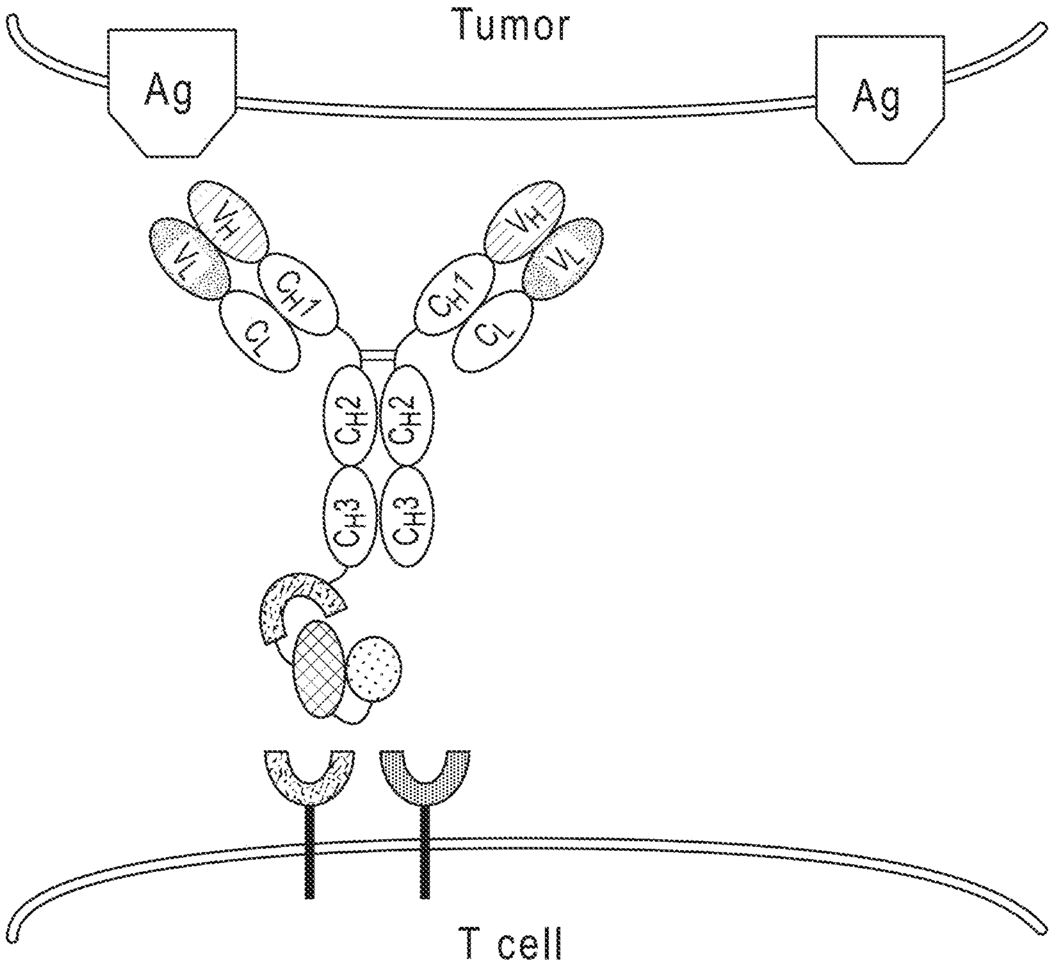
Figure 5U:
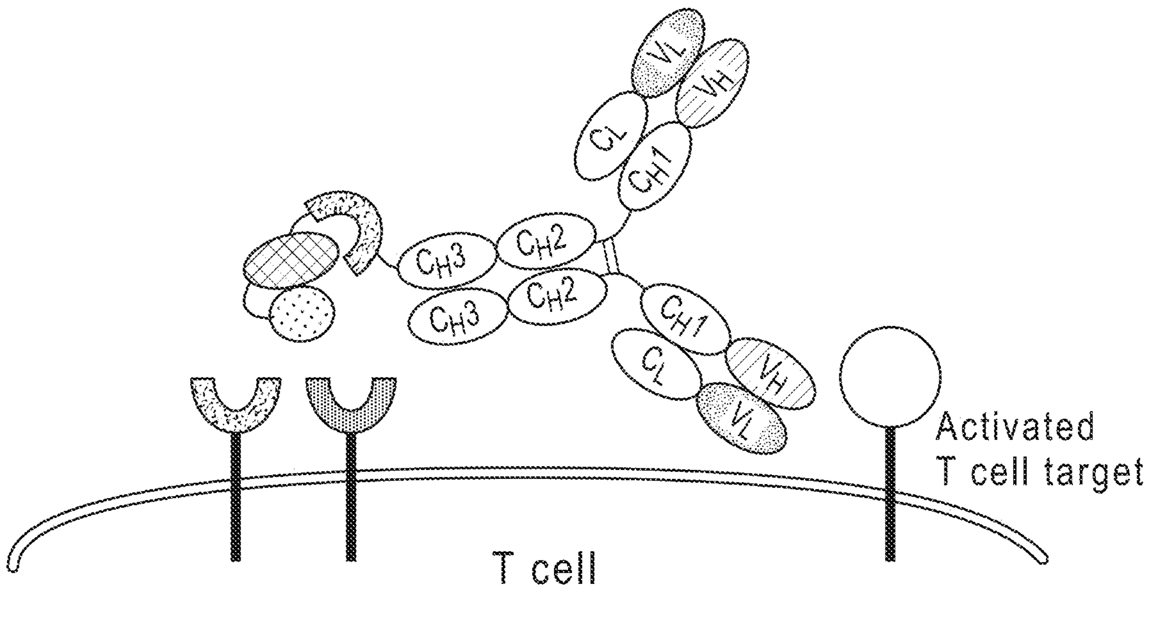
Figure 5V:
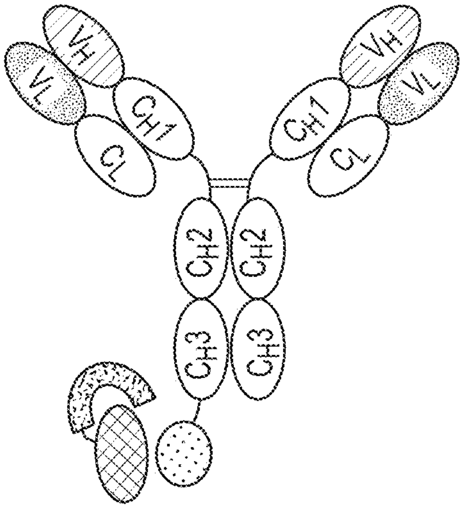

In some embodiments, the present disclosure provides an IL12 receptor agonist comprising Exemplary Monomer 19 and Exemplary Monomer 33, where Exemplary Monomer 19 is associated with monomeric p40 (see e.g., FIG. 5V (left monomer)). In some embodiments, the monomeric p40 is masked, monomeric p40 (see e.g., FIG. 5V). The mask can be, e.g., an IL12Rβ11-based or an anti-p40 antibody-based mask.

Figure 5W:
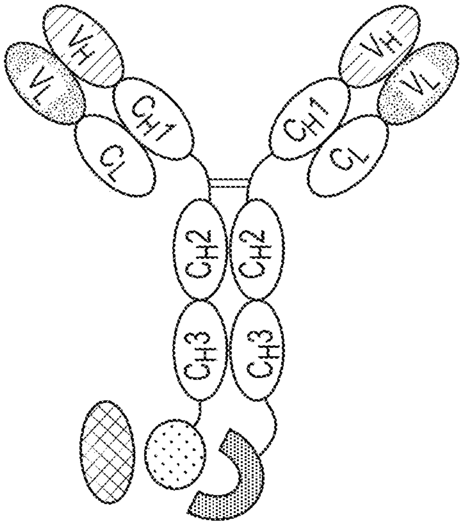
Figure 5X:
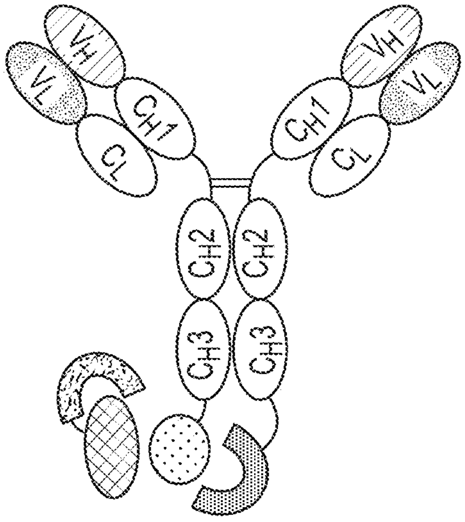

In some embodiments, the present disclosure provides an IL12 receptor agonist comprising Exemplary Monomer 19 and Exemplary Monomer 57, where Exemplary Monomer 19 is associated with monomeric p40 (see e.g., FIG. 5W (left monomer) and FIG. 5X (left monomer). In some embodiments, the monomeric p40 is masked, monomeric p40 (see, e.g., FIG. 5X). The mask can be, e.g., an IL12Rβ1-based or an anti-p40 antibody-based mask.

In some embodiments, the present disclosure provides an IL12 receptor agonist comprising two monomers according to Exemplary Monomer 25 (see, e.g., FIG. 5F).

In some embodiments, the present disclosure provides an IL12 receptor agonist comprising two monomers according to Exemplary Monomer 28 (see e.g., FIG. 5D).

In some embodiments, the present disclosure provides an IL12 receptor agonist comprising Exemplary Monomer 28 and Exemplary Monomer 33 (see e.g., FIG. 5C).

In some embodiments, the present disclosure provides an IL12 receptor agonist comprising Exemplary Monomer 28 and Exemplary Monomer 57 (see e.g., FIGS. 5I, and 5J). In one embodiment, the IL12Rβ moiety in Exemplary Monomer 57 is an IL12Rβ1 moiety. In another embodiment, the IL12Rβ moiety in Exemplary Monomer 57 is an IL12Rβ2 moiety.

In some embodiments, the present disclosure provides an IL12 receptor agonist comprising Exemplary Monomer 28 and Exemplary Monomer 59 (see e.g., FIGS. 5M, 5N, 39C and 39D).

In some embodiments, the present disclosure provides an IL12 receptor agonist comprising Exemplary Monomer 33 and Exemplary Monomer 35 (see, e.g., FIGS. 5H and 5R). In one embodiment, the IL12Rβ moiety in Exemplary Monomer 35 is an IL12Rβ1 moiety. In another embodiment, the IL12Rβ moiety in Exemplary Monomer 35 is an IL12Rβ2 moiety.

In some embodiments, the present disclosure provides an IL12 receptor agonist comprising Exemplary Monomer 33 and Exemplary Monomer 58 (see e.g., FIG. 5L).

In some embodiments, the present disclosure provides an IL12 receptor agonist comprising Exemplary Monomer 35 and Exemplary Monomer 57 (see e.g., FIG. 5K). The IL12Rβ moieties in Exemplary Monomer 35 and Exemplary Monomer 57 can both be IL12Rβ1 moieties, can both be IL12Rβ2 moieties, or can be a combination of IL12Rβ1 and IL12Rβ2 moieties. In one embodiment, the IL12Rβ moiety in Exemplary Monomer 35 is an IL12Rβ1 moiety and the IL12Rβ moiety in Exemplary Monomer 57 is an IL12Rβ2 moiety. In another embodiment, the IL12Rβ moiety in Exemplary Monomer 35 is an IL12Rβ2 moiety and the IL12Rβ moiety in Exemplary Monomer 57 is an IL12Rβ1 moiety.

In some embodiments, the present disclosure provides an IL12 receptor agonist comprising Exemplary Monomer 55 and Exemplary Monomer 60 (see, e.g., FIGS. 4O and 4P).

In some embodiments, the present disclosure provides an IL12 receptor agonist comprising Exemplary Monomer 57 and Exemplary Monomer 63 (see, e.g., FIG. 5S).

Additional embodiments of Exemplary Monomer pairings are set forth in the numbered embodiments disclosed in Section 7.

In embodiments of the foregoing IL12 receptor agonists comprising two exemplary monomers having IL12Rβ moieties, the IL12Rβ moieties can both be IL12Rβ1 moieties, can both be IL12Rβ2 moieties, or can be a combination of IL12Rβ1 and IL12Rβ2 moieties.

In the IL12 receptor agonists of the disclosure, when the targeting moiety is an antigen binding domain ("ABD") of an antibody, each monomer can be composed of two polypeptide chains, one polypeptide chain bearing the heavy chain variable region and the other polypeptide chain bearing the light chain variable region. The targeting moiety itself can comprise heavy and light chain variable domains on separate polypeptide chains. For example, with respect to an IL12 receptor agonist monomer including a targeting moiety, the monomer can be composed of a Polypeptide A and a Polypeptide B. Polypeptide A can include, for example, from N-terminus to C-terminus: the heavy chain variable domain of a targeting moiety-optional linker-multimerization moiety-optional linker-IL12 p40 moiety-IL12 p35 moiety; and Polypeptide B can comprise the light chain variable domain of a targeting moiety.

Alternatively, an scFv can be used as a targeting moiety, in which the heavy and light chain variable regions of the targeting moiety are fused to one another in a single polypeptide.

In certain aspects, an IL12 receptor agonist of the disclosure has a therapeutic index of greater than 1, and preferably greater than 2, and even more preferably greater than 10. In particular embodiments, the therapeutic index is about 10, about 20, about 100, or about 200.

In various embodiments, the IL12 receptor agonist does not comprise (a) a cytokine other than IL12; (b) an anti-IL12 antibody or antibody fragment; (c) an anti-DNA antibody or antibody fragment; (b) a non-binding antibody variable domain; or any combination of two, three or all four of these.

Further details of the components of the IL12 receptor agonists of the disclosure are presented below.

6.2.1. Biochemical Properties of IL12 Receptor Agonists

In vivo, large complexes of antibodies can be rapidly eliminated by phagocytosis, leading to reduced efficacy of the antibody. Large complexes can also increase immunogenicity of a therapeutic antibody. See, e.g., WO2020047067A1. During manufacturing, aggregation is a common issue that compromises the quality, safety, and efficacy of antibodies. The IL12 receptor agonists of the disclosure (e.g., masked IL12 receptor agonists comprising a single receptor domain type (e.g., D1 of IL12Rβ1 or IL12Rβ2)) can be less prone to aggregation, for example in vivo or ex vivo as compared to receptor agonists having alternative structures (e.g., masked IL12 receptor agonists comprising two receptor domain types (e.g., D1 and D2 of IL12Rβ1 or IL12Rβ2). Thus, in some embodiments, the IL12 receptor agonists of the disclosure have at least 50%, at least 60%, at least 70%, at least 80%, at least 95%, or at least 99% less aggregation during recombinant production in a mammalian cell line than IL12 receptor agonists having alternative structures. The oligomerization state of the IL12 receptor agonists can be determined by, for example, size-exclusion ultra-performance liquid chromatography.

In some embodiments, IL12 receptor agonists of the disclosure are believed to have good thermal stability. High thermostability and low aggregation propensity facilitate antibody manufacturing and storage, and promote long serum half-life. Carter and Merchant, 1997, Curr Opin Biotechnol, 8(4):449-454. Thermal stability can be measured by methods known in the art, including differential scanning fluorimetry (DSF).

6.3. The IL12 p40 and p35 Moieties

The present disclosure provides IL12 receptor agonists with p35 and p40 moieties with wild type or variant p35 and p40 sequences. The present disclosure further provides p35 and p40 moieties with variant p35 and p40 sequences, respectively. Exemplary p40 moieties are disclosed in Section 6.3.1 and exemplary p35 moieties are disclosed in Section 6.3.2.

6.3.1. IL12 p40 Moiety

Each IL12 p40 moiety of the IL12 receptor agonists of the disclosure comprises a wild type or variant IL12 p40 moiety. In some embodiments, an IL12 receptor agonist of the disclosure comprises a single IL12 p40 moiety (e.g., an IL12 p40 moiety on a first monomer or on a second monomer in embodiments where the IL12 receptor agonist is monovalent for IL12). In some embodiments, an IL12 receptor agonist of the disclosure comprises two IL12 p40 moieties (e.g., a first IL12 p40 moiety on a first monomer and a second IL12 p40 moiety on a second monomer in embodiments where the IL12 agonist is bivalent for IL12). In such embodiments, the two IL12 p40 moieties can be identical, or they can be different.

In eukaryotic cells, the human IL12 p40 subunit is synthesized as a precursor polypeptide of 328 amino acids, from which 22 amino acids are removed to generate mature IL12 p40. In some embodiments, an IL12 p40 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12Rβ1 binding portion of a mammalian, e.g., human or murine, p40 (sometimes referred to as the beta subunit of IL12 or IL12β). In some embodiments, the mammalian p40 is full-length human p40. In other embodiments, the mammalian p40 is mature human p40. The sequence of human p40 has the Uniprot identifier P29460 (uniprot.org/uniprot/P29460). In some embodiments, the mammalian p40 is full-length murine p40. In some embodiments, the mammalian p40 is mature murine p40. The sequence of murine p40 has the Uniprot identifier P43432 (uniprot.org/uniprot/P43432).

In some embodiments, the p40 moiety comprises p40 D2 and D3 domains, to the exclusion of the p40 D1 domain. In other embodiments, the p40 moiety comprises p40 D1, D2, and D3 domains.

Full-length human IL12 p40 has the following amino acid sequence (signal sequence=underlined; D1 domain=italicized; D2 domain=bold; D3 domain=bold and underlined):

(SEQ ID NO: 5)

MCHQQLVISWFSLVFLASPLVA*IWELKKDVYVVELDWYPDAPGEMVVLTC*

*DTPEEDGITWTLDQSSEVLGSGKTLTIQVKEFGDAGQYTCHKGGEVLSHS*

*LLLLHKKEDGIWSTDILKDQKEPKNKTF*LRCEAKNYSGRFTCWWLTTIST

DLTFSVKSSRGSSDPQGVTCGAATLSAERVRGDNKEYEYSVECQEDSACP

AAEESLPIEVMVDAVHKLKYENYTSSFFIRDIIKPDPPKNLQLKPLKNSR

QVEVSWEYPDTWSTPHSYFSLTFCVQVQGKSKREKKDRVFTDKTSATVIC

RKNASISVRAQDRYYSSSWSEWASVPCS.

Amino acid 23 of full-length human p40 is amino acid 1 of mature human p40.

In certain embodiments, the IL12 p40 moiety comprises one or more amino acid substitutions that reduce binding to IL12Rβ1. For example, in some embodiments, the IL12 p40 moiety can have up to 1,000-fold attenuated binding to human IL12Rβ1 as compared to wild type human IL12 p40. In some embodiments, the IL12 moiety can have up to 100-fold, up to 50-fold, up to 25-fold, up to 20-fold, up to 15-fold, up to 10-fold, or up to 5-fold attenuated binding to human IL12Rβ1 as compared to wild type human IL12 p40.

Other characteristics of useful IL12 p40 variants may include the ability to destabilize dimerization with IL12 p35.

Exemplary amino acid substitutions include, but are not limited to substitutions at positions K6, W15, D18, E32, E33, D34, Q42, S43, E45, Q56, E59, F60, D62, E73, K84, D87, D93, K96, K99, E100, N103, K104, N113, Q144, R159, D161, K163, E187, N200, N218, Q229, E235, Y246, C252, Q256, K258, K260, E262, K264, N281, Y292, and E299, wherein amino acid positions, unless otherwise noted, are relative to the mature human IL12 p40 amino acid sequence, excluding the 22-amino acid signal sequence. Corresponding amino acid positions in the full-length human sequence, full-length murine sequence, and mature murine sequence are provided in Table 1. Table 1 also provides exemplary substitutions at each noted positions.

TABLE 1

| IL12 p40 moiety Amino Acid Substitutions | | | | |
|---|---|---|---|---|
| Amino Acid (Human - Full Length) | Amino Acid (Human - Mature) | Amino Acid (Murine - Full Length) | Amino Acid (Murine - Mature) | Exemplary substitutions |
| K28 | K6 | K28 | K6 | A |
| W37 | W15 | W37 | W15 | A |
| D40 | D18 | D40 | D18 | N, K, A |
| E54 | E32 | E54 | E32 | Q, A |
| E55 | E33 | E55 | E33 | Q, A |
| D56 | D34 | D56 | D34 | N, K, A |
| Q64 | Q42 | Q64 | Q42 | E |
| S65 | S43 | S65 | S43 | E, K |
| E67 | E45 | E67 | E45 | Q |
| Q78 | Q56 | T78 | T56 | E |
| E81 | E59 | E81 | E59 | K, Q, A |
| F82 | F60 | F82 | F60 | A |
| D84 | D62 | D84 | D62 | N |
| E95 | E73 | E95 | E73 | Q |
| K106 | K84 | K106 | K84 | A |
| D109 | D87 | N109 | N87 | A |
| D115 | D93 | E115 | E93 | A |
| K118 | K96 | K118 | K96 | A |
| K121 | K99 | K121 | K99 | E, Y, A |
| E122 | E100 | | | Q |
| N125 | N103 | N122 | N100 | D, Q |
| K126 | K104 | K123 | K101 | A |
| N135 | N113 | N132 | N110 | D, Q |
| Q166 | Q144 | R163 | R141 | E |
| R181 | R159 | T178 | T156 | E |
| D183 | D161 | D180 | D158 | N |
| K185 | K163 | R182 | R160 | E |
| C199 | C177 | C197 | C175 | S |
| E209 | E187 | E207 | E185 | Q |
| K219 | K197 | K217 | K195 | A |
| N222 | N200 | N220 | N198 | D, Q |
| N240 | N218 | N238 | N216 | Q |
| Q251 | Q229 | Q248 | Q226 | E |
| E257 | E235 | E254 | E232 | Q |
| Y268 | Y246 | Y265 | Y243 | V, F |
| C274 | C252 | F271 | F249 | S |
| Q278 | Q256 | Q275 | Q253 | N |
| K280 | K258 | K277 | K255 | E |
| K282 | K260 | E279 | K257 | E |
| E284 | E262 | N289 | N267 | Q |
| K286 | K264 | K291 | K269 | E |
| N303 | N281 | G307 | G285 | D, Q |
| Y314 | Y292 | Y318 | Y296 | F |
| E321 | E299 | K325 | K303 | Q |

An exemplary amino acid substitution at mature human K6 is K6A.

An exemplary amino acid substitution at mature human W15 is W15A.

Exemplary amino acid substitutions at mature human D18 include D18N, D18K, and D18A.

Exemplary amino acid substitutions at mature human E32 include E32Q and E32A.

Exemplary amino acid substitutions at mature human E33 include E33Q and E33A.

Exemplary amino acid substitutions at mature human D34 include D34N, D34K, and D34A.

An exemplary amino acid substitution at mature human Q42 is Q42E.

Exemplary amino acid substitutions at mature human S43 include S43E and S34K.

An exemplary amino acid substitution at mature human E45 is E45Q.

An exemplary amino acid substitution at mature human Q56 is Q56E.

Exemplary amino acid substitutions at mature human E59 include E59K, E59Q, and E59A.

An exemplary amino acid substitution at mature human F60 is F60A.

An exemplary amino acid substitution at mature human D62 is D62N.

An exemplary amino acid substitution at mature human E73 is E73Q.

An exemplary amino acid substitution at mature human K84 is K84A.

An exemplary amino acid substitution at mature human D87 is D87N.

An exemplary amino acid substitution at mature human D93 is D93A.

An exemplary amino acid substitution at mature human K96 is E93A.

Exemplary amino acid substitutions at mature human K99 include K99E, K99Y, and K99A.

An exemplary amino acid substitution at mature human E100 is E100 Q.

Exemplary amino acid substitutions at mature human N103 include N103D and N103Q.

An exemplary amino acid substitution at mature human K104 is K104A.

Exemplary amino acid substitutions at mature human N113 include N113D and N113Q.

An exemplary amino acid substitution at mature human Q144 is Q144E.

An exemplary amino acid substitution at mature human R159 is R159 E.

An exemplary amino acid substitution at mature human D161 is D161N.

An exemplary amino acid substitution at mature human K163 is K163E.

An exemplary amino acid substitution at mature human E187 is E187Q.

Exemplary amino acid substitutions at mature human N200 include N200D and N200Q.

An exemplary amino acid substitution at mature human N218 is N218Q.

An exemplary amino acid substitution at mature human Q229 is Q229E.

An exemplary amino acid substitution at mature human E235 is E235Q.

Exemplary amino acid substitutions at mature human Y246 include Y246V and Y246F.

An exemplary amino acid substitution at mature human C252 is C252S.

An exemplary amino acid substitution at mature human Q256 is Q256N.

An exemplary amino acid substitution at mature human K258 is K258E.

An exemplary amino acid substitution at mature human K260 is K260E.

An exemplary amino acid substitution at mature human E262 is E262Q.

An exemplary amino acid substitution at mature human K264 is K264E.

Exemplary amino acid substitutions at mature human N281 include N281D and N281Q.

An exemplary amino acid substitution at mature human Y292 is Y292F.

An exemplary amino acid substitution at mature human E299 is E299Q.

In certain embodiments, amino acid substitutions at mature human Y246 and/or Y292 destabilize the p40/p35 heterodimer by preventing formation of a disulfide bond between the two subunits. Exemplary amino acid substitutions at Y246 include Y246V and Y246F. An exemplary amino acid substitution at Y292 is Y292F.

In some embodiments, the p40 moiety is fused, either directly or indirectly, to an IL12 p40 binding domain of IL12Rβ1 (i.e., the IL12Rβ1 moiety, e.g., as described in Section 6.4.1), optionally via a linker (e.g., as described in Section 6.8). When present, the IL12 p40 binding domain of IL12Rβ1 can be N-terminal or C-terminal to the IL12 p40 moiety. When the p40 moiety is "directly" fused to the IL12 p40 binding domain of IL12Rβ1, the p40 moiety and the IL12 p40 binding domain of IL12Rβ1 are positioned adjacently on the same monomer, separated only by a linker, if present. When the p40 moiety is "indirectly" fused to the IL12 p40 binding domain of IL12Rβ1, the p40 moiety and the IL12 p40 binding domain of IL12Rβ1 are separated by one or more other domains (e.g., an IL12 p35 moiety) on the same monomer, or are located on separate monomers.

6.3.2. IL12 p35 Moiety

Each IL12 p35 moiety of the IL12 receptor agonists of the disclosure comprises a wild type or variant IL12 p35 moiety. In some embodiments, an IL12 receptor agonist of the disclosure comprises a single IL12 p35 moiety (e.g., an IL12 p35 moiety on a first monomer or on a second monomer in embodiments where the IL12 receptor agonist is monovalent for IL12). In some embodiments, an IL12 receptor agonist of the disclosure comprises two IL12 p35 moieties. In such embodiments, the two IL12 p35 moieties can be identical, or they can be different.

In eukaryotic cells, the human IL12 p35 subunit is synthesized as a precursor polypeptide of 219 amino acids, from which 22 amino acids are removed to generate mature IL12 p35. In some embodiments, an IL12 p35 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12Rβ2 binding portion of a mammalian, e.g., human or murine, p35 (sometimes referred to as the alpha subunit of IL12 or IL12a). In some embodiments, the mammalian p35 is full-length human p35. In other embodiments, the mammalian p40 is mature human p35. The sequence of human p35 has the Uniprot identifier P29459 (uniprot.org/uniprot/P29459). In some embodiments, the mammalian p35 is full-length murine p35. In some embodiments, the mammalian p35 is mature murine p40. The sequence of murine p40 has the Uniprot identifier P43431 (uniprot.org/uniprot/P43431).

Full-length human IL12 p35 has the following amino acid sequence (signal sequence=underlined):

(SEQ ID NO: 6)

MCPARSLLLVATLVLLDHLSLARNLPVATPDPGMFPCLHHSQNLLRAVSN

MLQKARQTLEFYPCTSEEIDHEDITKDKTSTVEACLPLELTKNESCLNSR

ETSFITNGSCLASRKTSFMMALCLSSIYEDLKMYQVEFKTMNAKLLMDPK

RQIFLDQNMLAVIDELMQALNFNSETVPQKSSLEEPDFYKTKIKLCILLH

AFRIRAVTIDRVMSYLNAS.

Amino acid 23 of full-length human p35 is amino acid 1 of mature human p35.

In certain embodiments, the IL12 p35 moiety comprises one or more amino acid substitutions that reduce binding to IL12Rβ2. For example, in some embodiments, the IL12 p35 moiety can have up to 1,000-fold attenuated binding to human IL12Rβ1 as compared to wild type human IL12 p35. In some embodiments, the IL12 moiety can have up to 100-fold, up to 50-fold, up to 25-fold, up to 20-fold, up to 15-fold, up to 10-fold, or up to 5-fold attenuated binding to human IL12Rβ2 as compared to wild type human IL12 p35.

Other characteristics of useful IL12 p35 variants may include the ability to destabilize dimerization with IL12 p40.

Exemplary amino acid substitutions include, but are not limited to substitutions at N21, Q35, E38, E45, D55, N71, L75, N76, E79, N85, L89, F96, M97, L124, M125, Q130, Q135, N136, E143, Q146, Y167, I171, and R189, wherein amino acid positions are relative to the mature human IL12 p35 amino acid sequence, excluding the 22-amino acid signal sequence. Corresponding amino acid positions in the full-length human sequence, full-length murine sequence, and mature murine sequence are provided in Table 2. Table 2 also provides exemplary substitutions at each noted positions.

TABLE 2

IL12 p35 moiety Amino Acid Substitutions

| Amino Acid (Human - Full Length) | Amino Acid (Human - Mature) | Amino Acid (Murine - Full Length) | Amino Acid (Murine - Mature) | Exemplary substitutions |
|---|---|---|---|---|
| N43 | N21 | N39 | N17 | D |
| Q57 | Q35 | E53 | E31 | D |
| E60 | E38 | K56 | K34 | Q |
| E67 | E45 | E63 | E41 | Q |
| D77 | D55 | D73 | D51 | Q, K |
| N93 | N71 | N89 | N67 | D |
| L97 | L75 | L93 | L71 | A |
| N98 | N76 | A94 | A72 | D |
| E101 | E79 | E97 | E75 | Q |
| N107 | N85 | R103 | R81 | D, Q |
| L111 | L89 | L107 | L85 | A |
| F118 | F96 | L114 | L92 | A |
| M119 | M97 | M115 | M93 | A |
| L146 | L124 | Q142 | Q120 | A |
| M147 | M125 | N143 | N121 | A |
| Q152 | Q130 | Q156 | Q126 | E |
| Q157 | Q135 | K153 | K131 | E |
| N158 | N136 | G154 | G132 | D |
| E165 | E143 | E161 | E139 | Q |
| Q168 | Q146 | Q164 | Q142 | E |
| Y189 | Y167 | Y185 | Y163 | A, V, R, E |
| I193 | I171 | M189 | M167 | A, V, E |
| R211 | R189 | R207 | R185 | A, K |

An exemplary amino acid substitution at mature human N21 is N21D.

An exemplary amino acid substitution at mature human Q35 is Q35D.

An exemplary amino acid substitution at mature human E38 is E38Q.

An exemplary amino acid substitution at mature human E45 is E45Q.

Exemplary amino acid substitutions at mature human D55 include D55Q and D55K.

An exemplary amino acid substitution at mature human N71 is N71D.

An exemplary amino acid substitution at mature human L75 is L75A.

An exemplary amino acid substitution at mature human N76 is N76D.

An exemplary amino acid substitution at mature human E79 is E79Q.

Exemplary amino acid substitutions at mature human N85 include N85D and N85Q.

An exemplary amino acid substitution at mature human L89 is L89A.

An exemplary amino acid substitution at mature human F96 is F96A.

An exemplary amino acid substitution at mature human M97 is M97A.

An exemplary amino acid substitution at mature human L124 is L124A.

An exemplary amino acid substitution at mature human M125 is M125A.

An exemplary amino acid substitution at mature human Q130 is Q130E.

An exemplary amino acid substitution at mature human Q135 is Q135E.

An exemplary amino acid substitution at mature human N136 is N136D.

An exemplary amino acid substitution at mature human E143 is E143Q.

An exemplary amino acid substitution at mature human Q146 is Q146E.

Exemplary amino acid substitutions at mature human Y167 include Y167A, Y167V, Y167R, and Y167E.

Exemplary amino acid substitutions at mature human I171 include I171A, I171V, and I171E.

In certain embodiments, an amino acid substitution at mature human R189 destabilizes the p40/p35 heterodimer by preventing formation of a disulfide bond between the two subunits. Exemplary amino acid substitutions at mature human R189 include R189A and R189K.

In some embodiments, the p35 moiety is fused, either directly or indirectly, to an IL12 p35 binding domain of IL12Rβ2 (i.e., the IL12Rβ2 moiety, e.g., as described in Section 6.4.2), optionally via a linker (e.g., as described in Section 6.8). When present, the IL12 p35 binding domain of IL12Rβ2 can be N-terminal or C-terminal to the IL12 p35 moiety. When the p35 moiety is "directly" fused to the IL12 p35 binding domain of IL12Rβ2, the p35 moiety and the IL12 p35 binding domain of IL12Rβ2 are positioned adjacently on the same monomer, separated only by a linker, if present. When the p35 moiety is "indirectly" fused to the IL12 p35 binding domain of IL12Rβ2, the p35 moiety and the IL12 p35 binding domain of IL12Rβ2 are separated by one or more other domains (e.g., an IL12 p40 moiety) on the same monomer, or are located on separate monomers.

6.4. IL12 Masking Moieties

The present disclosure provides IL12 receptor agonists with one or more IL12 masking moieties capable of binding IL12 p40 and/or p35 moieties. In some aspects, the IL12 making moieties described herein bind IL12 p40 and/or p35 moieties, thereby attenuating IL12 activity on a target cell. In some embodiments, the IL12 masking moiety is an IL12Rβ1 moiety capable of binding an IL12 p40 moiety. In other embodiments, the IL12 masking moiety is an IL12Rβ2 moiety capable of binding an IL12 p35 moiety. Exemplary IL12Rβ1 moieties are disclosed in Section 6.4.1 and exemplary IL12Rβ2 moieties are disclosed in Section 6.4.2. In other embodiments, the IL12 masking moiety is an IL12 antibody fragment. Exemplary IL12 antibody fragments are disclosed in Section 6.4.3.

6.4.1. IL12Rβ1 Moiety

IL12 receptor agonists of the disclosure optionally include one or more IL12Rβ1 moieties. Each of the one or more IL12Rβ1 moieties is capable of binding an IL12 p40 moiety of the disclosure. An IL12Rβ1 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12 p40 binding portion of a mammalian, e.g., human or murine, IL12 receptor subunit beta-1 (IL12Rβ1). The IL12 p40 binding portion of IL12Rβ1 comprises or consists of the extracellular domain of the receptor subunit. The sequence of human IL12Rβ1 has the Uniprot identifier P42701 (uniprot.org/uniprot/P42701) (SEQ ID NO:33), with amino acids 24 to 545 (SEQ ID NO:134) making up the extracellular domain. The sequence of murine IL12Rβ1 has the Uniprot identifier Q60837 (uniprot.org/uniprot/Q60837), with amino acids 24 to 565 making up the extracellular domain.

In some embodiments, the IL12Rβ1 moiety includes an extracellular domain (or an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the extracellular domain) of a mammalian, e.g., human or murine, IL12Rβ1.

In certain aspects, the IL12Rβ1 moiety can comprise or consist of an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to amino acids 24 to 545 of full-length human IL12Rβ1 (i.e., Uniprot identifier P42701), optionally wherein the binding portion has an amino acid sequence of (a) at least 160 amino acids, at least 161 amino acids, at least 162 amino acids, at least 164 amino acids or at least 165 amino acids and/or (b) up to 251, up to 240, up to 230, up to 220, up to 210, up to 200, up to 190, up to 180 or up to 170 amino acids from amino acids 24 to 545 of full-length human IL12Rβ1. In particular embodiments, the portion of human IL12Rβ1 is bounded by any one of (a) and (b) in the preceding sentence, e.g., at least 160 and up to 180 amino acids from human IL12Rβ1, at least 162 and up to 200 amino acids from human IL12Rβ1, at least 160 and up to 220 amino acids from human IL12Rβ1, at least 164 and up to 190 amino acids from human IL12Rβ1, and so on and so forth.

In some embodiments, the IL12Rβ1 moiety comprises or consists of an amino acid sequence having at least about 90%, at least about 95%, at least about 96%, at least about 97%, at least about 98%, at least about 99% or 100% sequence identity to amino acids 24 to 545 of full-length human IL12Rβ1, with or without an additional up to 5 amino acids, up to 10 amino acids, up to 15 amino acids, up to 20 amino acids, up to 30 amino acids, or up to 40 amino acids C-terminal to amino acid residue 545, of IL12Rβ1.

The IL12Rβ1 moiety-containing IL12 receptor agonists of the disclosure can have the IL12Rβ1 extracellular domain at the N- or C-terminus of the IL12 p40 moiety when located on the same monomer. In some embodiments, the IL12Rβ1 moiety-containing IL12 receptor agonists of the disclosure preferably have the IL12Rβ1 extracellular domain at the N-terminus of the IL12 p40 moiety.

6.4.2. IL12Rβ2 Moiety

IL12 receptor agonists of the disclosure optionally include one or more IL12Rβ2 moieties. Each of the one or more IL12Rβ2 moieties is capable of binding an IL12 p35 moiety of the disclosure. An IL12Rβ2 moiety is an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, to an IL12 p35 binding portion of a mammalian, e.g., human or murine, IL12 receptor subunit beta-2 (IL12Rβ2). The IL12 p35 binding portion of IL12Rβ2 comprises or consists of the extracellular domain of the receptor subunit. The sequence of human IL12Rβ2 has the Uniprot identifier Q99665 (uniprot.org/uniprot/Q99665) (SEQ ID NO: 135), with amino acids 24 to 622 (SEQ ID NO: 136) making up the extracellular domain.

In some embodiments, the IL12Rβ2 moiety includes an extracellular domain (or an amino acid sequence comprising at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to the extracellular domain) of a mammalian, e.g., human or murine, IL12Rβ2.

In certain aspects, the IL12Rβ2 moiety can comprise or consist of an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to amino acids 24 to 637 or full-length human IL12Rβ2 (i.e., Uniprot identifier Q99665), optionally wherein the binding portion has an amino acid sequence of (a) at least 160 amino acids, at least 161 amino acids, at least 162 amino acids, at least 164 amino acids or at least 165 amino acids and/or (b) up to 251, up to 240, up to 230, up to 220, up to 210, up to 200, up to 190, up to 180 or up to 170 amino acids from amino acids 24 to 637 of full-length IL12Rβ2. In particular embodiments, the portion of human IL12Rβ2 is bounded by any one of (a) and (b) in the preceding sentence, e.g., at least 160 and up to 180 amino acids from human IL12Rβ2, at least 162 and up to 200 amino acids from human IL12Rβ2, at least 160 and up to 220 amino acids from human IL12Rβ2, at least 164 and up to 190 amino acids from human IL12Rβ2, and so on and so forth.

In some embodiments, the IL12Rβ2 moiety comprises or consists of an amino acid sequence having at least about 90%, at least about 95%, at least about 96%, at least about 97%, at least about 98%, at least about 99% or 100% sequence identity to amino acids 24 to 637 of full-length IL12Rβ2, with or without an additional up to 5 amino acids, up to 10 amino acids, up to 15 amino acids, up to 20 amino acids, up to 30 amino acids, or up to 40 amino acids C-terminal to amino acid residue 637, of IL12Rβ2.

The IL12Rβ2 moiety-containing IL12 receptor agonists of the disclosure can have the IL12Rβ2 extracellular domain at the N- or C-terminus of the IL12 p35 moiety when located on the same monomer. In some embodiments, the IL12Rβ2 moiety-containing IL12 receptor agonists of the disclosure preferably have the IL12Rβ2 extracellular domain at the N-terminus of the IL12 p35 moiety.

6.4.3. IL12 Antibody Fragments

In some aspects, IL12 receptor agonists of the disclosure include an IL12 antibody fragment. In some embodiments, an IL12 monomer comprises a p40 moiety and a p35 moiety connected to the N- or C-terminus of a multimerization moiety (e.g., an Fc domain), with the IL12 antibody fragment positioned N- or C-terminal to the p40 and p35 moieties (see e.g., FIGS. 4O and 4P, left monomers). In other embodiments, an IL12 monomer lacking both p40 and p35 moieties comprises a multimerization moiety (e.g., an Fc domain) and an IL12 antibody fragment connected to the N- or C-terminus thereof. In some embodiments, an IL12 receptor agonist comprises a single IL12 antibody fragment (e.g., one of two IL12 monomers making up an IL12 receptor agonist comprises an IL12 antibody fragment; see e.g., FIGS. 4O-4R). In other embodiments, an IL12 receptor agonist comprises two IL12 antibody fragments (e.g., both IL12 monomers making up an IL12 receptor agonist comprise an IL12 antibody fragment; e.g., two left monomer of FIG. 4O, two left monomers of FIG. 4P, or one left monomer of FIG. 4O and one left monomer of FIG. 4P). In such embodiments, the two IL12 antibody fragments can be identical, or they can be different. In some embodiments a first IL12 antibody fragment can target a p40 moiety and a second IL12 antibody fragment can target a p35 moiety. In other embodiments, both IL12 antibody fragments can target p40 moieties or both IL12 antibody fragments can target p35 moieties.

In some embodiments, the IL12 antibody fragment comprises an antibody binding domain of any known anti-IL12 antibody. Examples of known anti-IL12 antibodies include, but are not limited to ustekinumab; briakinumab; anti-IL12 antibodies described in WO/2017/172771; anti-IL12 antibodies described in WO/2012/094623; anti-IL12 antibodies described in WO/2006/069036; anti-IL12 antibodies described in WO/2009/068627; clone B-T21 (Diaclone); MAB219 (R&D Systems); MAB1510 (R&D Systems); clone C17.8 (Bio X Cell); clone R1-5D9 (Bio X Cell); AP-MAB0853 (ab80682) (abcam); and ab9992 (abcam). An anti-IL12 antibody can bind to p35 and/or p40 (e.g., to p35, to p40, or to both p35 and p40).

In some embodiments, the IL12 antibody fragment comprises an antibody domain that binds to the same epitope as and/or competes for binding to IL12 with ustekinumab; briakinumab; anti-IL12 antibodies described in WO/2017/172771; anti-IL12 antibodies described in WO/2012/094623; anti-IL12 antibodies described in WO/2006/069036; anti-IL12 antibodies described in WO/2009/068627; clone B-T21 (Diaclone); MAB219 (R&D Systems); MAB1510 (R&D Systems); clone C17.8 (Bio X Cell); clone R1-5D9 (Bio X Cell); AP-MAB0853 (ab80682) (abcam); and ab9992 (abcam). Assays for measuring antibody competition are known in the art. For example, a sample of IL12 can be bound to a solid support. Then, a first antibody and a second antibody are added. One of the two antibodies is labelled. If the labelled antibody and the unlabeled antibody bind to separate and discrete sites on IL12, the labelled antibody will bind at the same level whether or not the unlabeled antibody is present. However, if the sites of interaction are identical or overlapping, the unlabeled antibody will compete, and the amount of labelled antibody bound to the antigen will be lowered. If the unlabeled antibody is present in excess, very little, if any, labelled antibody will bind. In some embodiments, a competing antibody is an antibody that decrease the binding of another antibody to IL12 by about 50%, about 60%, about 70%, about 80%, about 85%, about 90%, about 95%, or about 99%. Details of procedures for carrying out such competition assays are well known in the art and can be found, for example, in Greenfield, Ed., Antibodies, A Laboratory Manual, Cold Spring Harbor Laboratory Press, Cold Spring Harbor, New York, 2014. Such assays can be made quantitative by using purified antibodies. A standard curve can be established by titrating one antibody against itself, i.e., the same antibody is used for both the label and the competitor. The capacity of an unlabeled competing antibody to inhibit the binding of the labeled antibody to the plate is titrated. The results can be plotted, and the concentrations necessary to achieve the desired degree of binding inhibition are compared. In some embodiments, competition for binding to a target molecule can be determined, for example, using a real time, label-free bio-layer interferometry assay on the Octet HTX biosensor platform (Pall ForteBio Corp.).

For example, the IL12 antibody fragment can be formatted according to any of the formats described in Section 6.5.2 for targeting moieties. For example, the IL12 antibody fragment can be in the format of an scFv, as described in Section 6.5.2.1, or in the format a Fab, as described in Section 6.5.2.2. Other formats (e.g., nanobodies) can also suitably be used. In some embodiments, the VH of an scFV is N-terminal to the VL. In other embodiments, the VH of an scFv is C-terminal to the VL.

The antigen binding fragments of an anti-IL12 antibody can be incorporated into an IL12 receptor agonist having any of the configurations described herein. The IL12 receptor agonists are typically composed of a plurality of polypeptide chains, for example as represented by the Exemplary Monomers described in Section 6.2. As set forth in Section 6.2, IL12 antibody fragments can be incorporated into any one of Exemplary Monomers 8, 28, 33, and 59, forming Exemplary Monomers 54, 57, 58, and 55, respectively. Exemplary IL12 receptor agonists that incorporate one or more of Exemplary Monomers 54, 55, 57, and 58 are detailed in Section 6.2.

6.5. The Targeting Moiety

The incorporation of targeting moieties in the IL12 receptor agonists of the disclosure permits the delivery of high concentrations of IL12 into the tumor microenvironment or to tumor reactive lymphocytes (including CART lymphocytes) with a concomitant reduction of systemic exposure, resulting in fewer side effects than obtained with wild type IL12.

Suitable targeting moiety formats are described in Section 6.5.2. The targeting moiety is preferably an antigen binding moiety, for example an antibody or an antigen-binding portion of an antibody, e.g., an scFv, as described in Section 6.5.2.1, or a Fab, as described in Section 6.5.2.2.

The antibodies and antigen-binding portions generally bind to specific antigenic determinants and are able to direct the IL12 receptor agonist to a target site, for example to a specific type of tumor cell or tumor stroma that bears the antigenic determinant. Exemplary target molecules recognized by the targeting moieties of the disclosure are described in Section 6.5.1.

In other embodiments, the targeting moiety is a peptide-MHC complex, as described in Section 6.5.3, e.g., a peptide-MHC complex that is recognized by tumor lymphocytes.

6.5.1. Target Molecules

The target molecules recognized by the targeting moieties of the IL12 receptor agonists of the disclosure are generally found, for example, on the surfaces of activated T cells, on the surfaces of tumor cells, on the surfaces of virus-infected cells, on the surfaces of other diseased cells, free in blood serum, in the extracellular matrix (ECM), or immune cells present in the target site, e.g., tumor reactive lymphocytes. Where the immune cells are exogenously administered (e.g., chimeric antigen receptor ("CAR") expressing T cells), the targeting moiety can recognize the chimeric antigen receptor (CAR) or another molecule found on the surface of the CAR T cells. In various embodiments, the CAR comprises CDRs or VH and VL sequences (e.g., in the format of an scFv) that specifically recognize a TAA or a pMHC complex.

Exemplary target molecules are Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low affinity IgE receptor), CD30 (cytokine receptor), CD33 (myeloid cell surface antigen), CD40 (tumor necrosis factor receptor), IL-6R-(IL6 receptor), CD20, MCSP, PDGFβR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, CA166-9, the extra domain A (EDA) and extra domain B (EDB) of fibronectin and the A1 domain of tenascin-C (TnC A1).

In some embodiments, the target molecule is CD20. In such embodiments, the targeting moiety comprises an antibody binding domain of any known anti-CD20 antibody. In a non-limiting example, a CD20 targeting moiety comprises an antigen binding domain from the following heavy chain variable region (VH) and one of the following light chain variable regions (VL):

```
anti-CD20 VH
                                                   (SEQ ID NO: 7)
Glu Val Gln Leu Val Glu Ser Gly Gly Gly Leu Val Gln Pro Gly Arg

Ser Leu Arg Leu Ser Cys Val Ala Ser Gly Phe Thr Phe Asn Asp Tyr

Ala Met His Trp Val Arg Gln Ala Pro Gly Lys Gly Leu Glu Trp Val

Ser Val Ile Ser Trp Asn Ser Asp Ser Ile Gly Tyr Ala Asp Ser Val

Lys Gly Arg Phe Thr Ile Ser Arg Asp Asn Ala Lys Asn Ser Leu Tyr

Leu Gln Met His Ser Leu Arg Ala Glu Asp Thr Ala Leu Tyr Tyr Cys

Ala Lys Asp Asn His Tyr Gly Ser Gly Ser Tyr Tyr Tyr Tyr Gln Tyr

Gly Met Asp Val Trp Gly Gln Gly Thr Thr Val Thr Val Ser Ser;

anti-CD20 VL1
                                                   (SEQ ID NO: 8)
Ala Glu Ile Val Met Thr Gln Ser Pro Ala Thr Leu Ser Val Ser Pro

Gly Glu Arg Ala Thr Leu Ser Cys Arg Ala Ser Gln Ser Val Ser Ser

Asn Leu Ala Trp Tyr Gln Gln Lys Pro Gly Gln Ala Pro Arg Leu Leu

Ile Tyr Gly Ala Ser Thr Arg Ala Thr Gly Ile Pro Ala Arg Phe Ser

Gly Ser Gly Ser Gly Thr Glu Phe Thr Leu Thr Ile Ser Ser Leu Gln

Ser Glu Asp Phe Ala Val Tyr Tyr Cys Gln His Tyr Ile Asn Trp Pro

Leu Thr Phe Gly Gly Gly Thr Lys Val Glu Ile Lys;

anti-CD20 VL2
                                                   (SEQ ID NO: 9)
Glu Ile Val Met Thr Gln Ser Pro Ala Thr Leu Ser Val Ser Pro Gly

Glu Arg Ala Thr Leu Ser Cys Arg Ala Ser His Ser Val Ser Arg Asn

Ser Ala Trp Tyr Gln Gln Lys Pro Gly Gln Ala Pro Arg Leu Leu Ile
```

-continued

Tyr Gly Ala Ser Thr Arg Ala Thr Gly Ile Pro Ala Arg Phe Ser Gly

Ser Gly Ser Gly Thr Glu Phe Thr Leu Thr Ile Ser Ser Leu Gln Ser

Glu Asp Phe Ala Ile Tyr Tyr Cys Gln Gln Tyr Asn Asn Trp Pro Leu

Thr Phe Gly Gly Gly Thr Lys Val Glu Ile Lys;

anti-CD20 VL3

(SEQ ID NO: 10)

Glu Ile Val Met Thr Gln Ser Pro Ala Thr Leu Ser Val Ser Pro Gly

Glu Arg Ala Thr Leu Ser Cys Arg Ala Ser Gln Ser Val Ser Ser Asn

Leu Ala Trp Tyr Gln Gln Lys Pro Gly Gln Ala Pro Arg Leu Leu Ile

Tyr Gly Ala Ser Thr Arg Ala Thr Gly Ile Pro Ala Arg Phe Ser Gly

Ser Gly Ser Gly Thr Glu Phe Thr Leu Thr Ile Ser Ser Leu Gln Ser

Glu Asp Phe Ala Val Tyr Tyr Cys Gln His Tyr Ile Asn Trp Pro Leu

Thr Phe Gly Gly Gly Thr Lys Val Glu Ile Lys;

anti-CD20 VL4

(SEQ ID NO: 11)

Glu Ile Val Met Thr Gln Ser Pro Ala Thr Leu Ser Val Ser Pro Gly

Glu Arg Ala Thr Leu Ser Cys Arg Ala Ser Gln Ser Val Ser Arg Asn

Leu Ala Trp Tyr Gln Gln Lys Pro Gly Gln Ala Pro Arg Leu Leu Ile

Tyr Gly Ala Ser Thr Arg Ala Thr Gly Ile Pro Ala Arg Phe Ser Gly

Ser Gly Ser Gly Thr Asp Phe Thr Leu Thr Ile Ser Ser Leu Gln Ser

Glu Asp Phe Ala Val Tyr Tyr Cys Gln Gln Tyr Asn Asn Trp Pro Leu

Thr Phe Gly Gly Gly Thr Lys Val Val Ile Lys;

anti-CD20 VL5

(SEQ ID NO: 12)

Glu Ile Val Met Thr Gln Ser Pro Ala Thr Leu Ser Val Ser Pro Gly

Glu Arg Ala Thr Leu Ser Cys Arg Ala Ser Gln Arg Ile Ser Ser Asn

Leu Ala Trp Tyr Gln Gln Lys Pro Gly Gln Ala Pro Arg Leu Leu Ile

Tyr Gly Ala Ser Thr Arg Ala Thr Gly Ser Pro Ala Arg Phe Ser Gly

Ser Gly Ser Gly Thr Asp Phe Thr Leu Thr Ile Ser Ser Leu Gln Ser

Glu Asp Val Ala Val Tyr Tyr Cys Gln Gln His His Asn Trp Pro Leu

Thr Phe Gly Gly Gly Thr Lys Val Glu Ile Lys;

anti-CD20 VL6

(SEQ ID NO: 13)

Asp Ile Val Leu Thr Gln Ser Pro Ala Thr Leu Ser Leu Ser Pro Gly

Glu Arg Ala Thr Leu Ser Cys Arg Ala Ser Gln Ser Val Ser Tyr Met

Asn Trp Tyr Gln Gln Lys Pro Gly Lys Ala Pro Lys Arg Trp Ile Tyr

Asp Thr Ser Lys Val Ala Ser Gly Val Pro Ala Arg Phe Ser Gly Ser

Gly Ser Gly Thr Asp Tyr Ser Leu Thr Ile Asn Ser Leu Glu Ala Glu

Asp Ala Ala Thr Tyr Tyr Cys Gln Gln Trp Ser Ser Asn Pro Leu Thr

Phe Gly Gly Gly Thr Lys Val Glu Ile Lys.

Non-limiting examples of viral antigens include an EBV antigen (e.g., Epstein-Barr virus LMP-1), a hepatitis C virus antigen (e.g., hepatitis C virus E2 glycoprotein), an HIV antigen (e.g., HIV gp160, and HIV gp120); a CMV antigen; a HPV-specific antigen, or an influenza virus antigen (e.g., influenza virus hemagglutinin).

Non-limiting examples of ECM antigens include syndecan, heparanase, integrins, osteopontin, link, cadherins, laminin, laminin type EGF, lectin, fibronectin, extra domain B (ED-B) of fibronectin, notch, tenascin, collagen and matrixin.

Other target molecules are cell surface molecules of tumor or viral lymphocytes, for example T-cell co-stimulatory proteins such as CD27, CD28, 4-1BB (CD137), OX40, CD30, CD40, ICOS, lymphocyte function-associated antigen-1 (LFA-1), CD2, CD7, LIGHT, NKG2C, and B7-H3.

In particular embodiments, the target molecules are checkpoint inhibitors, for example CTLA-4, PD1, PDL1, PDL2, B7-H3, B7-H4, BTLA, HVEM, TIM3, GAL9, LAG3, VISTA, KIR, 2B4, CD160, CGEN-15049, CHK1, CHK2. In particular embodiments, the target molecule is PD1. In other embodiments, the target molecule is LAG3.

In some embodiments, the target molecule is PD1. In such embodiments, the targeting moiety comprises an antibody binding domain of any known anti-PD1 antibody. In a non-limiting example, a PD1 targeting moiety comprises an antigen binding domain from the following heavy chain variable region (VH) and light chain variable region (VL):

```
anti-1 PD1 VH
                                    (SEQ ID NO: 14)
Glu Val Gln Leu Leu Glu Ser Gly Gly Val

Leu Val Gln Pro Gly Gly Ser Leu Arg Leu

Ser Cys Ala Ala Ser Gly Phe Thr Phe Ser

Asn Phe Gly Met Thr Trp Val Arg Gln Ala
```

-continued

```
Pro Gly Lys Gly Leu Glu Trp Val Ser Gly

Ile Ser Gly Gly Gly Arg Asp Thr Tyr Phe

Ala Asp Ser Val Lys Gly Arg Phe Thr Ile

Ser Arg Asp Asn Ser Lys Asn Thr Leu Tyr

Leu Gln Met Asn Ser Leu Lys Gly Glu Asp

Thr Ala Val Tyr Tyr Cys Val Lys Trp Gly

Asn Ile Tyr Phe Asp Tyr Trp Gly Gln Gly

Thr Leu Val Thr Val Ser Ser;

anti-PD1 VL
                                    (SEQ ID NO: 15)
Asp Ile Gln Met Thr Gln Ser Pro Ser Ser

Leu Ser Ala Ser Val Gly Asp Ser Ile Thr

Ile Thr Cys Arg Ala Ser Leu Ser Ile Asn

Thr Phe Leu Asn Trp Tyr Gln Gln Lys Pro

Gly Lys Ala Pro Asn Leu Leu Ile Tyr Ala

Ala Ser Ser Leu His Gly Gly Val Pro Ser

Arg Phe Ser Gly Ser Gly Ser Gly Thr Asp

Phe Thr Leu Thr Ile Arg Thr Leu Gln Pro

Glu Asp Phe Ala Thr Tyr Tyr Cys Gln Gln

Ser Ser Asn Thr Pro Phe Thr Phe Gly Pro

Gly Thr Val Val Asp Phe Arg.
```

Additional CD20 and PD1 targeting moieties are set forth in Table 3 below.

In some embodiments, the targeting moieties target the exemplary target molecules set forth in Table 3 below, together with references to exemplary antibodies or antibody sequences upon which the targeting moiety can be based.

TABLE 3

Exemplary Target Molecules

| Target | Antibody Name and/or Binding Sequences |
|---|---|
| 1-92-LFA-3 | Amevive ™ (alefacept) |
| 5T4 | GEN1044 |
| Activin Receptor Type II | Bimagrumab<br>VH: SEQ ID NOs:107, 109 of U.S. Pat. No. 8,388,968 B2<br>VL: SEQ ID NOs:93, 95 of U.S. Pat. No. 8,388,968 B2 |
| B7-H3 | Obrindatamab (MGD009) |
| B7-H3 (CD276) | Enoblituzumab (MGA271) |
| B7-H3 (CD276) | MGC018 |
| B7-H3 (CD276) | MGA012 |
| B7-H3 (CD276) | 8H9 |
| B7-H3 (CD276) | VH: the VH sequence of the heavy chain of SEQ ID NO:21, 26 or 31 of US 2021/0171641 A1.<br>VL: the VL sequence of the light chain of SEQ ID NO:20, 22 or 30 of US 2021/0171641 A1. |
| B7-H3 (CD276) | VH: the VH sequence of the heavy chain of SEQ ID NO:21, 29 or 37 of US 2019/0002563 A1.<br>VL: the VL sequence of the light chain of SEQ ID NO:17, 25 or 33 of US 2019/0002563 A1. |
| B7-H3 (CD276) | VH: the VH sequence of the heavy chain of SEQ ID NO:146, 147 or 148 of U.S. Pat. No. 10,640,563.<br>VL: the VL sequence of the light chain of SEQ ID NO:143, 144 or 145 of U.S. Pat. No. 10,640,563. |
| BAFF/B Lymphocyte Stimulator | Benlysta ™ (velimumab) |
| BAFF/B Lymphocyte Stimulator | VH: amino acids 1-123 of SEQ ID NO:327 of U.S. Pat. No. 7,138,501 |

TABLE 3-continued

| Exemplary Target Molecules | |
|---|---|
| Target | Antibody Name and/or Binding Sequences |
| | VL: amino acids 139-249 of SEQ ID NO:327 of U.S. Pat. No. 7,138,501. |
| BAFF/B Lymphocyte Stimulator | VH: amino acids 1-126 of SEQ ID NO:1321 of U.S. Pat. No. 7,605,236;<br>VL: amino acids 143-251 of SEQ ID NO:1049 of U.S. Pat. No. 7,605,236. |
| BAFF/B Lymphocyte Stimulator | Belimumab |
| BCMA | VH: the VH sequence of the heavy chain of SEQ ID NO. 126 of US 2021/0206865 A1<br>VL: the VL sequence of the light chain of SEQ ID NO. 129 or SEQ ID NO. 132 of US 2021/0206865 A1 |
| CA125 | Igobumab |
| CA125 | OvaRex ™ (oregobumab) |
| Cadherin | The antibodies described in US Pub. No. US 2006/0039915. |
| N-cadherin | An antibody that binds to the amino acid sequence of SEQ ID NO: 10, 17 or 18 of US Pub. No. US 2010/0278821. |
| CD11a | Raptiva ™ (efalizumab)<br>Sequence in Werther et al., 1996, The Journal of Immunology 157(11): 4986-4995. |
| CD19 | Blincyto ™ (blinatumomab) |
| CD19 | SGN-CD19A |
| CD20 | Bexxar ™ (tositumomab)<br>VH: the VH sequence of the heavy chain of SEQ ID NO:124 of US Patent Pub. US 2017/0002060 A1<br>VL: the VL sequence of the light chain of SEQ ID NO:125 of US Patent Pub. US 2017/0002060 A1 |
| CD20 | Zevalin ™ (ibritumomab tiuxetan)<br>VH: SEQ ID NO:9 of U.S. Pat. No. 5,736,137<br>VL: SEQ ID NO:6 of U.S. Pat. No. 5,736,137 |
| CD20 | Rituxan ™ (rituximab)<br>VH: SEQ ID NO:9 of U.S. Pat. No. 5,736,137<br>VL: SEQ ID NO:6 of U.S. Pat. No. 5,736,137 |
| CD20 | Ocrevus ™ (ocrelizumab) |
| CD20 | Okaratuzumab |
| CD20 | Arzerra ™ (ofatumumab)<br>VH: SEQ ID NO:2 of U.S. Pat. No. 8,529,902<br>VL: SEQ ID NO:4 of U.S. Pat. No. 8,529,902 |
| CD20 | Gazyva ™ (obinutuzumab) |
| CD20 | VH: SEQ ID NO: 4 of US 2021/0206870 A1<br>VL of SEQ ID NO:6 of US 2021/0206870 A1 |
| CD20 | Epcoritamab |
| CD22 | Belimumab |
| CD22 | Epratuzumab |
| CD22 | Besponsa ™ (inotuzumab ozogamicin) |
| CD22 | Lumoxiti ™ (moxetumumab pasudox) |
| CD22 | pinatuzumab vedotin |
| CD25 | Zenapax ™ (daclizumab)<br>VH: SEQ ID NO:9 of U.S. Pat. No. 7,060,269<br>VL: SEQ ID NO:10 of U.S. Pat. No. 7,060,269 |
| CD30 | Adcetris ™ (brentuximab vedotin)<br>VH: SEQ ID NO:2 of U.S. Pat. No. 7,090,843<br>VL: SEQ ID NO:10 of U.S. Pat. No. 7,090,843 |
| CD33 | Myelotarg™ (gemtuzumab)<br>Sequence in Man Sung, et al., 1993, Molecular immunology 30:1361-1367 |
| CD33 | Lintuzumab |
| CD38 | Darzalex ™ (daratumumab) |
| CD40 | Lukatumumab |
| CD40 | Dacetuzumab |
| CD40L | Hu5c8 (ruplizumab) |
| CD44v6 | vibatuzumab mertansine |
| CD52 | Campath ™ (alemtuzumab)<br>VH: SEQ ID NO:1 of US Patent Pub. US 2017/0002060 A1<br>VL: SEQ ID NO:2 of US Patent Pub. US 2017/0002060 A1 |
| CD70 | Blenrep ™ (borsetuzumab mafodotin) |
| CD123 | Flotetuzumab |
| CD221 | Tepezza ™ (teprotumumab) |
| CEA | Hybri-Ceaker® (altumomab pentetate) |
| CEA | Scintimun ™ (besilesomab) |
| CEA | CEA-CIDE ™ (labetuzumab)) |
| CEA | CEA-Scan ™ (arcitumomab) |
| CEA | hMN-15<br>CDR-H1, CDR-H2 and CDR-H3 sequences of SEQ ID NOs:4-6 of U.S. Pat. No. 8,771,690 B2 |

TABLE 3-continued

| Exemplary Target Molecules | |
|---|---|
| Target | Antibody Name and/or Binding Sequences |
| | CDR-L1, CDR-L2 and CDR-L3 sequences of SEQ ID NOs:1-3 of U.S. Pat. No. 8,771,690 B2 |
| CEA | CEA binding portion of RO6958688/RG7802 from clinical trial NCT02324257 |
| CEA | Cibisatamab |
| CEA | CEA binding portion of MEDI-565/MT110/AMG211 from clinical trials NCT01284231 and NCT02291614<br>VH: SEQ ID NO:49 or 51 of PCT Publication No. WO 2013/012414 A1<br>VL: SEQ ID NO:48 of PCT Publication No. WO 2013/012414 A1. |
| CEA | Rabetuzumab |
| CEA | Atezolizumab |
| CEA | Cibisatamab |
| CEA | MEDI-565 (AMG211, MT111) |
| CEA | RO6958688! |
| CEA | VH: SEQ ID No. 9 described in WO2022/048883A1<br>VL: SEQ ID No. 10 described in WO2022/048883A1 |
| CLDN18.2 | AMG910 |
| Collagen alpha-4 chain | TRC093 (MT293) |
| Collagen | The collagen binding antibody fragment described in Liang, H. et al. A collagen-binding EGFR antibody fragment targeting tumors with a collagen-rich extracellular matrix. Sci. Rep. 5, 18205; doi: 10.1038/srep18205 (2016). |
| Collagen type I | Cetuximab (Erbitux) |
| Collagen type X | The amino acid sequences of SEQ ID NO: 1 or 2 of PCT Pub No. WO 2019/020797. |
| Collagen type X | The amino acid sequences of SEQ ID NO: 1 of PCT Pub No. WO 2014/180992. |
| Collagen type X | Antibody X34 as described in I. Girkontaite et al., "Immunolocalization of type X collagen in normal fetal and adult osteoarthritic cartilage with monoclonal antibodies," Matrix Biol 15, 231-238 (1996). |
| Collagen type X | Antibodies X53 or 1H8 or ARC0659 or JF0961 collagen X polyclonal antibody sold under catalog number PA5-115039 or PA5-116871 or PA5-97603 or PA5-49198 from ThermoFisher Scientific. |
| Collagen type X | Antibody sold under catalog number RDI-COLL10abr from RDI. |
| Complement C5 | Soliris ™ (eculizumab)<br>VH: amino acids 1-122 of SEQ ID NO: 10 of U.S. Pat. No. 6,355,245<br>VL: amino acids 3-110 of SEQ ID NO: 9 of U.S. Pat. No. 6,355,245 |
| CTLA-4 | Yervoy ™ (ipilimumab)<br>VH: SEQ ID NO: 17 of WO 2001/014424 A2<br>VL: SEQ ID NO: 7 of WO 2001/014424 A2 |
| CTLA-4 | (tremelimumab) |
| CTLA-4 | Orencia ™ (abatacept) |
| DLL3 | AMG757 |
| EGFR | Erbitux ™ (cetuximab)<br>VH: SEQ ID NO: 11 of U.S. Pat. No. 6,217,866<br>VL: SEQ ID NO: 13 of U.S. Pat. No. 6,217,866 |
| EGFR | Vectibix ™ (panitumumab)<br>VH: SEQ ID NO: 37 of U.S. Pat. No. 6,235,883<br>VL: SEQ ID NO: 38 of U.S. Pat. No. 6,235,883 |
| EGFR | Zalutumumab<br>VH: SEQ ID NO: 64 of WO 2018/140831 A2<br>VL: SEQ ID NO: 69 of WO 2018/140831 A2 |
| EGFR | mapatumumab |
| EGFR | Matuzumab |
| EGFR | Nimotuzumab<br>VH: SEQ ID NO: 51 of WO 2018/140831 A2<br>VL: SEQ ID NO: 56 of WO 2018/140831 A2 |
| EGFR | ICR62 |
| EGFR | mAb 528 |
| EGFR | CH806 |
| EGFRv3 | AMG596 |
| EGFRv3 | AMG404 |
| EGFR/CD64 | MDX-447 |
| EpCAM | Panorex ™ (edrecolomab)<br>VH: SEQ ID NO:129 of WO 2018/140831 A2<br>VL: SEQ ID NO:134 of WO 2018/140831 A2 |
| EpCAM | Adecatumumab<br>VH: SEQ ID NO:142 of WO 2018/140831 A2<br>VL: SEQ ID NO:147 of WO 2018/140831 A2 |
| EpCAM | tucotuzumab celmoleukin |
| EpCAM | citatuzumab bogatox |
| EpCAM | EP1629013 B1<br>VH: SEQ ID NOs: 80, 84, 88, 92 or 96<br>VL: SEQ ID NOs: 82, 86, 90, 94 or 98 |

TABLE 3-continued

Exemplary Target Molecules

| Target | Antibody Name and/or Binding Sequences |
|---|---|
| EpCAM | G8.8<br>HC: SEQ ID NO: 4 of US Patent Pub. No. US 2020/0317806 A1<br>HL: SEQ ID NO: 3 of US Patent Pub. No. US 2020/0317806 A1 |
| EpCAM | VH: SEQ ID NOs: 17-22 of WO 2021/211510 A2.<br>VL: SEQ ID NO: 15-16 of WO 2021/211510 A2. |
| EpCAM | Removab ™ (catumaxomab) |
| EpCAM | Vicineum ™ (oportuzumab monatox) |
| EpCAM | M701 |
| F protein of RSV | Synagic ™ (palivizumab) |
| GD2 | 3F8 |
| Glycoprotein receptor IIb/IIIa | ReoPro™ (abiciximab) |
| gpA33 | MGD007 |
| GPC3 | ERY974 |
| GUCY2C | PF-07062119 |
| Heparanase | An antibody selected from HP130, HP 239, HP 108.264, HP 115.140, HP 152.197, HP 110.662, HP 144.141, HP 108.371, HP 135.108, HP 151.316, HP 117.372, HP 37/33, HP3/17, HP 201 or HP 102 or an amino acid sequence of SEQ ID NO: 1-11 described in US Patent Pub. US 2004/0170631. |
| Her2 | Herceptin ™ (trastuzumab) |
| Her2 | Aldesleukin (proleukine) |
| Her2 | Sargramustim (leukine) |
| Her2 | M802 |
| Her2 | Runimotamab (BTRC4017A, R07227780) |
| Her2 | ISB1302 |
| Her2-neu | Perjeta™ (pertuzumab)<br>VH: SEQ ID NO: 16 of WO 2013/096812 A1.<br>VL: SEQ ID NO:15 of WO 2013/096812 A1. |
| Her2-neu | Rexomun ™ (ertumaxomab) |
| IgE | Xolair ™ (omalizumab) |
| IGFIR | (figitumumab) |
| IL1β | Ilaris ™ (canakinumab)<br>VH: SEQ ID NO:1 of U.S. Pat. No. 7,446,175.<br>VL: SEQ ID NO: 2 of U.S. Pat. No. 7,446,175 |
| IL1Rα | Antril ™, Kineret ™ (ankinra) |
| IL2R | Simulect™ (basiliximab)<br>VH: SEQ ID NO: 3 of U.S. Pat. No. 6,383,487<br>VL: SEQ ID NO: 6 of U.S. Pat. No. 6,383,487 |
| IL6 | Clazakizumab |
| IL6 receptor | Actemra™ (tocilizumab)<br>VH: SEQ ID NO: 31 of U.S. Pat. No. 7,479,543<br>VL: SEQ ID NO: 29 of U.S. Pat. No. 7,479,543 |
| Integrinα4 | Tysabri ™ (natalizumab)<br>VH: SEQ ID NOs: 11-13 of U.S. Pat. No. 5,840,299<br>VL: SEQ ID NOs: 7-8 of U.S. Pat. No. 5,840,299 |
| Integrinα4 β7 | Entyvio ™ (vedolizumab)<br>HC: SEQ ID NO: 2 of US Patent Pub. US 2012/0282249.<br>LC: SEQ ID NO: 4 of US Patent Pub. US 2012/0282249. |
| Integrinα5 β1 | VH: SEQ ID NO: 2 of European Patent No. 1 755 659.<br>VL: SEQ ID NO: 4 of European Patent No. 1 755 659. |
| Integrin β1 | VH: SEQ ID NO:2, 6, 8, 10, 12, 14, 29-43 or 91-100 of US Patent Pub. US 2022/0089744.<br>VL:, SEQ ID NO:4, 16, 18, 20, 22, 44-57 or 107-116 of US Patent Pub. US 2022/0089744. |
| LAG3 | Relatlimab (BMS-98016) |
| LAG3 | Sym022 |
| LAG3 | HLX26 |
| LAG3 | TSR-033 |
| LAG3 | ABL501 |
| LAG3 | INCAGN02385 |
| LAG3 | Fianlimab (REGN3767) |
| LAG3 | RO7247669 |
| LAG3 | EMB-02 |
| LAG3 | FS118 |
| LAG3 | GSK2831781 |
| LAG3 | IBI323 |
| LAG3 | IBI110 |
| LAG3 | LAG525 |
| LAG3 | XmAb ®22841 |
| LAG3 | LBL-007 |
| LAG3 | VH: SEQ ID NO:1, 8, 10 or 12 of U.S. Pat. No. 9,902,772.<br>VL: SEQ ID NO:2, 3, 4, 5, 6, 7, 9, 11, 13 or 14 of U.S. Pat. No. 9,902,772. |
| LAG3 | VH: SEQ ID NO: 182 of US Patent Pub. US 2021/0095026.<br>VL: SEQ ID NO: 88 of US Patent Pub. US 2021/0095026. |

TABLE 3-continued

Exemplary Target Molecules

| Target | Antibody Name and/or Binding Sequences |
|---|---|
| LAG3 | Antibodies having VH/VL amino acid sequences of SEQ ID NOs 23/24, 3/4 and 11/12 of US Pub. US2022/0056126A1. |
| Laminin | Lam-89 from Sigma Aldrich |
| Mesothelin | Amatuximab |
| Mesothelin | HPN536 |
| MUC1 | civatuzumab tetraxetane |
| MUC1 | Pankomab ™ (gatipotuzumab) |
| MUC1 | Femtumumab |
| MUC1 | Cantuzumab ravtansine |
| MUC16 (CA125) | Anti-MUC16 antibodies having VH and VL sequences having the amino acid sequences of any one of the following SEQ ID NO: pairs from US 2018/0118848A1: 18/26; 82/858; 98/170 |
| MUC17 | AMG199 |
| Nectin-4 | Enfortumab (ASP7465, ASG-22CE, ASG-22ME)<br>VH: SEQ ID NO:3 of PCT Pub. WO 2021/151984.<br>VL: SEQ ID NO: 4 of PCT Pub. WO 2021/151984. |
| Nectin-4 | SBT290 |
| Nectin-4 | VH: SEQ ID NO:1 of U.S. Pat. No. 11,274,160.<br>VL: SEQ ID NO:2 of U.S. Pat. No. 11,274,160. |
| NGF | (tanezumab) |
| Osteopontin | HC: SEQ ID NO: 22 of PCT Pub. WO 2021/030209.<br>LC: SEQ ID NO: 24 of PCT Pub. WO 2021/030209. |
| PD1 | MDX-1106/BMS-936558 (nivolumab), a human IgG4 mAb with the structure described in WHO Drug Information, Vol. 27, No. 1, pages 68-69 (2013) and whose heavy and light chain sequences are disclosed in FIG. 7 of US Pub. No. US20190270812A1 |
| PD1 | MK-3475 (pembrolizumab), a humanized IgG4 mAb with the structure described in WHO Drug Information, Vol. 27, No. 2, pages 161-162 (2013) and whose heavy and light chain sequences are disclosed in FIG. 6 of US Pub. No. US20190270812A1 |
| PD1 | REGN2810 (disclosed as H4H7798N in US Pub No. 20150203579) |
| PD1 | Anti-PD1 antibodies having CDR H1-H3 and CDR L1-L3 sequences corresponding to the following SEQ ID NOs. of U.S. Pat. No. 11,034,765 B2:<br>a) SEQ ID NOs: 18, 19, 20, 21, 22, and 23, respectively;<br>b) SEQ ID NOs: 24, 25, 26, 27, 28, and 29, respectively;<br>c) SEQ ID NOs: 30, 31, 32, 33, 34, and 35, respectively;<br>d) SEQ ID NOs: 36, 37, 38, 39, 40, and 41, respectively;<br>e) SEQ ID NOs: 42, 43, 44, 45, 46, and 47, respectively;<br>f) SEQ ID NOs: 48, 49, 50, 51, 52, and 53, respectively;<br>g) SEQ ID NOs: 54, 55, 56, 57, 58, and 59, respectively; and<br>h) SEQ ID NOs: 60, 61, 62, 63, 64, and 65, respectively. |
| PD1 | Anti-PD1 antibodies disclosed in Tables 1-3 of PCT Pub. WO2015112800A1, including but not limited to anti-PD1 antibodies having VH/VL pairs having SEQ ID NOs: 2/10, 18/26, 34/42, 50/58, 66/74, 82/90, 98/106, 1 14/122, 130/138, 146/154, 162/170, 178/186, 194/202, 210/202, 218/202, 226/202, 234/202, 242/202, 250/202, 258/202, 266/202, 274/202, 282/202, 290/202, 298/186, 306/186 and 314/186 of PCT Pub. WO2015112800A1. |
| PD1 | Anti-PD1 antibodies disclosed in U.S. Pat. No. 10,294,299 B2 as having the following SEQ ID NO. pair for heavy and light chain variable domains:<br>SEQ ID NOs. 164/178<br>SEQ ID NOs. 165/179<br>SEQ ID NOs. 166/180<br>SEQ ID NOs. 167/181<br>SEQ ID NOs. 168/182<br>SEQ ID NOs. 169/183<br>SEQ ID NOs. 170/184<br>SEQ ID NOs. 171/185<br>SEQ ID NOs. 172/186<br>SEQ ID NOs. 173/187<br>SEQ ID NOs. 174/188<br>SEQ ID NOs. 175/189<br>SEQ ID NOs. 176/190<br>SEQ ID NOs. 177/190 |
| PD1 | MEDI-0680 (AMP-514) |
| PD1 | PDR001 |
| PD1 | BGB-108 |
| PD1 | h409A11, described in WO2008/156712 |
| PD1 | h409A16, described in WO2008/156712 |
| PD1 | h409A17, described in WO2008/156712 |
| PD1 | Anti-PD1 antibodies described in U.S. Pat. No. 7,488,802 |
| PD1 | Anti-PD1 antibodies described in U.S. Pat. No. 7,521,051 |
| PD1 | Anti-PD1 antibodies described in U.S. Pat. No. 8,008,449 |
| PD1 | Anti-PD1 antibodies described in U.S. Pat. No. 8,354,509 |

TABLE 3-continued

| Exemplary Target Molecules | |
|---|---|
| Target | Antibody Name and/or Binding Sequences |
| PD1 | Anti-PD1 antibodies described in U.S. Pat. No. 8,168,757 |
| PD1 | Anti-PD1 antibodies described in PCT Pub. No. W02004/004771 |
| PD1 | Anti-PD1 antibodies described in PCT Pub. No. W02004/056875 |
| PD1 | Anti-PD1 antibodies described in PCT Pub. No. W02004/072286 |
| PD1 | Anti-PD1 antibodies described in US Pub. No. US2011/0271358 |
| PDL1 | Durvalumab (MEDI4736) |
| PDL1 | Atezolizumab (Tecentriq, MPDL3280A)) |
| PDL1 | MDX 1105 (BMS-936559) |
| PDL1 | Avelumab |
| PDL1 | ZKAB001 (Socazolimab) |
| PDL1 | TQB2450 |
| PDL1 | MEDI4736 |
| PDL1 | HLX20 |
| PDL1 | KN035 |
| PDL1 | LY3434172 |
| PDL1 | LY3300054 |
| PDL1 | LDP |
| PDL1 | EMB-09 |
| PDL1 | ABL501 |
| PDL1 | INBRX-105 |
| PDL1 | SHR-1210 |
| PDL1 | STI-3031 (IMC-001) |
| PDL1 | MPDL3280A (RG7446) |
| PDL1 | KN035 |
| PDL1 | BGB-A333 |
| PDL1 | HLX301 |
| PDL1 | Y101D |
| PDL1 | ES101 |
| PDL1 | IBI322 |
| PDL1 | Envafolimab |
| PDL1 | VH: SEQ ID NO:46, 48, 50 or 52 of U.S. Pat. No. 11,168,144.<br>VL: SEQ ID NO:58, 137 or 12 of U.S. Pat. No. 11,168,144. |
| PDL1 | VH: SEQ ID NO:23, 124, 126, 127, 128, 130, 140 or 145 of U.S. Pat. No. 11,208,486.<br>VL: SEQ ID NO:24 or 125 of U.S. Pat. No. 11,208,486. |
| Phosphatidylserine | (bavituximab) |
| PSCA | GEM3PSCA |
| PSMA | huJ591 |
| PSMA | Anti-PSMA antibodies having VH and VL sequences having the amino acid sequences of any one of the following SEQ ID NO: pairs from WO 2017/023761A1: 2/1642; 10/1642; 18/1642; 26/1642; 34/1642; 42/1642; 50/1642; 58/1642; 66/1642; 74/1642; 82/1642; 90/1642; 98/1642; 106/1642; 1 14/1642; 122/130; and 138/146. |
| PSMA | An antibody such as: PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgemx 4.219.3, Abgenix 4.288.1, Abgenix 4.333.1, Abgemx 4.54.1, Abgenix 4.153.1, Abgenix 4.232.3, Abgenix 4.292.3, Abgenix 4.304.1, Abgenix 4.78.1 and Abgenix 4.152.1 described in WO2003034903A2<br>A hybridoma cell line such as: PSMA 3.7 (PTA-3257), PSMA 3.8, PSMA 3.9 (PTA- 3258), PSMA 3.11 (PTA-3269), PSMA 5.4 (PTA-3268), PSMA 7.1 (PTA-3292), PSMA 7.3 (PTA-3293), PSMA 10.3 (PTA-3247) , PSMA 1.8.3 (PTA-3906), PSMA A3.1.3 (PTA- 3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgemx 4.152.1 (PTA-4653) described in WO 2003/034903A2.<br>VH of SEQ ID NOs: 2-7 described in WO 2003/034903A2<br>VL of SEQ ID NOs: 8-13 described in WO 2003/034903A2 |
| PMSA | VH: SEQ ID NOs: 225, 239, 253, 267, 281, 295, 309, 323, 337, 351, 365, 379, 393, 407, 421, 435, 449, 463, 477, 491, 505, 519, 533, 547, 561, 575, 589, 603 or 617 described in WO 2011/121110A1.<br>VL SEQ ID NOs: 230, 244, 258, 272, 286, 300, 314, 328, 342, 356, 370, 384, 398, 412, 426, 440, 454, 468, 482, 496, 510, 524, 538, 552, 566, 580, 594, 608 or 622 described in WO 2011 /121110A1.<br>VH and VL SEQ ID Nos: 235, 249, 263, 277, 291, 305, 319, 333, 347, |

TABLE 3-continued

| Exemplary Target Molecules | |
|---|---|
| Target | Antibody Name and/or Binding Sequences |
| | 361, 375, 389, 403, 417, 431, 445, 459, 473, 487, 501, 515, 529, 543, 557, 571, 585, 599, 613 or 627 described in WO 2011/121110A1. |
| PMSA | An anti-PMSA antibody having a VL amino acid sequence of any one of SEQ ID NOs: 229-312 of US 2022/0119525 A1 and a VH of SEQ ID NO: 217 of US 2022/0119525 A1. |
| PMSA | ES414 |
| PMSA | BAY2010112 (pasotuxizumab) |
| PMSA | CCW702 |
| PMSA | JNJ-63898081 |
| PMSA | CC-1 |
| PMSA | Acapatamab |
| PSMA | HPN424 |
| RAAG12 | RAV12 |
| RANKL | Prolia ™ (denosumab)<br>VH: SEQ ID NO:51 of US Patent Pub. 2017/0002060<br>VL: SEQ ID NO:52 of US Patent Pub. 2017/0002060 |
| SLAMF7 | Empliciti ™ (elotuzumab) |
| SSTR2 | XmAb ® 18087 |
| STEAP1 | VHCDR1 SEQ ID NOs: 14, 33, 182, 184 or 185 described in US20210179731A1.<br>VHCDR2 SEQ ID NOs: 15, 21, 34, 182, 184 or 185 described in US20210179731A1.<br>VHCDR3 SEQ ID NOs: 16 and 35 described in US20210179731A1.<br>VH SEQ ID NOs: 182 or 184 described in US20210179731A1.<br>VLCDR1 SEQ ID NOs: 11 or 30 described in US20210179731A1.<br>VLCDR2 SEQ ID NOs: 12 or 31 described in US20210179731A1.<br>VLCDR3 SEQ ID NOs: 13 or 32 described in US20210179731A1.<br>VL SEQ ID NOs: 183 or 186 described in US20210179731A1. |
| STEAP1 | AMG509 |
| STEAP2 | Anti-STEAP 2 antibodies having CDR-H1, CDR-H2, CDR-H3, CDR-L1, CDR-L2 and CDR-L3 sequences selected from SEQ ID NOS: (1) 4-6-8-12-14-16; (2) 20-22-24-28-30-32; (3) 36-38-40-44-46-48; (4) 52-54-56-60-62-64; (5) 68-70-72-60-62-64; (6) 76-78-80-60-62-64; (7) 84-86-88-60-62-64; (8) 92-94-96-60-62-64; (9) 100-102-104-60-62-64; (10) 108-110-112-116-118-120; (11) 124-126-128-132-134-136; (12) 140-142-144-148-150-152; (13) 156-158-160-164-166-168; (14) 172-174-176-180-182-184; (15) 188-190-192-196-198-200; (16) 204-206-208-212-214-216; (17) 220-222-224-228-230-232; (18) 236-238-240-244-246-248; (19) 252-254-256-260-262-264; (20) 268-270-272-276-278-280; (21) 284-286-288-292-294-296; (22) 300-302-304-308-310-312; (23) 316-318-320-324-326-328; (24) 332-334-336-340-342-344; (25) 348-350-352-356-358-360; (26) 364-366-368-372-374-376; and (27) 380-382-384-388-390-392 of U.S. Pat. No. 10,772,972 B2.<br>Anti-STEAP 2 antibodies having (a) a VH comprising the amino acid of any one of SEQ ID NOs: 2, 18, 34, 50, 66, 74, 82, 90, 98, 106, 122, 138, 154, 170, 186, 202, 218, 234, 250, 266, 282, 298, 314, 330, 346, 362, and 378 of U.S. Pat. No. 10,772,972 B2; and (b) a VL comprising the amino acid sequence of any one of SEQ ID NOs: 10; 26; 42; 58; 114; 130; 146; 162; 178; 194; 210; 226, 242; 258; 274; 290; 306; 322; 338; 354; 370; and 386 of U.S. Pat. No. 10,772,972 B2.<br>Anti-STEAP 2 antibodies having a VH/VL pair comprising the amino acid sequences of any of the following pairs of SEQ ID NOs of U.S. Pat. No. 10,772,972 B2: 2/10; 18/26; 34/42; 50/58; 66/58; 74/58; 82/58; 90/58; 98/58; 106/114; 122/130; 138/146; 154/162; 170/178; 186/194; 202/210; 218/226; 234/242; 250/258; 266/274; 282/290; 298/306; 314/322; 330/338; 346/354; 362/370; and 378/386. |
| Syndecan-1 (CD 138) | The B-B4 antibody described in Wijdenes et al. (1996) Br. J. Haematol., 94: 318-323 |
| Syndecan-4 | The amino acid sequence of amino acids 93 and 121 of SEQ ID NO: 1 or the amino acid sequence of amino acids 92 and 122 of SEQ ID NO:2 described in European Patent Pub. EP 2 603 236. |
| TGFβ | GC1008 |
| TNFR | Enbrel ™ (etanercept) |
| TNFα | Remicade ™ (infliximab)<br>VH: SEQ ID NO:2 of Int. Patent Publication WO201/3087911 A1<br>VH: SEQ ID NO:3 of Int. Patent Publication WO2013/ A1087911 |
| TNFα | Humira ™ (adalimumab)<br>VH: SEQ ID NO:4 of U.S. Pat. No. 6,258,562<br>VL: SEQ ID NO:3 of U.S. Pat. No. 6,258,562 |
| TNFα | Cimzia ™ (certolizumab pegol)<br>VH: SEQ ID NO:14 of U.S. Pat. No. 7,012,135<br>VL: SEQ ID NO:9 of U.S. Pat. No. 7,012,135 |
| TNFα | Simponi™ (golimumab)<br>VH: SEQ ID NO:7 of U.S. Pat. No. 7,250,165<br>VL: SEQ ID NO:8 of U.S. Pat. No. 7,250,165 |

TABLE 3-continued

| Exemplary Target Molecules | |
|---|---|
| Target | Antibody Name and/or Binding Sequences |
| VEGF | Avastin ™ (bevacizumab)<br>VH: SEQ ID NO:9 of U.S. Pat. No. 7,060,269<br>VL: SEQ ID NO:10 of U.S. Pat. No. 7,060,269 |
| VEGF | Lucentis ™ (ranibizumab)<br>VH: SEQ ID NO:4 of U.S. Pat. No. 9,914,770<br>VL: SEQ ID NO:2 of U.S. Pat. No. 9,914,770 |

In some aspects, the targeting moiety competes with an antibody set forth above, including in Table 3, for binding to the target molecule. In further aspects, the targeting moiety comprises CDRs having CDR sequences of an antibody set forth above, including in Table 3. In some embodiments, the targeting moiety comprises all 6 CDR sequences of the antibody set forth above, including the antibody set forth in Table 3. In other embodiments, the targeting moiety comprises at least the heavy chain CDR sequences (CDR-H1, CDR-H2, CDR-H3) of such antibody and the light chain CDR sequences of a universal light chain. In further aspects, a targeting moiety comprises a VH comprising the amino acid sequence of the VH of an antibody set forth above, e.g., in Table 3. In some embodiments, the targeting moiety further comprises a VL comprising the amino acid sequence of the VL of the antibody set forth above, e.g., in Table 3. In other embodiments, the targeting moiety further comprises a universal light chain VL sequence.

In some embodiments, the checkpoint inhibitor targeting moiety is non-blocking or poorly-blocking of ligand-receptor binding. Examples of non-blocking or poorly-blocking anti-PD1 antibodies includes antibodies having VH/VL amino acid sequences of SEQ ID NOs: 2/10 of PCT Pub. No. WO2015/112800A1; SEQ ID NOs: 16/17 of U.S. Pat. No. 11,034,765 B2; SEQ ID NOs. 164/178, 165/179, 166/180, 167/181, 168/182, 169/183, 170/184, 171/185, 172/186, 173/187, 174/188, 175/189, 176/190 and 177/190 of U.S. Pat. No. 10,294,299 B2. Examples of non-blocking or poorly-blocking anti-LAG3 antibodies includes antibodies having VH/VL amino acid sequences of SEQ ID NOs 23/24, 3/4 and 11/12 of US Pub. US2022/0056126A1.

Additional target molecules that can be targeted by the IL12 receptor agonists are disclosed in Table 6 below and in, e.g., Hafeez et al., 2020, Molecules 25:4764, doi:10.3390/molecules25204764, particularly in Table 1. Table 1 of Hafeez et al. is incorporated by reference in its entirety herein.

6.5.2. Targeting Moiety Format

In certain aspects, the targeting moiety can be any type of antibody or fragment thereof that retains specific binding to an antigenic determinant. In one embodiment the antigen binding moiety is a full-length antibody. In one embodiment the antigen binding moiety is an immunoglobulin molecule, particularly an IgG class immunoglobulin molecule, more particularly an $IgG_1$ or $IgG_4$ immunoglobulin molecule. Antibody fragments include, but are not limited to, VH (or $V_H$) fragments, VL (or $V_L$) fragments, Fab fragments, $F(ab')_2$ fragments, scFv fragments, Fv fragments, minibodies, diabodies, triabodies, and tetrabodies.

6.5.2.1. scFv

Single chain Fv or "scFv" antibody fragments comprise the VH and VL domains of an antibody in a single polypeptide chain, are capable of being expressed as a single chain polypeptide, and retain the specificity of the intact antibodies from which they are derived. Generally, the scFv polypeptide further comprises a polypeptide linker between the VH and VL domain that enables the scFv to form the desired structure for target binding. Examples of linkers suitable for connecting the VH and VL chains of an scFv are the linkers identified in Section 6.5.3.

Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The scFv can comprise VH and VL sequences from any suitable species, such as murine, human or humanized VH and VL sequences.

To create an scFv-encoding nucleic acid, the VH and VL-encoding DNA fragments are operably linked to another fragment encoding a linker, e.g., encoding any of the linkers described in Section 6.5.3 (typically a repeat of a sequence containing the amino acids glycine and serine, such as the amino acid sequence $(Gly4\sim Ser)_3$ (SEQ ID NO: 16), such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348:552-554).

6.5.2.2. Fab

Fab domains were traditionally produced by proteolytic cleavage of immunoglobulin molecules using enzymes such as papain. In the IL12 receptor agonists of the disclosure, the Fab domains are typically recombinantly expressed as part of the IL12 receptor agonist.

The Fab domains can comprise constant domain and variable region sequences from any suitable species, and thus can be murine, chimeric, human or humanized.

Fab domains typically comprise a CH1 domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

For the IL12 receptor agonists of the disclosure, particularly when the light chain is not a common or universal light chain, it is advantageous to use Fab heterodimerization strategies to permit the correct association of Fab domains belonging to the same ABD and minimize aberrant pairing of Fab domains belonging to different ABDs. For example, the Fab heterodimerization strategies shown in Table 4 below can be used:

TABLE 4

Fab Heterodimerization Strategies

| STRATEGY | VH | CH1 | VL | CL | REFERENCE |
|---|---|---|---|---|---|
| CrossMabCH1-CL | WT | CL domain | WT | CH1 domain | Schaefer et al., 2011, Cancer Cell 2011; 20:472-86; PMID:22014573. |
| orthogonal Fab VHVRD1CH1CRD2-VLVRD1CλCRD2 | 39K, 62E | H172A, F174G | 1R, 38D, (36F) | L135Y, S176W | Lewis et al., 2014, Nat Biotechnol 32:191-8 |
| orthogonal Fab VHVRD2CH1wt - VLVRD2CλWt | 39Y | WT | 38R | WT | Lewis et al., 2014, Nat Biotechnol 32:191-8 |
| TCR CαCβ | 39K | TCR Cα | 38D | TCR Cβ | Wu et al., 2015, MAbs 7:364-76 |
| CR3 | WT | T192E | WT | N137K, S114A | Golay at al., 2016, J Immunol 196:3199-211. |
| MUT4 | WT | L143Q, S188V | WT | V133T, S176V | Golay at al., 2016, J Immunol 196:3199-211. |
| DuetMab | WT | F126C | WT | S121C | Mazor et al., 2015, MAbs 7:377-89; Mazor et al., 2015, MAbs 7:461-669. |
| Domain exchanged | WT | CH3 + knob or hole mutation | WT | CH3 + hole or knob mutation | Wozniak-Knopp et al., 2018, PLoSONE13(4):e0195442 |

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or more amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179, the contents of which are hereby incorporated by reference.

In some embodiments, the Fab domain comprises a 192E substitution in the CH1 domain and 114A and 137K substitutions in the CL domain, which introduces a salt-bridge between the CH1 and CL domains (see, e.g., Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, e.g., Golay et al., 2016, J Immunol 196:3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1 R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121 C in the CL domain (see, e.g., Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the a T cell receptor and substituting the CL domain with the b domain of the T cell receptor, and pairing these domain replacements with an additional charge-charge interaction between the VL and VH domains by introducing a 38D modification in the VL domain and a 39K modification in the VH domain.

In lieu of, or in addition to, the use of Fab heterodimerization strategies to promote correct VH-VL pairings, the VL of common light chain (also referred to as a universal light chain) can be used for each Fab VL region of an IL12 receptor agonist of the disclosure. In various embodiments, employing a common light chain as described herein reduces the number of inappropriate species of IL12 receptor agonists as compared to employing original cognate VLs. In various embodiments, the VL domains of the IL12 receptor agonists are identified from monospecific antibodies comprising a common light chain. In various embodiments, the VH regions of the IL12 receptor agonists comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate an antibody repertoire containing a plurality of human VHs that are cognate with one or one of two possible human VLs, wherein the antibody repertoire specific for the antigen of interest. Common light chains are those derived from a rearranged human Vκ1-39Jκ5 sequence or a rearranged human Vκ3-20Jκ1 sequence, and include somatically mutated (e.g., affinity matured) versions. See, for example, U.S. Pat. No. 10,412,940.

6.5.3. MHC-Peptide Fusions

The targeting moiety of an IL12 receptor agonist of the disclosure can be a peptide-MHC complex (a "pMHC complex"), e.g., a peptide complexed with an MHC class I domain or a peptide complexed with an MHC class II domain, in each case optionally with a β2 microglobulin domain.

The peptide in the pMHC complex can have the amino acid sequence of a peptide which can be associated with, e.g., presented by, an MHC class I molecule. In certain embodiments, the sequence can comprise from 6 to 20 contiguous amino acids. In certain embodiments, a peptide sequence can be that of a protein fragment, wherein the protein is a derived from, e.g., a portion of, a cellular protein, such as, for example, a protein associated with cancer or cancer neoantigen, and wherein the peptide can be bound to the MHC class I heavy chain.

In some embodiments, a pMHC complex targeting moiety comprises an antigenic peptide, MHC polypeptide or a fragment, mutant or derivative thereof, and optionally, a β2 microglobulin polypeptide or a fragment, mutant or derivative thereof having features and/or configurations described in Section 6.4.3 of PCT Pub. WO 2021/127487 A2, which section is specifically incorporated by reference herein. In some embodiments, one or more components of a pMHC complex are connected via a pMHC linker as described in Section 6.7.1 of PCT Pub. WO 2021/127487 A2, which section is specifically incorporated by reference herein.

The peptides in the pMHC complexes of the disclosure typically at least a portion, e.g., an antigenic determinant, of proteins of infectious agents (e.g., bacterial, viral or parasitic organisms), allergens, and tumor associated proteins. Preferably, the pMHC complexes comprise an antigenic determinant of cancer cells. Exemplary antigenic determinants of cancer cells include Exemplary antigenic determinants of cancer cells include LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYES01 (157-165, C165A), NYES1 (157-165, C165V), p54 WT (264-272), PAP-3 (136-143), PSMA (4-12), PSMA (135-145), Survivin (96-014), Tyrosinase (369-377, 371 D), and WT1 (126-134). Further antigenic determinant of cancer cells are described in Section 6.4.3 and Table 3 of PCT Pub. WO 2021/127487 A2, which section and table are specifically incorporated by reference herein.

6.6. The Multimerization Moiety 6.6.1. Fc Domains

In some embodiments, the IL12 agonists and IL12 monomers of the disclosure include one or more multimerization moieties, for example one or more multimerization moieties that are or comprise an Fc domain. In certain embodiments, an IL12 monomer of the disclosure comprises a single multimerization moiety (e.g., a single Fc domain) and/or an IL12 agonist of the disclosure comprises two multimerization moieties (e.g., two Fc domains that can associate to form an Fc region).

The IL12 receptor agonists and IL12 monomers of the disclosure can include an Fc domain, or a pair of Fc domains that associate to form an Fc region, derived from any suitable species operably linked to an IL12 moiety. In one embodiment the Fc domain is derived from a human Fc domain. In preferred embodiments, the IL12 moiety is fused to an IgG Fc molecule.

The IL12 moiety may be fused to the N-terminus or the C-terminus of the IgG Fc domain. As shown in the Examples, IL12 agonists comprising IL12 moieties fused to the C-terminus of the IgG Fc domain maintains the IL12 activity to a greater extent than when the IL12 moieties are fused to the N-terminus of the IgG Fc.

One embodiment of the present disclosure is directed to a dimer comprising two Fc-fusion polypeptides created by fusing one or more IL12 moieties (e.g., a p35 moiety and a p40 moiety) to the Fc region of an antibody, e.g., by fusing both a p35 moiety and a p40 moiety to an Fc domain that can upon expression form an IL12 monomer capable of homodimerization or by fusing p35 moiety to a first Fc domain and a p40 moiety to a second Fc domain that upon expression form two different IL12 monomers that are capable of heterodimerizing. The dimer can be made by, for example, inserting a gene fusion encoding the fusion protein(s) into an appropriate expression vector, expressing the gene fusion(s) in host cells transformed with the recombinant expression vector, and allowing the expressed fusion protein(s) to assemble much like antibody molecules, whereupon interchain bonds form between the Fc moieties to yield the dimer.

The Fc domains that can be incorporated into IL12 monomers can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from IgG1, IgG2, IgG3 or IgG4. In one embodiment the Fc domain is derived from IgG1. In one embodiment the Fc domain is derived from IgG4.

The two Fc domains within the Fc region can be the same or different from one another. In a native antibody the Fc domains are typically identical, but for the purpose of producing multispecific binding molecules, e.g., the IL12 receptor agonists of the disclosure, the Fc domains might advantageously be different to allow for heterodimerization, as described in Section 6.6.1.2 below.

In native antibodies, the heavy chain Fc domain of IgA, IgD and IgG is composed of two heavy chain constant domains (CH2 and CH3) and that of IgE and IgM is composed of three heavy chain constant domains (CH2, CH3 and CH4). These dimerize to create an Fc region.

In IL12 receptor agonists of the present disclosure, the Fc region, and/or the Fc domains within it, can comprise heavy chain constant domains from one or more different classes of antibody, for example one, two or three different classes.

In one embodiment the Fc region comprises CH2 and CH3 domains derived from IgG1.

In one embodiment the Fc region comprises CH2 and CH3 domains derived from IgG2.

In one embodiment the Fc region comprises CH2 and CH3 domains derived from IgG3.

In one embodiment the Fc region comprises CH2 and CH3 domains derived from IgG4.

In one embodiment the Fc region comprises a CH4 domain from IgM. The IgM CH4 domain is typically located at the C-terminus of the CH3 domain.

In one embodiment the Fc region comprises CH2 and CH3 domains derived from IgG and a CH4 domain derived from IgM.

It will be appreciated that the heavy chain constant domains for use in producing an Fc region for the IL12 receptor agonists of the present disclosure may include variants of the naturally occurring constant domains described above. Such variants may comprise one or more amino acid variations compared to wild type constant domains. In one example the Fc region of the present disclosure comprises at least one constant domain that varies in sequence from the wild type constant domain. It will be appreciated that the variant constant domains may be longer or shorter than the wild type constant domain. Preferably the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the IL12 receptor agonists of the present disclosure do not comprise a tailpiece.

The Fc domains that are incorporated into the IL12 receptor agonists of the present disclosure may comprise one or more modifications that alter the functional properties of the proteins, for example, binding to Fc-receptors such as FcRn or leukocyte receptors, binding to complement, modified disulfide bond architecture, or altered glycosylation patterns. Exemplary Fc modifications that alter effector function are described in Section 6.6.1.1

The Fc domains can also be altered to include modifications that improve manufacturability of asymmetric IL12 receptor agonists, for example by allowing heterodimerization, which is the preferential pairing of non-identical Fc domains over identical Fc domains. Heterodimerization permits the production of IL12 receptor agonists in which different polypeptide components are connected to one another by an Fc region containing Fc domains that differ in sequence. Examples of heterodimerization strategies are exemplified in Section 6.6.1.2.

It will be appreciated that any of the modifications mentioned above can be combined in any suitable manner to achieve the desired functional properties and/or combined with other modifications to alter the properties of the IL12 receptor agonists.

6.6.1.1. Fc Domains with Altered Effector Function

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

In one embodiment, the Fc domain (e.g., an Fc domain of an IL12 monomer) or the Fc region (e.g., one or both Fc domains of an IL12 receptor agonist that can associate to form an Fc region) comprises an amino acid substitution at a position selected from the group of E233, L234, L235, N297, P331 and P329 (numberings according to Kabat EU index). In a more specific embodiment, the Fc domain or the Fc region comprises an amino acid substitution at a position selected from the group of L234, L235 and P329 (numberings according to Kabat EU index). In some embodiments, the Fc domain or the Fc region comprises the amino acid substitutions L234A and L235A (numberings according to Kabat EU index). In one such embodiment, the Fc domain or region is an Igd Fc domain or region, particularly a human Igd Fc domain or region. In one embodiment, the Fc domain or the Fc region comprises an amino acid substitution at position P329. In a more specific embodiment, the amino acid substitution is P329A or P329G, particularly P329G (numberings according to Kabat EU index). In one embodiment, the Fc domain or the Fc region comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain or the Fc region comprises amino acid substitutions at positions P329, L234 and L235 (numberings according to Kabat EU index). In more particular embodiments, the Fc domain comprises the amino acid mutations L234A, L235A and P329G ("P329G LALA", "PGLALA" or "LALAPG").

Typically, the same one or more amino acid substitution is present in each of the two Fc domains of an Fc region.

Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc domain. In some embodiments, the IgG1 Fc domain is a variant IgG1 comprising D265A, N297A mutations (EU numbering) to reduce effector function.

In another embodiment, the Fc domain is an IgG4 Fc domain with reduced binding to Fc receptors. Exemplary IgG4 Fc domains with reduced binding to Fc receptors may comprise an amino acid sequence selected from Table 5 below: In some embodiments, the Fc domain includes only the bolded portion of the sequences shown below:

TABLE 5

| Fc Domain | Sequence |
|---|---|
| SEQ ID NO: 1 of WO2014/121087 | Asp Lys Arg Val Glu Ser Lys Tyr Gly Pro Cys Pro Pro Cys Pro<br>Ala Pro Pro Val Ala Gly Pro Ser Val Phe Leu Phe Pro Pro Lys<br>Pro Lys Asp Thr Leu Met Ile Ser Arg Thr Pro Glu Val Thr Cys<br>Val Val Val Asp Val Ser Gln Glu Asp Pro Glu Val Gln Phe Asn<br>Trp Tyr Val Asp Gly Val Glu Val His Asn Ala Lys Thr Lys Pro<br>Arg Glu Glu Gln Phe Asn Ser Thr Tyr Arg Val Val Ser Val Leu<br>Thr Val Leu His Gln Asp Trp Leu Asn Gly Lys Glu Tyr Lys Cys<br>Lys Val Ser Asn Lys Gly Leu Pro Ser Ser Ile Glu Lys Thr Ile<br>Ser Lys Ala Lys Gly Gln Pro Arg Glu Pro Gln Val Tyr Thr Leu<br>Pro Pro Ser Gln Glu Glu Met Thr Lys Asn Gln Val Ser Leu Thr<br>Cys Leu Val Lys Gly Phe Tyr Pro Ser Asp Ile Ala Val Glu Trp<br>Glu Ser Asn Gly Gln Pro Glu Asn Asn Tyr Lys Thr Thr Pro Pro<br>Val Leu Asp Ser Asp Gly Ser Phe Phe Leu Tyr Ser Arg Leu Thr<br>Val Asp Lys Ser Arg Trp Gln Glu Gly Asn Val Phe Ser Cys Ser<br>Val Met His Glu Ala Leu His Asn His Tyr Thr Gln Lys Ser Leu<br>Ser Leu Ser Leu Gly Lys (SEQ ID NO: 17) |
| SEQ ID NO: 2 of WO2014/121087 | Asp Lys Lys Val Glu Pro Lys Ser Cys Asp Lys Thr His Thr Cys<br>Pro Pro Cys Pro Ala Pro Pro Val Ala Gly Pro Ser Val Phe Leu<br>Phe Pro Pro Lys Pro Lys Asp Thr Leu Met Ile Ser Arg Thr Pro<br>Glu Val Thr Cys Val Val Val Asp Val Ser Gln Glu Asp Pro Glu<br>Val Gln Phe Asn Trp Tyr Val Asp Gly Val Glu Val His Asn Ala<br>Lys Thr Lys Pro Arg Glu Glu Gln Phe Asn Ser Thr Tyr Arg Val<br>Val Ser Val Leu Thr Val Leu His Gln Asp Trp Leu Asn Gly Lys<br>Glu Tyr Lys Cys Lys Val Ser Asn Lys Gly Leu Pro Ser Ser Ile<br>Glu Lys Thr Ile Ser Lys Ala Lys Gly Gln Pro Arg Glu Pro Gln<br>Val Tyr Thr Leu Pro Pro Ser Arg Asp Glu Leu Thr Lys Asn Gln<br>Val Ser Leu Thr Cys Leu Val Lys Gly Phe Tyr Pro Ser Asp Ile<br>Ala Val Glu Trp Glu Ser Asn Gly Gln Pro Glu Asn Asn Tyr Lys<br>Thr Thr Pro Pro Val Leu Asp Ser Asp Gly Ser Phe Phe Leu Tyr<br>Ser Lys Leu Thr Val Asp Lys Ser Arg Trp Gln Gln Gly Asn Val<br>Phe Ser Cys Ser Val Met His Glu Ala Leu His Asn His Tyr Thr<br>Gln Lys Ser Leu Ser Leu Ser Pro Gly Lys (SEQ ID NO: 18) |
| SEQ ID NO: 30 of WO2014/121087 | Ala Ser Thr Lys Gly Pro Ser Val Phe Pro Leu Ala Pro Ser Ser<br>Lys<br>Ser Thr Ser Gly Gly Thr Ala Ala Leu Gly Cys Leu Val Lys Asp<br>Tyr<br>Phe Pro Glu Pro Val Thr Val Ser Trp Asn Ser Gly Ala Leu Thr<br>Ser Gly Val His Thr Phe Pro Ala Val Leu Gln Ser Ser Gly Leu<br>Tyr Ser Leu Ser Ser Val Val Thr Val Pro Ser Ser Ser Leu Gly<br>Thr Gln Thr Tyr Ile Cys Asn Val Asn His Lys Pro Ser Asn Thr<br>Lys Val Asp Lys Lys Val **Glu Pro Lys Ser Cys Asp Lys Thr**<br>**His Thr Cys Pro Pro Cys Pro Ala Pro Pro Val Ala Gly Pro**<br>**Ser Val Phe Leu Phe Pro Pro Lys Pro Lys Asp Thr Leu Met**<br>**Ile Ser Arg Thr Pro Glu Val Thr Cys Val Val Val Asp Val Ser**<br>**Gln Glu Asp Pro Glu Val Gln Phe Asn Trp Tyr Val Asp Gly**<br>**Val Glu Val His Asn Ala Lys Thr Lys Pro Arg Glu Glu Gln**<br>**Phe Asn Ser Thr Tyr Arg Val Val Ser Val Leu Thr Val Leu**<br>**His Gln Asp Trp Leu Asn Gly Lys Glu Tyr Lys Cys Lys Val**<br>**Ser Asn Lys Gly Leu Pro Ser Ser Ile Glu Lys Thr Ile Ser Lys**<br>**Ala Lys Gly Gln Pro Arg Glu Pro Gln Val Tyr Thr Leu Pro**<br>**Pro Ser Arg Asp Glu Leu Thr Lys Asn Gln Val Ser Leu Thr**<br>**Cys Leu Val Lys Gly Phe Tyr Pro Ser Asp Ile Ala Val Glu**<br>**Trp Glu Ser Asn Gly Gln Pro Glu Asn Asn**<br>**Tyr Lys Thr Thr Pro Pro Val Leu Asp Ser Asp Gly Ser Phe**<br>**Phe Leu Tyr Ser Lys Leu Thr Val Asp Lys Ser Arg Trp Gln**<br>**Gln Gly Asn Val Phe Ser Cys Ser Val Met His Glu Ala Leu**<br>**His Asn His Tyr Thr Gln Lys Ser Leu Ser Leu Ser Pro Gly**<br>**Lys** (SEQ ID NO: 19) |
| SEQ ID NO: 31 of WO2014/121087 | Ala Ser Thr Lys Gly Pro Ser Val Phe Pro Leu Ala Pro Cys Ser<br>Arg Ser Thr Ser Glu Ser Thr Ala Ala Leu Gly Cys Leu Val Lys |

TABLE 5-continued

| Fc Domain | Sequence |
|---|---|
| | Asp Tyr Phe Pro Glu Pro Val Thr Val Ser Trp Asn Ser Gly Ala<br>Leu Thr Ser Gly Val His Thr Phe Pro Ala Val Leu Gln Ser Ser<br>Gly Leu Tyr Ser Leu Ser Ser Val Val Thr Val Pro Ser Ser Ser<br>Leu Gly Thr Lys Thr Tyr Thr Cys Asn Val Asp His Lys Pro Ser<br>Asn Thr Lys Val Asp Lys Arg Val **Glu Ser Lys Tyr Gly Pro Pro**<br>**Cys Pro Pro Cys Pro Ala Pro Pro Val Ala Gly Pro Ser Val**<br>**Phe Leu Phe Pro Pro Lys Pro Lys Asp Thr Leu Met Ile Ser**<br>**Arg Thr Pro Glu Val Thr Cys Val Val Val Asp Val Ser Gln**<br>**Glu Asp Pro Glu Val Gln Phe Asn Trp Tyr Val Asp Gly Val**<br>**Glu Val His Asn Ala Lys Thr Lys Pro Arg Glu Glu Gln Phe**<br>**Asn Ser Thr Tyr Arg Val Val Ser Val Leu Thr Val Leu His**<br>**Gln Asp Trp Leu Asn Gly Lys Glu Tyr Lys Cys Lys Val Ser**<br>**Asn Lys Gly Leu Pro Ser Ser Ile Glu Lys Thr Ile Ser Lys Ala**<br>**Lys Gly Gln Pro Arg Glu Pro Gln Val Tyr Thr Leu Pro Pro**<br>**Ser Gln Glu Glu Met Thr Lys Asn**<br>**Gln Val Ser Leu Thr Cys Leu Val Lys Gly Phe Tyr Pro Ser**<br>**Asp Ile Ala Val Glu Trp Glu Ser Asn Gly Gln Pro Glu Asn**<br>**Asn Tyr Lys Thr Thr Pro Pro Val Leu Asp Ser Asp Gly Ser**<br>**Phe Phe Leu Tyr Ser Arg Leu Thr Val Asp Lys Ser Arg Trp**<br>**Gln Glu Gly Asn Val Phe Ser Cys Ser Val Met His Glu Ala**<br>**Leu His Asn His Tyr Thr Gln Lys Ser Leu Ser Leu Ser Leu**<br>**Gly Lys** (SEQ ID NO: 20) |
| SEQ ID NO: 37 of WO2014/121087 | Ala Ser Thr Lys Gly Pro Ser Val Phe Pro Leu Ala Pro Ser Ser<br>Lys<br>Ser Thr Ser Gly Gly Thr Ala Ala Leu Gly Cys Leu Val Lys Asp<br>Tyr<br>Phe Pro Glu Pro Val Thr Val Ser Trp Asn Ser Gly Ala Leu Thr<br>Ser Gly Val His Thr Phe Pro Ala Val Leu Gln Ser Ser Gly Leu<br>Tyr Ser Leu Ser Ser Val Val Thr Val Pro Ser Ser Ser Leu Gly<br>Thr Gln Thr Tyr Ile Cys Asn Val Asn His Lys Pro Ser Asn Thr<br>Lys Val Asp Lys Lys Val **Glu Pro Lys Ser Cys Asp Lys Thr**<br>**His Thr Cys Pro Pro Cys Pro Ala Pro Pro Val Ala Gly Pro**<br>**Ser Val Phe Leu Phe Pro Pro Lys Pro Lys Asp Thr Leu Met**<br>**Ile Ser Arg Thr Pro Glu Val Thr Cys Val Val Val Asp Val Ser**<br>**Gln Glu Asp Pro Glu Val Gln Phe Asn Trp Tyr Val Asp Gly**<br>**Val Glu Val His Asn Ala Lys Thr Lys Pro Arg Glu Glu Gln**<br>**Phe Asn Ser Thr Tyr Arg Val Val Ser Val Leu Thr Val Leu**<br>**His Gln Asp Trp Leu Asn Gly Lys Glu Tyr Lys Cys Lys Val**<br>**Ser Asn Lys Gly Leu Pro Ser Ser Ile Glu Lys Thr Ile Ser Lys**<br>**Ala Lys Gly Gln Pro Arg Glu Pro Gln Val Tyr Thr Leu Pro**<br>**Pro Ser Arg Asp Glu Leu Thr Lys Asn Gln Val Ser Leu Thr**<br>**Cys Leu Val Lys Gly Phe Tyr Pro Ser Asp Ile Ala Val Glu**<br>**Trp Glu Ser Asn Gly Gln Pro Glu Asn Asn**<br>**Tyr Lys Thr Thr Pro Pro Val Leu Asp Ser Asp Gly Ser Phe**<br>**Phe Leu Tyr Ser Lys Leu Thr Val Asp Lys Ser Arg Trp Gln**<br>**Gln Gly Asn Val Phe Ser Cys Ser Val Met His Glu Ala Leu**<br>**His Asn Arg Phe Thr Gln Lys Ser Leu Ser Leu Ser Pro Gly**<br>**Lys** (SEQ ID NO: 21) |
| SEQ ID NO: 38 of WO2014/121087 | Ala Ser Thr Lys Gly Pro Ser Val Phe Pro Leu Ala Pro Cys Ser<br>Arg Ser Thr Ser Glu Ser Thr Ala Ala Leu Gly Cys Leu Val Lys<br>Asp Tyr Phe Pro Glu Pro Val Thr Val Ser Trp Asn Ser Gly Ala<br>Leu Thr Ser Gly Val His Thr Phe Pro Ala Val Leu Gln Ser Ser<br>Gly Leu Tyr Ser Leu Ser Ser Val Val Thr Val Pro Ser Ser Ser<br>Leu Gly Thr Lys Thr Tyr Thr Cys Asn Val Asp His Lys Pro Ser<br>Asn Thr Lys Val Asp Lys Arg Val **Glu Ser Lys Tyr Gly Pro Pro**<br>**Cys Pro Pro Cys Pro Ala Pro Pro Val Ala Gly Pro Ser Val**<br>**Phe Leu Phe Pro Pro Lys Pro Lys Asp Thr Leu Met Ile Ser**<br>**Arg Thr Pro Glu Val Thr Cys Val Val Val Asp Val Ser Gln**<br>**Glu Asp Pro Glu Val Gln Phe Asn Trp Tyr Val Asp Gly Val**<br>**Glu Val His Asn Ala Lys Thr Lys Pro Arg Glu Glu Gln Phe**<br>**Asn Ser Thr Tyr Arg Val Val Ser Val Leu Thr Val Leu His**<br>**Gln Asp Trp Leu Asn Gly Lys Glu Tyr Lys Cys Lys Val Ser**<br>**Asn Lys Gly Leu Pro Ser Ser Ile Glu Lys Thr Ile Ser Lys Ala**<br>**Lys Gly Gln Pro Arg Glu Pro Gln Val Tyr Thr Leu Pro Pro**<br>**Ser Gln Glu Glu Met Thr Lys Asn**<br>**Gln Val Ser Leu Thr Cys Leu Val Lys Gly Phe Tyr Pro Ser**<br>**Asp Ile Ala Val Glu Trp Glu Ser Asn Gly Gln Pro Glu Asn**<br>**Asn Tyr Lys Thr Thr Pro Pro Val Leu Asp Ser Asp Gly Ser**<br>**Phe Phe Leu Tyr Ser Arg Leu Thr Val Asp Lys Ser Arg Trp**<br>**Gln Glu Gly Asn Val Phe Ser Cys Ser Val Met His Glu Ala**<br>**Leu His Asn Arg Phe Thr Gln Lys Ser Leu Ser Leu Ser Leu**<br>**Gly Lys** (SEQ ID NO: 22) |

In a particular embodiment, the IgG4 with reduced effector function comprises the bolded portion of the amino acid sequence of SEQ ID NO:31 of WO2014/121087 (SEQ ID NO: 20), sometimes referred to herein as IgG4s or hIgG4s.

For heterodimeric Fc regions, it is possible to incorporate a combination of the variant IgG4 Fc sequences set forth above, for example an Fc region comprising an Fc domain comprising the amino acid sequence of SEQ ID NO:30 of WO2014/121087 (SEQ ID NO: 19) (or the bolded portion thereof) and an Fc domain comprising the amino acid sequence of SEQ ID NO:37 of WO2014/121087 (SEQ ID NO: 21) (or the bolded portion thereof) or an Fc region comprising an Fc domain comprising the amino acid sequence of SEQ ID NO:31 of WO2014/121087 (SEQ ID NO: 20) (or the bolded portion thereof) and an Fc domain comprising the amino acid sequence of SEQ ID NO:38 of WO2014/121087 (SEQ ID NO: 22) (or the bolded portion thereof).

6.6.1.2. Fc Heterodimerization Variants

Certain IL12 receptor agonists entail dimerization between two Fc domains that, unlike a native immunoglobulin, are operably linked to non-identical N-terminal regions, e.g., one Fc domain connected to a Fab and the other Fc domain connected to an IL12 moiety. Inadequate heterodimerization of two Fc domains to form an Fc region has can be an obstacle for increasing the yield of desired heterodimeric molecules and represents challenges for purification. A variety of approaches available in the art can be used in for enhancing dimerization of Fc domains that might be present in the IL12 receptor agonists of the disclosure, for example as disclosed in EP 1870459A1; U.S. Pat. Nos. 5,582,996; 5,731,168; 5,910,573; 5,932,448; 6,833,441; 7,183,076; U.S. Patent Application Publication No. 2006204493A1; and PCT Publication No. WO 2009/089004A1.

The present disclosure provides IL12 receptor agonists comprising Fc heterodimers, i.e., Fc regions comprising heterologous, non-identical Fc domains. Typically, each Fc domain in the Fc heterodimer comprises a CH3 domain of an antibody. The CH3 domains are derived from the constant region of an antibody of any isotype, class or subclass, and preferably of IgG (IgG1, IgG2, IgG3 and IgG4) class, as described in the preceding section.

Heterodimerization of the two different heavy chains at CH3 domains give rise to the desired IL12 receptor agonist, while homodimerization of identical heavy chains will reduce yield of the desired IL12 receptor agonist. Thus, in a preferred embodiment, the polypeptides that associate to form an IL12 receptor agonist of the disclosure will contain CH3 domains with modifications that favor heterodimeric association relative to unmodified Fc domains.

In a specific embodiment said modification promoting the formation of Fc heterodimers is a so-called “knob-into-hole” or “knob-in-hole” modification, comprising a “knob” modification in one of the Fc domains and a “hole” modification in the other Fc domain. The knob-into-hole technology is described e.g., in U.S. Pat. Nos. 5,731,168; 7,695,936; Ridgway et al., 1996, Prot Eng 9:617-621, and Carter, 2001, Immunol Meth 248:7-15. Generally, the method involves introducing a protuberance (“knob”) at the interface of a first polypeptide and a corresponding cavity (“hole”) in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g., by site-specific mutagenesis, or by peptide synthesis. An exemplary substitution is Y470T.

In a specific such embodiment, in the first Fc domain the threonine residue at position 366 is replaced with a tryptophan residue (T366W), and in the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second Fc domain additionally the tyrosine residue at position 349 is replaced by a cysteine residue (Y349C) (numbering according to Kabat EU index). In a particular embodiment, the first Fc domain comprises the amino acid substitutions S354C and T366W, and the second Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second Fc domains of the Fc region.

As an alternative, or in addition, to the use of Fc domains that are modified to promote heterodimerization, an Fc domain can be modified to allow a purification strategy that enables selections of Fc heterodimers. In one such embodiment, one polypeptide comprises a modified Fc domain that abrogates its binding to Protein A, thus enabling a purification method that yields a heterodimeric protein. See, for example, U.S. Pat. No. 8,586,713. As such, the IL12 receptor agonists comprise a first CH3 domain and a second Ig CH3 domain, wherein the first and second Ig CH3 domains differ from one another by at least one amino acid, and wherein at least one amino acid difference reduces binding of the IL12 receptor agonist to Protein A as compared to a corresponding IL12 receptor agonist lacking the amino acid difference. In one embodiment, the first CH3 domain binds Protein A and the second CH3 domain contains a mutation/modification that reduces or abolishes Protein A binding such as an H95R modification (by IMGT exon numbering; H435R by EU numbering). The second CH3 may further comprise a Y96F modification (by IMGT; Y436F by EU). This class of modifications is referred to herein as "star" mutations.

In some embodiments, the Fc can contain one or more mutations (e.g., knob and hole mutations) to facilitate heterodimerization as well as star mutations to facilitate purification.

6.7. Stabilization Moieties

The IL12 receptor agonists of the disclosure can comprise a stabilization moiety that can extend the molecule's serum half-life in vivo. Serum half-life is often divided into an alpha phase and a beta phase. Either or both phases may be improved significantly by addition of an appropriate stabilization moiety. For example, the stabilization moiety can increase the serum half-life of the IL12 receptor agonist by more than 5, 10, 20, 30, 40, 50, 60, 70, 80, 90, 100, 120, 150, 200, 400, 600, 800, 1000% or more relative to a corresponding IL12 receptor agonist not containing the stabilization moiety. For the purpose of this disclosure, serum half-life can refer to the half-life in humans or other mammals (e.g., mice or non-human primates).

Wild type IL12 has a serum half-life of less than 10 minutes. The IL12 receptor agonists of the disclosure have preferably a serum half-life in humans and/or mice of at least about 2 hours, at least about 4 hours, at least about 6 hours, or at least about 8 hours. In some embodiments, the IL12 receptor agonists of the disclosure have a serum half-life of at least 10 hours, at least 12 hours at least 15 hours, at least 18 hours, at least 24 hours, at least 36 hours, at least 48 hours, at least 60 hours, or at least 72 hours.

Stabilization moieties, include polyoxyalkylene moieties (e.g., polyethylene glycol), sugars (e.g., sialic acid), and well-tolerated protein moieties (e.g., Fc and fragments and variants thereof, transferrin, or serum albumin).

Other stabilization moieties that can be used in the IL12 receptor agonists of the disclosure include those described in Kontermann et al., 2011, Current Opinion in Biotechnology 22:868-76. Such Stabilization moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the disclosure provides an IL12 receptor agonist comprising a stabilization moiety that is a polymeric sugar.

Serum albumin can also be engaged in half-life extension through modules with the capacity to non-covalently interact with albumin. Accordingly, the IL12 receptor agonists of the disclosure can include as a stabilization moiety an albumin-binding protein. The albumin-binding protein can be either conjugated or genetically fused to one or more other components of the IL12 receptor agonist of the disclosure. Proteins with albumin-binding activity are known from certain bacteria. For example, streptococcal protein G contains several small albumin-binding domains composed of roughly 50 amino acid residues (6 kDa). Additional examples of serum albumin binding proteins such as those described in U.S. Publication Nos. 2007/0178082 and 2007/0269422. Fusion of an albumin binding domain to a protein results in a strongly extended half-life (see Kontermann et al., 2011, Current Opinion in Biotechnology 22:868-76).

In other embodiments the stabilization moiety is human serum albumin. In other embodiments, the stabilization moiety is transferrin.

In some embodiments, the stabilization moiety is an Fc domain, for example any of the Fc domains described in Section 6.6.1 and subsections thereof, incorporated by reference herein. The Fc domains described in Section 6.6.1 are generally capable of dimerization. However, for the purpose of stabilization the Fc domain can be a soluble monomeric Fc domain that has a reduced ability to self-associate. See, e.g., Helm et al., 1996, J. Biol. Chem. 271: 7494-7500 and Ying et al., 2012, J Biol Chem. 287(23):19399-19408. An example of a soluble monomeric Fc domain comprises amino acid substitutions in the positions corresponding to T366 and/or Y407 in CH3, as described in U.S. Patent Publication No. 2019/0367611. The monomeric Fc domains can be of any Ig subtype and can include additional substitutions that reduce effector function, as described in Section 6.6.1 and subsections thereof.

In yet other embodiments, the stabilization moiety is a polyethylene glycol moiety or another polymer, as described in Section 6.7.1 below.

The stabilization moiety can be connected to one or more other components of the IL12 receptor agonists of the disclosure via a linker, for example as described in Section 6.8 below.

In some embodiments, the IL12 receptor agonist comprises polyethylene glycol (PEG) or another hydrophilic polymer as a stabilization moiety, for example a copolymer of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran or poly(n-vinyl pyrrolidone)polyethylene glycol, a propropylene glycol homopolymer, a prolypropylene oxide/ethylene oxide copolymer, a polyoxyethylated polyol (e.g., glycerol), polyvinyl alcohol, and mixtures thereof. The polymer may be of any molecular weight, and may be branched or unbranched.

6.8. Linkers

In certain aspects, the present disclosure provides IL12 receptor agonists in which two or more components of an IL12 receptor agonist are connected to one another by a peptide linker. By way of example and not limitation, linkers can be used to connect (a) an IL12 moiety and a multimerization moiety; (b) an IL12 moiety and a targeting moiety; (c) a targeting moiety and a multimerization moiety (e.g., a Fab domain and an Fc domain); (d) different domains within an IL12 moiety (e.g., an IL12 domain and an IL-Rα domain); or (e) different domains within a targeting moiety (e.g., different components of a peptide-MHC complex or the VH and VL domains in a scFv).

A peptide linker can range from 2 amino acids to 60 or more amino acids, and in certain aspects a peptide linker ranges from 3 amino acids to 50 amino acids, from 4 to 30 amino acids, from 5 to 25 amino acids, from 10 to 25 amino acids, 10 amino acids to 60 amino acids, from 12 amino acids to 20 amino acids, from 20 amino acids to 50 amino acids, or from 25 amino acids to 35 amino acids in length.

In particular aspects, a peptide linker is at least 5 amino acids, at least 6 amino acids or at least 7 amino acids in length and optionally is up to 30 amino acids, up to 40 amino acids, up to 50 amino acids or up to 60 amino acids in length.

In some embodiments of the foregoing, the linker ranges from 5 amino acids to 50 amino acids in length, e.g., ranges from 5 to 50, from 5 to 45, from 5 to 40, from 5 to 35, from 5 to 30, from 5 to 25, or from 5 to 20 amino acids in length. In other embodiments of the foregoing, the linker ranges from 6 amino acids to 50 amino acids in length, e.g., ranges from 6 to 50, from 6 to 45, from 6 to 40, from 6 to 35, from 6 to 30, from 6 to 25, or from 6 to 20 amino acids in length. In yet other embodiments of the foregoing, the linker ranges from 7 amino acids to 50 amino acids in length, e.g., ranges from 7 to 50, from 7 to 45, from 7 to 40, from 7 to 35, from 7 to 30, from 7 to 25, or from 7 to 20 amino acids in length.

Charged (e.g., charged hydrophilic linkers) and/or flexible linkers are particularly preferred.

Examples of flexible linkers that can be used in the IL12 receptor agonists of the disclosure include those disclosed by Chen et al., 2013, Adv Drug Deliv Rev. 65(10): 1357-1369 and Klein et al., 2014, Protein Engineering, Design & Selection 27(10): 325-330. Particularly useful flexible linkers are or comprise repeats of glycines and serines, e.g., a monomer or multimer of $G_nS$ (SEQ ID NO: 23) or $SG_n$, where n is an integer from 1 to 10, e.g., 1 2, 3, 4, 5, 6, 7, 8, 9 or 10 (SEQ ID NO: 24). In one embodiment, the linker is or comprises a monomer or multimer of repeat of $G_4S$ (SEQ ID NO: 25) e.g., $(GGGGS)_n$ (SEQ ID NO: 26).

Polyglycine linkers can suitably be used in the IL12 receptor agonists of the disclosure. In some embodiments, a peptide linker comprises two consecutive glycines (2Gly), three consecutive glycines (3Gly), four consecutive glycines (4Gly) (SEQ ID NO: 27), five consecutive glycines (5Gly) (SEQ ID NO: 28), six consecutive glycines (6Gly) (SEQ ID NO: 29), seven consecutive glycines (7Gly) (SEQ ID NO: 30), eight consecutive glycines (8Gly) (SEQ ID NO: 31) or nine consecutive glycines (9Gly) (SEQ ID NO: 32).

6.8.1. pMHC Linkers

For pMHC complexes, suitable linkers can range from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. In addition to the linkers above, pMHC linkers include glycine polymers (G)n, glycine-serine polymers (including, for example, (GS)n, (GSGGS)n (SEQ ID NO: 33) and (GGGS)n, where n is an integer of at least one (SEQ ID NO: 34)), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, 1992, Rev. Computational Chem. 1 1173-142, incorporated herein in its entirety by reference). Exemplary linkers can comprise amino acid sequences including, but not limited to, GGSG (SEQ ID NO: 35), GGSGG (SEQ ID NO: 36), GSGSG (SEQ ID NO: 37), GSGGG (SEQ ID NO: 38), GGGSG (SEQ ID NO: 39), GSSSG (SEQ ID NO: 40), GCGASGGGGSGGGGS (SEQ ID NO: 41), GGGGSGGGGS (SEQ ID NO: 42), GGGASGGGGSGGGGS (SEQ ID NO: 43), GGGGSGGGGSGGGGS (SEQ ID NO: 44), GGGASGGGGS (SEQ ID NO: 45), GGGGSGGGGSGGGGSGGGGS (SEQ ID NO: 46), GCGGS (SEQ ID NO: 47), and the like. In some embodiments, a linker polypeptide includes a cysteine residue that can form a disulfide bond with a cysteine residue present in another portion of the pMHC complex. In certain embodiments, the linker comprises the amino acid sequence GCGGS (SEQ ID NO: 47). The substitution of a glycine in the $G_4S$ linker (SEQ ID NO: 25) with cysteine can result in the formation of a disulfide bond, for example an MHC targeting moiety with a corresponding cysteine substitution in HLA.A2 that stabilizes the MHC peptide within the MHC complex.

6.8.2. Hinge Sequences

In other embodiments, the IL12 receptor agonists of the disclosure comprise a linker that is a hinge region. In particular, where an IL12 receptor agonist contains an immunoglobulin-based targeting moiety, the hinge can be used to connect the targeting moiety, e.g., a Fab domain, to a multimerization domain, e.g., an Fc domain. The hinge region can be a native or a modified hinge region. Hinge regions are typically found at the N-termini of Fc regions. The term "hinge region", unless the context dictates otherwise, refers to a naturally or non-naturally occurring hinge sequence that in the context of a single or monomeric polypeptide chain is a monomeric hinge domain and in the context of a dimeric polypeptide (e.g., a homodimeric or heterodimeric IL12 receptor agonist formed by the association of two Fc domains) can comprise two associated hinge sequences on separate polypeptide chains.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc domain or Fc region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO 99/15549, WO 2005/003170, WO 2005/003169, WO 2005/003170, WO 98/25971 and WO 2005/003171 and these are incorporated herein by reference.

In one embodiment, an IL12 receptor agonist of the disclosure comprises an Fc region in which one or both Fc domains possesses an intact hinge region at its N-terminus.

In various embodiments, positions 233-236 within a hinge region may be G, G, G and unoccupied; G, G, unoccupied, and unoccupied; G, unoccupied, unoccupied, and unoccupied; or all unoccupied, with positions numbered by EU numbering.

In some embodiments, the IL12 receptor agonists of the disclosure comprise a modified hinge region that reduces binding affinity for an Fcγ receptor relative to a wild-type hinge region of the same isotype (e.g., human IgG1 or human IgG4).

In one embodiment, the IL12 receptor agonists of the disclosure comprise an Fc region in which each Fc domain possesses an intact hinge region at its N-terminus, where each Fc domain and hinge region is derived from IgG4 and each hinge region comprise the modified sequence CPPC (SEQ ID NO: 48). The core hinge region of human IgG4 contains the sequence CPSC (SEQ ID NO: 49) compared to IgG1 that contains the sequence CPPC (SEQ ID NO: 48). The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide. (Angel et al., 1993, Mol Immunol 30(1):105-108). Changing the serine residue to a proline to give the same core sequence as IgG1 allows complete formation of inter-chain disulfides in the IgG4 hinge region, thus reducing heterogeneity in the purified product. This altered isotype is termed IgG4P.

6.8.2.1. Chimeric Hinge Sequences

The hinge region can be a chimeric hinge region.

For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region.

In particular embodiments, a chimeric hinge region comprises the amino acid sequence EPKSCDKTHTCPPCPAPPVA (SEQ ID NO: 50) (previously disclosed as SEQ ID NO:8 of WO2014/121087, which is incorporated by reference in its entirety herein) or ESKYGPPCPPCPAPPVA (SEQ ID NO: 51) (previously disclosed as SEQ ID NO:9 of WO2014/121087). Such chimeric hinge sequences can be suitably linked to an IgG4 CH2 region (for example by incorporation into an IgG4 Fc domain, for example a human or murine Fc domain, which can be further modified in the CH2 and/or CH3 domain to reduce effector function, for example as described in Section 6.6.1.1).

6.8.2.2. Hinge Sequences with Reduced Effector Function

Figure 1:
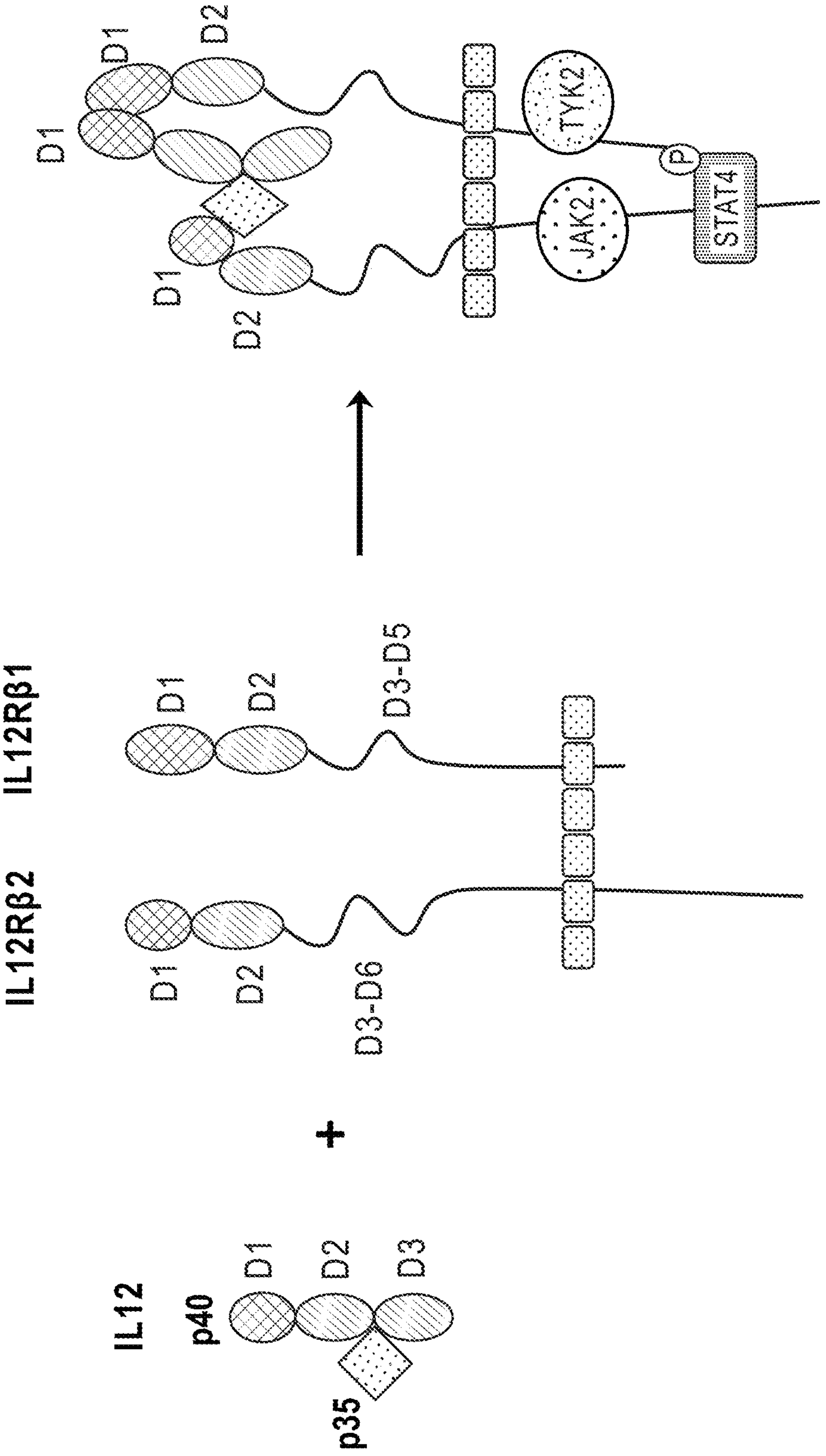

In further embodiments, the hinge region can be modified to reduce effector function, for example as described in WO2016161010A2, which is incorporated by reference in its entirety herein. In various embodiments, the positions 233-236 of the modified hinge region are G, G, G and unoccupied; G, G, unoccupied, and unoccupied; G, unoccupied, unoccupied, and unoccupied; or all unoccupied, with positions numbered by EU numbering (as shown in FIG. 1 of WO2016161010A2). These segments can be represented as GGG-, GG- -, G- - - or - - - - with "-" representing an unoccupied position.

Position 236 is unoccupied in canonical human IgG2 but is occupied by in other canonical human IgG isotypes. Positions 233-235 are occupied by residues other than G in all four human isotypes (as shown in FIG. 1 of WO2016161010A2).

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies. Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG- -(233-236), G- - -(233-236) and no G(233-236). Optionally, the hinge domain amino acid sequence comprises CPPCPAPGGG-GPSVF (SEQ ID NO: 52) (previously disclosed as SEQ ID NO:1 of WO2016161010A2), CPPCPAPGG- -GPSVF (SEQ ID NO: 53) (previously disclosed as SEQ ID NO:2 of WO2016161010A2), CPPCPAPG- - -GPSVF (SEQ ID NO: 54) (previously disclosed as SEQ ID NO:3 of WO2016161010A2), or CPPCPAP- - - -GPSVF (SEQ ID NO: 55) (previously disclosed as SEQ ID NO:4 of WO2016161010A2).

The modified hinge regions described above can be incorporated into a heavy chain constant region, which typically include CH2 and CH3 domains, and which may have an additional hinge segment (e.g., an upper hinge) flanking the designated region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4 of WO2016161010A2.

In specific embodiments, the modified hinge sequences can be linked to an IgG4 CH2 region (for example by incorporation into an IgG4 Fc domain, for example a human or murine Fc domain, which can be further modified in the CH2 and/or CH3 domain to reduce effector function, for example as described in Section 6.6.1.1).

6.9. Nucleic Acids and Host Cells

In another aspect, the disclosure provides nucleic acids encoding the IL12 receptor agonists of the disclosure. In some embodiments, the IL12 receptor agonists are encoded by a single nucleic acid. In other embodiments, for example in the case of a heterodimeric molecule or a molecule comprising a targeting moiety composed of more than one polypeptide chain, the IL12 receptor agonists can be encoded by a plurality (e.g., two, three, four or more) nucleic acids.

A single nucleic acid can encode an IL12 receptor agonist that comprises a single polypeptide chain, an IL12 receptor agonist that comprises two or more polypeptide chains, or a portion of an IL12 receptor agonist that comprises more than two polypeptide chains (for example, a single nucleic acid can encode two polypeptide chains of an IL12 receptor agonist comprising three, four or more polypeptide chains, or three polypeptide chains of an IL12 receptor agonist comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, and separated by internal ribosome entry site (IRES) sequences allowing for translation into separate polypeptides.

In some embodiments, an IL12 receptor agonist comprising two or more polypeptide chains is encoded by two or more nucleic acids. The number of nucleic acids encoding an IL12 receptor agonist can be equal to or less than the number of polypeptide chains in the IL12 receptor agonist (for example, when more than one polypeptide chains are encoded by a single nucleic acid).

The nucleic acids of the disclosure can be DNA or RNA (e.g., mRNA).

In another aspect, the disclosure provides host cells and vectors containing the nucleic acids of the disclosure. The nucleic acids may be present in a single vector or separate vectors present in the same host cell or separate host cell, as described in more detail herein below.

6.9.1. Vectors

The disclosure provides vectors comprising nucleotide sequences encoding an IL12 receptor agonist or an IL12 receptor agonist component described herein, for example one or two of the polypeptide chains of a half antibody. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors can be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and may be varied or optimized depending upon the specific expression vector and mammalian host cell employed, based upon the present description.

6.9.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

6.10. Pharmaceutical Compositions 6.10.1. Pharmaceutical Compositions Comprising IL12 Receptor Agonist Polypeptide The IL12 receptor agonists of the disclosure may be in the form of compositions comprising the IL12 receptor agonist and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the IL12 receptor agonist and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an IL12 receptor agonist of the disclosure per dose. The quantity of IL12 receptor agonist included in a unit dose will depend on the disease being treated, as well as other factors as are well known in the art. Such unit dosages may be in the form of a lyophilized dry powder containing an amount of IL12 receptor agonist suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of IL12 receptor agonist suitable for a single administration.

The pharmaceutical compositions may also be supplied in bulk from containing quantities of IL12 receptor agonist suitable for multiple administrations.

Pharmaceutical compositions may be prepared for storage as lyophilized formulations or aqueous solutions by mixing an IL12 receptor agonist having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of IL12 receptor agonist.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.10.2. Pharmaceutical Compositions for Delivery of IL12 Receptor Agonist Encoding Nucleic Acids An IL12 receptor agonist of the disclosure can be delivered by any method useful for gene therapy, for example as mRNA or through viral vectors encoding the IL12 receptor agonist under the control of a suitable promoter.

Exemplary gene therapy vectors include adenovirus- or AAV-based therapeutics. Non-limiting examples of adenovirus-based or AAV-based therapeutics for use in the methods, uses or compositions herein include, but are not limited to: rAd-p53, which is a recombinant adenoviral vector encoding the wild-type human tumor suppressor protein p53, for example, for the use in treating a cancer (also known as Gendicine®, Genkaxin®, Qi et al., 2006, Modern Oncology, 14:1295-1297); Ad5_d11520, which is an adenovirus lacking the E1B gene for inactivating host p53 (also called H101 or ONYX-015; see, e.g., Russell et al., 2012, Nature Biotechnology 30:658-670); AD5-D24-GM-CSF, an adenovirus containing the cytokine GM-CSF, for example, for the use in treating a cancer (Cerullo et al., 2010, Cancer Res. 70:4297); rAd-HSVtk, a replication deficient adenovirus with HSV thymidine kinase gene, for example, for the treatment of cancer (developed as Cerepro®, Ark Therapeutics, see e.g. U.S. Pat. No. 6,579,855; developed as ProstAtak™ by Advantagene; International PCT Appl. No. WO2005/049094); rAd-TNFα, a replication-deficient adenoviral vector expressing human tumor necrosis factor alpha (TNFα) under the control of the chemoradiation-inducible EGR-1 promoter, for example, for the treatment of cancer (TNFerade™, GenVec; Rasmussen et al., 2002, Cancer Gene Ther. 9:951-7; Ad-IFNβ, an adenovirus serotype 5 vector from which the E1 and E3 genes have been deleted expressing the human interferon-beta gene under the direction of the cytomegalovirus (CMV) immediate-early promoter, for example for treating cancers (BG00001 and H5.110CMVhIFN-β, Biogen; Sterman et al., 2010, Mol. Ther. 18:852-860).

The nucleic acid molecule (e.g., mRNA) or virus can be formulated as the sole pharmaceutically active ingredient in a pharmaceutical composition or can be combined with other active agents for the particular disorder treated. Optionally, other medicinal agents, pharmaceutical agents, carriers, adjuvants, diluents can be included in the compositions provided herein. For example, any one or more of a wetting agents, emulsifiers and lubricants, such as sodium lauryl sulfate and magnesium stearate, as well as coloring agents, release agents, coating agents, sweetening, flavoring and perfuming agents, preservatives, antioxidants, chelating agents and inert gases also can be present in the compositions. Exemplary other agents and excipients that can be included in the compositions include, for example, water soluble antioxidants, such as ascorbic acid, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, α-tocopherol; and metal chelating agents, such as citric acid, ethylenediamine tetraacetic acid (EDTA), sorbitol, tartaric acid and phosphoric acid.

6.11. Therapeutic Indications and Methods of Treatment

The present disclosure provides methods for using and applications for the IL12 receptor agonists of the disclosure.

IL12 receptor agonists of the disclosure are useful in treating disease states where stimulation of the immune system of the host is beneficial, in particular conditions where an enhanced cellular immune response is desirable. These may include disease states where the host immune response is insufficient or deficient.

Disease states for which the IL12 receptor agonists of the disclosure can be administered comprise, for example, a tumor or infection where a cellular immune response would be a critical mechanism for specific immunity. Specific disease states for which IL12 receptor agonists of the present disclosure can be employed include cancer, including breast cancer, prostate cancer, and colorectal cancer. The IL12 receptor agonists of the disclosure may be administered per se or in any suitable pharmaceutical composition.

In one aspect, IL12 receptor agonists of the disclosure for use as a medicament are provided. In further aspects, IL12 receptor agonists of the disclosure for use in treating a disease are provided. In certain embodiments, IL12 receptor agonists of the disclosure for use in a method of treatment are provided. In one embodiment, the disclosure provides an IL12 receptor agonist as described herein for use in the treatment of a disease in a subject in need thereof. In certain embodiments, the disclosure provides an IL12 receptor agonist for use in a method of treating a subject having a disease comprising administering to the individual a therapeutically effective amount of the IL12 receptor agonist. In certain embodiments the disease to be treated is a proliferative disorder. In a preferred embodiment the disease is cancer. In certain embodiments the method further comprises administering to the individual a therapeutically effective amount of at least one additional therapeutic agent, e.g., an anti-cancer agent if the disease to be treated is cancer. In further embodiments, the disclosure provides an IL12 receptor agonist for use in stimulating the immune system. In certain embodiments, the disclosure provides an IL12 receptor agonist for use in a method of stimulating the immune system in a subject comprising administering to the individual an effective amount of the IL12 receptor agonist to stimulate the immune system. An "individual" according to any of the above embodiments is a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL12 receptors, an increase in T cell responsiveness, an increase in natural killer cell activity or lymphokine-activated killer (LAK) cell activity, and the like.

In a further aspect, the disclosure provides for the use of an IL12 receptor agonist of the disclosure in the manufacture or preparation of a medicament for the treatment of a disease in a subject in need thereof. In one embodiment, the medicament is for use in a method of treating a disease comprising administering to a subject having the disease a therapeutically effective amount of the medicament. In certain embodiments the disease to be treated is a proliferative disorder. In a preferred embodiment the disease is cancer. In one such embodiment, the method further comprises administering to the individual a therapeutically effective amount of at least one additional therapeutic agent, e.g., an anti-cancer agent if the disease to be treated is cancer. In a further embodiment, the medicament is for stimulating the immune system. In a further embodiment, the medicament is for use in a method of stimulating the immune system in a subject comprising administering to the individual an amount effective of the medicament to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL12 receptors, an increase in T cell responsiveness, an increase in natural killer cell activity or lymphokine-activated killer (LAK) cell activity, and the like.

In a further aspect, the disclosure provides a method for treating a disease in a subject, comprising administering to said individual a therapeutically effective amount of an IL12 receptor agonist of the disclosure. In one embodiment a composition is administered to said individual, comprising the IL12 receptor agonist of the disclosure in a pharmaceutically acceptable form. In certain embodiments the disease to be treated is a proliferative disorder. In a preferred embodiment the disease is cancer. In certain embodiments the method further comprises administering to the individual a therapeutically effective amount of at least one additional therapeutic agent, e.g., an anti-cancer agent if the disease to be treated is cancer. In a further aspect, the disclosure provides a method for stimulating the immune system in a subject, comprising administering to the individual an effective amount of an IL12 receptor agonist to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL12 receptors, an increase in T cell responsiveness, an increase in natural killer cell activity or lymphokine-activated killer (LAK) cell activity, and the like.

In certain aspects, the disclosure provides a method of treating cancer, comprising administering to a subject in need thereof an IL12 receptor agonist or pharmaceutical composition as described herein.

In some embodiments, the disclosure provides a method of treating cancer with an IL12 receptor agonist protein that is targeted to cancer tissue, comprising administering to a subject in need thereof an IL12 receptor agonist or pharmaceutical composition as described herein, where the IL12 receptor agonist comprises a targeting moiety that recognizes a target molecule that is expressed in the tumor tissue (e.g., the cancer cells, the extracellular matrix, tumor lymphocytes, etc.).

The present disclosure further provides a method of localized delivery of an IL12 protein, comprising administering to a subject an IL12 receptor agonist or pharmaceutical composition as described herein, where the IL12 receptor agonist comprises a targeting moiety that recognizes a target molecule that is expressed by a tissue to which the IL12 receptor agonist is to be locally delivered. As used herein, the term "locally delivered" does not require local administration but rather indicates that the IL12 receptor agonist be selectively localized to a tissue of interest following administration.

The present disclosure further provides a method of administering to the subject IL12 therapy with reduced systemic exposure and/or reduced systemic toxicity, comprising administering to a subject the IL12 therapy in the form of an IL12 receptor agonist or pharmaceutical composition as described herein. Accordingly, the foregoing methods permit IL12 therapy with reduced off-target side effects by virtue of preferential targeting of an IL12 receptor agonist to a particular target tissue and/or attenuation and/or masking of the IL12 moiety until at the site of intended activity.

The present disclosure further provides method of locally inducing an immune response in a target tissue, comprising administering to a subject IL12 receptor agonist or pharmaceutical composition as described herein which has one or more targeting moieties capable of binding a target molecule expressed in the target tissue. The IL12 receptor agonist can then induce the immune response against at least one cell type in the target tissue.

In some embodiments, the administration is not local to the tissue. For example, when the target tissue is cancer tissue, the administration can be systemic or subcutaneous.

In certain embodiments the disease to be treated is a proliferative disorder, preferably cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using an IL12 receptor agonist of the present disclosure include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. Similarly, other cell proliferation disorders can also be treated by the IL12 receptor agonists of the present disclosure. Examples of such cell proliferation disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other cell proliferation disease, besides neoplasia, located in an organ system listed above.

Table 6 below shows exemplary indications for which IL12 receptor agonists targeting particular target molecules can be used.

TABLE 6

Examples of Target Molecule Indications

| Target | Exemplary Indication(s) |
|---|---|
| ADRB3 | Ewing sarcoma |
| ALK | NSCLC, ALCL, IMT, neuroblastoma |
| B7H3 | melanoma, osteosarcoma, leukemia, breast, prostate, ovarian, pancreatic, colorectal cancers |
| BCMA | multiple myeloma, leukemia (e.g., acute lymphoblastic leukemia ("ALL"), acute myeloid leukemia ("AML"), chronic lymphocytic leukemia ("CLL"), chronic myeloid leukemia ("CML") and hairy cell leukemia ("HCL")); lymphoma (e.g., Hodgkin's lymphoma, non-Hodgkin's lymphoma, including diffuse large B-cell lymphoma ("DLBCL")) |
| Cadherin 17 | gastric, pancreatic, and colorectal adenocarcinomas |
| CAIX | clear-cell renal cell carcinoma, hypoxic solid tumors, head and neck squamous carcinoma |
| CD123 | leukemia (e.g., ALL, CLL, AML, CML, HCL); lymphoma (e.g., Hodgkin's lymphoma, non-Hodgkin's lymphoma, e.g., DLBCL); multiple myeloma. In a preferred embodiment, the indication is AML. |
| CD171 | neuroblastoma, paraganglioma |
| CD179a | B cell malignancies |
| CD19 | leukemia (e.g., ALL, CLL, AML, CML, HCL); lymphoma (e.g., Hodgkin's lymphoma, non-Hodgkin's lymphoma, e.g., DLBCL); multiple myeloma. |
| CD20 | leukemia (e.g., ALL, CLL, AML, CML, HCL); lymphoma (e.g., Hodgkin's lymphoma, non-Hodgkin's lymphoma, e.g., DLBCL); multiple myeloma. |
| CD22 | leukemia (e.g., ALL, CLL, AML, CML, HCL); lymphoma (e.g., Hodgkin's lymphoma, non-Hodgkin's lymphoma, e.g., DLBCL); multiple myeloma; lung cancer |
| CD24 | ovarian, breast, prostate, bladder, renal, non-small cell carcinomas |
| CD30 | anaplastic large cell lymphoma, embryonal carcinoma, Hodgkin Lymphoma |
| CD32b | B cell malignancies, gastric, pancreatic, esophageal, glioblastoma, breast, colorectal |
| CD33 | leukemia (e.g., ALL, CLL, AML, CML, HCL); lymphoma (e.g., Hodgkin's lymphoma, non-Hodgkin's lymphoma, e.g., DLBCL); multiple myeloma. In a preferred embodiment, the indication is AML. |
| CD38 | leukemia (e.g., ALL, CLL, AML, CML, HCL); lymphoma (e.g., Hodgkin's lymphoma, non-Hodgkin's lymphoma, e.g., DLBCL); multiple myeloma |
| CD44v6 | colon cancer, head and neck small cell carcinoma |
| CD97 | B cell malignancies, gastric, pancreatic, esophageal, glioblastoma, breast, colorectal |
| CEA (CEACAM5) | colorectal carcinoma, gastric carcinoma, pancreatic carcinoma, lung cancer, breast cancer, medullary thyroid carcinoma |
| CLDN6 | ovarian, breast, lung cancer |
| CLL-1 | leukemia (e.g., ALL, CLL, AML, CML, HCL); lymphoma (e.g., Hodgkin's lymphoma, non-Hodgkin's lymphoma, e.g., DLBCL); multiple myeloma. In a preferred embodiment, the indication is AML. |
| CS1 (SLAMF7) | multiple myeloma |
| EGFR | squamous cell carcinoma of lung, anal cancer, glioblastoma, epithelial tumors of head and neck, colon cancer |

TABLE 6-continued

Examples of Target Molecule Indications

| Target | Exemplary Indication(s) |
|---|---|
| EGFRvIII | Glioblastoma |
| EPCAM | gastrointestestinal carcinoma, colorectal cancer |
| EphA2 | kaposi's sarcoma, glioblastoma, solid tumors, glioma |
| Ephrin B2 | thyroid cancer, breast cancer, malignant melanoma |
| ERBB2 (Her2/neu) | breast, ovarian, gastric cancers, lung adenocarcinoma, non-small cell lung cancer, uterine cancer, uterine serous endometrial carcinoma, salivary duct carcinoma |
| FAP | pancreatic cancer, colorectal cancer, metastasis, epithelial cancers, soft tissue sarcomas |
| FCRL5 | multiple myeloma |
| FLT3 | leukemia (e.g., ALL, CLL, AML, CML, HCL), lymphoma (e.g., Hodgkin's lymphoma, non-Hodgkin's lymphoma, e.g., DLBCL), multiple myeloma |
| Folate receptor alpha | ovarian, breast, renal, lung, colorectal, brain cancers |
| Folate receptor beta | ovarian cancer |
| Fucosyl GM1 | AML, myeloma |
| GD2 | malignant melanoma, neuroblastoma |
| GD3 | Melanoma |
| GloboH | ovarian, gastric, prostate, lung, breast, and pancreatic cancers |
| gp100 | Melanoma |
| GPNMB | breast cancer, head and neck cancers |
| GPR20 | GIST |
| GPR64 | Ewing sarcoma, prostate, kidney and lung sarcomas |
| GPRC5D | multiple myeloma |
| HAVCR1 | renal cancer |
| HER2 | HER-2 (+) adenocarcinoma of gastroesophageal junction, HER-2 positive gastric adenocarcinoma, HER2 positive carcinoma of breast |
| HER3 | colon and gastric cancers |
| HMWMAA | melanoma, glioblastoma, breast cancer |
| IGF-I receptor | breast, prostate, lung cancers |
| IL11Rα | papillary thyroid cancer, osteosarcoma, colorectal adenocarcinoma, lymphocytic leukemia |
| IL13Rα2 | renal cell carcinoma, prostate cancer, gliomas, head and neck cancer, astrocytoma |
| KIT | myeloid leukemia, kaposi's sarcoma, erythroleukemia, gastrointestinal stromal tumors |
| KLRG2 | breast cancers, lung cancers and ovarian cancers. |
| LewisY | squamous cell lung carcinoma, lung adenocarcinoma, ovarian carcinoma, and colorectal adenocarcinoma |
| LMP2 | prostate cancer, Hodgkin's lymphoma, nasopharyngeal carcinoma |
| LRP6 | breast cancer |
| LY6K | breast, lung, ovarian, and cervical cancer |
| LYPD8 | colorectal and gastric cancers |
| Mesothelin | mesothelioma, pancreatic cancer, ovarian cancer, stomach cancer, lung cancer, endometrial cancer |
| MUC1 | breast and ovarian cancers, lung, stomach, pancreatic, prostate cancers |
| NCAM | melanoma, Wilms' tumor, small cell lung cancer, neuroblastoma, myeloma, paraganglioma, pancreatic acinar cell carcinoma, myeloid leukemia |
| NY-BR-1 | breast cancer |
| o-acetyl GD2 | neuroblastoma, melanoma |
| OR51E2 | prostate cancer |
| PANX3 | Osteosarcoma |
| PLAC1 | hepatocellular carcinoma |
| Polysialic acid | small cell lung cancer |
| PDGFR-beta | myelomonocytic leukemia, chronic myeloid leukemia, acute myelogenous leukemia, acute lymphoblastic leukemia |
| PRSS21 | colon cancer, testicular cancer, ovarian cancer |
| PSCA | prostate cancer, gastric and bladder cancers |
| PSMA | prostate cancer |
| ROR1 | metastatic cancers, chronic lymphocytic leukemia, solid tumors in lung, breast, ovarian, colon, pancreatic, sarcoma |
| SLC34A2 | bladder cancer |
| SLC39A6 | breast cancer, esophageal cancer |
| SLITRK6 | breast cancer, urothelial cancer, lung cancer |
| SSEA-4 | breast cancer, cancer stem cells, epithelial ovarian carcinoma |
| STEAP1 | prostate cancer |
| STEAP2 | prostate cancer (including castrate-resistant prostate cancer), bladder cancer, cervical cancer, lung cancer, colon cancer, kidney cancer, breast cancer, pancreatic cancer, stomach cancer, uterine cancer, ovarian cancer, preferably prostate cancer |
| TACSTD2 | carcinomas, e.g., non-small-cell lung cancer |
| TAG72 | ovarian, breast, colon, lung, pancreatic cancers, gastric cancer |
| TEM1/CD248 | colorectal cancer |
| TEM7R | colorectal cancer |
| Tn | colorectal, breast cancers, cervical, lung, stomach cancers |

TABLE 6-continued

| Examples of Target Molecule Indications | |
|---|---|
| Target | Exemplary Indication(s) |
| TSHR | thyroid cancer, multiple myeloma |
| Tyrosinase | prostate cancer, melanoma |
| UPK2 | bladder cancer |
| VEGFR2 | ovarian and pancreatic cancers, renal cell carcinoma, colorectal cancer, medullary thyroid carcinoma |

Additional target molecules and corresponding indications are disclosed in, e.g., Hafeez et al., 2020, Molecules 25:4764, doi:10.3390/molecules25204764, particularly in Table 1. Table 1 is incorporated by reference in its entirety here.

In another embodiment, the disease is related to autoimmunity, transplantation rejection, post-traumatic immune responses and infectious diseases (e.g., HIV). More specifically, the IL12 receptor agonists may be used in eliminating cells involved in immune cell-mediated disorders, including lymphoma; autoimmunity, transplantation rejection, graft-versus-host disease, ischemia and stroke.

A skilled artisan readily recognizes that in many cases the IL12 receptor agonists may not provide a cure but may only provide partial benefit. In some embodiments, a physiological change having some benefit is also considered therapeutically beneficial. Thus, in some embodiments, an amount of IL12 receptor agonist that provides a physiological change is considered an "effective amount" or a "therapeutically effective amount".

The subject, patient, or individual in need of treatment is typically a mammal, more specifically a human.

For the prevention or treatment of disease, the appropriate dosage of an IL12 receptor agonist of the disclosure (when used alone or in combination with one or more other additional therapeutic agents) will depend on the type of disease to be treated, the route of administration, the body weight of the patient, the particular IL12 receptor agonist, the severity and course of the disease, whether the antibody is administered for preventive or therapeutic purposes, previous or concurrent therapeutic interventions, the patient's clinical history and response to the IL12 receptor agonist, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

A single administration of unconjugated IL12 can range from about 50,000 IU/kg to about 1,000,000 IU/kg or more, more typically about 600,000 IU/kg of IL12. This may be repeated several times a day (e.g., 2-3 times), for several days (e.g., about 3-5 consecutive days) and then may be repeated one or more times following a period of rest (e.g., about 7-14 days). Thus, a therapeutically effective amount may comprise only a single administration or many administrations over a period of time (e.g., about 20-30 individual administrations of about 600,000 IU/kg of IL12 each given over about a 10-20 day period).

Similarly, the IL12 receptor agonist is suitably administered to the patient at one time or over a series of treatments. Depending on the type and severity of the disease, about 1 μg/kg to 15 mg/kg (e.g., 0.1 mg/kg-10 mg/kg) of IL12 receptor agonist can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the IL12 receptor agonist would be in the range from about 0.005 mg/kg to about 10 mg/kg. In other non-limiting examples, a dose may also comprise from about 1 μg/kg/body weight, about 5 μg/kg/body weight, about 10 μg/kg/body weight, about 50 μg/kg/body weight, about 100 μg/kg/body weight, about 200 μg/kg/body weight, about 350 μg/kg/body weight, about 500 μg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 μg/kg/body weight to about 500 mg/kg/body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the IL12 receptor agonist). An initial higher loading dose, followed by one or more lower doses may be administered. However, other dosage regimens may be useful. The progress of this therapy is easily monitored by conventional techniques and assays.

The IL12 receptor agonists of the disclosure will generally be used in an amount effective to achieve the intended purpose. For use to treat or prevent a disease condition, the IL12 receptor agonists of the disclosure, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $EC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the IL12 receptor agonists which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by ELISA HPLC.

In cases of local administration or selective uptake, the effective local concentration of the IL12 receptor agonists may not be related to plasma concentration. One having skill in the art will be able to optimize therapeutically effective local dosages without undue experimentation.

A therapeutically effective dose of the IL12 receptor agonists described herein will generally provide therapeutic benefit without causing substantial toxicity. Toxicity and therapeutic efficacy of an IL12 receptor agonist can be determined by standard pharmaceutical procedures in cell culture or experimental animals (see, e.g., Examples 7 and 8). Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. IL12 receptor agonists that exhibit large therapeutic indices are preferred. In one embodiment, the IL12 receptor agonist according to the present disclosure exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. (See, e.g., Fingl et al., 1975, In: The Pharmacological Basis of Therapeutics, Ch. 1, p. 1, incorporated herein by reference in its entirety).

The attending physician for patients treated with IL12 receptor agonists of the disclosure would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Due to lower toxicity, the IL12 receptor agonists of the disclosure can have higher maximum therapeutic doses than wild type IL12, although, IL12 receptor agonists containing a stabilization moiety are typically administered at lower doses than wild type IL12 due to the prolonged half-lives.

6.12. Combination Therapy

The IL12 receptor agonists according to the disclosure may be administered in combination with one or more other agents in therapy. For instance, an IL12 receptor agonist of the disclosure may be co-administered with at least one additional therapeutic agent. The term "therapeutic agent" encompasses any agent administered to treat a symptom or disease in a subject in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of IL12 receptor agonist used, the type of disorder or treatment, and other factors discussed above. The IL12 receptor agonists are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the IL12 receptor agonist of the disclosure can occur prior to, simultaneously, and/or following, administration of the additional therapeutic agent and/or adjuvant. IL12 receptor agonists of the disclosure can also be used in combination with radiation therapy.

The IL12 receptor agonists of the disclosure can be advantageously used in combination with chimeric antigen receptor ("CAR")-expressing cells, e.g., CAR-expressing T ("CAR-T") cells, for example CAR-T in the treatment of cancer or autoimmune diseases. In some embodiments, the CAR-T cells are recognized by a targeting moiety in the IL12 receptor agonist. The targeting moiety can recognize a T cell receptor or another cell surface molecule on the CART cells. In some embodiments, a targeting moiety in the IL12 receptor agonist is capable of binding to an extracellular domain of the CAR, for example the antigen binding domain.

Exemplary CAR structures, preparations, administration protocols and combination therapy regimens are disclosed in, e.g., Section 6.11.1 of PCT Pub. WO 2021/127487 A2, which section is specifically incorporated by reference herein and applied mutatis mutandis to the IL12 receptor agonists of the disclosure.

7. NUMBERED EMBODIMENTS

While various specific embodiments have been illustrated and described, it will be appreciated that various changes can be made without departing from the spirit and scope of the disclosure(s). The present disclosure is exemplified by the numbered embodiments set forth below. Unless otherwise specified, features of any of the concepts, aspects and/or embodiments described in the detailed description above are applicable mutatis mutandis to any of the following numbered embodiments.

1. A p35 moiety comprising a variant p35 moiety having an amino acid sequence with at least 90%, at least 95% or at least 97% sequence identity to a receptor binding domain of mature human or mature murine p35 and comprising one or more amino acid substitutions at the position corresponding to:

(a) amino acid Y189 of full length human p35 or amino acid Y185 of full length murine p35, wherein the substitution is optionally A, V, R or E;

(b) amino acid I193 of full length human p35 or amino acid M189 of full length murine p35, wherein the substitution is optionally A, V, or E, (c) amino acid R211 of full length human p35 or amino acid R207 of full length murine p35, wherein the substitution is optionally A or K; or (d) any combination of (a) to (c);

optionally wherein the variant comprises one or more additional substitutions recited in Table 2 or any combination of substitutions recited in any one of embodiments 676 to 719.

2. A p40 moiety comprising a variant p40 moiety having an amino acid sequence with at least 90%, at least 95% or at least 97% sequence identity to a receptor binding domain of mature human or mature murine p40 and comprising one or more amino acid substitutions at the position corresponding to:

(a) amino acid K28 of full length human p40 or amino acid K28 of full length murine p40, wherein the substitution is optionally A;

(b) amino acid W37 of full length human p40 or amino acid W37 of full length murine p40, wherein the substitution is optionally A, (c) amino acid D115 of full length human p40 or amino acid E115 of full length murine p40, wherein the substitution is optionally A;

(d) amino acid K118 of full length human p40 or amino acid K118 of full length murine p40, wherein the substitution is optionally A;

(e) amino acid K126 of full length human p40 or amino acid K126 of full length murine p40, wherein the substitution is optionally A, (f) amino acid Y268 of full length human p40 or amino acid Y265 of full length murine p40, wherein the substitution is optionally V or F;

(g) amino acid Y314 of full length human p40 or amino acid Y318 of full length murine p40, wherein the substitution is optionally F; or (h) any combination of (a) to (g);

optionally wherein the variant comprises one or more additional substitutions recited in Table 1 or any combination of substitutions recited in any one of embodiments 589 to 674.

3. An IL12 receptor agonist comprising:

(a) a first polypeptide chain comprising, in an N- to C-terminal orientation, a first targeting moiety or targeting moiety component, a first Fc domain and a p35 moiety, optionally wherein the p35 moiety has an attenuating substitution, e.g., one or more of the attenuating substitutions set forth in Table 2;

(b) a second polypeptide chain comprising in an N- to C-terminal orientation, a second targeting moiety or targeting moiety component and a second Fc domain;

(c) a p40 moiety between the first Fc domain and the p35 moiety or in the form of a monomeric p40, optionally wherein the p40 moiety has an attenuating substitution, e.g., an attenuating substitution at the position corresponding to amino acid W37 of full length human p40 or amino acid W37 of full length murine p40 and/or one or more of the attenuating substitutions set forth in Table 1;

(d) an IL12Rβ moiety or an IL12 antibody fragment configured to mask the p35 moiety or the p40 moiety.

4. An IL12 receptor agonist comprising an IL12 mutein, wherein the IL12 receptor agonist has at least 500-fold attenuation as compared to wild-type IL12, wherein the IL12 receptor agonist comprises:

(a) a first polypeptide chain and a second polypeptide chain dimerized through a first Fc domain and a second Fc domain;

(b) an optional first targeting moiety or targeting moiety component on the first polypeptide chain and an optional second targeting moiety or targeting moiety component on the second polypeptide chain;

(c) a p35 moiety and a p40 moiety; and (d) an IL12Rβ moiety or an IL12 antibody fragment configured to mask the p35 moiety or the p40 moiety.

5. An IL12 receptor agonist comprising on a first polypeptide chain and a second polypeptide chain dimerized through a first Fc domain and a second Fc domain:

(a) an optional first targeting moiety and an optional second targeting moiety;

(b) an IL12 mutein comprising a p35 moiety and a p40 moiety, wherein:

(i) the p35 moiety comprises an attenuating amino acid substitution, optionally wherein the attenuating amino acid substitution is at (A) amino acid Y189 of full length human p35 or amino acid Y185 of full length murine p35, wherein the substitution is optionally A, V, R or E; (B) amino acid I193 of full length human p35 or amino acid M189 of full length murine p35, wherein the substitution is optionally A, V, or E; (C) amino acid R211 of full length human p35 or amino acid R207 of full length murine p35, wherein the substitution is optionally A or K; or (D) any combination of (A)-(C); and/or (ii) the p40 moiety comprises an attenuating amino acid substitution optionally wherein the attenuating amino acid substitution is at (A) amino acid K28 of full length human p40 or amino acid K28 of full length murine p40, wherein the substitution is optionally A; (B) amino acid W37 of full length human p40 or amino acid W37 of full length murine p40, wherein the substitution is optionally A; (C) amino acid D115 of full length human p40 or amino acid E115 of full length murine p40, wherein the substitution is optionally A; (D) amino acid K118 of full length human p40 or amino acid K118 of full length murine p40, wherein the substitution is optionally A; (E) amino acid K126 of full length human p40 or amino acid K126 of full length murine p40, wherein the substitution is optionally A; (F) amino acid Y268 of full length human p40 or amino acid Y265 of full length murine p40, wherein the substitution is optionally V or F; (G) amino acid Y314 of full length human p40 or amino acid Y318 of full length murine p40, wherein the substitution is optionally F; or (H) any combination of (A) to (G);

(iii) an IL12Rβ moiety or an IL12 antibody fragment configured to mask the p35 moiety or the p40 moiety.

6. An IL12 receptor agonist comprising an IL12 mutein which optionally comprises:
   (a) the p35 moiety of embodiment 1 and/or the p40 moiety of embodiment;
   (b) a p35 moiety having at least 90%, at least 95%, or at least 97% sequence identity to a receptor binding domain of mature human or mature murine p35 and/or a p40 moiety having at least 90%, at least 95%, or at least 97% sequence identity to a receptor binding domain of mature human or mature murine p40; and/or
   (c) a polypeptide chain or pair of polypeptide chains having any of the configurations shown in any one of FIGS. 2B-2P, 3B-3I, 4B-4Y, 5B-5T, 5V-5X and 39A-39D.
7. An IL12 receptor agonist, which is optionally an IL12 receptor agonist according to any one of embodiments 3 to 6, which comprises one, two or more IL12 monomers.
8. An IL12 receptor agonist, which is optionally an IL12 agonist according to any one of embodiments 3 to 7, comprising a first IL12 monomer having the configuration of Exemplary Monomer 1 and a second IL12 monomer having the configuration of Exemplary Monomer 2.
9. An IL12 receptor agonist, which is optionally an IL12 agonist according to any one of embodiments 3 to 7, comprising a first IL12 monomer having the configuration of Exemplary Monomer 1 and a second IL12 monomer having the configuration of Exemplary Monomer 18.
10. An IL12 receptor agonist, which is optionally an IL12 agonist according to any one of embodiments 3 to 7, comprising a first IL12 monomer having the configuration of Exemplary Monomer 1 and a second IL12 monomer having the configuration of Exemplary Monomer 22.
11. An IL12 receptor agonist, which is optionally an IL12 agonist according to any one of embodiments 3 to 7, comprising a first IL12 monomer having the configuration of Exemplary Monomer 2 and a second IL12 monomer having the configuration of Exemplary Monomer 17.
12. An IL12 receptor agonist, which is optionally an IL12 agonist according to any one of embodiments 3 to 7, comprising a first IL12 monomer having the configuration of Exemplary Monomer 2 and a second IL12 monomer having the configuration of Exemplary Monomer 21.
13. An IL12 receptor agonist, which is optionally an IL12 agonist according to any one of embodiments 3 to 7, comprising a first IL12 monomer having the configuration of Exemplary Monomer 3 and a second IL12 monomer having the configuration of Exemplary Monomer 4.
14. An IL12 receptor agonist, which is optionally an IL12 agonist according to any one of embodiments 3 to 7, comprising a first IL12 monomer having the configuration of Exemplary Monomer 3 and a second IL12 monomer having the configuration of Exemplary Monomer 20.
15. An IL12 receptor agonist, which is optionally an IL12 agonist according to any one of embodiments 3 to 7, comprising a first IL12 monomer having the configuration of Exemplary Monomer 3 and a second IL12 monomer having the configuration of Exemplary Monomer 24.
16. An IL12 receptor agonist, which is optionally an IL12 agonist according to any one of embodiments 3 to 7, comprising a first IL12 monomer having the configuration of Exemplary Monomer 3 and a second IL12 monomer having the configuration of Exemplary Monomer 53.
17. An IL12 receptor agonist, which is optionally an IL12 agonist according to any one of embodiments 3 to 7, comprising a first IL12 monomer having the configuration of Exemplary Monomer 3 associated with a monomeric p40 (which is optionally a masked, monomeric p40) and a second IL12 monomer having the configuration of Exemplary Monomer 51, optionally wherein the monomeric p40 comprises a p40 moiety according to embodiment 2.
18. An IL12 receptor agonist, which is optionally an IL12 agonist according to any one of embodiments 3 to 7, comprising a first IL12 monomer having the configuration of Exemplary Monomer 3 associated with a monomeric p40 (which is optionally a masked, monomeric p40) and a second IL12 monomer having the configuration of Exemplary Monomer 60, optionally wherein the monomeric p40 comprises a p40 moiety according to embodiment 2.
19. An IL12 receptor agonist, which is optionally an IL12 agonist according to any one of embodiments 3 to 7, comprising a first IL12 monomer having the configuration of Exemplary Monomer 4 and a second IL12 monomer having the configuration of Exemplary Monomer 19.
20. An IL12 receptor agonist, which is optionally an IL12 agonist according to any one of embodiments 3 to 7, comprising a first IL12 monomer having the configuration of Exemplary Monomer 4 and a second IL12 monomer having the configuration of Exemplary Monomer 23.
21. An IL12 receptor agonist, which is optionally an IL12 agonist according to any one of embodiments 3 to 7, comprising a first IL12 monomer having the configuration of Exemplary Monomer 4 and a second IL12 monomer having the configuration of Exemplary Monomer 52.
22. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 5.
23. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 6.
24. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 13.
25. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 14.

26. An IL12 receptor agonist, which is optionally an IL12 agonist a according to any one of embodiments 3 to 7, comprising a first IL12 monomer having the configuration of Exemplary Monomer 5 and a second IL12 monomer having the configuration of Exemplary Monomer 15.
27. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 16.
28. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 25.
29. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 26.
30. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 29.
31. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 30.
32. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 33.
33. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 34.
34. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 43.
35. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 44.
36. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 45.
37. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 46.
38. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 47.
39. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 48.
40. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 49.
41. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 50.
42. An IL12 receptor agonist, which is optionally an IL12 agonist according to any one of embodiments 3 to 7, comprising a first IL12 monomer having the configuration of Exemplary Monomer 5 and a second IL12 monomer having the configuration of Exemplary Monomer 51.
43. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 6.
44. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 13.
45. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 14.
46. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 15.
47. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 16.

48. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 25.
49. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 26.
50. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 29.
51. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 30.
52. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 33.
53. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 34.
54. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 43.
55. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 44.
56. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 45.
57. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 46.
58. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 47.
59. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 48.
60. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 49.
61. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 50
62. An IL12 receptor agonist, which is optionally an IL12 agonist according to any one of embodiments 3 to 7, comprising a first IL12 monomer having the configuration of Exemplary Monomer 6 and a second IL12 monomer having the configuration of Exemplary Monomer 51.
63. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 7.
64. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 60.
65. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 8.
66. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 9.
67. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 10.
68. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 11.
69. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 12.

70. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 27.
71. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 28.
72. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 31.
73. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 32.
74. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 33.
75. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 34.
76. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 35.
77. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 36.
78. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 37.
79. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 38.
80. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 39.
81. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 40.
82. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 41.
83. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 42.
84. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 51.
85. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 59.
86. An IL12 receptor agonist, which is optionally an IL12 agonist according to any one of embodiments 3 to 7, comprising a first IL12 monomer having the configuration of Exemplary Monomer 7 and a second IL12 monomer having the configuration of Exemplary Monomer 63.
87. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 8.
88. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 60.
89. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 9.
90. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 10.
91. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 11.

92. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 12.

93. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 27.

94. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 28.

95. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 31.

96. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 32.

97. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 33.

98. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 34.

99. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 35.

100. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 36.

101. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 37.

102. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 38.

103. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 39.

104. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 40.

105. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 41.

106. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 42.

107. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 51.

108. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 55.

109. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 59.

110. An IL12 receptor agonist, which is optionally an IL12 agonist according to any one of embodiments 3 to 7, comprising a first IL12 monomer having the configuration of Exemplary Monomer 8 and a second IL12 monomer having the configuration of Exemplary Monomer 63.

111. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 9, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

112. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 60.

113. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 10, optionally wherein:
(a) the IL12Rβ moieties in Exemplary Monomer 9 and Exemplary Monomer 10 are both IL12Rβ1 moieties;
(b) the IL12Rβ moieties in Exemplary Monomer 9 and Exemplary Monomer 10 are both IL12Rβ2 moieties
(c) the IL12Rβ moiety in Exemplary Monomer 9 is an IL12Rβ1 moiety and the IL12Rβ moiety in Exemplary Monomer 10 is an IL12Rβ2 moiety; or
(d) the IL12Rβ moiety in Exemplary Monomer 9 is an IL12Rβ2 moiety and the IL12Rβ moiety in Exemplary Monomer 10 is an IL12Rβ1 moiety.

114. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 11, optionally wherein:
(a) the IL12Rβ moieties in Exemplary Monomer 9 and Exemplary Monomer 11 are both IL12Rβ1 moieties;
(b) the IL12Rβ moieties in Exemplary Monomer 9 and Exemplary Monomer 1 are both IL12Rβ2 moieties
(c) the IL12Rβ moiety in Exemplary Monomer 9 is an IL12Rβ1 moiety and the IL12Rβ moiety in Exemplary Monomer 11 is an IL12Rβ2 moiety; or
(d) the IL12Rβ moiety in Exemplary Monomer 9 is an IL12Rβ2 moiety and the IL12Rβ moiety in Exemplary Monomer 11 is an IL12Rβ1 moiety.

115. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 12, optionally wherein:
(a) the IL12Rβ moieties in Exemplary Monomer 9 and Exemplary Monomer 12 are both IL12Rβ1 moieties;
(b) the IL12Rβ moieties in Exemplary Monomer 9 and Exemplary Monomer 12 are both IL12Rβ2 moieties
(c) the IL12Rβ moiety in Exemplary Monomer 9 is an IL12Rβ1 moiety and the IL12Rβ moiety in Exemplary Monomer 12 is an IL12Rβ2 moiety; or
(d) the IL12Rβ moiety in Exemplary Monomer 9 is an IL12Rβ2 moiety and the IL12Rβ moiety in Exemplary Monomer 12 is an IL12Rβ1 moiety.

116. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 27.

117. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 28.

118. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 31.

119. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 32.

120. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 33.

121. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 34.

122. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 35, optionally wherein:
(a) the IL12Rβ moieties in Exemplary Monomer 9 and Exemplary Monomer 35 are both IL12Rβ1 moieties;
(b) the IL12Rβ moieties in Exemplary Monomer 9 and Exemplary Monomer 35 are both IL12Rβ2 moieties
(c) the IL12Rβ moiety in Exemplary Monomer 9 is an IL12Rβ1 moiety and the IL12Rβ moiety in Exemplary Monomer 35 is an IL12Rβ2 moiety; or
(d) the IL12Rβ moiety in Exemplary Monomer 9 is an IL12Rβ2 moiety and the IL12Rβ moiety in Exemplary Monomer 35 is an IL12Rβ1 moiety.

123. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 36, optionally wherein:
(a) the IL12Rβ moieties in Exemplary Monomer 9 and Exemplary Monomer 36 are both IL12Rβ1 moieties;
(b) the IL12Rβ moieties in Exemplary Monomer 9 and Exemplary Monomer 36 are both IL12Rβ2 moieties
(c) the IL12Rβ moiety in Exemplary Monomer 9 is an IL12Rβ1 moiety and the IL12Rβ moiety in Exemplary Monomer 36 is an IL12Rβ2 moiety; or
(d) the IL12Rβ moiety in Exemplary Monomer 9 is an IL12Rβ2 moiety and the IL12Rβ moiety in Exemplary Monomer 36 is an IL12Rβ1 moiety.

124. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 37, optionally wherein:
(a) the IL12Rβ moieties in Exemplary Monomer 9 and Exemplary Monomer 37 are both IL12Rβ1 moieties;
(b) the IL12Rβ moieties in Exemplary Monomer 9 and Exemplary Monomer 37 are both IL12Rβ2 moieties
(c) the IL12Rβ moiety in Exemplary Monomer 9 is an IL12Rβ1 moiety and the IL12Rβ moiety in Exemplary Monomer 37 is an IL12Rβ2 moiety; or (d) the IL12Rβ moiety in Exemplary Monomer 9 is an IL12Rβ2 moiety and the IL12Rβ moiety in Exemplary Monomer 37 is an IL12Rβ1 moiety.

125. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 38, optionally wherein:

(a) the IL12Rβ moieties in Exemplary Monomer 9 and Exemplary Monomer 38 are both IL12Rβ1 moieties;

(b) the IL12Rβ moieties in Exemplary Monomer 9 and Exemplary Monomer 38 are both IL12Rβ2 moieties (c) the IL12Rβ moiety in Exemplary Monomer 9 is an IL12Rβ1 moiety and the IL12Rβ moiety in Exemplary Monomer 38 is an IL12Rβ2 moiety; or (d) the IL12Rβ moiety in Exemplary Monomer 9 is an IL12Rβ2 moiety and the IL12Rβ moiety in Exemplary Monomer 38 is an IL12Rβ1 moiety.

126. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 39, optionally wherein:

(a) the IL12Rβ moieties in Exemplary Monomer 9 and Exemplary Monomer 10 are both IL12Rβ1 moieties;

(b) the IL12Rβ moieties in Exemplary Monomer 9 and Exemplary Monomer 10 are both IL12Rβ2 moieties (c) the IL12Rβ moiety in Exemplary Monomer 9 is an IL12Rβ1 moiety and the IL12Rβ moiety in Exemplary Monomer 10 is an IL12Rβ2 moiety; or (d) the IL12Rβ moiety in Exemplary Monomer 9 is an IL12Rβ2 moiety and the IL12Rβ moiety in Exemplary Monomer 10 is an IL12Rβ1 moiety.

127. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 40, optionally wherein:

(a) the IL12Rβ moieties in Exemplary Monomer 9 and Exemplary Monomer 40 are both IL12Rβ1 moieties;

(b) the IL12Rβ moieties in Exemplary Monomer 9 and Exemplary Monomer 40 are both IL12Rβ2 moieties (c) the IL12Rβ moiety in Exemplary Monomer 9 is an IL12Rβ1 moiety and the IL12Rβ moiety in Exemplary Monomer 40 is an IL12Rβ2 moiety; or (d) the IL12Rβ moiety in Exemplary Monomer 9 is an IL12Rβ2 moiety and the IL12Rβ moiety in Exemplary Monomer 40 is an IL12Rβ1 moiety.

128. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 41, optionally wherein:

(a) the IL12Rβ moieties in Exemplary Monomer 9 and Exemplary Monomer 41 are both IL12Rβ1 moieties;

(b) the IL12Rβ moieties in Exemplary Monomer 9 and Exemplary Monomer 41 are both IL12Rβ2 moieties (c) the IL12Rβ moiety in Exemplary Monomer 9 is an IL12Rβ1 moiety and the IL12Rβ moiety in Exemplary Monomer 41 is an IL12Rβ2 moiety; or (d) the IL12Rβ moiety in Exemplary Monomer 9 is an IL12Rβ2 moiety and the IL12Rβ moiety in Exemplary Monomer 41 is an IL12Rβ1 moiety.

129. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 42, optionally wherein:

(a) the IL12Rβ moieties in Exemplary Monomer 9 and Exemplary Monomer 42 are both IL12Rβ1 moieties;

(b) the IL12Rβ moieties in Exemplary Monomer 9 and Exemplary Monomer 42

(c) the IL12Rβ moiety in Exemplary Monomer 9 is an IL12Rβ1 moiety and the IL12Rβ moiety in Exemplary Monomer 42 is an IL12Rβ2 moiety; or (d) the IL12Rβ moiety in Exemplary Monomer 9 is an IL12Rβ2 moiety and the IL12Rβ moiety in Exemplary Monomer 42 is an IL12Rβ1 moiety.

130. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 51, optionally wherein:

(a) the IL12Rβ moieties in Exemplary Monomer 9 and Exemplary Monomer 51 are both IL12Rβ1 moieties;

(b) the IL12Rβ moieties in Exemplary Monomer 9 and Exemplary Monomer 51 are both IL12Rβ2 moieties (c) the IL12Rβ moiety in Exemplary Monomer 9 is an IL12Rβ1 moiety and the IL12Rβ moiety in Exemplary Monomer 51 is an IL12Rβ2 moiety; or (d) the IL12Rβ moiety in Exemplary Monomer 9 is an IL12Rβ2 moiety and the IL12Rβ moiety in Exemplary Monomer 51 is an IL12Rβ1 moiety.

131. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 24.

132. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 60.

133. An IL12 receptor agonist, which is optionally an IL12 agonist according to any one of embodiments 3 to 7, comprising a first IL12 monomer having the configuration of Exemplary Monomer 9 and a second IL12 monomer having the configuration of Exemplary Monomer 63.

134. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 10, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

135. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 11, optionally wherein:
   (a) the IL12Rβ moieties in Exemplary Monomer 10 and Exemplary Monomer 11 are both IL12Rβ1 moieties;
   (b) the IL12Rβ moieties in Exemplary Monomer 10 and Exemplary Monomer 11 are both IL12Rβ2 moieties
   (c) the IL12Rβ moiety in Exemplary Monomer 10 is an IL12Rβ1 moiety and the IL12Rβ moiety in Exemplary Monomer 11 is an IL12Rβ2 moiety; or
   (d) the IL12Rβ moiety in Exemplary Monomer 10 is an IL12Rβ2 moiety and the IL12Rβ moiety in Exemplary Monomer 11 is an IL12Rβ1 moiety.
136. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 12, optionally wherein:
   (a) the IL12Rβ moieties in Exemplary Monomer 10 and Exemplary Monomer 12 are both IL12Rβ1 moieties;
   (b) the IL12Rβ moieties in Exemplary Monomer 10 and Exemplary Monomer 12 are both IL12Rβ2 moieties
   (c) the IL12Rβ moiety in Exemplary Monomer 10 is an IL12Rβ1 moiety and the IL12Rβ moiety in Exemplary Monomer 12 is an IL12Rβ2 moiety; or
   (d) the IL12Rβ moiety in Exemplary Monomer 10 is an IL12Rβ2 moiety and the IL12Rβ moiety in Exemplary Monomer 12 is an IL12Rβ1 moiety.
137. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 27.
138. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 28.
139. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 31.
140. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 32.
141. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 33.
142. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 34.
143. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 35, optionally wherein:
   (a) the IL12Rβ moieties in Exemplary Monomer 10 and Exemplary Monomer 35 are both IL12Rβ1 moieties;
   (b) the IL12Rβ moieties in Exemplary Monomer 10 and Exemplary Monomer 35 are both IL12Rβ2 moieties
   (c) the IL12Rβ moiety in Exemplary Monomer 10 is an IL12Rβ1 moiety and the IL12Rβ moiety in Exemplary Monomer 35 is an IL12Rβ2 moiety; or
   (d) the IL12Rβ moiety in Exemplary Monomer 10 is an IL12Rβ2 moiety and the IL12Rβ moiety in Exemplary Monomer 35 is an IL12Rβ1 moiety.
144. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 36, optionally wherein:
   (a) the IL12Rβ moieties in Exemplary Monomer 10 and Exemplary Monomer 36 are both IL12Rβ1 moieties;
   (b) the IL12Rβ moieties in Exemplary Monomer 10 and Exemplary Monomer 36 are both IL12Rβ2 moieties
   (c) the IL12Rβ moiety in Exemplary Monomer 10 is an IL12Rβ1 moiety and the IL12Rβ moiety in Exemplary Monomer 36 is an IL12Rβ2 moiety; or
   (d) the IL12Rβ moiety in Exemplary Monomer 10 is an IL12Rβ2 moiety and the IL12Rβ moiety in Exemplary Monomer 36 is an IL12Rβ1 moiety.
145. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 37, optionally wherein:
   (a) the IL12Rβ moieties in Exemplary Monomer 10 and Exemplary Monomer 37 are both IL12Rβ1 moieties;
   (b) the IL12Rβ moieties in Exemplary Monomer 10 and Exemplary Monomer 37 are both IL12Rβ2 moieties
   (c) the IL12Rβ moiety in Exemplary Monomer 10 is an IL12Rβ1 moiety and the IL12Rβ moiety in Exemplary Monomer 37 is an IL12Rβ2 moiety; or
   (d) the IL12Rβ moiety in Exemplary Monomer 10 is an IL12Rβ2 moiety and the IL12Rβ moiety in Exemplary Monomer 37 is an IL12Rβ1 moiety.
146. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 38, optionally wherein:

(a) the IL12Rβ moieties in Exemplary Monomer 10 and Exemplary Monomer 38 are both IL12Rβ1 moieties;

(b) the IL12Rβ moieties in Exemplary Monomer 10 and Exemplary Monomer 38 are both IL12Rβ2 moieties (c) the IL12Rβ moiety in Exemplary Monomer 10 is an IL12Rβ1 moiety and the IL12Rβ moiety in Exemplary Monomer 38 is an IL12Rβ2 moiety; or (d) the IL12Rβ moiety in Exemplary Monomer 10 is an IL12Rβ2 moiety and the IL12Rβ moiety in Exemplary Monomer 38 is an IL12Rβ1 moiety.

147. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 39, optionally wherein:

(a) the IL12Rβ moieties in Exemplary Monomer 10 and Exemplary Monomer 39 are both IL12Rβ1 moieties;

(b) the IL12Rβ moieties in Exemplary Monomer 10 and Exemplary Monomer 39 are both IL12Rβ2 moieties (c) the IL12Rβ moiety in Exemplary Monomer 10 is an IL12Rβ1 moiety and the IL12Rβ moiety in Exemplary Monomer 39 is an IL12Rβ2 moiety; or (d) the IL12Rβ moiety in Exemplary Monomer 10 is an IL12Rβ2 moiety and the IL12Rβ moiety in Exemplary Monomer 39 is an IL12Rβ1 moiety.

148. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 40, optionally wherein:

(a) the IL12Rβ moieties in Exemplary Monomer 10 and Exemplary Monomer 40 are both IL12Rβ1 moieties;

(b) the IL12Rβ moieties in Exemplary Monomer 10 and Exemplary Monomer 40 are both IL12Rβ2 moieties (c) the IL12Rβ moiety in Exemplary Monomer 10 is an IL12Rβ1 moiety and the IL12Rβ moiety in Exemplary Monomer 40 is an IL12Rβ2 moiety; or (d) the IL12Rβ moiety in Exemplary Monomer 10 is an IL12Rβ2 moiety and the IL12Rβ moiety in Exemplary Monomer 40 is an IL12Rβ1 moiety.

149. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 41, optionally wherein:

(a) the IL12Rβ moieties in Exemplary Monomer 10 and Exemplary Monomer 41 are both IL12Rβ1 moieties;

(b) the IL12Rβ moieties in Exemplary Monomer 10 and Exemplary Monomer 41 are both IL12Rβ2 moieties (c) the IL12Rβ moiety in Exemplary Monomer 10 is an IL12Rβ1 moiety and the IL12Rβ moiety in Exemplary Monomer 41 is an IL12Rβ2 moiety; or (d) the IL12Rβ moiety in Exemplary Monomer 10 is an IL12Rβ2 moiety and the IL12Rβ moiety in Exemplary Monomer 41 is an IL12Rβ1 moiety.

150. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 42, optionally wherein:

(a) the IL12Rβ moieties in Exemplary Monomer 10 and Exemplary Monomer 42 are both IL12Rβ1 moieties;

(b) the IL12Rβ moieties in Exemplary Monomer 10 and Exemplary Monomer 42 are both IL12Rβ2 moieties (c) the IL12Rβ moiety in Exemplary Monomer 10 is an IL12Rβ1 moiety and the IL12Rβ moiety in Exemplary Monomer 42 is an IL12Rβ2 moiety; or (d) the IL12Rβ moiety in Exemplary Monomer 10 is an IL12Rβ2 moiety and the IL12Rβ moiety in Exemplary Monomer 42 is an IL12Rβ1 moiety.

151. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 51, optionally wherein:

(a) the IL12Rβ moieties in Exemplary Monomer 10 and Exemplary Monomer 51 are both IL12Rβ1 moieties;

(b) the IL12Rβ moieties in Exemplary Monomer 10 and Exemplary Monomer 51 are both IL12Rβ2 moieties (c) the IL12Rβ moiety in Exemplary Monomer 10 is an IL12Rβ1 moiety and the IL12Rβ moiety in Exemplary Monomer 51 is an IL12Rβ2 moiety; or (d) the IL12Rβ moiety in Exemplary Monomer 10 is an IL12Rβ2 moiety and the IL12Rβ moiety in Exemplary Monomer 51 is an IL12Rβ1 moiety.

152. An IL12 receptor agonist, which is optionally an IL12 agonist according to any one of embodiments 3 to 7, comprising a first IL12 monomer having the configuration of Exemplary Monomer 10 and a second IL12 monomer having the configuration of Exemplary Monomer 63.

153. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 11, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

154. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 60.

155. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 12, optionally wherein:

(a) the IL12Rβ moieties in Exemplary Monomer 11 and Exemplary Monomer 12 are both IL12Rβ1 moieties;

(b) the IL12Rβ moieties in Exemplary Monomer 11 and Exemplary Monomer 12 are both IL12Rβ2 moieties (c) the IL12Rβ moiety in Exemplary Monomer 11 is an IL12Rβ1 moiety and the IL12Rβ moiety in Exemplary Monomer 12 is an IL12Rβ2 moiety; or (d) the IL12Rβ moiety in Exemplary Monomer 11 is an IL12Rβ2 moiety and the IL12Rβ moiety in Exemplary Monomer 12 is an IL12Rβ1 moiety.

156. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 27.

157. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 28.

158. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 31.

159. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 32.

160. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 33.

161. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 34.

162. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 35, optionally wherein:

(a) the IL12Rβ moieties in Exemplary Monomer 11 and Exemplary Monomer 35 are both IL12Rβ1 moieties;

(b) the IL12Rβ moieties in Exemplary Monomer 11 and Exemplary Monomer 35 are both IL12Rβ2 moieties (c) the IL12Rβ moiety in Exemplary Monomer 11 is an IL12Rβ1 moiety and the IL12Rβ moiety in Exemplary Monomer 35 is an IL12Rβ2 moiety; or (d) the IL12Rβ moiety in Exemplary Monomer 11 is an IL12Rβ2 moiety and the IL12Rβ moiety in Exemplary Monomer 35 is an IL12Rβ1 moiety.

163. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 36, optionally wherein:

(a) the IL12Rβ moieties in Exemplary Monomer 11 and Exemplary Monomer 36 are both IL12Rβ1 moieties;

(b) the IL12Rβ moieties in Exemplary Monomer 11 and Exemplary Monomer 36 are both IL12Rβ2 moieties (c) the IL12Rβ moiety in Exemplary Monomer 11 is an IL12Rβ1 moiety and the IL12Rβ moiety in Exemplary Monomer 36 is an IL12Rβ2 moiety; or (d) the IL12Rβ moiety in Exemplary Monomer 11 is an IL12Rβ2 moiety and the IL12Rβ moiety in Exemplary Monomer 36 is an IL12Rβ1 moiety.

164. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 37, optionally wherein:

(a) the IL12Rβ moieties in Exemplary Monomer 11 and Exemplary Monomer 37 are both IL12Rβ1 moieties;

(b) the IL12Rβ moieties in Exemplary Monomer 11 and Exemplary Monomer 7

(c) the IL12Rβ moiety in Exemplary Monomer 11 is an IL12Rβ1 moiety and the IL12Rβ moiety in Exemplary Monomer 37 is an IL12Rβ2 moiety; or (d) the IL12Rβ moiety in Exemplary Monomer 11 is an IL12Rβ2 moiety and the IL12Rβ moiety in Exemplary Monomer 37 is an IL12Rβ1 moiety.

165. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 38, optionally wherein:

(a) the IL12Rβ moieties in Exemplary Monomer 11 and Exemplary Monomer 38 are both IL12Rβ1 moieties;

(b) the IL12Rβ moieties in Exemplary Monomer 11 and Exemplary Monomer 38 are both IL12Rβ2 moieties (c) the IL12Rβ moiety in Exemplary Monomer 11 is an IL12Rβ1 moiety and the IL12Rβ moiety in Exemplary Monomer 38 is an IL12Rβ2 moiety; or (d) the IL12Rβ moiety in Exemplary Monomer 11 is an IL12Rβ2 moiety and the IL12Rβ moiety in Exemplary Monomer 38 is an IL12Rβ1 moiety.

166. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 39, optionally wherein:

(a) the IL12Rβ moieties in Exemplary Monomer 11 and Exemplary Monomer 39 are both IL12Rβ1 moieties;

(b) the IL12Rβ moieties in Exemplary Monomer 11 and Exemplary Monomer 39 are both IL12Rβ2 moieties (c) the IL12Rβ moiety in Exemplary Monomer 11 is an IL12Rβ1 moiety and the IL12Rβ moiety in Exemplary Monomer 39 is an IL12Rβ2 moiety; or (d) the IL12Rβ moiety in Exemplary Monomer 11 is an IL12Rβ2 moiety and the IL12Rβ moiety in Exemplary Monomer 39 is an IL12Rβ1 moiety.

167. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 40, optionally wherein:

(a) the IL12Rβ moieties in Exemplary Monomer 11 and Exemplary Monomer 40 are both IL12Rβ1 moieties;

(b) the IL12Rβ moieties in Exemplary Monomer 11 and Exemplary Monomer 40 are both IL12Rβ2 moieties (c) the IL12Rβ moiety in Exemplary Monomer 11 is an IL12Rβ1 moiety and the IL12Rβ moiety in Exemplary Monomer 40 is an IL12Rβ2 moiety; or (d) the IL12Rβ moiety in Exemplary Monomer 11 is an IL12Rβ2 moiety and the IL12Rβ moiety in Exemplary Monomer 40 is an IL12Rβ1 moiety.

168. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 41, optionally wherein:

(a) the IL12Rβ moieties in Exemplary Monomer 11 and Exemplary Monomer 41 are both IL12Rβ1 moieties;

(b) the IL12Rβ moieties in Exemplary Monomer 11 and Exemplary Monomer 41 are both IL12Rβ2 moieties (c) the IL12Rβ moiety in Exemplary Monomer 11 is an IL12Rβ1 moiety and the IL12Rβ moiety in Exemplary Monomer 41 is an IL12Rβ2 moiety; or (d) the IL12Rβ moiety in Exemplary Monomer 11 is an IL12Rβ2 moiety and the IL12Rβ moiety in Exemplary Monomer 41 is an IL12Rβ1 moiety.

169. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 42, optionally wherein:

(a) the IL12Rβ moieties in Exemplary Monomer 11 and Exemplary Monomer 42 are both IL12Rβ1 moieties;

(b) the IL12Rβ moieties in Exemplary Monomer 11 and Exemplary Monomer 42 are both IL12Rβ2 moieties (c) the IL12Rβ moiety in Exemplary Monomer 11 is an IL12Rβ1 moiety and the IL12Rβ moiety in Exemplary Monomer 42 is an IL12Rβ2 moiety; or (d) the IL12Rβ moiety in Exemplary Monomer 11 is an IL12Rβ2 moiety and the IL12Rβ moiety in Exemplary Monomer 42 is an IL12Rβ1 moiety.

170. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 51, optionally wherein:

(a) the IL12Rβ moieties in Exemplary Monomer 11 and Exemplary Monomer 51 are both IL12Rβ1 moieties;

(b) the IL12Rβ moieties in Exemplary Monomer 11 and Exemplary Monomer 51 are both IL12Rβ2 moieties (c) the IL12Rβ moiety in Exemplary Monomer 11 is an IL12Rβ1 moiety and the IL12Rβ moiety in Exemplary Monomer 51 is an IL12Rβ2 moiety; or (d) the IL12Rβ moiety in Exemplary Monomer 11 is an IL12Rβ2 moiety and the IL12Rβ moiety in Exemplary Monomer 51 is an IL12Rβ1 moiety.

171. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 59.

172. An IL12 receptor agonist, which is optionally an IL12 agonist according to any one of embodiments 3 to 7, comprising a first IL12 monomer having the configuration of Exemplary Monomer 11 and a second IL12 monomer having the configuration of Exemplary Monomer 63.

173. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 12, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

174. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 27.

175. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 28.

176. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 31.

177. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 32.

178. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 33.

179. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 34.

180. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 35, optionally wherein:
(a) the IL12Rβ moieties in Exemplary Monomer 12 and Exemplary Monomer 35 are both IL12Rβ1 moieties;
(b) the IL12Rβ moieties in Exemplary Monomer 12 and Exemplary Monomer 35 are both IL12Rβ2 moieties
(c) the IL12Rβ moiety in Exemplary Monomer 12 is an IL12Rβ1 moiety and the IL12Rβ moiety in Exemplary Monomer 35 is an IL12Rβ2 moiety; or
(d) the IL12Rβ moiety in Exemplary Monomer 12 is an IL12Rβ2 moiety and the IL12Rβ moiety in Exemplary Monomer 35 is an IL12Rβ1 moiety.

181. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 36, optionally wherein:
(a) the IL12Rβ moieties in Exemplary Monomer 12 and Exemplary Monomer 36 are both IL12Rβ1 moieties;
(b) the IL12Rβ moieties in Exemplary Monomer 12 and Exemplary Monomer 36 are both IL12Rβ2 moieties
(c) the IL12Rβ moiety in Exemplary Monomer 12 is an IL12Rβ1 moiety and the IL12Rβ moiety in Exemplary Monomer 36 is an IL12Rβ2 moiety; or
(d) the IL12Rβ moiety in Exemplary Monomer 12 is an IL12Rβ2 moiety and the IL12Rβ moiety in Exemplary Monomer 36 is an IL12Rβ1 moiety.

182. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 37, optionally wherein:
(a) the IL12Rβ moieties in Exemplary Monomer 12 and Exemplary Monomer 37 are both IL12Rβ1 moieties;
(b) the IL12Rβ moieties in Exemplary Monomer 12 and Exemplary Monomer 37 are both IL12Rβ2 moieties
(c) the IL12Rβ moiety in Exemplary Monomer 12 is an IL12Rβ1 moiety and the IL12Rβ moiety in Exemplary Monomer 37 is an IL12Rβ2 moiety; or
(d) the IL12Rβ moiety in Exemplary Monomer 12 is an IL12Rβ2 moiety and the IL12Rβ moiety in Exemplary Monomer 37 is an IL12Rβ1 moiety.

183. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 38, optionally wherein:
(a) the IL12Rβ moieties in Exemplary Monomer 12 and Exemplary Monomer 38 are both IL12Rβ1 moieties;
(b) the IL12Rβ moieties in Exemplary Monomer 12 and Exemplary Monomer 38 are both IL12Rβ2 moieties
(c) the IL12Rβ moiety in Exemplary Monomer 12 is an IL12Rβ1 moiety and the IL12Rβ moiety in Exemplary Monomer 38 is an IL12Rβ2 moiety; or
(d) the IL12Rβ moiety in Exemplary Monomer 12 is an IL12Rβ2 moiety and the IL12Rβ moiety in Exemplary Monomer 38 is an IL12Rβ1 moiety.

184. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 39, optionally wherein:
(a) the IL12Rβ moieties in Exemplary Monomer 12 and Exemplary Monomer 39 are both IL12Rβ1 moieties;
(b) the IL12Rβ moieties in Exemplary Monomer 12 and Exemplary Monomer 39 are both IL12Rβ2 moieties
(c) the IL12Rβ moiety in Exemplary Monomer 12 is an IL12Rβ1 moiety and the IL12Rβ moiety in Exemplary Monomer 39 is an IL12Rβ2 moiety; or
(d) the IL12Rβ moiety in Exemplary Monomer 12 is an IL12Rβ2 moiety and the IL12Rβ moiety in Exemplary Monomer 39 is an IL12Rβ1 moiety.

185. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 40, optionally wherein:
(a) the IL12Rβ moieties in Exemplary Monomer 12 and Exemplary Monomer 40 are both IL12Rβ1 moieties;
(b) the IL12Rβ moieties in Exemplary Monomer 12 and Exemplary Monomer 40 are both IL12Rβ2 moieties
(c) the IL12Rβ moiety in Exemplary Monomer 12 is an IL12Rβ1 moiety and the IL12Rβ moiety in Exemplary Monomer 40 is an IL12Rβ2 moiety; or
(d) the IL12Rβ moiety in Exemplary Monomer 12 is an IL12Rβ2 moiety and the IL12Rβ moiety in Exemplary Monomer 40 is an IL12Rβ1 moiety.

186. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 41, optionally wherein:
(a) the IL12Rβ moieties in Exemplary Monomer 12 and Exemplary Monomer 41 are both IL12Rβ1 moieties;
(b) the IL12Rβ moieties in Exemplary Monomer 12 and Exemplary Monomer 41 are both IL12Rβ2 moieties
(c) the IL12Rβ moiety in Exemplary Monomer 12 is an IL12Rβ1 moiety and the IL12Rβ moiety in Exemplary Monomer 41 is an IL12Rβ2 moiety; or
(d) the IL12Rβ moiety in Exemplary Monomer 12 is an IL12Rβ2 moiety and the IL12Rβ moiety in Exemplary Monomer 41 is an IL12Rβ1 moiety.

187. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 42, optionally wherein:

(a) the IL12Rβ moieties in Exemplary Monomer 12 and Exemplary Monomer 42 are both IL12Rβ1 moieties;

(b) the IL12Rβ moieties in Exemplary Monomer 12 and Exemplary Monomer 42 are both IL12Rβ2 moieties (c) the IL12Rβ moiety in Exemplary Monomer 12 is an IL12Rβ1 moiety and the IL12Rβ moiety in Exemplary Monomer 42 is an IL12Rβ2 moiety; or (d) the IL12Rβ moiety in Exemplary Monomer 12 is an IL12Rβ2 moiety and the IL12Rβ moiety in Exemplary Monomer 42 is an IL12Rβ1 moiety.

188. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 51, optionally wherein:

(a) the IL12Rβ moieties in Exemplary Monomer 12 and Exemplary Monomer 51 are both IL12Rβ1 moieties;

(b) the IL12Rβ moieties in Exemplary Monomer 12 and Exemplary Monomer 51 are both IL12Rβ2 moieties (c) the IL12Rβ moiety in Exemplary Monomer 12 is an IL12Rβ1 moiety and the IL12Rβ moiety in Exemplary Monomer 51 is an IL12Rβ2 moiety; or (d) the IL12Rβ moiety in Exemplary Monomer 12 is an IL12Rβ2 moiety and the IL12Rβ moiety in Exemplary Monomer 51 is an IL12Rβ1 moiety.

189. An IL12 receptor agonist, which is optionally an IL12 agonist according to any one of embodiments 3 to 7, comprising a first IL12 monomer having the configuration of Exemplary Monomer 12 and a second IL12 monomer having the configuration of Exemplary Monomer 63.

190. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 13, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

191. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 14, optionally wherein:

(a) the IL12Rβ moieties in Exemplary Monomer 13 and Exemplary Monomer 14 are both IL12Rβ1 moieties;

(b) the IL12Rβ moieties in Exemplary Monomer 13 and Exemplary Monomer 14 are both IL12Rβ2 moieties (c) the IL12Rβ moiety in Exemplary Monomer 13 is an IL12Rβ1 moiety and the IL12Rβ moiety in Exemplary Monomer 14 is an IL12Rβ2 moiety; or (d) the IL12Rβ moiety in Exemplary Monomer 13 is an IL12Rβ2 moiety and the IL12Rβ moiety in Exemplary Monomer 4 is an IL12Rβ1 moiety.

192. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 15, optionally wherein:

(a) the IL12Rβ moieties in Exemplary Monomer 13 and Exemplary Monomer 15 are both IL12Rβ1 moieties;

(b) the IL12Rβ moieties in Exemplary Monomer 13 and Exemplary Monomer 15 are both IL12Rβ2 moieties (c) the IL12Rβ moiety in Exemplary Monomer 13 is an IL12Rβ1 moiety and the IL12Rβ moiety in Exemplary Monomer 15 is an IL12Rβ2 moiety; or (d) the IL12Rβ moiety in Exemplary Monomer 13 is an IL12Rβ2 moiety and the IL12Rβ moiety in Exemplary Monomer 15 is an IL12Rβ1 moiety.

193. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 16, optionally wherein:

(a) the IL12Rβ moieties in Exemplary Monomer 13 and Exemplary Monomer 16 are both IL12Rβ1 moieties;

(b) the IL12Rβ moieties in Exemplary Monomer 13 and Exemplary Monomer 16 are both IL12Rβ2 moieties (c) the IL12Rβ moiety in Exemplary Monomer 13 is an IL12Rβ1 moiety and the IL12Rβ moiety in Exemplary Monomer 16 is an IL12Rβ2 moiety; or (d) the IL12Rβ moiety in Exemplary Monomer 13 is an IL12Rβ2 moiety and the IL12Rβ moiety in Exemplary Monomer 16 is an IL12Rβ1 moiety.

194. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 25.

195. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 26.

196. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 29.

197. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 30.

198. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 33.
199. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 34.
200. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 43, optionally wherein:
   (a) the IL12Rβ moieties in Exemplary Monomer 13 and Exemplary Monomer 43 are both IL12Rβ1 moieties;
   (b) the IL12Rβ moieties in Exemplary Monomer 13 and Exemplary Monomer 43 are both IL12Rβ2 moieties
   (c) the IL12Rβ moiety in Exemplary Monomer 13 is an IL12Rβ1 moiety and the IL12Rβ moiety in Exemplary Monomer 43 is an IL12Rβ2 moiety; or
   (d) the IL12Rβ moiety in Exemplary Monomer 13 is an IL12Rβ2 moiety and the IL12Rβ moiety in Exemplary Monomer 43 is an IL12Rβ1 moiety.
201. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 44, optionally wherein:
   (a) the IL12Rβ moieties in Exemplary Monomer 13 and Exemplary Monomer 44 are both IL12Rβ1 moieties;
   (b) the IL12Rβ moieties in Exemplary Monomer 13 and Exemplary Monomer 44 are both IL12Rβ2 moieties
   (c) the IL12Rβ moiety in Exemplary Monomer 13 is an IL12Rβ1 moiety and the IL12Rβ moiety in Exemplary Monomer 44 is an IL12Rβ2 moiety; or
   (d) the IL12Rβ moiety in Exemplary Monomer 13 is an IL12Rβ2 moiety and the IL12Rβ moiety in Exemplary Monomer 44 is an IL12Rβ1 moiety.
202. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 45, optionally wherein:
   (a) the IL12Rβ moieties in Exemplary Monomer 13 and Exemplary Monomer 45 are both IL12Rβ1 moieties;
   (b) the IL12Rβ moieties in Exemplary Monomer 13 and Exemplary Monomer 45 are both IL12Rβ2 moieties
   (c) the IL12Rβ moiety in Exemplary Monomer 13 is an IL12Rβ1 moiety and the IL12Rβ moiety in Exemplary Monomer 45 is an IL12Rβ2 moiety; or
   (d) the IL12Rβ moiety in Exemplary Monomer 13 is an IL12Rβ2 moiety and the IL12Rβ moiety in Exemplary Monomer 45 is an IL12Rβ1 moiety.
203. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 46, optionally wherein:
   (a) the IL12Rβ moieties in Exemplary Monomer 13 and Exemplary Monomer 46 are both IL12Rβ1 moieties;
   (b) the IL12Rβ moieties in Exemplary Monomer 13 and Exemplary Monomer 46 are both IL12Rβ2 moieties
   (c) the IL12Rβ moiety in Exemplary Monomer 13 is an IL12Rβ1 moiety and the IL12Rβ moiety in Exemplary Monomer 46 is an IL12Rβ2 moiety; or
   (d) the IL12Rβ moiety in Exemplary Monomer 13 is an IL12Rβ2 moiety and the IL12Rβ moiety in Exemplary Monomer 46 is an IL12Rβ1 moiety.
204. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 47, optionally wherein:
   (a) the IL12Rβ moieties in Exemplary Monomer 13 and Exemplary Monomer 47 are both IL12Rβ1 moieties;
   (b) the IL12Rβ moieties in Exemplary Monomer 13 and Exemplary Monomer 47 are both IL12Rβ2 moieties
   (c) the IL12Rβ moiety in Exemplary Monomer 13 is an IL12Rβ1 moiety and the IL12Rβ moiety in Exemplary Monomer 47 is an IL12Rβ2 moiety; or
   (d) the IL12Rβ moiety in Exemplary Monomer 13 is an IL12Rβ2 moiety and the IL12Rβ moiety in Exemplary Monomer 47 is an IL12Rβ1 moiety.
205. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 48, optionally wherein:
   (a) the IL12Rβ moieties in Exemplary Monomer 13 and Exemplary Monomer 48 are both IL12Rβ1 moieties;
   (b) the IL12Rβ moieties in Exemplary Monomer 13 and Exemplary Monomer 48 are both IL12Rβ2 moieties
   (c) the IL12Rβ moiety in Exemplary Monomer 13 is an IL12Rβ1 moiety and the IL12Rβ moiety in Exemplary Monomer 48 is an IL12Rβ2 moiety; or
   (d) the IL12Rβ moiety in Exemplary Monomer 13 is an IL12Rβ2 moiety and the IL12Rβ moiety in Exemplary Monomer 48 is an IL12Rβ1 moiety.
206. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 49, optionally wherein:
   (a) the IL12Rβ moieties in Exemplary Monomer 13 and Exemplary Monomer 49 are both IL12Rβ1 moieties;
   (b) the IL12Rβ moieties in Exemplary Monomer 13 and Exemplary Monomer 49 are both IL12Rβ2 moieties (c) the IL12Rβ moiety in Exemplary Monomer 13 is an IL12Rβ1 moiety and the IL12Rβ moiety in Exemplary Monomer 49 is an IL12Rβ2 moiety; or
(d) the IL12Rβ moiety in Exemplary Monomer 13 is an IL12Rβ2 moiety and the IL12Rβ moiety in Exemplary Monomer 49 is an IL12Rβ1 moiety.

207. An IL12 receptor agonist, which is optionally an IL12 agonist according to any one of embodiments 3 to 7, comprising a first IL12 monomer having the configuration of Exemplary Monomer 13 and a second IL12 monomer having the configuration of Exemplary Monomer 50, optionally wherein:
(a) the IL12Rβ moieties in Exemplary Monomer 13 and Exemplary Monomer 50 are both IL12Rβ1 moieties;
(b) the IL12Rβ moieties in Exemplary Monomer 13 and Exemplary Monomer 50 are both IL12Rβ2 moieties
(c) the IL12Rβ moiety in Exemplary Monomer 13 is an IL12Rβ1 moiety and the IL12Rβ moiety in Exemplary Monomer 50 is an IL12Rβ2 moiety; or
(d) the IL12Rβ moiety in Exemplary Monomer 13 is an IL12Rβ2 moiety and the IL12Rβ moiety in Exemplary Monomer 50 is an IL12Rβ1 moiety.

208. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 14, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

209. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 15, optionally wherein:
(a) the IL12Rβ moieties in Exemplary Monomer 14 and Exemplary Monomer 15 are both IL12Rβ1 moieties;
(b) the IL12Rβ moieties in Exemplary Monomer 14 and Exemplary Monomer 15 are both IL12Rβ2 moieties
(c) the IL12Rβ moiety in Exemplary Monomer 14 is an IL12Rβ1 moiety and the IL12Rβ moiety in Exemplary Monomer 15 is an IL12Rβ2 moiety; or
(d) the IL12Rβ moiety in Exemplary Monomer 14 is an IL12Rβ2 moiety and the IL12Rβ moiety in Exemplary Monomer 15 is an IL12Rβ1 moiety.

210. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 16, optionally wherein:
(a) the IL12Rβ moieties in Exemplary Monomer 14 and Exemplary Monomer 16 are both IL12Rβ1 moieties;
(b) the IL12Rβ moieties in Exemplary Monomer 14 and Exemplary Monomer 16 are both IL12Rβ2 moieties
(c) the IL12Rβ moiety in Exemplary Monomer 16 is an IL12Rβ1 moiety and the IL12Rβ moiety in Exemplary Monomer 14 is an IL12Rβ2 moiety; or
(d) the IL12Rβ moiety in Exemplary Monomer 16 is an IL12Rβ2 moiety and the IL12Rβ moiety in Exemplary Monomer 14 is an IL12Rβ1 moiety.

211. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 25.

212. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 26.

213. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 29.

214. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 30.

215. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 33.

216. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 34.

217. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 43, optionally wherein:
(a) the IL12Rβ moieties in Exemplary Monomer 14 and Exemplary Monomer 43 are both IL12Rβ1 moieties;
(b) the IL12Rβ moieties in Exemplary Monomer 14 and Exemplary Monomer 43 are both IL12Rβ2 moieties
(c) the IL12Rβ moiety in Exemplary Monomer 14 is an IL12Rβ1 moiety and the IL12Rβ moiety in Exemplary Monomer 43 is an IL12Rβ2 moiety; or
(d) the IL12Rβ moiety in Exemplary Monomer 14 is an IL12Rβ2 moiety and the IL12Rβ moiety in Exemplary Monomer 43 is an IL12Rβ1 moiety.

218. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 44, optionally wherein:
   (a) the IL12Rβ moieties in Exemplary Monomer 14 and Exemplary Monomer 44 are both IL12Rβ1 moieties;
   (b) the IL12Rβ moieties in Exemplary Monomer 14 and Exemplary Monomer 44 are both IL12Rβ2 moieties
   (c) the IL12Rβ moiety in Exemplary Monomer 14 is an IL12Rβ1 moiety and the IL12Rβ moiety in Exemplary Monomer 44 is an IL12Rβ2 moiety; or
   (d) the IL12Rβ moiety in Exemplary Monomer 14 is an IL12Rβ2 moiety and the IL12Rβ moiety in Exemplary Monomer 4 is an IL12Rβ1 moiety.
219. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 45, optionally wherein:
   (a) the IL12Rβ moieties in Exemplary Monomer 14 and Exemplary Monomer 45 are both IL12Rβ1 moieties;
   (b) the IL12Rβ moieties in Exemplary Monomer 14 and Exemplary Monomer 45 are both IL12Rβ2 moieties
   (c) the IL12Rβ moiety in Exemplary Monomer 45 is an IL12Rβ1 moiety and the IL12Rβ moiety in Exemplary Monomer 15 is an IL12Rβ2 moiety; or
   (d) the IL12Rβ moiety in Exemplary Monomer 45 is an IL12Rβ2 moiety and the IL12Rβ moiety in Exemplary Monomer 15 is an IL12Rβ1 moiety.
220. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 46, optionally wherein:
   (a) the IL12Rβ moieties in Exemplary Monomer 14 and Exemplary Monomer 46 are both IL12Rβ1 moieties;
   (b) the IL12Rβ moieties in Exemplary Monomer 14 and Exemplary Monomer 46 are both IL12Rβ2 moieties
   (c) the IL12Rβ moiety in Exemplary Monomer 14 is an IL12Rβ1 moiety and the IL12Rβ moiety in Exemplary Monomer 46 is an IL12Rβ2 moiety; or
   (d) the IL12Rβ moiety in Exemplary Monomer 14 is an IL12Rβ2 moiety and the IL12Rβ moiety in Exemplary Monomer 46 is an IL12Rβ1 moiety.
221. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 47, optionally wherein:
   (a) the IL12Rβ moieties in Exemplary Monomer 14 and Exemplary Monomer 47 are both IL12Rβ1 moieties;
   (b) the IL12Rβ moieties in Exemplary Monomer 14 and Exemplary Monomer 47 are both IL12Rβ2 moieties
   (c) the IL12Rβ moiety in Exemplary Monomer 47 is an IL12Rβ1 moiety and the IL12Rβ moiety in Exemplary Monomer 15 is an IL12Rβ2 moiety; or
   (d) the IL12Rβ moiety in Exemplary Monomer 47 is an IL12Rβ2 moiety and the IL12Rβ moiety in Exemplary Monomer 15 is an IL12Rβ1 moiety.
222. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 48, optionally wherein:
   (a) the IL12Rβ moieties in Exemplary Monomer 14 and Exemplary Monomer 48 are both IL12Rβ1 moieties;
   (b) the IL12Rβ moieties in Exemplary Monomer 14 and Exemplary Monomer 48 are both IL12Rβ2 moieties
   (c) the IL12Rβ moiety in Exemplary Monomer 14 is an IL12Rβ1 moiety and the IL12Rβ moiety in Exemplary Monomer 48 is an IL12Rβ2 moiety; or
   (d) the IL12Rβ moiety in Exemplary Monomer 14 is an IL12Rβ2 moiety and the IL12Rβ moiety in Exemplary Monomer 48 is an IL12Rβ1 moiety.
223. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 49, optionally wherein:
   (a) the IL12Rβ moieties in Exemplary Monomer 14 and Exemplary Monomer 49 are both IL12Rβ1 moieties;
   (b) the IL12Rβ moieties in Exemplary Monomer 14 and Exemplary Monomer 49 are both IL12Rβ2 moieties
   (c) the IL12Rβ moiety in Exemplary Monomer 14 is an IL12Rβ1 moiety and the IL12Rβ moiety in Exemplary Monomer 49 is an IL12Rβ2 moiety; or
   (d) the IL12Rβ moiety in Exemplary Monomer 14 is an IL12Rβ2 moiety and the IL12Rβ moiety in Exemplary Monomer 49 is an IL12Rβ1 moiety.
224. An IL12 receptor agonist, which is optionally an IL12 agonist according to any one of embodiments 3 to 7, comprising a first IL12 monomer having the configuration of Exemplary Monomer 14 and a second IL12 monomer having the configuration of Exemplary Monomer 50, optionally wherein:
   (a) the IL12Rβ moieties in Exemplary Monomer 14 and Exemplary Monomer 50 are both IL12Rβ1 moieties;
   (b) the IL12Rβ moieties in Exemplary Monomer 14 and Exemplary Monomer 50 are both IL12Rβ2 moieties
   (c) the IL12Rβ moiety in Exemplary Monomer 14 is an IL12Rβ1 moiety and the IL12Rβ moiety in Exemplary Monomer 50 is an IL12Rβ2 moiety; or
   (d) the IL12Rβ moiety in Exemplary Monomer 14 is an IL12Rβ2 moiety and the IL12Rβ moiety in Exemplary Monomer 50 is an IL12Rβ1 moiety.
225. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 15, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

226. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 16, optionally wherein:

(a) the IL12Rβ moieties in Exemplary Monomer 15 and Exemplary Monomer 16 are both IL12Rβ1 moieties;

(b) the IL12Rβ moieties in Exemplary Monomer 15 and Exemplary Monomer 16 are both IL12Rβ2 moieties (c) the IL12Rβ moiety in Exemplary Monomer 15 is an IL12Rβ1 moiety and the IL12Rβ moiety in Exemplary Monomer 16 is an IL12Rβ2 moiety; or (d) the IL12Rβ moiety in Exemplary Monomer 15 is an IL12Rβ2 moiety and the IL12Rβ moiety in Exemplary Monomer 16 is an IL12Rβ1 moiety.

227. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 25.

228. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 26.

229. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 29.

230. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 30.

231. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 33.

232. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 34.

233. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 43, optionally wherein:

(a) the IL12Rβ moieties in Exemplary Monomer 15 and Exemplary Monomer 43 are both IL12Rβ1 moieties;

(b) the IL12Rβ moieties in Exemplary Monomer 15 and Exemplary Monomer 43 are both IL12Rβ2 moieties (c) the IL12Rβ moiety in Exemplary Monomer 15 is an IL12Rβ1 moiety and the IL12Rβ moiety in Exemplary Monomer 43 is an IL12Rβ2 moiety; or (d) the IL12Rβ moiety in Exemplary Monomer 15 is an IL12Rβ2 moiety and the IL12Rβ moiety in Exemplary Monomer 3 is an IL12Rβ1 moiety.

234. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 44, optionally wherein:

(a) the IL12Rβ moieties in Exemplary Monomer 15 and Exemplary Monomer 44 are both IL12Rβ1 moieties;

(b) the IL12Rβ moieties in Exemplary Monomer 15 and Exemplary Monomer 44 are both IL12Rβ2 moieties (c) the IL12Rβ moiety in Exemplary Monomer 15 is an IL12Rβ1 moiety and the IL12Rβ moiety in Exemplary Monomer 44 is an IL12Rβ2 moiety; or (d) the IL12Rβ moiety in Exemplary Monomer 15 is an IL12Rβ2 moiety and the IL12Rβ moiety in Exemplary Monomer 44 is an IL12Rβ1 moiety.

235. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 45, optionally wherein:

(a) the IL12Rβ moieties in Exemplary Monomer 15 and Exemplary Monomer 45 are both IL12Rβ1 moieties;

(b) the IL12Rβ moieties in Exemplary Monomer 15 and Exemplary Monomer 45 are both IL12Rβ2 moieties (c) the IL12Rβ moiety in Exemplary Monomer 15 is an IL12Rβ1 moiety and the IL12Rβ moiety in Exemplary Monomer 45 is an IL12Rβ2 moiety; or (d) the IL12Rβ moiety in Exemplary Monomer 15 is an IL12Rβ2 moiety and the IL12Rβ moiety in Exemplary Monomer 45 is an IL12Rβ1 moiety.

236. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 46, optionally wherein:

(a) the IL12Rβ moieties in Exemplary Monomer 15 and Exemplary Monomer 46 are both IL12Rβ1 moieties;

(b) the IL12Rβ moieties in Exemplary Monomer 15 and Exemplary Monomer 46 are both IL12Rβ2 moieties (c) the IL12Rβ moiety in Exemplary Monomer 15 is an IL12Rβ1 moiety and the IL12Rβ moiety in Exemplary Monomer 46 is an IL12Rβ2 moiety; or (d) the IL12Rβ moiety in Exemplary Monomer 15 is an IL12Rβ2 moiety and the IL12Rβ moiety in Exemplary Monomer 46 is an IL12Rβ1 moiety.

237. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 47, optionally wherein:

(a) the IL12Rβ moieties in Exemplary Monomer 15 and Exemplary Monomer 47 are both IL12Rβ1 moieties;

(b) the IL12Rβ moieties in Exemplary Monomer 15 and Exemplary Monomer 47 are both IL12Rβ2 moieties (c) the IL12Rβ moiety in Exemplary Monomer 15 is an IL12Rβ1 moiety and the IL12Rβ moiety in Exemplary Monomer 47 is an IL12Rβ2 moiety; or (d) the IL12Rβ moiety in Exemplary Monomer 15 is an IL12Rβ2 moiety and the IL12Rβ moiety in Exemplary Monomer 47 is an IL12Rβ1 moiety.

238. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 48, optionally wherein:

(a) the IL12Rβ moieties in Exemplary Monomer 15 and Exemplary Monomer 48 are both IL12Rβ1 moieties;

(b) the IL12Rβ moieties in Exemplary Monomer 15 and Exemplary Monomer 48 are both IL12Rβ2 moieties (c) the IL12Rβ moiety in Exemplary Monomer 15 is an IL12Rβ1 moiety and the IL12Rβ moiety in Exemplary Monomer 48 is an IL12Rβ2 moiety; or (d) the IL12Rβ moiety in Exemplary Monomer 15 is an IL12Rβ2 moiety and the IL12Rβ moiety in Exemplary Monomer 48 is an IL12Rβ1 moiety.

239. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 49, optionally wherein:

(a) the IL12Rβ moieties in Exemplary Monomer 15 and Exemplary Monomer 49 are both IL12Rβ1 moieties;

(b) the IL12Rβ moieties in Exemplary Monomer 15 and Exemplary Monomer 49 are both IL12Rβ2 moieties (c) the IL12Rβ moiety in Exemplary Monomer 15 is an IL12Rβ1 moiety and the IL12Rβ moiety in Exemplary Monomer 49 is an IL12Rβ2 moiety; or (d) the IL12Rβ moiety in Exemplary Monomer 15 is an IL12Rβ2 moiety and the IL12Rβ moiety in Exemplary Monomer 49 is an IL12Rβ1 moiety.

240. An IL12 receptor agonist, which is optionally an IL12 agonist according to any one of embodiments 3 to 7, comprising a first IL12 monomer having the configuration of Exemplary Monomer 15 and a second IL12 monomer having the configuration of Exemplary Monomer 50, optionally wherein:

(a) the IL12Rβ moieties in Exemplary Monomer 15 and Exemplary Monomer 50 are both IL12Rβ1 moieties;

(b) the IL12Rβ moieties in Exemplary Monomer 15 and Exemplary Monomer 50 are both IL12Rβ2 moieties (c) the IL12Rβ moiety in Exemplary Monomer 15 is an IL12Rβ1 moiety and the IL12Rβ moiety in Exemplary Monomer 50 is an IL12Rβ2 moiety; or (d) the IL12Rβ moiety in Exemplary Monomer 15 is an IL12Rβ2 moiety and the IL12Rβ moiety in Exemplary Monomer 50 is an IL12Rβ1 moiety.

241. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 16, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

242. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 25.

243. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 26.

244. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 29.

245. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 30.

246. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 33.

247. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 34.

248. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 43, optionally wherein:
- (a) the IL12Rβ moieties in Exemplary Monomer 16 and Exemplary Monomer 43 are both IL12Rβ1 moieties;
- (b) the IL12Rβ moieties in Exemplary Monomer 16 and Exemplary Monomer 43 are both IL12Rβ2 moieties
- (c) the IL12Rβ moiety in Exemplary Monomer 16 is an IL12Rβ1 moiety and the IL12Rβ moiety in Exemplary Monomer 43 is an IL12Rβ2 moiety; or
- (d) the IL12Rβ moiety in Exemplary Monomer 16 is an IL12Rβ2 moiety and the IL12Rβ moiety in Exemplary Monomer 43 is an IL12Rβ1 moiety.

249. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 44, optionally wherein:
- (a) the IL12Rβ moieties in Exemplary Monomer 16 and Exemplary Monomer 44 are both IL12Rβ1 moieties;
- (b) the IL12Rβ moieties in Exemplary Monomer 16 and Exemplary Monomer 44 are both IL12Rβ2 moieties
- (c) the IL12Rβ moiety in Exemplary Monomer 16 is an IL12Rβ1 moiety and the IL12Rβ moiety in Exemplary Monomer 44 is an IL12Rβ2 moiety; or
- (d) the IL12Rβ moiety in Exemplary Monomer 16 is an IL12Rβ2 moiety and the IL12Rβ moiety in Exemplary Monomer 44 is an IL12Rβ1 moiety.

250. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 45, optionally wherein:
- (a) the IL12Rβ moieties in Exemplary Monomer 16 and Exemplary Monomer 45 are both IL12Rβ1 moieties;
- (b) the IL12Rβ moieties in Exemplary Monomer 16 and Exemplary Monomer 45 are both IL12Rβ2 moieties
- (c) the IL12Rβ moiety in Exemplary Monomer 16 is an IL12Rβ1 moiety and the IL12Rβ moiety in Exemplary Monomer 45 is an IL12Rβ2 moiety; or
- (d) the IL12Rβ moiety in Exemplary Monomer 16 is an IL12Rβ2 moiety and the IL12Rβ moiety in Exemplary Monomer 45 is an IL12Rβ1 moiety.

251. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 46, optionally wherein:
- (a) the IL12Rβ moieties in Exemplary Monomer 16 and Exemplary Monomer 46 are both IL12Rβ1 moieties;
- (b) the IL12Rβ moieties in Exemplary Monomer 16 and Exemplary Monomer 46 are both IL12Rβ2 moieties
- (c) the IL12Rβ moiety in Exemplary Monomer 16 is an IL12Rβ1 moiety and the IL12Rβ moiety in Exemplary Monomer 46 is an IL12Rβ2 moiety; or
- (d) the IL12Rβ moiety in Exemplary Monomer 16 is an IL12Rβ2 moiety and the IL12Rβ moiety in Exemplary Monomer 46 is an IL12Rβ1 moiety.

252. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 47, optionally wherein:
- (a) the IL12Rβ moieties in Exemplary Monomer 16 and Exemplary Monomer 47 are both IL12Rβ1 moieties;
- (b) the IL12Rβ moieties in Exemplary Monomer 16 and Exemplary Monomer 47 are both IL12Rβ2 moieties
- (c) the IL12Rβ moiety in Exemplary Monomer 16 is an IL12Rβ1 moiety and the IL12Rβ moiety in Exemplary Monomer 47 is an IL12Rβ2 moiety; or
- (d) the IL12Rβ moiety in Exemplary Monomer 16 is an IL12Rβ2 moiety and the IL12Rβ moiety in Exemplary Monomer 47 is an IL12Rβ1 moiety.

253. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 48, optionally wherein:
- (a) the IL12Rβ moieties in Exemplary Monomer 16 and Exemplary Monomer 48 are both IL12Rβ1 moieties;
- (b) the IL12Rβ moieties in Exemplary Monomer 16 and Exemplary Monomer 48 are both IL12Rβ2 moieties
- (c) the IL12Rβ moiety in Exemplary Monomer 16 is an IL12Rβ1 moiety and the IL12Rβ moiety in Exemplary Monomer 48 is an IL12Rβ2 moiety; or
- (d) the IL12Rβ moiety in Exemplary Monomer 16 is an IL12Rβ2 moiety and the IL12Rβ moiety in Exemplary Monomer 48 is an IL12Rβ1 moiety.

254. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 49, optionally wherein:
- (a) the IL12Rβ moieties in Exemplary Monomer 16 and Exemplary Monomer 49 are both IL12Rβ1 moieties;
- (b) the IL12Rβ moieties in Exemplary Monomer 16 and Exemplary Monomer 49 are both IL12Rβ2 moieties
- (c) the IL12Rβ moiety in Exemplary Monomer 16 is an IL12Rβ1 moiety and the IL12Rβ moiety in Exemplary Monomer 49 is an IL12Rβ2 moiety; or
- (d) the IL12Rβ moiety in Exemplary Monomer 16 is an IL12Rβ2 moiety and the IL12Rβ moiety in Exemplary Monomer 49 is an IL12Rβ1 moiety.

255. An IL12 receptor agonist, which is optionally an IL12 agonist according to any one of embodiments 3 to 7, comprising a first IL12 monomer having the configuration of Exemplary Monomer 16 and a second IL12 monomer having the configuration of Exemplary Monomer 50, optionally wherein:
- (a) the IL12Rβ moieties in Exemplary Monomer 16 and Exemplary Monomer 50 are both IL12Rβ1 moieties;

(b) the IL12Rβ moieties in Exemplary Monomer 16 and Exemplary Monomer 50 are both IL12Rβ2 moieties
(c) the IL12Rβ moiety in Exemplary Monomer 16 is an IL12Rβ1 moiety and the IL12Rβ moiety in Exemplary Monomer 50 is an IL12Rβ2 moiety; or
(d) the IL12Rβ moiety in Exemplary Monomer 16 is an IL12Rβ2 moiety and the IL12Rβ moiety in Exemplary Monomer 50 is an IL12Rβ1 moiety.

256. An IL12 receptor agonist, which is optionally an IL12 agonist according to any one of embodiments 3 to 7, comprising a first IL12 monomer having the configuration of Exemplary Monomer 17 and a second IL12 monomer having the configuration of Exemplary Monomer 18.

257. An IL12 receptor agonist, which is optionally an IL12 agonist according to any one of embodiments 3 to 7, comprising a first IL12 monomer having the configuration of Exemplary Monomer 19 and a second IL12 monomer having the configuration of Exemplary Monomer 20.

258. An IL12 receptor agonist, which is optionally an IL12 agonist according to any one of embodiments 3 to 7, comprising a first IL12 monomer having the configuration of Exemplary Monomer 19 associated with a monomeric p40 (which is optionally a masked, monomeric p40) and a second IL12 monomer having the configuration of Exemplary Monomer 33.

259. An IL12 receptor agonist, which is optionally an IL12 agonist according to any one of embodiments 3 to 7, comprising a first IL12 monomer having the configuration of Exemplary Monomer 19 associated with a monomeric p40 (which is optionally a masked, monomeric p40) and a second IL12 monomer having the configuration of Exemplary Monomer 57.

260. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 25.

261. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 26.

262. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 29.

263. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 30.

264. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 33.

265. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 34.

266. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 43.

267. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 44.

268. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 45.

269. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 46.

270. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 47.

271. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 48.

272. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 49.

273. An IL12 receptor agonist, which is optionally an IL12 agonist according to any one of embodiments 3 to 7, comprising a first IL12 monomer having the configuration of Exemplary Monomer 25 and a second IL12 monomer having the configuration of Exemplary Monomer 50.

274. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 26.

275. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 29.

276. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 30.

277. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 33.

278. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 34.

279. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 43.

280. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 44.

281. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 45.

282. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 46.

283. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 47.

284. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 48.

285. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 49.

286. An IL12 receptor agonist, which is optionally an IL12 agonist according to any one of embodiments 3 to 7, comprising a first IL12 monomer having the configuration of Exemplary Monomer 26 and a second IL12 monomer having the configuration of Exemplary Monomer 50.

287. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 27.

288. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 28.

289. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 31.

290. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 32.

291. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 33.

292. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 34.

293. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 35.

294. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 36.

295. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 37.

296. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 38.

297. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 39.

298. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 40.

299. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 41.

300. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 42.

301. An IL12 receptor agonist, which is optionally an IL12 agonist according to any one of embodiments 3 to 7, comprising a first IL12 monomer having the configuration of Exemplary Monomer 27 and a second IL12 monomer having the configuration of Exemplary Monomer 51.

302. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 28.

303. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 31.

304. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 32.

305. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 33.

306. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 34.

307. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 35.

308. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 36.

309. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 37.

310. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 38.

311. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 39.

312. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 40.

313. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 41.

314. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 42.

315. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 51.

316. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 59.

317. An IL12 receptor agonist, which is optionally an IL12 agonist according to any one of embodiments 3 to 7, comprising a first IL12 monomer having the configuration of Exemplary Monomer 28 and a second IL12 monomer having the configuration of Exemplary Monomer 63.

318. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 29.

319. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 30.

320. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 33.

321. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 34.

322. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 43.

323. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 44.

324. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 45.

325. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 46.

326. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 47.

327. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 48.

328. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 49.

329. An IL12 receptor agonist, which is optionally an IL12 agonist according to any one of embodiments 3 to 7, comprising a first IL12 monomer having the configuration of Exemplary Monomer 29 and a second IL12 monomer having the configuration of Exemplary Monomer 50.

330. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 30.

331. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 34.

332. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 43.

333. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 44.

334. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 45.

335. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 46.

336. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 47.

337. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 48.

338. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 49.

339. An IL12 receptor agonist, which is optionally an IL12 agonist according to any one of embodiments 3 to 7, comprising a first IL12 monomer having the configuration of Exemplary Monomer 30 and a second IL12 monomer having the configuration of Exemplary Monomer 50.

340. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 31.

341. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 32.

342. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 33.

343. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 34.

344. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 35.

345. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 36.

346. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 37.

347. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 38.

348. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 39.

349. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 40.

350. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 41.

351. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 42.

352. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 51.

353. An IL12 receptor agonist, which is optionally an IL12 agonist according to any one of embodiments 3 to 7, comprising a first IL12 monomer having the configuration of Exemplary Monomer 31 and a second IL12 monomer having the configuration of Exemplary Monomer 63.

354. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 32.

355. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 33.

356. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 34.

357. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 35.

358. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 36.

359. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 37.

360. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 38.

361. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 39.

362. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 40.

363. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 41.

364. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 42.

365. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 51.

366. An IL12 receptor agonist, which is optionally an IL12 agonist according to any one of embodiments 3 to 7, comprising a first IL12 monomer having the configuration of Exemplary Monomer 32 and a second IL12 monomer having the configuration of Exemplary Monomer 63.

367. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 34.

368. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 35.

369. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 36.

370. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 37.

371. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 38.

372. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 39.

373. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 40.

374. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 41.

375. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 42.

376. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 43.

377. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 44.

378. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 45.

379. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 46.

380. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 47.

381. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 48.

382. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 49.

383. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 50.

384. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 51.

385. An IL12 receptor agonist, which is optionally an IL12 agonist according to any one of embodiments 3 to 7, comprising a first IL12 monomer having the configuration of Exemplary Monomer 33 and a second IL12 monomer having the configuration of Exemplary Monomer 63.

386. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 35.

387. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 36.

388. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 37.

389. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 38.

390. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 39.

391. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 40.

392. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 41.

393. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 42.

394. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 51.

395. An IL12 receptor agonist, which is optionally an IL12 agonist according to any one of embodiments 3 to 7, comprising a first IL12 monomer having the configuration of Exemplary Monomer 34 and a second IL12 monomer having the configuration of Exemplary Monomer 63.

396. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 35, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

397. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 36, optionally wherein:

(a) the IL12Rβ moieties in Exemplary Monomer 35 and Exemplary Monomer 36 are both IL12Rβ1 moieties;

(b) the IL12Rβ moieties in Exemplary Monomer 35 and Exemplary Monomer 36 are both IL12Rβ2 moieties (c) the IL12Rβ moiety in Exemplary Monomer 35 is an IL12Rβ1 moiety and the IL12Rβ moiety in Exemplary Monomer 36 is an IL12Rβ2 moiety; or (d) the IL12Rβ moiety in Exemplary Monomer 35 is an IL12Rβ2 moiety and the IL12Rβ moiety in Exemplary Monomer 36 is an IL12Rβ1 moiety.

398. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 37, optionally wherein:

(a) the IL12Rβ moieties in Exemplary Monomer 35 and Exemplary Monomer 37 are both IL12Rβ1 moieties;

(b) the IL12Rβ moieties in Exemplary Monomer 35 and Exemplary Monomer 37 are both IL12Rβ2 moieties (c) the IL12Rβ moiety in Exemplary Monomer 35 is an IL12Rβ1 moiety and the IL12Rβ moiety in Exemplary Monomer 37 is an IL12Rβ2 moiety; or (d) the IL12Rβ moiety in Exemplary Monomer 35 is an IL12Rβ2 moiety and the IL12Rβ moiety in Exemplary Monomer 37 is an IL12Rβ1 moiety.

399. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 38, optionally wherein:

(a) the IL12Rβ moieties in Exemplary Monomer 35 and Exemplary Monomer 38 are both IL12Rβ1 moieties;

(b) the IL12Rβ moieties in Exemplary Monomer 35 and Exemplary Monomer 38 are both IL12Rβ2 moieties (c) the IL12Rβ moiety in Exemplary Monomer 35 is an IL12Rβ1 moiety and the IL12Rβ moiety in Exemplary Monomer 38 is an IL12Rβ2 moiety; or (d) the IL12Rβ moiety in Exemplary Monomer 35 is an IL12Rβ2 moiety and the IL12Rβ moiety in Exemplary Monomer 38 is an IL12Rβ1 moiety.

400. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 39, optionally wherein:
(a) the IL12Rβ moieties in Exemplary Monomer 35 and Exemplary Monomer 39 are both IL12Rβ1 moieties;
(b) the IL12Rβ moieties in Exemplary Monomer 35 and Exemplary Monomer 39 are both IL12Rβ2 moieties
(c) the IL12Rβ moiety in Exemplary Monomer 35 is an IL12Rβ1 moiety and the IL12Rβ moiety in Exemplary Monomer 39 is an IL12Rβ2 moiety; or
(d) the IL12Rβ moiety in Exemplary Monomer 35 is an IL12Rβ2 moiety and the IL12Rβ moiety in Exemplary Monomer 39 is an IL12Rβ1 moiety.

401. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 40, optionally wherein:
(a) the IL12Rβ moieties in Exemplary Monomer 35 and Exemplary Monomer 40 are both IL12Rβ1 moieties;
(b) the IL12Rβ moieties in Exemplary Monomer 35 and Exemplary Monomer 40 are both IL12Rβ2 moieties
(c) the IL12Rβ moiety in Exemplary Monomer 35 is an IL12Rβ1 moiety and the IL12Rβ moiety in Exemplary Monomer 40 is an IL12Rβ2 moiety; or
(d) the IL12Rβ moiety in Exemplary Monomer 35 is an IL12Rβ2 moiety and the IL12Rβ moiety in Exemplary Monomer 40 is an IL12Rβ1 moiety.

402. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 41, optionally wherein:
(a) the IL12Rβ moieties in Exemplary Monomer 35 and Exemplary Monomer 41 are both IL12Rβ1 moieties;
(b) the IL12Rβ moieties in Exemplary Monomer 35 and Exemplary Monomer 41 are both IL12Rβ2 moieties
(c) the IL12Rβ moiety in Exemplary Monomer 35 is an IL12Rβ1 moiety and the IL12Rβ moiety in Exemplary Monomer 41 is an IL12Rβ2 moiety; or
(d) the IL12Rβ moiety in Exemplary Monomer 35 is an IL12Rβ2 moiety and the IL12Rβ moiety in Exemplary Monomer 41 is an IL12Rβ1 moiety.

403. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 42, optionally wherein:
(a) the IL12Rβ moieties in Exemplary Monomer 35 and Exemplary Monomer 42 are both IL12Rβ1 moieties;
(b) the IL12Rβ moieties in Exemplary Monomer 35 and Exemplary Monomer 42 are both IL12Rβ2 moieties
(c) the IL12Rβ moiety in Exemplary Monomer 35 is an IL12Rβ1 moiety and the IL12Rβ moiety in Exemplary Monomer 42 is an IL12Rβ2 moiety; or
(d) the IL12Rβ moiety in Exemplary Monomer 35 is an IL12Rβ2 moiety and the IL12Rβ moiety in Exemplary Monomer 42 is an IL12Rβ1 moiety.

404. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 51, optionally wherein:
(a) the IL12Rβ moieties in Exemplary Monomer 35 and Exemplary Monomer 51 are both IL12Rβ1 moieties;
(b) the IL12Rβ moieties in Exemplary Monomer 35 and Exemplary Monomer 51 are both IL12Rβ2 moieties
(c) the IL12Rβ moiety in Exemplary Monomer 35 is an IL12Rβ1 moiety and the IL12Rβ moiety in Exemplary Monomer 51 is an IL12Rβ2 moiety; or
(d) the IL12Rβ moiety in Exemplary Monomer 35 is an IL12Rβ2 moiety and the IL12Rβ moiety in Exemplary Monomer 51 is an IL12Rβ1 moiety.

405. An IL12 receptor agonist, which is optionally an IL12 agonist according to any one of embodiments 3 to 7, comprising a first IL12 monomer having the configuration of Exemplary Monomer 35 and a second IL12 monomer having the configuration of Exemplary Monomer 63.

406. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 36, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

407. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 37, optionally wherein:
(a) the IL12Rβ moieties in Exemplary Monomer 36 and Exemplary Monomer 37 are both IL12Rβ1 moieties;
(b) the IL12Rβ moieties in Exemplary Monomer 36 and Exemplary Monomer 37 are both IL12Rβ2 moieties
(c) the IL12Rβ moiety in Exemplary Monomer 36 is an IL12Rβ1 moiety and the IL12Rβ moiety in Exemplary Monomer 37 is an IL12Rβ2 moiety; or
(d) the IL12Rβ moiety in Exemplary Monomer 36 is an IL12Rβ2 moiety and the IL12Rβ moiety in Exemplary Monomer 37 is an IL12Rβ1 moiety.

408. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 38, optionally wherein:

(a) the IL12Rβ moieties in Exemplary Monomer 36 and Exemplary Monomer 38 are both IL12Rβ1 moieties;

(b) the IL12Rβ moieties in Exemplary Monomer 36 and Exemplary Monomer 38 are both IL12Rβ2 moieties (c) the IL12Rβ moiety in Exemplary Monomer 36 is an IL12Rβ1 moiety and the IL12Rβ moiety in Exemplary Monomer 38 is an IL12Rβ2 moiety; or (d) the IL12Rβ moiety in Exemplary Monomer 36 is an IL12Rβ2 moiety and the IL12Rβ moiety in Exemplary Monomer 38 is an IL12Rβ1 moiety.

409. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 39, optionally wherein:

(a) the IL12Rβ moieties in Exemplary Monomer 36 and Exemplary Monomer 39 are both IL12Rβ1 moieties;

(b) the IL12Rβ moieties in Exemplary Monomer 36 and Exemplary Monomer 39 are both IL12Rβ2 moieties (c) the IL12Rβ moiety in Exemplary Monomer 36 is an IL12Rβ1 moiety and the IL12Rβ moiety in Exemplary Monomer 39 is an IL12Rβ2 moiety; or (d) the IL12Rβ moiety in Exemplary Monomer 36 is an IL12Rβ2 moiety and the IL12Rβ moiety in Exemplary Monomer 39 is an IL12Rβ1 moiety.

410. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 40, optionally wherein:

(a) the IL12Rβ moieties in Exemplary Monomer 36 and Exemplary Monomer 40 are both IL12Rβ1 moieties;

(b) the IL12Rβ moieties in Exemplary Monomer 36 and Exemplary Monomer 40 are both IL12Rβ2 moieties (c) the IL12Rβ moiety in Exemplary Monomer 36 is an IL12Rβ1 moiety and the IL12Rβ moiety in Exemplary Monomer 40 is an IL12Rβ2 moiety; or (d) the IL12Rβ moiety in Exemplary Monomer 36 is an IL12Rβ2 moiety and the IL12Rβ moiety in Exemplary Monomer 40 is an IL12Rβ1 moiety.

411. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 41, optionally wherein:

(a) the IL12Rβ moieties in Exemplary Monomer 36 and Exemplary Monomer 41 are both IL12Rβ1 moieties;

(b) the IL12Rβ moieties in Exemplary Monomer 36 and Exemplary Monomer 41 are both IL12Rβ2 moieties (c) the IL12Rβ moiety in Exemplary Monomer 36 is an IL12Rβ1 moiety and the IL12Rβ moiety in Exemplary Monomer 41 is an IL12Rβ2 moiety; or (d) the IL12Rβ moiety in Exemplary Monomer 36 is an IL12Rβ2 moiety and the IL12Rβ moiety in Exemplary Monomer 41 is an IL12Rβ1 moiety.

412. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 42, optionally wherein:

(a) the IL12Rβ moieties in Exemplary Monomer 36 and Exemplary Monomer 42 are both IL12Rβ1 moieties;

(b) the IL12Rβ moieties in Exemplary Monomer 36 and Exemplary Monomer 42 are both IL12Rβ2 moieties (c) the IL12Rβ moiety in Exemplary Monomer 36 is an IL12Rβ1 moiety and the IL12Rβ moiety in Exemplary Monomer 42 is an IL12Rβ2 moiety; or (d) the IL12Rβ moiety in Exemplary Monomer 36 is an IL12Rβ2 moiety and the IL12Rβ moiety in Exemplary Monomer 42 is an IL12Rβ1 moiety.

413. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 51, optionally wherein:

(a) the IL12Rβ moieties in Exemplary Monomer 36 and Exemplary Monomer 51 are both IL12Rβ1 moieties;

(b) the IL12Rβ moieties in Exemplary Monomer 36 and Exemplary Monomer 51 are both IL12Rβ2 moieties (c) the IL12Rβ moiety in Exemplary Monomer 36 is an IL12Rβ1 moiety and the IL12Rβ moiety in Exemplary Monomer 51 is an IL12Rβ2 moiety; or (d) the IL12Rβ moiety in Exemplary Monomer 36 is an IL12Rβ2 moiety and the IL12Rβ moiety in Exemplary Monomer 51 is an IL12Rβ1 moiety.

414. An IL12 receptor agonist, which is optionally an IL12 agonist according to any one of embodiments 3 to 7, comprising a first IL12 monomer having the configuration of Exemplary Monomer 36 and a second IL12 monomer having the configuration of Exemplary Monomer 63.

415. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 37, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

416. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 38, optionally wherein:

(a) the IL12Rβ moieties in Exemplary Monomer 37 and Exemplary Monomer 38 are both IL12Rβ1 moieties;

(b) the IL12Rβ moieties in Exemplary Monomer 37 and Exemplary Monomer 38 are both IL12Rβ2 moieties (c) the IL12Rβ moiety in Exemplary Monomer 37 is an IL12Rβ1 moiety and the IL12Rβ moiety in Exemplary Monomer 38 is an IL12Rβ2 moiety; or (d) the IL12Rβ moiety in Exemplary Monomer 37 is an IL12Rβ2 moiety and the IL12Rβ moiety in Exemplary Monomer 38 is an IL12Rβ1 moiety.

417. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 39, optionally wherein:

(a) the IL12Rβ moieties in Exemplary Monomer 37 and Exemplary Monomer 39 are both IL12Rβ1 moieties;

(b) the IL12Rβ moieties in Exemplary Monomer 37 and Exemplary Monomer 39 are both IL12Rβ2 moieties (c) the IL12Rβ moiety in Exemplary Monomer 37 is an IL12Rβ1 moiety and the IL12Rβ moiety in Exemplary Monomer 39 is an IL12Rβ2 moiety; or (d) the IL12Rβ moiety in Exemplary Monomer 37 is an IL12Rβ2 moiety and the IL12Rβ moiety in Exemplary Monomer 39 is an IL12Rβ1 moiety.

418. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 40, optionally wherein:

(a) the IL12Rβ moieties in Exemplary Monomer 37 and Exemplary Monomer 40 are both IL12Rβ1 moieties;

(b) the IL12Rβ moieties in Exemplary Monomer 37 and Exemplary Monomer 40 are both IL12Rβ2 moieties (c) the IL12Rβ moiety in Exemplary Monomer 37 is an IL12Rβ1 moiety and the IL12Rβ moiety in Exemplary Monomer 40 is an IL12Rβ2 moiety; or (d) the IL12Rβ moiety in Exemplary Monomer 37 is an IL12Rβ2 moiety and the IL12Rβ moiety in Exemplary Monomer 40 is an IL12Rβ1 moiety.

419. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 41, optionally wherein:

(a) the IL12Rβ moieties in Exemplary Monomer 37 and Exemplary Monomer 41 are both IL12Rβ1 moieties;

(b) the IL12Rβ moieties in Exemplary Monomer 37 and Exemplary Monomer 41 are both IL12Rβ2 moieties (c) the IL12Rβ moiety in Exemplary Monomer 37 is an IL12Rβ1 moiety and the IL12Rβ moiety in Exemplary Monomer 41 is an IL12Rβ2 moiety; or (d) the IL12Rβ moiety in Exemplary Monomer 37 is an IL12Rβ2 moiety and the IL12Rβ moiety in Exemplary Monomer 41 is an IL12Rβ1 moiety.

420. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 42, optionally wherein:

(a) the IL12Rβ moieties in Exemplary Monomer 37 and Exemplary Monomer 42 are both IL12Rβ1 moieties;

(b) the IL12Rβ moieties in Exemplary Monomer 37 and Exemplary Monomer 42 are both IL12Rβ2 moieties (c) the IL12Rβ moiety in Exemplary Monomer 37 is an IL12Rβ1 moiety and the IL12Rβ moiety in Exemplary Monomer 42 is an IL12Rβ2 moiety; or (d) the IL12Rβ moiety in Exemplary Monomer 37 is an IL12Rβ2 moiety and the IL12Rβ moiety in Exemplary Monomer 42 is an IL12Rβ1 moiety.

421. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 51, optionally wherein:

(a) the IL12Rβ moieties in Exemplary Monomer 37 and Exemplary Monomer 51 are both IL12Rβ1 moieties;

(b) the IL12Rβ moieties in Exemplary Monomer 37 and Exemplary Monomer 51 are both IL12Rβ2 moieties (c) the IL12Rβ moiety in Exemplary Monomer 37 is an IL12Rβ1 moiety and the IL12Rβ moiety in Exemplary Monomer 51 is an IL12Rβ2 moiety; or (d) the IL12Rβ moiety in Exemplary Monomer 37 is an IL12Rβ2 moiety and the IL12Rβ moiety in Exemplary Monomer 51 is an IL12Rβ1 moiety.

422. An IL12 receptor agonist, which is optionally an IL12 agonist according to any one of embodiments 3 to 7, comprising a first IL12 monomer having the configuration of Exemplary Monomer 37 and a second IL12 monomer having the configuration of Exemplary Monomer 63.

423. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 38, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

424. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 39, optionally wherein:

(a) the IL12Rβ moieties in Exemplary Monomer 38 and Exemplary Monomer 39 are both IL12Rβ1 moieties;

(b) the IL12Rβ moieties in Exemplary Monomer 38 and Exemplary Monomer 39 are both IL12Rβ2 moieties (c) the IL12Rβ moiety in Exemplary Monomer 38 is an IL12Rβ1 moiety and the IL12Rβ moiety in Exemplary Monomer 39 is an IL12Rβ2 moiety; or (d) the IL12Rβ moiety in Exemplary Monomer 38 is an IL12Rβ2 moiety and the IL12Rβ moiety in Exemplary Monomer 39 is an IL12Rβ1 moiety.

425. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 40, optionally wherein:

(a) the IL12Rβ moieties in Exemplary Monomer 38 and Exemplary Monomer 40 are both IL12Rβ1 moieties;

(b) the IL12Rβ moieties in Exemplary Monomer 38 and Exemplary Monomer 40 are both IL12Rβ2 moieties (c) the IL12Rβ moiety in Exemplary Monomer 38 is an IL12Rβ1 moiety and the IL12Rβ moiety in Exemplary Monomer 40 is an IL12Rβ2 moiety; or (d) the IL12Rβ moiety in Exemplary Monomer 38 is an IL12Rβ2 moiety and the IL12Rβ moiety in Exemplary Monomer 40 is an IL12Rβ1 moiety.

426. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 41, optionally wherein:

(a) the IL12Rβ moieties in Exemplary Monomer 38 and Exemplary Monomer 41 are both IL12Rβ1 moieties;

(b) the IL12Rβ moieties in Exemplary Monomer 38 and Exemplary Monomer 41 are both IL12Rβ2 moieties (c) the IL12Rβ moiety in Exemplary Monomer 38 is an IL12Rβ1 moiety and the IL12Rβ moiety in Exemplary Monomer 41 is an IL12Rβ2 moiety; or (d) the IL12Rβ moiety in Exemplary Monomer 38 is an IL12Rβ2 moiety and the IL12Rβ moiety in Exemplary Monomer 41 is an IL12Rβ1 moiety.

427. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 42, optionally wherein:

(a) the IL12Rβ moieties in Exemplary Monomer 38 and Exemplary Monomer 42 are both IL12Rβ1 moieties;

(b) the IL12Rβ moieties in Exemplary Monomer 38 and Exemplary Monomer 42 are both IL12Rβ2 moieties (c) the IL12Rβ moiety in Exemplary Monomer 38 is an IL12Rβ1 moiety and the IL12Rβ moiety in Exemplary Monomer 42 is an IL12Rβ2 moiety; or (d) the IL12Rβ moiety in Exemplary Monomer 38 is an IL12Rβ2 moiety and the IL12Rβ moiety in Exemplary Monomer 42 is an IL12Rβ1 moiety.

428. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 51, optionally wherein:

(a) the IL12Rβ moieties in Exemplary Monomer 38 and Exemplary Monomer 51 are both IL12Rβ1 moieties;

(b) the IL12Rβ moieties in Exemplary Monomer 38 and Exemplary Monomer 51 are both IL12Rβ2 moieties (c) the IL12Rβ moiety in Exemplary Monomer 38 is an IL12Rβ1 moiety and the IL12Rβ moiety in Exemplary Monomer 51 is an IL12Rβ2 moiety; or (d) the IL12Rβ moiety in Exemplary Monomer 38 is an IL12Rβ2 moiety and the IL12Rβ moiety in Exemplary Monomer 51 is an IL12Rβ1 moiety.

429. An IL12 receptor agonist, which is optionally an IL12 agonist according to any one of embodiments 3 to 7, comprising a first IL12 monomer having the configuration of Exemplary Monomer 38 and a second IL12 monomer having the configuration of Exemplary Monomer 63.

430. An IL12 receptor agonist, which is optionally an IL12 agonist according to any one of embodiments 3 to 7, comprising a first IL12 monomer having the configuration of Exemplary Monomer 39 and a second IL12 monomer having the configuration of Exemplary Monomer 39, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

431. An IL12 receptor agonist, which is optionally an IL12 agonist according to any one of embodiments 3 to 7, comprising a first IL12 monomer having the configuration of Exemplary Monomer 39 and a second IL12 monomer having the configuration of Exemplary Monomer 40, optionally wherein:

(a) the IL12Rβ moieties in Exemplary Monomer 39 and Exemplary Monomer 40 are both IL12Rβ1 moieties;

(b) the IL12Rβ moieties in Exemplary Monomer 39 and Exemplary Monomer 40 are both IL12Rβ2 moieties (c) the IL12Rβ moiety in Exemplary Monomer 39 is an IL12Rβ1 moiety and the IL12Rβ moiety in Exemplary Monomer 40 is an IL12Rβ2 moiety; or (d) the IL12Rβ moiety in Exemplary Monomer 39 is an IL12Rβ2 moiety and the IL12Rβ moiety in Exemplary Monomer 40 is an IL12Rβ1 moiety.

432. An IL12 receptor agonist, which is optionally an IL12 agonist according to any one of embodiments 3 to 7, comprising a first IL12 monomer having the configuration of Exemplary Monomer 39 and a second IL12 monomer having the configuration of Exemplary Monomer 41, optionally wherein:
(a) the IL12Rβ moieties in Exemplary Monomer 39 and Exemplary Monomer 41 are both IL12Rβ1 moieties;
(b) the IL12Rβ moieties in Exemplary Monomer 39 and Exemplary Monomer 41 are both IL12Rβ2 moieties
(c) the IL12Rβ moiety in Exemplary Monomer 39 is an IL12Rβ1 moiety and the IL12Rβ moiety in Exemplary Monomer 41 is an IL12Rβ2 moiety; or
(d) the IL12Rβ moiety in Exemplary Monomer 39 is an IL12Rβ2 moiety and the IL12Rβ moiety in Exemplary Monomer 41 is an IL12Rβ1 moiety.

433. An IL12 receptor agonist, which is optionally an IL12 agonist according to any one of embodiments 3 to 7, comprising a first IL12 monomer having the configuration of Exemplary Monomer 39 and a second IL12 monomer having the configuration of Exemplary Monomer 42, optionally wherein:
(a) the IL12Rβ moieties in Exemplary Monomer 39 and Exemplary Monomer 42 are both IL12Rβ1 moieties;
(b) the IL12Rβ moieties in Exemplary Monomer 39 and Exemplary Monomer 42 are both IL12Rβ2 moieties
(c) the IL12Rβ moiety in Exemplary Monomer 39 is an IL12Rβ1 moiety and the IL12Rβ moiety in Exemplary Monomer 42 is an IL12Rβ2 moiety; or
(d) the IL12Rβ moiety in Exemplary Monomer 39 is an IL12Rβ2 moiety and the IL12Rβ moiety in Exemplary Monomer 42 is an IL12Rβ1 moiety.

434. An IL12 receptor agonist, which is optionally an IL12 agonist according to any one of embodiments 3 to 7, comprising a first IL12 monomer having the configuration of Exemplary Monomer 39 and a second IL12 monomer having the configuration of Exemplary Monomer 51, optionally wherein:
(a) the IL12Rβ moieties in Exemplary Monomer 39 and Exemplary Monomer 51 are both IL12Rβ1 moieties;
(b) the IL12Rβ moieties in Exemplary Monomer 39 and Exemplary Monomer 51 are both IL12Rβ2 moieties
(c) the IL12Rβ moiety in Exemplary Monomer 39 is an IL12Rβ1 moiety and the IL12Rβ moiety in Exemplary Monomer 51 is an IL12Rβ2 moiety; or
(d) the IL12Rβ moiety in Exemplary Monomer 39 is an IL12Rβ2 moiety and the IL12Rβ moiety in Exemplary Monomer 51 is an IL12Rβ1 moiety.

435. An IL12 receptor agonist, which is optionally an IL12 agonist according to any one of embodiments 3 to 7, comprising a first IL12 monomer having the configuration of Exemplary Monomer 39 and a second IL12 monomer having the configuration of Exemplary Monomer 63.

436. An IL12 receptor agonist, which is optionally an IL12 agonist according to any one of embodiments 3 to 7, comprising a first IL12 monomer having the configuration of Exemplary Monomer 40 and a second IL12 monomer having the configuration of Exemplary Monomer 40, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

437. An IL12 receptor agonist, which is optionally an IL12 agonist according to any one of embodiments 3 to 7, comprising a first IL12 monomer having the configuration of Exemplary Monomer 40 and a second IL12 monomer having the configuration of Exemplary Monomer 41, optionally wherein:
(a) the IL12Rβ moieties in Exemplary Monomer 40 and Exemplary Monomer 41 are both IL12Rβ1 moieties;
(b) the IL12Rβ moieties in Exemplary Monomer 40 and Exemplary Monomer 41 are both IL12Rβ2 moieties
(c) the IL12Rβ moiety in Exemplary Monomer 40 is an IL12Rβ1 moiety and the IL12Rβ moiety in Exemplary Monomer 41 is an IL12Rβ2 moiety; or
(d) the IL12Rβ moiety in Exemplary Monomer 40 is an IL12Rβ2 moiety and the IL12Rβ moiety in Exemplary Monomer 41 is an IL12Rβ1 moiety.

438. An IL12 receptor agonist, which is optionally an IL12 agonist according to any one of embodiments 3 to 7, comprising a first IL12 monomer having the configuration of Exemplary Monomer 40 and a second IL12 monomer having the configuration of Exemplary Monomer 42, optionally wherein:
(a) the IL12Rβ moieties in Exemplary Monomer 40 and Exemplary Monomer 42 are both IL12Rβ1 moieties;
(b) the IL12Rβ moieties in Exemplary Monomer 40 and Exemplary Monomer 42 are both IL12Rβ2 moieties
(c) the IL12Rβ moiety in Exemplary Monomer 40 is an IL12Rβ1 moiety and the IL12Rβ moiety in Exemplary Monomer 42 is an IL12Rβ2 moiety; or
(d) the IL12Rβ moiety in Exemplary Monomer 40 is an IL12Rβ2 moiety and the IL12Rβ moiety in Exemplary Monomer 42 is an IL12Rβ1 moiety.

439. An IL12 receptor agonist, which is optionally an IL12 agonist according to any one of embodiments 3 to 7, comprising a first IL12 monomer having the configuration of Exemplary Monomer 40 and a second IL12 monomer having the configuration of Exemplary Monomer 51, optionally wherein:
(a) the IL12Rβ moieties in Exemplary Monomer 40 and Exemplary Monomer 51 are both IL12Rβ1 moieties;
(b) the IL12Rβ moieties in Exemplary Monomer 40 and Exemplary Monomer 51 are both IL12Rβ2 moieties
(c) the IL12Rβ moiety in Exemplary Monomer 40 is an IL12Rβ1 moiety and the IL12Rβ moiety in Exemplary Monomer 51 is an IL12Rβ2 moiety; or
(d) the IL12Rβ moiety in Exemplary Monomer 40 is an IL12Rβ2 moiety and the IL12Rβ moiety in Exemplary Monomer 51 is an IL12Rβ1 moiety.

440. An IL12 receptor agonist, which is optionally an IL12 agonist according to any one of embodiments 3 to 7, comprising a first IL12 monomer having the configuration of Exemplary Monomer 40 and a second IL12 monomer having the configuration of Exemplary Monomer 63.

441. An IL12 receptor agonist, which is optionally an IL12 agonist according to any one of embodiments 3 to 7, comprising a first IL12 monomer having the configuration of Exemplary Monomer 41 and a second IL12 monomer having the configuration of Exemplary Monomer 41, optionally wherein:
 (a) the IL12Rβ moieties in the first IL12 monomer and in the second IL12 monomer are both IL12Rβ1 moieties;
 (b) the IL12Rβ moieties in the first IL12 monomer and in the second IL12 monomer are both IL12Rβ2;
 (c) the IL12Rβ moiety in the first IL12 monomer is an IL12Rβ1 moiety and the IL12Rβ moiety in the second IL12 monomer is an IL12Rβ2 moiety;
 (d) the IL12Rβ moiety in the first IL12 monomer is an IL12Rβ2 moiety and the IL12Rβ moiety in the second IL12 monomer is an IL12Rβ1 moiety.

442. An IL12 receptor agonist, which is optionally an IL12 agonist according to any one of embodiments 3 to 7, comprising a first IL12 monomer having the configuration of Exemplary Monomer 41 and a second IL12 monomer having the configuration of Exemplary Monomer 42, optionally wherein:
 (a) the IL12Rβ moieties in Exemplary Monomer 41 and Exemplary Monomer 42 are both IL12Rβ1 moieties;
 (b) the IL12Rβ moieties in Exemplary Monomer 41 and Exemplary Monomer 42 are both IL12Rβ2 moieties
 (c) the IL12Rβ moiety in Exemplary Monomer 41 is an IL12Rβ1 moiety and the IL12Rβ moiety in Exemplary Monomer 42 is an IL12Rβ2 moiety; or
 (d) the IL12Rβ moiety in Exemplary Monomer 41 is an IL12Rβ2 moiety and the IL12Rβ moiety in Exemplary Monomer 42 is an IL12Rβ1 moiety.

443. An IL12 receptor agonist, which is optionally an IL12 agonist according to any one of embodiments 3 to 7, comprising a first IL12 monomer having the configuration of Exemplary Monomer 41 and a second IL12 monomer having the configuration of Exemplary Monomer 51, optionally wherein:
 (a) the IL12Rβ moieties in Exemplary Monomer 41 and Exemplary Monomer 51 are both IL12Rβ1 moieties;
 (b) the IL12Rβ moieties in Exemplary Monomer 41 and Exemplary Monomer 51 are both IL12Rβ2 moieties
 (c) the IL12Rβ moiety in Exemplary Monomer 41 is an IL12Rβ1 moiety and the IL12Rβ moiety in Exemplary Monomer 51 is an IL12Rβ2 moiety; or
 (d) the IL12Rβ moiety in Exemplary Monomer 41 is an IL12Rβ2 moiety and the IL12Rβ moiety in Exemplary Monomer 51 is an IL12Rβ1 moiety.

444. An IL12 receptor agonist, which is optionally an IL12 agonist according to any one of embodiments 3 to 7, comprising a first IL12 monomer having the configuration of Exemplary Monomer 41 and a second IL12 monomer having the configuration of Exemplary Monomer 63.

445. An IL12 receptor agonist, which is optionally an IL12 agonist according to any one of embodiments 3 to 7, comprising a first IL12 monomer having the configuration of Exemplary Monomer 42 and a second IL12 monomer having the configuration of Exemplary Monomer 42, optionally wherein:
 (a) the IL12Rβ moieties in the first IL12 monomer and in the second IL12 monomer are both IL12Rβ1 moieties;
 (b) the IL12Rβ moieties in the first IL12 monomer and in the second IL12 monomer are both IL12Rβ2;
 (c) the IL12Rβ moiety in the first IL12 monomer is an IL12Rβ1 moiety and the IL12Rβ moiety in the second IL12 monomer is an IL12Rβ2 moiety;
 (d) the IL12Rβ moiety in the first IL12 monomer is an IL12Rβ2 moiety and the IL12Rβ moiety in the second IL12 monomer is an IL12Rβ1 moiety.

446. An IL12 receptor agonist, which is optionally an IL12 agonist according to any one of embodiments 3 to 7, comprising a first IL12 monomer having the configuration of Exemplary Monomer 42 and a second IL12 monomer having the configuration of Exemplary Monomer 51, optionally wherein:
 (a) the IL12Rβ moieties in Exemplary Monomer 42 and Exemplary Monomer 51 are both IL12Rβ1 moieties;
 (b) the IL12Rβ moieties in Exemplary Monomer 42 and Exemplary Monomer 51 are both IL12Rβ2 moieties
 (c) the IL12Rβ moiety in Exemplary Monomer 42 is an IL12Rβ1 moiety and the IL12Rβ moiety in Exemplary Monomer 51 is an IL12Rβ2 moiety; or
 (d) the IL12Rβ moiety in Exemplary Monomer 42 is an IL12Rβ2 moiety and the IL12Rβ moiety in Exemplary Monomer 51 is an IL12Rβ1 moiety.

447. An IL12 receptor agonist, which is optionally an IL12 agonist according to any one of embodiments 3 to 7, comprising a first IL12 monomer having the configuration of Exemplary Monomer 42 and a second IL12 monomer having the configuration of Exemplary Monomer 63.

448. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 43, optionally wherein:
 (a) the IL12Rβ moieties in the first IL12 monomer and in the second IL12 monomer are both IL12Rβ1 moieties;
 (b) the IL12Rβ moieties in the first IL12 monomer and in the second IL12 monomer are both IL12Rβ2;
 (c) the IL12Rβ moiety in the first IL12 monomer is an IL12Rβ1 moiety and the IL12Rβ moiety in the second IL12 monomer is an IL12Rβ2 moiety;
 (d) the IL12Rβ moiety in the first IL12 monomer is an IL12Rβ2 moiety and the IL12Rβ moiety in the second IL12 monomer is an IL12Rβ1 moiety.

449. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 44, optionally wherein:
 (a) the IL12Rβ moieties in Exemplary Monomer 43 and Exemplary Monomer 44 are both IL12Rβ1 moieties;
 (b) the IL12Rβ moieties in Exemplary Monomer 43 and Exemplary Monomer 44 are both IL12Rβ2 moieties
 (c) the IL12Rβ moiety in Exemplary Monomer 43 is an IL12Rβ1 moiety and the IL12Rβ moiety in Exemplary Monomer 44 is an IL12Rβ2 moiety; or (d) the IL12Rβ moiety in Exemplary Monomer 43 is an IL12Rβ2 moiety and the IL12Rβ moiety in Exemplary Monomer 44 is an IL12Rβ1 moiety.

450. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 45, optionally wherein:

(a) the IL12Rβ moieties in Exemplary Monomer 43 and Exemplary Monomer 45 are both IL12Rβ1 moieties;

(b) the IL12Rβ moieties in Exemplary Monomer 43 and Exemplary Monomer 45 are both IL12Rβ2 moieties (c) the IL12Rβ moiety in Exemplary Monomer 43 is an IL12Rβ1 moiety and the IL12Rβ moiety in Exemplary Monomer 45 is an IL12Rβ2 moiety; or (d) the IL12Rβ moiety in Exemplary Monomer 43 is an IL12Rβ2 moiety and the IL12Rβ moiety in Exemplary Monomer 45 is an IL12Rβ1 moiety.

451. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 46, optionally wherein:

(a) the IL12Rβ moieties in Exemplary Monomer 43 and Exemplary Monomer 46 are both IL12Rβ1 moieties;

(b) the IL12Rβ moieties in Exemplary Monomer 43 and Exemplary Monomer 46 are both IL12Rβ2 moieties (c) the IL12Rβ moiety in Exemplary Monomer 43 is an IL12Rβ1 moiety and the IL12Rβ moiety in Exemplary Monomer 46 is an IL12Rβ2 moiety; or (d) the IL12Rβ moiety in Exemplary Monomer 43 is an IL12Rβ2 moiety and the IL12Rβ moiety in Exemplary Monomer 46 is an IL12Rβ1 moiety.

452. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 47, optionally wherein:

(a) the IL12Rβ moieties in Exemplary Monomer 43 and Exemplary Monomer 47 are both IL12Rβ1 moieties;

(b) the IL12Rβ moieties in Exemplary Monomer 43 and Exemplary Monomer 47 are both IL12Rβ2 moieties (c) the IL12Rβ moiety in Exemplary Monomer 43 is an IL12Rβ1 moiety and the IL12Rβ moiety in Exemplary Monomer 47 is an IL12Rβ2 moiety; or (d) the IL12Rβ moiety in Exemplary Monomer 43 is an IL12Rβ2 moiety and the IL12Rβ moiety in Exemplary Monomer 47 is an IL12Rβ1 moiety.

453. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 48, optionally wherein:

(a) the IL12Rβ moieties in Exemplary Monomer 43 and Exemplary Monomer 48 are both IL12Rβ1 moieties;

(b) the IL12Rβ moieties in Exemplary Monomer 43 and Exemplary Monomer 48 are both IL12Rβ2 moieties (c) the IL12Rβ moiety in Exemplary Monomer 43 is an IL12Rβ1 moiety and the IL12Rβ moiety in Exemplary Monomer 48 is an IL12Rβ2 moiety; or (d) the IL12Rβ moiety in Exemplary Monomer 43 is an IL12Rβ2 moiety and the IL12Rβ moiety in Exemplary Monomer 48 is an IL12Rβ1 moiety.

454. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 49, optionally wherein:

(a) the IL12Rβ moieties in Exemplary Monomer 43 and Exemplary Monomer 49 are both IL12Rβ1 moieties;

(b) the IL12Rβ moieties in Exemplary Monomer 43 and Exemplary Monomer 49 are both IL12Rβ2 moieties (c) the IL12Rβ moiety in Exemplary Monomer 43 is an IL12Rβ1 moiety and the IL12Rβ moiety in Exemplary Monomer 49 is an IL12Rβ2 moiety; or (d) the IL12Rβ moiety in Exemplary Monomer 43 is an IL12Rβ2 moiety and the IL12Rβ moiety in Exemplary Monomer 49 is an IL12Rβ1 moiety.

455. An IL12 receptor agonist, which is optionally an IL12 agonist according to any one of embodiments 3 to 7, comprising a first IL12 monomer having the configuration of Exemplary Monomer 43 and a second IL12 monomer having the configuration of Exemplary Monomer 50, optionally wherein:

(a) the IL12Rβ moieties in Exemplary Monomer 43 and Exemplary Monomer 50 are both IL12Rβ1 moieties;

(b) the IL12Rβ moieties in Exemplary Monomer 43 and Exemplary Monomer 50 are both IL12Rβ2 moieties (c) the IL12Rβ moiety in Exemplary Monomer 43 is an IL12Rβ1 moiety and the IL12Rβ moiety in Exemplary Monomer 50 is an IL12Rβ2 moiety; or (d) the IL12Rβ moiety in Exemplary Monomer 43 is an IL12Rβ2 moiety and the IL12Rβ moiety in Exemplary Monomer 50 is an IL12Rβ1 moiety.

456. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 44, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

457. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 45, optionally wherein:
(a) the IL12Rβ moieties in Exemplary Monomer 44 and Exemplary Monomer 45 are both IL12Rβ1 moieties;
(b) the IL12Rβ moieties in Exemplary Monomer 44 and Exemplary Monomer 45 are both IL12Rβ2 moieties
(c) the IL12Rβ moiety in Exemplary Monomer 44 is an IL12Rβ1 moiety and the IL12Rβ moiety in Exemplary Monomer 45 is an IL12Rβ2 moiety; or
(d) the IL12Rβ moiety in Exemplary Monomer 44 is an IL12Rβ2 moiety and the IL12Rβ moiety in Exemplary Monomer 45 is an IL12Rβ1 moiety.

458. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 46, optionally wherein:
(a) the IL12Rβ moieties in Exemplary Monomer 44 and Exemplary Monomer 46 are both IL12Rβ1 moieties;
(b) the IL12Rβ moieties in Exemplary Monomer 44 and Exemplary Monomer 46 are both IL12Rβ2 moieties
(c) the IL12Rβ moiety in Exemplary Monomer 44 is an IL12Rβ1 moiety and the IL12Rβ moiety in Exemplary Monomer 46 is an IL12Rβ2 moiety; or
(d) the IL12Rβ moiety in Exemplary Monomer 44 is an IL12Rβ2 moiety and the IL12Rβ moiety in Exemplary Monomer 46 is an IL12Rβ1 moiety.

459. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 47, optionally wherein:
(a) the IL12Rβ moieties in Exemplary Monomer 44 and Exemplary Monomer 47 are both IL12Rβ1 moieties;
(b) the IL12Rβ moieties in Exemplary Monomer 44 and Exemplary Monomer 47 are both IL12Rβ2 moieties
(c) the IL12Rβ moiety in Exemplary Monomer 44 is an IL12Rβ1 moiety and the IL12Rβ moiety in Exemplary Monomer 47 is an IL12Rβ2 moiety; or
(d) the IL12Rβ moiety in Exemplary Monomer 44 is an IL12Rβ2 moiety and the IL12Rβ moiety in Exemplary Monomer 47 is an IL12Rβ1 moiety.

460. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 48, optionally wherein:
(a) the IL12Rβ moieties in Exemplary Monomer 44 and Exemplary Monomer 48 are both IL12Rβ1 moieties;
(b) the IL12Rβ moieties in Exemplary Monomer 44 and Exemplary Monomer 48 are both IL12Rβ2 moieties
(c) the IL12Rβ moiety in Exemplary Monomer 44 is an IL12Rβ1 moiety and the IL12Rβ moiety in Exemplary Monomer 48 is an IL12Rβ2 moiety; or
(d) the IL12Rβ moiety in Exemplary Monomer 44 is an IL12Rβ2 moiety and the IL12Rβ moiety in Exemplary Monomer 48 is an IL12Rβ1 moiety.

461. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 49, optionally wherein:
(a) the IL12Rβ moieties in Exemplary Monomer 44 and Exemplary Monomer 49 are both IL12Rβ1 moieties;
(b) the IL12Rβ moieties in Exemplary Monomer 44 and Exemplary Monomer 49 are both IL12Rβ2 moieties
(c) the IL12Rβ moiety in Exemplary Monomer 44 is an IL12Rβ1 moiety and the IL12Rβ moiety in Exemplary Monomer 49 is an IL12Rβ2 moiety; or
(d) the IL12Rβ moiety in Exemplary Monomer 44 is an IL12Rβ2 moiety and the IL12Rβ moiety in Exemplary Monomer 49 is an IL12Rβ1 moiety.

462. An IL12 receptor agonist, which is optionally an IL12 agonist according to any one of embodiments 3 to 7, comprising a first IL12 monomer having the configuration of Exemplary Monomer 44 and a second IL12 monomer having the configuration of Exemplary Monomer 50, optionally wherein:
(a) the IL12Rβ moieties in Exemplary Monomer 44 and Exemplary Monomer 50 are both IL12Rβ1 moieties;
(b) the IL12Rβ moieties in Exemplary Monomer 44 and Exemplary Monomer 50 are both IL12Rβ2 moieties
(c) the IL12Rβ moiety in Exemplary Monomer 44 is an IL12Rβ1 moiety and the IL12Rβ moiety in Exemplary Monomer 50 is an IL12Rβ2 moiety; or
(d) the IL12Rβ moiety in Exemplary Monomer 44 is an IL12Rβ2 moiety and the IL12Rβ moiety in Exemplary Monomer 50 is an IL12Rβ1 moiety.

463. An IL12 receptor agonist, which is optionally an IL12 agonist according to any one of embodiments 3 to 7, comprising a first IL12 monomer having the configuration of Exemplary Monomer 45 and a second IL12 monomer having the configuration of Exemplary Monomer 45, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

464. An IL12 receptor agonist, which is optionally an IL12 agonist according to any one of embodiments 3 to 7, comprising a first IL12 monomer having the configuration of Exemplary Monomer 45 and a second IL12 monomer having the configuration of Exemplary Monomer 46, optionally wherein:
(a) the IL12Rβ moieties in Exemplary Monomer 45 and Exemplary Monomer 46 are both IL12Rβ1 moieties;

(b) the IL12Rβ moieties in Exemplary Monomer 45 and Exemplary Monomer 46 are both IL12Rβ2 moieties (c) the IL12Rβ moiety in Exemplary Monomer 45 is an IL12Rβ1 moiety and the IL12Rβ moiety in Exemplary Monomer 46 is an IL12Rβ2 moiety; or (d) the IL12Rβ moiety in Exemplary Monomer 45 is an IL12Rβ2 moiety and the IL12Rβ moiety in Exemplary Monomer 46 is an IL12Rβ1 moiety.

465. An IL12 receptor agonist, which is optionally an IL12 agonist according to any one of embodiments 3 to 7, comprising a first IL12 monomer having the configuration of Exemplary Monomer 45 and a second IL12 monomer having the configuration of Exemplary Monomer 47, optionally wherein:

(a) the IL12Rβ moieties in Exemplary Monomer 45 and Exemplary Monomer 47 are both IL12Rβ1 moieties;

(b) the IL12Rβ moieties in Exemplary Monomer 45 and Exemplary Monomer 47 are both IL12Rβ2 moieties (c) the IL12Rβ moiety in Exemplary Monomer 45 is an IL12Rβ1 moiety and the IL12Rβ moiety in Exemplary Monomer 47 is an IL12Rβ2 moiety; or (d) the IL12Rβ moiety in Exemplary Monomer 45 is an IL12Rβ2 moiety and the IL12Rβ moiety in Exemplary Monomer 47 is an IL12Rβ1 moiety.

466. An IL12 receptor agonist, which is optionally an IL12 agonist according to any one of embodiments 3 to 7, comprising a first IL12 monomer having the configuration of Exemplary Monomer 45 and a second IL12 monomer having the configuration of Exemplary Monomer 48, optionally wherein:

(a) the IL12Rβ moieties in Exemplary Monomer 45 and Exemplary Monomer 48 are both IL12Rβ1 moieties;

(b) the IL12Rβ moieties in Exemplary Monomer 45 and Exemplary Monomer 48 are both IL12Rβ2 moieties (c) the IL12Rβ moiety in Exemplary Monomer 45 is an IL12Rβ1 moiety and the IL12Rβ moiety in Exemplary Monomer 48 is an IL12Rβ2 moiety; or (d) the IL12Rβ moiety in Exemplary Monomer 45 is an IL12Rβ2 moiety and the IL12Rβ moiety in Exemplary Monomer 48 is an IL12Rβ1 moiety.

467. An IL12 receptor agonist, which is optionally an IL12 agonist according to any one of embodiments 3 to 7, comprising a first IL12 monomer having the configuration of Exemplary Monomer 45 and a second IL12 monomer having the configuration of Exemplary Monomer 49, optionally wherein:

(a) the IL12Rβ moieties in Exemplary Monomer 45 and Exemplary Monomer 49 are both IL12Rβ1 moieties;

(b) the IL12Rβ moieties in Exemplary Monomer 45 and Exemplary Monomer 49 are both IL12Rβ2 moieties (c) the IL12Rβ moiety in Exemplary Monomer 45 is an IL12Rβ1 moiety and the IL12Rβ moiety in Exemplary Monomer 49 is an IL12Rβ2 moiety; or (d) the IL12Rβ moiety in Exemplary Monomer 45 is an IL12Rβ2 moiety and the IL12Rβ moiety in Exemplary Monomer 49 is an IL12Rβ1 moiety.

468. An IL12 receptor agonist, which is optionally an IL12 agonist according to any one of embodiments 3 to 7, comprising a first IL12 monomer having the configuration of Exemplary Monomer 45 and a second IL12 monomer having the configuration of Exemplary Monomer 50, optionally wherein:

(a) the IL12Rβ moieties in Exemplary Monomer 45 and Exemplary Monomer 50 are both IL12Rβ1 moieties;

(b) the IL12Rβ moieties in Exemplary Monomer 45 and Exemplary Monomer 50 are both IL12Rβ2 moieties (c) the IL12Rβ moiety in Exemplary Monomer 45 is an IL12Rβ1 moiety and the IL12Rβ moiety in Exemplary Monomer 50 is an IL12Rβ2 moiety; or (d) the IL12Rβ moiety in Exemplary Monomer 45 is an IL12Rβ2 moiety and the IL12Rβ moiety in Exemplary Monomer 50 is an IL12Rβ1 moiety.

469. An IL12 receptor agonist, which is optionally an IL12 agonist according to any one of embodiments 3 to 7, comprising a first IL12 monomer having the configuration of Exemplary Monomer 46 and a second IL12 monomer having the configuration of Exemplary Monomer 46, optionally wherein:

(a) the IL12Rβ moieties in the first IL12 monomer and in the second IL12 monomer are both IL12Rβ1 moieties;

(b) the IL12Rβ moieties in the first IL12 monomer and in the second IL12 monomer are both IL12Rβ2;

(c) the IL12Rβ moiety in the first IL12 monomer is an IL12Rβ1 moiety and the IL12Rβ moiety in the second IL12 monomer is an IL12Rβ2 moiety;

(d) the IL12Rβ moiety in the first IL12 monomer is an IL12Rβ2 moiety and the IL12Rβ moiety in the second IL12 monomer is an IL12Rβ1 moiety.

470. An IL12 receptor agonist, which is optionally an IL12 agonist according to any one of embodiments 3 to 7, comprising a first IL12 monomer having the configuration of Exemplary Monomer 46 and a second IL12 monomer having the configuration of Exemplary Monomer 47, optionally wherein:

(a) the IL12Rβ moieties in Exemplary Monomer 46 and Exemplary Monomer 50 are both IL12Rβ1 moieties;

(b) the IL12Rβ moieties in Exemplary Monomer 46 and Exemplary Monomer 50 are both IL12Rβ2 moieties (c) the IL12Rβ moiety in Exemplary Monomer 46 is an IL12Rβ1 moiety and the IL12Rβ moiety in Exemplary Monomer 50 is an IL12Rβ2 moiety; or (d) the IL12Rβ moiety in Exemplary Monomer 46 is an IL12Rβ2 moiety and the IL12Rβ moiety in Exemplary Monomer 50 is an IL12Rβ1 moiety.

471. An IL12 receptor agonist, which is optionally an IL12 agonist according to any one of embodiments 3 to 7, comprising a first IL12 monomer having the configuration of Exemplary Monomer 46 and a second IL12 monomer having the configuration of Exemplary Monomer 48, optionally wherein:

(a) the IL12Rβ moieties in Exemplary Monomer 46 and Exemplary Monomer 48 are both IL12Rβ1 moieties;

(b) the IL12Rβ moieties in Exemplary Monomer 46 and Exemplary Monomer 48 are both IL12Rβ2 moieties (c) the IL12Rβ moiety in Exemplary Monomer 46 is an IL12Rβ1 moiety and the IL12Rβ moiety in Exemplary Monomer 48 is an IL12Rβ2 moiety; or (d) the IL12Rβ moiety in Exemplary Monomer 46 is an IL12Rβ2 moiety and the IL12Rβ moiety in Exemplary Monomer 48 is an IL12Rβ1 moiety.

472. An IL12 receptor agonist, which is optionally an IL12 agonist according to any one of embodiments 3 to 7, comprising a first IL12 monomer having the configuration of Exemplary Monomer 46 and a second IL12 monomer having the configuration of Exemplary Monomer 49, optionally wherein:
   (a) the IL12Rβ moieties in Exemplary Monomer 46 and Exemplary Monomer 49 are both IL12Rβ1 moieties;
   (b) the IL12Rβ moieties in Exemplary Monomer 46 and Exemplary Monomer 49 are both IL12Rβ2 moieties
   (c) the IL12Rβ moiety in Exemplary Monomer 46 is an IL12Rβ1 moiety and the IL12Rβ moiety in Exemplary Monomer 49 is an IL12Rβ2 moiety; or
   (d) the IL12Rβ moiety in Exemplary Monomer 46 is an IL12Rβ2 moiety and the IL12Rβ moiety in Exemplary Monomer 49 is an IL12Rβ1 moiety.
473. An IL12 receptor agonist, which is optionally an IL12 agonist according to any one of embodiments 3 to 7, comprising a first IL12 monomer having the configuration of Exemplary Monomer 46 and a second IL12 monomer having the configuration of Exemplary Monomer 50, optionally wherein:
   (a) the IL12Rβ moieties in Exemplary Monomer 46 and Exemplary Monomer 50 are both IL12Rβ1 moieties;
   (b) the IL12Rβ moieties in Exemplary Monomer 46 and Exemplary Monomer 50 are both IL12Rβ2 moieties
   (c) the IL12Rβ moiety in Exemplary Monomer 46 is an IL12Rβ1 moiety and the IL12Rβ moiety in Exemplary Monomer 50 is an IL12Rβ2 moiety; or
   (d) the IL12Rβ moiety in Exemplary Monomer 46 is an IL12Rβ2 moiety and the IL12Rβ moiety in Exemplary Monomer 50 is an IL12Rβ1 moiety.
474. An IL12 receptor agonist, which is optionally an IL12 agonist according to any one of embodiments 3 to 7, comprising a first IL12 monomer having the configuration of Exemplary Monomer 47 and a second IL12 monomer having the configuration of Exemplary Monomer 47, optionally wherein:
   (a) the IL12Rβ moieties in the first IL12 monomer and in the second IL12 monomer are both IL12Rβ1 moieties;
   (b) the IL12Rβ moieties in the first IL12 monomer and in the second IL12 monomer are both IL12Rβ2;
   (c) the IL12Rβ moiety in the first IL12 monomer is an IL12Rβ1 moiety and the IL12Rβ moiety in the second IL12 monomer is an IL12Rβ2 moiety;
   (d) the IL12Rβ moiety in the first IL12 monomer is an IL12Rβ2 moiety and the IL12Rβ moiety in the second IL12 monomer is an IL12Rβ1 moiety.
475. An IL12 receptor agonist, which is optionally an IL12 agonist according to any one of embodiments 3 to 7, comprising a first IL12 monomer having the configuration of Exemplary Monomer 47 and a second IL12 monomer having the configuration of Exemplary Monomer 48, optionally wherein:
   (a) the IL12Rβ moieties in Exemplary Monomer 47 and Exemplary Monomer 48 are both IL12Rβ1 moieties;
   (b) the IL12Rβ moieties in Exemplary Monomer 47 and Exemplary Monomer 48 are both IL12Rβ2 moieties
   (c) the IL12Rβ moiety in Exemplary Monomer 47 is an IL12Rβ1 moiety and the IL12Rβ moiety in Exemplary Monomer 48 is an IL12Rβ2 moiety; or
   (d) the IL12Rβ moiety in Exemplary Monomer 47 is an IL12Rβ2 moiety and the IL12Rβ moiety in Exemplary Monomer 48 is an IL12Rβ1 moiety.
476. An IL12 receptor agonist, which is optionally an IL12 agonist according to any one of embodiments 3 to 7, comprising a first IL12 monomer having the configuration of Exemplary Monomer 47 and a second IL12 monomer having the configuration of Exemplary Monomer 49, optionally wherein:
   (a) the IL12Rβ moieties in Exemplary Monomer 47 and Exemplary Monomer 49 are both IL12Rβ1 moieties;
   (b) the IL12Rβ moieties in Exemplary Monomer 47 and Exemplary Monomer 49 are both IL12Rβ2 moieties
   (c) the IL12Rβ moiety in Exemplary Monomer 47 is an IL12Rβ1 moiety and the IL12Rβ moiety in Exemplary Monomer 49 is an IL12Rβ2 moiety; or
   (d) the IL12Rβ moiety in Exemplary Monomer 47 is an IL12Rβ2 moiety and the IL12Rβ moiety in Exemplary Monomer 49 is an IL12Rβ1 moiety.
477. An IL12 receptor agonist, which is optionally an IL12 agonist according to any one of embodiments 3 to 7, comprising a first IL12 monomer having the configuration of Exemplary Monomer 47 and a second IL12 monomer having the configuration of Exemplary Monomer 50, optionally wherein:
   (a) the IL12Rβ moieties in Exemplary Monomer 47 and Exemplary Monomer 50 are both IL12Rβ1 moieties;
   (b) the IL12Rβ moieties in Exemplary Monomer 47 and Exemplary Monomer 50 are both IL12Rβ2 moieties
   (c) the IL12Rβ moiety in Exemplary Monomer 47 is an IL12Rβ1 moiety and the IL12Rβ moiety in Exemplary Monomer 50 is an IL12Rβ2 moiety; or
   (d) the IL12Rβ moiety in Exemplary Monomer 47 is an IL12Rβ2 moiety and the IL12Rβ moiety in Exemplary Monomer 50 is an IL12Rβ1 moiety.
478. An IL12 receptor agonist, which is optionally an IL12 agonist according to any one of embodiments 3 to 7, comprising a first IL12 monomer having the configuration of Exemplary Monomer 48 and a second IL12 monomer having the configuration of Exemplary Monomer 48, optionally wherein:
   (a) the IL12Rβ moieties in the first IL12 monomer and in the second IL12 monomer are both IL12Rβ1 moieties;
   (b) the IL12Rβ moieties in the first IL12 monomer and in the second IL12 monomer are both IL12Rβ2;
   (c) the IL12Rβ moiety in the first IL12 monomer is an IL12Rβ1 moiety and the IL12Rβ moiety in the second IL12 monomer is an IL12Rβ2 moiety;
   (d) the IL12Rβ moiety in the first IL12 monomer is an IL12Rβ2 moiety and the IL12Rβ moiety in the second IL12 monomer is an IL12Rβ1 moiety.
479. An IL12 receptor agonist, which is optionally an IL12 agonist according to any one of embodiments 3 to 7, comprising a first IL12 monomer having the configuration of Exemplary Monomer 48 and a second IL12 monomer having the configuration of Exemplary Monomer 49, optionally wherein:

(a) the IL12Rβ moieties in Exemplary Monomer 48 and Exemplary Monomer 49 are both IL12Rβ1 moieties;
(b) the IL12Rβ moieties in Exemplary Monomer 48 and Exemplary Monomer 49 are both IL12Rβ2 moieties
(c) the IL12Rβ moiety in Exemplary Monomer 48 is an IL12Rβ1 moiety and the IL12Rβ moiety in Exemplary Monomer 49 is an IL12Rβ2 moiety; or
(d) the IL12Rβ moiety in Exemplary Monomer 48 is an IL12Rβ2 moiety and the IL12Rβ moiety in Exemplary Monomer 49 is an IL12Rβ1 moiety.

480. An IL12 receptor agonist, which is optionally an IL12 agonist according to any one of embodiments 3 to 7, comprising a first IL12 monomer having the configuration of Exemplary Monomer 48 and a second IL12 monomer having the configuration of Exemplary Monomer 50, optionally wherein:
(a) the IL12Rβ moieties in Exemplary Monomer 48 and Exemplary Monomer 50 are both IL12Rβ1 moieties;
(b) the IL12Rβ moieties in Exemplary Monomer 48 and Exemplary Monomer 50 are both IL12Rβ2 moieties
(c) the IL12Rβ moiety in Exemplary Monomer 48 is an IL12Rβ1 moiety and the IL12Rβ moiety in Exemplary Monomer 50 is an IL12Rβ2 moiety; or
(d) the IL12Rβ moiety in Exemplary Monomer 48 is an IL12Rβ2 moiety and the IL12Rβ moiety in Exemplary Monomer 50 is an IL12Rβ1 moiety.

481. An IL12 receptor agonist, which is optionally an IL12 agonist according to any one of embodiments 3 to 7, comprising a first IL12 monomer having the configuration of Exemplary Monomer 49 and a second IL12 monomer having the configuration of Exemplary Monomer 49, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

482. An IL12 receptor agonist, which is optionally an IL12 agonist according to any one of embodiments 3 to 7, comprising a first IL12 monomer having the configuration of Exemplary Monomer 49 and a second IL12 monomer having the configuration of Exemplary Monomer 50, optionally wherein:
(a) the IL12Rβ moieties in Exemplary Monomer 49 and Exemplary Monomer 50 are both IL12Rβ1 moieties;
(b) the IL12Rβ moieties in Exemplary Monomer 49 and Exemplary Monomer 50 are both IL12Rβ2 moieties
(c) the IL12Rβ moiety in Exemplary Monomer 49 is an IL12Rβ1 moiety and the IL12Rβ moiety in Exemplary Monomer 50 is an IL12Rβ2 moiety; or
(d) the IL12Rβ moiety in Exemplary Monomer 49 is an IL12Rβ2 moiety and the IL12Rβ moiety in Exemplary Monomer 50 is an IL12Rβ1 moiety.

483. An IL12 receptor agonist, which is optionally an IL12 agonist according to any one of embodiments 3 to 7, comprising a first IL12 monomer having the configuration of Exemplary Monomer 50 and a second IL12 monomer having the configuration of Exemplary Monomer 50, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

484. An IL12 receptor agonist, which is optionally an IL12 agonist according to any one of embodiments 3 to 7, comprising a first IL12 monomer having the configuration of Exemplary Monomer 51 and a second IL12 monomer having the configuration of Exemplary Monomer 51, optionally wherein:
(a) the IL12Rβ moieties in the first IL12 monomer and in the second IL12 monomer are both IL12Rβ1 moieties;
(b) the IL12Rβ moieties in the first IL12 monomer and in the second IL12 monomer are both IL12Rβ2;
(c) the IL12Rβ moiety in the first IL12 monomer is an IL12Rβ1 moiety and the IL12Rβ moiety in the second IL12 monomer is an IL12Rβ2 moiety;
(d) the IL12Rβ moiety in the first IL12 monomer is an IL12Rβ2 moiety and the IL12Rβ moiety in the second IL12 monomer is an IL12Rβ1 moiety.

485. An IL12 receptor agonist, which is optionally an IL12 agonist according to any one of embodiments 3 to 7, comprising a first IL12 monomer having the configuration of Exemplary Monomer 51 and a second IL12 monomer having the configuration of Exemplary Monomer 63.

486. An IL12 receptor agonist, which is optionally an IL12 agonist according to any one of embodiments 3 to 7, comprising a first IL12 monomer having the configuration of Exemplary Monomer 55 and a second IL12 monomer having the configuration of Exemplary Monomer 60.

487. An IL12 receptor agonist, which is optionally an IL12 agonist according to any one of embodiments 3 to 7, comprising a first IL12 monomer having the configuration of Exemplary Monomer 55 and a second IL12 monomer having the configuration of Exemplary Monomer 60.

488. An IL12 receptor agonist, which is optionally an IL12 agonist according to any one of embodiments 3 to 7, comprising a first IL12 monomer having the configuration of Exemplary Monomer 57 and a second IL12 monomer having the configuration of Exemplary Monomer 63.

489. An IL12 receptor agonist, which is optionally an IL12 agonist according to any one of embodiments 3 to 7, comprising a first IL12 monomer having the configuration of Exemplary Monomer 61 and a second IL12 monomer having the configuration of Exemplary Monomer 61.

490. An IL12 receptor agonist, which is optionally an IL12 agonist according to any one of embodiments 3 to 7, comprising a first IL12 monomer having the configuration of Exemplary Monomer 61 and a second IL12 monomer having the configuration of Exemplary Monomer 62.

491. An IL12 receptor agonist, which is optionally an IL12 agonist according to any one of embodiments 3 to 7, comprising a first IL12 monomer having the configuration of Exemplary Monomer 63 and a second IL12 monomer having the configuration of Exemplary Monomer 63.

492. The IL12 receptor agonist of any one of embodiments 6 to 491, which comprises a first p40 moiety and a first p35 moiety and which optionally comprises a first polypeptide chain and a second polypeptide chain.

493. An IL12 receptor agonist, which is optionally an IL12 agonist according to any one of embodiments 3 to 7, comprising:

(a) a first polypeptide chain comprising:
  (i) optionally, a first multimerization moiety;
  (ii) optionally, a first targeting moiety or a first targeting moiety component; and
  (iii) optionally, a stabilization moiety; and (b) a second polypeptide chain comprising:
  (i) optionally, a second multimerization moiety;
  (ii) optionally, a second targeting moiety or a second targeting moiety component; and
  (iii) optionally, a stabilization moiety;

(c) a first p40 moiety comprising a p40 D2 domain and a p40 D3 domain; and (d) a first p35 moiety.

494. The IL12 receptor agonist of embodiment 493, wherein the first p40 moiety further comprises a p40 D1 domain.

495. The IL12 receptor agonist of embodiment 493 or embodiment 494, wherein the first p40 moiety is on the first polypeptide chain or the second polypeptide chain.

496. The IL12 receptor agonist of any one of embodiments 493 or embodiment 494, wherein the first p40 moiety is in the form of a monomeric p40 polypeptide.

497. The IL12 receptor agonist of any one of embodiments 493 to 495, which is bivalent for IL12 and comprises a second p40 moiety comprising a p40 D2 domain and a p40 D3 domain and a second p35 moiety.

498. The IL12 receptor agonist of embodiment 497, wherein the second p40 moiety further comprises a p40 D1 domain.

499. The IL12 receptor agonist of any one of embodiments 493 to 498, wherein:

(a) the first polypeptide comprises the first p40 moiety and the first p35 moiety; and (b) the second polypeptide comprises a second p40 moiety comprising a p40 D2 domain and a p40 D3 domain, and a second p35 moiety.

500. The IL12 receptor agonist of embodiment 499, wherein the second p40 moiety further comprises a p40 D1 domain.

501. The IL12 receptor agonist of any one of embodiments 493 to 500, which comprises a first IL12 monomer and a second IL12 monomer.

502. The IL12 receptor agonist of embodiment 501, wherein the first IL12 monomer and the second IL12 monomer are not identical.

503. The IL12 receptor agonist of embodiment 494, wherein the first IL12 monomer and the second IL12 monomer are identical.

504. The IL12 receptor agonist of any one of embodiments 493 to 496, which comprises a first multimerization moiety and a second multimerization moiety and wherein the first p40 moiety and the first p35 moiety are N-terminal to the first multimerization moiety, and the second p40 moiety and the second p35 moiety are N-terminal to the second multimerization moiety.

505. The IL12 receptor agonist of any one of embodiments 486 to 503, which comprises a first multimerization moiety and a second multimerization moiety and wherein the first p40 moiety and the first p35 moiety are C-terminal to the first multimerization moiety, and the second p40 moiety and the second p35 moiety are C-terminal to the second multimerization moiety.

506. The IL agonist of any one of embodiments 493 to 505, wherein the first p40 moiety is N-terminal to the first p35 moiety and the second p40 moiety is N-terminal to the p35 moiety of the second IL12 moiety.

507. The IL agonist of any one of embodiments 493 to 505, wherein the first p40 moiety is C-terminal to the first p35 moiety and the second p40 moiety is C-terminal to the p35 moiety of the second IL12 moiety.

508. The IL12 receptor agonist of any one of embodiments 493 to 507, which comprises a first multimerization moiety and a second multimerization moiety and wherein:

(a) the first multimerization moiety and either the first p40 moiety or the first p35 moiety are connected via a first multimerization moiety linker; and (b) the second multimerization moiety and either the second p40 moiety or the second p35 moiety are connected via a second multimerization moiety linker.

509. The IL12 receptor agonist of embodiment 508, wherein each of the first multimerization moiety linker and the second multimerization moiety linker is at least 5 or at least 10 amino acids in length.

510. The IL12 receptor agonist of embodiment 508 or embodiment 509, wherein each of the first multimerization moiety linker and the second multimerization moiety linker is or comprises a glycine-serine linker.

511. The IL12 receptor agonist of any one of embodiments 508 to 510, wherein each of the first multimerization moiety linker and the second multimerization moiety linker comprises the amino acid sequence $G_4S$ (SEQ ID NO: 25).

512. The IL12 receptor agonist of embodiment 511, wherein each of the first multimerization moiety linker and the second multimerization moiety linker is or comprises a multimer of the amino acid sequence $G_4S$ (SEQ ID NO: 25).

513. The IL12 receptor agonist of embodiment 512, wherein the multimer comprises, 2, 3, 4, 5, 6, or more repeats of the amino acid sequence $G_4S$ (SEQ ID NO: 25).

514. The IL12 receptor agonist of any one of embodiments 493 to 507, wherein the first p40 moiety and the first p35 moiety are connected via a first intra-IL12 moiety linker, and the second p40 moiety and the second p35 moiety are connected via a second intra-IL12 moiety linker.

515. The IL12 receptor agonist of embodiment 514, wherein each of the first intra-IL12 moiety linker and the second intra-IL12 moiety linker is at least 5 or at least 10 amino acids in length.

516. The IL12 receptor agonist of embodiment 507 or 515, wherein each of the first intra-IL12 moiety linker and the second intra-IL12 moiety linker is or comprises a glycine-serine linker.

517. The IL12 receptor agonist of embodiment 516, wherein each of the first intra-IL12 moiety linker and the second intra-IL12 moiety linker comprises the amino acid sequence $G_4S$ (SEQ ID NO: 25).
518. The IL12 receptor agonist of embodiment 517, wherein each of the first intra-IL12 moiety linker and the second linker is or comprises a multimer of the amino acid sequence $G_4S$ (SEQ ID NO: 25).
519. The IL12 receptor agonist of embodiment 518, wherein the multimer comprises, 2, 3, 4, 5, 6, or more repeats of the amino acid sequence $G_4S$ (SEQ ID NO: 25).
520. The IL12 receptor agonist of any one of embodiments 6 to 496, which is monovalent for IL12.
521. The IL12 receptor agonist of any one of embodiments 6 to 491 and 520, which comprises a first polypeptide chain, a second polypeptide chain, a first p40 moiety comprising a p40 D2 domain and a p40 D3 domain, and a first p35 moiety.
522. The IL12 receptor agonist of embodiment 521, wherein:
   (a) the first polypeptide comprises the first p40 moiety; and
   (b) the second polypeptide comprises the first p35 moiety.
523. The IL12 receptor agonist of embodiment 522, which comprises a first multimerization moiety and a second multimerization moiety and wherein the first p40 moiety is N-terminal to the first multimerization moiety and the first p35 moiety is N-terminal to the second multimerization moiety.
524. The IL12 receptor agonist of embodiment 522, which comprises a first multimerization moiety and a second multimerization moiety and wherein the first p40 moiety is C-terminal to the first multimerization moiety and the first p35 moiety is C-terminal to the second multimerization moiety.
525. The IL12 receptor agonist of any one of embodiments 522 to 524, which comprises a first multimerization moiety and a second multimerization moiety and wherein
   (a) the first multimerization moiety and the first p40 moiety are connected via a first multimerization moiety linker; and
   (b) the second multimerization moiety and the first p35 moiety are connected via a second multimerization moiety linker.
526. The IL12 receptor agonist of embodiment 525, wherein each of the first multimerization moiety linker and the second multimerization moiety linker is at least 5 or at least 10 amino acids in length.
527. The IL12 receptor agonist of embodiment 525 or embodiment 526, wherein each of the first multimerization moiety linker and the second multimerization moiety linker is or comprises a glycine-serine linker.
528. The IL12 receptor agonist of any one of embodiments 525 to 527, wherein each of the first multimerization moiety linker and the second multimerization moiety linker comprises the amino acid sequence $G_4S$ (SEQ ID NO: 25).
529. The IL12 receptor agonist of embodiment 528, wherein each of the first multimerization moiety linker and the second multimerization moiety linker is or comprises a multimer of the amino acid sequence $G_4S$ (SEQ ID NO: 25).
530. The IL12 receptor agonist of embodiment 529, wherein the multimer comprises, 2, 3, 4, 5, 6, or more repeats of the amino acid sequence $G_4S$ (SEQ ID NO: 25).
531. The IL12 receptor agonist of embodiment 521, wherein:
   (a) the first polypeptide comprises the first p40 moiety and the first p35 moiety; and
   (b) the second polypeptide does not comprise a p40 moiety or a p35 moiety.
532. The IL12 receptor agonist of embodiment 531, which comprises a first multimerization moiety and a second multimerization moiety and wherein the first p40 moiety and the first p35 moiety are N-terminal to the first multimerization moiety.
533. The IL12 receptor agonist of embodiment 531, which comprises a first multimerization moiety and a second multimerization moiety and wherein the first p40 moiety and the first p35 moiety are C-terminal to the first multimerization moiety.
534. The IL12 agonist of any one of embodiments 531 to 533, wherein the first p40 moiety is N-terminal to the first p35 moiety.
535. The IL12 agonist of any one of embodiments 531 to 533, wherein the first p40 moiety is C-terminal to the first p35 moiety.
536. The IL12 receptor agonist of any one of embodiments 531 to 535, which comprises a first multimerization moiety and a second multimerization moiety and wherein the first multimerization moiety and either the first p40 moiety or the first p35 moiety are connected via a first multimerization moiety linker.
537. The IL12 receptor agonist of embodiment 536, wherein the first multimerization moiety linker is at least 5 or at least 10 amino acids in length.
538. The IL12 receptor agonist of embodiment 536 or embodiment 537, wherein the first multimerization moiety linker is or comprises a glycine-serine linker.
539. The IL12 receptor agonist of embodiment 538, wherein the first multimerization moiety linker comprises the amino acid sequence $G_4S$ (SEQ ID NO: 25).
540. The IL12 receptor agonist of embodiment 539, wherein the multimer comprises, 2, 3, 4, 5, 6, or more repeats of the amino acid sequence $G_4S$ (SEQ ID NO: 25).
541. The IL12 receptor agonist of any one of embodiments 531 to 540, wherein the first p40 moiety and the first p35 moiety are connected via a first intra-IL12 moiety linker.
542. The IL12 receptor agonist of embodiment 541, wherein the intra-IL12 moiety linker is at least 5 or at least 10 amino acids in length.
543. The IL12 agonist of embodiment 541 or embodiment 542, wherein the first intra-IL12 moiety linker is or comprises a glycine-serine linker.
544. The IL12 receptor agonist of embodiment 543, wherein the first intra-IL12 moiety linker comprises the amino acid sequence $G_4S$ (SEQ ID NO: 25).
545. The IL12 receptor agonist of embodiment 544, wherein first intra-IL12 moiety linker is or comprises a multimer of the amino acid sequence $G_4S$ (SEQ ID NO: 25).
546. The IL12 receptor agonist of embodiment 545, wherein the multimer comprises, 2, 3, 4, 5, 6, or more repeats of the amino acid sequence $G_4S$ (SEQ ID NO: 25).

547. The IL12 receptor agonist of any one of embodiments 6 to 546, which comprises a first p40 moiety and wherein the first p40 moiety is a human p40 or a variant thereof.
548. The IL12 receptor agonist of embodiment 547, wherein the first p40 moiety comprises an amino acid sequence having at least about 90% sequence identity to mature human p40.
549. The IL12 receptor agonist of embodiment 547 or embodiment 548, wherein the first p40 moiety comprises an amino acid sequence having at least about 93% sequence identity to mature human p40.
550. The IL12 receptor agonist of any one of embodiments 547 to 549, wherein the first p40 moiety comprises an amino acid sequence having at least about 96% sequence identity to mature human p40.
551. The IL12 receptor agonist of any one of embodiments 547 to 550, wherein the first p40 moiety comprises an amino acid sequence having at least about 98% sequence identity to mature human p40.
552. The IL12 receptor agonist of any one of embodiments 6 to 551, which comprises a first p35 moiety and wherein the first p35 moiety is a human p35 moiety or a variant thereof.
553. The IL12 receptor agonist of embodiment 552, wherein the first p35 moiety comprises an amino acid sequence having at least about 90% sequence identity to mature human p35.
554. The IL12 receptor agonist of embodiment 552 or embodiment 553, wherein the first p35 moiety comprises an amino acid sequence having at least about 93% sequence identity to mature human p35.
555. The IL12 receptor agonist of any one of embodiments 552 to 554, wherein the first p35 moiety comprises an amino acid sequence having at least about 96% sequence identity to mature human p35.
556. The IL12 receptor agonist of any one of embodiments 552 to 555, wherein the first p35 moiety comprises an amino acid sequence having at least about 98% sequence identity to mature human p35.
557. The IL12 receptor agonist of any one of embodiments 6 to 546, which comprises a first p40 moiety and wherein the first p40 moiety is a murine p40 or a variant thereof.
558. The IL12 receptor agonist of embodiment 557, wherein the first p40 moiety comprises an amino acid sequence having at least about 90% sequence identity to mature murine p40.
559. The IL12 receptor agonist of embodiment 557 or embodiment 558, wherein the first p40 moiety comprises an amino acid sequence having at least about 93% sequence identity to mature murine p40.
560. The IL12 receptor agonist of any one of embodiments 557 to 559, wherein the first p40 moiety comprises an amino acid sequence having at least about 96% sequence identity to mature murine p40.
561. The IL12 receptor agonist of any one of embodiments 557 to 560, wherein the first p40 moiety comprises an amino acid sequence having at least about 98% sequence identity to mature murine p40.
562. The IL12 receptor agonist of any one of embodiments 6 to 546 and 557 to 561, wherein the first p35 moiety is a murine p35 moiety or a variant thereof.
563. The IL12 receptor agonist of embodiment 562, wherein the first p35 moiety comprises an amino acid sequence having at least about 90% sequence identity to mature murine p35.
564. The IL12 receptor agonist of embodiment 562 or embodiment 563, wherein the first p35 moiety comprises an amino acid sequence having at least about 93% sequence identity to mature murine p35.
565. The IL12 receptor agonist of any one of embodiments 562 to 564, wherein the first p35 moiety comprises an amino acid sequence having at least about 96% sequence identity to mature murine p35.
566. The IL12 receptor agonist of any one of embodiments 562 to 565, wherein the first p35 moiety comprises an amino acid sequence having at least about 98% sequence identity to mature murine p35.
567. The IL12 receptor agonist of any one of embodiments 497 to 519 and embodiments 547 to 551 when dependent thereon, wherein the second p40 moiety is a human p40 or a variant thereof.
568. The IL12 receptor agonist of embodiment 567, wherein the second p40 moiety comprises an amino acid sequence having at least about 90% sequence identity to mature human p40.
569. The IL12 receptor agonist of embodiment 567 or embodiment 568, wherein the second p40 moiety comprises an amino acid sequence having at least about 93% sequence identity to mature human p40.
570. The IL12 receptor agonist of any one of embodiments 567 to 569, wherein the second p40 moiety comprises an amino acid sequence having at least about 96% sequence identity to mature human p40.
571. The IL12 receptor agonist of any one of embodiments 567 to 570, wherein the second p40 moiety comprises an amino acid sequence having at least about 98% sequence identity to mature human p40.
572. The IL12 receptor agonist of any one of embodiments 497 to 519, embodiments 552 to 556 when dependent thereon, and 567 to 571, wherein the second p35 moiety is a human p35 moiety or a variant thereof.
573. The IL12 receptor agonist of embodiment 572, wherein the second p35 moiety comprises an amino acid sequence having at least about 90% sequence identity to mature human p35.
574. The IL12 receptor agonist of embodiment 572 or embodiment 545, wherein the second p35 moiety comprises an amino acid sequence having at least about 93% sequence identity to mature human p35.
575. The IL12 receptor agonist of any one of embodiments 572 to 546, wherein the second p35 moiety comprises an amino acid sequence having at least about 96% sequence identity to mature human p35.
576. The IL12 receptor agonist of any one of embodiments 572 to 547, wherein the second p35 moiety comprises an amino acid sequence having at least about 98% sequence identity to mature human p35.
577. The IL12 receptor agonist of any one of embodiments 497 to 519 and embodiments 557 to 561 when dependent thereon, wherein the second p40 moiety is a murine p40 or a variant thereof.
578. The IL12 receptor agonist of embodiment 577, wherein the second p40 moiety comprises an amino acid sequence having at least about 90% sequence identity to mature murine p40.
579. The IL12 receptor agonist of embodiment 577 or embodiment 578, wherein the second p40 moiety comprises an amino acid sequence having at least about 93% sequence identity to mature murine p40.
580. The IL12 receptor agonist of any one of embodiments 577 to 579, wherein the second p40 moiety comprises an amino acid sequence having at least about 96% sequence identity to mature murine p40.

581. The IL12 receptor agonist of any one of embodiments 577 to 580, wherein the second p40 moiety comprises an amino acid sequence having at least about 98% sequence identity to mature murine p40.

582. The IL12 receptor agonist of any one of embodiments 497 to 519, embodiments 562 to 566 when dependent thereon, and embodiments 577 to 581, wherein the second p35 moiety is a murine p35 moiety or a variant thereof.

583. The IL12 receptor agonist of embodiment 582, wherein the second p35 moiety comprises an amino acid sequence having at least about 90% sequence identity to mature human p35.

584. The IL12 receptor agonist of embodiment 582 or embodiment 583, wherein the second p35 moiety comprises an amino acid sequence having at least about 93% sequence identity to mature human p35.

585. The IL12 receptor agonist of any one of embodiments 582 to 584, wherein the second p35 moiety comprises an amino acid sequence having at least about 96% sequence identity to mature human p35.

586. The IL12 receptor agonist of any one of embodiments 582 to 585, wherein the second p35 moiety comprises an amino acid sequence having at least about 98% sequence identity to mature human p35.

587. The IL12 receptor agonist of any one of embodiments 6 to 586, wherein neither the first polypeptide nor the second polypeptide comprise a cytokine moiety other than an IL12 (e.g., p35 or p40) moiety.

588. The IL12 receptor agonist of any one of embodiments 6 to 587, wherein the first p40 moiety, and if present, the second p40 moiety comprise(s) at least one amino acid substitution.

589. The IL12 receptor agonist of any one of embodiments 6 to 588, wherein the first p40 moiety, and if present, the second p40 moiety comprise(s) an amino acid substitution at a position corresponding to residue 6 of mature murine p40 (e.g., mature murine p40 residue 6).

590. An IL12 receptor agonist, which is optionally an IL12 receptor agonist according to embodiment 589, which comprises a first p40 moiety having an alanine substitution at a position corresponding to residue 6 of mature human p40 (e.g., mature murine p40 residue 6), and which optionally further comprises a second p40 moiety having an alanine substitution at a position corresponding to residue 6 of mature human p40 (e.g., mature murine p40 residue 6).

591. The IL12 receptor agonist of any one of embodiments 6 to 590, wherein the first p40 moiety, and if present, the second p40 moiety comprise(s) an amino acid substitution at a position corresponding to residue 15 of mature human p40 (e.g., mature murine p40 residue 15).

592. An IL12 receptor agonist, which is optionally an IL12 receptor agonist according to embodiment 591, which comprises a first p40 moiety having an alanine substitution at a position corresponding to residue 15 of mature human p40 (e.g., mature murine p40 residue 15), and which optionally further comprises a second IL12 p40 moiety having an alanine substitution at a position corresponding to residue 15 of mature human p40 (e.g., mature murine p40 residue 15).

593. The IL12 receptor agonist of any one of embodiments 6 to 592, wherein the first p40 moiety, and if present, the second p40 moiety comprise(s) comprises an amino acid substitution at a position corresponding to residue 18 of mature human p40 (e.g., mature murine p40 residue 18).

594. The IL12 receptor agonist of embodiment 593, wherein the amino acid substitution is D18A, D18N, or D18K.

595. The IL12 receptor agonist of any one of embodiments 6 to 594, wherein the first p40 moiety, and if present, the second p40 moiety comprise(s) comprises an amino acid substitution at a position corresponding to residue 32 of mature human p40 (e.g., mature murine p40 residue 32).

596. The IL12 receptor agonist of embodiment 595, wherein the amino acid substitution is E32Q.

597. The IL12 receptor agonist of any one of embodiments 6 to 596, wherein the first p40 moiety, and if present, the second p40 moiety comprise(s) an amino acid substitution at a position corresponding to residue 33 of mature human p40 (e.g., mature murine p40 residue 33).

598. The IL12 receptor agonist of embodiment 597, wherein the amino acid substitution is E33Q.

599. The IL12 receptor agonist of any one of embodiments 6 to 598, wherein the first p40 moiety, and if present, the second p40 moiety comprise(s) an amino acid substitution at a position corresponding to residue 34 of mature human p40 (e.g., mature murine p40 residue 40).

600. The IL12 receptor agonist of embodiment 599, wherein the amino acid substitution is D34N or D34K.

601. The IL12 receptor agonist of any one of embodiments 6 to 600, wherein the first p40 moiety, and if present, the second p40 moiety comprise(s) an amino acid substitution at a position corresponding to residue 42 of mature human p40 (e.g., mature murine p40 residue 42).

602. The IL12 receptor agonist of embodiment 601, wherein the amino acid substitution is Q42E.

603. The IL12 receptor agonist of any one of embodiments 6 to 602, wherein the first p40 moiety, and if present, the second p40 moiety comprise(s) an amino acid substitution at a position corresponding to residue 43 of mature human p40 (e.g., mature murine p40 residue 43).

604. The IL12 receptor agonist of embodiment 603, wherein the amino acid substitution is S43E or S43K.

605. The IL12 receptor agonist of any one of embodiments 6 to 604, wherein the first p40 moiety, and if present, the second p40 moiety comprise(s) an amino acid substitution at a position corresponding to residue 45 of mature human p40 (e.g., mature murine p40 residue 45).

606. The IL12 receptor agonist of embodiment 605, wherein the amino acid substitution is E45Q.

607. The IL12 receptor agonist of any one of embodiments 6 to 606, wherein the first p40 moiety, and if present, the second p40 moiety comprise(s) an amino acid substitution at a position corresponding to residue 56 of mature human p40 (e.g., mature murine p40 residue 56).

608. The IL12 receptor agonist of embodiment 607, wherein the amino acid substitution is Q56E.

609. The IL12 receptor agonist of any one of embodiments 6 to 608, wherein the first p40 moiety, and if present, the second p40 moiety comprise(s) an amino acid substitution at a position corresponding to residue 59 of mature human p40 (e.g., mature murine p40 residue 59).

610. The IL12 receptor agonist of embodiment 609, wherein the amino acid substitution is E59A, E59K, or E59Q.

611. The IL12 receptor agonist of any one of embodiments 6 to 610, wherein the first p40 moiety, and if present, the second p40 moiety comprise(s) an amino acid substitution at a position corresponding to residue 60 of mature human p40 (e.g., mature murine p40 residue 60).

612. The IL12 receptor agonist of embodiment 611, wherein the amino acid substitution is F60A.

613. The IL12 receptor agonist of any one of embodiments 6 to 612, wherein the first p40 moiety, and if present, the second p40 moiety comprise(s) an amino acid substitution at a position corresponding to residue 62 of mature human p40 (e.g., mature murine p40 residue 62).

614. The IL12 receptor agonist of embodiment 613, wherein the amino acid substitution is D62N.

615. The IL12 receptor agonist of any one of embodiments 6 to 614, wherein the first p40 moiety, and if present, the second p40 moiety comprise(s) an amino acid substitution at a position corresponding to residue 73 of mature human p40 (e.g., mature murine p40 residue 73).

616. The IL12 receptor agonist of embodiment 615, wherein the amino acid substitution is E73Q.

617. The IL12 receptor agonist of any one of embodiments 6 to 616, wherein the first p40 moiety, and if present, the second p40 moiety comprise(s) an amino acid substitution at a position corresponding to residue 84 of mature human p40 (e.g., mature murine p40 residue 84).

618. The IL12 receptor agonist of embodiment 617, wherein the amino acid substitution is K84A.

619. The IL12 receptor agonist of any one of embodiments 6 to 618, wherein the first p40 moiety, and if present, the second p40 moiety comprise(s) an amino acid substitution at a position corresponding to residue 87 of mature human p40 (e.g., mature murine p40 residue 87).

620. The IL12 receptor agonist of embodiment 619, wherein the amino acid substitution is D87N.

621. The IL12 receptor agonist of any one of embodiments 6 to 620, wherein the first p40 moiety, and if present, the second p40 moiety comprise(s) an amino acid substitution at a position corresponding to residue 93 of mature human p40 (e.g., mature murine p40 residue 93).

622. An IL12 receptor agonist, which is optionally an IL12 receptor agonist according to embodiment 621, which comprises a first p40 moiety having alanine substitution at a position corresponding to residue 93 of mature human p40 (e.g., mature murine p40 residue 93), and which optionally further comprises a second p40 moiety having alanine substitution at a position corresponding to residue 93 of mature human p40 (e.g., mature murine p40 residue 93).

623. The IL12 receptor agonist of any one of embodiments 6 to 622, wherein the first p40 moiety, and if present, the second p40 moiety comprise(s) an amino acid substitution at a position corresponding to residue 96 of mature human p40 (e.g., mature murine p40 residue 96).

624. An IL12 receptor agonist, which is optionally an IL12 receptor agonist according to embodiment 623, which comprises a first p40 moiety having an alanine substitution at a position corresponding to residue 96 of mature human p40 (e.g., mature murine p40 residue 96), and which optionally further comprises a second p40 moiety having an alanine substitution at a position corresponding to residue 96 of mature human p40 (e.g., mature murine p40 residue 96).

625. The IL12 receptor agonist of any one of embodiments 6 to 624, wherein the first p40 moiety, and if present, the second p40 moiety comprise(s) an amino acid substitution at a position corresponding to residue 99 of mature human p40 (e.g., mature murine p40 residue 99).

626. The IL12 receptor agonist of embodiment 625 wherein the amino acid substitution is K99A, K99E, or K99Y.

627. The IL12 receptor agonist of any one of embodiments 6 to 626, wherein the first p40 moiety, and if present, the second p40 moiety comprise(s) an amino acid substitution at a position corresponding to residue 100 of mature human p40.

628. The IL12 receptor agonist of embodiment 627, wherein the amino acid substitution is E100Q.

629. The IL12 receptor agonist of any one of embodiments 6 to 628, wherein the first p40 moiety, and if present, the second p40 moiety comprise(s) an amino acid substitution at a position corresponding to residue 104 of mature human p40 (e.g., mature murine p40 residue 101).

630. An IL12 receptor agonist, which is optionally an IL12 receptor agonist according to embodiment 629, which comprises a first p40 moiety having an alanine substitution at a position corresponding to residue 104 of mature human p40 (e.g., mature murine p40 residue 101), and which optionally further comprises a second p40 moiety having an alanine substitution at a position corresponding to residue 104 of mature human p40 (e.g., mature murine p40 residue 101).

631. The IL12 receptor agonist of any one of embodiments 6 to 630, wherein the first p40 moiety, and if present, the second p40 moiety comprise(s) an amino acid substitution at a position corresponding to residue 103 of mature human p40 (e.g., mature murine p40 residue 100).

632. The IL12 receptor agonist of embodiment 631, wherein the amino acid substitution is N103D, N103Q.

633. The IL12 receptor agonist of any one of embodiments 6 to 632, wherein the first p40 moiety, and if present, the second p40 moiety comprise(s) an amino acid substitution at a position corresponding to residue 113 of mature human p40 (e.g., mature murine p40 residue 110).

634. The IL12 receptor agonist of embodiment 633, wherein the amino acid substitution is N113D, N113Q.

635. The IL12 receptor agonist of any one of embodiments 6 to 634, wherein the first p40 moiety, and if present, the second p40 moiety comprise(s) an amino acid substitution at a position corresponding to residue 144 of mature human p40 (e.g., mature murine p40 residue 141).

636. The IL12 receptor agonist of embodiment 635, wherein the amino acid substitution is Q144E.

637. The IL12 receptor agonist of any one of embodiments 6 to 636, wherein the first p40 moiety, and if present, the second p40 moiety comprise(s) an amino acid substitution at a position corresponding to residue 159 of mature human p40 (e.g., mature murine p40 residue 156).

638. The IL12 receptor agonist of embodiment 637, wherein the amino acid substitution is R159E.

639. The IL12 receptor agonist of any one of embodiments 6 to 638, wherein the first p40 moiety, and if present, the second p40 moiety comprise(s) an amino acid substitution at a position corresponding to residue 161 of mature human p40 (e.g., mature murine p40 residue 158).

640. The IL12 receptor agonist of embodiment 639, wherein the amino acid substitution is D161N.

641. The IL12 receptor agonist of any one of embodiments 6 to 640, wherein v an amino acid substitution at a position corresponding to residue 163 of mature human p40 (e.g., mature murine p40 residue 160).

642. The IL12 receptor agonist of embodiment 641, wherein the amino acid substitution is K163E.

643. The IL12 receptor agonist of any one of embodiments 6 to 642, wherein the first p40 moiety, and if present, the second p40 moiety comprise(s) an amino acid substitution at a position corresponding to residue 177 of mature human p40 (e.g., mature murine p40 residue 175).

644. The IL12 receptor agonist of embodiment 643, wherein the amino acid substitution is C177S.

645. The IL12 receptor agonist of any one of embodiments 6 to 644, wherein the first p40 moiety, and if present, the second p40 moiety comprise(s) an amino acid substitution at a position corresponding to residue 187 of mature human p40 (e.g., mature murine p40 residue 185).

646. The IL12 receptor agonist of embodiment 645, wherein the amino acid substitution is E187Q.

647. The IL12 receptor agonist of any one of embodiments 6 to 646, wherein the first p40 moiety, and if present, the second p40 moiety comprise(s) an amino acid substitution at a position corresponding to residue 200 of mature human p40 (e.g., mature murine p40 residue 198).

648. The IL12 receptor agonist of embodiment 647, wherein the amino acid substitution is N200D or N200Q.

649. The IL12 receptor agonist of any one of embodiments 6 to 648, wherein the first p40 moiety, and if present, the second p40 moiety comprise(s) an amino acid substitution at a position corresponding to residue 218 of mature human p40 (e.g., mature murine p40 residue 216).

650. The IL12 receptor agonist of embodiment 649, wherein the amino acid substitution is N218Q.

651. The IL12 receptor agonist of any one of embodiments 6 to 650, wherein the first p40 moiety, and if present, the second p40 moiety comprise(s) an amino acid substitution at a position corresponding to residue 229 of mature human p40 (e.g., mature murine p40 residue 226).

652. The IL12 receptor agonist of embodiment 651, wherein the amino acid substitution is Q229E.

653. The IL12 receptor agonist of any one of embodiments 6 to 652, wherein the first p40 moiety, and if present, the second p40 moiety comprise(s) an amino acid substitution at a position corresponding to residue 235 of mature human p40 (e.g., mature murine p40 residue 232).

654. The IL12 receptor agonist of embodiment 653, wherein the amino acid substitution is E235Q.

655. The IL12 receptor agonist of any one of embodiments 6 to 654, wherein the first p40 moiety, and if present, the second p40 moiety comprise(s) an amino acid substitution at a position corresponding to residue 246 of mature human p40 (e.g., mature murine p40 residue 243).

656. An IL12 receptor agonist, which is optionally an IL12 receptor agonist according to embodiment 655, which comprises a first p40 moiety having a valine substitution or a phenylalanine substitution at a position corresponding to residue 246 of mature human p40 (e.g., murine p40 residue 243), and which optionally further comprises a second p40 moiety having a valine substitution or a phenylalanine substitution at a position corresponding to residue 246 of mature human p40 (e.g., mature murine p40 residue 243).

657. The IL12 receptor agonist of any one of embodiments 6 to 656, wherein the first p40 moiety, and if present, the second p40 moiety comprise(s) an amino acid substitution at a position corresponding to residue 252 of mature human p40 (e.g., mature murine p40 residue 249).

658. The IL12 receptor agonist of embodiment 657, wherein the amino acid substitution is C252S.

659. The IL12 receptor agonist of any one of embodiments 6 to 658, wherein the first p40 moiety, and if present, the second p40 moiety comprise(s) an amino acid substitution at a position corresponding to residue 256 of mature human p40 (e.g., mature murine p40 residue 253).

660. The IL12 receptor agonist of embodiment 659, wherein the amino acid substitution is Q256N.

661. The IL12 receptor agonist of any one of embodiments 6 to 660, wherein the first p40 moiety, and if present, the second p40 moiety comprise(s) an amino acid substitution at a position corresponding to residue 258 of mature human p40 (e.g., mature murine p40 residue 255).

662. The IL12 receptor agonist of embodiment 661, wherein the amino acid substitution is K258E.

663. The IL12 receptor agonist of any one of embodiments 6 to 662, wherein the first p40 moiety, and if present, the second p40 moiety comprise(s) an amino acid substitution at a position corresponding to residue 260 of mature human p40 (e.g., mature murine p40 residue 257).

664. The IL12 receptor agonist of embodiment 663, wherein the amino acid substitution is K260E.

665. The IL12 receptor agonist of any one of embodiments 6 to 664, wherein the first p40 moiety, and if present, the second p40 moiety comprise(s) an amino acid substitution at a position corresponding to residue 262 of mature human p40 (e.g., mature murine p40 residue 267).

666. The IL12 receptor agonist of embodiment 665, wherein the amino acid substitution is E262Q.

667. The IL12 receptor agonist of any one of embodiments 6 to 666, wherein the first p40 moiety, and if present, the second p40 moiety comprise(s) an amino acid substitution at a position corresponding to residue 264 of mature human p40 (e.g., mature murine p40 residue 269).

668. The IL12 receptor agonist of embodiment 667, wherein the amino acid substitution is K264E.

669. The IL12 receptor agonist of any one of embodiments 6 to 668, wherein the first p40 moiety, and if present, the second p40 moiety comprise(s) an amino acid substitution at a position corresponding to residue 281 of mature human p40 (e.g., mature murine p40 residue 285).

670. The IL12 receptor agonist of embodiment 669, wherein the amino acid substitution is N281D or N281Q.

671. The IL12 receptor agonist of any one of embodiments 6 to 670, wherein the first p40 moiety, and if present, the second p40 moiety comprise(s) an amino acid substitution at a position corresponding to residue 292 of mature human p40 (e.g., mature murine p40 residue 296).

672. An IL12 receptor agonist, which is optionally an IL12 receptor agonist according to embodiment 671, which comprises a first p40 moiety having a phenylalanine substitution at a position corresponding to residue 292 of mature human p40 (e.g., murine p40 residue 296), and which optionally further comprises a second p40 moiety having a phenylalanine substitution at a position corresponding to residue 292 of mature human p40 (e.g., mature murine p40 residue 296).

673. The IL12 receptor agonist of any one of embodiments 6 to 672, wherein the first p40 moiety, and if present, the second p40 moiety comprise(s) an amino acid substitution at a position corresponding to residue 299 of mature human p40 (e.g., mature murine p40 residue 303).

674. The IL12 receptor agonist of embodiment 673, wherein the amino acid substitution is E299Q.

675. The IL12 receptor agonist of any one of embodiments 6 to 674, wherein the first p35 moiety, and if present, the second p35 moiety comprise(s) at least one amino acid substitution.

676. The IL12 receptor agonist of any one of embodiments 6 to 675, wherein the first p35 moiety, and if present, the second p35 moiety comprise(s) an amino acid substitution at a position corresponding to residue 21 of mature human p35 (e.g., mature murine p35 residue 17).

677. The IL12 receptor agonist of embodiment 676, wherein the amino acid substitution is N21D.

678. The IL12 receptor agonist of any one of embodiments 6 to 677, wherein the first p35 moiety, and if present, the second p35 moiety comprise(s) an amino acid substitution at a position corresponding to residue 35 of mature human p35 (e.g., mature murine p35 residue 31).

679. The IL12 receptor agonist of embodiment 678, wherein the amino acid substitution is Q35D.

680. The IL12 receptor agonist of any one of embodiments 6 to 679, wherein the first p35 moiety, and if present, the second p35 moiety comprise(s) an amino acid substitution at a position corresponding to residue 38 of mature human p35 (e.g., mature murine p35 residue 34).

681. The IL12 receptor agonist of embodiment 680, wherein the amino acid substitution is E38Q.

682. The IL12 receptor agonist of any one of embodiments 6 to 681, wherein the first p35 moiety, and if present, the second p35 moiety comprise(s) an amino acid substitution at a position corresponding to residue 55 of mature human p35 (e.g., mature murine p35 residue 51).

683. The IL12 receptor agonist of embodiment 682, wherein the amino acid substitution is D55Q or D55K.

684. The IL12 receptor agonist of any one of embodiments 6 to 683, wherein the first p35 moiety, and if present, the second p35 moiety comprise(s) an amino acid substitution at a position corresponding to residue 71 of mature human p35 (e.g., mature murine p35 residue 67).

685. The IL12 receptor agonist of embodiment 684, wherein the amino acid substitution is N71D.

686. The IL12 receptor agonist of any one of embodiments 6 to 685, wherein the first p35 moiety, and if present, the second p35 moiety comprise(s) an amino acid substitution at a position corresponding to residue 75 of mature human p35 (e.g., mature murine p35 residue 7571).

687. The IL12 receptor agonist of embodiment 686, wherein the amino acid substitution is L75A.

688. The IL12 receptor agonist of any one of embodiments 6 to 687, wherein the first p35 moiety, and if present, the second p35 moiety comprise(s) an amino acid substitution at a position corresponding to residue 76 of mature human p35 (e.g., mature murine p35 residue 72).

689. The IL12 receptor agonist of embodiment 688, wherein the amino acid substitution is N76D.

690. The IL12 receptor agonist of any one of embodiments 6 to 689, wherein the first p35 moiety, and if present, the second p35 moiety comprise(s) an amino acid substitution at a position corresponding to residue 79 of mature human p35 (e.g., mature murine p35 residue 75).

691. The IL12 receptor agonist of embodiment 690, wherein the amino acid substitution is E79Q.

692. The IL12 receptor agonist of any one of embodiments 6 to 691, wherein the first p35 moiety, and if present, the second p35 moiety comprise(s) an amino acid substitution at a position corresponding to residue 85 of mature human p35 (e.g., mature murine p35 residue 81).

693. The IL12 receptor agonist of embodiment 692, wherein the amino acid substitution is N85D or N85Q.

694. The IL12 receptor agonist of any one of embodiments 6 to 693, wherein the first p35 moiety, and if present, the second p35 moiety comprise(s) an amino acid substitution at a position corresponding to residue 89 of mature human p35 (e.g., mature murine p35 residue 85).

695. The IL12 receptor agonist of embodiment 694, wherein the amino acid substitution is L89A.

696. The IL12 receptor agonist of any one of embodiments 6 to 695, wherein the first p35 moiety, and if present, the second p35 moiety comprise(s) an amino acid substitution at a position corresponding to residue 96 of mature human p35 (e.g., mature murine p35 residue 92).

697. The IL12 receptor agonist of embodiment 696, wherein the amino acid substitution is F96A.

698. The IL12 receptor agonist of any one of embodiments 6 to 697, wherein the first p35 moiety, and if present, the second p35 moiety comprise(s) an amino acid substitution at a position corresponding to residue 97 of mature human p35 (e.g., mature murine p35 residue 93).

699. The IL12 receptor agonist of embodiment 698, wherein the amino acid substitution is M97A.

700. The IL12 receptor agonist of any one of embodiments 6 to 699, wherein the first p35 moiety, and if present, the second p35 moiety comprise(s) an amino acid substitution at a position corresponding to residue 124 of mature human p35 (e.g., mature murine p35 residue 120).

701. The IL12 receptor agonist of embodiment 700, wherein the amino acid substitution is L124A.

702. The IL12 receptor agonist of any one of embodiments 6 to 701, wherein the first p35 moiety, and if present, the second p35 moiety comprise(s) an amino acid substitution at a position corresponding to residue 125 of mature human p35 (e.g., mature murine p35 residue 121).

703. The IL12 receptor agonist of embodiment 702, wherein the amino acid substitution is M125A.

704. The IL12 receptor agonist of any one of embodiments 6 to 703, wherein the first p35 moiety, and if present, the second p35 moiety comprise(s) an amino acid substitution at a position corresponding to residue 130 of mature human p35 (e.g., mature murine p35 residue 126).

705. The IL12 receptor agonist of embodiment 704, wherein the amino acid substitution is Q130E.

706. The IL12 receptor agonist of any one of embodiments 6 to 705, wherein the first p35 moiety, and if present, the second p35 moiety comprise(s) an amino acid substitution at a position corresponding to residue 135 of mature human p35 (e.g., mature murine p35 residue 131).

707. The IL12 receptor agonist of embodiment 706, wherein the amino acid substitution is Q135E.

708. The IL12 receptor agonist of any one of embodiments 6 to 707, wherein the first p35 moiety, and if present, the second p35 moiety comprise(s) an amino acid substitution at a position corresponding to residue 136 of mature human p35 (e.g., mature murine p35 residue 132).

709. The IL12 receptor agonist of embodiment 708, wherein the amino acid substitution is N136D.

710. The IL12 receptor agonist of any one of embodiments 6 to 709, wherein the first p35 moiety, and if present, the second p35 moiety comprise(s) an amino acid substitution at a position corresponding to residue 143 of mature human p35 (e.g., mature murine p35 residue 139).

711. The IL12 receptor agonist of embodiment 710, wherein the amino acid substitution is E143Q.

712. The IL12 receptor agonist of any one of embodiments 6 to 711, wherein the first p35 moiety, and if present, the second p35 moiety comprise(s) an amino acid substitution at a position corresponding to residue 146 of mature human p35 (e.g., mature murine p35 residue 142).

713. The IL12 receptor agonist of embodiment 712, wherein the amino acid substitution is Q146E.

714. The IL12 receptor agonist of any one of embodiments 6 to 713, wherein the first p35 moiety, and if present, the second p35 moiety comprise(s) an amino acid substitution at a position corresponding to residue 167 of mature human p35 (e.g., mature murine p35 residue 163).

715. An IL12 receptor agonist, which is optionally an IL12 receptor agonist according to embodiment 714, which comprises a first p35 moiety having an alanine substitution, a valine substitution, an arginine substitution, or a glutamic acid substitution at a position corresponding to residue 167 of mature human p35 (e.g., mature murine p35 residue 163), and which optionally further comprises a second p35 moiety having an alanine substitution, a valine substitution, an arginine substitution, or a glutamic acid substitution at a position corresponding to residue 167 of mature human p35 (e.g., mature murine p35 residue 163).

716. The IL12 receptor agonist of any one of embodiments 6 to 715, wherein the first p35 moiety, and if present, the second p35 moiety comprise(s) an amino acid substitution at a position corresponding to residue 171 of mature human p35 (e.g., mature murine p35 residue 167).

717. An IL12 receptor agonist, which is optionally an IL12 receptor agonist according to embodiment 716, which comprises a first p35 moiety having an alanine substitution, a valine substitution, or a glutamic acid substitution at a position corresponding to residue 171 of mature human p35 (e.g., murine p35 residue 167), and which optionally further comprises a second p35 moiety having an alanine substitution, a valine substitution, or a glutamic acid substitution at a position corresponding to residue 171 of mature human p35 (e.g., mature murine p35 residue 167).

718. The IL12 receptor agonist of any one of embodiments 6 to 717, wherein the first p35 moiety, and if present, the second p35 moiety comprise(s) an amino acid substitution at a position corresponding to residue 189 of mature human p35 (e.g., mature murine p35 residue 185).

719. An IL12 receptor agonist, which is optionally an IL12 receptor agonist according to embodiment 718, which comprises a first p35 moiety having an alanine substitution or a lysine substitution at a position corresponding to residue 189 of mature human p35 (e.g., mature murine p35 residue 185), and which optionally further comprises a second p35 moiety having an alanine substitution or a lysine substitution at a position corresponding to residue 189 of mature human p35 (e.g., mature murine p35 residue 185).

720. The IL12 receptor agonist of any one of embodiments 6 to 719, wherein either the first polypeptide or the second polypeptide further comprises a first IL12 masking moiety.

721. The IL12 receptor agonist of embodiment 720, wherein the first IL12 masking moiety is a first IL12 receptor moiety.

722. The IL12 receptor agonist of embodiment 721, wherein the first IL12 receptor moiety comprises IL12Rβ1, a p40-binding fragment thereof or a variant thereof having at least 90%, at least 95% or at least 97% sequence identity to IL12Rβ1 or the p40-binding fragment thereof.

723. The IL12 receptor agonist of embodiment 722, wherein the first IL12 receptor moiety comprises IL12Rβ2, a p35-binding fragment thereof or a variant thereof having at least 90%, at least 95% or at least 97% sequence identity to IL12Rβ2 or the p35-binding fragment thereof.

724. The IL12 receptor agonist of any one of embodiments 720 to 723, wherein the first polypeptide comprises the first IL12 receptor moiety and the second polypeptide comprises a second IL12 receptor moiety.

725. The IL12 receptor agonist of embodiment 724, wherein the first or second IL12 receptor moiety comprises IL12Rβ1, a p40-binding fragment thereof or a variant thereof having at least 90%, at least 95% or at least 97% sequence identity to IL12Rβ1 the p40-binding fragment thereof.

726. The IL12 receptor agonist of embodiment 724, wherein the first or second IL12 receptor moiety comprises IL12Rβ2, a p35-binding fragment thereof, or a variant thereof having at least 90%, at least 95% or at least 97% sequence identity to IL12Rβ2 or the p35-binding fragment thereof.

727. The IL12 receptor agonist of any one of embodiments 724 to 726, wherein the first IL12 receptor moiety and the second IL12 receptor moiety are identical.

728. The IL12 receptor agonist of any one of embodiments 724 to 726, wherein the first IL12 receptor moiety and the second IL12 receptor moiety are not identical.

729. The IL12 receptor agonist of any one of embodiments 720 to 728, which comprises a first multimerization moiety and a second multimerization moiety and wherein the first IL12 receptor moiety is between the first multimerization moiety and the first p40 moiety or first p35 moiety.

730. The IL12 receptor agonist of any one of embodiments 720 to 728, which comprises a first multimerization moiety and a second multimerization moiety and wherein the first IL12 receptor moiety is distal to the first multimerization moiety relative to the first p40 and first p35 moieties.

731. The IL12 receptor agonist of any one of embodiments 720 to 730, which comprises a first multimerization moiety and a second multimerization moiety and wherein the second IL12 receptor moiety is between the second multimerization moiety and the second p40 moiety or second p35 moiety.

732. The IL12 receptor agonist of any one of embodiments 720 to 730, which comprises a first multimerization moiety and a second multimerization moiety and wherein the second IL12 receptor moiety is distal to the second multimerization moiety relative to the second p40 and second p35 moieties.

733. The IL12 receptor agonist of any one of embodiments 720 to 732, wherein the first p40 moiety or the first p35 moiety, and the first IL12 receptor moiety are connected via a first receptor moiety linker.

734. The IL12 receptor agonist of any one of embodiments 724 to 733, wherein the second p40 moiety or the second p35 moiety, and the second IL12 receptor moiety are connected via a second receptor moiety linker.

735. The IL12 receptor agonist of embodiment 733 or 734 wherein the first receptor moiety linker, and when present, the second receptor moiety linker is(are) at least 10 or at least 15 amino acids in length.

736. The IL12 receptor agonist of any one of embodiments 733 to 735, wherein the first receptor moiety linker, and when present, the second receptor moiety linker is(are) or comprises a glycine-serine linker.

737. The IL12 receptor agonist of embodiment 736, wherein the glycine-serine linker comprises amino acid sequence $G_4S$ (SEQ ID NO: 25).

738. The IL12 receptor agonist of embodiment 737, wherein each of the first receptor moiety linker and the second receptor moiety linker is or comprises a multimer of the amino acid sequence $G_4S$ (SEQ ID NO: 25).

739. The IL12 receptor agonist of embodiment 738, wherein the multimer comprises, 2, 3, 4, 5, 6, or more repeats of the amino acid sequence $G_4S$ (SEQ ID NO: 25).

740. The IL12 receptor agonist of any one of embodiments 720 to 739, which comprises a first multimerization moiety and a second multimerization moiety and wherein the first IL12 receptor moiety and the first multimerization moiety are connected via a first linker.

741. The IL12 receptor agonist of any one of embodiments 724 to 740, which comprises a first multimerization moiety and a second multimerization moiety and wherein second IL12 receptor moiety and the second multimerization moiety are connected via a second linker.

742. The IL12 receptor agonist of embodiment 740 or embodiment 741, wherein the first linker, and when present, the second linker is (are) at least 10 or at least 15 amino acids in length.

743. The IL12 receptor agonist of any one of embodiments 740 to 742, wherein the first linker, and when present, the second linker is (are) or comprises a glycine-serine linker.

744. The IL12 receptor agonist of any one of embodiments 740 to 743, wherein the first linker, and when present, the second linker comprises the amino acid sequence $G_4S$ (SEQ ID NO: 25).

745. The IL12 receptor agonist of embodiment 744, wherein each of the first linker and the second linker is or comprises a multimer of the amino acid sequence $G_4S$ (SEQ ID NO: 25).

746. The IL12 receptor agonist of embodiment 745, wherein the multimer comprises, 2, 3, 4, 5, 6, or more repeats of the amino acid sequence $G_4S$ (SEQ ID NO: 25).

747. The IL12 receptor agonist of embodiment 720, wherein the first IL12 masking moiety is an IL12 antibody fragment.

748. The IL12 receptor agonist of embodiment 747, wherein the IL12 antibody fragment is in the form of a Fab, an Fv, an scFv, or an sdAb.

749. The IL12 receptor agonist of embodiment 747 or embodiment 748, wherein the IL12 antibody fragment is an antigen binding fragment of an anti-IL12 antibody.

750. The IL12 receptor agonist of embodiment 750, wherein the IL12 antibody fragment:

(a) comprises an antibody fragment of an antibody selected from ustekinumab; briakinumab; anti-IL12 antibodies described in WO/2017/172771; anti-IL12 antibodies described in WO/2012/094623; anti-IL12 antibodies described in WO/2006/069036; anti-IL12 antibodies described in WO/2009/068627; clone B-T21 (Diaclone); MAB219 (R&D Systems); MAB1510 (R&D Systems); clone C17.8 (Bio X Cell); clone R1-5D9 (Bio X Cell); AP-MAB0853 (ab80682) (abcam); and ab9992 (abcam); or (b) competes for binding to IL12 with and/or binds to the same epitope as an anti-IL12 antibody selected from ustekinumab; briakinumab; anti-IL12 antibodies described in WO/2017/172771; anti-IL12 antibodies described in WO/2012/094623; anti-IL12 antibodies described in WO/2006/069036; anti-IL12 antibodies described in WO/2009/068627; clone B-T21 (Diaclone); MAB219 (R&D Systems); MAB1510 (R&D Systems); clone C17.8 (Bio X Cell); clone R1-5D9 (Bio X Cell); AP-MAB0853 (ab80682) (abcam); and ab9992 (abcam).

751. The IL12 receptor agonist of any one of embodiments 747 to 750, which comprises a first multimerization moiety and a second multimerization moiety and wherein the IL12 antibody fragment is distal to the first multimerization moiety relative to the first p40 and first p35 moieties.

752. The IL12 receptor agonist of embodiment 751, wherein the first p40 moiety or the first p35 moiety, and the IL12 antibody fragment are connected via an antibody fragment linker.

753. The IL12 receptor agonist of any one of embodiments 747 to 752, which comprises a first multimerization moiety and a second multimerization moiety and wherein the first p40 and first p35 moieties are connected to the first multimerization moiety and the IL12 antibody fragment is connected to the second multimerization moiety.

754. The IL12 receptor agonist of embodiment 753, wherein the second multimerization moiety and the IL12 antibody fragment are connected via an antibody fragment linker.

755. The IL12 receptor agonist of embodiment 752 or embodiment 754, wherein the antibody fragment linker is at least 10 or at least 15 amino acids in length.

756. The IL12 receptor agonist of any one of embodiments 752, 754, and 755 wherein the antibody fragment linker is or comprises a glycine-serine linker.

757. The IL12 receptor agonist of embodiment 756, wherein the glycine-serine linker comprises amino acid sequence $G_4S$ (SEQ ID NO: 25).

758. The IL12 receptor agonist of embodiment 757, wherein the antibody fragment linker is or comprises a multimer of the amino acid sequence $G_4S$ (SEQ ID NO: 25).

759. The IL12 receptor agonist of embodiment 758, wherein the multimer comprises, 2, 3, 4, 5, 6, or more repeats of the amino acid sequence $G_4S$ (SEQ ID NO: 25).

760. The IL12 receptor agonist of any one of embodiments 6 to 731, which comprises a first multimerization moiety and a second multimerization moiety and wherein the first multimerization moiety and the second multimerization moiety are configured to dimerize together.

761. The IL12 receptor agonist of any one of embodiments 6 to 760, which comprises a first multimerization moiety and a second multimerization moiety and wherein the first multimerization moiety and the second multimerization moiety each is or comprises an Fc domain.

762. The IL12 receptor agonist of embodiment 761, wherein the Fc domain is an IgG1, IgG2, IgG3, or IgG4 Fc domain.

763. The IL12 receptor agonist of embodiment 761 or embodiment 762, wherein the Fc domain has reduced effector function.

764. The IL12 receptor agonist of any one of embodiment 761 to 763, wherein the Fc domain is an IgG4 Fc domain.

765. The IL12 receptor agonist of any one of embodiments 761 to 764, wherein the Fc domain comprises the amino acid sequence ESKYGPPCPPCPAPPVAGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 60) or a portion thereof.

766. The IL12 receptor agonist of any one of embodiments 6 to 765, which comprises a first targeting moiety.

767. The IL12 receptor agonist of embodiment 766, which comprises a first targeting moiety component on the first polypeptide chain and further comprises a third targeting moiety component configured to associate with the first targeting moiety component to form the first targeting moiety, wherein the third targeting moiety component is not part of the first polypeptide or the second polypeptide.

768. The IL12 receptor agonist of any one of embodiments 6 to 767, which comprises a second targeting moiety.

769. The IL12 receptor agonist of embodiment 768, which comprises a second targeting moiety component on the second polypeptide chain and further comprises a fourth targeting moiety component configured to associate with the second targeting moiety component to form the second targeting moiety, wherein the fourth targeting moiety component is not part of the first polypeptide or the second polypeptide.

770. The IL12 receptor of any one of embodiments 766 to 769, wherein (a) the first targeting moiety or first targeting moiety component, if present on the first polypeptide chain, is N-terminal to the first multimerization moiety and/or (b) the second targeting moiety or second targeting moiety component, if present on the second polypeptide chain, is N-terminal to the second multimerization moiety.

771. The IL12 receptor of embodiment 766 to 769, wherein (a) the first targeting moiety or first targeting moiety component, if present on the first polypeptide chain, is C-terminal to the first multimerization moiety and/or (b) the second targeting moiety or second targeting moiety component, if present on the second polypeptide chain, is C-terminal to the second multimerization moiety.

772. The IL12 receptor agonist of any one of embodiments 766 to 771, which comprises a first targeting moiety and/or a second targeting moiety, and wherein the first and/or second target moiety:

(a) binds to a tumor associated antigen;
(b) binds to a tumor microenvironment antigen;
(c) binds to a cell surface molecule of tumor reactive lymphocytes;
(d) binds to a checkpoint inhibitor;
(e) binds to a peptide-MHC complex;
(f) is a peptide-MHC complex;
(g) binds to an antigen associated with or targeted by an autoimmune response; or
(h) is independently selected from (a) to (g) above.

773. The IL12 receptor agonist of embodiment 768 or 769, wherein the first targeting moiety and the second targeting moiety are the same.

774. The IL12 receptor agonist of embodiment 772 or embodiment 773, wherein the first targeting moiety and/or second targeting moiety binds to a tumor associated antigen.

775. The IL12 receptor agonist of embodiment 774, wherein the tumor associated antigen is Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (AD-Abp), cyclophilin b, colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) or an immunogenic epitopes thereoPSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low binding affinity IgE receptor), CD30 (cytokine receptor), CD33 (myeloid cell surface antigen), CD40 (tumor necrosis factor receptor), IL-6R-(IL6 receptor), CD20, MCSP, PDGFβR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) or extra domain B (EDB) of fibronectin, or the A1 domain of tenascin-C (TnC A1).

776. The IL12 receptor agonist of embodiment 772 or embodiment 773, wherein the tumor associated antigen is CD20.

777. The IL12 receptor agonist of embodiment 772 or embodiment 773, wherein the tumor associated antigen is a viral antigen.

778. The IL12 receptor agonist of embodiment 777, wherein the viral antigen is Epstein-Barr virus LMP-1, hepatitis C virus E2 glycoprotein, HIV gp160, or HIV gp120, HPV E6, HPV E7, CMV early membrane antigen (EMA) or CMV late membrane antigen (LMA).

779. The IL12 receptor agonist of embodiment 772 or embodiment 773, wherein the first targeting moiety and/or second targeting moiety binds to a tumor microenvironment antigen.

780. The IL12 receptor agonist of embodiment 779, wherein the tumor microenvironment antigen is an extracellular matrix protein.

781. The IL12 receptor agonist of embodiment 780, wherein the extracellular matrix protein is syndecan, heparanase, integrins, osteopontin, link, cadherins, laminin, laminin type EGF, lectin, fibronectin, notch, tenascin, collagen and matrixin.

782. The IL12 receptor agonist of embodiment 772 or embodiment 773, wherein the first targeting moiety and/or second targeting moiety binds to a cell surface molecule of tumor lymphocytes.

783. The IL12 receptor agonist of embodiment 782, wherein the cell surface molecule is CD27, CD28, 4-1BB (CD137), OX40, CD30, CD40, PD1, ICOS, lymphocyte function-associated antigen-1 (LFA-1), CD2, CD7, LIGHT, NKG2C, LAG3, TIM3, or B7-H3.

784. The IL12 receptor agonist of embodiment 772 or embodiment 773, wherein the cell surface molecule is PD1.

785. The IL12 receptor agonist of embodiment 784, wherein the first targeting moiety and/or second targeting moiety is an anti-PD1 antibody or antigen binding fragment thereof.

786. The IL12 receptor agonist of embodiment 785, wherein the anti-PD1 antibody or antigen binding fragment thereof inhibits PD1 signaling.

787. The IL12 receptor agonist of embodiment 785, wherein the anti-PD1 antibody or antigen binding fragment thereof does not inhibit PD1 signaling.

788. The IL12 receptor agonist of embodiment 782, wherein the cell surface molecule is LAG3.

789. The IL12 receptor agonist of embodiment 772 or embodiment 773, wherein the first targeting moiety and/or second targeting moiety binds to a checkpoint inhibitor.

790. The IL12 receptor agonist of embodiment 789, wherein the checkpoint inhibitor is CTLA-4, PD1, PDL1, PDL2, PD1, B7-H3, B7-H4, BTLA, HVEM, TIM3, GAL9, LAG3, VISTA, KIR, 2B4, CD160, CGEN-15049, CHK1, VISTA, PSGL1, or CHK2.

791. The IL12 receptor agonist of embodiment 790, wherein the checkpoint inhibitor is PD1.

792. The IL12 receptor agonist of embodiment 791, wherein the first targeting moiety and/or second targeting moiety is an anti-PD1 antibody or antigen binding fragment thereof.

793. The IL12 receptor agonist of embodiment 792, wherein the anti-PD1 antibody or antigen binding fragment thereof inhibits PD1 signaling.

794. The IL12 receptor agonist of embodiment 792, wherein the anti-PD1 antibody or antigen binding fragment thereof does not inhibit PD1 signaling.

795. The IL12 receptor agonist of embodiment 790, wherein the checkpoint inhibitor is LAG3.

796. The IL12 receptor agonist of embodiment 772 or embodiment 773, wherein the first targeting moiety and/or second targeting moiety binds to an MHC-peptide complex.

797. The IL12 receptor agonist of embodiment 797 wherein the peptide in the peptide-MHC complex comprises a tumor neoantigen.

798. The IL12 receptor agonist of embodiment 798, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

799. The IL12 receptor agonist of any one of embodiments 796 to 798, wherein the first targeting moiety and/or second targeting moiety comprises an antibody or antigen binding fragment thereof having complementarity determining regions ("CDRs") comprising:
   (a) a CDR-H1 having an amino acid sequence selected from any of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524 of International Patent Publication No. WO 2019005897 A1, which are incorporated by reference herein;
   (b) a CDR-H2 having an amino acid sequence selected from any of SEQ ID NOs: 6, 22, 38, 54, 70, 86, 102, 118, 134, 150, 166, 182, 198, 214, 222, 238, 254, 270, 286, 302, 318, 334, 350, 366, 382, 414, 430, 446, 462, 478, 494, 510, and 526 of International Patent Publication No. WO 2019005897 A1, which are incorporated by reference herein;
   (c) a CDR-H3 having an amino acid sequence selected from any of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528 of International Patent Publication No. WO 2019005897 A1, which are incorporated by reference herein;
   (d) a CDR-L1 having an amino acid sequence selected from any of SEQ ID NOs: 12, 28, 44, 60, 76, 92, 108, 124, 140, 156, 172, 188, 204, 204, 228, 244, 260, 276, 292, 308, 324, 340, 356, 372, 388, 404, 420, 436, 452, 468, 484, 500, 516, and 532 of International Patent Publication No. WO 2019005897 A1, which are incorporated by reference herein;
   (e) a CDR-L2 having an amino acid sequence selected from any of SEQ ID NOs: 14, 30, 46, 62, 78, 94, 110, 126, 142, 158,174, 190, 206, 230, 246, 262, 278, 294, 310, 326, 342, 358, 374, 390, 406, 422, 438, 454, 470, 486, 502, 518, and 534 of International Patent Publication No. WO 2019005897 A1, which are incorporated by reference herein; and
   (f) a CDR-L3 having an amino acid sequence selected from an of SEQ ID NOs: 16. 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536 of International Patent Publication No. WO 2019005897 A1, which are incorporated by reference herein.

800. The IL12 receptor agonist of embodiment 799, wherein the antibody or antigen binding fragment has VH-VL amino acid sequences selected from any of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530 of International Patent Publication No. WO 2019005897 A1, which are incorporated by reference herein.

801. The IL12 receptor agonist of embodiment 800, wherein the antibody or antigen binding fragment has VH-VL amino acid sequences selected from any of SEQ ID NOs: 2/10, 34/42, 82/90, 194/202, 282/290, and 506/514 of International Patent Publication No. WO 2019005897 A1, which are incorporated by reference herein.

802. The IL12 receptor agonist of embodiment 772 or embodiment 773, wherein the first targeting moiety and/or second targeting moiety binds to an antigen associated with or targeted by an autoimmune response.

803. The IL12 receptor agonist of embodiment 802, wherein the peptide is derived from gliadin, GAD 65, IA-2, insulin B chain, glatiramer acetate (GA), achetylcholine receptor (AChR), p205, insulin, thyroid-stimulating hormone, tyrosinase, TRP I, or a myelin antigen.

804. The IL12 receptor agonist of embodiment 803, wherein the peptide is derived from IL-4R, IL-6R, or DLL4.

805. The IL12 receptor agonist of any one of embodiments 767 to 804, wherein the first targeting moiety and, if present, second targeting moiety is an antibody or antigen binding fragment thereof.

806. The IL12 receptor agonist of embodiment 805, wherein the targeting moiety is a Fab.

807. The IL12 receptor agonist of embodiment 805, wherein the targeting moiety is an scFv.

808. The IL12 receptor agonist any one of embodiments 767 to 804, wherein the first targeting moiety and, if present, second targeting moiety is a peptide-MHC complex.

809. The IL12 receptor agonist of embodiment 808, wherein the peptide-MHC complex binds to the T cell receptor of tumor lymphocytes.

810. The IL12 receptor agonist of embodiment 808 or embodiment 809, wherein the peptide in the peptide-MHC complex comprises a tumor neoantigen.

811. The IL12 receptor agonist of embodiment 810, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

812. The IL12 receptor agonist of embodiment 808, wherein the peptide in peptide-MHC complex comprises a viral antigen.

813. The IL12 receptor agonist of embodiment 812, wherein the viral antigen is CMVpp65 or HPV16E7.

814. The IL12 receptor agonist of any one of embodiments 808 to 813, wherein the peptide-MHC complex further comprises P2 microglobulin or a fragment thereof.

815. The IL12 receptor agonist of embodiment 814, wherein the peptide MHC complex comprises a type I MHC domain.
816. The IL12 receptor agonist of embodiment 815, wherein the peptide MHC complex comprises, in an N- to C-terminal orientation a MHC peptide, a linker, a β2-microglobulin domain, a linker, and a type I MHC domain.
817. The IL12 receptor agonist of embodiment 816, wherein the linker connecting the MHC peptide and the β2-microglobulin domain comprises the amino acid sequence GCGGS (SEQ ID NO: 47).
818. The IL12 receptor agonist of any one of embodiment 808 to 813, wherein the peptide-MHC complex does not comprise β2 microglobulin or a fragment thereof.
819. The IL12 receptor agonist of embodiment 818, wherein the peptide MHC complex comprises a type II MHC domain.
820. The IL12 receptor agonist of any one of embodiments 6 to 819, which comprises a stabilization moiety.
821. The IL12 receptor agonist of embodiment 820, wherein the stabilization moiety is human serum albumin, a human serum albumin binder, an XTEN, a PAS, a carbohydrate, a polysialic acid, a hydrophilic polymer, or a fatty acid.
822. The IL12 receptor agonist of embodiment 821, wherein the stabilization moiety is a human serum albumin binder.
823. The IL12 receptor agonist of embodiment of 822, wherein the human serum albumin binder is Adnectin PKE, AlbudAb, or an albumin binding domain.
824. The IL12 receptor agonist of embodiment 820, wherein the stabilization moiety is a hydrophilic polymer.
825. The IL12 receptor agonist of embodiment 824, wherein the hydrophilic polymer is polyethylene glycol (PEG).
826. The IL12 receptor agonist of embodiment 825, wherein the PEG has a molecular weight ranging from about 7.5 kDa to about 80 kDa.
827. The IL12 receptor agonist of embodiment 826, wherein the PEG has a molecular weight ranging from about 30 kDa to about 60 kDa, optionally wherein the molecular weight is about 50 kDa.
828. The IL12 receptor agonist of any one of embodiments 824 to 827, wherein the hydrophilic polymer is attached to an IL12Rβ1-binding surface of the p40 moiety.
829. The IL12 receptor agonist of any one of embodiments 824 to 828, wherein the hydrophilic polymer is attached to an IL12Rβ2-binding surface of the p35 moiety.
830. The IL12 receptor agonist of any one of embodiments 6 to 829, wherein the first p40 and first p35 moieties, when present the second p40 and second p35 moieties, and/or the IL12 receptor agonist has 50-fold to 1,000-fold or 1.5-fold to 10-fold attenuated binding to human IL12 receptor complex as compared to wild type IL12.
831. The IL12 receptor agonist of any one of embodiments 6 to 829, wherein the first p40 and first p35 moieties, when present the second p40 and second p35 moieties, and/or the IL12 receptor agonist has up to 100-fold, up to 500-fold, up to 1,000-fold or up to 5,000-fold attenuated binding to human IL12 receptor complex as compared to wild-type human IL12.
832. The IL12 receptor agonist of any one of embodiments 6 to 831 wherein the first p40 and first p35 moieties, when present the second p40 and second p35 moieties, and/or the IL12 receptor agonist has higher cytokine activity on tumor-reactive lymphocytes than on peripheral lymphocytes.
833. The IL12 receptor agonist of embodiment 832, wherein the first p40 and first p35 moieties, when present the second p40 and second p35 moieties, and/or the IL12 receptor agonist has at least 5-fold or at least 10-fold higher cytokine activity on tumor reactive lymphocytes than on peripheral lymphocytes.
834. The IL12 receptor agonist of any one of embodiments 6 to 833, which has a therapeutic index of at least 1.
835. The IL12 receptor agonist of embodiment 834, which has a therapeutic index of at least 2.
836. The IL12 receptor agonist of embodiment 834, which has a therapeutic index of at least 5.
837. The IL12 receptor agonist of embodiment 834, which has a therapeutic index of at least 10.
838. The IL12 receptor agonist of embodiment 834, which has a therapeutic index of at least 20.
839. The IL12 receptor agonist of embodiment 834, which has a therapeutic index of at least 50.
840. The IL12 receptor agonist of any one of embodiments 834 to 839, which has a therapeutic index of up to 500.
841. The IL12 receptor agonist of any one of embodiments 806 to 839, which has a therapeutic index of up to 250.
842. The IL12 receptor agonist of any one of embodiments 6 to 841, which has a therapeutic index of about 2.
843. The IL12 receptor agonist of any one of embodiments 6 to 841, which has a therapeutic index of about 10.
844. The IL12 receptor agonist of any one of embodiments 6 to 841, which has a therapeutic index of about 20.
845. The IL12 receptor agonist of any one of embodiments 6 to 841, which has a therapeutic index of about 50.
846. The IL12 receptor agonist of any one of embodiments 6 to 841, which has a therapeutic index of about 100.
847. The IL12 receptor agonist of any one of embodiments 6 to 841, which has a therapeutic index of about 200.
848. A nucleic acid or plurality of nucleic acids encoding the p35 moiety of embodiment 1, the p40 moiety of embodiment 2, or the IL12 receptor agonist of any one of embodiments 6 to 847.
849. A host cell engineered to express the p35 moiety of embodiment 1, the p40 moiety of embodiment 2, the IL12 receptor agonist of any one of embodiments 6 to 847 or the nucleic acid(s) of embodiment 848.
850. A method of producing the p35 moiety of embodiment 1, the p40 moiety of embodiment 2, the IL12 receptor agonist of any one of embodiments 6 to 847, comprising culturing the host cell of embodiment 849 and recovering the p35 moiety, p40 moiety or IL12 receptor agonist expressed thereby.
851. A pharmaceutical composition comprising the p35 moiety of embodiment 1, the p40 moiety of embodiment 2, the IL12 receptor agonist of any one of embodiments 6 to 847 and an excipient.

852. A method of treating cancer, comprising administering to a subject in need thereof the p35 moiety of embodiment 1, the p40 moiety of embodiment 2, the IL12 receptor agonist of any one of embodiments 6 to 847 or the pharmaceutical composition of embodiment 816.

853. A method of targeted treatment of cancer, comprising administering to a subject in need thereof an IL12 receptor agonist according to any one of embodiments 6 to 847 or a pharmaceutical composition comprising an IL12 receptor agonist according to any one of embodiments 6 to 847, wherein the IL12 receptor agonist comprises one or two targeting moieties, optionally wherein the one or two targeting moieties are as defined in any one of embodiments 766 to 819 or as described in Section 6.5.

854. A method of localized delivery of an IL12 protein, comprising administering to a subject in need thereof an IL12 receptor agonist according to any one of embodiments 6 to 847 or a pharmaceutical composition comprising an IL12 receptor agonist according to any one of embodiments 6 to 847, wherein the IL12 receptor agonist comprises one or two targeting moieties, optionally wherein the one or two targeting moieties are as defined in any one of embodiments 766 to 819 or as described in Section 6.5.

855. A method of administering to the subject IL12 therapy with reduced systemic exposure and/or reduced systemic toxicity, comprising administering to a subject the IL12 therapy in the form of an IL12 receptor agonist according to any one of embodiments 6 to 847 or a pharmaceutical composition comprising an IL12 receptor agonist according to any one of embodiments 6 to 847, wherein the IL12 receptor agonist comprises (a) one or two targeting moieties, optionally wherein the one or two targeting moieties are as defined in any one of embodiments 766 to 819 or as described in Section 6.5 and/or (b) an IL12 moiety that is attenuated through mutation and/or masking (e.g., by an IL12 receptor or an anti-IL12 antibody or antigen-binding fragment thereof, e.g., as described in Section 6.4).

856. A method of locally inducing an immune response in a target tissue, comprising administering to a subject in need thereof an IL12 receptor agonist according to any one of embodiments 6 to 847 or a pharmaceutical composition comprising an IL12 receptor agonist according to any one of embodiments 6 to 847, wherein the IL12 receptor agonist comprises (a) one or two targeting moieties, optionally wherein the one or two targeting moieties are as defined in any one of embodiments 766 to 819 or as described in Section 6.5 and/or (b) an IL12 moiety that is attenuated through mutation and/or masking (e.g., by an IL12 receptor or an anti-IL12 antibody or antigen-binding fragment thereof, e.g., as described in Section 6.4).

857. The method of any one of embodiments 852 to 856, wherein the administration is systemic, optionally intravenous.

858. The method of any one of embodiments 852 to 856, wherein the administration is subcutaneous.

859. The method of any one of embodiments 852 to 858, which further comprises administering an anti-PD1 antibody to the subject.

860. The method of embodiment 859, wherein the anti-PD1 antibody is MDX-1106 (nivolumab), MK-3475 (pembrolizumab), MEDI-0680 (AMP-514), PDR001, or BGB-108.

8. EXAMPLES

8.1. Materials and Methods

8.1.1. Production of IL12 Receptor Agonists

Constructs encoding IL12, IL12-Fc fusion proteins, and the IL12 mutein-Fc fusion proteins in Tables 7 to 10 below and Fc controls were generated. The IL12-Fc fusion proteins and IL12 mutein-Fc fusion proteins included different configurations of murine or human IL12 p40 and p35 subunits, an IgG4 Fc domain, and linkers of different lengths from different repeats of $G_4S$ (SEQ ID NO: 25). A 29-amino acid signal sequence from murine inactive tyrosine-protein kinase transmembrane receptor ROR1 (mROR1) was added to the N-termini of the constructs. All IL12-Fc fusion proteins and IL12 mutein-Fc fusion proteins were expressed as preproteins containing the signal sequence. The signal sequence was cleaved by intracellular processing to produce a mature protein.

TABLE A

| Sequences of components of constructs exemplified herein | |
|---|---|
| Human IL12 p40 (mature): | IWELKKDVYVVELDWYPDAPGEMVV LTCDTPEEDGITWTLDQSSEVLGSG KTLTIQVKEFGDAGQYTCHKGGEVL SHSLLLLHKKEDGIWSTDILKDQKE PKNKTFLRCEAKNYSGRFTCWWLTT ISTDLTFSVKSSRGSSDPQGVTCGA ATLSAERVRGDNKEYEYSVECQEDS ACPAAEESLPIEVMVDAVHKLKYEN YTSSFFIRDIIKPDPPKNLQLKPLK NSRQVEVSWEYPDTWSTPHSYFSLT FCVQVQGKSKREKKDRVFTDKTSAT VICRKNASISVRAQDRYYSSSWSEW ASVPCS (SEQ ID NO: 56) |
| Murine IL12 p40 (mature): | MWELEKDVYVVEVDWTPDAPGETVN LTCDTPEEDDITWTSDQRHGVIGSG KTLTITVKEFLDAGQYTCHKGGETL SHSHLLLHKKENGIWSTEILKNFKN KTFLKCEAPNYSGRFTCSWLVQRNM DLKFNIKSSSSSPDSRAVTCGMASL SAEKVTLDQRDYEKYSVSCQEDVTC PTAEETLPIELALEARQQNKYENYS TSFFIRDIIKPDPPKNLQMKPLKNS QVEVSWEYPDSWSTPHSYFSLKFFV RIQRKKEKMKETEEGCNQKGAFLVE KTSTEVQCKGGNVCVQAQDRYYNSS CSKWACVPCRVRS (SEQ ID NO: 57) |
| Human IL12 p35 (mature): | RNLPVATPDPGMFPCLHHSQNLLRA VSNMLQKARQTLEFYPCTSEEIDHE DITKDKTSTVEACLPLELTKNESCL NSRETSFITNGSCLASRKTSFMMAL CLSSIYEDLKMYQVEFKTMNAKLLM DPKRQIFLDQNMLAVIDELMQALNF NSETVPQKSSLEEPDFYKTKIKLCI LLHAFRIRAVTIDRVMSYLNAS (SEQ ID NO: 58) |
| Murine IL12 p35 (mature): | RVIPVSGPARCLSQSRNLLKTTDDM VKTAREKLKHYSCTAEDIDHEDITR DQTSTLKTCLPLELHKNESCLATRE TSSTTRGSCLPPQKTSLMMTLCLGS IYEDLKMYQTEFQAINAALQNHNHQ QIILDKGMLVAIDELMQSLNHNGET LRQKPPVGEADPYRVKMKLCILLHA FSTRVVTINRVMGYLSSA (SEQ ID NO: 59) |
| hIgG4s-Fc Variant hIgG4 | ESKYGPPCPPCPAPPVAGPSVFLFP PKPKDTLMISRTPEVTCVVVDVSQE |

TABLE A-continued

| Sequences of components of constructs exemplified herein | |
|---|---|
| with IgG2-based hinge region (hIgG4E99-105 hIgG2_HingeC106-A115 hIgG4_CH2_CH3 G117-K237) | DPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 60) |
| hIgG4s(Knob)-Fc Variant hIgG4 with IgG2-based hinge region and mutations to facilitate heterodimerization with hIgG4s (HoleStar)-Fc | ESKYGPPCPPCPAPPVAGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLGK (SEQ ID NO: 61) |
| hIgG4s(Hole-Star)-Fc Variant hIgG4 with IgG2-based hinge region and mutations to facilitate heterodimerization with hIgG4s(Knob)-Fc | ESKYGPPCPPCPAPPVAGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVMHEALHNRFTQKSLSLSPGK (SEQ ID NO: 62) |

TABLE A-continued

| Sequences of components of constructs exemplified herein | |
|---|---|
| mIgG1-Fc IgG1 with N276D, N278D | VPRDCGCKPCICTVPEVSSVFIFPPKPKDVLTITLTPKVTCVVVDISKDDPEVQFSWFVDDVEVHTAQTQPREEQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQPIMDTDGSYFVYSKLNVQKSNWEAGNTFTCSVLHEGLHNHHTEKSLSHSPGK (SEQ ID NO: 63) |
| $G_4S$: | GGGGS (SEQ ID NO: 25) |

The constructs were expressed in Expi293F™ cells by transient transfection (Thermo Fisher Scientific). Proteins in Expi293F supernatant were purified using the ProteinMaker system (Protein BioSolutions, Gaithersburg, MD) with either HiTrap™ Protein G HP or MabSelect SuRe pcc columns (Cytiva). After single step elution, the antibodies were neutralized, dialyzed into a final buffer of phosphate buffered saline (PBS) with 5% glycerol, aliquoted and stored at −80° C.

Figure 6:
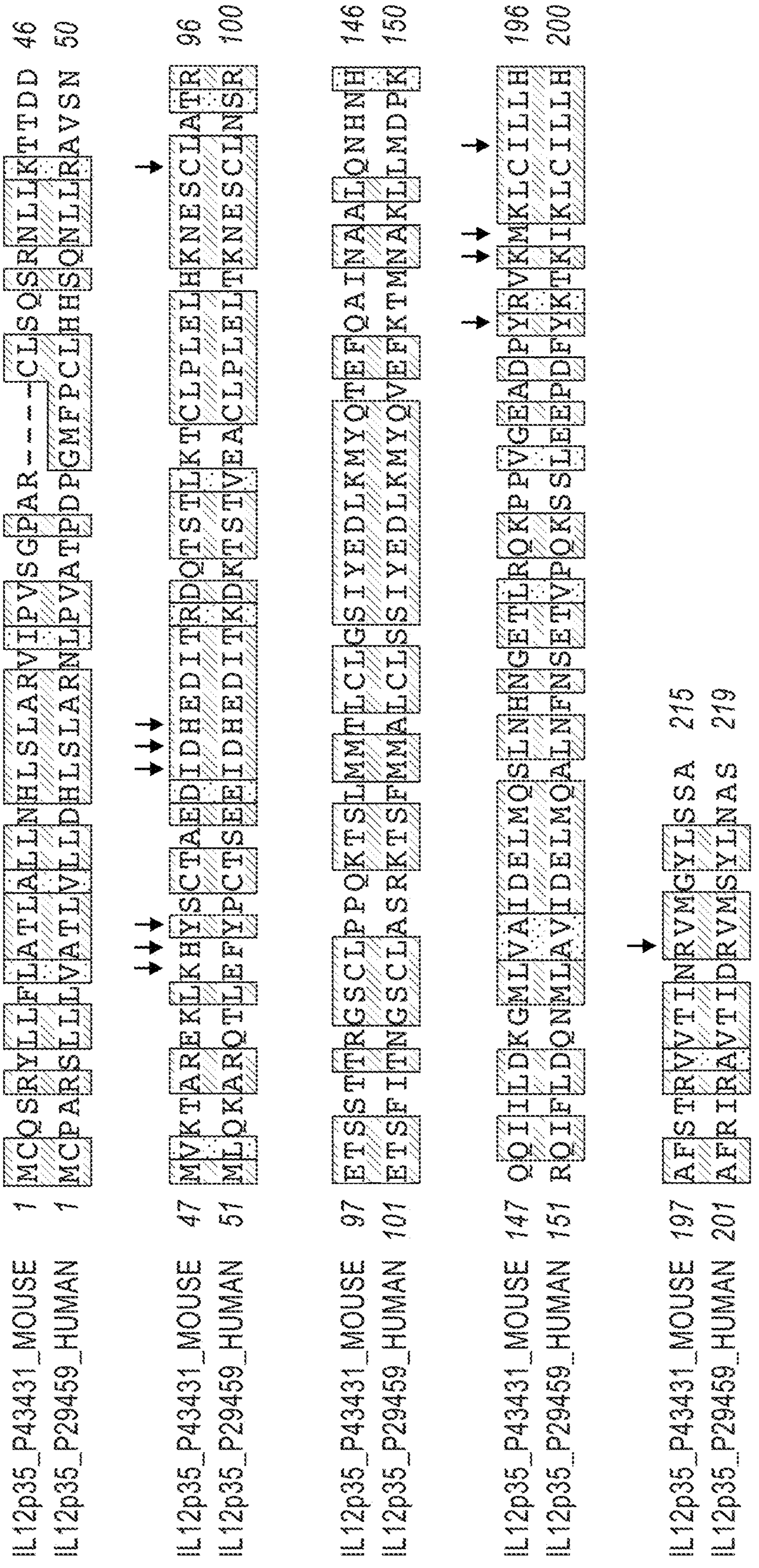
FIG. 6 depicts an alignment of mouse and human IL12 p35, with arrows depicting examples of representative mutein positions.
Figure 7:
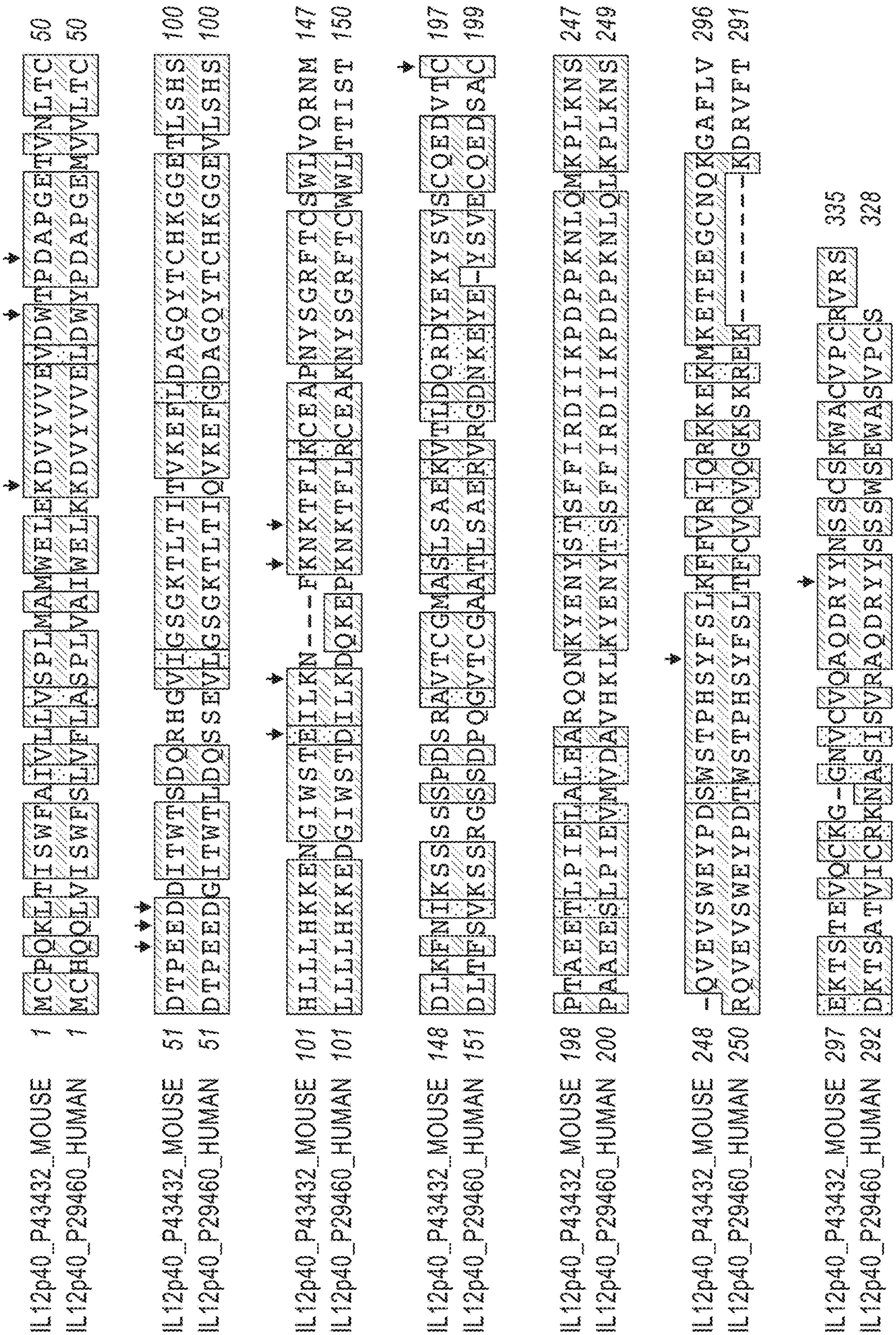
FIG. 7 depicts an alignment of mouse and human IL12 p40, with arrows depicting examples of representative mutein positions.

Alignments and selected mutein positions in IL12 p35 and p40 are depicted in FIGS. 6 and 7, respectively. Alignments were generated using MacVector. A sequence alignment of IL12 p35 with other representative IL6 family cytokines is provided in FIG. 8. FIG. 9 depicts the 3-dimensional structure of IL12, including potential residues involved in p35 interaction with IL12Rβ2, residues at the p35/p40 heterodimer interface, and surface-exposed hydrophobic or charged residues located on D1 or the D1-D2 junction of p40.

TABLE 7

IL12 Constructs

| Molecule | Description | Sequence |
|---|---|---|
| hIgG4s | Human IgG4 Fc isotype control. Fc is IgG4s (control antibody with hIgG4s sequence) | Heavy Chain VR+ hIgG4s QVQLVESGGGLVKPGGSLRLSCAASGFTFSNYYMSWVRQAPGKGLEWISYISGRGSTIFYADSVKGRITISRDNAKNSLFLQMNSLRAEDTAVYFCVKDRGGYSPYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPPVAGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 64) Light Chain VR+ human Kappa DIQMTQSPSSLSASVGDRVTITCRASQSISTYLNWYQQKPGKAPKLLIYTASSLQSGVPSRFSGSGSGTDFTLTISSLQPEDFATYYCQQSYSTPPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 65) |
| IL12 p40 (D1, D2, D3) | Recombinant human IL12 p40 (mature protein) | IWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRK |

TABLE 7-continued

| IL12 Constructs | | |
|---|---|---|
| Molecule | Description | Sequence |
| | | NASISVRAQDRYYSSSWSEWASVPCS (SEQ ID NO: 56) |
| IL12 p40 (D2, D3) | Recombinant human IL12 p40 (D2 and D3 domains) | DGIWSTDILKDQKEPKNKTFLRCEAKNYSGRFTCW WLTTISTDLTFSVKSSRGSSDPQGVTCGAATLSAE RVRGDNKEYEYSVECQEDSACPAAEESLPIEVMVD AVHKLKYENYTSSFFIRDIIKPDPPKNLQLKPLKN SRQVEVSWEYPDTWSTPHSYFSLTFCVQVQGKSKR EKKDRVFTDKTSATVICRKNASISVRAQDRYYSSS WSEWASVPCS (SEQ ID NO: 66) |
| IL12 p35 | Recombinant human IL12 p35 (mature protein) | RNLPVATPDPGMFPCLHHSQNLLRAVSNMLQKARQ TLEFYPCTSEEIDHEDITKDKTSTVEACLPLELTK NESCLNSRETSFITNGSCLASRKTSFMMALCLSSI YEDLKMYQVEFKTMNAKLLMDPKRQIFLDQNMLAV IDELMQALNFNSETVPQKSSLEEPDFYKTKIKLCI LLHAFRIRAVTIDRVMSYLNAS (SEQ ID NO: 58) |
| mIL12(p35)-Fc | Heterodimerize with IL12(p40)-Fc to form monovalent murine IL12(p35xp40)-Fc Fc is human IgG4s(Knob) | RVIPVSGPARCLSQSRNLLKTTDDMVKTAREKLKH YSCTAEDIDHEDITRDQTSTLKTCLPLELHKNESC LATRETSSTTRGSCLPPQKTSLMMTLCLGSIYEDL KMYQTEFQAINAALQNHNHQQIILDKGMLVAIDEL MQSLNHNGETLRQKPPVGEADPYRVKMKLCILLHA FSTRVVTINRVMGYLSSAGGGGSGGGGSGGGGSES KYGPPCPPCPAPPVAGPSVFLFPPKPKDTLMISRT PEVTCVVVDVSQEDPEVQFNWYVDGVEVHNAKTKP REEQFNSTYRVVSVLTVLHQDWLNGKEYKCKVSNK GLPSSIEKTISKAKGQPREPQVYTLPPSQEEMTKN QVSLWCLVKGFYPSDIAVEWESNGQPENNYKTTPP VLDSDGSFFLYSRLTVDKSRWQEGNVFSCSVMHEA LHNHYTQKSLSLSLGK (SEQ ID NO: 67) |
| mIL12(p40)-Fc | Heterodimerize with IL12(p35)-Fc to form monovalent murine IL12(p35xp40)-Fc Fc is human IgG4s(HoleStar) | MWELEKDVYVVEVDWTPDAPGETVNLTCDTPEEDD ITWTSDQRHGVIGSGKTLTITVKEFLDAGQYTCHK GGETLSHSHLLLHKKENGIWSTEILKNFKNKTFLK CEAPNYSGRFTCSWLVQRNMDLKFNIKSSSSSPDS RAVTCGMASLSAEKVTLDQRDYEKYSVSCQEDVTC PTAEETLPIELALEARQQNKYENYSTSFFIRDIIK PDPPKNLQMKPLKNSQVEVSWEYPDSWSTPHSYFS LKFFVRIQRKKEKMKETEEGCNQKGAFLVEKTSTE VQCKGGNVCVQAQDRYYNSSCSKWACVPCRVRSGG GGSGGGGSGGGGSESKYGPPCPPCPAPPVAGPSVF LFPPKPKDTLMISRTPEVTCVVVDVSQEDPEVQFN WYVDGVEVHNAKTKPREEQFNSTYRVVSVLTVLHQ DWLNGKEYKCKVSNKGLPSSIEKTISKAKGQPREP QVYTLPPSQEEMTKNQVSLSCAVKGFYPSDIAVEW ESNGQPENNYKTTPPVLDSDGSFFLVSRLTVDKSR WQEGNVFSCSVMHEALHNRFTQKSLSLSPGK (SEQ ID NO: 68) |
| mIL12(p35*)-Fc | Heterodimerize with IL12(p40*)-Fc to form monovalent murine IL12*(p35*xp40*)-Fc Fc is human IgG4s(Knob) IL12* mutein lacking disulfide bond between p40 and p35 | RVIPVSGPARCLSQSRNLLKTTDDMVKTAREKLKH YSCTAEDIDHEDITRDQTSTLKTCLPLELHKNESS LATRETSSTTRGSCLPPQKTSLMMTLCLGSIYEDL KMYQTEFQAINAALQNHNHQQIILDKGMLVAIDEL MQSLNHNGETLRQKPPVGEADPYRVKMKLCILLHA FSTRVVTINRVMGYLSSAGGGGSGGGGSGGGGSES KYGPPCPPCPAPPVAGPSVFLFPPKPKDTLMISRT PEVTCVVVDVSQEDPEVQFNWYVDGVEVHNAKTKP REEQFNSTYRVVSVLTVLHQDWLNGKEYKCKVSNK GLPSSIEKTISKAKGQPREPQVYTLPPSQEEMTKN QVSLWCLVKGFYPSDIAVEWESNGQPENNYKTTPP VLDSDGSFFLYSRLTVDKSRWQEGNVFSCSVMHEA LHNHYTQKSLSLSLGK (SEQ ID NO: 69) |
| mIL12(p40*)-Fc | Heterodimerize with IL12(p35*)-Fc to form monovalent murine IL12*(p35*xp40*)-Fc Fc is human | MWELEKDVYVVEVDWTPDAPGETVNLTCDTPEEDD ITWTSDQRHGVIGSGKTLTITVKEFLDAGQYTCHK GGETLSHSHLLLHKKENGIWSTEILKNFKNKTFLK CEAPNYSGRFTCSWLVQRNMDLKFNIKSSSSSPDS RAVTCGMASLSAEKVTLDQRDYEKYSVSCQEDVTS PTAEETLPIELALEARQQNKYENYSTSFFIRDIIK PDPPKNLQMKPLKNSQVEVSWEYPDSWSTPHSYFS LKFFVRIQRKKEKMKETEEGCNQKGAFLVEKTSTE |

TABLE 7-continued

| IL12 Constructs | | |
|---|---|---|
| Molecule | Description | Sequence |
| | IgG4s(HoleStar) IL12* mutein lacking disulfide bond between p40 and p35 | VQCKGGNVCVQAQDRYYNSSCSKWACVPCRVRSGG GGSGGGGSGGGGSESKYGPPCPPCPAPPVAGPSVF LFPPKPKDTLMISRTPEVTCVVVDVSQEDPEVQFN WYVDGVEVHNAKTKPREEQFNSTYRVVSVLTVLHQ DWLNGKEYKCKVSNKGLPSSIEKTISKAKGQPREP QVYTLPPSQEEMTKNQVSLSCAVKGFYPSDIAVEW ESNGQPENNYKTTPPVLDSDGSFFLVSRLTVDKSR WQEGNVFSCSVMHEALHNRFTQKSLSLSPGK (SEQ ID NO: 70) |
| Fc-mIL12(p35) | Heterodimerize with Fc-mIL12(p40) to form monovalent Fc-mIL12(p35xp40) Fc is human IgG4s(Knob) | ESKYGPPCPPCPAPPVAGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMT KNQVSLWCLVKGFYPSDIAVEWESNGQPENNYKTT PPVLDSDGSFFLYSRLTVDKSRWQEGNVFSCSVMH EALHNHYTQKSLSLSLGKGGGGSGGGGSGGGGSRV IPVSGPARCLSQSRNLLKTTDDMVKTAREKLKHYS CTAEDIDHEDITRDQTSTLKTCLPLELHKNESCLA TRETSSTTRGSCLPPQKTSLMMTLCLGSIYEDLKM YQTEFQAINAALQNHNHQQIILDKGMLVAIDELMQ SLNHNGETLRQKPPVGEADPYRVKMKLCILLHAFS TRVVTINRVMGYLSSA (SEQ ID NO: 71) |
| Fc-mIL12(p40) | Fc-monovalent murine IL12(p40) Heterodimerize with Fc-mIL12(p35) to form monovalent Fc-mIL12(p35xp40) Fc is human IgG4s(HoleStar) | ESKYGPPCPPCPAPPVAGPSVFLFPPKPKDTLMIS RTPEVTCVVVDVSQEDPEVQFNWYVDGVEVHNAKT KPREEQFNSTYRVVSVLTVLHQDWLNGKEYKCKVS NKGLPSSIEKTISKAKGQPREPQVYTLPPSQEEMT KNQVSLSCAVKGFYPSDIAVEWESNGQPENNYKTT PPVLDSDGSFFLVSRLTVDKSRWQEGNVFSCSVMH EALHNRFTQKSLSLSPGKGGGGSGGGGSGGGGSMW ELEKDVYVVEVDWTPDAPGETVNLTCDTPEEDDIT WTSDQRHGVIGSGKTLTITVKEFLDAGQYTCHKGG ETLSHSHLLLHKKENGIWSTEILKNFKNKTFLKCE APNYSGRFTCSWLVQRNMDLKFNIKSSSSSPDSRA VTCGMASLSAEKVTLDQRDYEKYSVSCQEDVTCPT AEETLPIELALEARQQNKYENYSTSFFIRDIIKPD PPKNLQMKPLKNSQVEVSWEYPDSWSTPHSYFSLK FFVRIQRKKEKMKETEEGCNQKGAFLVEKTSTEVQ CKGGNVCVQAQDRYYNSSCSKWACVPCRVRS (SEQ ID NO: 72) |
| mIL12(p40-p35)-Fc | Bivalent murine IL12(p40-p35)-Fc Fc is human IgG4s | MWELEKDVYVVEVDWTPDAPGETVNLTCDTPEEDD ITWTSDQRHGVIGSGKTLTITVKEFLDAGQYTCHK GGETLSHSHLLLHKKENGIWSTEILKNFKNKTFLK CEAPNYSGRFTCSWLVQRNMDLKFNIKSSSSSPDS RAVTCGMASLSAEKVTLDQRDYEKYSVSCQEDVTC PTAEETLPIELALEARQQNKYENYSTSFFIRDIIK PDPPKNLQMKPLKNSQVEVSWEYPDSWSTPHSYFS LKFFVRIQRKKEKMKETEEGCNQKGAFLVEKTSTE VQCKGGNVCVQAQDRYYNSSCSKWACVPCRVRSGG GGSGGGGSGGGGSRVIPVSGPARCLSQSRNLLKTT DDMVKTAREKLKHYSCTAEDIDHEDITRDQTSTLK TCLPLELHKNESCLATRETSSTTRGSCLPPQKTSL MMTLCLGSIYEDLKMYQTEFQAINAALQNHNHQQI ILDKGMLVAIDELMQSLNHNGETLRQKPPVGEADP YRVKMKLCILLHAFSTRVVTINRVMGYLSSAGGGG SGGGGSGGGGSESKYGPPCPPCPAPPVAGPSVFLF PPKPKDTLMISRTPEVTCVVVDVSQEDPEVQFNWY VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNHYTQKSLSLSLGK (SEQ ID NO: 73) |
| mIL12*(p40*-p35*)-Fc | Bivalent murine IL12*(p40* p35*)-Fc Fc is human IgG4s *IL12 mutein lacking disulfide bond between | MWELEKDVYVVEVDWTPDAPGETVNLTCDTPEEDD ITWTSDQRHGVIGSGKTLTITVKEFLDAGQYTCHK GGETLSHSHLLLHKKENGIWSTEILKNFKNKTFLK CEAPNYSGRFTCSWLVQRNMDLKFNIKSSSSSPDS RAVTCGMASLSAEKVTLDQRDYEKYSVSCQEDVTS PTAEETLPIELALEARQQNKYENYSTSFFIRDIIK PDPPKNLQMKPLKNSQVEVSWEYPDSWSTPHSYFS LKFFVRIQRKKEKMKETEEGCNQKGAFLVEKTSTE VQCKGGNVCVQAQDRYYNSSCSKWACVPCRVRSGG |

TABLE 7-continued

IL12 Constructs

| Molecule | Description | Sequence |
|---|---|---|
| | p40 and p35 | GGSGGGGSGGGGSRVIPVSGPARCLSQSRNLLKTT<br>DDMVKTAREKLKHYSCTAEDIDHEDITRDQTSTLK<br>TCLPLELHKNESSLATRETSSTTRGSCLPPQKTSL<br>MMTLCLGSIYEDLKMYQTEFQAINAALQNHNHQQI<br>ILDKGMLVAIDELMQSLNHNGETLRQKPPVGEADP<br>YRVKMKLCILLHAFSTRVVTINRVMGYLSSAGGGG<br>SGGGGSGGGGSESKYGPPCPPCPAPPVAGPSVFLF<br>PPKPKDTLMISRTPEVTCVVVDVSQEDPEVQFNWY<br>VDGVEVHNAKTKPREEQFNSTYRVVSVLTVLHQDW<br>LNGKEYKCKVSNKGLPSSIEKTISKAKGQPREPQV<br>YTLPPSQEEMTKNQVSLTCLVKGFYPSDIAVEWES<br>NGQPENNYKTTPPVLDSDGSFFLYSRLTVDKSRWQ<br>EGNVFSCSVMHEALHNHYTQKSLSLSLGK<br>(SEQ ID NO: 74) |
| mIL12(p35-p40)-Fc | Bivalent murine IL12(p35-p40)-Fc<br>Fc is human IgG4s | RVIPVSGPARCLSQSRNLLKTTDDMVKTAREKLKH<br>YSCTAEDIDHEDITRDQTSTLKTCLPLELHKNESC<br>LATRETSSTTRGSCLPPQKTSLMMTLCLGSIYEDL<br>KMYQTEFQAINAALQNHNHQQIILDKGMLVAIDEL<br>MQSLNHNGETLRQKPPVGEADPYRVKMKLCILLHA<br>FSTRVVTINRVMGYLSSAGGGGSGGGGSGGGGSGG<br>GGSGGGGSMWELEKDVYVVEVDWTPDAPGETVNLT<br>CDTPEEDDITWTSDQRHGVIGSGKTLTITVKEFLD<br>AGQYTCHKGGETLSHSHLLLHKKENGIWSTEILKN<br>FKNKTFLKCEAPNYSGRFTCSWLVQRNMDLKFNIK<br>SSSSSPDSRAVTCGMASLSAEKVTLDQRDYEKYSV<br>SCQEDVTCPTAEETLPIELALEARQQNKYENYSTS<br>FFIRDIIKPDPPKNLQMKPLKNSQVEVSWEYPDSW<br>STPHSYFSLKFFVRIQRKKEKMKETEEGCNQKGAF<br>LVEKTSTEVQCKGGNVCVQAQDRYYNSSCSKWACV<br>PCRVRSGGGGSGGGGSGGGGSESKYGPPCPPCPAP<br>PVAGPSVFLFPPKPKDTLMISRTPEVTCVVVDVSQ<br>EDPEVQFNWYVDGVEVHNAKTKPREEQFNSTYRVV<br>SVLTVLHQDWLNGKEYKCKVSNKGLPSSIEKTISK<br>AKGQPREPQVYTLPPSQEEMTKNQVSLTCLVKGFY<br>PSDIAVEWESNGQPENNYKTTPPVLDSDGSFFLYS<br>RLTVDKSRWQEGNVFSCSVMHEALHNHYTQKSLSL<br>SLGK (SEQ ID NO: 75) |
| mIL12*(p35*-p40*)-Fc | Bivalent murine IL12*(p35*-p40*)-Fc<br>Fc is human IgG4s<br>*IL12 mutein lacking disulfide bond between p40 and p35 | RVIPVSGPARCLSQSRNLLKTTDDMVKTAREKLKH<br>YSCTAEDIDHEDITRDQTSTLKTCLPLELHKNESS<br>LATRETSSTTRGSCLPPQKTSLMMTLCLGSIYEDL<br>KMYQTEFQAINAALQNHNHQQIILDKGMLVAIDEL<br>MQSLNHNGETLRQKPPVGEADPYRVKMKLCILLHA<br>FSTRVVTINRVMGYLSSAGGGGSGGGGSGGGGSGG<br>GGSGGGGSMWELEKDVYVVEVDWTPDAPGETVNLT<br>CDTPEEDDITWTSDQRHGVIGSGKTLTITVKEFLD<br>AGQYTCHKGGETLSHSHLLLHKKENGIWSTEILKN<br>FKNKTFLKCEAPNYSGRFTCSWLVQRNMDLKFNIK<br>SSSSSPDSRAVTCGMASLSAEKVTLDQRDYEKYSV<br>SCQEDVTSPTAEETLPIELALEARQQNKYENYSTS<br>FFIRDIIKPDPPKNLQMKPLKNSQVEVSWEYPDSW<br>STPHSYFSLKFFVRIQRKKEKMKETEEGCNQKGAF<br>LVEKTSTEVQCKGGNVCVQAQDRYYNSSCSKWACV<br>PCRVRSGGGGSGGGGSGGGGSESKYGPPCPPCPAP<br>PVAGPSVFLFPPKPKDTLMISRTPEVTCVVVDVSQ<br>EDPEVQFNWYVDGVEVHNAKTKPREEQFNSTYRVV<br>SVLTVLHQDWLNGKEYKCKVSNKGLPSSIEKTISK<br>AKGQPREPQVYTLPPSQEEMTKNQVSLTCLVKGFY<br>PSDIAVEWESNGQPENNYKTTPPVLDSDGSFFLYS<br>RLTVDKSRWQEGNVFSCSVMHEALHNHYTQKSLSL<br>SLGK (SEQ ID NO: 76) |
| Fc-mIL12(p40-p35) | Fc-bivalent murine IL12(p40-p35)<br>Fc is human IgG4s | ESKYGPPCPPCPAPPVAGPSVFLFPPKPKDTLMIS<br>RTPEVTCVVVDVSQEDPEVQFNWYVDGVEVHNAKT<br>KPREEQFNSTYRVVSVLTVLHQDWLNGKEYKCKVS<br>NKGLPSSIEKTISKAKGQPREPQVYTLPPSQEEMT<br>KNQVSLTCLVKGFYPSDIAVEWESNGQPENNYKTT<br>PPVLDSDGSFFLYSRLTVDKSRWQEGNVFSCSVMH<br>EALHNHYTQKSLSLSLGKGGGGSGGGGSGGGGSMW<br>ELEKDVYVVEVDWTPDAPGETVNLTCDTPEEDDIT<br>WTSDQRHGVIGSGKTLTITVKEFLDAGQYTCHKGG<br>ETLSHSHLLLHKKENGIWSTEILKNFKNKTFLKCE<br>APNYSGRFTCSWLVQRNMDLKFNIKSSSSSPDSRA<br>VTCGMASLSAEKVTLDQRDYEKYSVSCQEDVTCPT<br>AEETLPIELALEARQQNKYENYSTSFFIRDIIKPD |

TABLE 7-continued

IL12 Constructs

| Molecule | Description | Sequence |
|---|---|---|
| | | PPKNLQMKPLKNSQVEVSWEYPDSWSTPHSYFSLK<br>FFVRIQRKKEKMKETEEGCNQKGAFLVEKTSTEVQ<br>CKGGNVCVQAQDRYYNSSCSKWACVPCRVRSGGGG<br>SGGGGSGGGGSRVIPVSGPARCLSQSRNLLKTTDD<br>MVKTAREKLKHYSCTAEDIDHEDITRDQTSTLKTC<br>LPLELHKNESCLATRETSSTTRGSCLPPQKTSLMM<br>TLCLGSIYEDLKMYQTEFQAINAALQNHNHQQIIL<br>DKGMLVAIDELMQSLNHNGETLRQKPPVGEADPYR<br>VKMKLCILLHAFSTRVVTINRVMGYLSSA<br>(SEQ ID NO: 77) |
| Fc-mIL12*<br>(p40*-p35*) | Fc-bivalent<br>murine<br>IL12*(p40*-<br>p35*)<br>Fc is human<br>IgG4s<br>*IL12 mutein<br>lacking<br>disulfide<br>bond between<br>p40 and p35 | ESKYGPPCPPCPAPPVAGPSVFLFPPKPKDTLMIS<br>RTPEVTCVVVDVSQEDPEVQFNWYVDGVEVHNAKT<br>KPREEQFNSTYRVVSVLTVLHQDWLNGKEYKCKVS<br>NKGLPSSIEKTISKAKGQPREPQVYTLPPSQEEMT<br>KNQVSLTCLVKGFYPSDIAVEWESNGQPENNYKTT<br>PPVLDSDGSFFLYSRLTVDKSRWQEGNVFSCSVMH<br>EALHNHYTQKSLSLSLGKGGGGSGGGGSGGGGSMW<br>ELEKDVYVVEVDWTPDAPGETVNLTCDTPEEDDIT<br>WTSDQRHGVIGSGKTLTITVKEFLDAGQYTCHKGG<br>ETLSHSHLLLHKKENGIWSTEILKNFKNKTFLKCE<br>APNYSGRFTCSWLVQRNMDLKFNIKSSSSSPDSRA<br>VTCGMASLSAEKVTLDQRDYEKYSVSCQEDVTSPT<br>AEETLPIELALEARQQNKYENYSTSFFIRDIIKPD<br>PPKNLQMKPLKNSQVEVSWEYPDSWSTPHSYFSLK<br>FFVRIQRKKEKMKETEEGCNQKGAFLVEKTSTEVQ<br>CKGGNVCVQAQDRYYNSSCSKWACVPCRVRSGGGG<br>SGGGGSGGGGSRVIPVSGPARCLSQSRNLLKTTDD<br>MVKTAREKLKHYSCTAEDIDHEDITRDQTSTLKTC<br>LPLELHKNESSLATRETSSTTRGSCLPPQKTSLMM<br>TLCLGSIYEDLKMYQTEFQAINAALQNHNHQQIIL<br>DKGMLVAIDELMQSLNHNGETLRQKPPVGEADP<br>YRVKMKLCILLHAFSTRVVTINRVMGYLSSA<br>(SEQ ID NO: 78) |
| Fc-mIL12(p35-p40) | Fc-bivalent<br>murine IL12(p35-<br>p40)<br>Fc is human<br>IgG4s | ESKYGPPCPPCPAPPVAGPSVFLFPPKPKDTLMIS<br>RTPEVTCVVVDVSQEDPEVQFNWYVDGVEVHNAKT<br>KPREEQFNSTYRVVSVLTVLHQDWLNGKEYKCKVS<br>NKGLPSSIEKTISKAKGQPREPQVYTLPPSQEEMT<br>KNQVSLTCLVKGFYPSDIAVEWESNGQPENNYKTT<br>PPVLDSDGSFFLYSRLTVDKSRWQEGNVFSCSVMH<br>EALHNHYTQKSLSLSLGKGGGGSGGGGSGGGGSRV<br>IPVSGPARCLSQSRNLLKTTDDMVKTAREKLKHYS<br>CTAEDIDHEDITRDQTSTLKTCLPLELHKNESCLA<br>TRETSSTTRGSCLPPQKTSLMMTLCLGSIYEDLKM<br>YQTEFQAINAALQNHNHQQIILDKGMLVAIDELMQ<br>SLNHNGETLRQKPPVGEADPYRVKMKLCILLHAFS<br>TRVVTINRVMGYLSSAGGGGSGGGGSGGGGSGGGG<br>SGGGGSMWELEKDVYVVEVDWTPDAPGETVNLTCD<br>TPEEDDITWTSDQRHGVIGSGKTLTITVKEFLDAG<br>QYTCHKGGETLSHSHLLLHKKENGIWSTEILKNFK<br>NKTFLKCEAPNYSGRFTCSWLVQRNMDLKFNIKSS<br>SSSPDSRAVTCGMASLSAEKVTLDQRDYEKYSVSC<br>QEDVTCPTAEETLPIELALEARQQNKYENYSTSFF<br>IRDIIKPDPPKNLQMKPLKNSQVEVSWEYPDSWST<br>PHSYFSLKFFVRIQRKKEKMKETEEGCNQKGAFLV<br>EKTSTEVQCKGGNVCVQAQDRYYNSSCSKWACVPC<br>RVRS (SEQ ID NO: 79) |
| Fc-mIL12*<br>(p35*-p40*) | Fc-bivalent<br>murine<br>IL12*(p35*-<br>p40*)<br>Fc is<br>human IgG4s<br>*IL12 mutein<br>lacking<br>disulfide<br>bond between<br>p40 and p35 | ESKYGPPCPPCPAPPVAGPSVFLFPPKPKDTLMIS<br>RTPEVTCVVVDVSQEDPEVQFNWYVDGVEVHNAKT<br>KPREEQFNSTYRVVSVLTVLHQDWLNGKEYKCKVS<br>NKGLPSSIEKTISKAKGQPREPQVYTLPPSQEEMT<br>KNQVSLTCLVKGFYPSDIAVEWESNGQPENNYKTT<br>PPVLDSDGSFFLYSRLTVDKSRWQEGNVFSCSVMH<br>EALHNHYTQKSLSLSLGKGGGGSGGGGSGGGGSRV<br>IPVSGPARCLSQSRNLLKTTDDMVKTAREKLKHYS<br>CTAEDIDHEDITRDQTSTLKTCLPLELHKNESSLA<br>TRETSSTTRGSCLPPQKTSLMMTLCLGSIYEDLKM<br>YQTEFQAINAALQNHNHQQIILDKGMLVAIDELMQ<br>SLNHNGETLRQKPPVGEADPYRVKMKLCILLHAFS<br>TRVVTINRVMGYLSSAGGGGSGGGGSGGGGSGGGG<br>SGGGGSMWELEKDVYVVEVDWTPDAPGETVNLTCD<br>TPEEDDITWTSDQRHGVIGSGKTLTITVKEFLDAG<br>QYTCHKGGETLSHSHLLLHKKENGIWSTEILKNFK<br>NKTFLKCEAPNYSGRFTCSWLVQRNMDLKFNIKSS |

TABLE 7-continued

| IL12 Constructs | | |
|---|---|---|
| Molecule | Description | Sequence |
| | | SSSPDSRAVTCGMASLSAEKVTLDQRDYEKYSVSC QEDVTSPTAEETLPIELALEARQQNKYENYSTSFF IRDIIKPDPPKNLQMKPLKNSQVEVSWEYPDSWST PHSYFSLKFFVRIQRKKEKMKETEEGCNQKGAFLV EKTSTEVQCKGGNVCVQAQDRYYNSSCSKWACVPC RVRS (SEQ ID NO: 80) |

TABLE 8A

| Attenuated IL12 mutein-Fc fusion proteins: p35 binding interface muteins | |
|---|---|
| Molecule | Sequence |
| Fc-IL12(mutein 1) IgG4sFc-3xG4S-mIL12p40-3xG4S-mIL12p35(Y185A) | ESKYGPPCPPCPAPPVAGPSVFLFP PKPKDTLMISRTPEVTCVVVDVSQE DPEVQFNWYVDGVEVHNAKTKPREE QFNSTYRVVSVLTVLHQDWLNGKEY KCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LGKGGGGSGGGGSGGGGSMWELEKD VYVVEVDWTPDAPGETVNLTCDTPE EDDITWTSDQRHGVIGSGKTLTITV KEFLDAGQYTCHKGGETLSHSHLLL HKKENGIWSTEILKNFKNKTFLKCE APNYSGRFTCSWLVQRNMDLKFNIK SSSSSPDSRAVTCGMASLSAEKVTL DQRDYEKYSVSCQEDVTCPTAEETL PIELALEARQQNKYENYSTSFFIRD IIKPDPPKNLQMKPLKNSQVEVSWE YPDSWSTPHSYFSLKFFVRIQRKKE KMKETEEGCNQKGAFLVEKTSTEVQ CKGGNVCVQAQDRYYNSSCSKWACV PCRVRSGGGGSGGGGSGGGGSRVIP VSGPARCLSQSRNLLKTTDDMVKTA REKLKHYSCTAEDIDHEDITRDQTS TLKTCLPLELHKNESCLATRETSST TRGSCLPPQKTSLMMTLCLGSIYED LKMYQTEFQAINAALQNHNHQQIIL DKGMLVAIDELMQSLNHNGETLRQK PPVGEADPARVKMKLCILLHAFSTR VVTINRVMGYLSSA (SEQ ID NO: 81) |
| Fc-IL12(mutein 2) IgG4sFc-3xG4S-mIL12p40-3xG4S-mIL12p35(Y185V) | ESKYGPPCPPCPAPPVAGPSVFLFP PKPKDTLMISRTPEVTCVVVDVSQE DPEVQFNWYVDGVEVHNAKTKPREE QFNSTYRVVSVLTVLHQDWLNGKEY KCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LGKGGGGSGGGGSGGGGSMWELEKD VYVVEVDWTPDAPGETVNLTCDTPE EDDITWTSDQRHGVIGSGKTLTITV KEFLDAGQYTCHKGGETLSHSHLLL HKKENGIWSTEILKNFKNKTFLKCE APNYSGRFTCSWLVQRNMDLKFNIK SSSSSPDSRAVTCGMASLSAEKVTL DQRDYEKYSVSCQEDVTCPTAEETL PIELALEARQQNKYENYSTSFFIRD IIKPDPPKNLQMKPLKNSQVEVSWE YPDSWSTPHSYFSLKFFVRIQRKKE KMKETEEGCNQKGAFLVEKTSTEVQ CKGGNVCVQAQDRYYNSSCSKWACV PCRVRSGGGGSGGGGSGGGGSRVIP VSGPARCLSQSRNLLKTTDDMVKTA REKLKHYSCTAEDIDHEDITRDQTS TLKTCLPLELHKNESCLATRETSST |

TABLE 8A-continued

| Attenuated IL12 mutein-Fc fusion proteins: p35 binding interface muteins | |
|---|---|
| Molecule | Sequence |
| | TRGSCLPPQKTSLMMTLCLGSIYED LKMYQTEFQAINAALQNHNHQQIIL DKGMLVAIDELMQSLNHNGETLRQK PPVGEADPVRVKMKLCILLHAFSTR VVTINRVMGYLSSA (SEQ ID NO: 82) |
| Fc-IL12(mutein 3) IgG4sFc-3xG4S-mIL12p40-3xG4S-mIL12p35(Y185R) | ESKYGPPCPPCPAPPVAGPSVFLFP PKPKDTLMISRTPEVTCVVVDVSQE DPEVQFNWYVDGVEVHNAKTKPREE QFNSTYRVVSVLTVLHQDWLNGKEY KCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LGKGGGGSGGGGSGGGGSMWELEKD VYVVEVDWTPDAPGETVNLTCDTPE EDDITWTSDQRHGVIGSGKTLTITV KEFLDAGQYTCHKGGETLSHSHLLL HKKENGIWSTEILKNFKNKTFLKCE APNYSGRFTCSWLVQRNMDLKFNIK SSSSSPDSRAVTCGMASLSAEKVTL DQRDYEKYSVSCQEDVTCPTAEETL PIELALEARQQNKYENYSTSFFIRD IIKPDPPKNLQMKPLKNSQVEVSWE YPDSWSTPHSYFSLKFFVRIQRKKE KMKETEEGCNQKGAFLVEKTSTEVQ CKGGNVCVQAQDRYYNSSCSKWACV PCRVRSGGGGSGGGGSGGGGSRVIP VSGPARCLSQSRNLLKTTDDMVKTA REKLKHYSCTAEDIDHEDITRDQTS TLKTCLPLELHKNESCLATRETSST TRGSCLPPQKTSLMMTLCLGSIYED LKMYQTEFQAINAALQNHNHQQIIL DKGMLVAIDELMQSLNHNGETLRQK PPVGEADPRRVKMKLCILLHAFSTR VVTINRVMGYLSSA (SEQ ID NO: 83) |
| Fc-IL12(mutein 4) IgG4sFc-3xG4S-mIL12p40-3xG4S-mIL12p35(Y185E) | ESKYGPPCPPCPAPPVAGPSVFLFP PKPKDTLMISRTPEVTCVVVDVSQE DPEVQFNWYVDGVEVHNAKTKPREE QFNSTYRVVSVLTVLHQDWLNGKEY KCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LGKGGGGSGGGGSGGGGSMWELEKD VYVVEVDWTPDAPGETVNLTCDTPE EDDITWTSDQRHGVIGSGKTLTITV KEFLDAGQYTCHKGGETLSHSHLLL HKKENGIWSTEILKNFKNKTFLKCE APNYSGRFTCSWLVQRNMDLKFNIK SSSSSPDSRAVTCGMASLSAEKVTL DQRDYEKYSVSCQEDVTCPTAEETL PIELALEARQQNKYENYSTSFFIRD IIKPDPPKNLQMKPLKNSQVEVSWE |

TABLE 8A-continued

| Attenuated IL12 mutein-Fc fusion proteins: p35 binding interface muteins | |
|---|---|
| Molecule | Sequence |
| | YPDSWSTPHSYFSLKFFVRIQRKKE<br>KMKETEEGCNQKGAFLVEKTSTEVQ<br>CKGGNVCVQAQDRYYNSSCSKWACV<br>PCRVRSGGGGSGGGGSGGGGSRVIP<br>VSGPARCLSQSRNLLKTTDDMVKTA<br>REKLKHYSCTAEDIDHEDITRDQTS<br>TLKTCLPLELHKNESCLATRETSST<br>TRGSCLPPQKTSLMMTLCLGSIYED<br>LKMYQTEFQAINAALQNHNHQQIIL<br>DKGMLVAIDELMQSLNHNGETLRQK<br>PPVGEADPERVKMKLCILLHAFSTR<br>VVTINRVMGYLSSA<br>(SEQ ID NO: 84) |
| Fc-IL12(mutein 5)<br>IgG4sFc-3xG4S-<br>mIL12p40-3xG4S-<br>mIL12p35(M189A) | ESKYGPPCPPCPAPPVAGPSVFLFP<br>PKPKDTLMISRTPEVTCVVVDVSQE<br>DPEVQFNWYVDGVEVHNAKTKPREE<br>QFNSTYRVVSVLTVLHQDWLNGKEY<br>KCKVSNKGLPSSIEKTISKAKGQPR<br>EPQVYTLPPSQEEMTKNQVSLTCLV<br>KGFYPSDIAVEWESNGQPENNYKTT<br>PPVLDSDGSFFLYSRLTVDKSRWQE<br>GNVFSCSVMHEALHNHYTQKSLSLS<br>LGKGGGGSGGGGSGGGGSMWELEKD<br>VYVVEVDWTPDAPGETVNLTCDTPE<br>EDDITWTSDQRHGVIGSGKTLTITV<br>KEFLDAGQYTCHKGGETLSHSHLLL<br>HKKENGIWSTEILKNFKNKTFLKCE<br>APNYSGRFTCSWLVQRNMDLKFNIK<br>SSSSSPDSRAVTCGMASLSAEKVTL<br>DQRDYEKYSVSCQEDVTCPTAEETL<br>PIELALEARQQNKYENYSTSFFIRD<br>IIKPDPPKNLQMKPLKNSQVEVSWE<br>YPDSWSTPHSYFSLKFFVRIQRKKE<br>KMKETEEGCNQKGAFLVEKTSTEVQ<br>CKGGNVCVQAQDRYYNSSCSKWACV<br>PCRVRSGGGGSGGGGSGGGGSRVIP<br>VSGPARCLSQSRNLLKTTDDMVKTA<br>REKLKHYSCTAEDIDHEDITRDQTS<br>TLKTCLPLELHKNESCLATRETSST<br>TRGSCLPPQKTSLMMTLCLGSIYED<br>LKMYQTEFQAINAALQNHNHQQIIL<br>DKGMLVAIDELMQSLNHNGETLRQK<br>PPVGEADPYRVKAKLCILLHAFSTR<br>VVTINRVMGYLSSA<br>(SEQ ID NO: 85) |
| Fc-IL12(mutein 6)<br>IgG4sFc-3xG4S-<br>mIL12p40-3xG4S-<br>mIL12p35(M189E) | ESKYGPPCPPCPAPPVAGPSVFLFP<br>PKPKDTLMISRTPEVTCVVVDVSQE<br>DPEVQFNWYVDGVEVHNAKTKPREE<br>QFNSTYRVVSVLTVLHQDWLNGKEY<br>KCKVSNKGLPSSIEKTISKAKGQPR<br>EPQVYTLPPSQEEMTKNQVSLTCLV<br>KGFYPSDIAVEWESNGQPENNYKTT<br>PPVLDSDGSFFLYSRLTVDKSRWQE<br>GNVFSCSVMHEALHNHYTQKSLSLS<br>LGKGGGGSGGGGSGGGGSMWELEKD<br>VYVVEVDWTPDAPGETVNLTCDTPE<br>EDDITWTSDQRHGVIGSGKTLTITV<br>KEFLDAGQYTCHKGGETLSHSHLLL<br>HKKENGIWSTEILKNFKNKTFLKCE<br>APNYSGRFTCSWLVQRNMDLKFNIK<br>SSSSSPDSRAVTCGMASLSAEKVTL<br>DQRDYEKYSVSCQEDVTCPTAEETL<br>PIELALEARQQNKYENYSTSFFIRD<br>IIKPDPPKNLQMKPLKNSQVEVSWE<br>YPDSWSTPHSYFSLKFFVRIQRKKE<br>KMKETEEGCNQKGAFLVEKTSTEVQ<br>CKGGNVCVQAQDRYYNSSCSKWACV<br>PCRVRSGGGGSGGGGSGGGGSRVIP<br>VSGPARCLSQSRNLLKTTDDMVKTA<br>REKLKHYSCTAEDIDHEDITRDQTS<br>TLKTCLPLELHKNESCLATRETSST<br>TRGSCLPPQKTSLMMTLCLGSIYED<br>LKMYQTEFQAINAALQNHNHQQIIL<br>DKGMLVAIDELMQSLNHNGETLRQK<br>PPVGEADPYRVKEKLCILLHAFSTR<br>VVTINRVMGYLSSA<br>(SEQ ID NO: 86) |

TABLE 8B

| Attenuated IL12 mutein-Fc fusion proteins: Potential p40 binding interface muteins | |
|---|---|
| Molecule | Sequence |
| Fc-IL12(mutein 7)<br>IgG4sFc-3xG4S-<br>mIL12p40(K28A)-<br>3xG4S-mIL12p35 | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEADVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA (SEQ ID NO: 87) |
| Fc-IL12(mutein 8)<br>IgG4sFc-3xG4S-<br>mIL12p40(W37A)-<br>3xG4S-mIL12p35 | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDATPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS |

TABLE 8B-continued

Attenuated IL12 mutein-Fc fusion proteins: Potential p40 binding interface muteins

| Molecule | Sequence |
| --- | --- |
| | IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 88) |
| Fc-IL12(mutein 9) IgG4sFc-3xG4S-mIL12p40(D40A)-3xG4S-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPAAPGETVNLTCDTPEEDDITWTSDQRHGVIGSGKTLTITVKEFLD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 89) |
| Fc-IL12(mutein 10) IgG4sFc-3xG4S-mIL12p40(E54A, E55A, D56A)-3xG4S-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPAAADITWTSDQRHGVIGSGKTLTITVKEFLD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 90) |
| Fc-IL12(mutein 11) IgG4sFc-3xG4S-mIL12p40(E115A, K118A, K121A, K123A)-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKEFLD AGQYTCHKGGETLSHSHLLLHKKENGIWSTAILANFANATFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 91) |
| Fc-IL12(mutein 12) mIL12p40(D2-D3)-3xG4S-mIL12p35-3xG4S-IgG4sFc | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSN GIWSTEILKNFKNKTFLKCEAPNYSGRFTCSWLVQRNMDLKFNIKSSSSSPDSRAVTCGMA SLSAEKVTLDQRDYEKYSVSCQEDVTCPTAEETLPIELALEARQQNKYENYSTSFFIRDII KPDPPKNLQMKPLKNSQVEVSWEYPDSWSTPHSYFSLKFFVRIQRKKEKMKETEEGCNQKG AFLVEKTSTEVQCKGGNVCVQAQDRYYNSSCSKWACVPCRVRSGGGGSGGGGSGGGGSRVI PVSGPARCLSQSRNLLKTTDDMVKTAREKLKHYSCTAEDIDHEDITRDQTSTLKTCLPLEL HKNESCLATRETSSTTRGSCLPPQKTSLMMTLCLGSIYEDLKMYQTEFQAINAALQNHNHQ QIILDKGMLVAIDELMQSLNHNGETLRQKPPVGEADPYRVKMKLCILLHAFSTRVVTINRV MGYLSSA (SEQ ID NO: 92) |
| IL12(mutein 13)-Fc mIL12p40(D2-D3)-3xG4S-mIL12p35-3xG4S-IgG4sFc | NGIWSTEILKNFKNKTFLKCEAPNYSGRFTCSWLVQRNMDLKFNIKSSSSSPDSRAVTCGM ASLSAEKVTLDQRDYEKYSVSCQEDVTCPTAEETLPIELALEARQQNKYENYSTSFFIRDI IKPDPPKNLQMKPLKNSQVEVSWEYPDSWSTPHSYFSLKFFVRIQRKKEKMKETEEGCNQK GAFLVEKTSTEVQCKGGNVCVQAQDRYYNSSCSKWACVPCRVRSGGGGSGGGGSGGGGSRV IPVSGPARCLSQSRNLLKTTDDMVKTAREKLKHYSCTAEDIDHEDITRDQTSTLKTCLPLE LHKNESCLATRETSSTTRGSCLPPQKTSLMMTLCLGSIYEDLKMYQTEFQAINAALQNHNH QQIILDKGMLVAIDELMQSLNHNGETLRQKPPVGEADPYRVKMKLCILLHAFSTRVVTINR VMGYLSSAGGGGSGGGGSGGGGSESKYGPPCPPCPAPPVAGPSVFLFPPKPKDTLMISRTP EVTCVVVDVSQEDPEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHEALHNHYTQKS LSLSLGK (SEQ ID NO: 93) |
| Fc-IL12(mutein 14) IgG4sFc-3xG4S-mIL12p40(2xAla)-3xG4S-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKAALD |

TABLE 8B-continued

Attenuated IL12 mutein-Fc fusion proteins: Potential p40 binding interface muteins

| Molecule | Sequence |
|---|---|
| | AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 94) |
| Fc-IL12(mutein 15) IgG4sFc-3xG4S-mIL12p40(3xAla)-3xG4S-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKAALD AGQYTCHKGGETLSHSHLLLHAKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 95) |
| Fc-IL12(mutein 16) IgG4sFc-3xG4S-mIL12p40(W37A, F82A)-3xG4S-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDATPDAPGETVNLTCDTPEEDDITWTSDQRHGVIGSGKTLTITVKEALD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 96) |
| Fc-IL12(mutein 17) IgG4sFc-3xG4S-mIL12p40(E115A, K217A)-3xG4S-mIL12p35 | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKEFLD AGQYTCHKGGETLSHSHLLLHKKENGIWSTAILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNAYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 97) |

TABLE 8C

Attenuated IL12 mutein-Fc fusion proteins: p35/p40 heterodimeric Interface

| Molecule | Sequence |
|---|---|
| Fc-IL12(mutein 18) IgG4sFc-3xG4S-mIL12p40*-5xG4S-mIL12p35* p40*: C197S p35*: C92S | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKEFLD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTSPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSGGGGSGGGGSRVIPVSGPARCLSQSRNLLKTTDDMVKTA REKLKHYSCTAEDIDHEDITRDQTSTLKTCLPLELHKNESSLATRETSSTTRGSCLPPQKT SLMMTLCLGSIYEDLKMYQTEFQAINAALQNHNHQQIILDKGMLVAIDELMQSLNHNGETL RQKPPVGEADPYRVKMKLCILLHAFSTRVVTINRVMGYLSSA (SEQ ID NO: 98) |
| Fc-IL12(mutein 19) IgG4sFc-3xG4S- | ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG |

TABLE 8C-continued

| Attenuated IL12 mutein-Fc fusion proteins: p35/p40 heterodimeric Interface | |
|---|---|
| Molecule | Sequence |
| mIL12p40*-5xG4S-<br>mIL12p35*(R207A) | QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTSPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSGGGGSGGGGSRVIPVSGPARCLSQSRNLLKTTDDMVKTA<br>REKLKHYSCTAEDIDHEDITRDQTSTLKTCLPLELHKNESSLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINAVMGYLSSA (SEQ ID NO: 99) |
| Fc-IL12(mutein 20)<br>IgG4sFc-3xG4S-<br>mIL12p40*-5xG4S-<br>mIL12p35*(R207K) | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTSPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSGGGGSGGGGSRVIPVSGPARCLSQSRNLLKTTDDMVKTA<br>REKLKHYSCTAEDIDHEDITRDQTSTLKTCLPLELHKNESSLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINKVMGYLSSA (SEQ ID NO: 100) |
| Fc-IL12(mutein 21)<br>IgG4sFc-3xG4S-<br>mIL12p40*(Y265V)-<br>5xG4S-mIL12p35* | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTSPTAEETLPI<br>ELALEARQQNKYENYSTSFFIRDIIKPDPPKNLQMKPLKNSQVEVSWEYPDSWSTPHSVFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSGGGGSGGGGSRVIPVSGPARCLSQSRNLLKTTDDMVKTA<br>REKLKHYSCTAEDIDHEDITRDQTSTLKTCLPLELHKNESSLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINRVMGYLSSA (SEQ ID NO: 101) |
| Fc-IL12(mutein 22)<br>IgG4sFc-3xG4S-<br>mIL12p40*(Y265F)-<br>5xG4S-mIL12p35* | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTSPTAEETLPI<br>ELALEARQQNKYENYSTSFFIRDIIKPDPPKNLQMKPLKNSQVEVSWEYPDSWSTPHSFFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSGGGGSGGGGSRVIPVSGPARCLSQSRNLLKTTDDMVKTA<br>REKLKHYSCTAEDIDHEDITRDQTSTLKTCLPLELHKNESSLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINRVMGYLSSA (SEQ ID NO: 102) |
| Fc-IL12(mutein 23)<br>IgG4sFc-3xG4S-<br>mIL12p40*(Y318F)-<br>5xG4S-mIL12p35* | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTSPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRFYNSSCSKWAC<br>VPCRVRSGGGGSGGGGSGGGGSGGGGSGGGGSRVIPVSGPARCLSQSRNLLKTTDDMVKTA<br>REKLKHYSCTAEDIDHEDITRDQTSTLKTCLPLELHKNESSLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINRVMGYLSSA (SEQ ID NO: 103) |

TABLE 8D

Attenuated IL12 mutein-Fc fusion proteins: Receptor fusion constructs

| Molecule | Sequence |
| --- | --- |
| Fc-mIL12p40-<br>p35-mIL12Rb1(D1) | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSAGGGGSGGGGSGGGGSGGGGSGGGGSQLGA<br>SGPGDGCCVEKTSFPEGASGSPLGPRNLSCYRVSKTDYECSWQYDGPEDNVSHVLWCCFVP<br>PNHTHTGQERCRYFSSGPDRTVQFWEQDGIPVLSKVNFWVESRLGNRTMKSQKISQYLYNW<br>TKTTPPL (SEQ ID NO: 104) |
| Fc-mIL12p40-<br>p35-mIL12Rb2(D1) | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSAGGGGSGGGGSGGGGSGGGGSNIDVCKLGT<br>VTVQPAPVIPLGSAANISCSLNPKQGCSHYPSSNELILLKFVNDVLVENLHGKKVHDHTGH<br>SSTFQVTNLSLGMTLFVCKLNCSNSQKKPPVPVCGVEISVGV (SEQ ID NO: 105) |
| Fc-mIL12Rb2(D1)-<br>mIL12p40-p35 | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSN<br>IDVCKLGTVTVQPAPVIPLGSAANISCSLNPKQGCSHYPSSNELILLKFVNDVLVENLHGK<br>KVHDHTGHSSTFQVTNLSLGMTLFVCKLNCSNSQKKPPVPVCGVEISVGVGGGGSGGGGSG<br>GGGSGGGGSGGGGSMWELEKDVYVVEVDWTPDAPGETVNLTCDTPEEDDITWTSDQRHGVI<br>GSGKTLTITVKEFLDAGQYTCHKGGETLSHSHLLLHKKENGIWSTEILKNFKNKTFLKCEA<br>PNYSGRFTCSWLVQRNMDLKFNIKSSSSSPDSRAVTCGMASLSAEKVTLDQRDYEKYSVSC<br>QEDVTCPTAEETLPIELALEARQQNKYENYSTSFFIRDIIKPDPPKNLQMKPLKNSQVEVS<br>WEYPDSWSTPHSYFSLKFFVRIQRKKEKMKETEEGCNQKGAFLVEKTSTEVQCKGGNVCVQ<br>AQDRYYNSSCSKWACVPCRVRSGGGGSGGGGSGGGGSRVIPVSGPARCLSQSRNLLKTTDD<br>MVKTAREKLKHYSCTAEDIDHEDITRDQTSTLKTCLPLELHKNESCLATRETSSTTRGSCL<br>PPQKTSLMMTLCLGSIYEDLKMYQTEFQAINAALQNHNHQQIILDKGMLVAIDELMQSLNH<br>NGETLRQKPPVGEADPYRVKMKLCILLHAFSTRVVTINRVMGYLSSA (SEQ ID NO:<br>106) |
| Fc-p40-p35 x Fc<br>Chain 1: hIgG4s(HoleStar)<br>Chain 2: hIgG4s(Knob)-<br>p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA (SEQ ID NO: 107) |
| Fc x Fc-mIL12p40-<br>p35-mIL12Rb2(D1-2)<br>Chain 1: hIgG4s(HoleStar)<br>Chain 2: hIgG4s(Knob)-<br>mIL12p40-p35-<br>mIL12Rb2(D1-2) | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2: |

TABLE 8D-continued

Attenuated IL12 mutein-Fc fusion proteins: Receptor fusion constructs

| Molecule | Sequence |
|---|---|
| | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSAGGGGSGGGGSGGGGSGGGGSNIDVCKLGT<br>VTVQPAPVIPLGSAANISCSLNPKQGCSHYPSSNELILLKFVNDVLVENLHGKKVHDHTGH<br>SSTFQVTNLSLGMTLFVCKLNCSNSQKKPPVPVCGVEISVGVAPEPPQNISCVQEGENGTV<br>ACSWNSGKVTYLKTNYTLQLSGPNNLTCQKQCFSDNRQNCNRLDLGINLSPDLAESRFIVR<br>VTAINDLGNSSSLPHTFTFLDI (SEQ ID NO: 108) |
| Fc x Fc-mIL12p40-<br>p35-mIL12Rb1(D1-2)<br>Chain 1: hIgG4s(HoleStar)<br>Chain 2: hIgG4s(Knob)-<br>mIL12p40-p35-mIL12Rb1(D1-2) | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSAGGGGSGGGGSGGGGSGGGGSGGGGSQLGA<br>SGPGDGCCVEKTSFPEGASGSPLGPRNLSCYRVSKTDYECSWQYDGPEDNVSHVLWCCFVP<br>PNHTHTGQERCRYFSSGPDRTVQFWEQDGIPVLSKVNFWVESRLGNRTMKSQKISQYLYNW<br>TKTTPPLGHIKVSQSHRQLRMDWNVSEEAGAEVQFRRRMPTTNWTLGDCGPQVNSGSGVLG<br>DIRGSMSESCLCPSENMAQEIQIRRRRRLSSGAPGGPWSDWSMPVCVPPEVL (SEQ ID<br>NO: 109) |
| Fc x Fc-mIL12Rb1(D1)-<br>mIL12p40-p35<br>Chain 1: hIgG4s(HoleStar)<br>Chain 2: hIgG4s(Knob)<br>-mIL12Rb1(D1)-mIL12p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGGGGSGGGGSGGGGSMWELEKDVYVVEVDWTPDAPGETVNLTCDTPEEDDI<br>TWTSDQRHGVIGSGKTLTITVKEFLDAGQYTCHKGGETLSHSHLLLHKKENGIWSTEILKN<br>FKNKTFLKCEAPNYSGRFTCSWLVQRNMDLKFNIKSSSSPDSRAVTCGMASLSAEKVTLD<br>QRDYEKYSVSCQEDVTCPTAEETLPIELALEARQQNKYENYSTSFFIRDIIKPDPPKNLQM<br>KPLKNSQVEVSWEYPDSWSTPHSYFSLKFFVRIQRKKEKMKETEEGCNQKGAFLVEKTSTE<br>VQCKGGNVCVQAQDRYYNSSCSKWACVPCRVRSGGGGSGGGGSGGGGSRVIPVSGPARCLS<br>QSRNLLKTTDDMVKTAREKLKHYSCTAEDIDHEDITRDQTSTLKTCLPLELHKNESCLATR<br>ETSSTTRGSCLPPQKTSLMMTLCLGSIYEDLKMYQTEFQAINAALQNHNHQQIILDKGMLV<br>AIDELMQSLNHNGETLRQKPPVGEADPYRVKMKLCILLHAFSTRVVTINRVMGYLSSA<br>(SEQ ID NO: 110) |
| Fc-<mIL12Rb1(D1-2) x<br>mIL12p40-p35><br>Chain 1:<br>hIgG4s(HoleStar)-<br>mIL12Rb1(D1-2)<br>Chain 2:<br>hIgG4s(Knob)-mIL12p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGHIKVSQSHRQLRMDWNVSEEAGAEVQFRRRMPTTNWTLGDCGPQVNSGSG<br>VLGDIRGSMSESCLCPSENMAQEIQIRRRRRLSSGAPGGPWSDWSMPVCVPPEVL (SEQ<br>ID NO: 111) |

TABLE 8D-continued

| Attenuated IL12 mutein-Fc fusion proteins: Receptor fusion constructs | |
|---|---|
| Molecule | Sequence |
| | Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA (SEQ ID NO: 107) |
| Fc-<mIL12p35 x mIL12p40-mIL12Rb1(D1-2)><br>Chain 1: hIgG4s(HoleStar)-mIL12p40-mIL12Rb1(D1-2)<br>Chain 2: hIgG4s(Knob)-mIL12p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSGGGGSQLGASGPGDGCCVEKTSFPEGASGSPLGPRNLSC<br>YRVSKTDYECSWQYDGPEDNVSHVLWCCFVPPNHTHTGQERCRYFSSGPDRTVQFWEQDGI<br>PVLSKVNFWVESRLGNRTMKSQKISQYLYNWTKTTPPLGHIKVSQSHRQLRMDWNVSEEAG<br>AEVQFRRRMPTTNWTLGDCGPQVNSGSGVLGDIRGSMSESCLCPSENMAQEIQIRRRRRLS<br>SGAPGGPWSDWSMPVCVPPEVL (SEQ ID NO: 112)<br>Chain 2:<br>RVIPVSGPARCLSQSRNLLKTTDDMVKTAREKLKHYSCTAEDIDHEDITRDQTSTLKTCLP<br>LELHKNESCLATRETSSTTRGSCLPPQKTSLMMTLCLGSIYEDLKMYQTEFQAINAALQNH<br>NHQQIILDKGMLVAIDELMQSLNHNGETLRQKPPVGEADPYRVKMKLCILLHAFSTRVVTI<br>NRVMGYLSSAGGGGSGGGGSGGGGSESKYGPPCPPCPAPPVAGPSVFLFPPKPKDTLMISR<br>TPEVTCVVVDVSQEDPEVQFNWYVDGVEVHNAKTKPREEQFNSTYRVVSVLTVLHQDWLNG<br>KEYKCKVSNKGLPSSIEKTISKAKGQPREPQVYTLPPSQEEMTKNQVSLWCLVKGFYPSDI<br>AVEWESNGQPENNYKTTPPVLDSDGSFFLYSRLTVDKSRWQEGNVFSCSVMHEALHNHYTQ<br>KSLSLSLGK (SEQ ID NO: 67) |
| Fc-IL12Rβ1(D1)-p40-p35 | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGGGGSGGGGSGGGGSMWELEKDVYVVEVDWTPDAPGETVNLTCDTPEEDDI<br>TWTSDQRHGVIGSGKTLTITVKEFLDAGQYTCHKGGETLSHSHLLLHKKENGIWSTEILKN<br>FKNKTFLKCEAPNYSGRFTCSWLVQRNMDLKFNIKSSSSSPDSRAVTCGMASLSAEKVTLD<br>QRDYEKYSVSCQEDVTCPTAEETLPIELALEARQQNKYENYSTSFFIRDIIKPDPPKNLQM<br>KPLKNSQVEVSWEYPDSWSTPHSYFSLKFFVRIQRKKEKMKETEEGCNQKGAFLVEKTSTE<br>VQCKGGNVCVQAQDRYYNSSCSKWACVPCRVRSGGGGSGGGGSGGGGSRVIPVSGPARCLS<br>QSRNLLKTTDDMVKTAREKLKHYSCTAEDIDHEDITRDQTSTLKTCLPLELHKNESCLATR<br>ETSSTTRGSCLPPQKTSLMMTLCLGSIYEDLKMYQTEFQAINAALQNHNHQQIILDKGMLV<br>AIDELMQSLNHNGETLRQKPPVGEADPYRVKMKLCILLHAFSTRVVTINRVMGYLSSA<br>(SEQ ID NO: 113) |
| Fc-p40-p35 x Fc-IL12Rβ1(D1)<br>Chain 1: hIgG4s(HoleStar)-mIL12Rb1(D1)<br>Chain2: hIgG4s(Knob)-mIL12p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPL (SEQ ID NO: 114)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT |

TABLE 8D-continued

| Attenuated IL12 mutein-Fc fusion proteins: Receptor fusion constructs | |
|---|---|
| Molecule | Sequence |
| | AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 107) |
| Fc-p40-p35 x Fc-IL12Rβ2(D1)<br>Chain 1: hIgG4s(HoleStar)-mIL12Rb2(D1)<br>Chain2: hIgG4s(Knob)-mIL12p40-p35 | Chain 1:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGSN IDVCKLGTVTVQPAPVIPLGSAANISCSLNPKQGCSHYPSSNELILLKFVNDVLVENLHGK KVHDHTGHSSTFQVTNLSLGMTLFVCKLNCSNSQKKPPVPVCGVEISVGV (SEQ ID NO: 115)<br>Chain 2:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKEFLD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 107) |
| Fc-IL12Rβ1(D1)-p40-p35 x Fc-IL12Rβ2(D1)<br>Chain 1: hIgG4s(HoleStar)-mIL12Rb2(D1)<br>Chain 2: hIgG4s(Knob)-mIL12Rb1(D1)-mIL12p40-p35 | Chain 1:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGSN IDVCKLGTVTVQPAPVIPLGSAANISCSLNPKQGCSHYPSSNELILLKFVNDVLVENLHGK KVHDHTGHSSTFQVTNLSLGMTLFVCKLNCSNSQKKPPVPVCGVEISVGV (SEQ ID NO: 115)<br>Chain 2:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSQ LGASGPGDGCCVEKTSFPEGASGSPLGPRNLSCYRVSKTDYECSWQYDGPEDNVSHVLWCC FVPPNHTHTGQERCRYFSSGPDRTVQFWEQDGIPVLSKVNFWVESRLGNRTMKSQKISQYL YNWTKTTPPLGGGGSGGGGSGGGGSMWELEKDVYVVEVDWTPDAPGETVNLTCDTPEEDDI TWTSDQRHGVIGSGKTLTITVKEFLDAGQYTCHKGGETLSHSHLLLHKKENGIWSTEILKN FKNKTFLKCEAPNYSGRFTCSWLVQRNMDLKFNIKSSSSSPDSRAVTCGMASLSAEKVTLD QRDYEKYSVSCQEDVTCPTAEETLPIELALEARQQNKYENYSTSFFIRDIIKPDPPKNLQM KPLKNSQVEVSWEYPDSWSTPHSYFSLKFFVRIQRKKEKMKETEEGCNQKGAFLVEKTSTE VQCKGGNVCVQAQDRYYNSSCSKWACVPCRVRSGGGGSGGGGSGGGGSRVIPVSGPARCLS QSRNLLKTTDDMVKTAREKLKHYSCTAEDIDHEDITRDQTSTLKTCLPLELHKNESCLATR ETSSTTRGSCLPPQKTSLMMTLCLGSIYEDLKMYQTEFQAINAALQNHNHQQIILDKGMLV AIDELMQSLNHNGETLRQKPPVGEADPYRVKMKLCILLHAFSTRVVTINRVMGYLSSA (SEQ ID NO: 110) |
| Fc-p35 x Fc x p40<br>Chain 1: hIgG4s(HoleStar)<br>Chain 2: hIgG4s(Knob)-mp35<br>Chain 3: mp40 | Chain 1:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSR VIPVSGPARCLSQSRNLLKTTDDMVKTAREKLKHYSCTAEDIDHEDITRDQTSTLKTCLPL ELHKNESCLATRETSSTTRGSCLPPQKTSLMMTLCLGSIYEDLKMYQTEFQAINAALQNHN HQQIILDKGMLVAIDELMQSLNHNGETLRQKPPVGEADPYRVKMKLCILLHAFSTRVVTIN RVMGYLSSA (SEQ ID NO: 71)<br>Chain 3:<br>MWELEKDVYVVEVDWTPDAPGETVNLTCDTPEEDDITWTSDQRHGVIGSGKTLTITVKEFL DAGQYTCHKGGETLSHSHLLLHKKENGIWSTEILKNFKNKTFLKCEAPNYSGRFTCSWLVQ RNMDLKFNIKSSSSSPDSRAVTCGMASLSAEKVTLDQRDYEKYSVSCQEDVTCPTAEETLP IELALEARQQNKYENYSTSFFIRDIIKPDPPKNLQMKPLKNSQVEVSWEYPDSWSTPHSYF SLKFFVRIQRKKEKMKETEEGCNQKGAFLVEKTSTEVQCKGGNVCVQAQDRYYNSSCSKWA CVPCRVRS (SEQ ID NO: 57) |

TABLE 8D-continued

Attenuated IL12 mutein-Fc fusion proteins: Receptor fusion constructs

| Molecule | Sequence |
|---|---|
| Fc-p35 x Fc x IL12Rβ1(D1)-p40<br>Chain 1: hIgG4s(HoleStar)<br>Chain 2: hIgG4s(Knob)-mp35<br>Chain 3: mIL12Rb1(D1)-mp40 | Chain 1:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSR VIPVSGPARCLSQSRNLLKTTDDMVKTAREKLKHYSCTAEDIDHEDITRDQTSTLKTCLPL ELHKNESCLATRETSSTTRGSCLPPQKTSLMMTLCLGSIYEDLKMYQTEFQAINAALQNHN HQQIILDKGMLVAIDELMQSLNHNGETLRQKPPVGEADPYRVKMKLCILLHAFSTRVVTIN RVMGYLSSA (SEQ ID NO: 71)<br>Chain 3:<br>QLGASGPGDGCCVEKTSFPEGASGSPLGPRNLSCYRVSKTDYECSWQYDGPEDNVSHVLWC CFVPPNHTHTGQERCRYFSSGPDRTVQFWEQDGIPVLSKVNFWVESRLGNRTMKSQKISQY LYNWTKTTPPLGGGGSGGGGSMWELEKDVYVVEVDWTPDAPGETVNLTCDTPEEDDITWTS DQRHGVIGSGKTLTITVKEFLDAGQYTCHKGGETLSHSHLLLHKKENGIWSTEILKNFKNK TFLKCEAPNYSGRFTCSWLVQRNMDLKFNIKSSSSSPDSRAVTCGMASLSAEKVTLDQRDY EKYSVSCQEDVTCPTAEETLPIELALEARQQNKYENYSTSFFIRDIIKPDPPKNLQMKPLK NSQVEVSWEYPDSWSTPHSYFSLKFFVRIQRKKEKMKETEEGCNQKGAFLVEKTSTEVQCK GGNVCVQAQDRYYNSSCSKWACVPCRVRS (SEQ ID NO: 116) |
| Fc-p35 x Fc-IL12Rβ2(D1) x p40<br>Chain 1: hIgG4s(HoleStar)-mIL12Rb2(D1)<br>Chain 2: hIgG4s(Knob)-mp35<br>Chain 3: mp40 | Chain 1:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGSN IDVCKLGTVTVQPAPVIPLGSAANISCSLNPKQGCSHYPSSNELILLKFVNDVLVENLHGK KVHDHTGHSSTFQVTNLSLGMTLFVCKLNCSNSQKKPPVPVCGVEISVGV (SEQ ID NO: 115)<br>Chain 2:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSR VIPVSGPARCLSQSRNLLKTTDDMVKTAREKLKHYSCTAEDIDHEDITRDQTSTLKTCLPL ELHKNESCLATRETSSTTRGSCLPPQKTSLMMTLCLGSIYEDLKMYQTEFQAINAALQNHN HQQIILDKGMLVAIDELMQSLNHNGETLRQKPPVGEADPYRVKMKLCILLHAFSTRVVTIN RVMGYLSSA (SEQ ID NO: 71)<br>Chain 3:<br>MWELEKDVYVVEVDWTPDAPGETVNLTCDTPEEDDITWTSDQRHGVIGSGKTLTITVKEFL DAGQYTCHKGGETLSHSHLLLHKKENGIWSTEILKNFKNKTFLKCEAPNYSGRFTCSWLVQ RNMDLKFNIKSSSSSPDSRAVTCGMASLSAEKVTLDQRDYEKYSVSCQEDVTCPTAEETLP IELALEARQQNKYENYSTSFFIRDIIKPDPPKNLQMKPLKNSQVEVSWEYPDSWSTPHSYF SLKFFVRIQRKKEKMKETEEGCNQKGAFLVEKTSTEVQCKGGNVCVQAQDRYYNSSCSKWA CVPCRVRS (SEQ ID NO: 57) |
| Fc-p35 x Fc-IL12Rβ2(D1) x IL12R81 (D1)-p40<br>Chain 1: hIgG4s(HoleStar)-mIL12Rb2(D1)<br>Chain 2: hIgG4s(Knob)-mp35<br>Chain 3: IL12Rb1(D1)-p40 | Chain 1:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGSN IDVCKLGTVTVQPAPVIPLGSAANISCSLNPKQGCSHYPSSNELILLKFVNDVLVENLHGK KVHDHTGHSSTFQVTNLSLGMTLFVCKLNCSNSQKKPPVPVCGVEISVGV (SEQ ID NO: 115)<br>Chain 2:<br>ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSR VIPVSGPARCLSQSRNLLKTTDDMVKTAREKLKHYSCTAEDIDHEDITRDQTSTLKTCLPL ELHKNESCLATRETSSTTRGSCLPPQKTSLMMTLCLGSIYEDLKMYQTEFQAINAALQNHN HQQIILDKGMLVAIDELMQSLNHNGETLRQKPPVGEADPYRVKMKLCILLHAFSTRVVTIN RVMGYLSSA (SEQ ID NO: 71)<br>Chain 3:<br>QLGASGPGDGCCVEKTSFPEGASGSPLGPRNLSCYRVSKTDYECSWQYDGPEDNVSHVLWC CFVPPNHTHTGQERCRYFSSGPDRTVQFWEQDGIPVLSKVNFWVESRLGNRTMKSQKISQY LYNWTKTTPPLGGGGSGGGGSMWELEKDVYVVEVDWTPDAPGETVNLTCDTPEEDDITWTS DQRHGVIGSGKTLTITVKEFLDAGQYTCHKGGETLSHSHLLLHKKENGIWSTEILKNFKNK TFLKCEAPNYSGRFTCSWLVQRNMDLKFNIKSSSSSPDSRAVTCGMASLSAEKVTLDQRDY EKYSVSCQEDVTCPTAEETLPIELALEARQQNKYENYSTSFFIRDIIKPDPPKNLQMKPLK NSQVEVSWEYPDSWSTPHSYFSLKFFVRIQRKKEKMKETEEGCNQKGAFLVEKTSTEVQCK GGNVCVQAQDRYYNSSCSKWACVPCRVRS (SEQ ID NO: 116) |

TABLE 8D-continued

Attenuated IL12 mutein-Fc fusion proteins: Receptor fusion constructs

| Molecule | Sequence |
|---|---|
| Fc-p40(mutein24)-p35 x<br>Fc-IL12Rβ2(D1)<br>Chain 1: hIgG4s(HoleStar)-<br>mIL12Rb2(D1)<br>Chain 2: hIgG4s(Knob)-<br>p40(W37G)-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGSN<br>IDVCKLGTVTVQPAPVIPLGSAANISCSLNPKQGCSHYPSSNELILLKFVNDVLVENLHGK<br>KVHDHTGHSSTFQVTNLSLGMTLFVCKLNCSNSQKKPPVPVCGVEISVGV (SEQ ID<br>NO: 115)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDGTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA (SEQ ID NO: 117) |
| Fc-IL12Rβ1(D1)-p40-<br>p35(mutein 25)<br>Chain 1: hIgG4s(HoleStar)<br>Chain 2: hIgG4s(Knob)-<br>mIL12Rb1(D1)-mIL12p40-<br>p35(Y185G) | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGGGGSGGGGSGGGGSMWELEKDVYVVEVDWTPDAPGETVNLTCDTPEEDDI<br>TWTSDQRHGVIGSGKTLTITVKEFLDAGQYTCHKGGETLSHSHLLLHKKENGIWSTEILKN<br>FKNKTFLKCEAPNYSGRFTCSWLVQRNMDLKFNIKSSSSSPDSRAVTCGMASLSAEKVTLD<br>QRDYEKYSVSCQEDVTCPTAEETLPIELALEARQQNKYENYSTSFFIRDIIKPDPPKNLQM<br>KPLKNSQVEVSWEYPDSWSTPHSYFSLKFFVRIQRKKEKMKETEEGCNQKGAFLVEKTSTE<br>VQCKGGNVCVQAQDRYYNSSCSKWACVPCRVRSGGGGSGGGGSGGGGSRVIPVSGPARCLS<br>QSRNLLKTTDDMVKTAREKLKHYSCTAEDIDHEDITRDQTSTLKTCLPLELHKNESCLATR<br>ETSSTTRGSCLPPQKTSLMMTLCLGSIYEDLKMYQTEFQAINAALQNHNHQQIILDKGMLV<br>AIDELMQSLNHNGETLRQKPPVGEADPGRVKMKLCILLHAFSTRVVTINRVMGYLSSA<br>(SEQ ID NO: 118) |
| Fc-IL12Rβ1(D1)-p40-<br>p35(mutein 26)<br>Chain 1: hIgG4s(HoleStar)<br>Chain 2: hIgG4s(Knob)-<br>mIL12Rb1(D1)-mIL12p40-<br>p35(Y185L) | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGGGGSGGGGSGGGGSMWELEKDVYVVEVDWTPDAPGETVNLTCDTPEEDDI<br>TWTSDQRHGVIGSGKTLTITVKEFLDAGQYTCHKGGETLSHSHLLLHKKENGIWSTEILKN<br>FKNKTFLKCEAPNYSGRFTCSWLVQRNMDLKFNIKSSSSSPDSRAVTCGMASLSAEKVTLD<br>QRDYEKYSVSCQEDVTCPTAEETLPIELALEARQQNKYENYSTSFFIRDIIKPDPPKNLQM<br>KPLKNSQVEVSWEYPDSWSTPHSYFSLKFFVRIQRKKEKMKETEEGCNQKGAFLVEKTSTE<br>VQCKGGNVCVQAQDRYYNSSCSKWACVPCRVRSGGGGSGGGGSGGGGSRVIPVSGPARCLS<br>QSRNLLKTTDDMVKTAREKLKHYSCTAEDIDHEDITRDQTSTLKTCLPLELHKNESCLATR<br>ETSSTTRGSCLPPQKTSLMMTLCLGSIYEDLKMYQTEFQAINAALQNHNHQQIILDKGMLV<br>AIDELMQSLNHNGETLRQKPPVGEADPLRVKMKLCILLHAFSTRVVTINRVMGYLSSA<br>(SEQ ID NO: 119) |
| Fc-IL12Rβ1(D1)-p40-<br>p35(mutein 27)<br>Chain 1: hIgG4s(HoleStar)<br>Chain 2: hIgG4s(Knob)-<br>mIL12Rb1(D1)-mIL12p40-<br>p35(Y185V) | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2: |

TABLE 8D-continued

| Attenuated IL12 mutein-Fc fusion proteins: Receptor fusion constructs | |
|---|---|
| Molecule | Sequence |
| | ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGGGGSGGGGSGGGGSMWELEKDVYVVEVDWTPDAPGETVNLTCDTPEEDDI<br>TWTSDQRHGVIGSGKTLTITVKEFLDAGQYTCHKGGETLSHSHLLLHKKENGIWSTEILKN<br>FKNKTFLKCEAPNYSGRFTCSWLVQRNMDLKFNIKSSSSSPDSRAVTCGMASLSAEKVTLD<br>QRDYEKYSVSCQEDVTCPTAEETLPIELALEARQQNKYENYSTSFFIRDIIKPDPPKNLQM<br>KPLKNSQVEVSWEYPDSWSTPHSYFSLKFFVRIQRKKEKMKETEEGCNQKGAFLVEKTSTE<br>VQCKGGNVCVQAQDRYYNSSCSKWACVPCRVRSGGGGSGGGGSGGGGSRVIPVSGPARCLS<br>QSRNLLKTTDDMVKTAREKLKHYSCTAEDIDHEDITRDQTSTLKTCLPLELHKNESCLATR<br>ETSSTTRGSCLPPQKTSLMMTLCLGSIYEDLKMYQTEFQAINAALQNHNHQQIILDKGMLV<br>AIDELMQSLNHNGETLRQKPPVGEADPVRVKMKLCILLHAFSTRVVTINRVMGYLSSA<br>(SEQ ID NO: 120) |
| Fc-IL12Rβ1(D1)-p40-p35(mutein 28)<br>Chain 1: hIgG4s(HoleStar)<br>Chain 2: hIgG4s(Knob)-mIL12Rb1(D1)-mIL12p40-p35(Y185A) | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGK (SEQ ID NO: 62)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGGGGSGGGGSGGGGSMWELEKDVYVVEVDWTPDAPGETVNLTCDTPEEDDI<br>TWTSDQRHGVIGSGKTLTITVKEFLDAGQYTCHKGGETLSHSHLLLHKKENGIWSTEILKN<br>FKNKTFLKCEAPNYSGRFTCSWLVQRNMDLKFNIKSSSSSPDSRAVTCGMASLSAEKVTLD<br>QRDYEKYSVSCQEDVTCPTAEETLPIELALEARQQNKYENYSTSFFIRDIIKPDPPKNLQM<br>KPLKNSQVEVSWEYPDSWSTPHSYFSLKFFVRIQRKKEKMKETEEGCNQKGAFLVEKTSTE<br>VQCKGGNVCVQAQDRYYNSSCSKWACVPCRVRSGGGGSGGGGSGGGGSRVIPVSGPARCLS<br>QSRNLLKTTDDMVKTAREKLKHYSCTAEDIDHEDITRDQTSTLKTCLPLELHKNESCLATR<br>ETSSTTRGSCLPPQKTSLMMTLCLGSIYEDLKMYQTEFQAINAALQNHNHQQIILDKGMLV<br>AIDELMQSLNHNGETLRQKPPVGEADPARVKMKLCILLHAFSTRVVTINRVMGYLSSA<br>(SEQ ID NO: 121) |
| Fc-p40-p35xFc-IL12Rβ1(D1-2)<br>Chain 1: hIgG4s(HoleStar)-mIL12Rb1(D1-2)<br>Chain2: hIgG4s(Knob)-mIL12p40-p35 | Chain 1:<br>ESKYGPPCPPCPAPPVAGPSVFLFPPKPKDTLMISRTPEVTCVVVDVSQEDPEVQFNWY<br>VDGVEVHNAKTKPREEQFNSTYRVVSVLTVLHQDWLNGKEYKCKVSNKGLPSSIEKTIS<br>KAKGQPREPQVYTLPPSQEEMTKNQVSLSCAVKGFYPSDIAVEWESNGQPENNYKTTPP<br>VLDSDGSFFLVSRLTVDKSRWQEGNVFSCSVMHEALHNRFTQKSLSLSPGKGGGGSGGG<br>GSGGGGSQLGASGPGDGCCVEKTSFPEGASGSPLGPRNLSCYRVSKTDYECSWQYDGPE<br>DNVSHVLWCCFVPPNHTHTGQERCRYFSSGPDRTVQFWEQDGIPVLSKVNFWVESRLGN<br>RTMKSQKISQYLYNWTKTTPPLGHIKVSQSHRQLRMDWNVSEEAGAEVQFRRRMPTTNW<br>TLGDCGPQVNSGSGVLGDIRGSMSESCLCPSENMAQEIQIRRRRRLSSGAPGGPWSDWS<br>MPVCVPPEVL (SEQ ID NO: 111)<br>Chain 2:<br>ESKYGPPCPPCPAPPVAGPSVFLFPPKPKDTLMISRTPEVTCVVVDVSQEDPEVQFNWY<br>VDGVEVHNAKTKPREEQFNSTYRVVSVLTVLHQDWLNGKEYKCKVSNKGLPSSIEKTIS<br>KAKGQPREPQVYTLPPSQEEMTKNQVSLWCLVKGFYPSDIAVEWESNGQPENNYKTTPP<br>VLDSDGSFFLYSRLTVDKSRWQEGNVFSCSVMHEALHNHYTQKSLSLSLGKGGGGSGGG<br>GSGGGGSMWELEKDVYVVEVDWTPDAPGETVNLTCDTPEEDDITWTSDQRHGVIGSGKT<br>LTITVKEFLDAGQYTCHKGGETLSHSHLLLHKKENGIWSTEILKNFKNKTFLKCEAPNY<br>SGRFTCSWLVQRNMDLKFNIKSSSSSPDSRAVTCGMASLSAEKVTLDQRDYEKYSVSCQ<br>EDVTCPTAEETLPIELALEARQQNKYENYSTSFFIRDIIKPDPPKNLQMKPLKNSQVEV<br>SWEYPDSWSTPHSYFSLKFFVRIQRKKEKMKETEEGCNQKGAFLVEKTSTEVQCKGGNV<br>CVQAQDRYYNSSCSKWACVPCRVRSGGGGSGGGGSGGGGSRVIPVSGPARCLSQSRNLL<br>KTTDDMVKTAREKLKHYSCTAEDIDHEDITRDQTSTLKTCLPLELHKNESCLATRETSS<br>TTRGSCLPPQKTSLMMTLCLGSIYEDLKMYQTEFQAINAALQNHNHQQIILDKGMLVAI<br>DELMQSLNHNGETLRQKPPVGEADPYRVKMKLCILLHAFSTRVVTINRVMGYLSSA<br>(SEQ ID NO: 107) |
| Fc-p40-p35 x Fc-IL12Rβ2(D1-2)<br>Chain 1: hIgG4s(HoleStar)-mIL12Rb2(D1-2)<br>Chain2: hIgG4s(Knob)-mIL12p40-p35 | Chain 1:<br>ESKYGPPCPPCPAPPVAGPSVFLFPPKPKDTLMISRTPEVTCVVVDVSQEDPEVQFNWY<br>VDGVEVHNAKTKPREEQFNSTYRVVSVLTVLHQDWLNGKEYKCKVSNKGLPSSIEKTIS<br>KAKGQPREPQVYTLPPSQEEMTKNQVSLSCAVKGFYPSDIAVEWESNGQPENNYKTTPP<br>VLDSDGSFFLVSRLTVDKSRWQEGNVFSCSVMHEALHNRFTQKSLSLSPGKGGGGSGGG<br>GSGGGGSNIDVCKLGTVTVQPAPVIPLGSAANISCSLNPKQGCSHYPSSNELILLKFVN<br>DVLVENLHGKKVHDHTGHSSTFQVTNLSLGMTLFVCKLNCSNSQKKPPVPVCGVEISVG<br>VAPEPPQNISCVQEGENGTVACSWNSGKVTYLKTNYTLQLSGPNNLTCQKQCFSDNRQN<br>CNRLDLGINLSPDLAESRFIVRVTAINDLGNSSSLPHTFTFLDI (SEQ ID NO:<br>122) |

TABLE 8D-continued

| Attenuated IL12 mutein-Fc fusion proteins: Receptor fusion constructs | |
|---|---|
| Molecule | Sequence |
| | Chain 2: ESKYGPPCPPCPAPPVAGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTIS KAKGQPREPQVYTLPPSQEEMTKNQVSLWCLVKGFYPSDIAVEWESNGQPENNYKTTPP VLDSDGSFFLYSRLTVDKSRWQEGNVFSCSVMHEALHNHYTQKSLSLSLGKGGGGSGGG GSGGGGSMWELEKDVYVVEVDWTPDAPGETVNLTCDTPEEDDITWTSDQRHGVIGSGKT LTITVKEFLDAGQYTCHKGGETLSHSHLLLHKKENGIWSTEILKNFKNKTFLKCEAPNY SGRFTCSWLVQRNMDLKFNIKSSSSSPDSRAVTCGMASLSAEKVTLDQRDYEKYSVSCQ EDVTCPTAEETLPIELALEARQQNKYENYSTSFFIRDIIKPDPPKNLQMKPLKNSQVEV SWEYPDSWSTPHSYFSLKFFVRIQRKKEKMKETEEGCNQKGAFLVEKTSTEVQCKGGNV CVQAQDRYYNSSCSKWACVPCRVRSGGGGSGGGGSGGGGSRVIPVSGPARCLSQSRNLL KTTDDMVKTAREKLKHYSCTAEDIDHEDITRDQTSTLKTCLPLELHKNESCLATRETSS TTRGSCLPPQKTSLMMTLCLGSIYEDLKMYQTEFQAINAALQNHNHQQIILDKGMLVAI DELMQSLNHNGETLRQKPPVGEADPYRVKMKLCILLHAFSTRVVTINRVMGYLSSA (SEQ ID NO: 107) |

TABLE 8E

| Attenuated IL12 mutein-Fc fusion proteins: Ab mask-fusion constructs | |
|---|---|
| Molecule | Sequence |
| Fc-p40-p35 x Fc-scFv#A(VL-VH) Chain 1: hIgG4s(HoleStar)-scFV#A(VL-VH) Chain2: hIgG4s(Knob)-mIL12p40-p35 | Chain 1: ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGS-scFV#A (VL-VH; binds to IL12 p40) (SEQ ID NO: 123) Chain 2: ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKEFLD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 107) |
| Fc-p40-p35 x Fc-scFv#A(VH-VL) Chain 1: hIgG4s(HoleStar)-scFV#A(VH-VL) Chain 2: hIgG4s(Knob)-mIL12p40-p35 | Chain 1: ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGS-scFV#A (VL-VH; binds to IL12 p40) (SEQ ID NO: 123) Chain 2: ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLWCLVKGFYPSDIAVEWESNGQPENNYKTTPPVLDSDG SFFLYSRLTVDKSRWQEGNVFSCSVMHEALHNHYTQKSLSLSLGKGGGGSGGGGSGGGGSM WELEKDVYVVEVDWTPDAPGETVNLTCDTPEEDDITWTSDQRHGVIGSGKTLTITVKEFLD AGQYTCHKGGETLSHSHLLLHKKENGIWSTEILKNFKNKTFLKCEAPNYSGRFTCSWLVQR NMDLKFNIKSSSSSPDSRAVTCGMASLSAEKVTLDQRDYEKYSVSCQEDVTCPTAEETLPI ELALEARQQNKYENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQDRYYNSSCSKWAC VPCRVRSGGGGSGGGGSGGGGSRVIPVSGPARCLSQSRNLLKTTDDMVKTAREKLKHYSCT AEDIDHEDITRDQTSTLKTCLPLELHKNESCLATRETSSTTRGSCLPPQKTSLMMTLCLGS IYEDLKMYQTEFQAINAALQNHNHQQIILDKGMLVAIDELMQSLNHNGETLRQKPPVGEAD PYRVKMKLCILLHAFSTRVVTINRVMGYLSSA (SEQ ID NO: 107) |
| Fc-p40-p35 x Fc-Fab#A Chain 1: hIgG4s(HoleStar)-Fab#A(VH-CH1) Chain2: hIgG4s(Knob)-mIL12p40-p35 Chain3: Fab#A_light chain | Chain 1: ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG QPREPQVYTLPPSQEEMTKNQVSLSCAVKGFYPSDIAVEWESNGQPENNYKTTPPVLDSDG SFFLVSRLTVDKSRWQEGNVFSCSVMHEALHNRFTQKSLSLSPGKGGGGSGGGGSGGGGS-Fab#A (VH-CH1; Fab#A binds to IL12 p40) (SEQ ID NO: 123) Chain 2: ESKYGPPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKG |

TABLE 8E-continued

| Attenuated IL12 mutein-Fc fusion proteins: Ab mask-fusion constructs | |
|---|---|
| Molecule | Sequence |
| | QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA (SEQ ID NO: 107)<br>Chain 3:<br>Fab#A (VL-CL; Fab#A binds to IL12 p40) |
| Fc-p40-p35 x<br>scFv#B(VL-VH)<br>Chain 1:<br>hIgG4s(HoleStar)-<br>scFV#B(VL-VH)<br>Chain2:<br>hIgG4s(Knob)-<br>mIL12p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGS-<br>scFV#B(VL-VH; binds to IL12 p40) (SEQ ID NO: 123)<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA (SEQ ID NO: 107) |
| Fc-p40-p35 x<br>Fc-IL12Rβ1 (D1-2)<br>Chain 1:<br>hIgG4s(HoleStar)-<br>mIL12Rb1(D1-2)<br>Chain2: hIgG4s(Knob)-<br>mIL12p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGSQ<br>LGASGPGDGCCVEKTSFPEGASGSPLGPRNLSCYRVSKTDYECSWQYDGPEDNVSHVLWCC<br>FVPPNHTHTGQERCRYFSSGPDRTVQFWEQDGIPVLSKVNFWVESRLGNRTMKSQKISQYL<br>YNWTKTTPPLGHIKVSQSHRQLRMDWNVSEEAGAEVQFRRRMPTTNWTLGDCGPQVNSGSG<br>VLGDIRGSMSESCLCPSENMAQEIQIRRRRRLSSGAPGGPWSDWSMPVCVPPEVL<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI<br>ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA |
| Fc-p40-p35 x<br>Fc-IL12Rβ2(D1-2)<br>Chain 1:<br>hIgG4s(HoleStar)-<br>mIL12Rb2(D1-2)<br>Chain2: hIgG4s(Knob)-<br>mIL12p40-p35 | Chain 1:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLSCAVKGFYPSDIAVEWESNGQPENNYKTTPPVLDSDG<br>SFFLVSRLTVDKSRWQEGNVFSCSVMHEALHNRFTQKSLSLSPGKGGGGSGGGGSGGGGSN<br>IDVCKLGTVTVQPAPVIPLGSAANISCSLNPKQGCSHYPSSNELILLKFVNDVLVENLHGK<br>KVHDHTGHSSTFQVTNLSLGMTLFVCKLNCSNSQKKPPVPVCGVEISVGVAPEPPQNISCV<br>QEGENGTVACSWNSGKVTYLKTNYTLQLSGPNNLTCQKQCFSDNRQNCNRLDLGINLSPDL<br>AESRFIVRVTAINDLGNSSSLPHTFTFLDI<br>Chain 2:<br>ESKYGPPCPPCPAPPVAGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGLPSSIEKTISKAKG<br>QPREPQVYTLPPSQEEMTKNQVSLWCLVKGFYPSDIAVEWESNGQPENNYKTTPPVLDSDG<br>SFFLYSRLTVDKSRWQEGNVFSCSVMHEALHNHYTQKSLSLSLGKGGGGSGGGGSGGGGSM<br>WELEKDVYVVEVDWTPDAPGETVNLTCDTPEEDDITWTSDQRHGVIGSGKTLTITVKEFLD<br>AGQYTCHKGGETLSHSHLLLHKKENGIWSTEILKNFKNKTFLKCEAPNYSGRFTCSWLVQR<br>NMDLKFNIKSSSSSPDSRAVTCGMASLSAEKVTLDQRDYEKYSVSCQEDVTCPTAEETLPI |

TABLE 8E-continued

Attenuated IL12 mutein-Fc fusion proteins: Ab mask-fusion constructs

| Molecule | Sequence |
|---|---|
| | ELALEARQQNKYENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQDRYYNSSCSKWAC<br>VPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGS<br>IYEDLKMYQTEFQAINAALQNHNHQQIILDKGMLVAIDELMQSLNHNGETLRQKPPVGEAD<br>PYRVKMKLCILLHAFSTRVVTINRVMGYLSSA |

TABLE 9 mAb-targeted IL12 mutein-Fc fusion proteins: PD1-fusion

| Molecule | Sequence |
|---|---|
| αhPD1-<IL12Rβ1(D1)-<br>p40-p35 (monovalent)><br>Chain 1:<br>αhPD1-hIgG4s(HoleStar)<br>Chain2:<br>αhPD1-hIgG4s(Knob)-<br>mIL12Rb1(D1)-mIL12p40-<br>p35<br>Chain3:<br>αhPD1_light chain | Chain 1:<br>anti-hPD1 Fab (VH-CH1; binds to hPD1)-ESKYGPPCPPCPAPPVA<br>GPSVFLFPPKPKDTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREPQVYTLPPSQEEM<br>TKNQVSLSCAVKGFYPSDIAVEWESNGQPENNYKTTPPVLDSDGSFFLVSRLTVDKSRWQE<br>GNVFSCSVMHEALHNRFTQKSLSLSPGK (SEQ ID NO: 62)<br>Chain 2:<br>anti-hPD1 Fab (VH-CH1; binds to hPD1)-ESKYGPPCPPCPAPPVA<br>GPSVFLFPPKPKDTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREPQVYTLPPSQEEM<br>TKNQVSLWCLVKGFYPSDIAVEWESNGQPENNYKTTPPVLDSDGSFFLYSRLTVDKSRWQE<br>GNVFSCSVMHEALHNHYTQKSLSLSLGKGGGGSGGGGSGGGGSQLGASGPGDGCCVEKTSF<br>PEGASGSPLGPRNLSCYRVSKTDYECSWQYDGPEDNVSHVLWCCFVPPNHTHTGQERCRYF<br>SSGPDRTVQFWEQDGIPVLSKVNFWVESRLGNRTMKSQKISQYLYNWTKTTPPLGGGGSGG<br>GGSGGGGSMWELEKDVYVVEVDWTPDAPGETVNLTCDTPEEDDITWTSDQRHGVIGSGKTL<br>TITVKEFLDAGQYTCHKGGETLSHSHLLLHKKENGIWSTEILKNFKNKTFLKCEAPNYSGR<br>FTCSWLVQRNMDLKFNIKSSSSSPDSRAVTCGMASLSAEKVTLDQRDYEKYSVSCQEDVTC<br>PTAEETLPIELALEARQQNKYENYSTSFFIRDIIKPDPPKNLQMKPLKNSQVEVSWEYPDS<br>WSTPHSYFSLKFFVRIQRKKEKMKETEEGCNQKGAFLVEKTSTEVQCKGGNVCVQAQDRYY<br>NSSCSKWACVPCRVRSGGGGSGGGGSGGGGSRVIPVSGPARCLSQSRNLLKTTDDMVKTAR<br>EKLKHYSCTAEDIDHEDITRDQTSTLKTCLPLELHKNESCLATRETSSTTRGSCLPPQKTS<br>LMMTLCLGSIYEDLKMYQTEFQAINAALQNHNHQQIILDKGMLVAIDELMQSLNHNGETLR<br>QKPPVGEADPYRVKMKLCILLHAFSTRVVTINRVMGYLSSA (SEQ ID NO: 110)<br>Chain 3:<br>anti-hPD1 Fab (VL-CL; binds to hPD1) |
| αhCD20-<IL12R81(D1)-<br>p40-p35 (monovalent)><br>Chain 1: αhCD20-<br>hIgG4s(HoleStar)<br>Chain2:<br>αhCD20-hIgG4s(Knob)-<br>mIL12Rb1(D1)-mIL12p40-<br>p35<br>Chain3:<br>αhCD20_light chain | Chain 1:<br>anti-hCD20 Fab (VH-CH1; binds to hCD20)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGK (SEQ ID NO: 62)<br>Chain 2:<br>anti-hCD20 Fab (VH-CH1; binds to hCD20)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSQLGASGPGDGCCVEKTS<br>FPEGASGSPLGPRNLSCYRVSKTDYECSWQYDGPEDNVSHVLWCCFVPPNHTHTGQERCRY<br>FSSGPDRTVQFWEQDGIPVLSKVNFWVESRLGNRTMKSQKISQYLYNWTKTTPPLGGGGSG<br>GGGSGGGGSMWELEKDVYVVEVDWTPDAPGETVNLTCDTPEEDDITWTSDQRHGVIGSGKT<br>LTITVKEFLDAGQYTCHKGGETLSHSHLLLHKKENGIWSTEILKNFKNKTFLKCEAPNYSG<br>RFTCSWLVQRNMDLKFNIKSSSSSPDSRAVTCGMASLSAEKVTLDQRDYEKYSVSCQEDVT<br>CPTAEETLPIELALEARQQNKYENYSTSFFIRDIIKPDPPKNLQMKPLKNSQVEVSWEYPD<br>SWSTPHSYFSLKFFVRIQRKKEKMKETEEGCNQKGAFLVEKTSTEVQCKGGNVCVQAQDRY<br>YNSSCSKWACVPCRVRSGGGGSGGGGSGGGGSRVIPVSGPARCLSQSRNLLKTTDDMVKTA<br>REKLKHYSCTAEDIDHEDITRDQTSTLKTCLPLELHKNESCLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINRVMGYLSSA (SEQ ID NO: 110)<br>Chain 3:<br>anti-hCD20 Fab (VL-CL; binds to hCD20) |
| αhPD1-<p40-p35 x<br>IL12R32(D1)><br>Chain 1:<br>αhPD1-hIgG4s(HoleStar)-<br>mIL12Rb2(D1)<br>Chain2:<br>αhPD1-hIgG4s(Knob)-<br>mIL12p40-p35 | Chain 1:<br>anti-hPD1 Fab (VH-CH1; binds to hPD1)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGKGGGGSGGGGSGGGGSNIDVCKLGTVTVQPAPV<br>IPLGSAANISCSLNPKQGCSHYPSSNELILLKFVNDVLVENLHGKKVHDHTGHSSTFQVTN<br>LSLGMTLFVCKLNCSNSQKKPPVPVCGVEISVGV (SEQ ID NO: 115) |

TABLE 9-continued

| mAb-targeted IL12 mutein-Fc fusion proteins: PD1-fusion | |
|---|---|
| Molecule | Sequence |
| Chain3:<br>αhPD1_light chain | Chain 2:<br>anti-hPD1 Fab (VH-CH1; binds to hPD1)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSMWELEKDVYVVEVDWTP<br>DAPGETVNLTCDTPEEDDITWTSDQRHGVIGSGKTLTITVKEFLDAGQYTCHKGGETLSHS<br>HLLLHKKENGIWSTEILKNFKNKTFLKCEAPNYSGRFTCSWLVQRNMDLKFNIKSSSSSPD<br>SRAVTCGMASLSAEKVTLDQRDYEKYSVSCQEDVTCPTAEETLPIELALEARQQNKYENYS<br>TSFFIRDIIKPDPPKNLQMKPLKNSQVEVSWEYPDSWSTPHSYFSLKFFVRIQRKKEKMKE<br>TEEGCNQKGAFLVEKTSTEVQCKGGNVCVQAQDRYYNSSCSKWACVPCRVRSGGGGSGGGG<br>SGGGGSRVIPVSGPARCLSQSRNLLKTTDDMVKTAREKLKHYSCTAEDIDHEDITRDQTST<br>LKTCLPLELHKNESCLATRETSSTTRGSCLPPQKTSLMMTLCLGSIYEDLKMYQTEFQAIN<br>AALQNHNHQQIILDKGMLVAIDELMQSLNHNGETLRQKPPVGEADPYRVKMKLCILLHAFS<br>TRVVTINRVMGYLSSA (SEQ ID NO: 107)<br>Chain 3:<br>anti-hPD1 Fab (VL-CL; binds to hPD1) |
| αhCD20-<p40-p35 x<br>IL12R82(D1)><br>Chain 1:<br>αhCD20-hIgG4s(HoleStar)-<br>mIL12Rb2(D1)<br>Chain2:<br>αhCD20-hIgG4s(Knob)-<br>mIL12p40-p35<br>Chain3:<br>αhCD20_light<br>chain | Chain 1:<br>anti-hCD20 Fab (VH-CH1; binds to hCD20)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGKGGGGSGGGGSGGGGSNIDVCKLGTVTVQPAPV<br>IPLGSAANISCSLNPKQGCSHYPSSNELILLKFVNDVLVENLHGKKVHDHTGHSSTFQVTN<br>LSLGMTLFVCKLNCSNSQKKPPVPVCGVEISVGV (SEQ ID NO: 115)<br>Chain 2:<br>anti-hCD20 Fab (VH-CH1; binds to hCD2 0)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSMWELEKDVYVVEVDWTP<br>DAPGETVNLTCDTPEEDDITWTSDQRHGVIGSGKTLTITVKEFLDAGQYTCHKGGETLSHS<br>HLLLHKKENGIWSTEILKNFKNKTFLKCEAPNYSGRFTCSWLVQRNMDLKFNIKSSSSSPD<br>SRAVTCGMASLSAEKVTLDQRDYEKYSVSCQEDVTCPTAEETLPIELALEARQQNKYENYS<br>TSFFIRDIIKPDPPKNLQMKPLKNSQVEVSWEYPDSWSTPHSYFSLKFFVRIQRKKEKMKE<br>TEEGCNQKGAFLVEKTSTEVQCKGGNVCVQAQDRYYNSSCSKWACVPCRVRSGGGGSGGGG<br>SGGGGSRVIPVSGPARCLSQSRNLLKTTDDMVKTAREKLKHYSCTAEDIDHEDITRDQTST<br>LKTCLPLELHKNESCLATRETSSTTRGSCLPPQKTSLMMTLCLGSIYEDLKMYQTEFQAIN<br>AALQNHNHQQIILDKGMLVAIDELMQSLNHNGETLRQKPPVGEADPYRVKMKLCILLHAFS<br>TRVVTINRVMGYLSSA (SEQ ID NO: 107)<br>Chain 3:<br>anti-hCD20 Fab (VL-CL; binds to hCD20) |
| αhPD1-<IL12Rβ1(D1)-<br>p40-p35 x IL12Rβ2(D1)><br>Chain 1:<br>αhPD1-hIgG4s(HoleStar)-<br>mIL12Rb2(D1)<br>Chain2:<br>αhPD1-hIgG4s(Knob)-<br>mIL12Rb1 (D1)-mIL12p40-<br>p35<br>Chain3:<br>αhPD1_light chain | Chain 1:<br>anti-hPD1 Fab (VH-CH1; binds to hPD1)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGKGGGGSGGGGSGGGGSNIDVCKLGTVTVQPAPV<br>IPLGSAANISCSLNPKQGCSHYPSSNELILLKFVNDVLVENLHGKKVHDHTGHSSTFQVTN<br>LSLGMTLFVCKLNCSNSQKKPPVPVCGVEISVGV (SEQ ID NO: 115)<br>Chain 2:<br>anti-hPD1 Fab (VH-CH1; binds to hPD1)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSQLGASGPGDGCCVEKTS<br>FPEGASGSPLGPRNLSCYRVSKTDYECSWQYDGPEDNVSHVLWCCFVPPNHTHTGQERCRY<br>FSSGPDRTVQFWEQDGIPVLSKVNFWVESRLGNRTMKSQKISQYLYNWTKTTPPLGGGGSG<br>GGGSGGGGSMWELEKDVYVVEVDWTPDAPGETVNLTCDTPEEDDITWTSDQRHGVIGSGKT<br>LTITVKEFLDAGQYTCHKGGETLSHSHLLLHKKENGIWSTEILKNFKNKTFLKCEAPNYSG<br>RFTCSWLVQRNMDLKFNIKSSSSSPDSRAVTCGMASLSAEKVTLDQRDYEKYSVSCQEDVT<br>CPTAEETLPIELALEARQQNKYENYSTSFFIRDIIKPDPPKNLQMKPLKNSQVEVSWEYPD<br>SWSTPHSYFSLKFFVRIQRKKEKMKETEEGCNQKGAFLVEKTSTEVQCKGGNVCVQAQDRY<br>YNSSCSKWACVPCRVRSGGGGSGGGGSGGGGSRVIPVSGPARCLSQSRNLLKTTDDMVKTA<br>REKLKHYSCTAEDIDHEDITRDQTSTLKTCLPLELHKNESCLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINRVMGYLSSA (SEQ ID NO: 110)<br>Chain 3:<br>anti-hPD1 Fab (VL-CL; binds to hPD1) |
| αhCD20-<IL12Rβ1(D1)-<br>p40-p35 x IL12Rβ2(D1)><br>Chain 1:<br>αhCD20-hIgG4s(HoleStar)- | Chain 1:<br>anti-hCD20 Fab (VH-CH1; binds to hCD20)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE |

TABLE 9-continued mAb-targeted IL12 mutein-Fc fusion proteins: PD1-fusion

| Molecule | Sequence |
|---|---|
| mIL12Rb2(D1)<br>Chain2:<br>αhCD20-hIgG4s(Knob)-<br>mIL12Rb1(D1)-mIL12p40-<br>p35<br>Chain3:<br>αhCD20_light chain | MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGKGGGGSGGGGSGGGGSNIDVCKLGTVTVQPAPV<br>IPLGSAANISCSLNPKQGCSHYPSSNELILLKFVNDVLVENLHGKKVHDHTGHSSTFQVTN<br>LSLGMTLFVCKLNCSNSQKKPPVPVCGVEISVGV (SEQ ID NO: 115)<br>Chain 2:<br>anti-hCD20 Fab (VH-CH1; binds to hCD20)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSQLGASGPGDGCCVEKTS<br>FPEGASGSPLGPRNLSCYRVSKTDYECSWQYDGPEDNVSHVLWCCFVPPNHTHTGQERCRY<br>FSSGPDRTVQFWEQDGIPVLSKVNFWVESRLGNRTMKSQKISQYLYNWTKTTPPLGGGGSG<br>GGGSGGGGSMWELEKDVYVVEVDWTPDAPGETVNLTCDTPEEDDITWTSDQRHGVIGSGKT<br>LTITVKEFLDAGQYTCHKGGETLSHSHLLLHKKENGIWSTEILKNFKNKTFLKCEAPNYSG<br>RFTCSWLVQRNMDLKFNIKSSSSSPDSRAVTCGMASLSAEKVTLDQRDYEKYSVSCQEDVT<br>CPTAEETLPIELALEARQQNKYENYSTSFFIRDIIKPDPPKNLQMKPLKNSQVEVSWEYPD<br>SWSTPHSYFSLKFFVRIQRKKEKMKETEEGCNQKGAFLVEKTSTEVQCKGGNVCVQAQDRY<br>YNSSCSKWACVPCRVRSGGGGSGGGGSGGGGSRVIPVSGPARCLSQSRNLLKTTDDMVKTA<br>REKLKHYSCTAEDIDHEDITRDQTSTLKTCLPLELHKNESCLATRETSSTTRGSCLPPQKT<br>SLMMTLCLGSIYEDLKMYQTEFQAINAALQNHNHQQIILDKGMLVAIDELMQSLNHNGETL<br>RQKPPVGEADPYRVKMKLCILLHAFSTRVVTINRVMGYLSSA (SEQ ID NO: 110)<br>Chain 3:<br>anti-hCD20 Fab (VL-CL; binds to hCD20) |
| αhPD1-<mIL12Rb1(D1) x<br>mIL12p40-p35><br>Chain 1:<br>αhPD1-hIgG4s(HoleStar)-<br>mIL12Rb1(D1)<br>Chain2:<br>αhPD1-hIgG4s(Knob)-<br>mIL12p40-p35<br>Chain3:<br>αhPD1_light chain | Chain 1:<br>anti-hPD1 Fab (VH-CH1; binds to hPD1)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGKGGGGSGGGGSGGGGSQLGASGPGDGCCVEKTS<br>FPEGASGSPLGPRNLSCYRVSKTDYECSWQYDGPEDNVSHVLWCCFVPPNHTHTGQERCRY<br>FSSGPDRTVQFWEQDGIPVLSKVNFWVESRLGNRTMKSQKISQYLYNWTKTTPPL (SEQ<br>ID NO: 114)<br>Chain 2:<br>anti-hPD1 Fab (VH-CH1; binds to hPD1)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSMWELEKDVYVVEVDWTP<br>DAPGETVNLTCDTPEEDDITWTSDQRHGVIGSGKTLTITVKEFLDAGQYTCHKGGETLSHS<br>HLLLHKKENGIWSTEILKNFKNKTFLKCEAPNYSGRFTCSWLVQRNMDLKFNIKSSSSSPD<br>SRAVTCGMASLSAEKVTLDQRDYEKYSVSCQEDVTCPTAEETLPIELALEARQQNKYENYS<br>TSFFIRDIIKPDPPKNLQMKPLKNSQVEVSWEYPDSWSTPHSYFSLKFFVRIQRKKEKMKE<br>TEEGCNQKGAFLVEKTSTEVQCKGGNVCVQAQDRYYNSSCSKWACVPCRVRSGGGGSGGGG<br>SGGGGSRVIPVSGPARCLSQSRNLLKTTDDMVKTAREKLKHYSCTAEDIDHEDITRDQTST<br>LKTCLPLELHKNESCLATRETSSTTRGSCLPPQKTSLMMTLCLGSIYEDLKMYQTEFQAIN<br>AALQNHNHQQIILDKGMLVAIDELMQSLNHNGETLRQKPPVGEADPYRVKMKLCILLHAFS<br>TRVVTINRVMGYLSSA (SEQ ID NO: 107)<br>Chain 3:<br>anti-hPD1 Fab (VL-CL; binds to hPD1) |
| αhCD20-< mIL12Rb1 (D1) x<br>mIL12p40-p35><br>Chain 1:<br>αhCD20-hIgG4s(HoleStar)-<br>mIL12Rb1(D1)<br>Chain2:<br>αhCD20-hIgG4s(Knob)<br>-mIL12p40-p35<br>Chain3:<br>αhCD20_light chain | Chain 1:<br>anti-hCD20 Fab (VH-CH1; binds to hCD2 0)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLSCAVKGFYPSDIAVEWESNGQPENNYKTTPPVLDSDGSFFLVSRLTVDKSRWQ<br>EGNVFSCSVMHEALHNRFTQKSLSLSPGKGGGGSGGGGSGGGGSQLGASGPGDGCCVEKTS<br>FPEGASGSPLGPRNLSCYRVSKTDYECSWQYDGPEDNVSHVLWCCFVPPNHTHTGQERCRY<br>FSSGPDRTVQFWEQDGIPVLSKVNFWVESRLGNRTMKSQKISQYLYNWTKTTPPL (SEQ<br>ID NO: 114)<br>Chain 2:<br>anti-hCD20 Fab (VH-CH1; binds to hCD20)-ESKYGPPCPPCPAPPV<br>AGPSVFLFPPKPKDTLMISRTPEVTCVVVDVSQEDPEVQFNWYVDGVEVHNAKTKPREEQF<br>NSTYRVVSVLTVLHQDWLNGKEYKCKVSNKGLPSSIEKTISKAKGQPREPQVYTLPPSQEE<br>MTKNQVSLWCLVKGFYPSDIAVEWESNGQPENNYKTTPPVLDSDGSFFLYSRLTVDKSRWQ<br>EGNVFSCSVMHEALHNHYTQKSLSLSLGKGGGGSGGGGSGGGGSMWELEKDVYVVEVDWTP<br>DAPGETVNLTCDTPEEDDITWTSDQRHGVIGSGKTLTITVKEFLDAGQYTCHKGGETLSHS<br>HLLLHKKENGIWSTEILKNFKNKTFLKCEAPNYSGRFTCSWLVQRNMDLKFNIKSSSSSPD<br>SRAVTCGMASLSAEKVTLDQRDYEKYSVSCQEDVTCPTAEETLPIELALEARQQNKYENYS<br>TSFFIRDIIKPDPPKNLQMKPLKNSQVEVSWEYPDSWSTPHSYFSLKFFVRIQRKKEKMKE<br>TEEGCNQKGAFLVEKTSTEVQCKGGNVCVQAQDRYYNSSCSKWACVPCRVRSGGGGSGGGG<br>SGGGGSRVIPVSGPARCLSQSRNLLKTTDDMVKTAREKLKHYSCTAEDIDHEDITRDQTST<br>LKTCLPLELHKNESCLATRETSSTTRGSCLPPQKTSLMMTLCLGSIYEDLKMYQTEFQAIN |

TABLE 9-continued

| mAb-targeted IL12 mutein-Fc fusion proteins: PD1-fusion | |
|---|---|
| Molecule | Sequence |
| | AALQNHNHQQIILDKGMLVAIDELMQSLNHNGETLRQKPPVGEADPYRVKMKLCILLHAFS<br>TRVVTINRVMGYLSSA (SEQ ID NO: 107)<br>Chain 3:<br>anti-hCD20 Fab (VL-CL; binds to hCD20) |
| IL12Rβ1(D1)-IL12p40-<br>p35 x αhPD1<br>Chain 1:<br>αhPD1-hIgG4s(HoleStar)<br>Chain2:<br>mIL12Rb1(D1)-mIL12p40-<br>p35-hIgG4s(Knob)<br>Chain3:<br>αhPD1_light chain | Chain 1:<br>anti-hPD1 Fab (VH-CH1; binds to hPD1)-ESKYGPPCPPCPAPPVAGP<br>SVFLFPPKPKDTLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVYTLPPSQEEMTK<br>NQVSLSCAVKGFYPSDIAVEWESNGQPENNYKTTPPVLDSDGSFFLVSRLTVDKSRWQEGN<br>VFSCSVMHEALHNRFTQKSLSLSPGK (SEQ ID NO: 62)<br>Chain 2:<br>QLGASGPGDGCCVEKTSFPEGASGSPLGPRNLSCYRVSKTDYECSWQYDGPEDNVSHVLWC<br>CFVPPNHTHTGQERCRYFSSGPDRTVQFWEQDGIPVLSKVNFWVESRLGNRTMKSQKISQY<br>LYNWTKTTPPLGGGGSGGGGSMWELEKDVYVVEVDWTPDAPGETVNLTCDTPEEDDITWTS<br>DQRHGVIGSGKTLTITVKEFLDAGQYTCHKGGETLSHSHLLLHKKENGIWSTEILKNFKNK<br>TFLKCEAPNYSGRFTCSWLVQRNMDLKFNIKSSSSSPDSRAVTCGMASLSAEKVTLDQRDY<br>EKYSVSCQEDVTCPTAEETLPIELALEARQQNKYENYSTSFFIRDIIKPDPPKNLQMKPLK<br>NSQVEVSWEYPDSWSTPHSYFSLKFFVRIQRKKEKMKETEEGCNQKGAFLVEKTSTEVQCK<br>GGNVCVQAQDRYYNSSCSKWACVPCRVRSGGGGSGGGGSGGGGSRVIPVSGPARCLSQSRN<br>LLKTTDDMVKTAREKLKHYSCTAEDIDHEDITRDQTSTLKTCLPLELHKNESCLATRETSS<br>TTRGSCLPPQKTSLMMTLCLGSIYEDLKMYQTEFQAINAALQNHNHQQIILDKGMLVAIDE<br>LMQSLNHNGETLRQKPPVGEADPYRVKMKLCILLHAFSTRVVTINRVMGYLSSAGGGGSGG<br>GGSGGGGSESKYGPPCPPCPAPPVAGPSVFLFPPKPKDTLMISRTPEVTCVVVDVSQEDPE<br>VQFNWYVDGVEVHNAKTKPREEQFNSTYRVVSVLTVLHQDWLNGKEYKCKVSNKGLPSSIE<br>KTISKAKGQPREPQVYTLPPSQEEMTKNQVSLWCLVKGFYPSDIAVEWESNGQPENNYKTT<br>PPVLDSDGSFFLYSRLTVDKSRWQEGNVFSCSVMHEALHNHYTQKSLSLSLGK (SEQ ID<br>NO: 124)<br>Chain 3:<br>anti-hPD1 Fab (VL-CL; binds to hPD1) |
| IL12Rβ1(D1)-IL12p40-<br>p35 x αhCD20<br>Chain 1:<br>αhCD20-hIgG4s(HoleStar)<br>Chain2:<br>mIL12Rb1(D1)-<br>mIL12p40-p35-hIgG4s(Knob)<br>Chain3:<br>αhCD20_light chain | Chain 1:<br>anti-hCD20 Fab (VH-CH1; binds to hCD20)-ESKYGPPCPPCPAPP<br>VAGPSVFLFPPKPKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPREPQVYTLPPSQE<br>EMTKNQVSLSCAVKGFYPSDIAVEWESNGQPENNYKTTPPVLDSDGSFFLVSRLTVDKSRW<br>QEGNVFSCSVMHEALHNRFTQKSLSLSPGK (SEQ ID NO: 62)<br>Chain 2:<br>QLGASGPGDGCCVEKTSFPEGASGSPLGPRNLSCYRVSKTDYECSWQYDGPEDNVSHVLWC<br>CFVPPNHTHTGQERCRYFSSGPDRTVQFWEQDGIPVLSKVNFWVESRLGNRTMKSQKISQY<br>LYNWTKTTPPLGGGGSGGGGSMWELEKDVYVVEVDWTPDAPGETVNLTCDTPEEDDITWTS<br>DQRHGVIGSGKTLTITVKEFLDAGQYTCHKGGETLSHSHLLLHKKENGIWSTEILKNFKNK<br>TFLKCEAPNYSGRFTCSWLVQRNMDLKFNIKSSSSSPDSRAVTCGMASLSAEKVTLDQRDY<br>EKYSVSCQEDVTCPTAEETLPIELALEARQQNKYENYSTSFFIRDIIKPDPPKNLQMKPLK<br>NSQVEVSWEYPDSWSTPHSYFSLKFFVRIQRKKEKMKETEEGCNQKGAFLVEKTSTEVQCK<br>GGNVCVQAQDRYYNSSCSKWACVPCRVRSGGGGSGGGGSGGGGSRVIPVSGPARCLSQSRN<br>LLKTTDDMVKTAREKLKHYSCTAEDIDHEDITRDQTSTLKTCLPLELHKNESCLATRETSS<br>TTRGSCLPPQKTSLMMTLCLGSIYEDLKMYQTEFQAINAALQNHNHQQIILDKGMLVAIDE<br>LMQSLNHNGETLRQKPPVGEADPYRVKMKLCILLHAFSTRVVTINRVMGYLSSAGGGGSGG<br>GGSGGGGSESKYGPPCPPCPAPPVAGPSVFLFPPKPKDTLMISRTPEVTCVVVDVSQEDPE<br>VQFNWYVDGVEVHNAKTKPREEQFNSTYRVVSVLTVLHQDWLNGKEYKCKVSNKGLPSSIE<br>KTISKAKGQPREPQVYTLPPSQEEMTKNQVSLWCLVKGFYPSDIAVEWESNGQPENNYKTT<br>PPVLDSDGSFFLYSRLTVDKSRWQEGNVFSCSVMHEALHNHYTQKSLSLSLGK (SEQ ID<br>NO: 124)<br>Chain 3:<br>anti-hCD20 Fab (VL-CL; binds to hCD20) |
| αhPD1-<scFV#A(VL-VH) x<br>mIL12p40-p35><br>Chain 1:<br>αhPD1-hIgG4s(HoleStar)-<br>scFV#A(VL-VH)<br>Chain2:<br>αhPD1-hIgG4s(Knob)-<br>mIL12p40-p35<br>Chain 3:<br>αhPD1_light<br>chain | Chain 1:<br>anti-hPD1 Fab (VH-CH1; binds to hPD1)-ESKYGPPCPPCPAPPVA<br>GPSVFLFPPKPKDTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREPQVYTLPPSQEEM<br>TKNQVSLSCAVKGFYPSDIAVEWESNGQPENNYKTTPPVLDSDGSFFLVSRLTVDKSRWQE<br>GNVFSCSVMHEALHNRFTQKSLSLSPGKGGGGSGGGGSGGGGS-scFV#A (VL-VH;<br>binds to IL12 p40) (SEQ ID NO: 123)<br>Chain 2:<br>anti-hPD1 Fab (VH-CH1; binds to hPD1)-ESKYGPPCPPCPAPPVAGP<br>SVFLFPPKPKDTLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVYTLPPSQEEMTK<br>NQVSLWCLVKGFYPSDIAVEWESNGQPENNYKTTPPVLDSDGSFFLYSRLTVDKSRWQEGN<br>VFSCSVMHEALHNHYTQKSLSLSLGKGGGGSGGGGSGGGGSMWELEKDVYVVEVDWTPDAP<br>GETVNLTCDTPEEDDITWTSDQRHGVIGSGKTLTITVKEFLDAGQYTCHKGGETLSHSHLL<br>LHKKENGIWSTEILKNFKNKTFLKCEAPNYSGRFTCSWLVQRNMDLKFNIKSSSSSPDSRA<br>VTCGMASLSAEKVTLDQRDYEKYSVSCQEDVTCPTAEETLPIELALEARQQNKYENYSTSF<br>FIRDIIKPDPPKNLQMKPLKNSQVEVSWEYPDSWSTPHSYFSLKFFVRIQRKKEKMKETEE<br>GCNQKGAFLVEKTSTEVQCKGGNVCVQAQDRYYNSSCSKWACVPCRVRSGGGGSGGGGSGG<br>GGSRVIPVSGPARCLSQSRNLLKTTDDMVKTAREKLKHYSCTAEDIDHEDITRDQTSTLKT |

TABLE 9-continued

| mAb-targeted IL12 mutein-Fc fusion proteins: PD1-fusion | |
|---|---|
| Molecule | Sequence |
| | CLPLELHKNESCLATRETSSTTRGSCLPPQKTSLMMTLCLGSIYEDLKMYQTEFQAINAAL<br>QNHNHQQIILDKGMLVAIDELMQSLNHNGETLRQKPPVGEADPYRVKMKLCILLHAFSTRV<br>VTINRVMGYLSSA (SEQ ID NO: 107)<br>Chain 3:<br>anti-hPD1 Fab (VL-CL; binds to hPD1 |
| αhCD20-<scFV#A(VL-VH) x<br>mIL12p40-p35><br>Chain 1:<br>αhCD20-hIgG4s(HoleStar)-<br>scFV#A(VL-VH)<br>Chain2:<br>αhCD20-hIgG4s(Knob)-<br>mIL12p40-p35<br>Chain 3:<br>αhCD20_light<br>chain | Chain 1:<br>anti-hCD20 Fab (VH-CH1; binds to hCD20)-ESKYGPPCPPCPAPPVAG<br>PSVFLFPPKPKDTLMISRTPEVTCVVVDVSQEDPEVQFNWYVDGVEVHNAKTKPREEQFNS<br>TYRVVSVLTVLHQDWLNGKEYKCKVSNKGLPSSIEKTISKAKGQPREPQVYTLPPSQEEMT<br>KNQVSLSCAVKGFYPSDIAVEWESNGQPENNYKTTPPVLDSDGSFFLVSRLTVDKSRWQEG<br>NVFSCSVMHEALHNRFTQKSLSLSPGKGGGGSGGGGSGGGGS-scFV#A (VL-VH;<br>binds to IL12 p40) (SEQ ID NO: 123)<br>Chain 2:<br>anti-hCD20 Fab (VH-CH1; binds to hCD20)-ESKYGPPCPPCPAPPVAG<br>PSVFLFPPKPKDTLMISRTPEVTCVVVDVSQEDPEVQFNWYVDGVEVHNAKTKPREEQFNS<br>TYRVVSVLTVLHQDWLNGKEYKCKVSNKGLPSSIEKTISKAKGQPREPQVYTLPPSQEEMT<br>KNQVSLWCLVKGFYPSDIAVEWESNGQPENNYKTTPPVLDSDGSFFLYSRLTVDKSRWQEG<br>NVFSCSVMHEALHNHYTQKSLSLSLGKGGGGSGGGGSGGGGSMWELEKDVYVVEVDWTPDA<br>PGETVNLTCDTPEEDDITWTSDQRHGVIGSGKTLTITVKEFLDAGQYTCHKGGETLSHSHL<br>LLHKKENGIWSTEILKNFKNKTFLKCEAPNYSGRFTCSWLVQRNMDLKFNIKSSSSSPDSR<br>AVTCGMASLSAEKVTLDQRDYEKYSVSCQEDVTCPTAEETLPIELALEARQQNKYENYSTS<br>FFIRDIIKPDPPKNLQMKPLKNSQVEVSWEYPDSWSTPHSYFSLKFFVRIQRKKEKMKETE<br>EGCNQKGAFLVEKTSTEVQCKGGNVCVQAQDRYYNSSCSKWACVPCRVRSGGGGSGGGGSG<br>GGGSRVIPVSGPARCLSQSRNLLKTTDDMVKTAREKLKHYSCTAEDIDHEDITRDQTSTLK<br>TCLPLELHKNESCLATRETSSTTRGSCLPPQKTSLMMTLCLGSIYEDLKMYQTEFQAINAA<br>LQNHNHQQIILDKGMLVAIDELMQSLNHNGETLRQKPPVGEADPYRVKMKLCILLHAFSTR<br>VVTINRVMGYLSSA (SEQ ID NO: 107)<br>Chain 3:<br>anti-hCD20 Fab (VL-CL; binds to hCD20) |

TABLE 10

| Human IL12 construct | |
|---|---|
| Molecule | Sequence |
| Fc-hIL12p40-<br>p35 | ESKYGPPCPPCPAPPVAGPSVFLFPP<br>KPKDTLMISRTPEVTCVVVDVSQED<br>PEVQFNWYVDGVEVHNAKTKPREEQ<br>FNSTYRVVSVLTVLHQDWLNGKEYK<br>CKVSNKGLPSSIEKTISKAKGQPRE<br>PQVYTLPPSQEEMTKNQVSLTCLVK<br>GFYPSDIAVEWESNGQPENNYKTTP<br>PVLDSDGSFFLYSRLTVDKSRWQEG<br>NVFSCSVMHEALHNHYTQKSLSLSL<br>GKGGGGSGGGGSGGGGSIWELKKDV<br>YVVELDWYPDAPGEMVVLTCDTPEE<br>DGITWTLDQSSEVLGSGKTLTIQVK<br>EFGDAGQYTCHKGGEVLSHSLLLLH<br>KKEDGIWSTDILKDQKEPKNKTFLR<br>CEAKNYSGRFTCWWLTTISTDLTFS<br>VKSSRGSSDPQGVTCGAATLSAERV<br>RGDNKEYEYSVECQEDSACPAAEES<br>LPIEVMVDAVHKLKYENYTSSFFIR<br>DIIKPDPPKNLQLKPLKNSRQVEVS<br>WEYPDTWSTPHSYFSLTFCVQVQGK<br>SKREKKDRVFTDKTSATVICRKNAS<br>ISVRAQDRYYSSSWSEWASVPCSGG<br>GGSGGGGSGGGGSRNLPVATPDPGM<br>FPCLHHSQNLLRAVSNMLQKARQTL<br>EFYPCTSEEIDHEDITKDKTSTVEA<br>CLPLELTKNESCLNSRETSFITNGS<br>CLASRKTSFMMALCLSSIYEDLKMY<br>QVEFKTMNAKLLMDPKRQIFLDQNM<br>LAVIDELMQALNFNSETVPQKSSLE<br>EPDFYKTKIKLCILLHAFRIRAVTI<br>DRVMSYLNAS<br>(SEQ ID NO: 125) |

8.1.2. STAT3 Reporter Assay

A STAT3 driven luciferase-based reporter assay was used to evaluate the ability of IL12-Fc fusion proteins and IL12 mutein-Fc fusion proteins to activate STAT3-mediated transcription in CTLL-2, previously reported to respond to mIL12 (Khatri et al., 2007, J Immunol Methods. 326(1-2): 41-53).

8.1.2.1. Engineering of Reporter CTLL-2 Cells

CTLL2 (ATCC, #TIB-214) were transduced with a lentiviral vector encoding a STAT3 driven luciferase reporter (Cignal STAT3-Luc lenti reporter, SA Biosciences, CLS-6028L) in the presence of 5 ug/mL polybrene (Millipore TR-1003-G), then selected and maintained in RPMI-1640+10% fetal bovine serum (FBS)+L-Glutamine/Penicillin-Streptomycin+10 mM HEPES+1 mM Sodium Pyruvate+10% Rat T-Cell Culture Supplement with ConA (Corning, 354115)+3 ug/mL Puromycin and the resulting cell line renamed CTLL2/STAT3-Luc.

8.1.2.2. IL12 Stimulation of Reporter Cells

In this experiment, engineered reporter cells were stimulated via either recombinant IL12, IL12-Fc fusion proteins, or IL12 mutein-Fc fusion proteins. The cytokine, through binding to the IL12 receptors beta 1 (IL12Rβ1) and beta 2 (IL12Rβ2), activates the signaling complex and induces STAT3 phosphorylation. STAT3 phosphorylation leads to enhanced transcriptional activity of the STAT3 response elements driving the production of the reporter gene, luciferase.

8.1.2.3. Luciferase Assay Set Up

RPMI1640 supplemented with 10% FBS and P/S/G was used as assay medium to prepare cell suspensions and fusion protein dilutions.

A day prior to the assay, CTLL2/Stat3-Luc cells were spun down and resuspended at 3×10^5 cells/mL in RPMI-1640+10% fetal bovine serum (FBS)+L-Glutamine/Penicillin-Streptomycin+10 mM HEPES+1 mM Sodium Pyruvate. The day of the assay, cells were spun down and resuspended in assay medium at $5\times10^5$/mL. IL12, IL12-Fc fusion proteins, IL12 mutein-Fc fusion proteins, and controls were diluted 1:5 following an 11-point dilution (ranges indicated on figures), with the 12th point containing no recombinant protein. $2.5\times10^4$ reporter cells were added to 96 well white flat bottom plates and incubated with serially diluted IL12, IL12-Fc fusion protein, IL12 mutein-Fc fusion protein construct, or control proteins. Plates were incubated for 5 hours and 30 min at 37° C./5% $CO_2$, before the addition of 100 μL ONE-Glo™ (Promega) reagent to lyse cells and detect luciferase activity. The emitted light was captured in relative light units (RLU) on a multilabel plate reader Envision (PerkinElmer). All serial dilutions were tested in duplicates.

For determination of EC50 values, points leading to a hook effect, whereby concentrations of the protein higher than the max signal leads to a dose dependent decrease in signal, were excluded. The EC50 values were determined using the GraphPad Prism™ software from a four-parameter logistic equation over a 12-point dose-response curve where the 12th dilution point contained no recombinant protein. Induction fold at specific concentration as the ratio of the mean signal in presence of a fixed amount of protein divided by the mean signal in absence of that protein. Max induction was calculated as the ratio of the maximal mean signal across the protein dose range divided by the mean signal in absence of that protein 8.1.3. Activity of IL12-Fc Fusion Proteins and IL12 Mutein-Fc Fusion Proteins in MC38 Syngeneic Tumor Model 8-10-week-old female C57BL/6 mice (The Jackson Laboratory) were implanted with $3\times10^5$ MC38 tumor cells subcutaneously into the right hind flank.

Mice were randomized when tumor size reached 75-85 $mm^3$ and were treated intraperitoneally with different IL12-Fc fusion proteins. Treatment was administered intraperitoneally every 2 days, for a total of 5 doses (study #1, see FIG. 21) or every 3 days, for total of 3 doses (study #2 see FIG. 25A). One group of mice in study #1 also received intraperitoneal injections of anti-mPD1 twice per week for 2 weeks. Tumors were measured semiweekly using a digital caliper and the tumor sizes were calculated as length× $width^2/2$. Measurements were performed until the average tumor size of the control group reached 2250 $mm^3$, or until any mouse in any group needed to be euthanized due to ulceration or body weight loss of more than 20%. Observations were extended to Day 71 (7.5 weeks after the last treatment) to determine the frequency of tumor-free mice.

8.1.4. Determination of Oligomerization State of IL12-Fc Fusion Proteins by Size-Exclusion Chromatography Couple to Multi-Angle Light Scattering Detectors (SEC-MALS)

Size-exclusion ultra-performance liquid chromatography (SEC) coupled with multiangle light scattering (MALS) were employed to assess the oligomeric state of different fusion proteins. SEC analysis was conducted on a Waters Acquity UPLC H-Class system. 10 μg of each protein sample was injected into an Acquity BEH SEC columns (200 Å, 1.7 μm, 4.6×300 mm). Flow rate was set at 0.3 ml/min. Mobile phase buffer contains 10 mM sodium phosphate, 500 mM NaCl, pH 7.0. UV absorbance at 280 nm, light scattering and refractive index changes were monitored using Wyatt Optilab T-Rex and Wyatt-uDawn Treos LS Detector.

8.1.5. Primary T Cell Binding Assay

Spleens were harvested from C57BL/6 mice and dissociated manually. Splenocytes were stimulated by culturing for 48 hours in RPMI+10% FBS+2 mM L-glutamine/Pen/Strep in the presence of anti-CD3 and anti-CD28 activation beads (Thermo/11456D) at a 1:3 (beads:splenocytes) ratio and in the presence of 30 U/mL human IL-2 (proleukin). Beads were removed before cells were stained with a viability marker (Invitrogen/L34976) at 1:500 in PBS for 15 minutes room temperature, washed, then stained with anti-CD90.2(BD/563008), anti-CD8 (BD/563786), and anti-CD25 (BD/553072) for 30 minutes on ice. Cells were washed once before plating 200,000 cells per well in a 96-well plate and staining indicated concentration of test IL12-Fc fusion proteins or variant molecules for 2 hours on ice. Cells were washed twice before staining for the Fc portion using an ahuFC antibody (Jackson Immuno 109-136-170). Data was acquired using a BD LSRFortessa™ X-20 instrument. Data plots represent geometric mean fluorescence intensity (MFI) of the ahuFC signal from CD25+, CD8+CD90.2+ T cells.

8.1.6. pSTAT4 Assay on Primary T Cells from C57BL/6 Mice

Spleens were harvested from C57BL/6 mice and dissociated manually. Splenocytes were stimulated by culturing for 48 hours in RPMI+10% FBS+2 mM L-glutamine/Pen/Strep in the presence of aCD3 and aCD28 activation beads (Thermo/11456D) at a 1:3 (beads:splenocytes) ratio and in the presence of 30 U/mL human IL-2 (proleukin). Beads were removed before cells were stained with a viability marker (Invitrogen/L34976) at 1:500 in PBS for 15 minutes room temperature and washed. Cells were plated at 500,000 cells per well in 96-well plate and then stimulated with the indicated concentration of IL12-Fc fusion protein or IL12-Fc variant protein for 20 minutes at 37° C. before fixation with Cytofix buffer (BD/554655) for 12 minutes at 37° C. Cells were then permeabilization with pre-chilled Perm Buffer III (BD/558050) for 15 mins on ice and washed 2 times. Cells were then stained with aCD90.2 (BD/563008), aCD8 (BD/563786), aCD25 (BD/553072), and pSTAT4 (BD/558137) for 30 minutes on ice. Cells were washed twice before data was acquired using a BD LSRFortessa™ X-20 instrument. Data plots represents geometric mean fluorescence intensity (MFI) of the pSTAT4 signal from CD25+CD8+CD90.2+ T cells.

8.1.7. NK92 Reporter Assay

A STAT3 driven luciferase-based reporter assay was used to evaluate the ability of IL12-Fc fusion proteins and IL12-IL12R-Fc fusion proteins to activate STAT3-mediated transcription in NK92.

8.1.7.1. Engineering of Reporter NK92 Cells

The human natural killer cell line NK92 was transduced with a Signal Transducer and Activator of Transcription 3 (STAT3) response element driven luciferase reporter construct and maintained in alpha minimum essential medium without nucleosides+2 mM L-glutamine/Pen/Strep+1.5 g/L sodium bicarbonate+12.5% horse serum+12.5% FBS+0.2 mM inositol+0.1 mM 2-mercaptoethanol+0.02 mM folic acid+200 U/mL recombinant hIL-2+1 mg/mL puromycin. A single cell clone, having high responsiveness to IL12, was identified and renamed NK92/STAT3-Luc cl.7F7 and was used for assays as noted.

NK92/STAT3-Luc cl.7F7 were engineered to stably express human PD1 (amino acids M1-L288 of accession number NP_005009.2, with a 2QèE mutation) and cells selected in media supplemented with 0.5 mg/mL G418. Cells were validated by flow cytometry and renamed NK92/STAT3-Luc cl.7F7/hPD1.

8.1.7.2. Luciferase Assay Setup

RPMI1640 supplemented with 10% FBS and P/S/G was used as assay medium to prepare cell suspensions and fusion protein dilutions.

A day prior to the assay, NK92/STAT3-Luc and/or NK92/STAT3-Luc cl.7F7 cells were spun down and resuspended at $5\times10^5$ cells/mL in alpha minimum essential medium without nucleosides+2 mM L-glutamine/Pen/Strep+1.5 g/L sodium bicarbonate+12.5% horse serum+12.5% FBS+0.2 mM inositol+0.1 mM 2-mercaptoethanol+0.02 mM folic acid. The day of the assay, cells were spun down and resuspended in assay medium at $5\times10^5$/mL. IL12, IL12-Fc fusion proteins, or IL12-IL12R-Fc fusion proteins, and controls were diluted 1:5 following a 9-point dilution range (10 nM to 5.12 fM range for recombinant IL12 and 50 nM to 25.6 fM for IL12-Fc fusion proteins or IL12-IL12R-Fc fusion proteins), with the $10^{th}$ point containing no recombinant protein. $2.5\times10^5$ reporter cells were added to 96 well white flat bottom plates and incubated with serially diluted IL12, IL12-Fc fusion protein, IL12-IL12R-Fc fusion protein construct, or control proteins. Plates were incubated for 5 hours at 37° C./5% CO2, before the addition of 100 μL ONE-Glo™ (Promega) reagent to lyse cells and detect luciferase activity. The emitted light was captured in relative light units (RLU) on a multilabel plate reader Envision (PerkinElmer). All serial dilutions were tested in duplicates. $EC_{50}$ values of the antibodies were determined using GraphPad Prism™ software from a four-parameter logistic equation over a 10-point dose-response curve.

8.1.8. pSTAT4 Assay on Primary T Cells from PD-1×LAG3 Knock-In Mice

Spleens were harvested from PD-1×LAG3 knock-in mice (DOI: 10.1158/1535-7163.MCT-18-1376) and dissociated manually. Splenocytes were stimulated by culturing for 48 hours in RPMI+10% FBS+2 mM L-glutamine/Pen/Strep in the presence of anti-CD3 and anti-CD28 activation beads (Thermo/11456D) at a ratio of 1:3 (beads:splenocytes) in the presence of 30 U/mL human IL-2 (proleukin). Beads were removed before cells were stained with a viability marker (Invitrogen/L34976) at 1:500 in PBS for 15 minutes room temperature and washed. Cells were plated at 200,000 cells per well in 96-well plate and then stimulated with Fc-IL12 or Fc-IL12 variant protein for 20 minutes at 37° C. before fixation with Cytofix buffer (BD/554655) for 12 minutes at 37° C. Cells were then permeabilization with pre-chilled Perm Buffer III (BD/558050) for 15 mins on ice and washed 2 times. Cells were then stained with anti-CD90.2 (BD/563008), anti-CD8 (BD/563786), anti-CD25 (BD/553072), and pSTAT4 (BD/558137) for 30 minutes on ice. Cells were washed twice before data was acquired using a BD LSR-Fortessa™ X-20 instrument. Data plots represents geometric mean fluorescence intensity (MFI) of the pSTAT4 signal from CD25+CD8+CD90.2+ T cells.

8.1.9. Engineered HT-2 Reporter Cell Assay

The mouse lymphoblastic clonal cell line HT-2 clone A5E was transduced with a STAT3 driven luciferase reporter construct and maintained in RPMI-1640+10% FBS+10 mM HEPES+1 mM sodium pyruvate+50 mM beta-mercapto-ethanol+P/S/G+200 IU/mL proleukin+1 mg/mL puromycin. A single cell clone having high responsiveness to IL12 was identified and renamed HT-2/STAT3-Luc cl.94.

The engineered HT-2 reporter cells were stimulated via either recombinant IL12, or Fc-IL12 fusion proteins, including those comprising an IL12 antibody fragment. Functional IL12 receptors are formed by the differential assembly of IL12R subunits (IL12Rb1 and IL12Rb2). Binding of cytokine by IL12R leads to activation of STAT1/3/4, which drives luciferase production in the engineered cell line.

8.1.9.1. Assay Setup

RPMI-1640 supplemented with 10% fetal bovine serum (FBS) and penicillin/streptomycin/L-glutamine was used as assay medium to prepare cell suspensions and antibody dilutions. A day prior to screening, engineered reporter cells were spun and resuspended at $3\times10^5$ cells/mL in cognate media devoid of IL2. On the day of the assay, cells were spun down, resuspended in assay medium, plated at $2.5\times10^4$ reporter cells/well in 96 well white flat bottom plates and incubated with protein that was serially diluted (1:5) over an 11-point titration range with the $12^{th}$ point containing no recombinant protein. Plates were incubated for 5 hours at 37° C., 5% $CO_2$ and then 100 mL ONE-Glo™ (Promega) reagent was added to the wells to lyse the cells and detect luciferase activity. The emitted light was measured in RLU on a multilabel plate reader Envision (PerkinElmer). $EC_{50}$ values of the antibodies were determined using GraphPad Prism™ software from a four-parameter logistic equation over a 12-point dose-response curve.

8.2. Example 1: Cloning and Expressing of IL12 Mutein-Fc Fusion Proteins 8.2.1. Overview DNA fragments encoding various mouse or human p40, p35, various linker ($G_4S$ (SEQ ID NO: 25)) lengths, and IgG4s Fc domains with or without knob-forming mutations (T366W, EU numbering), hole-forming mutations (T366S, L368A, Y407V, EU numbering) and Star mutations (H435R, Y436F, EU numbering) were synthesized by Integrated DNA Technologies, Inc. (San Diego, California) or Geneart/Thermo Fisher Scientific (Regensburg, Germany)

Mammalian expression vectors for individual chains were created by either NEBuilder HiFi DNA Assembly Kit (New England BioLabs Inc.) or restriction digest followed by ligation following standard molecular cloning protocols provided by New England BioLabs Inc. DNAs were transfected as a single plasmid, heavy and light chain pair, or as a pair for knob-forming mutations (T366W, EU numbering), hole-forming mutations (T366S, L368A, Y407V, EU numbering) and Star mutations (H435R, Y436F, EU numbering) into Expi293F cells (ThermoFisher Scientific) following the manufacturer's protocol. 50 ml of cell culture supernatant was harvested and processed for purification via HiTrap™ Protein G HP or MabSelect SuRe pcc columns (Cytiva).

8.2.2. Results

The orientation of the fusion protein (N- vs. C-terminal Fc fusions) affected the ability to express IL12-Fc fusion proteins and IL12 mutein-Fc fusion proteins, as well as their proper assembly (e.g., assembly with minimal aggregation).

FIGS. 10A and 10B show that the various IL12 mutein-Fc fusion proteins can be expressed in vitro. In certain instances, however, the expressed fusion protein formed high molecular weight species, indicating protein aggregation.

Monovalent IL12-Fc fusion proteins were expressible to varying degrees and properly assembled species (see FIGS. 10A and 11-13 and Table 11). The C-terminal mIL12 orientation of Fc-IL12(p35×p40) reduced the final concentration of fusion protein and decreased properly assembled species relative to the N-terminal mIL12 orientation of IL12(p35×p40)-Fc (see Table 11 and FIGS. 11 and 12, with FIG. 12 showing detection of monomeric and trimeric oligomers in addition to the expected dimer). Disulfide bond removal in the N-terminal orientation caused a decrease in the covalently bound high molecular weight species (see FIG. 10A).

TABLE 11

Expression of Monovalent IL12-Fc Fusion Proteins

| Fusion Protein | Yield from 50 mL culture (mg) | Predicted MW (KDal) |
|---|---|---|
| IL12(p35xp40)-Fc | 8.4 | 110 |
| Fc-IL12(p35xp40) | 2.6 | 110 |
| IL12*(p35*xp40*)-Fc | 8.0 | 110 |

All bivalent IL12-Fc fusion proteins were expressible to varying degrees and purities (see FIGS. 10B and 14-18, and Tables 12 and 13). Generally, mIL12-Fc fusion proteins having an mIL12 orientation of p35-p40 were more difficult to express (see FIG. 10B and Table 12) and demonstrated the lowest purities (see FIGS. 14, 15, 16, and 17, and Table 12). Disulfide bond removal did not largely affect p35-p40 expression. Disulfide removal appears to decrease covalent high molecular weight species in several instances (see FIG. 10B). Both bivalent IL12(p35-p40) N (lane 5) and C (lane 7) terminal Fc fusions were largely expressed as covalent high molecular weight species while bivalent IL12*(p35*-p40*) N (lane 11) and C (lane 13) terminal Fc fusions had increased proportions of species of expected molecular weight on a non-reduced denaturing gel (FIG. 10B).

TABLE 12

Expression of Bivalent IL12-Fc Fusion Proteins

| Fusion Protein | Yield from 50 mL culture (mg) | Predicted MW (KDal) |
|---|---|---|
| IL12(p40-p35)-Fc | 1.7 | 170 |
| IL12(p35-p40)-Fc | 0.4 | 171 |
| Fc-IL12(p40-p35) | 3.2 | 170 |
| Fc-IL12(p35-p40) | 0.4 | 171 |
| IL12*(p40*-p35*)-Fc | 3.1 | 170 |
| IL12*(p35*-p40*)-Fc | 0.5 | 171 |
| Fc-IL12*(p40*-p35*) | 1.8 | 170 |
| Fc-IL12*(p35*-p40*) | 0.4 | 171 |

8.3. Example 2: Activity of IL12-Fc Fusion Proteins and IL12 Mutein-Fc Fusion Proteins in STAT3 Reporter Assay The ability of recombinant IL12, IL12-Fc fusion proteins, and IL12 mutein-Fc fusion proteins to stimulate IL12 receptor was assessed in a STAT3-reporter cell-based bioassay as described in Section 8.1.2.

8.3.1. Results

Activation curves are shown in FIGS. 19, 20A, and 20B. Incubation of the CTLL-2/STAT3-Luc reporter cells with mouse IL12 induced luciferase activity. Incubation of the CTLL-2/STAT3-Luc cells with the noted monovalent, bivalent, and disulfide-removed IL2-Fc fusion proteins also induced luciferase activity (FIG. 19). Table 13 provides the $EC_{50}$ and maximum STAT3-Luc activity for the IL12-Fc fusion proteins of FIG. 19. FIG. 20A shows luciferase activity from additional bivalent IL12 mutein-Fc fusion proteins. Table 14 provides the $EC_{50}$ and maximum STAT3-Luc activity for the IL12 mutein-Fc fusion proteins of FIG. 20A. FIG. 20B shows luciferase activity from additional bivalent IL12 mutein-Fc fusion proteins. Table 15 provides the $EC_{50}$ and maximum STAT3-Luc activity for the IL12-Fc fusion proteins of FIG. 20B.

Monovalent mIL12 N-terminal Fc fusions largely preserved the activity of mIL12 (FIG. 19). In the bivalent Fc fusions, the p40-p35 mIL12 orientation, whether N- or C-terminal, showed a lower maximum activity than recombinant mIL12 (FIG. 19). Elimination of the disulfide bond between p40 and p35 (i.e., disulfide-removed) had minimal effect on activity (FIG. 19).

TABLE 13

Bioactivity of IL12-Fc Fusion Proteins

| Construct | EC50 (M) | Fold induction at 6.25 nM⁺ | Max fold induction* |
|---|---|---|---|
| Recomb mIL12 | 5.56E−11 | 12.16 | 12.43 |
| Monovalent: IL12(p35xp40)-Fc | 6.47E−11 | 9.58 | 9.89 |
| Monovalent: IL12*(p35*xp40*)-Fc | 8.11E−11 | 8.93 | 9.62 |
| Bivalent: IL12(p40-p35)-Fc | 1.16E−11 | 7.52 | 15.45 |
| Bivalent: Fc-IL12(p40-p35) | 1.85E−11 | 6.73 | 7.66 |
| Bivalent: IL12*(p40*-p35*)-Fc | 1.72E−11 | 7.01 | 8.48 |
| Bivalent: Fc-p40*-p35* | 1.80E−11 | 5.96 | 7.83 |

TABLE 14

Bioactivity of Bivalent IL12 Mutein-Fc Fusion Proteins

| Construct | EC50 (M) | Fold induction at 20 nM⁺ | Max fold induction* |
|---|---|---|---|
| Recomb mIL12 | 3.46E−11 | 18.82 | 19.12 |
| Fc-IL12(p40-p35) | 6.11E−11 | 12.79 | 14.39 |
| Fc-IL12(mutein 1) | 1.76E−10 | 4.52 | 4.52 |
| Fc-IL12(mutein 2) | 2.60E−10 | 5.41 | 5.90 |
| Fc-IL12(mutein 3) | ND | 1.06 | 1.11 |
| Fc-IL12(mutein 4) | ND | 1.12 | 1.16 |
| Fc-IL12(mutein 8) | 8.05E−10 | 10.02 | 10.12 |
| Fc-IL12(mutein 11) | 1.33E−09 | 8.93 | 10.17 |
| Fc-IL12(mutein 12) | ND | 1.04 | 1.10 |
| Fc-IL12(mutein 13) | ND | 1.37 | 27.49 |

TABLE 15

Bioactivity of Bivalent IL12 Mutein-Fc Fusion Proteins

| Construct | EC50 (M) | Max fold induction* |
|---|---|---|
| Recomb mIL12 | 3.71E−10 | 17.78 |
| Fc-IL12(p40-p35) | 9.95E−11 | 12.17 |
| Fc-IL12(mutein 14) | 3.79E−09 | 7.31 |
| Fc-IL12(mutein 15) | ND | 1.18 |
| Fc-IL12(mutein 16) | 1.67E−08 | 2.48 |
| Fc-IL12(mutein 17) | 3.53E−10 | 9.67 |

8.4. Example 3: Anti-Tumor Activity of IL12-Fc Fusion Proteins and IL12 Mutein-Fc Fusion Proteins The activity of IL12-Fc fusion proteins and IL12 mutein-Fc fusion proteins in an MC38 tumor model was evaluated. MC38 tumor cells were implanted into C57BL/6 mice as described in Section 8.1.3. For FIGS. 21-24, once tumors had reached an average volume of 85 $mm^3$ on day 8 mice were randomized into groups (n=6/group) and dosed intraperitoneally (IP) with hIgG4s isotype control, monovalent IL12(p35×p40)-Fc fusion protein, or one of 4 bivalent IL12-Fc fusion proteins. The results are shown in FIGS. 22-24.

Referring to FIGS. 25A and 25B, once tumors had reached an average volume of 75 mm$^3$ on day 9 mice were randomized into groups (n=5-6/group) and dosed with hIgG4s isotype control, bivalent Fc-p40-p35, or bivalent test mutein fusion protein every 3 days for a total of 3 doses.

8.4.1. Results

FIGS. 22 and 23A-23F show the effect of the test fusion proteins on tumor volume. Each measurement represents the average of n=6/group+/−SEM. Monovalent IL12(p35×p40)-Fc, bivalent IL12(p40-p35)-Fc, bivalent IL12(p40-p35)-Fc combination with αPD1, and bivalent Fc-IL12(p40-p35) all demonstrated anti-tumor efficacy and tumor growth inhibition at doses tested. Individual tumor growth curves (FIGS. 23A-F) demonstrate proportion of mice that were tumor-free at the end of study along with proportion of mice that had >20% body-weight loss during the study and were euthanized. Treatment with monovalent: IL12(p35×p40)-Fc at 2 μg was efficacious for tumor regressions, however led to 4/6 mice having >20% bodyweight loss demonstrating substantial toxicity. Bivalent: IL12(p40-p35)-Fc at 2 μg led to tumor regressions with no mice having >20% bodyweight loss, however 3/6 tumors relapsed. The combination of bivalent: IL12(p40-p35)-Fc at 2 μg and aPD-1 at 100 μg led to enhanced anti-tumor efficacy with 5/6 mice tumor free. Bivalent: IL12(p40-p35)-Fc at 10 μg led to robust tumor control but led to 3/6 mice having >20% bodyweight loss demonstrating substantial toxicity. Bivalent: Fc-IL12(p40-p35) at 2 μg led to 5/6 mice being tumor free, with no mice having >20% bodyweight loss.

FIG. 24 shows the effect of the test fusion proteins on bodyweight. Bodyweight loss was used as a measurement of toxicity. IL12(p40-p35)-Fc at 2 μg led to minimal bodyweight loss and bivalent: Fc-IL12(p40-p35) at 2 μg led to low-level bodyweight loss. The combination of bivalent: IL12(p40-p35)-Fc at 2 μg and aPD-1 at 100 μg led to more severe bodyweight loss compared to bivalent: IL12(p40-p35)-Fc at 2 μg alone. Monovalent: IL12(p35×p40)-Fc at 2 μg and Bivalent: IL12(p40-p35)-Fc at 10 μg led to more severe bodyweight loss compared to bivalent: IL12(p40-p35)-Fc at 2 μg alone.

FIGS. 25A and 25B shows the effect of test muteins on tumor volume and bodyweight loss. Test muteins were administered IP every 3 days for 3 doses. Bivalent: Fc-IL12 (mutein 1) (20 μg) and bivalent: Fc-IL12(mutein 8) (20 μg) muteins maintained anti-tumor efficacy and tumor growth inhibition. Bivalent: Fc-IL12(mutein 8) (20 μg) had reduced bodyweight loss compared to a matched dose of Bivalent: Fc-IL12(mutein 1) (20 μg) or a reduced dose of wild-type Bivalent: Fc-IL12(p40-p35) (10 μg).

8.5. Example 4: Effect of Masking Moieties on IL12-Fc Fusion Proteins 8.5.1. Primary T Cell Binding Assay As observable in FIG. 26A, compared to the Fc-IL12 (p40-p35) control, Fc-IL12(mutein 1) and Fc-IL12(mutein 4) did not show major differences in binding to activated primary mouse T cells. Fc-IL12(mutein 16) and Fc-IL12 (mutein 15) demonstrated reduced binding to activated primary mouse T cells.

As observable in FIG. 26B, compared to the Fc-p40-p35×Fc control, Fc-p40-p35×Fc-IL12Rβ2(D1) did not show major differences in binding to activated primary mouse T cells while Fc-IL12Rβ1(D1)-p40-p35×Fc and Fc-p40-p35×Fc-IL12Rβ1(D1) had reduced binding to activated primary mouse T cells. These results suggest that the IL12Rβ1 subunit is critical for recruitment of IL12 to cells expressing the receptor complex.

In activated primary mouse T cells, compared to the Fc-IL12(p40-p35) control, Fc-IL12(mutein 1) showed minimally decreased pSTAT4 activity (FIG. 27A). Fc-IL12 (mutein 4) had no detectable pSTAT4 activity (FIG. 27A). Fc-IL12(mutein 16) and Fc-IL12(mutein 15) showed reduced pSTAT4 activity (FIG. 27A). Compared to Fc-p40-p35×Fc, Fc-p40-p35×Fc-IL12Rβ2(D1), Fc-IL12Rβ1(D1)-p40-p35×Fc, and Fc-p40-p35×Fc-IL12Rβ1(D1) had reduced pSTAT4 activity in activated primary mouse T cells (FIG. 27B).

8.5.1.1. Combined IL12Rβ1 and IL12Rβ2 Receptor-Masked Fc-IL12 has Further Reduced Activity than Either Mask Alone on Primary Mouse T Cells In activated primary mouse T cells, compared with the unmasked monovalent control Fc-p40-p35×Fc, Fc-IL12Rβ1 (D1)-p40-p35×Fc and Fc-p40-p35×Fc-IL12Rβ2(D1) had reduced potency for pSTAT4 activity (FIG. 30). The combination of both IL12Rβ1(D1) and IL12Rβ2(D1) masks in the same molecule as in Fc-IL12Rβ1(D1)-p40-p35×Fc-IL12Rβ2(D1) leads to further attenuation versus either mask alone (FIG. 30).

8.5.2. Engineered NK92 Reporter Assays

Engineered reporter cells were stimulated via either recombinant IL12, IL12-Fc fusion protein, or IL12-IL12R-Fc fusion proteins. The cytokine, through binding to the IL12 receptors beta 1 (IL12Rβ1) and beta 2 (IL12Rβ2), activated the signaling complex and induces STAT3 phosphorylation. STAT3 phosphorylation led to enhanced transcriptional activity of the STAT3 response elements driving the production of the reporter gene, luciferase. Compared with the unmasked bivalent control Fc-IL12(p40-p35), bivalent Fc-IL12Rβ1(D1)-p40-p35 had reduced potency of STAT3 bioactivity (FIG. 28). Compared with the unmasked monovalent control Fc-p40-p35×Fc, Fc-IL12Rβ1(D1)-p40-p35×Fc, Fc-p40-p35×Fc-IL12Rβ1(D1), and Fc-p40-p35×Fc-IL12Rβ2(D1) all had reduced potency of STAT3 bioactivity (FIG. 28). Fc-IL12Rβ1(D1)-p40-p35×Fc was the most attenuated molecule tested in this experiment.

Compared with the unmasked monovalent control Fc-p40-p35×Fc, Fc-IL12Rβ1(D1)-p40-p35×Fc and Fc-p40-p35×Fc-IL12Rβ2(D1) had reduced potency of STAT3 bioactivity (FIG. 29). The combination of both IL12Rβ1(D1) and IL12Rβ2(D1) masks in the same molecule as in Fc-IL12Rβ1 (D1)-p40-p35×Fc-IL12Rβ2(D1) lead to further attenuation versus either mask alone (FIG. 29).

8.5.2.1. IL12Rb1(D1 & D2) does not Further Attenuate IL12 Versus IL12Rb1(D1) Alone and IL12Rb2(D1 & D2) does not Further Attenuate IL12 Versus IL12Rb2(D1) Alone Engineered reporter cells were stimulated via either recombinant IL12, IL12-Fc fusion proteins, or IL12-IL12R-Fc fusion proteins. Compared to the unmasked Fc-p40-p35×Fc control, Fc-p40-p35×Fc-IL12Rβ1(D1) had attenuated STAT3 bioactivity (FIG. 31). The addition of IL12Rβ1 domain 2 (D2) as in Fc-p40-p35×Fc-IL12Rβ11(D1-2) did not lead to further attenuation versus IL12Rβ1 domain 1 (D1) alone as in Fc-p40-p35×Fc-IL12Rβ1(D1) (FIG. 31). Compared to the unmasked Fc-p40-p35×Fc control, Fc-p40-p35×Fc-IL12Rβ2(D1) had attenuated STAT3 bioactivity (FIG. 31). The addition of IL12Rβ2 domain 2 (D2) as in Fc-p40-p35×Fc-IL12Rβ2(D1-2) did not lead to further attenuation versus IL12Rβ2 domain 1 (D1) alone as in Fc-p40-p35×Fc-IL12Rβ2(D1) (FIG. 31).

8.5.2.2. mAb-Targeted IL12 Variant has Enhanced pSTAT3 Activity on Target-Expressing Cells Compared to an Untargeted Control Construct Reporter cells engineered to express hPD-1 were stimulated via either recombinant IL12, anti-hCD20-IL12 fusion proteins, or anti-hPD1-IL12 fusion proteins. Compared to recombinant mIL12 and the unmasked Fc-p40-p35×Fc control, non-targeted anti-hCD20-<IL12Rβ1(D1)-p40-p35 (monovalent)> and anti-hCD20-<p40-p35×IL12Rβ2(D1)> had attenuated STAT3 bioactivity on the engineered NK92 reporter cells overexpressing hPD1 (FIG. 32). Anti-hPD1-<IL12Rβ1(D1)-p40-p35 (monovalent)> had increased potency of STAT3 activity versus anti-hCD20-<IL12Rβ1 (D1)-p40-p35 (monovalent)>, and anti-hPD1-<p40-p35× IL12Rβ2(D1)> had increased potency of STAT3 activity versus anti-hCD20-<p40-p35×IL12Rβ2(D1)>, demonstrating target-enhanced STAT3 activity (FIG. 32).

8.5.2.3. mAb-Based Masking Attenuates IL12 Activity on Human NK92 Cells

Engineered reporter cells were stimulated via either recombinant IL12, IL12-Fc fusion proteins, or IL12 antibody fragment-masked Fc fusion proteins. Fc-p40-p35×Fc-scFv #A(VL-VH), Fc-p40-p35×Fc-scFv #A(VH-VL), Fc-p40-p35×Fc-Fab #A, and Fc-p40-p35×scFv #B(VL-VH) all had reduced potency of STAT3 bioactivity compared to recombinant mIL12 or the unmasked control Fc-p40-p35× Fc (FIG. 33). Fc-p40-p35×Fc-scFv #A(VL-VH) had further reduced potency of STAT3 bioactivity compared to Fc-p40-p35×scFv #B(VL-VH) (FIG. 33).

8.5.3. HT-2 Reporter Assay—IL12 Antibody Fragment-Based Masking Attenuates IL12 Activity on Murine HT-2 Cells Engineered HT-2 reporter cells were stimulated via either recombinant IL12, IL12-Fc fusion proteins, or IL12-mAb-based-mask-Fc fusion proteins. Fc-p40-p35×Fc-scFv #A(VL-VH), Fc-p40-p35×Fc-scFv #A(VH-VL), Fc-p40-p35×Fc-Fab #A, and Fc-p40-p35×scFv #B(VL-VH) all had reduced potency of STAT3 bioactivity compared to recombinant mIL12 or the unmasked control Fc-p40-p35×Fc (FIG. 34). Fc-p40-p35×Fc-scFv #A(VL-VH) had further reduced potency of STAT3 bioactivity compared to Fc-p40-p35× scFv #B(VL-VH) (FIG. 34).

8.6. Example 5: Receptor Masked Fc-IL12 have Attenuated Bioactivity and Reduced Toxicity In Vivo Referring to FIGS. 35A and 35B The anti-tumor activity of receptor masked Fc-IL12 fusion proteins in an MC38 tumor model was evaluated. $3\times10^5$ MC38 tumor cells were implanted subcutaneously into the right flanks of C57BL/6 mice. Once tumors had reached an average volume of 100 mm3 on day 10, mice were randomized into groups (n=6-7/group) and dosed on day 10 and 13 intraperitoneally (IP) with hIgG4s isotype control, or 10 micrograms of Fc-p40-p35×Fc, Fc-IL12Rβ1 (D1)-p40-p35×Fc, or Fc-p40-p35×Fc-IL12Rβ2(D1). Each tumor measurement represents the average+/−SEM. Both Fc-IL12Rβ11(D1)-p40-p35×Fc, and Fc-p40-p35×Fc-IL12Rβ2(D1) led to tumor growth inhibition compared to the isotype group. Fc-p40-p35×Fc measurements were only taken till day 16 when mice from that group were euthanized due to >20% body weight loss.

FIG. 35C demonstrates the percent change in body weight during the experiment in FIGS. 35A and 35B. Fc-IL12Rβ1 (D1)-p40-p35×Fc, or Fc-p40-p35×Fc-IL12Rβ2(D1) led to reduced body weight loss compared to Fc-p40-p35×Fc.

Figure 36A:
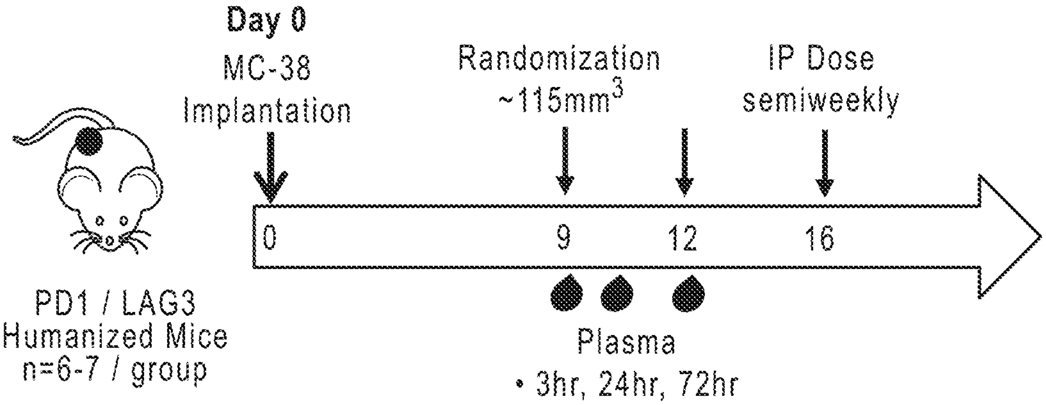
Figure 36B:
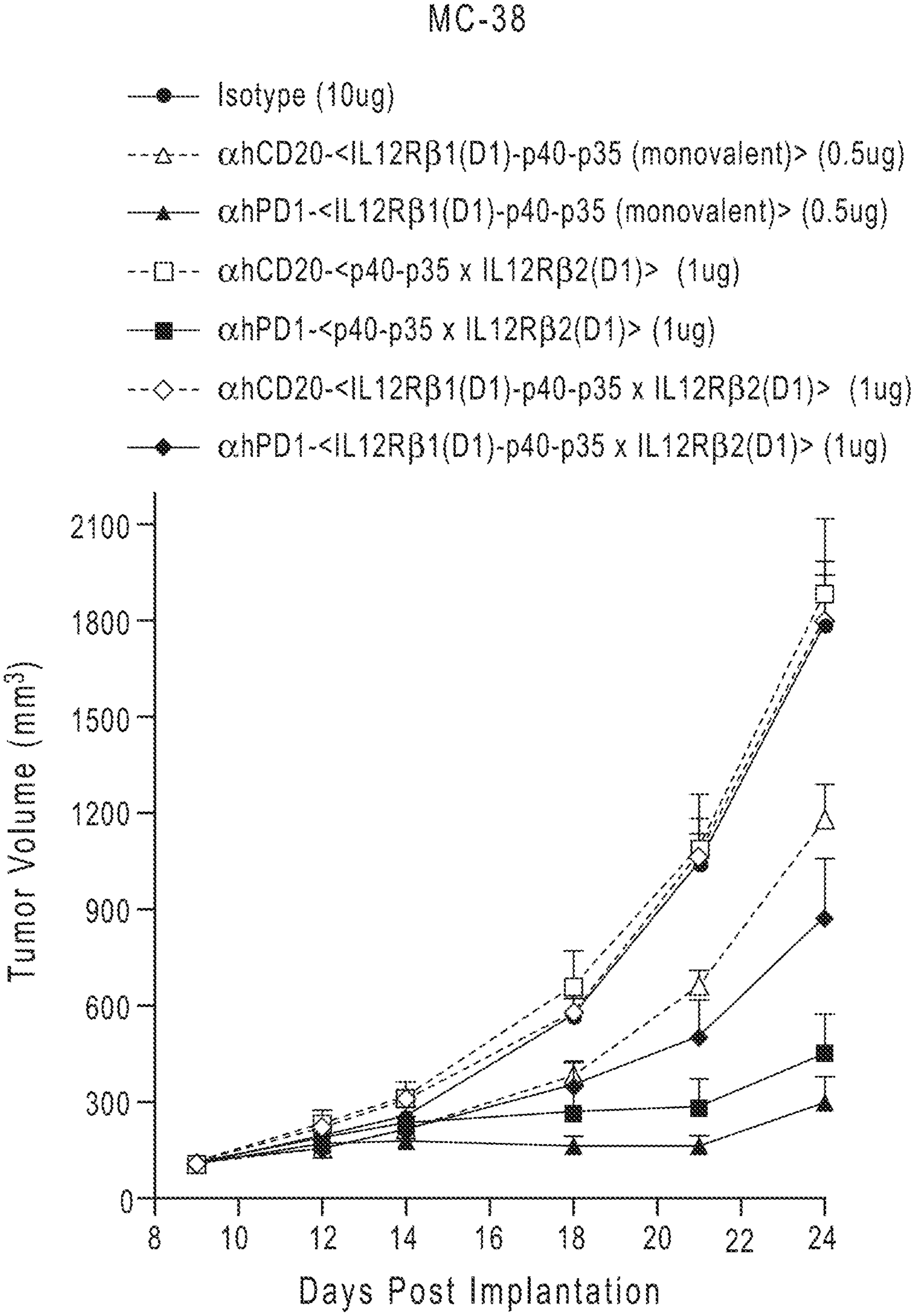

8.7. Example 6: Effect of PD1-Targeted-Receptor Masked IL12 Constructs on Anti-Tumor Efficacy and Toxicity FIGS. 36A and 36B depict the anti-tumor activity of PD1-targeted-receptor masked IL12 fusion proteins in an MC38 tumor model. $3\times10^5$ MC38 tumor cells were implanted subcutaneously into the right flanks of PD-1× LAG3 knock-in mice (doi: 10.1158/1535-7163.MCT-16-0665). Once tumors had reached an average volume of 115 mm3 on day 9, mice were randomized into groups (n=6-7/group) and dosed on day 9, 12, and 16 intraperitoneally (IP) with hIgG4s isotype control or indicated dose of PD1-targeted-receptor masked IL12 fusion proteins. αhPD1-<IL12Rβ1(D1)-p40-p35 (monovalent)> led to tumor growth inhibition compared to the isotype control or the αhCD20-<IL12Rβ1(D1)-p40-p35 (monovalent)> test protein that is targeted to an irrelevant antigen. αhPD1-<p40-p35× IL12Rβ2(D1)> led to tumor growth inhibition compared to the isotype control or the αhCD20-<p40-p35×IL12Rβ2 (D1)> test protein that is targeted to an irrelevant antigen. αhPD1-<IL12Rβ1 (D1)-p40-p35×IL12Rβ2(D1)> led to tumor growth inhibition compared to the isotype control or the αhCD20-<IL12Rβ1(D1)-p40-p35×IL12Rβ2(D1)> test protein that is targeted to an irrelevant antigen. Each tumor measurement represents the average+/−SEM.

Figure 36C:
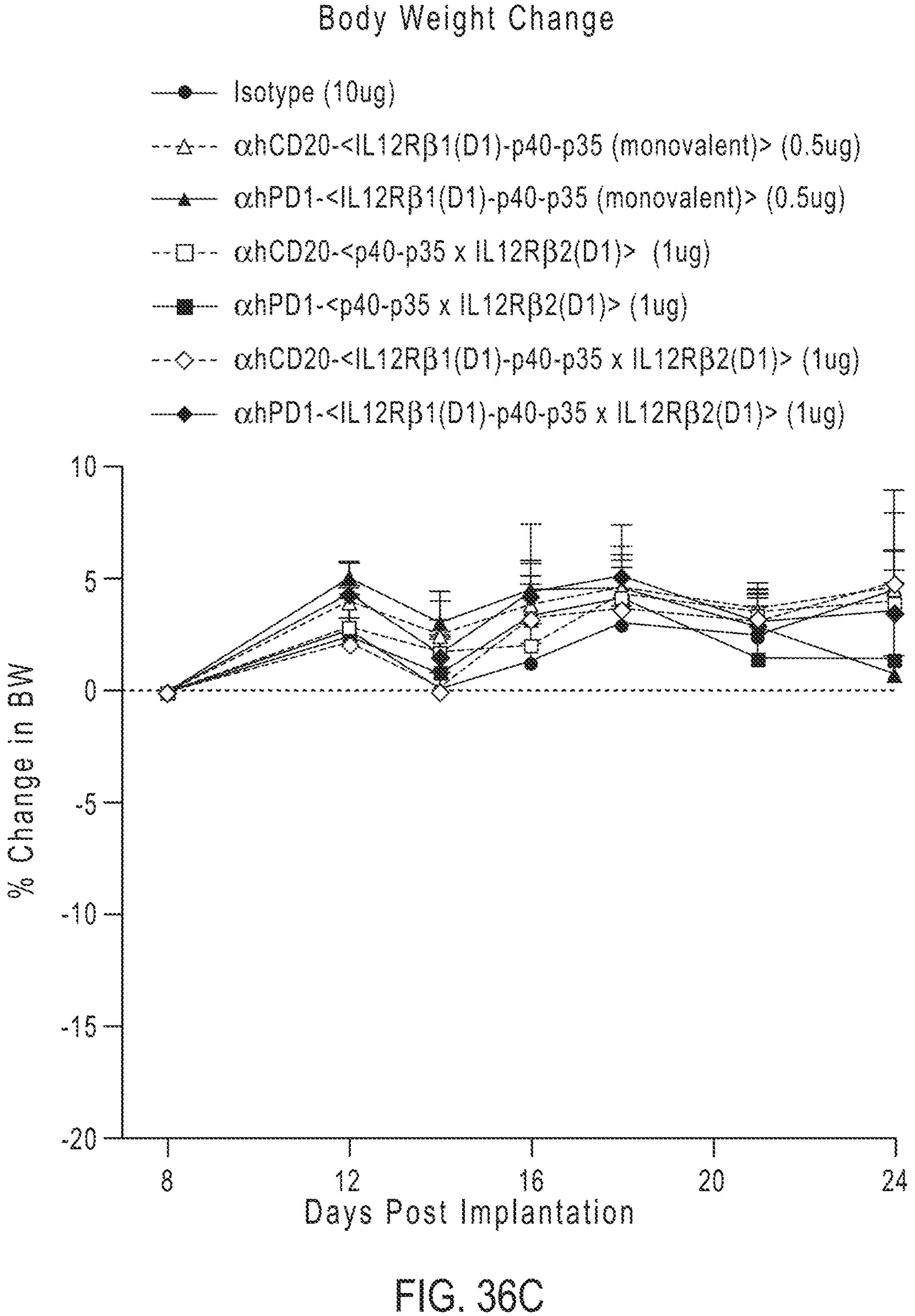

FIG. 36C depicts the percent body weight change from mice related to FIGS. 36A and 36B. Data represents the average+/−SEM. No treatment group demonstrated body weight loss (a measure of obvious toxicity) throughout the study.

Figure 36D:
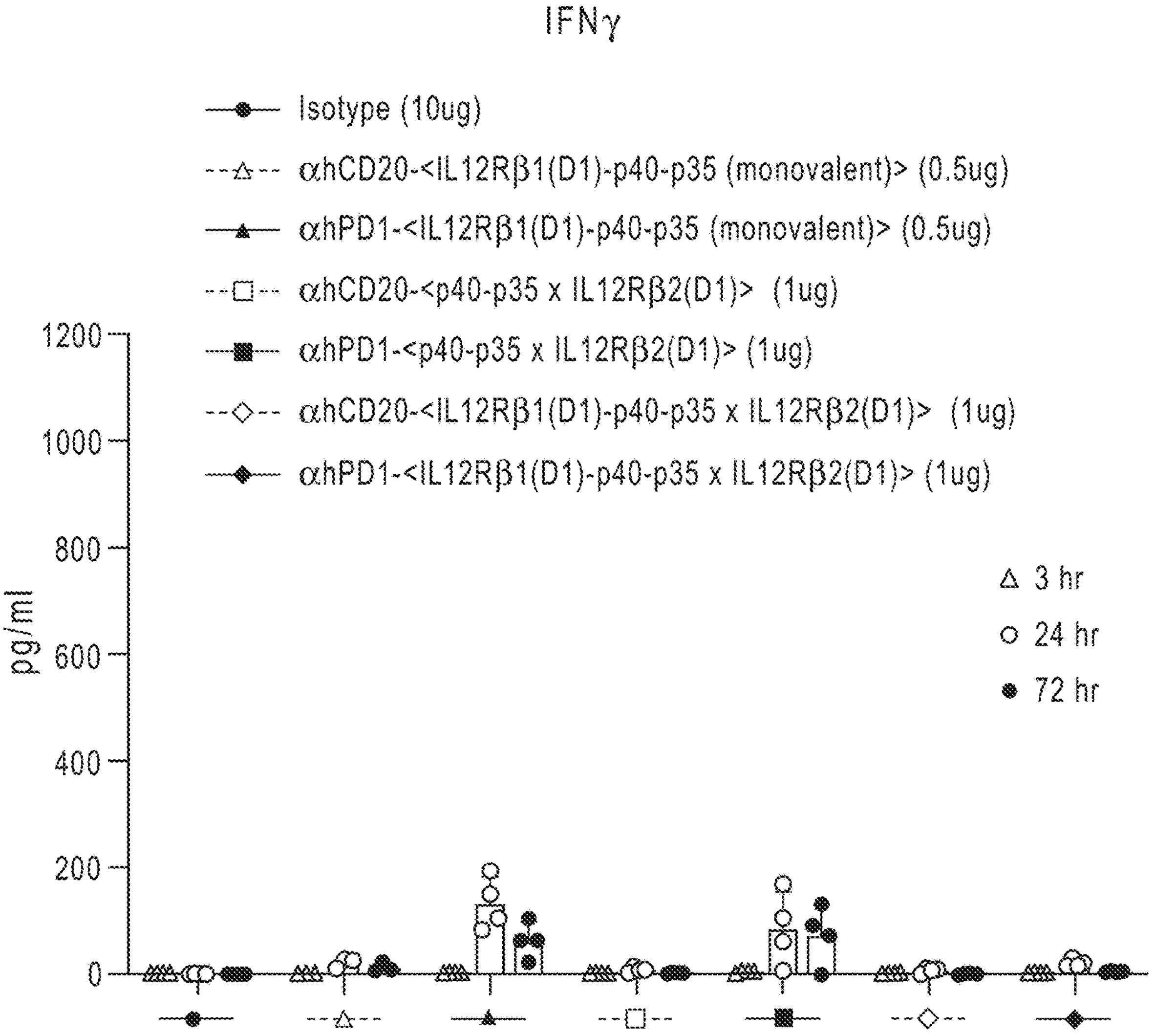
Figure 36E:
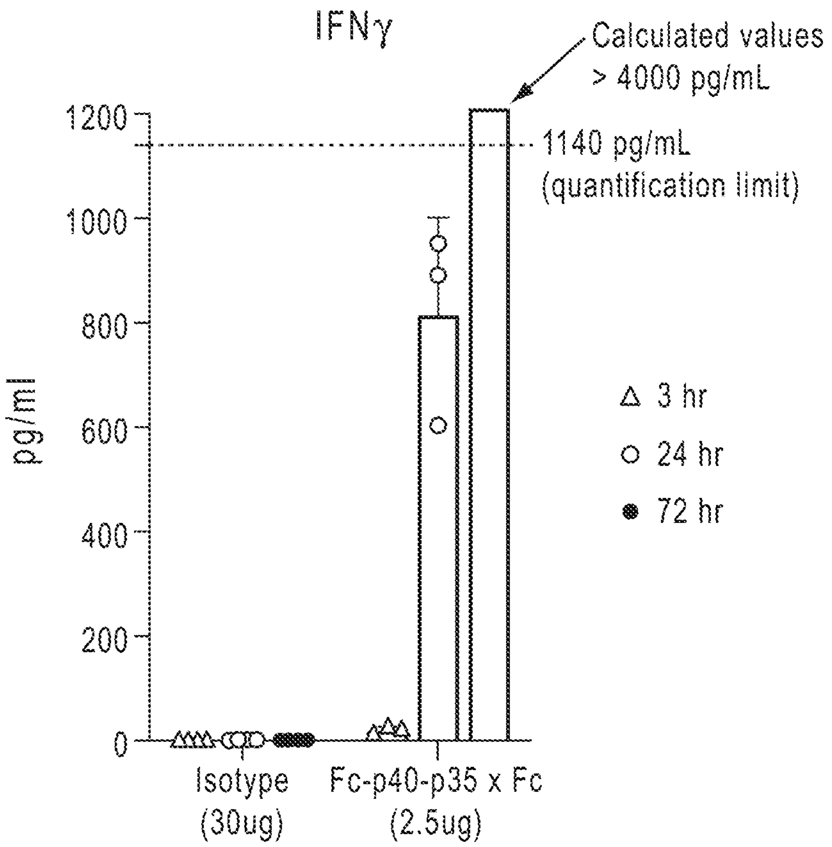

FIGS. 36D and 36E depicts the serum IFNγ levels after 3, 24 and 72 hrs post intraperitoneal dosing with the indicated proteins in mice bearing MC38 tumors. Serum IFNγ levels were measured using the V-PLEX Proinflammatory Panell (mouse) Kit (K15048D-1) from Meso Scale Discovery, LLC (Rockville, Maryland). αhPD1-<IL12Rβ1(D1)-p40-p35 (monovalent)>, irrelevant target αhCD20-<IL12Rβ1(D1)-p40-p35 (monovalent)>, αhPD1-<p40-p35×IL12Rβ2(D1)>, irrelevant target αhCD20-<p40-p35×IL12Rβ2(D1)>, αhPD1-<IL12Rβ1(D1)-p40-p35×IL12Rβ2(D1)>, and irrelevant target αhCD20-<IL12Rβ1(D1)-p40-p35×IL12Rβ2 (D1)> all led to lower serum IFNγ levels (a biomarker of toxicity) compared to data from the unmasked Fc-p40-p35× Fc control (FIG. 36E) at the same timepoints.

FIGS. 37A and 37B evaluate anti-tumor efficacy of αhPD1-<IL12Rβ1(D1)-p40-p35 (monovalent)> versus the combination of irrelevant target αhCD20-<p40-p35× IL12Rβ2(D1)> plus αPD1 (REGN2810) (doi: 10.1158/1535-7163.MCT-16-0665). $3\times10^5$ MC38 tumor cells were implanted subcutaneously into the right flanks of PD-1× LAG3 knock-in mice (doi: 10.1158/1535-7163.MCT-16-0665). Once tumors had reached an average volume of 125 $mm^3$ on day 9, mice were randomized into groups (n=5-7/group) and dosed on day 9, 12, and 16 intraperitoneally (IP) with hIgG4s isotype control or indicated dose of test protein. The monotherapy of αhPD1-<IL12Rβ1(D1)-p40-p35 (monovalent)> had superior anti-tumor efficacy than the combination of αhCD20-<p40-p35×IL12Rβ2(D1)> plus αPD1 (REGN2810).

Figure 38A:
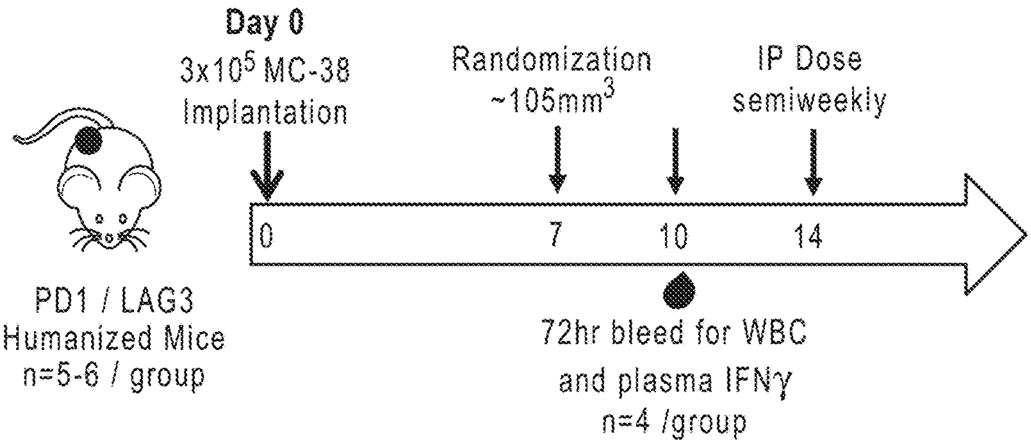
Figures 1, 38B:
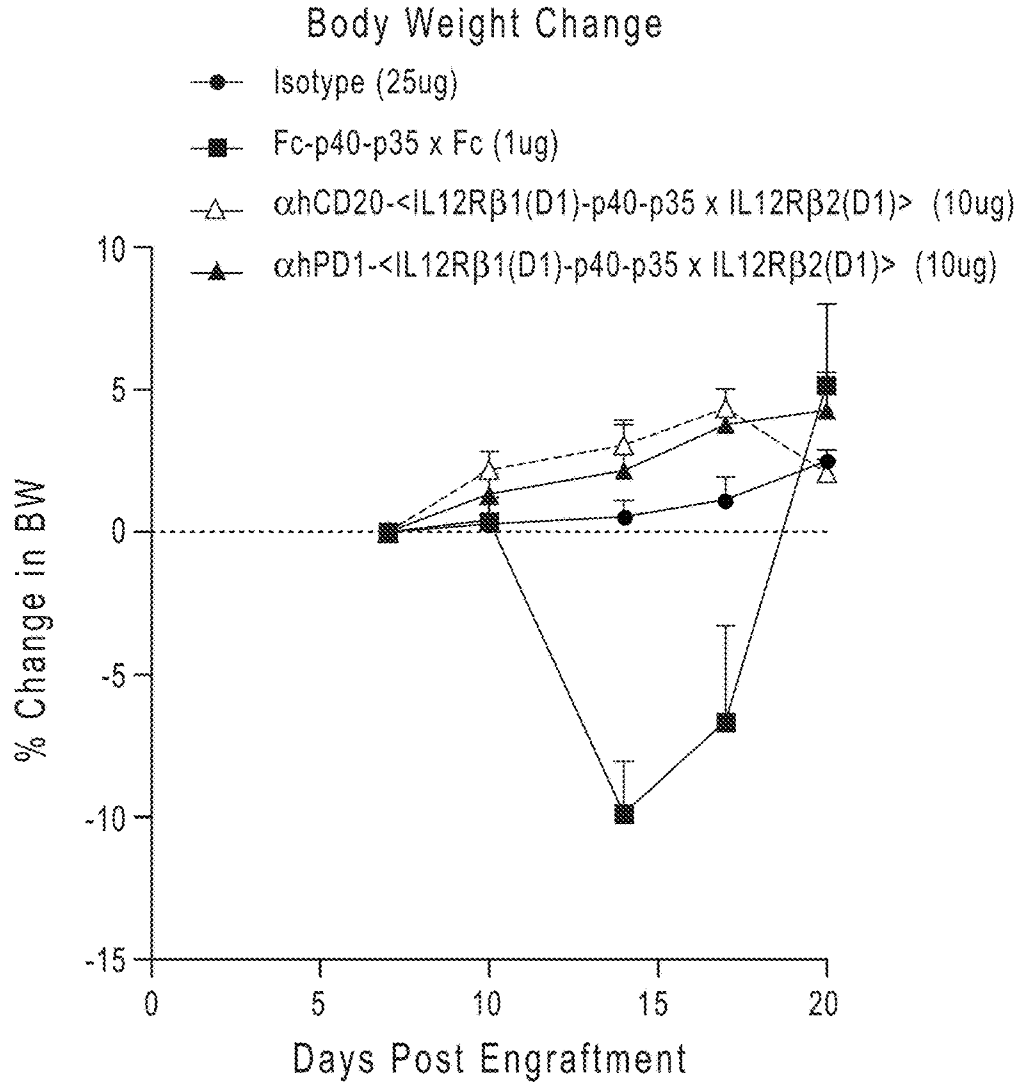
Figures 2, 38B:
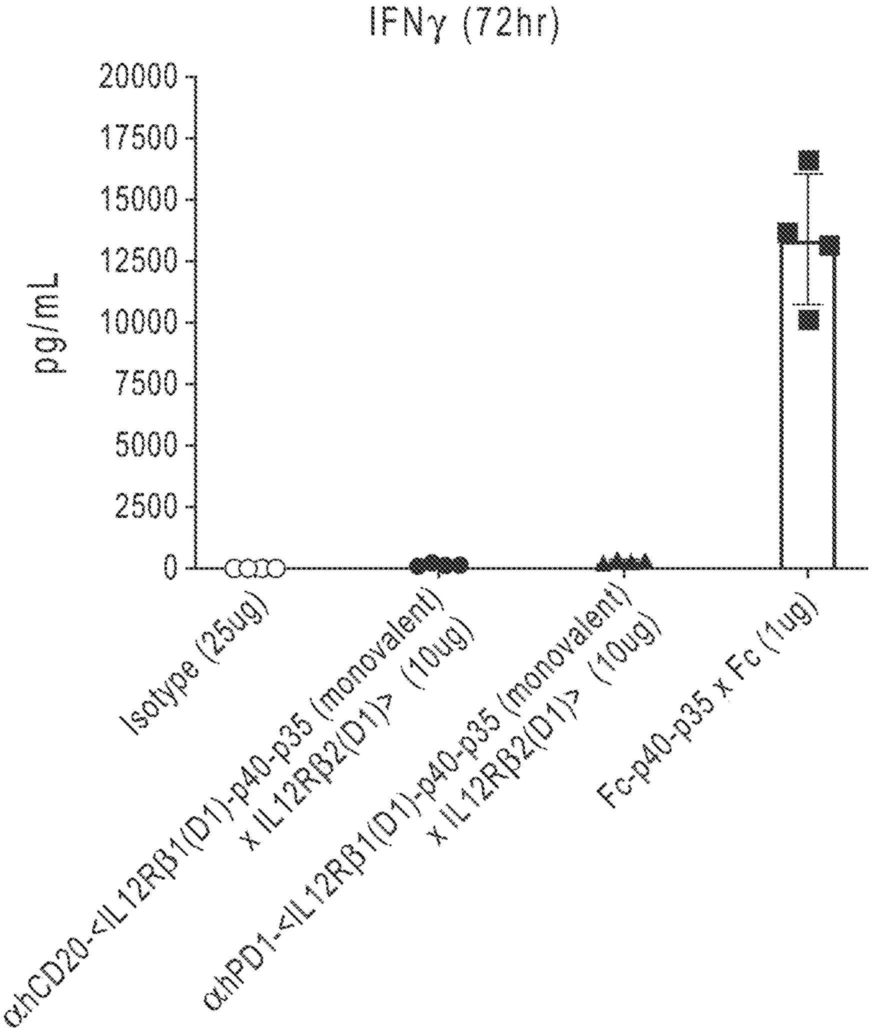
Figures 1, 38C:
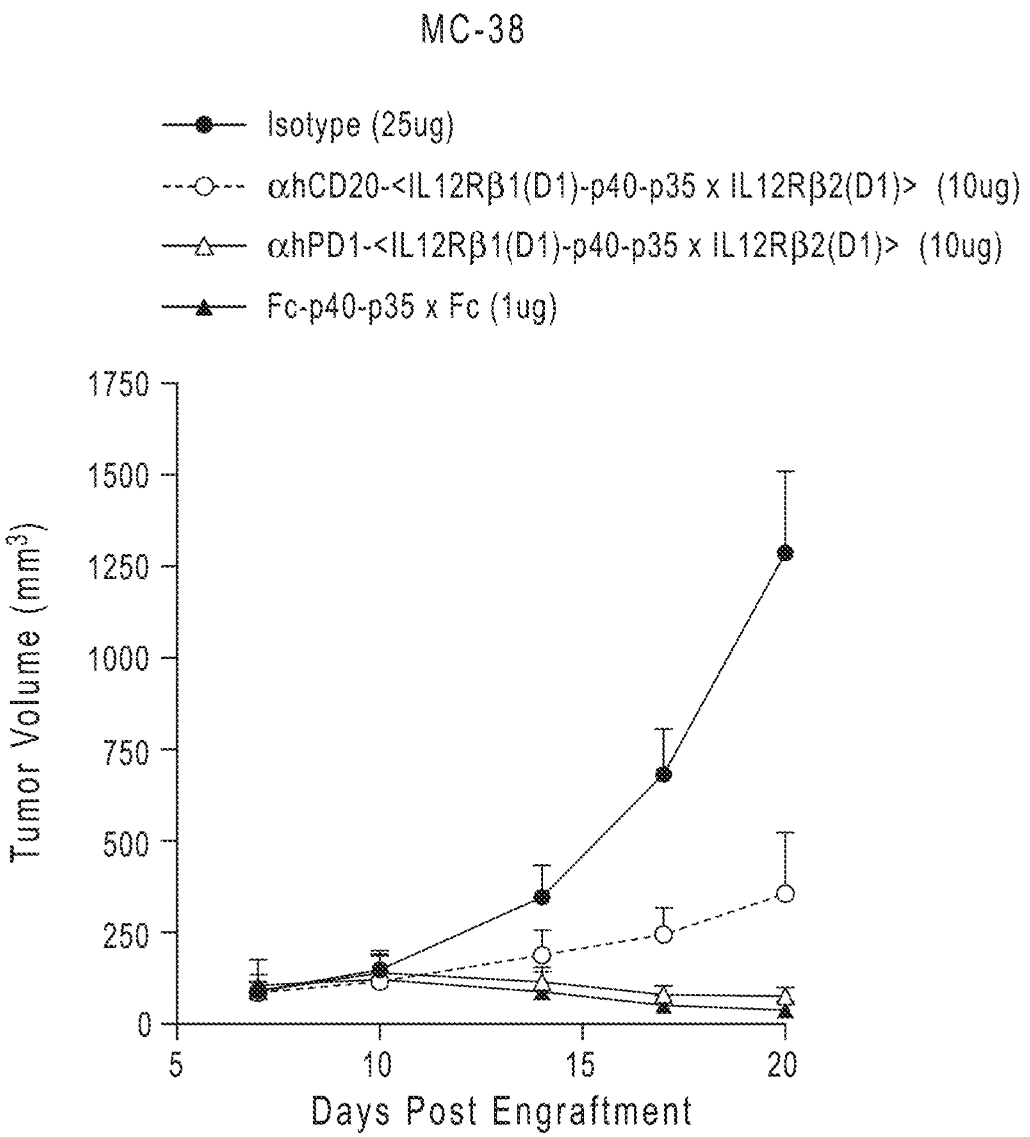
Figures 2, 38C:
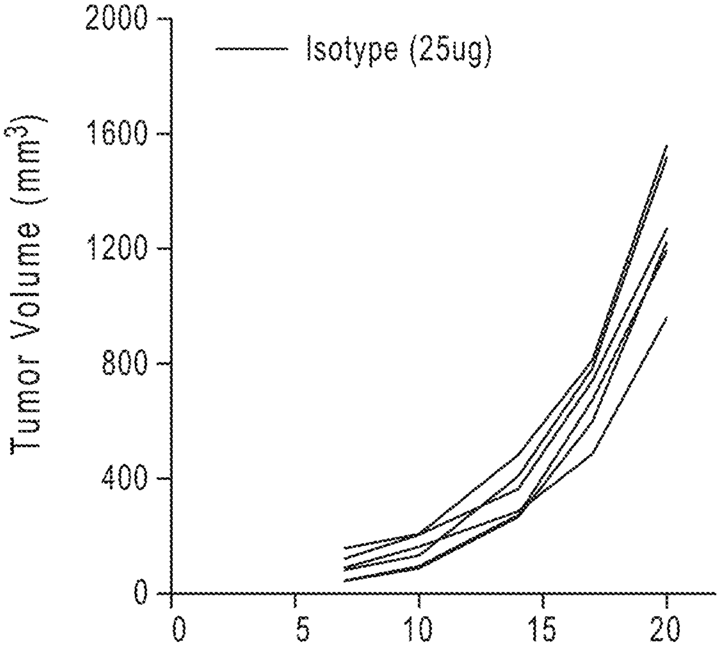
Figures 3, 38C:
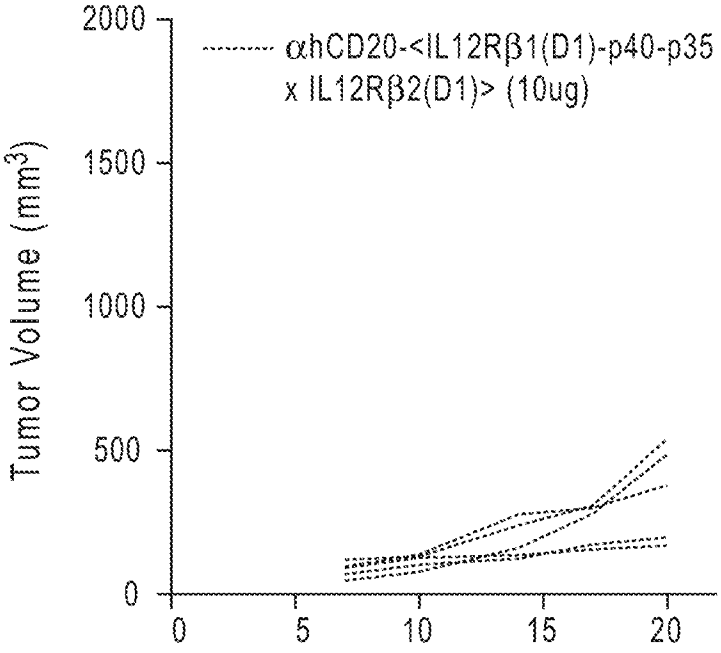
Figures 4, 38C:
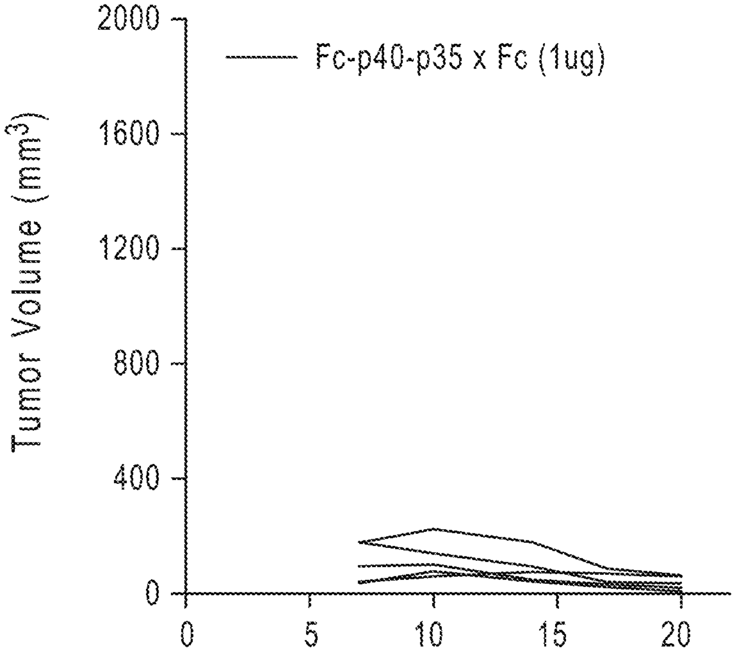
Figures 5, 38C:
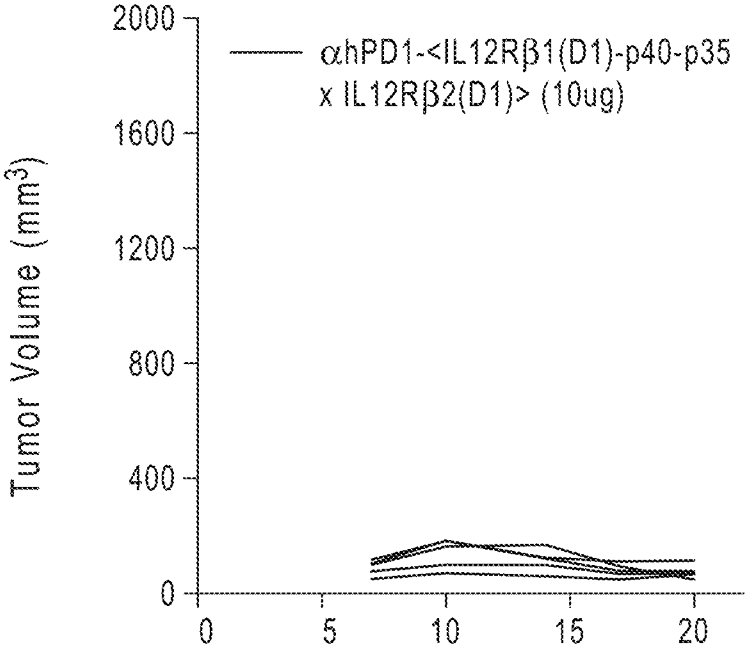

FIG. 38A depicts the experimental scheme for FIG. 38B and FIG. 38C. $3\times10^5$ MC38 tumor cells were implanted subcutaneously into the right flanks of PD-1×LAG3 knock-in mice (doi: 10.1158/1535-7163.MCT-16-0665). Once tumors had reached an average volume of 105 $mm^3$ on day 7, mice were randomized into groups (n=5-6/group) and dosed on day 7, 10, and 14 intraperitoneally (IP).

FIG. 38B-1 depicts the percent body weight change from the experiment as described in FIG. 38A. Mice treated with Fc-p40-p35×Fc (1 ug) had substantial body weight loss while mice treated with a higher dose of αhPD1-<IL12Rβ1 (D1)-p40-p35×IL12Rβ2(D1)> (10 ug) or αhCD20-<IL12Rβ1 (D1)-p40-p35×IL12Rβ2(D1)> (10 ug) targeting an irrelevant antigen did not have body weight loss.

FIG. 38B-2 depicts the level of serum IFNγ at 72 hours post first dose (and before the second dose) in mice from the experiment as described in FIG. 38A. IFNγ levels were measured by AlphaLISA (Perkin Elmer AL501C, Waltham, MA). Fc-p40-p35×Fc (1 ug) led to substantial serum IFNγ (a biomarker of toxicity) while αhPD1-<IL12Rβ11(D1)-p40-p35×IL12Rβ2(D1)> (10 ug) or αhCD20-<IL12Rβ11(D1)-p40-p35×IL12Rβ2(D1)> (10 ug) led to minimal serum IFNγ.

FIG. 38C-1 depicts the tumor growth of mice after $3\times10^5$ MC38 tumor cells were implanted subcutaneously into the right flanks of PD-1×LAG3 knock-in mice (doi: 10.1158/1535-7163.MCT-16-0665). Once tumors had reached an average volume of 105 $mm^3$ on day 7, mice were randomized into groups (n=5-6/group) and dosed on day 7, 10, and 14 intraperitoneally (IP). Fc-p40-p35×Fc (1 ug) led to robust tumor control (FIG. 38C-1) however also led to toxicity as evidenced by body weight loss (FIG. 38B-1). αhPD1-<IL12Rβ1(D1)-p40-p35×IL12Rβ2(D1)> (10 ug) led to tumor control comparable to Fc-p40-p35×Fc (1 ug) without any body weight loss (FIG. 38B-1).

FIGS. 38C-2, 3, 4, 5 depict individual tumor growth curves of the individual mice.

8.8. Example 7: Effect of PD1-Targeted-Antibody-Masked IL12 Constructs on Bioactivity, Anti-Tumor Efficacy, and Toxicity FIG. 40A: NK92/STAT3-Luc cl.7F7/hPD1 reporter cells engineered to express hPD-1 were stimulated via either Fc-p40-p35×Fc control, various targeted and untargeted antibody-masked IL12 protein constructs, or targeted and untargeted receptor masked IL12 protein constructs as described in Section 8.1.7. At the 4-hour timepoint, compared to the unmasked Fc-p40-p35×Fc control, the following constructs targeting the irrelevant antigen hCD20 had reduced STAT3 bioactivity: αhCD20-<scFV #A(VL-VH)×mIL12p40-p35>, αhCD20-<scFV #B(VL-VH)×mIL12p40-p35>, and αhCD20-<IL12Rβ1(D1)-p40-p35 (monovalent)>. αhPD1-<scFV #A(VL-VH)×mIL12p40-p35> had target enhanced activity compared to αhCD20-<scFV #A(VL-VH)×mIL12p40-p35>, αhPD1-<scFV #B(VL-VH)×mIL12p40-p35> had target-enhanced activity compared to αhCD20-<scFV #B(VL-VH)×mIL12p40-p35>, and αhPD1-<IL12Rβ1 (D1)-p40-p35 (monovalent)> had target-enhanced activity compared to αhCD20-<IL12Rβ1(D1)-p40-p35 (monovalent)>. FIG. 40A-1 depicts a zoomed axis of FIG. 40A to better illustrate the target-enhanced activity of αhPD1-<scFV #A(VL-VH)×mIL12p40-p35> compared to αhCD20-<scFV #A(VL-VH)×mIL12p40-p35> on NK92/STAT3-Luc/hPD1 cells. NK92/STAT3-Luc Parental does not express hPD-1. αhPD1-<scFV #A(VL-VH)×mIL12p40-p35> has similar bioactivity to αhCD20-<scFV #A(VL-VH)×mIL12p40-p35> on NK92/STAT3-Luc Parental demonstrating the target-independent activity of these proteins are similar.

FIG. 40B: NK92/STAT3-Luc cl.7F7/hPD1 reporter cells engineered to express hPD-1 were stimulated via either Fc-p40-p35×Fc control, various targeted and untargeted antibody-masked IL12 protein constructs, or targeted and untargeted receptor masked IL12 protein constructs as described in Section 8.1.7. At the 24-hour timepoint, αhPD1-<scFV #A(VL-VH)×mIL12p40-p35> had target enhanced activity compared to αhCD20-<scFV #A(VL-VH)×mIL12p40-p35>, and αhPD1-<scFV #B(VL-VH)×mIL12p40-p35> had target-enhanced activity compared to αhCD20-<scFV #B(VL-VH)×mIL12p40-p35>.

Figure 41A:
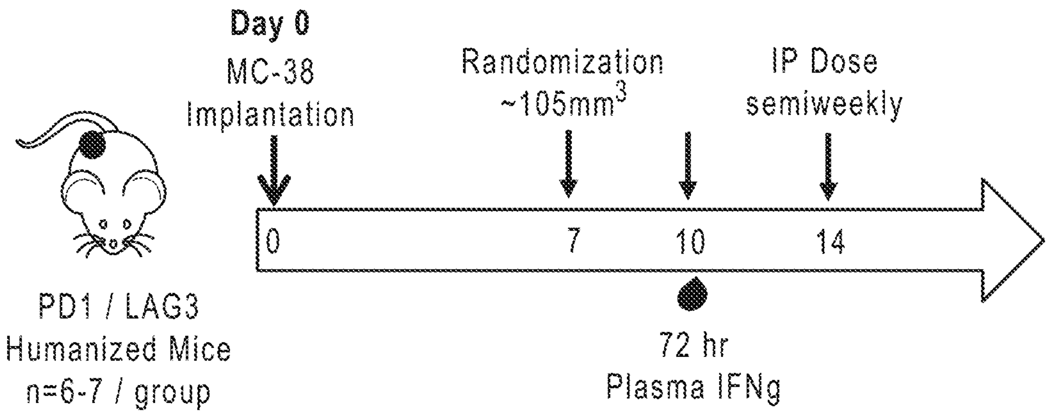
Figure 41B:
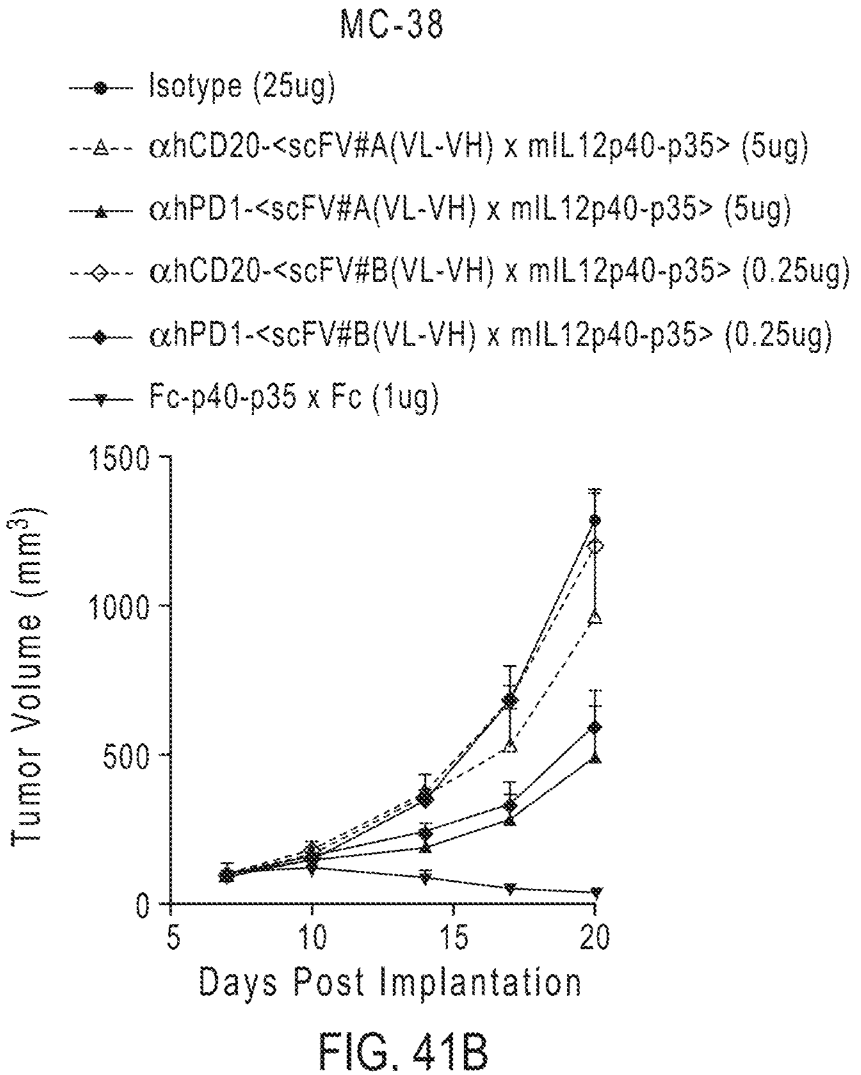
Figure 41C:
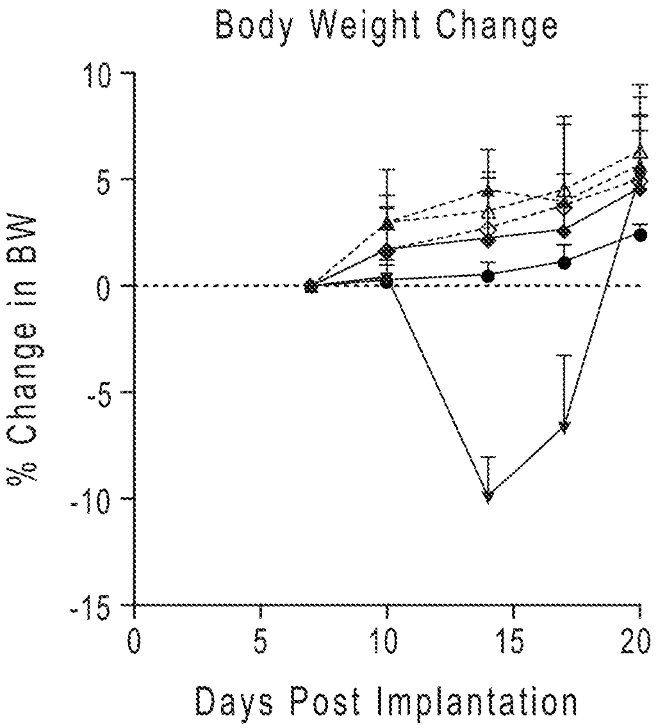
Figure 41D:
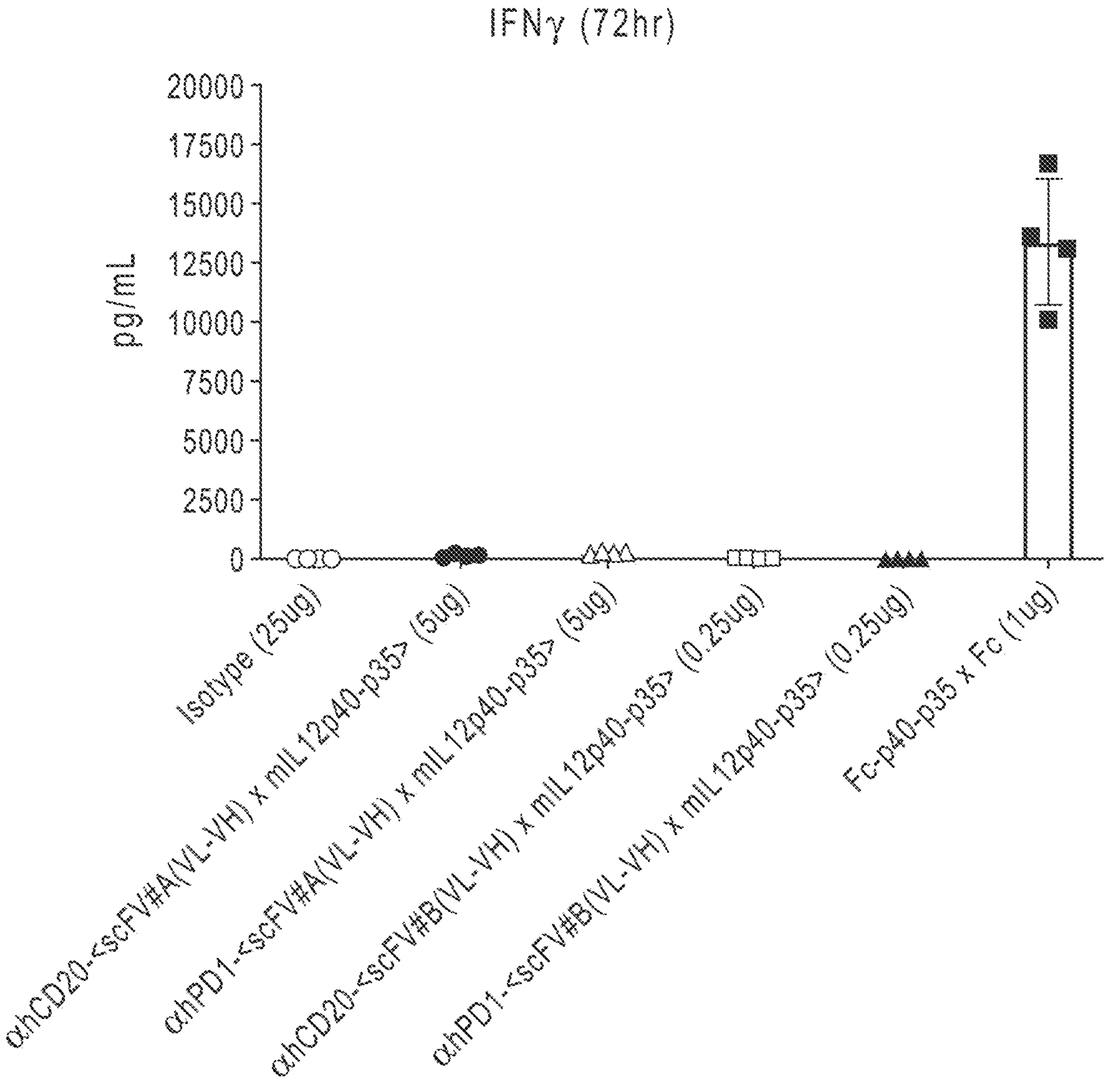

FIG. 41A depicts the experimental scheme for FIGS. 41B, 41C, and 41D. $3\times10^5$ MC38 tumor cells were implanted subcutaneously into the right flanks of PD-1×LAG3 knock-in mice (doi: 10.1158/1535-7163.MCT-16-0665). Once tumors had reached an average volume of 105 $mm^3$ on day 7, mice were randomized into groups (n=5-6/group) and dosed on day 7, 10, and 14 intraperitoneally (IP).

FIG. 41B depicts tumor growth curves for mice as described in FIG. 41A treated with indicated doses and proteins. αhPD1-<scFV #A(VL-VH)×mIL12p40-p35> treated mice had tumor growth inhibition compared to isotype-treated mice or αhCD20-<scFV #A(VL-VH)×mIL12p40-p35> (targeting irrelevant antigen) treated mice. αhPD1-<scFV #B(VL-VH)×mIL12p40-p35> treated mice had tumor growth inhibition compared to αhCD20-<scFV #B(VL-VH)×mIL12p40-p35> (targeting irrelevant antigen) treated mice.

FIG. 41C depicts the percent body weight change of mice as described in FIG. 41A treated with indicated doses and proteins. Mice treated with Fc-p40-p35×Fc (1 ug) had substantial body weight loss while mice treated with αhPD1-<scFV #A(VL-VH)×mIL12p40-p35> (5 ug), αhCD20-<scFV #A(VL-VH)×mIL12p40-p35> (5 ug) (targeting irrelevant antigen), αhPD1-<scFV #B(VL-VH)×mIL12p40-p35> (0.25 ug), or αhCD20-<scFV #B(VL-VH)×mIL12p40-p35> (0.25 ug) (targeting irrelevant antigen) did not have body weight loss.

FIG. 41D depicts the level of serum IFNγ at 72 hours post first dosing in mice from the experiment as described in FIG. 41A. IFNγ levels were measured by AlphaLISA (Perkin Elmer AL501C, Waltham, MA). Fc-p40-p35×Fc (1 ug) led to substantial serum IFNγ (a biomarker of toxicity) while αhPD1-<scFV #A(VL-VH)×mIL12p40-p35> (5 ug), αhCD20-<scFV #A(VL-VH)×mIL12p40-p35> (5 ug) (targeting irrelevant antigen), αhPD1-<scFV #B(VL-VH)×mIL12p40-p35> (0.25 ug), or αhCD20-<scFV #B(VL-VH)×mIL12p40-p35> (0.25 ug) (targeting irrelevant antigen) treatment led to minimal serum IFNγ.

8.9. Example 8: Effect of the Combination of Receptor Mask for One IL12 Subunit and Mutein on the Opposite Subunit Engineered HT-2 reporter cells were stimulated via either recombinant IL12, IL12-Fc fusion proteins, receptor-masked IL12-Fc fusion proteins, or receptor-masked IL12 (mutein)-Fc fusion proteins as described in Section 8.1.7. Referring to FIG. 42, compared to recombinant mIL12 and the unmasked Fc-p40-p35×Fc control, Fc-p40-p35×Fc-IL12Rβ2(D1) has reduced bioactivity. Fc-p40(mutein 24)-p35×Fc-IL12Rβ2(D1) has further reduced bioactivity demonstrating the combination attenuation effect of the IL12Rβ2 (D1) mask and a p40 mutein.

Referring to FIG. 43, engineered HT-2 reporter cells were stimulated via either recombinant IL12, IL12-Fc fusion proteins, receptor-masked IL12-Fc fusion proteins, or receptor-masked IL12(mutein)-Fc fusion proteins as described in Section 8.1.7. Compared to recombinant mIL12 and the unmasked Fc-p40-p35×Fc control, Fc-IL12Rβ1(D1)-p40-p35 has reduced bioactivity. Fc-IL12Rβ1 (D1)-p40-p35 (mutein 25), Fc-IL12Rβ1 (D1)-p40-p35(mutein 26), Fc-IL12Rβ1(D1)-p40-p35(mutein 27), and Fc-IL12Rβ1 (D1)-p40-p35(mutein 28) all have substantially further reduced bioactivity. This demonstrates the combination attenuation effect of the IL12Rβ1(D1) mask and a p35 mutein.

8.10. Example 9: '3 Chain' Format Protein Constructs with Receptor Masks Attenuate IL12 Bioactivity Engineered HT-2 reporter cells were stimulated via either recombinant mIL12, IL12-Fc fusion proteins, or receptor masked IL12 fusion proteins as described in Section 8.1.7. As shown in FIG. 44, compared to recombinant mIL12, the unmasked Fc-p35×Fc×p40 has comparable bioactivity. Fc-p35×Fc-IL12Rβ2(D1)×p40 and Fc-p35×Fc×IL12Rβ1 (D1)-p40 have reduced bioactivity compared to the unmasked Fc-p35×Fc×p40. Fc-p35×Fc-IL12Rβ2(D1)× IL12Rβ1(D1)-p40 had further reduced bioactivity compared to either the Fc-p35×Fc-IL12Rβ2(D1)×p40 and Fc-p35×Fc× IL12Rβ1(D1)-p40. Fc-p35×Fc-IL12Rβ2(D1)×IL12Rβ1 (D1)-p40 also had reduced bioactivity versus Fc-p40-p35× Fc, Fc-IL12Rβ1(D1)-p40-p35×Fc, Fc-p40-p35×Fc-IL12Rβ2 (D1), and Fc-IL12Rβ1(D1)-p40-p35×Fc-IL12Rβ2 (D1).

8.11. Example 10: Receptor-Masked IL12 has Target-Enhanced Bioactivity

Reporter cells engineered to express hPD-1 were stimulated via IL12 fusion proteins as described in Section 8.1.7. As shown in FIG. 45, compared to the unmasked Fc-p40-p35×Fc control, IL12Rβ1(D1)-IL12p40-p35×αhCD20 (which is targeted to an irrelevant CD20 antigen) has attenuated bioactivity. Compared to IL12Rβ1(D1)-IL12p40-p35× αhCD20, IL12Rβ1(D1)-IL12p40-p35×αhPD1 has target-enhanced bioactivity.

8.12. Example 11: Receptor-Masked IL12 has Target-Enhanced Bioactivity

8.12.1. Materials & Methods

The '3 chain' format protein constructs with receptor masks were evaluated for in vivo activity in an MC38 tumor model according to the protocol shown in FIG. 46A. $3\times10^5$ MC38 tumor cells were implanted subcutaneously into the right flanks of C57/BL6 female mice. Once tumors had reached an average volume of 80 $mm^3$ on day 10, mice were randomized into groups (n=5/group) and dosed on day 10, 13, and 16 intraperitoneally (IP) with hIgG4s isotype control or (1) Fc-p35×Fc×p40 (non-masked), (2) Fc-p35×Fc× IL12Rβ2(D1)-p40 (single masked), (3) Fc-p35×Fc-IL12Rβ1(D1)×p40 (single-masked), or (4) Fc-p35×Fc× IL12Rβ2(D1)×IL12Rβ2(D1)-p40 (double-masked).

Tumor growth, body weight and 72-hour serum IFNγ were measured (using AlphaLISA (Perkin Elmer AL501C, Waltham, MA)). Results are shown in FIGS. 46B, 46C and 46D, respectively.

8.12.2. Results

All '3 chain' format protein constructs showed efficacy in reducing tumor growth (FIG. 46B). Further, the double masked construct exhibited no toxicity, as measured by reduction in body weight (FIG. 46C) and systemic IFNγ levels (FIG. 46D).

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. An IL12 receptor agonist comprising:

(a) a first polypeptide chain comprising, in N- to C-terminal orientation:

(i) a first Fc domain; and (ii) a p35 moiety comprising an amino acid sequence having at least 90% sequence identity to amino acids 23-219 of SEQ ID NO:6;

(b) a second polypeptide chain comprising, in N- to C-terminal orientation:

(i) a second Fc domain associated with the first Fc domain to form an Fc heterodimer; and (ii) an IL12Rβ2 moiety comprising the amino acid sequence of SEQ ID NO:136 configured to mask the p35 moiety; and (c) a third polypeptide chain comprising:

(i) a p40 moiety comprising an amino acid sequence having at least 90% sequence identity to amino acids 129-328 of SEQ ID NO:5 or to amino acids 23-328 of SEQ ID NO: 5, associated with the p35 moiety; and (ii) an IL12Rβ1 moiety comprising the amino acid sequence of SEQ ID NO:134 configured to mask the p40 moiety.

2. The IL12 receptor agonist of claim 1, wherein the p40 moiety comprises an amino acid sequence having at least 95% sequence identity to amino acids 129-328 of SEQ ID NO:5.

3. The IL12 receptor agonist of claim 2, wherein the p35 moiety comprises an amino acid sequence having at least 95% sequence identity to amino acids 23-219 of SEQ ID NO:6.

4. The IL12 receptor agonist of claim 3, wherein the p40 moiety comprises an amino acid sequence having at least 98% sequence identity to amino acids 129-328 of SEQ ID NO:5.

5. The IL12 receptor agonist of claim 4, wherein the p35 moiety comprises an amino acid sequence having at least 98% sequence identity to amino acids 23-219 of SEQ ID NO:6.

6. The IL12 receptor agonist of claim 1, wherein the p40 moiety comprises an amino acid sequence having at least 95% sequence identity to amino acids 23-328 of SEQ ID NO:5.

7. The IL12 receptor agonist of claim 6, wherein the p35 moiety comprises an amino acid sequence having at least 95% sequence identity to amino acids 23-219 of SEQ ID NO:6.

8. The IL12 receptor agonist of claim 7, wherein the p40 moiety comprises an amino acid sequence having at least 98% sequence identity to amino acids 23-328 of SEQ ID NO:5.

9. The IL12 receptor agonist of claim 8, wherein the p35 moiety comprises an amino acid sequence having at least 98% sequence identity to amino acids 23-219 of SEQ ID NO:6.

10. The IL12 receptor agonist of claim 1, in which:

(a) the p35 moiety comprises the amino acid substitution (A) Y189A, Y189V, Y189R or Y189E; (B) 1193A, 1193V, or 1193E; (C) R211A or R211K; or (D) any combination of (A) to (C); and/or (b) the p40 moiety comprises the amino acid substitution (A) K28A; (B) W37A; (C) D115A; (D) K118A; (E) K126A; (F) Y268V or Y268F; (G) Y314F; or (H) any combination of (A) to (G).

11. The IL12 receptor agonist of claim 1, wherein the p40 moiety comprises the amino acid substitution W37A.

12. The IL12 receptor agonist of claim 3, wherein the p40 moiety comprises the amino acid substitution W37A.

13. A pharmaceutical composition comprising the IL12 receptor agonist of claim 1 and an excipient.

* * * * *